(12) United States Patent
Wu et al.

(10) Patent No.: US 11,596,692 B1
(45) Date of Patent: Mar. 7, 2023

(54) PD-L1/STING CONJUGATES AND METHODS OF USE

(71) Applicant: Incyte Corporation, Wilmington, DE (US)

(72) Inventors: Liangxing Wu, Wilmington, DE (US); Zhenwu Li, Wilmington, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 171 days.

(21) Appl. No.: 16/691,150

(22) Filed: Nov. 21, 2019

Related U.S. Application Data

(60) Provisional application No. 62/770,472, filed on Nov. 21, 2018.

(51) Int. Cl.
| | |
|---|---|
| *A61K 47/65* | (2017.01) |
| *A61K 31/519* | (2006.01) |
| *A61P 35/00* | (2006.01) |
| *A61K 47/60* | (2017.01) |
| *A61K 31/4184* | (2006.01) |
| *A61K 31/437* | (2006.01) |

(52) U.S. Cl.
CPC .......... *A61K 47/65* (2017.08); *A61K 31/4184* (2013.01); *A61K 31/437* (2013.01); *A61K 31/519* (2013.01); *A61K 47/60* (2017.08); *A61P 35/00* (2018.01)

(58) Field of Classification Search
CPC .... A61K 47/65; A61K 47/60; A61K 31/4184; A61K 31/437; A61K 31/519; A61P 35/00
See application file for complete search history.

(56) References Cited

U.S. PATENT DOCUMENTS

| | | | |
|---|---|---|---|
| 5,521,184 A | 5/1996 | Zimmermann et al. | |
| 2007/0225286 A1 | 9/2007 | Ren et al. | |
| 2014/0205653 A1 | 7/2014 | Dubensky et al. | |
| 2015/0056224 A1 | 2/2015 | Dubensky et al. | |
| 2017/0146519 A1 | 5/2017 | DeFillipis et al. | |
| 2017/0158772 A1 | 6/2017 | Thompson et al. | |
| 2017/0298139 A1 | 10/2017 | Thompson et al. | |
| 2018/0105514 A1 | 4/2018 | Mehlmann et al. | |
| 2018/0177784 A1 | 6/2018 | Wu et al. | |
| 2018/0177870 A1 | 6/2018 | Liu et al. | |
| 2018/0179179 A1 | 6/2018 | Wu et al. | |
| 2018/0179197 A1 | 6/2018 | Wu et al. | |
| 2018/0179201 A1 | 6/2018 | Wu et al. | |
| 2018/0179202 A1 | 6/2018 | Wu et al. | |
| 2018/0222982 A1 | 8/2018 | Dranoff et al. | |
| 2018/0305315 A1 | 10/2018 | Aktoudianakis et al. | |
| 2019/0270727 A1 | 9/2019 | Aktoudianakis et al. | |
| 2019/0300524 A1 | 10/2019 | Wu et al. | |
| 2019/0345170 A1 | 11/2019 | Wu et al. | |
| 2019/0359608 A1 | 11/2019 | Wu et al. | |
| 2020/0039994 A1 | 2/2020 | Wu et al. | |
| 2020/0040009 A1 | 2/2020 | Wu et al. | |

FOREIGN PATENT DOCUMENTS

| | | |
|---|---|---|
| CN | 105367617 | 3/2016 |
| CN | 107335049 | 11/2017 |
| WO | WO 2000/009495 | 2/2000 |
| WO | WO 2000/053595 | 9/2000 |
| WO | WO 2001/014402 | 3/2001 |
| WO | WO 2001/064655 | 9/2001 |
| WO | WO 2002/000196 | 1/2002 |
| WO | WO 2003/024967 | 3/2003 |
| WO | WO 2003/037347 | 5/2003 |
| WO | WO 2003/099771 | 12/2003 |
| WO | WO 2004/005281 | 1/2004 |
| WO | WO 2004/046120 | 6/2004 |
| WO | WO 2004/056786 | 7/2004 |
| WO | WO 2004/080980 | 9/2004 |
| WO | WO 2005/028444 | 3/2005 |
| WO | WO 2006/056399 | 6/2006 |
| WO | WO 2014/093936 | 6/2014 |
| WO | WO 2015/061294 | 4/2015 |
| WO | WO 2015/077354 | 5/2015 |
| WO | WO 2015/143161 | 9/2015 |
| WO | WO 2015/185565 | 12/2015 |
| WO | WO 2016/096577 | 6/2016 |
| WO | WO 2016/120305 | 8/2016 |
| WO | WO 2017/011444 | 1/2017 |
| WO | WO 2017/011622 | 1/2017 |
| WO | WO 2017/011920 | 1/2017 |
| WO | WO 2017/027645 | 2/2017 |
| WO | WO 2017/027646 | 2/2017 |
| WO | WO 2017/053537 | 3/2017 |
| WO | WO 2017/093933 | 6/2017 |
| WO | WO 2017/100305 | 6/2017 |

(Continued)

OTHER PUBLICATIONS

Ansell et al., "PD-1 blockade with nivolumab in relapsed or refractory Hodgkin's lymphoma," N Engl J Med., 2015, 372:311-319.
Atzrodt et al., "The Renaissance of H/D Exchange," Angew. Chem. Int. Ed., Oct. 4, 2007, 7744-7765.
Azzoni et al., "Pegylated Interferon Alfa-2a Monotherapy Results in Suppression of HIV Type 1 Replication and Decreased Cell-Associated HIV DNA Integration," J. Infect. Dis., Oct. 2012, 207:213-222.
Barber et al., "STING: infection, inflammation and cancer," Nat Rev Immunol., Dec. 2015, 15(12):760-770.
Beutler, "TLRs and innate immunity," Blood, Feb. 12, 2009, 113:1399-1407.
Blank et al., "Blockade of PD-L1 (B7-H1) augments human tumor-specific T cell responses in vitro," Int J Cancer., 2006, 119:317-327.
Blom et al., "Preparative LC-MS Purification: Improved Compound Specific Method Optimization," J. Combi. Chem., Sep. 11, 2014, 6:874-883.
Blom et al., "Optimizing Preparative LC-MS Configurations and Methods for Parallel Synthesis Purification," J. Combi. Chem., Jul. 29, 2003, 5:670-683.

(Continued)

*Primary Examiner* — Noble E Jarrell
(74) *Attorney, Agent, or Firm* — Fish & Richardson P.C.

(57) ABSTRACT

The present application relates to conjugates of STING agonists and small molecule modulators of the PD-1/PD-L1 protein/protein interaction, as well as methods of treating cancer using the conjugates.

40 Claims, 2 Drawing Sheets
(2 of 2 Drawing Sheet(s) Filed in Color)

(56) References Cited

FOREIGN PATENT DOCUMENTS

| WO | WO 2017/106740 | 6/2017 | |
|---|---|---|---|
| WO | WO 2017/123657 | 7/2017 | |
| WO | WO 2017/123669 | 7/2017 | |
| WO | WO 2017127729 | * 7/2017 | |
| WO | WO 2017/151922 | 9/2017 | |
| WO | WO 2017/161349 | 9/2017 | |
| WO | WO 2017/175147 | 10/2017 | |
| WO | WO 2017/175156 | 10/2017 | |
| WO | WO 2018/060323 | 4/2018 | |
| WO | WO 2018/067423 | 4/2018 | |
| WO | WO 2018/118664 | 6/2018 | |
| WO | WO 2018/140831 | 8/2018 | |
| WO | WO 2018/195321 | 10/2018 | |
| WO | WO 2018/234805 | 12/2018 | |
| WO | WO 2018/234807 | 12/2018 | |
| WO | WO 2018/234808 | 12/2018 | |
| WO | WO 2019/027857 | 2/2019 | |
| WO | WO 2019/027858 | 2/2019 | |
| WO | WO 2019/069269 | 4/2019 | |
| WO | WO 2019/069270 | 4/2019 | |
| WO | WO 2019/069275 | 4/2019 | |
| WO | WO 2019/134705 | 7/2019 | |
| WO | WO 2019/137707 | 7/2019 | |
| WO | WO 2019/204609 | 10/2019 | |
| WO | WO 2019/219820 | 11/2019 | |
| WO | WO 2020/006432 | 1/2020 | |
| WO | WO 2020/132549 | 6/2020 | |
| WO | WO 2020132582 | * 6/2020 | |
| WO | WO 2020/146237 | 7/2020 | |
| WO | WO 2017/186711 | 11/2020 | |

OTHER PUBLICATIONS

Blom et al., "Two-Pump at Column Dilution Configuration for Preparative LC-MS," Journal of Combinatorial Chemistry, Apr. 12, 2002, 4:295-301.

Burdette et al., "STING and the innate immune response to nucleic acids in the cytosol," Nat. Immunol. Jan. 2013, 14:19-26.

Cai et al., "The cGAS-cGAMP-STING Pathway of Cytosolic DNA Sensing and Signaling," Mol. Cell Review, Apr. 24, 2014, 54:289-296.

Cavlar et al., "Species-specific detection of the antiviral small-molecule compound CMA by STING," EMBO J. May 15, 2013, 32:1440-1450.

Chen et al., "Regulation and function of the cGAS-STING pathway of cytosolic DNA sensing," Nature Immunol., Oct. 2016, 17(10):1142-1149.

Cheng et al., "Pharmacologic Activation of the Innate Immune System to Prevent Respiratory Viral Infections," Am. J. Respir. Cell. Mol. Biol. Sep. 2011, 45:480-488.

Conlon et al., "Mouse, but not Human STING, Binds and Signals in Response to the Vascular Disrupting Agent 5,6-Dimethylxanthenone-4-Acetic Acid," J Immunol., 2013, 190:5216-5225.

Corrales et al., "Direct Activation of STING in the Tumor Microenvironment Leads to Potent and Systemic Tumor Regression and Immunity," Cell Reports, May 19, 2015, 11:1018-1030.

Crosse et al., "Interferon-Stimulated Genes as Enhancers of Antiviral Innate Immune Signaling," J. Innate Immun., Nov. 30, 2017, 10:85-93.

Diprivan, Reference ID No. 4089428, retrieved from https://www.accessdata.fda.gov/drugsatfda_docs/label/2017/019627s066lbl.pdf, Apr. 2017, 54 pages.

Enomoto et al., "Factors associated with the response to interferon-based antiviral therapies for chronic hepatitis C," World J. Hepatol, Nov. 18, 2015, 7:2681-2687.

Gao et al., "Structure-Function Analysis of STING Activation by c[G(20,50)pA(30,50)p]and Targeting by Antiviral DMXAA," Cell, Aug. 13, 2013, 154(4):748-762.

Garbe et al., "Diagnosis and treatment of cutaneous melanoma: state of the art 2006*," Melanoma Res. Apr. 2007, 17:117-127.

Garon et al., "Pembrolizumab for the treatment of non-small-cell lung cancer," N Engl J Med., 2015, 372:2018-2028.

Greenwald et al., "The B7 family revisited," Annu Rev Immunol., 2005, 23:515-548.

Guo et al., "STING agonists induce an innate antiviral immune response against hepatitis B virus," Antimicrobial Agents and Chemotherapy, Dec. 15, 2014, 59:1273-1281.

Herbst et al., "Predictive correlates of response to the anti-PD-L1 antibody in Cancer," Nature, 2014, 515:563-567.

Hervas-Stubbs et al., "Direct Effects of Type I Interferons on Cells of the Immune System," Clin. Cancer Res., May 1, 2011, 17:2619-2627.

International Search Report and Written Opinion in International Application No. PCT/US2019/033944, dated Sep. 19, 2019, 13 pages.

International Search Report and Written Opinion in International Application No. PCT/US2019/044499, dated Nov. 20, 2019, 13 pages.

International Search Report and Written Opinion in International Application No. PCT/US2019/044500, dated Nov. 20, 2019, 13 pages.

Ishikawa et al., "STING is an endoplasmic reticulum adaptor that facilitates innate immune signalling," Nature, Oct. 2, 2018, 455:674-678.

Iwai et al., "Involvement of PD-L1 on tumor cells in the escape from host immune system and tumor immunotherapy by PD-L1 blockade," PNAS., 2002, 99(19):12293-12297.

Berge et al., "Pharmaceutical Salts," Journal of Pharmaceutical Science, 1977, 66:1-19.

Kerekes et al., "Aurora Kinase Inhibitors Based on the Imidazo[1,2-a]pyrazine Core: Fluorine and Deuterium Incorporation Improve Oral Absorption and Exposure," J. Med. Chem., Dec. 3, 2010, 54:201-210.

Khiar et al., "Identification of a small molecule that primes the type I interferon response to cytosolic DNA," Scientific Reports, May 31, 2017, 7:2561.

Kim et al., "Anticancer Flavonoids Are Mouse-Selective STING Agonists," ACS Chem. Biol., May 17, 2013, 8:1396-1401.

Kirkwood, "Cancer Immunotherapy: The Interferon-Experience," Semin. Oncol., Jun. 1, 2002, 29:18-26.

Kramer et al., "Antiviral Activity of 10-Carboxymethyl-9-Acridanone," Antimicrobial Agents and Chemotherapy, Feb. 1, 1976, 9:233-238.

Lane et al., "Interferon-α in Patients with Asymptomatic Human Immunodeficiency Virus (HIV) Infection: A Randomized, Placebo-Controlled Trial," Ann. Intern. Med., Jun. 1, 1990, 112:805-811.

Larkin et al., "Cutting Edge: Activation of STING in T Cells Induces Type I IFN Responses and Cell Death," J Immunol., 2017, 199:397-402.

Liu et al., "A cell-based high throughput screening assay for the discovery of cGASSTING pathway agonists," Antiviral Research, 2017, 147:37-46.

McNab et al., "Type I interferons in infectious disease. Nature Reviews Immunology," Nat Rev Immunol, Feb. 2015, 15:87-103.

Okazaki et al., "The PD-1-PD-L pathway in immunological tolerance," Trends Immunol., 2006, 4:195-201.

Okudaira et al., "Blockade of B7-H1 or B7-DC induces an anti-tumor effect in a mouse pancreatic cancer model," Int J Oncol., 2009, 35:741-749.

Palm et al., "Pattern recognition receptors and control of adaptive immunity," Immunol Rev. Jan. 2009, 227:221-233.

Perera et al., "Activation of LPS-inducible genes by the antitumor agent 5,6-dimethylxanthenone-4-acetic acid in primary murine macrophages. Dissection of signaling pathways leading to gene induction and tyrosine phosphorylation," J. Immunol., Nov. 15, 1994, 153:4684-4697.

Peturssion et al., "Protecting Groups in Carbohydrate Chemistry," J Chem Educ., 1997, 74(11):1297-1303.

Pizzocaro et al., "Interferon Adjuvant to Radical Nephrectomy in Robson Stages II and III Renal Cell Carcinoma: A Multicentric Randomized Study," J. Clin. Oncol., Jan. 15, 2001, 19:425-431.

(56) References Cited

OTHER PUBLICATIONS

Powles et al., "MPDL3280A (anti-PD-L1) treatment leads to clinical activity in metastatic bladder cancer," Nature, 2014, 515:558-562.
Quesada et al., "Alpha Interferon for Induction of Remission in Hairy-Cell Leukemia," N. Engl. J. Med. Jan. 5, 1984, 310:15-18.
Ramanjulu et al., "Design of amidobenzimidazole STING receptor agonists with systemic activity," Nature, 2018, 564:439-443.
Ramanjulu et al., "Design of amidobenzimidazole STING receptor agonists with systemic activity," Nature, 2018, Supplementary Information, 66 pages.
Rao et al., "Anti-PD-1/PD-L1 therapy for infectious diseases: learning from the cancer paradigm," International Journal of Infectious Diseases, 2017, 56:221-228.
Remington et al., "Remington's Pharmaceutical Sciences," 17th ed., 1985, p. 1418.
Sali et al., "Characterization of a Novel Human-Specific STING Agonist that Elicits Antiviral Activity Against Emerging Alphaviruses," PLoS Pathog., Dec. 8, 2015, 11(12):e1005324.
SciFinder Search Results, generated Jun. 27, 2018, 1 page.
SciFinder Search Results, generated Jun. 27, 2018, 22 pages.
Siu et al., "Discovery of a Novel cGAMP Competitive Ligand of the Inactive Form of STING," ACS Med Chem Lett., 2019, 10(1):92-97.
Smith et al., "March's Advanced Organic Chemistry: Reactions, Mechanisms, and Structure," Wiley, 2007, 6th Ed., 2374 pages.
Sokolowska et al., "STING Signaling in Cancer Cells: Important or Not?," Arch Immunol Ther Exp., Jul. 26, 2017, 66:125-132.
Takeuchi et al., "Innate immunity to virus infection," Immunol Rev., Jan. 2009, 227:75-86.
Tang et al., "Benefits of Therapeutic Drug Monitoring of Vancomycin: A Systematic Review and Meta-Analysis," Plos One, Oct. 2013, 8:1-10.
Tang et al., "The chemotherapeutic agent DMXAA as a unique IRF3-dependent type-2 vaccine adjuvant," Plos One., 2013, 8(3):e60038.
Tarhini et al., "IFN-α in the Treatment of Melanoma," J. Immunol., Oct. 2012, 189:3789-3793.
Topalian et al., "Safety, Activity, and Immune Correlates of Anti-PD-1 Antibody in Cancer," N Engl J Med., 2012, 366:2443-2454.
Vannucchi et al., "Perspectives in Biomolecular Therapeutic Intervention in Cancer: From the Early to the New Strategies With Type I Interferons," Curr. Med. Chem., Mar. 1, 2007, 14:667-679.
Wallace et al., "The Vascular Disrupting Agent, DMXAA, Directly Activates Dendritic Cells through a MyD88-Independent Mechanism and Generates Antitumor Cytotoxic T Lymphocytes," Cancer Research, Jul. 2007, 67:7011-7019.
Wuts et al., "Protective Groups in Organic Synthesis," 4th Ed., Wiley, 2006, 1111 pages.
Xu et al., "Design, synthesis and biological evaluation of deuterated nintedanib for improving pharmacokinetic properties," J. Label Compd. Radiopharm. May 26, 2015, 58:308-312.
Zhou et al., "Blockade of programmed death-1 pathway rescues the effector function of tumor-infiltrating T cells and enhances the antitumor efficacy of lentivector immunization," J Immunol., 2010, 185:5082-5092.

* cited by examiner

PD-L1/STING CONJUGATES AND METHODS OF USE

This application claims the benefit of priority of U.S. Prov. Appl. No. 62/770,472, filed Nov. 21, 2018, which is incorporated herein by reference in its entirety.

TECHNICAL FIELD

The present application relates to conjugates of small molecule modulators of the PD-1/PD-L1 protein/protein interaction and STING agonists, as well as their compositions and methods of use.

BACKGROUND

The innate immune system is the first line of defense against infection from foreign microorganisms including bacteria, viruses, parasites and other infectious threats by responding to certain danger signals associated with cellular or tissue damage. This response is initiated by activation of so-called pattern recognition receptors that can detect different forms of foreign antigens, i.e., nucleic acids, peptides, carbohydrates, and more, which then lead to production of interferons (IFNs), proinflammatory chemokines and cytokines, and anti-microbial peptides to fight infection (Palm N W and Medzhitov R., "Pattern recognition receptors and control of adaptive immunity," *Immunol Rev* (2009) 227: 221-233; Takeuchi O and Akira S. "Innate immunity to virus infection," *Immunol Rev* (2009) 227:75-86; Beutler B A. TLRs and innate immunity. *Blood* (2009) 113:1399-1407). STING (stimulator of interferon genes), also known as MITA, MPYS, ERIS, and TMEM173, is one such pattern recognition receptor in the innate immune response that detects cytosolic nucleic acids (Ishikawa H and Barber G N., "STING is an endoplasmic reticulum adaptor that facilitates innate immune signaling," *Nature* (2008) 455:674-678). Direct binding of STING to its ligands induces a conformational change of the complex resulting in a downstream signaling cascade involving TBK1 activation, IRF-3 phosphorylation, and production of type I IFNs and other proinflammatory cytokines, such as TNF, IL-6 and IFNγ (Ishikawa and Barber, supra).

Type I IFNs play a central role in orchestrating host anti-viral response through inhibiting viral replication in infected cells, activating and enhancing antigen presentation and triggering the adaptive immune response through direct and indirect action on T and B cells (McNab F, et al., "Type I interferons in infectious disease," *Nat Rev Immunol* (2015) 15:87-103; Crosse K M, et al., "Interferon-Stimulated Genes as Enhancers of Antiviral Innate Immune Signaling," *J Innate Immun* (2018) 10:85-93). Therefore, this cytokine acts as a master regulator whose induction in the early stages of viral infection modulates downstream signaling cascades that promote both pro-inflammatory and anti-inflammatory responses. Thus type I IFNs have been evaluated as a therapeutic agent for chronic viral infection such as HCV and HIV (Enomoto H, et al., "Factors associated with the response to interferon-based antiviral therapies for chronic hepatitis C," *World J Hepatol* (2015) 7:2681-2687; Azzoni L, et al., "Pegylated interferon alfa-2a monotherapy results in suppression of HIV type 1 replication and decreased cell-associated HIV DNA integration," *J Infect Dis* (2013) 207:213-222; Lane H C, et al. "Interferon-alpha in patients with asymptomatic human immunodeficiency virus (HIV) infection: A randomized, placebo-controlled trial," *Ann Intern Med* (1990) 112:805-11).

The use of type I interferons (the IFNα family and IFNβ) as potential antitumor agents has also been investigated (Kirkwood J., "Cancer immunotherapy: the interferon-alpha experience," *Semin Oncol* (2002) 29:18-26; Tarhini A A, et al., "IFN-alpha in the treatment of melanoma," *J Immunol* (2012) 189:3789-3793). IFNs have multiple anticancer mechanisms that include: direct inhibition on tumor cell proliferation and angiogenesis; induction of tumor-specific cytotoxic T-cells; plus other immunoregulatory effects on antibody production, natural killer (NK) cell activation, macrophage function, delayed-type hypersensitivity, and major histocompatibility complex antigen expression (Hervas-Stubbs S, et al., "Direct effects of type I interferons on cells of the immune system," *Clin Cancer Res* (2011) 17:2619-2627; Vannucchi S, et al. "Perspectives in biomolecular therapeutic intervention in cancer: from the early to the new strategies with type I interferons," *Curr Med Chem* (2007) 14:667-679).

Anticancer activity of type I IFNs has been demonstrated in patients with hematological malignancies (e.g., hairy cell leukemia) and solid tumors (e.g., renal cell carcinoma and malignant melanoma) (Quesada J R, et al., "Alpha interferon for induction of remission in hairy-cell leukemia," *N Engl J Med* (1984) 310:15-18; Pizzocaro G, et al., "Interferon adjuvant to radical nephrectomy in Robson stages II and III renal cell carcinoma: a multicentric randomized study," *J Clin Oncol* (2001) 19:425-431; Garbe C, et al., "Diagnosis and treatment of cutaneous melanoma: state of the art," *Melanoma Res* (2007) 17:117-127). However, the results and overall efficacy have been modest. This may be due to intrinsic resistance to IFN-induced cell death, to the short half-life (~30 minutes) of intravenously or subcutaneously dosed IFN, to dose-limiting systemic toxicities, and/or to the development of neutralizing antibodies against recombinant IFN protein. Thus, the development of an agent like a STING agonist to induce production of type I interferons will be of interest to the field. Currently, there are two different classes of STING agonists: cyclic dinucleotides and small molecule structures.

Cyclic dinucleotides (CDNs) can directly bind and activate STING, and the complex of bacterial CDN and STING has been confirmed by X-ray crystallography recently (Burdette D L, et al., "STING and the innate immune response to nucleic acids in the cytosol," *Nat Immunol* (2013) 14:19-26). In mammalian cells, the primary sensor of cyclic double stranded DNA (dsDNA), namely cyclic GMP-AMP synthetase (cGAS), can convert those cyclic dsDNA into a mammalian CDN cGAMP (cyclic guanosine monophosphate-adenosine monophosphate) (Gao P, et al., "Structure-function analysis of STING activation by c[G(2',5')pA(3'5')] and targeting by antiviral DMXAA," *Cell* (2013) 154:748-762). The interaction of cGAMP and STING has also been confirmed by X-ray crystallography (Cai X, et al., "The cGAS-cGAMP-STING pathway of cytosolic DNA sensing and signaling," *Mol Cell* (2014) 54:289-296). Synthetic derivatives of cGAMP have been synthesized and showed excellent cellular potency to activate both mouse and human STING in vitro, as well as demonstrated good anti-tumor efficacy in preclinical mouse models (Corrales L, et al, "Direct activation of STING in the tumor microenvironment leads to potent and systemic tumor regression and immunity," *Cell Rep* (2015) 11:1018-1030).

Small molecules that can activate STING have also been identified, DMXAA (5,6-dimethylxanthenone-4-acetic acid) and CMA (10-carboxymethyl-9-acridanone) (Perera P Y, et al., "Activation of LPS-inducible genes by the antitumor agent 5, 6-dimethylxanthenone-4-acetic acid in primary murine macrophages. Dissection of signaling pathways leading to gene induction and tyrosine phosphorylation," *J Immunol* (1994) 153:4684-4697; Kramer M J, et al., "Antiviral activity of 10-carboxymethyl-9-acridanone," *Antimicrob Agents Chemother* (1976) 9:233-238). These two chemically-unrelated compounds can activate the STING pathway, and block multiple viruses from replication (Guo F, et al., "STING agonists induce an innate antiviral immune response against hepatitis B virus," *Agents Chemother* (2015) 59:1273-1281; Cheng G, et al., "Pharmacologic activation of the innate immune system to prevent respiratory viral infections," *Am J Respir Cell Mol Biol* (2011) 45:480-488). Intriguingly, DMXAA demonstrates excellent anti-tumor activity in preclinical mouse models by priming CD8+ T cells responses to promote rejection of established tumors in a STING-dependent manner, inducing tumor necrosis through disruption of tumor vasculature, as well as augmenting cancer vaccine effect (Corrales, supra; Wallace A, et al., "The vascular disrupting agent, DMXAA, directly activates dendritic cells through a MyD88-independent mechanism and generates antitumor cytotoxic T lymphocytes," *Cancer Res* (2007) 67:7011-7019; Tang C K, et al., "The chemotherapeutic agent DMXAA as a unique IRF3-dependent type-2 vaccine adjuvant," *Plos One* (2013) 8:1-6).

A major concern for systemic delivery of a STING agonist is the potential for the induction of a cytokine storm. One approach to restrict STING agonism to the tumor microenvironment while avoiding systemic toxicity is to co-target PD-L1, which is highly expressed in tumors and many tumor infiltrating antigen presenting cells. PD-L1 interacts with PD-1 receptor (also known as CD279) or CD80 (also known as B7.1) which are expressed on activated T cells, NK T cells, B cells, and macrophages (Greenwald R J, et al., "The B7 family revisited," *Annu. Rev. Immunol* 2005;23:515-548; Okazaki T, et al., "The PD-1-PD-L pathway in immunological tolerance," *Trends Immunol* 2006; 4:195-201).

Blockade of PD-L1/PD-1 signaling improves T cell responses in a range of preclinical cancer models. Antibodies against PD-L1 can enhance or restore T cell effector function, including cytokine production and cytolytic activity against tumor cells, as well as increased proliferation and/or infiltration of tumor-reactive CD8$^+$ T cells into established tumors (Iwai Y, et al., "Involvement of PD-L1 on tumor cells in the escape from host immune system and tumor immunotherapy by PD-L1 blockade," PNAS 2002; 99(19):12293-12297; Okudaira K, et al., "Blockade of B7-H1 or B7-DC induces an anti-tumor effect in a mouse pancreatic cancer model," *Int J Oncol* 2009; 35:741-749; Zhou Q, et al., "Blockade of programmed death-1 pathway rescues the effector function of tumor-infiltrating T cells and enhances the antitumor efficacy of lentivector immunization," *J Immunol* 2010; 185:5082-5092; Blank C, et al., "Blockade of PD-L1 (B7-H1) augments human tumor-specific T cell responses in vitro," *Int J Cancer* 2006; 119:317-327). Therapeutic use of blocking antibodies to PD-L1 has produced durable clinical responses in a wide variety of solid and hematologic malignancies (Topalian S L, et al., "Safety, Activity, and Immune Correlates of Anti-PD-1 Antibody in Cancer," *N Engl J Med* 2012; 366:2443-2454; Herbst R S, et al., "Predictive correlates of response to the anti-PD-L1 antibody in Cancer," *Nature* 2014; 515:563-567; Powles T, et al., "MPDL3280A (anti-PD-L1) treatment leads to clinical activity in metastatic bladder cancer," *Nature* 2014; 515:558-562; Garon E B, et al., "Pembrolizumab for the treatment of non-small-cell lung cancer," *N Engl J Med* 2015; 372:2018-2028; Ansell S M, et al., "PD-1 blockade with nivolumab in relapsed or refractory Hodgkin's lymphoma," *N Engl J Med* 2015; 372:311-319).

Hence, there is a need for small molecule entities that can activate human STING and induce upregulation of IRF3 and NFκB pathway, which can later lead to production of IFNs and other proinflammatory cytokines and chemokines in a PD-L1-dependent manner. This type of immunomodulatory agent may be useful not only in infectious disease to activate innate immunity, but also in cancer, and as vaccine adjuvants. There is a further need for to limit STING agonism to the tumor microenvironment. This application addresses these needs and others.

SUMMARY

The present disclosure provides, inter alia, compounds of Formula (I):

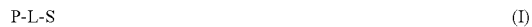

$$P\text{-}L\text{-}S \tag{I}$$

or a pharmaceutically acceptable salt thereof, wherein P is a ligand that binds to cell surface PD-L1 protein and induces PD-L1 internalization, L is a linking group, and S is a moiety that agonizes STING.

The P ligand is a small molecule compound (i.e., not an antibody). The P ligands of the compounds of Formula (I) target PD-L1 and have been shown to interrupt the PD-L1:PD-1 interaction (see e.g., Tables 2 and 3), and also internalize PD-L1 in the target cell population. This internalization process can thus selectively deliver the payload of STING agonists (the S moiety) to PD-L1-expressing cells, allowing for a targeted treatment of cancer.

The present disclosure further provides methods of treating cancer in a patient, comprising administering to the patient a compound described herein, or a pharmaceutically acceptable salt thereof.

The present disclosure also provides a method of activating or agonizing STING, comprising contacting a cell with a compound described herein, or a pharmaceutically acceptable salt thereof.

In some embodiments, the compound or salt selectively agonizes STING in high PD-L1 expressing cells as compared to low PD-L1 expressing cells, wherein the high PD-L1 expressing cells have 200-fold more surface PD-L1 expression than a negative control and the low PD-L1 expressing cells have about 10-fold more surface PD-L1 expression than a negative control. In some embodiments, the high PD-L1 and low PD-L1 expression are determined by measuring the mean fluorescence intensity of PD-L1 expression of high PD-L1 expressing cells and low PD-L1 expressing HEK-293T cell lines stained with phycoerythrin-conjugated anti-PD-L1 antibody.

Other features and advantages of the disclosure will be apparent from the following detailed description, and from the claims.

DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
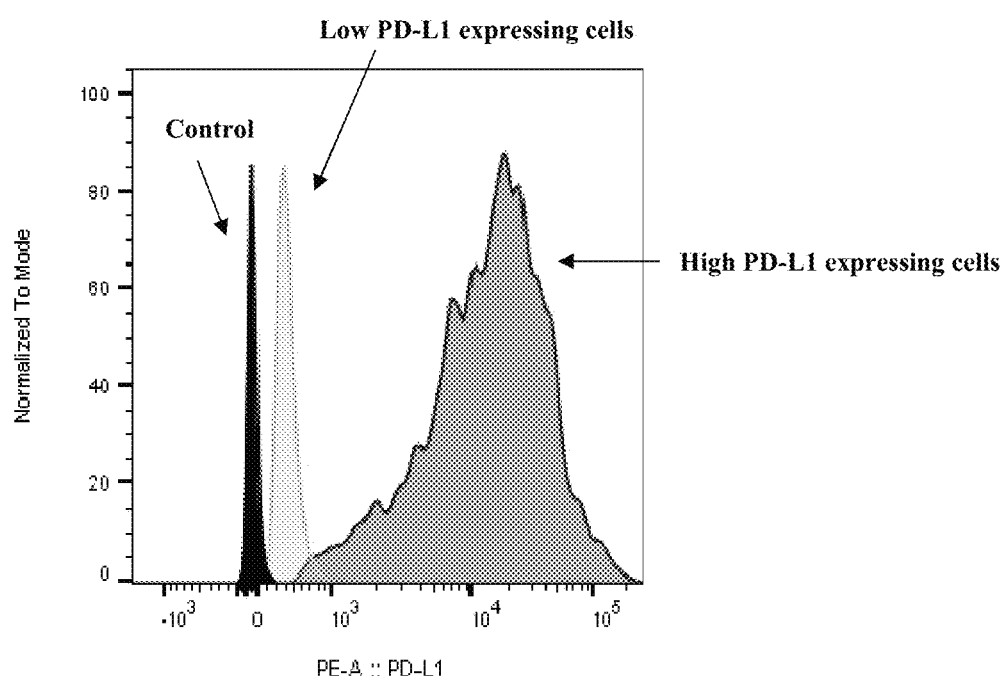
FIG. 1 depicts the mean fluorescence intensity of PD-L1 expression of high PD-L1 expressing cells and low PD-L1 expressing HEK-293T cell lines stained with phycoerythrin-conjugated anti-PD-L1 antibody.

The present disclosure provides, inter alia, compounds of Formula (I):

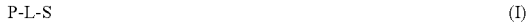

or a pharmaceutically acceptable salt thereof, wherein P is a ligand that binds to cell surface PD-L1 protein and induces PD-L1 internalization, L is a linking group, and S is a moiety that agonizes STING. Embodiments for each of the conjugate components are described infra.

Ligand P

In some embodiments P has Formula (P-1):

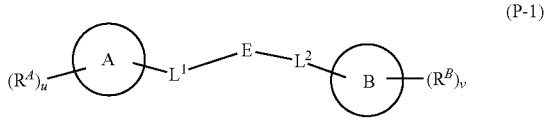

wherein:

L is attached to ring A or ring B by a direct bond or to an $R^A$ or $R^B$ substituent;

E is

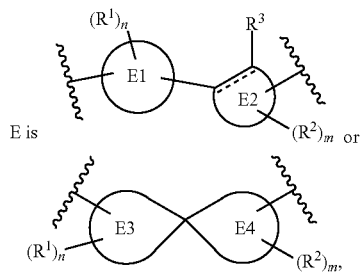

wherein ring E1 or ring E3 is attached to $L^1$ and ring E2 or ring E4 is attached to $L^2$;

==== is a single bond or a double bond;

ring E1 and E2 are each independently selected from $C_{6-10}$ aryl, 5- to 14-membered heteroaryl, 4- to 14-membered heterocycloalkyl, and $C_{3-14}$ cycloalkyl;

ring E3 and ring E4 are joined together through a quaternary ring carbon atom to form a spiro structure; and ring E3 and ring E4 are each independently selected from 4- to 14-membered heterocycloalkyl and $C_{3-14}$ cycloalkyl;

$L^1$ and $L^2$ are each independently selected from bond, —$(CR^{14}R^{15})_{t1}C(O)NR^{13}(CR^{14}R^{15})_{t1}$—, —$(CR^{14}R^{15})_{t1}NR^{13}C(O)(CR^{14}R^{15})_{t1}$—, —$(CR^{14}R^{15})_{t1}C(=NR^{13})NR^{13}(CR^{14}R^{15})_{t1}$—, —$(CR^{14}R^{15})_{t1}NR^{13}C(=NR^{13})(CR^{14}R^{15})_{t1}$—, —$(CR^{14}R^{15})_{t1}C(=NOR^{13})NR^{13}(CR^{14}R^{15})_{t1}$—, —$(CR^{14}R^{15})_{t1}NR^{13}C(=NOR^{13})(CR^{14}R^{15})_{t1}$—, —$(CR^{14}R^{15})_{t1}C(=NCN)NR^{13}(CR^{14}R^{15})_{t1}$—, —$(CR^{14}R^{15})_{t1}NR^{13}C(=NCN)(CR^{14}R^{15})_{t1}$—, —$(CR^{14}R^{15})_{t2}$—, —O—, —O—$(CR^{14}R^{15})_{t2}$—, —$(CR^{14}R^{15})_{t2}$—O—, —$(CR^{14}R^{15})_{t2}(CR^{14}R^{15})_{t2}$—, —$NR^{13}$—, —$(CR^{14}R^{15})_{t2}$—$NR^{13}$—, —$NR^{13}$—$(CR^{14}R^{15})_{t2}$—, —$(CR^{14}R^{15})_{t2}NR^{13}(CR^{14}R^{15})_{t2}$, —$CR^{14}=CR^{15}$—, —C≡C—, —$(CR^{14}R^{15})_{t1}$ $SO_2(CR^{14}R^{15})_{t1}$—, —$(CR^{14}R^{15})_{t1}SO_2NR^{13}(CR^{14}R^{15})_{t1}$—, —$(CR^{14}R^{15})_{t1}NR^{13}SO_2(CR^{14}R^{15})_{t1}$—, —$(CR^{14}R^{15})_{t1}NR^{13}S(O)_2NR^{13}$—$(CR^{14}R^{15})_{t1}$—, —$(CR^{14}R^{15})_{t1}NR^{13}C(O)O$—$(CR^{14}R^{15})_{t1}$—, —$(CR^{14}R^{15})_{t1}OC(O)NR^{13}(CR^{14}R^{15})_{t1}$—, —$(CR^{14}R^{15})_{t1}NR^{13}C(O)NR^{13}(CR^{14}R^{15})_{t1}$—, and —$(CR^{14}R^{15})_{t1}NR^{13}S(O)_2NR^{13}(CR^{14}R^{15})_{t1}$—;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —$N(C_{1-4}$ alkyl$)_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —$N(C_{1-4}$alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 4-, 5-, 6-or 7-membered heterocycloalkyl, each of which is optionally substituted with 1 or 2 independently selected $R^q$ substituents;

$R^1$ is $C_{1-4}$ alkyl, $C_{1-4}$ alkoxy, $C_{1-4}$ haloalkyl, $C_{1-4}$ haloalkoxy, CN, halo, OH, —C(O)OH, $NH_2$, -$C_{1-4}$ alkylamino, or di-($C_{1-4}$ alkyl)amino;

$R^2$ is $C_{1-4}$ alkyl, $C_{1-4}$ alkoxy, $C_{1-4}$ haloalkyl, $C_{1-4}$ haloalkoxy, CN, halo, OH, —C(O)OH, $NH_2$, -$C_{1-4}$ alkylamino, or di-($C_{1-4}$ alkyl)amino;

$R^3$ is $C_{1-4}$ alkyl, halo, CN, or $C_{1-4}$ haloalkyl;

ring A and ring B are each independently selected from 5-14 membered heteroaryl, 4-14 membered heterocycloalkyl, $C_{6-14}$ aryl, and $C_{3-14}$ cycloalkyl;

$R^A$ and $R^B$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-14}$ aryl, $C_{3-14}$ cycloalkyl, 5-14 membered heteroaryl, 4-14 membered heterocycloalkyl, $C_{6-14}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2 R^a$, $S(O)_2NR^aC(O)R^a$, —$P(O)R^aR^a$, —$P(O)(OR^a)$ $(OR^a)$, —$B(OH)_2$, —$B(OR^a)_2$ and $S(O)_2NR^aR^a$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- are each optionally substituted with 1, 2, 3, 4 or 5 independently selected $R^b$ substituents;

or two $R^A$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

or two $R^B$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- are each optionally substituted with 1, 2, 3, 4, or 5 independently selected $R^d$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $C(=NOH)R^c$, $C(=NOH)NR^c$, $C(=NCN)NR^cR^c$, $NR^cC(=NCN)NR^cR^c$, $C(=NR^c)NR^cR^c$, $NR^cC(=NR^c)NR^cR^c$, $NHR^c$, $NR^cR^c$, $NR^cC(O)R^c$, $NR^cC(=NR^c)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, $—P(O)R^cR^c$, $—P(O)(OR^c)(OR^c)$, $—B(OH)_2$, $—B(OR^c)_2$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2, 3, 4, or 5 independently selected $R^f$ substituents;

or two $R^c$ attached to the same nitrogen atom are taken together to form a 4-14 membered heterocycloalkyl ring which is optionally substituted with 1, 2, or 3 independently selected $R^f$ substituents;

each $R^d$ is independently selected from $C_{1-6}$ alkyl, $C_{1-6}$ haloalkyl, halo, $C_{2-6}$ alkenyl, $C_{2-6}$ alkynyl, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-10 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $C(O)NR^eS(O)_2R^e$, $OC(O)R^e$, $OC(O)NR^eR^e$, $NHR^e$, $NR^eR^e$, $NR^eC(O)R^e$, $NR^eC(=NR^e)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $S(O)_2NR^eC(O)R^e$, $NR^eS(O)_2R^e$, $NR^eS(O)_2NR^eR^e$, $—P(O)R^eR^e$, $—P(O)(OR^e)(OR^e)$, $—B(OH)_2$, $—B(OR^e)_2$ and $S(O)_2NR^eR^e$, wherein the $C_{1-6}$ alkyl, $C_{2-6}$ alkenyl, $C_{2-6}$ alkynyl, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-10 membered heteroaryl)-$C_{1-4}$ alkyl-, and (4-14 membered heterocycloalkyl)-$C_{1-4}$ alkyl- are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2 or 3 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $C(O)NR^gS(O)_2R^g$, $OC(O)R^g$, $OC(O)NR^gR^g$, $NHR^g$, $NR^gR^g$, $NR^gC(O)R^g$, $NR^gC(=NR^g)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $S(O)_2NR^gC(O)R^g$, $NR^gS(O)_2R^g$, $NR^gS(O)_2NR^gR^g$, $—P(O)R^gR^g$, $—P(O)(OR^g)(OR^g)$, $—B(OH)_2$, $—B(OR^g)_2$ and $S(O)_2NR^gR^g$; wherein the $C_{1-4}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 independently selected $R^n$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2, or 3 independently selected $R^p$ substituents;

each $R^n$ is substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $C(O)NR^oS(O)_2R^o$, $OC(O)R^o$, $OC(O)NR^oR^o$, $NHR^o$, $NR^oR^o$, $NR^oC(O)R^o$, $NR^oC(=NR^o)R^o$, $NR^oC(O)NR^oR^o$, $NR^oC(O)OR^o$, $C(=NR^oNR^oR^o$, $NR^oC(=NR^oNR^oR^o$, $S(O)R^o$, $S(O)NR^oR^o$, $S(O)_2R^o$, $S(O)_2NR^oC(O)R^o$, $NR^oS(O)_2R^o$, $NR^oS(O)_2NR^oR^o$, $—P(O)R^oR^o$, $—P(O)R^o(OR^o)$, $—B(OH)_2$, $—B(OR^o)_2$ and $S(O)_2NR^oR^o$, wherein the $C_{1-4}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are each optionally substituted with 1, 2 or 3 independently selected R$^q$ substituents;

each R$^p$ is independently selected from C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halo, CN, NHOR$^r$, OR$^r$, SR$^r$, C(O)R$^r$, C(O)NR$'$R$^r$, C(O)OR$^r$, C(O)NR$'$S(O)$_2$R$^r$, OC(O)R$^r$, OC(O)NR$'$R$^r$, NHR$^r$, NR$'$R$^r$, NR$'$C(O)R$^r$, NR$'$C(=NR$'$)R$^r$, NR$'$C(O)NR$'$R$^r$, NR$'$C(O)OR$^r$, C(=NR$'$)NR$'$R$^r$, NR$'$C(=NR$'$)NR$'$R$^r$, NR$'$C(=NOH)NR$'$R$^r$, NR$'$C(=NCN)NR$'$R$^r$, S(O)R$^r$, S(O)NR$'$R$^r$, S(O)$_2$R$^r$, S(O)$_2$NR$'$C(O)R$^r$, NR$'$S(O)$_2$R$^r$, NR$'$S(O)$_2$NR$'$R$^r$, —P(O)R$'$R$^r$, —P(O)(OR$'$)(0R$'$), —B(OH)$_2$, —B(OR$'$)$_2$ and S(O)$_2$NR$'$R$^r$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- is optionally substituted with 1, 2 or 3 independently selected R$^q$ substituents;

each R$^o$ or R$^r$ is independently selected from H, C$_{1-4}$ alkyl, C$_{3-6}$ cycloalkyl, C$_{6-10}$ aryl, 5 or 6-membered heteroaryl, 4-7 membered heterocycloalkyl, C$_{1-6}$ haloalkyl, C$_{1-6}$ haloalkoxy, C$_{2-4}$ alkenyl, and C$_{2-4}$ alkynyl, wherein the C$_{1-4}$ alkyl, C$_{3-6}$ cycloalkyl, C$_{6-10}$ aryl, 5 or 6-membered heteroaryl, 4-7 membered heterocycloalkyl, C$_{2-4}$ alkenyl, and C$_{2-4}$ alkynyl are each optionally substituted with 1, 2 or 3 independently selected R$^q$ substituents;

each R$^q$ is independently selected from OH, NO$_2$, CN, halo, C$_{1-6}$ alkyl, C$_{2-6}$ alkenyl, C$_{2-6}$ alkynyl, C$_{1-6}$ haloalkyl, phenyl, C$_{3-7}$ cycloalkyl, 4-6 membered heterocycloalkyl, and 5-6 membered heteroaryl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonyloxy, C$_{1-6}$ alkylcarbonylamino, C$_{1-6}$ alkoxycarbonylamino, C$_{1-6}$ alkylaminocarbonyloxy, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino, wherein the C$_{1-6}$ alkyl, phenyl, C$_{3-7}$ cycloalkyl, 4-6 membered heterocycloalkyl, and 5-6 membered heteroaryl are each optionally substituted with 1, 2 or 3 substituents independently selected from halo, OH, CN, —COOH, C$_{1-4}$ alkyl, C$_{1-4}$ alkoxy, C$_{1-4}$ haloalkyl, C$_{1-4}$ haloalkoxy, amino, C$_{1-3}$ alkylamino, and di(C$_{1-3}$ alkyl) amino;

each subscript t1 is independently an integer of 0, 1, 2, 3 or 4;

each subscript t2 is independently an integer of 1, 2, 3 or 4;

the subscript m is an integer of 0, 1, 2, 3, or 4;

the subscript n is an integer of 0, 1, 2, 3, or 4;

the subscript u is an integer of 0, 1, 2, 3, 4, 5, 6, 7 or 8; and the subscript v is an integer of 0, 1, 2, 3, 4, 5, 6, 7 or 8.

In some embodiments, E has formula:

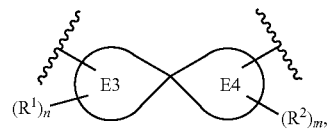

wherein ring E3 is attached to L$^1$ and ring E4 is attached to L$^2$.

In some embodiments, E has formula:

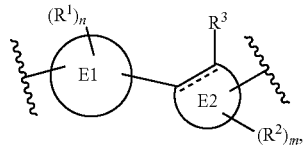

wherein ring E1 is attached to L$^1$ and ring E2 is attached to L$^2$.

In some embodiments, E has formula:

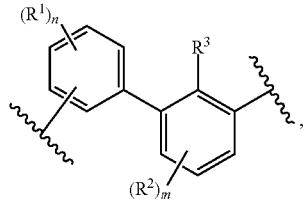

wherein the left (having (R$^1$)$_n$ substituents) phenyl ring is attached to L$^1$ and the right (having (R$^2$)$_m$ and R$^3$ substituents) phenyl ring is attached to L$^2$.

In some embodiments, E has formula:

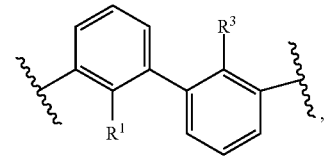

wherein the left (having (R$^1$)$_n$ substituents) phenyl ring is attached to L$^1$ and the right (having (R$^2$)$_m$ and R$^3$ substituents) phenyl ring is attached to L$^2$.

In some embodiments, P has Formula (P-1a):

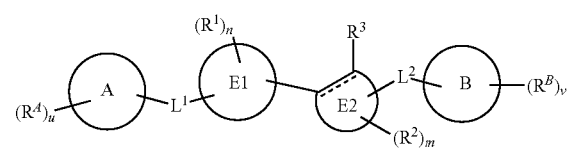

(P-1a)

wherein:

L$^1$ and L$^2$ are each independently selected from a bond, —C(O)NR$^{13}$—, —NR$^{13}$C(O)—, —C(=NR$^{13}$)NR$^{13}$—, —NR$^{13}$C(=NR$^{13}$)—, —C(=NOR$^{13}$)NR$^{13}$—, —NR$^{13}$C (=NOR$^{13}$)—, —C(=NCN)NR$^{13}$—, —NR$^{13}$C(=NCN)—, O, —(CR$^{14}$R$^{15}$)$_{t2}$—, —(CR$^{14}$R$^{15}$)$_{t2}$—O—, —O(CR$^{14}$R$^{15}$)$_{t2}$—, —NR$^{13}$—, —(CR$^{14}$R$^{15}$)$_{t2}$—NR$^{13}$—, —NR$^{13}$—(CR$^{14}$R$^{15}$)$_{t2}$—, —CH=CH—, —C≡C—, —S(O)$_2$NR$^{13}$—, —NR$^{13}$S(O)$_2$—, —NR$^{13}$S(O)$_2$NR$^{13}$—, —NR$^{13}$C(O)O—, —OC(O)NR$^{13}$— and —NR$^{13}$C(O)NR$^{13}$—;

R$^{13}$, R$^{14}$, and R$^{15}$ are independently selected from H and C$_{1-4}$ alkyl;

ring E1 and ring E2 are each independently selected from phenyl, 5- to 6-membered heteroaryl, 4- to 7-membered heterocycloalkyl, and C$_{3-7}$ cycloalkyl;

ring A and ring B are each independently selected from 5-10 membered heteroaryl, 4-10 membered heterocycloalkyl, C$_{6-10}$ aryl, and C$_{3-10}$ cycloalkyl;

R$^1$ is C$_{1-3}$ alkyl, C$_{1-3}$ alkoxy, C$_{1-3}$ haloalkyl, C$_{1-3}$ haloalkoxy, CN, halo, OH, —C(O)OH, NH$_2$, -C$_{1-3}$ alkylamino, or di-(C$_{1-3}$ alkyl)amino;

R$^2$ is C$_{1-3}$ alkyl, C$_{1-3}$ alkoxy, C$_{1-3}$ haloalkyl, C$_{1-3}$ haloalkoxy, CN, halo, OH, —C(O)OH, NH$_2$, -C$_{1-3}$ alkylamino, or di-(C$_{1-3}$ alkyl)amino;

R$^3$ is C$_{1-3}$ alkyl, halo, CN, or C$_{1-3}$ haloalkyl;

each subscript t2 is independently an integer of 1, 2, 3 or 4;

the subscript m is an integer of 0, 1, 2, or 3;
the subscript n is an integer of 0, 1, 2, or 3;
the subscript u is an integer of 0, 1, 2, 3, 4, or 5; and
the subscript v is an integer of 0, 1, 2, 3, 4, or 5.

In some embodiments, P has Formula (P-1b):

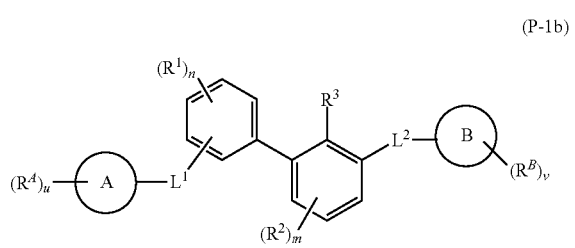

(P-1b)

wherein:
L$^1$ and L$^2$ are each independently selected from a bond, —C(O)NR$^{13}$—, —NR$^{13}$C(O)—, —O—, —(CR$^{14}$R$^{15}$)$_{t2}$—, —(CR$^{14}$R$^{15}$)$_{t2}$—O—, —O(CR$^{14}$R$^{15}$)$_{t2}$—, —NR$^{13}$—, —(CR$^{14}$R$^{15}$)$_{t2}$—NR$^{13}$—, —NR$^{13}$—(CR$^{14}$R$^{15}$)$_{t2}$—, —S(O)$_2$NR$^{13}$—, —NR$^{13}$S(O)$_2$—, —NR$^{13}$S(O)$_2$NR$^{13}$—, —NR$^{13}$C(O)O—, —OC(O)NR$^{13}$— and —NR$^{13}$C(O)NR$^{13}$—;

ring A and ring B are each independently selected from 5-10 membered heteroaryl, 4-10 membered heterocycloalkyl, C$_{6-10}$ aryl, and C$_{3-10}$ cycloalkyl;

R$^1$ is C$_{1-4}$ alkyl, C$_{1-4}$ alkoxy, C$_{1-4}$ haloalkyl, C$_{1-4}$ haloalkoxy, CN, halo, OH, —C(O)OH, NH$_2$, -C$_{1-4}$ alkylamino, or di-(C$_{1-4}$ alkyl)amino;

R$^2$ is C$_{1-4}$ alkyl, C$_{1-4}$ alkoxy, C$_{1-4}$ haloalkyl, C$_{1-4}$ haloalkoxy, CN, halo, OH, —C(O)OH, NH$_2$, -C$_{1-4}$ alkylamino, or di-(C$_{1-4}$ alkyl)amino;

R$^3$ is methyl, Cl, F, CN, or C$_{3-2}$ haloalkyl;

each subscript t2 is independently an integer of 1, 2, 3 or 4;

the subscript m is an integer of 0, 1, 2, or 3;
the subscript n is an integer of 0, 1, 2, or 3;
the subscript u is an integer of 0, 1, 2, 3, 4, or 5; and
the subscript v is an integer of 0, 1, 2, 3, 4, or 5.

In some embodiments, P has Formula (P-1b), wherein:
L$^1$ is a bond, —C(O)NH—, —OCH$_2$—, or —NH—;
L$^2$ is a bond, —NHC(O)—, —CH$_2$O—, or —NH—;

ring A and ring B are each independently selected from 5-10 membered heteroaryl, 4-10 membered heterocycloalkyl, C$_{6-10}$ aryl, and C$_{3-10}$ cycloalkyl;

R$^1$ is C$_{1-4}$ alkyl, C$_{1-4}$ alkoxy, C$_{1-4}$ haloalkyl, C$_{1-4}$ haloalkoxy, CN, halo, OH, —C(O)OH, NH$_2$, -C$_{1-4}$ alkylamino, or di-(C$_{1-4}$ alkyl)amino;

R$^2$ is C$_{1-4}$ alkyl, C$_{1-4}$ alkoxy, C$_{1-4}$ haloalkyl, C$_{1-4}$ haloalkoxy, CN, halo, OH, —C(O)OH, NH$_2$, -C$_{1-4}$ alkylamino, or di-(C$_{1-4}$ alkyl)amino;

R$^3$ is methyl, Cl, F, CN, or C$_{1-2}$ haloalkyl;
the subscript m is an integer of 0, 1, 2, or 3;
the subscript n is an integer of 0, 1, 2, or 3;
the subscript u is an integer of 0, 1, 2, 3, 4, or 5; and
the subscript v is an integer of 0, 1, 2, 3, 4, or 5.

In some embodiments, P has Formula (P-1c):

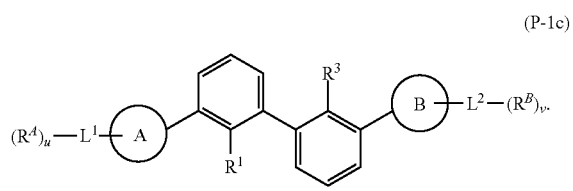

(P-1c)

In some embodiments, P has Formula (P-1c):

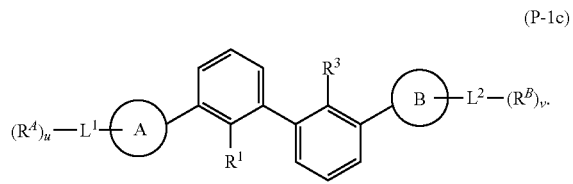

(P-1c)

wherein:
L$^1$ and L$^2$ are each independently selected from a bond, —C(O)NR$^{13}$—, —NR$^{13}$C(O)—, —O—, —(CR$^{14}$R$^{15}$)$_{t2}$—, —(CR$^{14}$R$^{15}$)$_{t2}$—O—, —O(CR$^{14}$R$^{15}$)$_{t2}$—, —NR$^{13}$—, —(CR$^{14}$R$^{15}$)$_{t2}$—NR$^{13}$—, —NR$^{13}$—(CR$^{14}$R$^{15}$)$_{t2}$—, —S(O)$_2$ NR$^{13}$—, —NR$^{13}$S(O)$_2$—, —NR$^{13}$S(O)$_2$NR$^{13}$—, —NR$^{13}$C(O)O—, —OC(O)NR$^{13}$— and —NR$^{13}$C(O)NR$^{13}$—;

ring A and ring B are each independently selected from 5-10 membered heteroaryl, 4-10 membered heterocycloalkyl, C$_{6-10}$ aryl, and C$_{3-10}$ cycloalkyl;

R$^1$ is C$_{1-4}$ alkyl, C$_{1-4}$ alkoxy, C$_{1-4}$ haloalkyl, C$_{1-4}$ haloalkoxy, CN, halo, OH, —C(O)OH, NH$_2$, -C$_{1-4}$ alkylamino, or di-(C$_{1-4}$ alkyl)amino;

R$^2$ is C$_{1-4}$ alkyl, C$_{1-4}$ alkoxy, C$_{1-4}$ haloalkyl, C$_{1-4}$ haloalkoxy, CN, halo, OH, —C(O)OH, NH$_2$, -C$_{1-4}$ alkylamino, or di-(C$_{1-4}$ alkyl)amino;

R$^3$ is methyl, Cl, F, CN, or C$_{1-2}$ haloalkyl;

each R$^{13}$ is independently H, C$_{1-6}$ haloalkyl or C$_{1-6}$ alkyl optionally substituted with a substituent selected from C$_{1-4}$ alkyl, C$_{1-4}$ alkoxy, C$_{1-4}$ haloalkyl, C$_{1-4}$ haloalkoxy, CN, halo, OH, —COOH, NH$_2$, —NHC$_{1-4}$ alkyl and —N(C$_{1-4}$ alkyl)$_2$;

R$^A$ and R$^B$ are each independently selected from H, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, CN, NO$_2$, OR$^a$, SR$^a$, NHOR$^a$, C(O)R$^a$, C(O)NR$^a$R$^a$, C(O)OR$^a$, C(O)NR$^a$S(O)$_2$R$^a$, OC(O)R$^a$, OC(O)NR$^a$R$^a$, NHR$^a$, NR$^a$R$^a$, NR$^a$C(O)R$^a$, NR$^a$C(=NR$^a$)R$^a$, NR$^a$C(O)

OR$^a$, NR$^a$C(O)NR$^a$R$^a$, C(=NR$^a$)R$^a$, C(=NOH)R$^a$, C(=NOH)NR$^a$, C(=NCN)NR$^a$R$^a$, NR$^a$C(=NCN)NR$^a$R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$ R$^a$, S(O)$_2$NR$^a$C(O)R$^a$, —P(O)R$^a$R$^a$, —P(O)(OR$^a$)(OR$^a$), —B(OH)$_2$, —B(OR$^a$)$_2$ and S(O)$_2$NR$^a$R$^a$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are each optionally substituted with 1, 2, 3, 4 or 5 independently selected R$^b$ substituents;

each R$^a$ is independently selected from H, CN, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are each optionally substituted with 1, 2, 3, 4, or 5 independently selected R$^d$ substituents;

each R$^b$ substituent is independently selected from halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, CN, OH, NH$_2$, NO$_2$, NHOR$^c$, OR$^c$, SR$^c$, C(O)R$^c$, C(O)NR$^c$R$^c$, C(O)OR$^c$, C(O)NR$^c$S(O)$_2$R$^c$, OC(O)R$^c$, OC(O)NR$^c$R$^c$, C(=NOH)R$^c$, C(=NOH)NR$^c$, C(=NCN)NR$^c$R$^c$, NR$^c$C(=NCN)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(=NR$^c$)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$, S(O)$_2$NR$^c$C(O)R$^c$, —P(O)R$^c$R$^c$, —P(O)(OR$^c$)(OR$^c$), —B(OH)$_2$, —B(OR$^c$)$_2$ and S(O)$_2$NR$^c$R$^c$; wherein the C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are each further optionally substituted with 1, 2 or 3 independently selected R$^d$ substituents;

each R$^c$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are each optionally substituted with 1, 2, 3, 4, or 5 independently selected R$^f$ substituents;

or two R$^c$ attached to the same nitrogen atom are taken together to form a 4-7 membered heterocycloalkyl ring which is optionally substituted with 1, 2, or 3 independently selected R$^f$ substituents;

each R$^d$ is independently selected from C$_{1-6}$ alkyl, C$_{1-6}$ haloalkyl, halo, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, CN, NH$_2$, NHOR$^e$, OR$^e$, SR$^e$, C(O)R$^e$, C(O)NR$^e$R$^e$, C(O)OR$^e$, C(O)NR$^e$S(O)$_2$R$^e$, OC(O)R$^e$, OC(O)NR$^e$R$^e$, NHR$^e$, NR$^e$R$^e$, NR$^e$C(O)R$^e$, NR$^e$C(=NR$^e$)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, S(O)$_2$NR$^e$C(O)R$^e$, NR$^e$S(O)$_2$R$^e$, NR$^e$S(O)$_2$NR$^e$R$^e$, —P(O)R$^e$R$^e$, —P(O)(OR$^e$)(OR$^e$), —B(OH)$_2$, —B(OR$^e$)$_2$ and S(O)$_2$NR$^e$R$^e$, wherein the C$_{1-6}$ alkyl, C$_{6-10}$ aryl, C$_{3-10}$ cycloalkyl, 5-10 membered heteroaryl, 4-10 membered heterocycloalkyl, C$_{6-10}$ aryl- C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- are each optionally substituted with 1, 2, or 3 independently selected R$^f$ substituents;

each R$^e$ is independently selected from H, C$_{1-6}$ alkyl, and C$_{1-6}$ haloalkyl; wherein the C$_{1-6}$ alkyl is optionally substituted with 1, 2 or 3 independently selected R$^f$ substituents; and each R$^f$ is independently selected from OH, NO$_2$, CN, halo, C$_{1-4}$ alkyl, C$_{2-4}$ alkenyl, C$_{2-4}$ alkynyl, C$_{1-4}$ haloalkyl, HO-C$_{1-4}$ alkylene, C$_{1-4}$ alkoxy-C$_{1-4}$ alkylene, CN-C$_{1-4}$ alkylene, C$_{3-7}$ cycloalkyl, C$_{1-4}$ alkoxy, C$_{1-4}$ haloalkoxy, amino, C$_{1-4}$ alkylamino, di(C$_{1-4}$ alkyl)amino, thio, C$_{1-4}$ alkylthio, C$_{1-4}$ alkylsulfinyl, C$_{1-4}$ alkylsulfonyl, carbamyl, C$_{1-4}$ alkylcarbamyl, di(C$_{1-4}$ alkyl)carbamyl, carboxy, C$_{1-4}$ alkylcarbonyl, C$_{1-4}$ alkoxycarbonyl, C$_{1-4}$ alkylcarbonyloxy, C$_{1-4}$ alkylcarbonylamino, C$_{1-4}$ alkoxycarbonylamino, C$_{1-4}$ alkylaminocarbonyloxy, C$_{1-4}$ alkylsulfonylamino, aminosulfonyl, C$_{1-4}$ alkylaminosulfonyl, di(C$_{1-4}$ alkyl)aminosulfonyl, aminosulfonylamino, C$_{1-4}$ alkylaminosulfonylamino, di(C$_{1-4}$ alkyl)aminosulfonylamino, aminocarbonylamino, C$_{1-4}$ alkylaminocarbonylamino, and di(C$_{1-4}$ alkyl)aminocarbonylamino;

each subscript t2 is independently an integer of 1, 2, 3 or 4;

the subscript m is an integer of 0, 1, 2, or 3;

the subscript n is an integer of 0, 1, 2, or 3;

the subscript u is an integer of 0, 1, 2, 3, 4, or 5; and the subscript v is an integer of 0, 1, 2, 3, 4, or 5.

In some embodiments, P has Formula (P-1c):

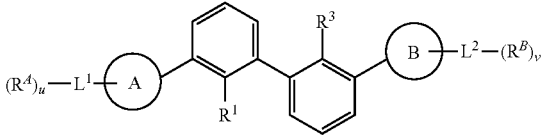

(P-1c)

wherein:

L$^1$ and L$^2$ are each independently selected from a bond, —C(O)NR$^{13}$—, —NR$^{13}$C(O)—, —O—, —(CR$^{14}$R$^{15}$)$_{t2}$—, —(CR$^{14}$R$^{15}$)$_{t2}$—O—, —O(CR$^{14}$R$^{15}$)$_{t2}$—, —NR$^{13}$—, —(CR$^{14}$R$^{15}$)$_{t2}$—NR$^{13}$—, —NR$^{13}$—(CR$^{14}$R$^{15}$)$_{t2}$—, —S(O)$_2$ NR$^{13}$—, —NR$^{13}$S(O)$_2$—, —NR$^{13}$S(O)$_2$NR$^{13}$—, —NR$^{13}$C(O)O—, —OC(O)NR$^{13}$— and —NR$^{13}$C(O)NR$^{13}$—;

ring A and ring B are each independently selected from 5-10 membered heteroaryl, 4-10 membered heterocycloalkyl, C$_{6-10}$ aryl, and C$_{3-10}$ cycloalkyl;

R$^1$ is C$_{1-4}$ alkyl, C$_{1-4}$ alkoxy, C$_{1-4}$ haloalkyl, C$_{1-4}$ haloalkoxy, CN, halo, OH, —C(O)OH, NH$_2$, -C$_{1-4}$ alkylamino, or di-(C$_{1-4}$ alkyl)amino;

$R^2$ is $C_{1-4}$ alkyl, $C_{1-4}$ alkoxy, $C_{1-4}$ haloalkyl, $C_{1-4}$ haloalkoxy, CN, halo, OH, —C(O)OH, $NH_2$, -$C_{1-4}$ alkylamino, or di-($C_{1-4}$ alkyl)amino;

$R^3$ is methyl, Cl, F, CN, or $C_{1-2}$ haloalkyl;

each subscript t2 is independently an integer of 1, 2, 3 or 4;

the subscript m is an integer of 0, 1, 2, or 3;
the subscript n is an integer of 0, 1, 2, or 3;
the subscript u is an integer of 0, 1, 2, 3, 4, or 5; and
the subscript v is an integer of 0, 1, 2, 3, 4, or 5.

In some embodiments, P has Formula (P-1c):

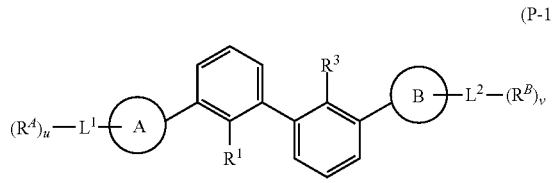

(P-1c)

wherein:
$L^1$ is a bond, —C(O)NH—, —OCH$_2$—, or —NH—;
$L^2$ is a bond, —NHC(O)—, —CH$_2$O—, or —NH—;
ring A and ring B are each independently selected from 5-10 membered heteroaryl, 4-10 membered heterocycloalkyl, $C_{6-10}$ aryl, and $C_{3-10}$ cycloalkyl;
$R^1$ is $C_{1-4}$ alkyl, $C_{1-4}$ alkoxy, $C_{1-4}$ haloalkyl, $C_{1-4}$ haloalkoxy, CN, halo, OH, —C(O)OH, $NH_2$, -$C_{1-4}$ alkylamino, or di-($C_{1-4}$ alkyl)amino;
$R^2$ is $C_{1-4}$ alkyl, $C_{1-4}$ alkoxy, $C_{1-4}$ haloalkyl, $C_{1-4}$ haloalkoxy, CN, halo, OH, —C(O)OH, $NH_2$, -$C_{1-4}$ alkylamino, or di-($C_{1-4}$ alkyl)amino;
$R^3$ is methyl, Cl, F, CN, or $C_{1-2}$ haloalkyl;
each subscript t2 is independently an integer of 1, 2, 3 or 4;
the subscript m is an integer of 0, 1, 2, or 3;
the subscript n is an integer of 0, 1, 2, or 3;
the subscript u is an integer of 0, 1, 2, 3, 4, or 5; and
the subscript v is an integer of 0, 1, 2, 3, 4, or 5.

In some embodiments, $L^1$ is a bond, —C(O)NH-, —OCH$_2$—, or —NH—. In some embodiments, $L^1$ is a bond. In some embodiments, $L^1$ is —C(O)NH—. In some embodiments, $L^1$ is —OCH$_2$—. In some embodiments, $L^1$ is —NH—. In some embodiments, $L^1$ is a bond.

In some embodiments, $L^2$ is a bond, —NHC(O)—, —CH$_2$O—, or —NH—. In some embodiments, $L^2$ is a bond. In some embodiments, $L^2$ is —NHC(O)—. In some embodiments, $L^2$ is —CH$_2$O—. In some embodiments, $L^2$ is —NH—. In some embodiments, $L^2$ is a bond.

In some embodiments, ring A is phenyl, 6-membered heterocycloalkyl having 1-2 heteroatom ring members independently selected from N, O, and S, 6-membered heteroaryl having 1-3 heteroatom ring members independently selected from N, O, and S, or a fused bicyclic moiety of formula:

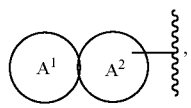

wherein $A^1$ is selected from phenyl, 5-6 membered heterocycloalkyl having 1-2 heteroatom ring members independently selected from N, O, and S, 5-6 membered heteroaryl having 1-3 heteroatom ring members independently selected from N, O, and S; and $A^2$ selected from phenyl, 5-6 membered heterocycloalkyl having 1-2 heteroatom ring members independently selected from N, O, and S, and 5-6 membered heteroaryl having 1-3 heteroatom ring members independently selected from N, O, and S. In some embodiments, ring A is phenyl. In some embodiments, ring A is 6-membered heterocycloalkyl having 1-2 heteroatom ring members independently selected from N, O, and S. In some embodiments, ring A is 6-membered heteroaryl having 1-3 heteroatom ring members independently selected from N, O, and S. In some embodiments, ring A is a fused bicyclic moiety of formula:

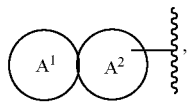

wherein $A^1$ is selected from phenyl, 5-6 membered heterocycloalkyl having 1-2 heteroatom ring members independently selected from N, O, and S, 5-6 membered heteroaryl having 1-3 heteroatom ring members independently selected from N, O, and S; and $A^2$ selected from phenyl, 5-6 membered heterocycloalkyl having 1-2 heteroatom ring members independently selected from N, O, and S, and 5-6 membered heteroaryl having 1-3 heteroatom ring members independently selected from N, O, and S.

In some embodiments, ring B is phenyl, 6-membered heterocycloalkyl having 1-2 heteroatom ring members independently selected from N, O, and S, 6-membered heteroaryl having 1-3 heteroatom ring members independently selected from N, O, and S, or a fused bicyclic moiety of formula:

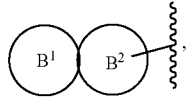

wherein $B^1$ is selected from phenyl, 5-6 membered heterocycloalkyl having 1-2 heteroatom ring members independently selected from N, O, and S, 5-6 membered heteroaryl having 1-3 heteroatom ring members independently selected from N, O, and S; and $B^2$ selected from phenyl, 5-6 membered heterocycloalkyl having 1-2 heteroatom ring members independently selected from N, O, and S, and 5-6 membered heteroaryl having 1-3 heteroatom ring members independently selected from N, O, and S.

In some embodiments, ring B is phenyl. In some embodiments, ring B is 6-membered heterocycloalkyl having 1-2 heteroatom ring members independently selected from N, O, and S. In some embodiments, ring B is 6-membered heteroaryl having 1-3 heteroatom ring members independently selected from N, O, and S. In some embodiments, ring B is a fused bicyclic moiety of formula:

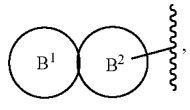

wherein B¹ is selected from phenyl, 5-6 membered heterocycloalkyl having 1-2 heteroatom ring members independently selected from N, O, and S, 5-6 membered heteroaryl having 1-3 heteroatom ring members independently selected from N, O, and S; and B² selected from phenyl, 5-6 membered heterocycloalkyl having 1-2 heteroatom ring members independently selected from N, O, and S, and 5-6 membered heteroaryl having 1-3 heteroatom ring members independently selected from N, O, and S.

In some embodiments, ring A is selected from:

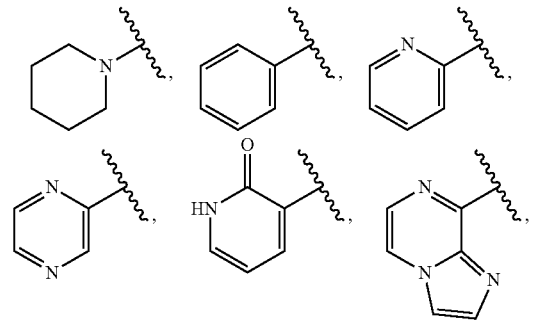

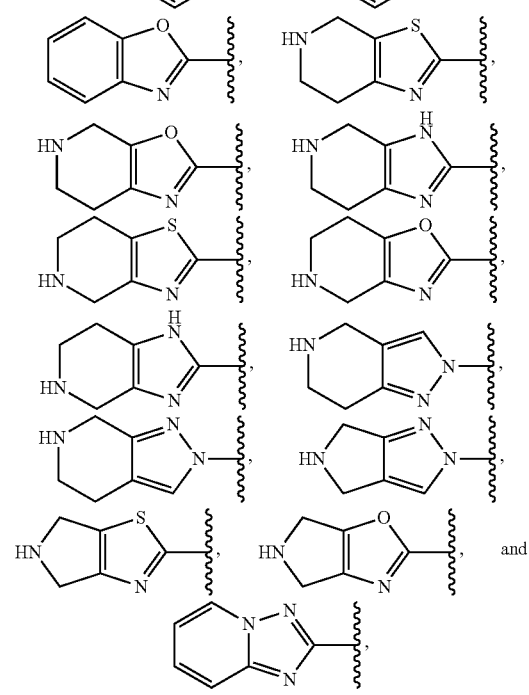

each of which is substituted with u independently selected $R^A$ groups; and wherein

designates the point of attachment to $L^1$.

In some embodiments, ring A is selected from:

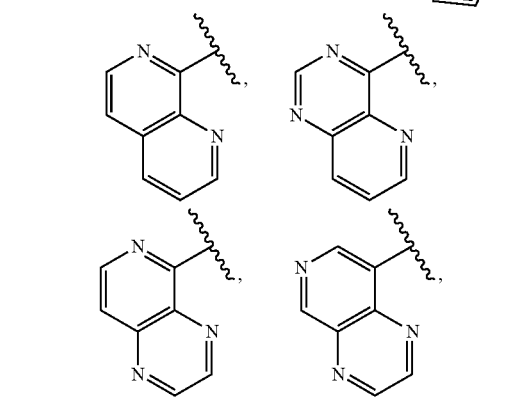

each of which is substituted with u independently selected $R^A$ groups; and wherein

designates the point of attachment to $L^1$.

In some embodiments, ring A is selected from:

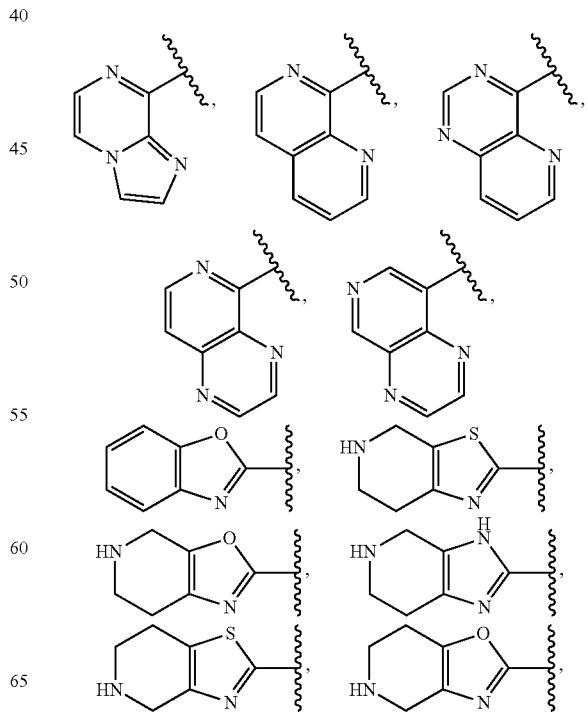

-continued

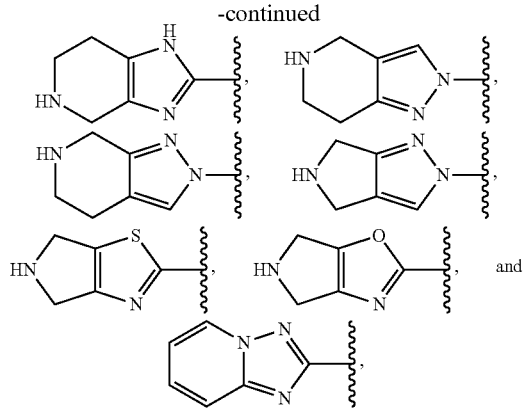

each of which is substituted with u independently selected $R^A$ groups; and wherein

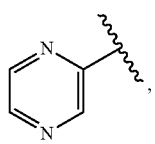 [SMILES: *c1cnccn1]

designates the point of attachment to $L^1$.

In some embodiments, ring A is selected from:

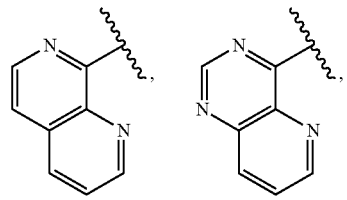

each of which is substituted with u independently selected $R^A$ groups; and wherein

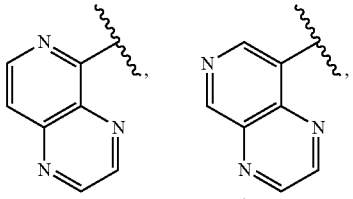

designates the point of attachment to $L^1$.

In some embodiments, ring A is:

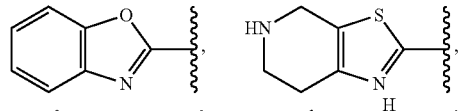

each of which is substituted with u independently selected $R^A$ groups; and wherein

designates the point of attachment to $L^1$.

In some embodiments, ring B is selected from:

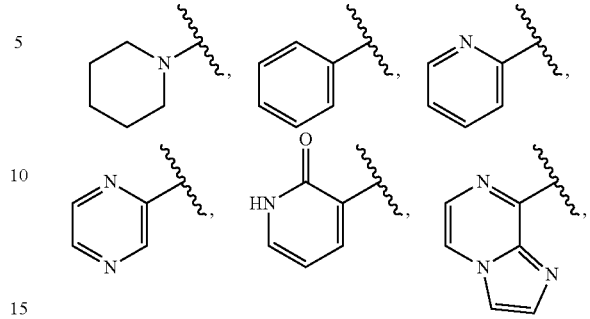

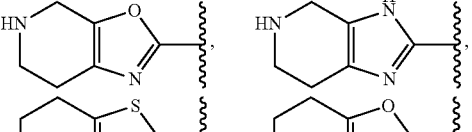

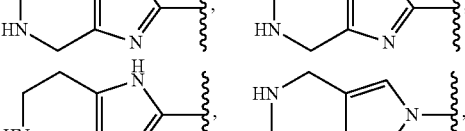

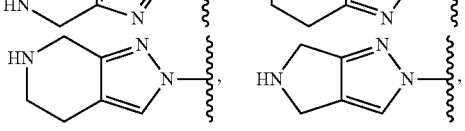

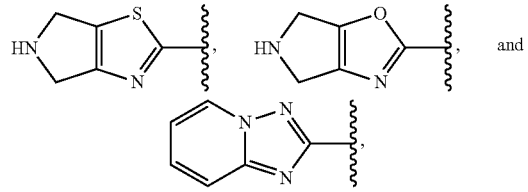

each of which is substituted with v independently selected $R^B$ groups; and wherein

designates the point of attachment to $L^2$.

In some embodiments, ring B is selected from:

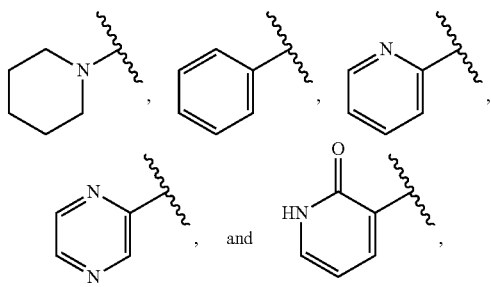

each of which is substituted with v independently selected $R^B$ groups; and wherein

designates the point of attachment to $L^2$.

In some embodiments, ring B is selected from:

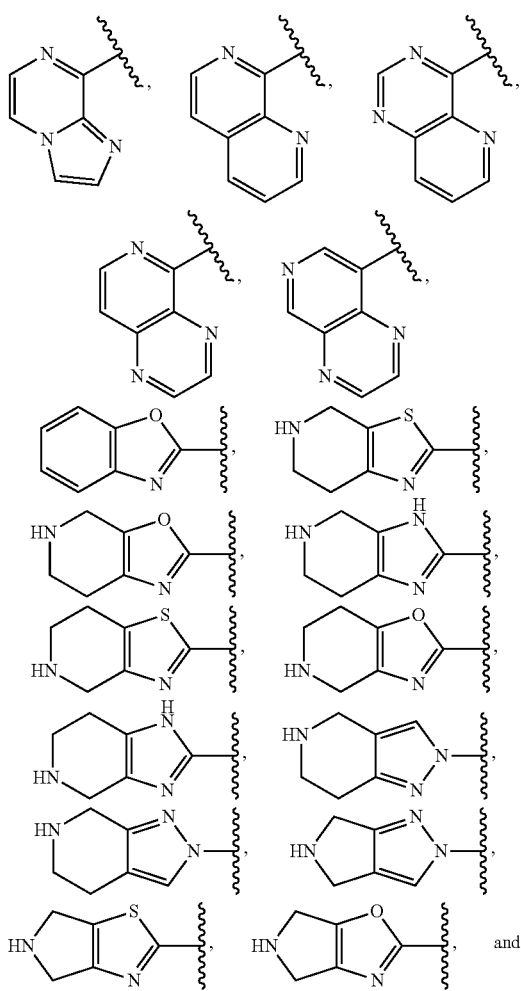

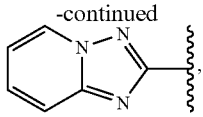

each of which is substituted with v independently selected $R^B$ groups; and wherein

designates the point of attachment to $L^2$.

In some embodiments, ring B is selected from:

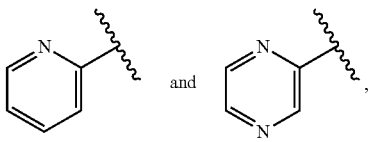 [SMILES: *c1ccccn1 ; *c1cnccn1]

each of which is substituted with u independently selected $R^B$ groups; and wherein

designates the point of attachment to $L^2$.

In some embodiments, ring B is:

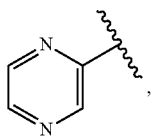

each of which is substituted with u independently selected $R^B$ groups; and wherein

designates the point of attachment to $L^2$.

In some embodiments, ring A is selected from:

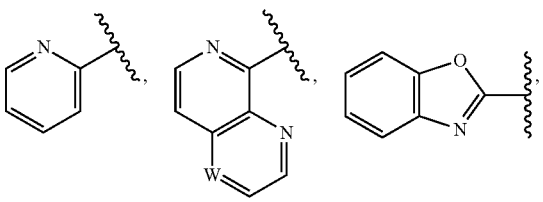

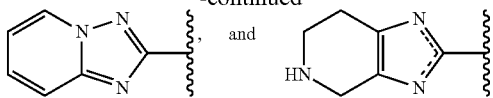 and each of which is optionally substituted with 1, 2, or 3 independently selected $R^A$ groups; wherein W is N or $CR^B$; wherein ------ is a single or double bond provided that the ring is aromatic; and; and wherein

designates the point of attachment to $L^1$.

In some embodiments, ring A is:

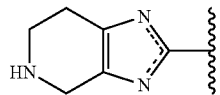

which is optionally substituted with 1, 2, or 3 independently selected $R^A$ groups; wherein ------ is a single or double bond provided that the ring is aromatic; and; and wherein

designates the point of attachment to $L^1$.

In some embodiments, ring B is selected from:

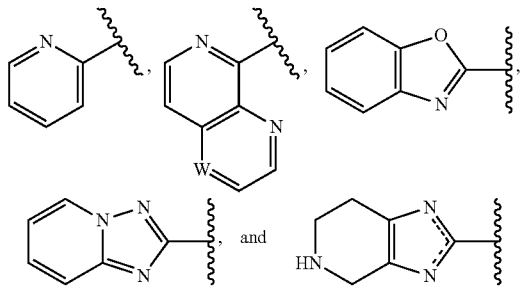

each of which is optionally substituted with 1, 2, or 3 independently selected $R^B$ groups; wherein W is N or $CR^B$; wherein ------ is a single or double bond provided that the ring is aromatic; and wherein

designates the point of attachment to $L^2$.

In some embodiments, ring B is:

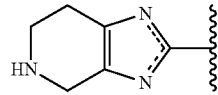

which is optionally substituted with 1, 2, or 3 independently selected $R^B$ groups; wherein ------ is a single or double bond provided that the ring is aromatic; and wherein

designates the point of attachment to $L^2$. In some embodiments, $R^1$ is $C_{1-4}$ alkyl, $C_{1-4}$ alkoxy, $C_{1-4}$ haloalkyl, $C_{1-4}$ haloalkoxy, CN, halo, OH, —C(O)OH, $NH_2$, -$C_{1-4}$ alkylamino, or di-($C_{1-4}$ alkyl)amino. In some embodiments, $R^1$ is $C_{1-4}$ alkyl, $C_{1-4}$ alkoxy, $C_{1-4}$ haloalkyl, $C_{1-4}$ haloalkoxy, CN, and halo. In some embodiments, $R^1$ is $C_{1-4}$ alkyl, $C_{1-4}$ alkoxy, CN, and halo. In some embodiments, $R^1$ is $C_{1-4}$ alkyl. In some embodiments, $R^1$ is halo.

In some embodiments, $R^2$ is $C_{1-4}$ alkyl, $C_{1-4}$ alkoxy, $C_{1-4}$ haloalkyl, $C_{1-4}$ haloalkoxy, CN, halo, OH, —C(O)OH, $NH_2$, -$C_{1-4}$ alkylamino, or di-($C_{1-4}$ alkyl)amino. In some embodiments, $R^2$ is $C_{1-4}$ alkyl, $C_{1-4}$ alkoxy, $C_{1-4}$ haloalkyl, $C_{1-4}$ haloalkoxy, CN, and halo. In some embodiments, $R^2$ is $C_{1-4}$ alkyl, $C_{1-4}$ alkoxy, CN, and halo. In some embodiments, $R^2$ is $C_{1-4}$ alkyl. In some embodiments, $R^2$ is halo.

In some embodiments, $R^3$ is methyl, Cl, F, or CN. In some embodiments, $R^3$ is methyl. In some embodiments, $R^3$ is Cl. In some embodiments, $R^3$ is F. In some embodiments, $R^3$ is CN.

In some embodiments, each $R^{13}$ is independently H, $C_{1-6}$ haloalkyl or $C_{1-6}$ alkyl optionally substituted with a substituent selected from $C_{1-4}$ alkoxy, $C_{1-4}$ haloalkoxy, CN, halo, OH, —COOH, $NH_2$, —$NHC_{1-4}$ alkyl and —$N(C_{1-4}$ alkyl$)_2$. In some embodiments, each $R^{13}$ is independently H or $C_{1-6}$ alkyl optionally substituted with a substituent selected from CN, halo, OH, —COOH, $NH_2$, —$NHC_{1-4}$ alkyl and —$N(C_{1-4}$ alkyl$)_2$. In some embodiments, each $R^{13}$ is independently H or $C_{1-6}$ alkyl. In some embodiments, each $R^{13}$ is H. In some embodiments, each $R^{13}$ is $C_{1-6}$ alkyl.

In some embodiments, the subscript m is an integer of 0 or 1. In some embodiments, the subscript m is an integer of 0. In some embodiments, the subscript m is an integer of 1.

In some embodiments, the subscript n is an integer of 0 or 1. In some embodiments, the subscript n is an integer of 0. In some embodiments, the subscript n is an integer of 1.

In some embodiments, the subscript u is an integer of 0, 1, 2, or 3. In some embodiments, the subscript u is an integer of 1. In some embodiments, the subscript u is an integer of 2. In some embodiments, the subscript u is an integer of 3.

In some embodiments, the subscript v is an integer of 0, 1, 2, or 3. In some embodiments, the subscript v is an integer of 1. In some embodiments, the subscript v is an integer of 2. In some embodiments, the subscript v is an integer of 3.

In some embodiments, one $R^A$ and one $R^B$ are each independently:

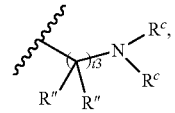

wherein:
    each R" is independently selected from H and $C_{1-3}$ alkyl;
    t3 is an integer from 1-4; and
    each $R^c$ is independently selected from H, $C_{1-6}$ alkyl, $C_{1-4}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl-, wherein the $C_{1-6}$ alkyl, $C_{2-6}$ alkenyl, $C_{2-6}$ alkynyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl- are each optionally substituted with 1, 2, 3, 4, or 5 independently selected $R^f$ substituents;
    or two $R^c$ attached to the same nitrogen atom are taken together to form a 4-7 membered heterocycloalkyl ring which is optionally substituted with 1, 2, or 3 independently selected $R^f$ substituents.

In some embodiments:
    $R^A$ and $R^B$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_6$-aryl-$C_{1-4}$ alkyl-, $C_{3-10}$cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2 R^a$, $S(O)_2NR^aC(O)R^a$, $-P(O)R^aR^a$, $-P(O)(OR^a)(OR^a)$, $-B(OH)_2$, $-B(OR^a)_2$ and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2, 3, 4 or 5 independently selected $R^b$ substituents;
    each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2, 3, 4, or 5 independently selected $R^d$ substituents;
    each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $OC(=NOH)R^c$, $C(=NOH)NR^c$, $C(=NCN)NR^cR^c$, $NR^cC(=NCN)NR^cR^c$, $C(=NR^c)NR^cR^c$, $NR^cC(=NR^c)NR^cR^c$, $NHR^c$, $NR^cR^c$, $NR^cC(O)R^c$, $NR^cC(=NR^c)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, $-P(O)R^cR^c$, $-P(O)(OR^c)(OR^c)$, $-B(OH)_2$, $-B(OR^c)_2$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each further optionally substituted with 1, 2 or 3 independently selected $R^d$ substituents;
    each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2, 3, 4, or 5 independently selected $R^f$ substituents;
    or two $R^c$ attached to the same nitrogen atom are taken together to form a 4-7 membered heterocycloalkyl ring which is optionally substituted with 1, 2, or 3 independently selected $R^f$ substituents;
    each $R^d$ is independently selected from $C_{1-6}$ alkyl, $C_{1-6}$ haloalkyl, halo, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $C(O)NR^eS(O)_2R^e$, $OC(O)R^e$, $OC(O)NR^eR^e$, $NHR^e$, $NR^eR^e$, $NR^eC(O)R^e$, $NR^eC(=NR^e)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $S(O)_2NR^eC(O)R^e$, $NR^eS(O)_2R^e$, $NR^eS(O)_2NR^eR^e$, $-P(O)R^eR^e$, $-P(O)(OR^e)(OR^e)$, $-B(OH)_2$, $-B(OR^e)_2$ and $S(O)_2NR^eR^e$, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2, or 3 independently selected $R^f$ substituents;
    each $R^e$ is independently selected from H, $C_{1-6}$ alkyl, and $C_{1-6}$ haloalkyl; wherein the $C_{1-6}$ alkyl is optionally substituted with 1, 2 or 3 independently selected $R^f$ substituents; and
    each $R^f$ is independently selected from OH, $NO_2$, CN, halo, $C_{1-4}$ alkyl, $C_{2-4}$ alkenyl, C2-4 alkynyl, $C_{1-4}$ haloalkyl, HO-$C_{1-4}$ alkylene, $C_{1-4}$ alkoxy-$C_{1-4}$ alkylene, CN-$C_{1-4}$ alkylene, $C_{3-7}$ cycloalkyl, $C_{1-4}$ alkoxy, $C_{1-4}$ haloalkoxy, amino, $C_{1-4}$ alkylamino, di($C_{1-4}$ alkyl)amino, thio, $C_{1-4}$ alkylthio, $C_{1-4}$ alkylsulfinyl, $C_{1-4}$ alkylsulfonyl, carbamyl, $C_{1-4}$ alkylcarbamyl, di($C_{1-4}$ alkyl)carbamyl, carboxy, $C_{1-4}$ alkylcarbonyl, $C_{1-4}$ alkoxycarbonyl, $C_{1-4}$ alkylcarbonyloxy, $C_{1-4}$ alkylcarbonylamino, $C_{1-4}$ alkoxycarbonylamino, $C_{1-4}$ alkylaminocarbonyloxy, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino.

In some embodiments, $R^A$ and $R^B$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NO$_2$, OR$^a$, SR$^a$, C(O)R$^a$, and C(O)NR$^a$R$^a$, C(O)OR$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2, or 3 independently selected $R^b$ substituents;

each $R^a$ is independently selected from H, CN, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, are each optionally substituted with 1, 2, or 3 independently selected $R^d$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NHR$^c$, NR$^c$R$^c$, OH, NH$_2$, NO$_2$, NHOR$^c$, OR$^c$, SR$^c$, C(O)R$^c$, C(O)NR$^c$R$^c$, and C(O)OR$^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, are each optionally substituted with 1, 2, or 3 independently selected $R^f$ substituents;

each $R^d$ is independently selected from $C_{1-6}$ alkyl, $C_{1-6}$ haloalkyl, halo, $C_{6-10}$ aryl, $C_{3-10}$ cycloalkyl, 5-10 membered heteroaryl, 4-10 membered heterocycloalkyl, CN, NH$_2$, NHOR$^e$, OR$^e$, SR$^e$, C(O)R$^e$, C(O)NR$^e$R$^e$, and C(O)OR$^e$, wherein the $C_{1-6}$ alkyl, $C_{6-10}$ aryl, $C_{3-10}$ cycloalkyl, 5-10 membered heteroaryl, and 4-10 membered heterocycloalkyl, are each optionally substituted with 1, 2, or 3 independently selected $R^f$ substituents;

each $R^e$ is independently selected from H and $C_{1-6}$ alkyl; and each $R^f$ is independently selected from OH, NO$_2$, CN, halo, $C_{1-4}$ alkyl, $C_{2-4}$ alkenyl, $C_{2-4}$ alkynyl, $C_{1-4}$ haloalkyl, and carboxy.

In some embodiments, $R^A$ and $R^B$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, and CN, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{14}$ alkyl- are each optionally substituted with 1, 2, or 3 independently selected $R^b$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, OR$^c$, NHR$^c$, NR$^c$R$^c$, C(O)R$^c$, C(O)NR$^c$, and C(O)OR$^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, are each optionally substituted with 1, 2, or 3 independently selected $R^f$ substituents;

each $R^d$ is independently selected from $C_{1-6}$ alkyl, $C_{1-6}$ haloalkyl, halo, OR$^e$, C(O)R$^e$, C(O)NR$^e$R$^e$, and C(O)OR$^e$, wherein the $C_{1-6}$ alkyl is optionally substituted with 1, 2, or 3 independently selected $R^f$ substituents;

each $R^e$ is independently selected from H and $C_{1-6}$ alkyl; and each $R^f$ is independently selected from OH, halo, $C_{1-4}$ alkyl, $C_{2-4}$ alkenyl, $C_{2-4}$ alkynyl, $C_{1-4}$ haloalkyl, and carboxy.

In some embodiments, $R^A$ and $R^B$ are each independently selected from H, halo, $C_{1-6}$ alkyl, $C_{2-6}$ alkenyl, $C_{2-6}$ alkynyl, $C_{1-6}$ haloalkyl, 4-10 membered heterocycloalkyl, (4-10 membered heterocycloalkyl)-$C_{1-4}$ alkyl-, and CN, wherein the $C_{1-6}$ alkyl, $C_{2-6}$ alkenyl, $C_{2-6}$ alkynyl, 4-10 membered heterocycloalkyl, and (4-10 membered heterocycloalkyl)-$C_{1-4}$ alkyl- are each optionally substituted with 1, 2, or 3 independently selected $R^b$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, 5-10 membered heteroaryl, 4-10 membered heterocycloalkyl, CN, OH, OR$^c$, NHR$^c$, NR$^c$R$^c$, C(O)R$^c$, C(O)NR$^c$R$^c$, and C(O)OR$^c$; wherein the $C_{1-6}$ alkyl, $C_{1-6}$ haloalkyl, 5-10 membered heteroaryl, and 4-10 membered heterocycloalkyl, are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, are each optionally substituted with 1, 2, or 3 independently selected $R^f$ substituents;

each $R^d$ is independently selected from $C_{1-6}$ alkyl and OR$^e$, C(O)R$^e$, wherein the $C_{1-6}$ alkyl is optionally substituted with 1, 2, or 3 independently selected $R^f$ substituents;

each $R^e$ is independently selected from H and $C_{1-6}$ alkyl; and each $R^f$ is independently selected from OH, halo, $C_{1-4}$ alkyl, $C_{2-4}$ alkenyl, $C_{2-4}$ alkynyl, and carboxy.

In some embodiments, P is a compound in Table 2 infra, wherein L is attached to a terminal ring by a direct bond or to a substituent attached to a terminal ring. A terminal ring is two of the outermost rings of the compounds (e.g., the two terminal rings in compound P15 in Table 2 are pyrrolidine rings).

In some embodiments, P is a compound or formula in US Patent Publ. Nos. 20180179201, 20180179197, 20180179179, 20180179202, 20180177784, 20180177870, 20190300524, and 20190345170, each of which is incorporated herein by reference in its entirety, wherein L is attached to a terminal ring by a direct bond or to a substituent attached to a terminal ring.

With respect to L being attached directly to Ring A or Ring B or to a $R^A$ or $R^B$ substituent, a hydrogen atom on Ring A or Ring B or on a $R^A$ or $R^B$ is replaced by L. In some embodiments, L is attached directly to Ring A. In some embodiments, L is attached directly to Ring B. In some embodiments, L is attached to a $R^A$ substituent. In some embodiments, L is attached to a $R^B$ substituent.

However, in the context of L being attached to a terminal ring or to a substituent attached to a terminal ring of a compound in Table 2, L replaces any atom or acyclic moiety on the terminal ring; or any atom or acyclic moiety on the substituent on the terminal ring. For example, L can replace hydrogen atom or an OH group on a substituent on a terminal ring; or a hydrogen atom or a methyl group on a terminal ring.

In some embodiments, P has formula:

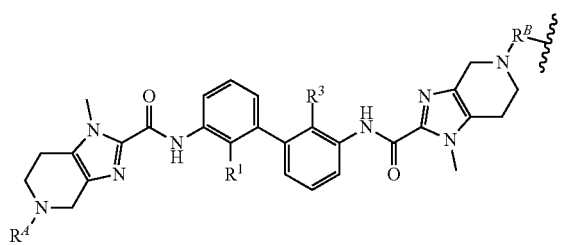

In some embodiments, P has formula:

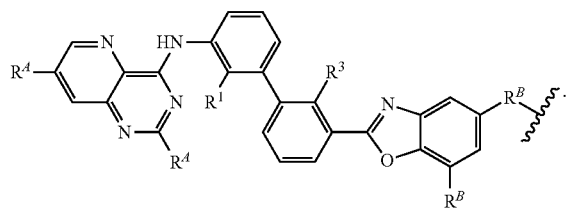

In some embodiments, P has formula:

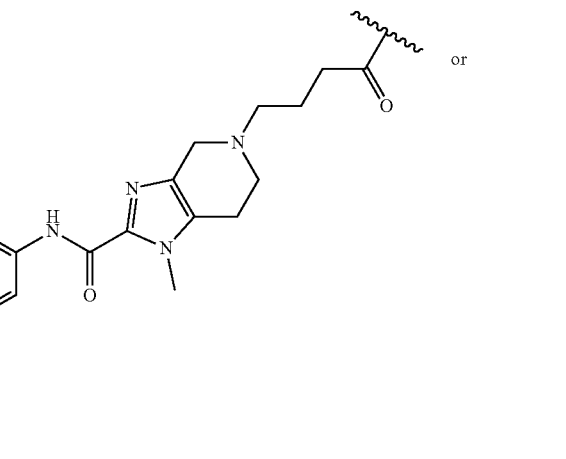

In some embodiments, P has formula:


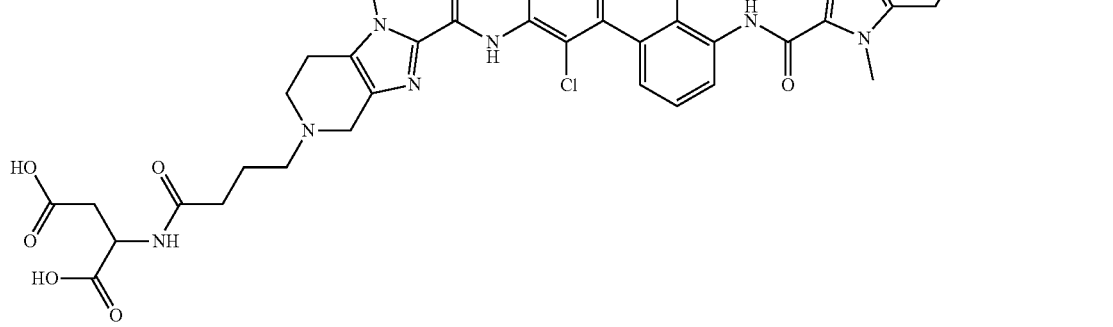

In some embodiments, P has formula has formula:

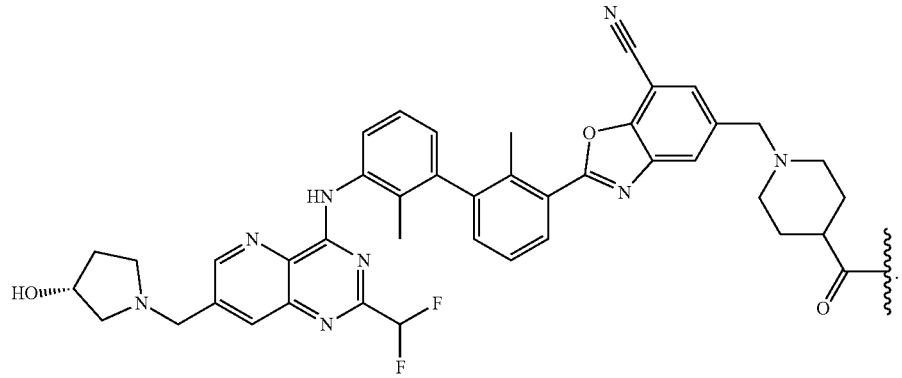 [SMILES: *C(=O)C1CCN(Cc2cc(C#N)c3oc(-c4cccc(-c5cccc(Nc6nc(C(F)F)nc7cc(CN8CC[C@@H](O)C8)cnc67)c5C)c4C)nc3c2)CC1]

or
In some embodiments, P has Formula (P-3):

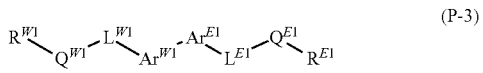
(P-3)

wherein:

L is attached to $Q^{W1}$, $R^{W1}$, $Q^{E1}$, $R^{E1}$, or to a substituent on $Q^{W1}$ or $Q^{E1}$;

$Ar^{W1}$ and $Ar^{E1}$ are each independently cycloalkyl, aryl, heteroaryl, or heterocyclyl; wherein each cycloalkyl, aryl, heteroaryl, or heterocyclyl is optionally substituted with 1 to 4 groups independently selected from halo, —$OR^a$, —$NO_2$, —CN, —$NR^aR^b$, —$N_3$, —$S(O)_2R^a$, -$C_{1-6}$ alkyl, -$C_{1-6}$ haloalkyl, -$C_{2-6}$ alkenyl, -$C_{2-6}$ alkynyl, —$OC_{1-6}$ alkyl, —$OC_{1-6}$ haloalkyl, -$C_{3-8}$ cycloalkyl, and -$C_{1-6}$ alkyl-$C_{3-8}$ cycloalkyl; wherein each alkyl, alkenyl, alkynyl, and cycloalkyl group is optionally substituted with 1 to 4 groups independently selected from oxo, halo, $NO_2$, —CN, —$N_3$, and —$OR^a$;

$L^{W1}$ and $L^{E1}$ are each independently a bond, —O—, —S—, —SO—, —$S(O)_2$—, —$(CR^3R^{3a})_m$—, —$(CR^3R^{3a})_m$O$(CR^3R^{3a})_m$—, —$(CR^3R^{3a})_mS(CR^3R^{3a})_m$—, —$(CR^3R^{3a})_mNR^3(CR^3R^{3a})_m$—, —C(O)—, —$(CR^3R^{3a})_mC(O)(CR^3R^{3a})_m$—, —$(CR^3R^{3a})_mC(O)NR^3(CR^3R^{3a})_m$—, —$(CR^3R^{3a})_mNR^3C(O)(CR^3R^{3a})_m$—, $C_{2-6}$ alkenylene, $C_{2-6}$ alkynylene, —$(CR^3R^{3a})_m$-(cycloprop-1,2-diyl)-$(CR^3R^{3a})_m$—, or —$(CR^3R^{3a})_m$-(cyclobut-1,4-diyl)-$(CR^3R^{3a})_m$—, wherein each m is independently 0, 1, 2, 3 or 4;

$Q^{W1}$ and $Q^{E1}$ are each independently aryl, heteroaryl, or heterocyclyl, wherein each aryl, heteroaryl, or heterocyclyl is optionally substituted with 1 to 4 groups independently selected from halo, oxo, —$OR^a$, —$N_3$, —$NO_2$, —CN, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, -$C_{1-6}$ alkyl, -$C_{2-6}$ alkenyl, -$C_{2-6}$ alkynyl, —$OC_{1-6}$ alkyl, -$C_{3-8}$ cycloalkyl, -$C_{1-6}$ alkyl-$C_{3-8}$ cycloalkyl, aryl, heteroaryl, heterocyclyl, and $R^N$; wherein each alkyl, alkenyl, alkynyl, -$C_{3-8}$ cycloalkyl, aryl, heteroaryl, or heterocyclyl is optionally substituted with 1 to 4 groups independently selected from oxo, halo, —$OR^a$, —$N_3$, —$NO_2$, —CN, —$NR^aR^b$, $C(O)R^a$, —C(O)$OR^a$, —$OC_{1-6}$ alkyl—CN, —$C(O)NR^aR^b$, —$NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$, and -$C_{3-8}$ cycloalkyl; and wherein the heteroaryl or heterocyclyl group may be oxidized on a nitrogen atom to form an N-oxide or oxidized on a sulfur atom to form a sulfoxide or sulfone;

$R^N$ is independently -$C_{1-6}$ alkyl$NR^1R^2$, —$OC_{1-6}$ alkyl$NR^1R^2$, -$C_{1-6}$ alkyl-O—$C_{1-6}$ alkyl-$NR^1R^2$, —$NR^aC_{1-6}$ alkyl$NR^1R^2$, -$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$ alkyl$NR^1R^2$, -$C_{1-6}$ alkyl$OR^a$, or -$L^1$-V-$L^2$-(ring A); wherein:

$L^1$ is independently a bond, O, $NR^a$, S, SO, or $SO_2$;

V is independently selected from a bond, -$C_{1-6}$ alkyl, -$C_{2-6}$ alkenyl, and -$C_{2-6}$ alkynyl, wherein each alkyl, alkenyl, or alkynyl is optionally independently substituted with $OR^a$, halo, cyano, —$NR^aR^b$ or -$C_{3-8}$ cycloalkyl;

$L^2$ is independently a bond, O, $NR^a$, S, SO, or $SO_2$;

ring A is independently cycloalkyl, aryl, heteroaryl, or heterocyclyl; wherein each cycloalkyl, aryl, heteroaryl, or heterocyclyl is optionally substituted with 1 to 4 groups independently selected from oxo, —$NO_2$, —$N_3$, —$OR^a$, halo, cyano, -$C_{1-6}$ alkyl, -$C_{1-6}$haloalkyl, -$C_{2-6}$ alkenyl, -$C_{2-6}$ alkynyl, —O—$C_{1-6}$ haloalkyl, $NR^aR^b$, —C(O)$R^a$, —C(O)$OR^a$, —$OC_{1-6}$ alkyl-CN, —C(O)$NR^aR^b$, $NR^aC(O)R^a$, —$NR^aC(O)OR^a$, —$NR^aC(O)OR^a$, —C(O)N($R^a$)$OR^b$, —$SO_2R^a$, —$SO_2NR^aR^b$, —$NR^aSO_2R^b$, —$NR^aSO_2NR^aR^b$, —C(O)$NR^aSO_2NR^aR^b$, $C_{3-8}$ cycloalkyl, and -$C_{1-6}$ alkyl-$C_{3-8}$ cycloalkyl;

wherein each alkyl, alkenyl, or alkynyl is optionally independently substituted with $OR^a$, halo, cyano, —$NR^aR^b$ and -$C_{3-8}$ cycloalkyl;

$R^{W1}$ and $R^{E1}$ are each independently —$NR^1R^2$, -$C_{1-6}$ alkyl$NR^1R^2$, —O-$C_{1-6}$ alkyl$NR^1R^2$, -$C_{1-6}$ alkylO-$C_{1-6}$ alkyl$NR^1R^2$, —$NR^aC_{1-6}$ alkyl$NR^1R^2$, -$C_{1-6}$ alkyl$N^+R^1R^2R^3$, —$SC_{1-6}$ alkyl$NR^1R^2$, —C(O)$NR^1R^2$, —$S(O)_2R^a$, —$(CH_2)_uS(O)_2NR^1R^2$, —$(CH_2)_uNR^aS(O)_2NR^1R^2$, —$S(O)_2NR^aC_{1-6}$ alkyl$NR^1R^2$, —$NR^aS(O)_2C_{1-6}$ alkyl$NR^1R^2$, —$(CH_2)_uC(O)NR^aS(O)_2NR^1R^2$, —$(CH_2)_uN^+R^1R^2O^-$, —$(CH_2)_uP^+R^bR^cR^d$, —$(CH_2)_uP^+R^bR^cO^-$, —$(CH_2)_uP^+O[NR^aR^b][NR^cR^d]$, —$(CH_2)_uNR^cP(O)(OR^c)_2$, —$(CH_2)_uNR^c(CH_2)_uP(O)(OR^c)_2$, —$(CH_2)_uCH_2P(O)(OR^c)(OR^d)$, —$(CH_2)_uOP(O)(OR^c)(OR^d)$, —$(CH_2)_uOP(O)NR^aR^b(OR^a)$, or —$V^2$—$(CR^cR^d)_p$—$L^3$-(ring B)-$(T)_z$; wherein:

$V^2$ is independently a bond, O, $NR^a$, S, SO, $SO_2$, C(O) $NR^a$, $NR^aC(O)$, $SO_2NR^1R^2$, or $NR^aSO_2$;

$L^3$ is independently a bond, $NR^a$, S, SO, $SO_2$, C(O)$NR^a$, $NR^aC(O)$, $SO_2NR^1R^2$, or $NR^aSO_2$;

ring B is independently cycloalkyl, aryl, heteroaryl, or heterocyclyl;

T is independently H, OR$^a$, (CH$_2$)$_q$NR$^1$R$^2$, (CH$_2$)$_q$NR$^a$C(O)R$^e$, (CH$_2$)$_q$OR$^a$, or (CH$_2$)$_q$C(O)R$^e$;

p is independently 0, 1, 2, 3, 4, or 5;

q is independently 0, 1, 2, 3, 4, or 5;

u is 0, 1, 2, 3, or 4; and z is 0, 1, 2, or 3;

wherein each cycloalkyl, aryl, heteroaryl, or heterocyclyl of R$^{E1}$ or R$^{W1}$ is optionally substituted with 1 to 3 substituents independently selected from NR$^a$R$^b$, halo, cyano, oxo, OR$^a$, -C$_{1-6}$ alkyl, -C$_{1-6}$ haloalkyl, -C$_{1-6}$ alkyl, -C$_{1-6}$ alkylCN, -C$_{1-6}$ alkylNR$^a$R$^b$, -C$_{1-6}$ alkylOH, -C$_{3-8}$ cycloalkyl, and -C$_{1-3}$ alkyl-C$_{3-8}$ cycloalkyl;

provided that at least one of V$^2$, L$^3$, ring B and T contains a nitrogen atom;

R$^1$ is independently selected from H, -C$_{1-8}$ alkyl, -C$_{2-6}$ alkenyl, -C$_{2-6}$ alkynyl, aryl, heteroaryl, heterocycloalkyl, C$_{3-6}$ cycloalkyl, -C$_{1-6}$ alkyl-aryl, -C$_{1-6}$ alkyl-heteroaryl, -C$_{1-6}$ alkyl-heterocycloalkyl, -C$_{1-6}$ alkyl-C(O)OR$^a$, -C$_{2-6}$ alkenyl-C(O)OR$^a$, —SO$_2$R$^a$, —SO$_2$NR$^a$R$^b$, —C(O)NR$^a$SO$_2$R$^a$, and -C$_{1-6}$ alkyl-C$_{3-8}$ cycloalkyl; wherein each alkyl, alkenyl, cycloalkyl, aryl, heteroaryl, or heterocycloalkyl is optionally substituted with 1 to 4 groups independently selected from —OR$^a$, —CN, halo, -C$_{1-6}$ alkyl, -C$_{1-6}$ alkyl-CN, -C$_{1-6}$ alkylOR$^a$, -C$_{1-6}$ haloalkyl, C$_{3-8}$ cycloalkyl, -C$_{1-3}$ alkyl-C$_{3-8}$ cycloalkyl, —C(O)R$^a$, -C$_{1-6}$ alkyl-C(O)R$^a$, —C(O)OR$^a$, -C$_{1-6}$alkylC(O)OR$^a$, —NR$^a$R$^b$, —OC(O)NR$^a$R$^b$, —NR$^a$C(O)OR$^a$, -C$_{1-6}$ alkyl-NR$^a$R$^b$, —C(O)NR$^a$R$^b$, -C$_{1-6}$ alkyl-C(O)NR$^a$R$^b$, —SO$_2$R$^a$, -C$_{1-6}$ alkyl-SO$_2$R$^a$, —SO$_2$NR$^a$R$^b$, -C$_{1-6}$ alkyl-SO$_2$NR$^a$R$^b$, —C(O)NR$^a$SO$_2$NR$^a$R$^b$, -C$_{1-6}$ alkyl-C(O)NR$^a$SO$_2$NR$^a$R$^b$, —NR$^a$C(O)R$^a$, and -C$_{1-6}$ alkyl-NR$^a$C(O)R$^a$;

R$^2$ is independently selected from H, -C$_{1-6}$ alkyl, -C$_{2-6}$ alkenyl, -C$_{2-6}$ alkynyl, aryl, heteroaryl, heterocycloalkyl, C$_{3-6}$ cycloalkyl, -C$_{1-6}$ alkylaryl, -C$_{1-6}$ alkyl-heteroaryl, -C$_{1-6}$ alkyl-heterocycloalkyl, -C$_{2-6}$ alkyl-OR$^a$, -C$_{1-6}$ alkyl-C(O)OR$^a$, and -C$_{2-6}$ alkenyl-C(O)OR$^a$; wherein each alkyl, alkenyl, cycloalkyl, aryl, heteroaryl, or heterocycloalkyl is optionally substituted with 1 to 4 groups independently selected from —OR$^a$, —CN, halo, -C$_{1-6}$ alkyl, -C$_{1-6}$ alkylCN, -C$_{1-6}$ alkyl-OR$^a$, -C$_{1-6}$ haloalkyl, C$_{3-8}$ cycloalkyl, -C$_{1-3}$ alkyl-C$_{3-8}$ cycloalkyl, —C(O)R$^a$, -C$_{1-6}$ alkyl-C(O)R$^a$, —C(O)OR$^a$, -C$_{1-6}$ alkyl-C(O)OR$^a$, —NR$^a$R$^b$, -C$_{1-6}$ alkyl-NR$^a$R$^b$, —C(O)NR$^a$R$^b$, -C$_{1-6}$ alkylC(O)NR$^a$R$^b$, —SO$_2$R$^a$, -C$_{1-6}$ alkyl-SO$_2$R$^a$, —SO$_2$NR$^a$R$^b$, -C$_{1-6}$ alkyl-SO$_2$NR$^a$R$^b$, and —NR$^a$C(O)R$^a$;

or R$^1$ and R$^2$ combine to form a heterocycloalkyl group optionally containing 1, 2, or 3 additional heteroatoms independently selected from oxygen, sulfur and nitrogen, and optionally substituted with 1 to 3 groups independently selected from oxo, -C$_{1-6}$ alkyl, C$_{3-8}$ cycloalkyl, -C$_{2-6}$ alkenyl, -C$_{2-6}$ alkynyl, —OR$^a$, —C(O)OR$^a$, -C$_{1-6}$ alkyl-CN, -C$_{1-6}$ alkyl-OR$^a$, -C$_{1-6}$ haloalkyl, -C$_{1-3}$ alkyl-C$_{3-8}$ cycloalkyl, —C(O)R$^a$, -C$_{1-6}$ alkyl-C(O)R$^a$, —C(O)OR$^a$, -C$_{1-6}$ alkyl-C(O)OR$^a$, —NR$^a$R$^b$, -C$_{1-6}$ alkyl-NR$^a$R$^b$, —C(O)NR$^a$R$^b$, -C$_{1-6}$ alkyl-C(O)NR$^a$R$^b$, —SO$_2$R$^a$, -C$_{1-6}$ alkyl-SO$_2$R$^a$, —SO$_2$NR$^a$R$^b$, and -C$_{1-6}$ alkyl-SO$_2$NR$^a$R$^b$;

R$^3$ is independently H, -C$_{1-6}$ alkyl, -C$_{2-6}$ alkenyl, C$_{3-6}$ cycloalkyl, aryl, heteroaryl, heterocycloalkyl, -C$_{1-6}$ alkyl-aryl, -C$_{1-6}$ alkyl-heteroaryl, -C$_{1-6}$ alkyl-heterocycloalkyl, -C$_{2-6}$ alkyl-OR$^a$, -C$_{1-6}$ alkyl-C(O)OR$^a$, or -C$_{2-6}$ alkenyl-C(O)OR$^a$;

R$^{3a}$ is independently H, -C$_{1-6}$ alkyl, -C$_{2-6}$ alkenyl, C$_{3-6}$ cycloalkyl, aryl, heteroaryl, heterocycloalkyl, -C$_{1-6}$ alkylaryl, -C$_{1-6}$ alkyl-heteroaryl, -C$_{1-6}$ alkyl-heterocycloalkyl, -C$_{2-6}$ alkyl-OR$^a$, -C$_{1-6}$ alkyl-C(O)OR$^a$, or -C$_{2-6}$ alkenyl-C(O)OR$^a$;

R$^a$ is independently selected from H, -C$_{1-6}$ alkyl, C$_{3-8}$ cycloalkyl, aryl, heteroaryl, heterocycloalkyl, -C$_{1-3}$ alkyl-C$_{3-8}$ cycloalkyl, -C$_{1-6}$ alkylaryl, -C$_{1-6}$ alkylheteroaryl, and -C$_{1-6}$ alkylheterocycloalkyl;

R$^b$ is independently selected from H, -C$_{1-6}$ alkyl, C$_{3-8}$ cycloalkyl, aryl, heteroaryl, heterocycloalkyl, -C$_{1-3}$ alkyl-C$_{3-8}$ cycloalkyl, -C$_{1-6}$ alkylaryl, -C$_{1-6}$ alkylheteroaryl, and -C$_{1-6}$ alkylheterocycloalkyl;

or R$^a$ and R$^b$ may combine together to form a ring consisting of 3-8 ring atoms that are C, N, O, or S; wherein the ring is optionally substituted with 1 to 4 groups independently selected from —OR$^f$, —CN, halo, -C$_{1-6}$ alkyl—CN, -C$_{1-6}$ alkyl—OR$^f$, -C$_{1-6}$ haloalkyl, C$_{3-8}$ cycloalkyl, -C$_{1-3}$ alkyl-C$_{3-8}$ cycloalkyl, —C(O)R$^f$, -C$_{1-6}$ alkyl-C(O)R$^f$, —C(O)OR$^f$, -C$_{1-6}$ alkyl-C(O)OR$^f$, —NR$^f$R$^g$, -C$_{1-6}$ alkyl-NR$^f$R$^g$, —C(O)NR$^f$R$^g$, -C$_{1-6}$ alkyl-C(O)NR$^f$R$^g$, —SO$_2$R$^f$, -C$_{1-6}$ alkyl-SO$_2$R$^f$, —SO$_2$NR$^f$R$^g$, -C$_{1-6}$ alkyl-SO$_2$NR$^f$R$^g$, —C(O)NR$^f$SO$_2$R$^g$, and —NR$^f$C(O)R$^g$;

R$^c$ is independently selected from H, OH, -C$_{1-6}$ alkyl, C$_{3-8}$ cycloalkyl, aryl, heteroaryl, heterocycloalkyl, -C$_{1-3}$ alkyl-C$_{3-8}$ cycloalkyl, -C$_{1-6}$ alkylaryl, -C$_{1-6}$ alkylheteroaryl, and -C$_{1-6}$ alkylheterocycloalkyl;

R$^d$ is independently selected from H, -C$_{1-6}$ alkyl, C$_{3-8}$ cycloalkyl, aryl, heteroaryl, heterocycloalkyl, -C$_{1-3}$ alkyl-C$_{3-8}$ cycloalkyl, -C$_{1-6}$ alkylaryl, -C$_{1-6}$ alkylheteroaryl, and -C$_{1-6}$ alkylheterocycloalkyl;

R$^e$ is independently selected from H, -C$_{1-6}$ alkyl, C$_{1-6}$ alkoxy, C$_{3-8}$ cycloalkyl, aryl, heteroaryl, heterocycloalkyl, —O-C$_{3-8}$ cycloalkyl, —O-aryl, —O-heteroaryl, —O-heterocycloalkyl, -C$_{1-3}$ alkyl-C$_{3-8}$ cycloalkyl, -C$_{1-6}$ alkylaryl, -C$_{1-6}$ alkylheteroaryl, —NR$^f$R$^g$, -C$_{1-6}$ alkyl-NR$^f$R$^g$, —C(O)NR$^f$R$^g$, -C$_{1-6}$ alkyl—C(O)NR$^f$R$^g$, —NHSO$_2$R$^f$, -C$_{1-6}$ alkyl—SO$_2$R$^f$, and -C$_{1-6}$ alkyl—SO$_2$NR$^f$R$^g$;

R$^f$ is independently selected from H, -C$_{1-6}$ alkyl, C$_{3-8}$ cycloalkyl, aryl, heteroaryl, heterocycloalkyl, -C$_{1-3}$ alkyl-C$_{3-8}$ cycloalkyl, -C$_{1-6}$ alkylaryl, -C$_{1-6}$ alkylheteroaryl, and -C$_{1-6}$ alkylheterocycloalkyl; and R$^g$ is independently selected from H, -C$_{1-6}$ alkyl, C$_{3-8}$ cycloalkyl, aryl, heteroaryl, heterocycloalkyl, -C$_{1-3}$ alkyl-C$_{3-8}$ cycloalkyl, -C$_{1-6}$ alkyl-aryl, -C$_{1-6}$ alkyl-heteroaryl, and -C$_{1-6}$ alkyl-heterocycloalkyl.

In some embodiments, the P moiety is an example compound disclosed in WO 2018195321 and US 20180305315, each of which is incorporated herein by reference in its entirety, wherein L is attached to a Q$^{W1}$ or Q$^{E1}$ ring or a substituent on Q$^{W1}$ or Q$^{E1}$ ring (e.g., R$^{E1}$ or R$^{W1}$ or other substituent).

With respect to L being attached directly to Q$^{W1}$ or Q$^{E1}$, or to a substituent on Q$^{W1}$ or Q$^{E1}$ (e.g., R$^{E1}$ or R$^{W1}$ or other substituent), a hydrogen atom on Q$^{W1}$ or Q$^{E1}$, or on the substituent is replaced by L.

However, in the context of L being attached to an example compound in WO 2018195321 or US 20180305315, L replaces any atom or acyclic moiety on a terminal ring, or on a substituent on a terminal ring.

In some embodiments, P is a moiety disclosed in US 20190270727 or WO 2019204609, each of which is incorporated herein by reference in its entirety, wherein L is attached to the ring to which the R$^W$ and R$^E$ substituents are attached (e.g., by attachment to R$^E$ or R$^W$ or other substituent; e.g., by replacement of a hydrogen atom of R$^E$ or R$^W$ or by replacement of any atom or acyclic moiety on R$^E$ or R$^W$).

Moiety S

In some embodiments, S has Formula (S-1):

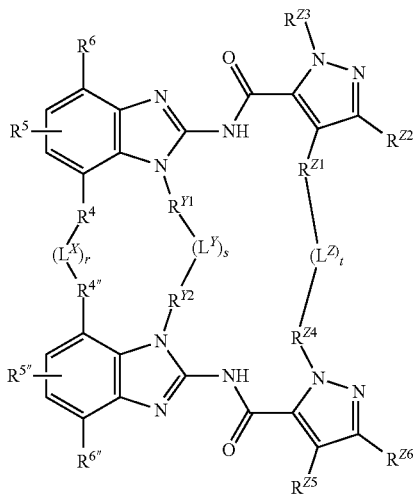

wherein:

L is attached to $R^4$, $R^5$, $R^6$, $R^{4'''}$, $R^{5''}$, $R^{6''}$, $R^{Z1}$, $R^{Z2}$, $R^{Z1}$, $R^{Z2}$, $R^{Z3}$, $R^{Z4}$, $R^{Z5}$, or $R^{Z6}$, provided that if L is attached to $R^4$ or $R^{4'''}$ then r is 0 or if L is attached to $R^{Z1}$ or $R^{Z4}$, then t is 0; provided that if L is attached to any of $R^4$, $R^5$, $R^6$, $R^{4'''}$, $R^{5''}$, $R^{6''}$, $R^{Z1}$, $R^{Z2}$, $R^{Z3}$, $R^{Z4}$, $R^{Z5}$, or $R^{Z6}$, then that $R^4$, $R^5$, $R^6$, $R^{4'''}$, $R^{5''}$, $R^{6''}$, $R^{Z1}$, $R^{Z2}$, $R^{Z3}$, $R^{Z4}$, $R^{Z5}$, or $R^{Z6}$ can additionally be a bond;

r is 0 or 1;

s is 0 or 1;

t is 0 or 1;

r+s+t=1 or 2;

when r is 0, $R^4$ and $R^{4'''}$ are each independently H, halo, OH, $OR^{a1}$, $OP(O)(OH)_2$, $OP(O)(R^IR^{II})_2$, $NR^{e1}R^{f1}$, $C(O)OR^{f1}$, $NR^{f1}C(O)R^{b1}$, $NR^{g1}S(O)_2(C_{1-4}$ alkyl)$NR^{e1}R^{f1}$, $NR^{g1}C(O)(C_{1-4}$ alkyl)$NR^{h1}R^{f1}$, optionally substituted $C_{1-6}$ alkyl, optionally substituted $C_{1-6}$ alkoxy, optionally substituted ($C_{1-6}$ alkyl)amino-, or optionally substituted ($C_{1-6}$ alkyl)($C_{1-4}$ alkyl)amino; wherein the $C_{1-6}$ alkyl moieties of said optionally substituted $C_{1-6}$ alkyl, optionally substituted $C_{1-6}$ alkoxy, optionally substituted ($C_{1-6}$ alkyl)amino, and optionally substituted ($C_{1-6}$ alkyl)($C_{1-4}$ alkyl)amino are each optionally substituted by 1, 2, 3, or 4 substituents independently selected from OH, $OP(O)(OH)_2$, $OP(O)(R^IR^{II})_2$, $C_{1-4}$ alkoxy, $NR^{e1}R^{f1}$, $C(O)OR^{f1}$, $C(O)NR^{e1}R^{f1}$, optionally substituted phenyl, optionally substituted 5-6 membered heterocycloalkyl, and optionally substituted 5-6 membered heteroaryl; wherein said optionally substituted phenyl, optionally substituted 5-6 membered heterocycloalkyl, and optionally substituted 5-6 membered heteroaryl are each optionally substituted by 1, 2, 3, or 4 substituents independently selected from halo, OH, $OP(O)(OH)_2$, $OP(O)(R^IR^{II})_2$, amino, ($C_{1-6}$ alkyl)amino, di-($C_{1-6}$ alkyl)($C_{1-6}$ alkyl) amino, $NH_2$-$C_{1-6}$ alkyl-, $C_{1-6}$ haloalkyl, HO-$C_{1-4}$ alkylene, $(OP(O)(OH)_2)$-$C_{1-4}$ alkyl-, $(OP(O)(R^IR^{II})_2)$-$C_{1-4}$ alkyl-, $C_{1-4}$ haloalkoxy, $C_{1-4}$ alkoxy, HO-$C_{2-4}$ alkoxy-, $(OP(O)(OH)_2)$-$C_{2-4}$ alkoxy, $(OP(O)(R^IR^{II})_2)$-$C_{2-4}$ alkoxy-, $C_{1-4}$ alkoxy-$C_{1-4}$ alkyl-, and $C_{1-4}$ alkoxy-$C_{1-4}$ alkyl-;

when s is 0, $R^{Y1}$ and $R^{Y2}$ are each independently H, optionally substituted $C_{1-6}$ alkyl, $C_{1-6}$ haloalkyl, optionally substituted $C_{2-6}$ alkenyl, optionally substituted $C_{2-6}$ alkynyl, optionally substituted $C_{3-6}$ cycloalkyl, optionally substituted 4-6 membered heterocycloalkyl, optionally substituted phenyl, optionally substituted 5-6 membered heteroaryl, or optionally substituted 9-10 membered heteroaryl; wherein said optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted 4-6 membered heterocycloalkyl, optionally substituted phenyl, optionally substituted 5-6 membered heteroaryl, and optionally substituted 9-10 membered heteroaryl are each optionally substituted by 1, 2, 3, or 4 substituents independently selected from halo, nitro, $-R^{e1}$, $-OH$, $OP(O)(OH)_2$, $OP(O)(R^IR^{II})_2$, $OR^{c1}$, $NH_2$, $NR^{c1}R^{d1}$, $OC(O)R^{c1}$, $C(O)OH$, $C(O)OR^{c1}$, $S(O)R^{c1}$, $S(O)_2R^{c1}$, $C(O)NH_2$, $C(O)NR^{c1}R^{d1}$, $S(O)_2NH_2$, $S(O)_2NR^{c1}R^{d1}$, $OC(O)NH_2$, $OC(O)NR^{c1}R^{d1}$, $NR^{d1}C(O)R^{c1}$, $NR^{d1}S(O)R^{c1}$, $NR^{d1}C(O)OR^{c1}$, and $NR^{d1}S(O)_2R^{c1}$;

when t is 0, $R^{Z1}$ is H, halo, or $C_{1-6}$ alkyl and $R^{Z4}$ is optionally substituted $C_{1-6}$ alkyl, wherein said optionally substituted $C_{1-6}$ alkyl group is optionally substituted by a substituent selected from $OR^{c1}$, $NR^{c1}R^{d1}$, $C(O)OR$, $C(O)NR^{c1}R^{d1}$, $S(O)_2NR^{c1}R^{d1}$, and $OC(O)NR^{c1}R^{d1}$;

when r is 1, then $R^4$ and $R^{4'''}$ are each independently selected from $CH_2$, $NR^{f1}$, and O, and $L^X$ taken together with $R^4$ and $R^{4'''}$ form a linking group, wherein $L^X$ is optionally substituted $C_{1-12}$ alkyl, optionally substituted $C_{1-12}$ haloalkyl, optionally substituted $C_{2-12}$ alkenyl, optionally substituted $C_{2-12}$ alkynyl, optionally substituted -$C_{1-6}$ alkyl-O-$C_{1-6}$ alkyl-, optionally substituted -$C_{1-6}$ alkyl-$NR^{a1}$-$C_{1-6}$ alkyl-, optionally substituted -$C_{1-6}$ alkyl-($C_{3-6}$ cycloalkyl)-$C_{1-6}$ alkyl-, optionally substituted -$C_{1-6}$ alkyl-phenyl-$C_{1-6}$ alkyl-, optionally substituted -$C_{1-6}$ alkyl-(4-6 membered heterocycloalkyl)-$C_{1-6}$ alkyl-, or optionally substituted -$C_{1-6}$ alkyl-(5-6 membered heteroaryl)-$C_{1-6}$ alkyl-; wherein the alkyl, alkenyl, or alkynyl moiety of optionally substituted $C_{1-12}$ alkyl, optionally substituted $C_{2-12}$ alkenyl, optionally substituted $C_{2-12}$ alkynyl, optionally substituted -$C_{1-6}$ alkyl-O-$C_{1-6}$ alkyl-, optionally substituted -$C_{1-6}$ alkyl-$NR^{a1}$-$C_{1-6}$ alkyl-, optionally substituted -$C_{1-6}$ alkyl-($C_{3-6}$ cycloalkyl)-$C_{1-6}$ alkyl-, optionally substituted -$C_{1-6}$ alkyl-phenyl-$C_{1-6}$ alkyl-, optionally substituted -$C_{1-6}$ alkyl-(4-6 membered heterocycloalkyl)-$C_{1-6}$ alkyl-, and optionally substituted -$C_{1-6}$ alkyl-(5-6 membered heteroaryl)-$C_{1-6}$ alkyl- are each optionally substituted by 1, 2, 3, or 4 substituents independently selected from halo, $C_{1-4}$ haloalkyl, OH, $OP(O)(OH)_2$, $OP(O)(R^IR^{II})_2$, $OR^{c1}$, $NH_2$, $NR^{c1}R^{d1}$, $OC(O)R^{c1}$, $C(O)OH$, $C(O)OR^{c1}$, $S(O)R^{c1}$, $S(O)_2R^{c1}$, $C(O)NH_2$, $C(O)NR^{c1}R^{d1}$, $S(O)_2NH_2$, $S(O)_2NR^{c1}R^{d1}$, $OC(O)NH_2$, $OC(O)NR^{c1}R^{d1}$, $NR^{d1}C(O)R^{c1}$, $NR^{d1}S(O)R^{c1}$, $NR^{d1}C(O)OR^{d1}$, and $NR^{d1}S(O)_2R^{c1}$; and the $C_{3-6}$ cycloalkyl, phenyl, 4-6 membered heterocycloalkyl, or 5-6 membered heteroaryl moiety of said optionally substituted -$C_{1-6}$ alkyl-($C_{3-6}$ cycloalkyl)-$C_{1-6}$ alkyl-, optionally substituted -$C_{1-6}$ alkyl-phenyl-$C_{1-6}$ alkyl-, optionally substituted -$C_{1-6}$ alkyl-(4-6 membered heterocycloalkyl)-$C_{1-6}$ alkyl-, and optionally substituted -$C_{1-6}$ alkyl-(5-6 membered heteroaryl)-$C_{1-6}$ alkyl- are each optionally substituted by 1, 2, 3, or 4 substituents independently selected from halo, OH, $OP(O)(OH)_2$, $OP(O)(R^IR^{II})_2$, amino, ($C_{1-4}$ alkyl)amino-, di-($C_{1-4}$ alkyl)amino-, $C_{1-4}$ alkyl, $C_{1-4}$ haloalkyl, $C_{1-4}$ haloalkoxy, $C_{1-4}$ alkoxy, OH-($C_{1-4}$ alkoxy), -($C_{1-4}$ alkoxyl)-O—P(O)(OH)$_2$, -($C_{1-4}$ alkoxyl)—OP(O)(R^IR^{II})$_2$, and $C_{1-4}$ alkoxy-($C_{1-4}$ alkoxy)-;

when s is 1, $R^{Y1}$ and $R^{Y2}$ are each independently a bond or —$CH_2$—, and $L^Y$, taken together with $R^{Y1}$ and $R^{Y2}$, forms a linking group, wherein $L^Y$ is a bond or $L^Y$ is $C_{1-10}$ haloalkyl, optionally substituted $C_{1-10}$ alkyl, optionally substituted $C_{2-10}$ alkenyl, optionally substituted $C_{2-10}$ alkynyl, optionally substituted -$C_{1-6}$ alkyl-O-$C_{1-6}$ alkyl-, optionally substituted -$C_{1-6}$ alkyl-$NR^{a1}$-$C_{1-6}$ alkyl-, optionally substituted $C_{3-6}$ cycloalkyl, optionally substituted phenyl, optionally substituted 4-6 membered heterocycloalkyl, optionally substituted 5-6 membered heteroaryl, optionally substituted -$C_{1-4}$ alkyl-($C_{3-6}$ cycloalkyl)-$C_{1-4}$ alkyl-, optionally substituted -$C_{1-4}$ alkyl-phenyl-$C_{1-4}$ alkyl-, optionally substituted -$C_{1-4}$ alkyl-(4-6 membered heterocycloalkyl)-$C_{1-4}$ alkyl-, or optionally substituted -$C1\_4$ alkyl-(5-6 membered heteroaryl)-$C_{1-4}$ alkyl-; wherein the alkyl, alkenyl, and alkynyl moieties of said optionally substituted $C_{1-10}$ alkyl, optionally substituted $C_{2-10}$ alkenyl, optionally substituted $C_{2-10}$ alkynyl, optionally substituted -$C_{1-6}$ alkyl-O-$C_{1-6}$ alkyl-, optionally substituted -$C_{1-6}$ alkyl-$NR^{a1}$-$C_{1-6}$ alkyl-, optionally substituted -$C_{1-4}$ alkyl-($C_{3-6}$ cycloalkyl)-$C_{1-4}$ alkyl-, optionally substituted -$C_{1-4}$ alkyl-phenyl-$C_{1-4}$ alkyl-, optionally substituted -$C_{1-4}$ alkyl-(4-6 membered heterocycloalkyl)-$C_{1-4}$ alkyl-, and optionally substituted -$C_{1-4}$ alkyl-(5-6 membered heteroaryl)-$C_{1-4}$ alkyl- are each optionally substituted by 1 or 2 substituents independently selected from halo, $C_{1-4}$ haloalkylOH, O—P(O)(OH)$_2$, O—P(O)($R^I R^{II}$)$_2$, $OR^{c1}$, $NH_2$, $NR^{c1}R^{d1}$, $OC(O)R^{c1}$, $C(O)OH$, $C(O)OR^{c1}$, $S(O)R^{c1}$, $S(O)_2R^{c1}$, $C(O)NH_2$, $C(O)NR^{c1}R^{d1}$, $S(O)_2NH_2$, $S(O)_2NR^{c1}R^{d1}$, $OC(O)NH_2$, $OC(O)NR^{c1}R^{d1}$, $NR^{d1}C(O)R^{c1}$, $NR^{d1}S(O)R^{c1}$, $NR^{d1}C(O)OR^{c1}$, and $NR^{d1}S(O)_2R^{c1}$; and wherein the $C_{3-6}$ cycloalkyl, phenyl, 4-6 membered heterocycloalkyl and 5-6 membered heteroaryl moieties of optionally substituted $C_{3-6}$ cycloalkyl, optionally substituted phenyl, optionally substituted 4-6 membered heterocycloalkyl, optionally substituted 5-6 membered heteroaryl, optionally substituted -$C_{1-4}$ alkyl-($C_{3-6}$ cycloalkyl)-$C_{1-4}$ alkyl-, optionally substituted -$C_{1-4}$ alkyl-phenyl-$C_{1-4}$ alkyl-, optionally substituted -$C_{1-4}$ alkyl-(4-6 membered heterocycloalkyl)-$C_{1-4}$ alkyl-, and optionally substituted -$C_{1-4}$ alkyl-(5-6 membered heteroaryl)-$C_{1-4}$ alkyl- are optionally substituted by 1, 2, 3, or 4 substituents independently selected from halo, OH, OP(O)(OH)$_2$, OP(O)($R^I R^{II}$)$_2$, amino, ($C_{1-4}$ alkyl)amino-, di-($C_{1-4}$ alkyl)amino-, $C_{1-4}$ alkyl, $C_{1-4}$ haloalkyl, $C_{1-4}$ haloalkoxy, $C_{1-4}$ alkoxy, OH-($C_{1-4}$ alkoxy), -($C_{1-4}$ alkoxyl)-O-P(O)(OH)$_2$, -($C_{1-4}$ alkoxyl)-OP(O)($R^I R^{II}$)$_2$, and $C_{1-4}$ alkoxy-($C_{1-4}$ alkoxy)-;

when t is 1, $R^{Z1}$ and $R^{Z4}$ are each independently —CH$_2$—, and $L^Z$, taken together with $R^{Z1}$ and $R^{Z4}$, forms a linking group, wherein $L^Z$ is $C_{1-10}$ haloalkyl, optionally substituted $C_{1-10}$ alkyl, optionally substituted $C_{2-10}$ alkenyl, optionally substituted $C_{2-10}$ alkynyl, optionally substituted -$C_{1-6}$ alkyl-O-$C_{1-6}$ alkyl-, optionally substituted -$C_{1-6}$ alkyl-$NR^{a1}$-$C_{1-6}$ alkyl-, optionally substituted $C_{3-6}$ cycloalkyl, optionally substituted phenyl, optionally substituted 4-6 membered heterocycloalkyl, optionally substituted 5-6 membered heteroaryl, optionally substituted -$C_{1-4}$ alkyl-($C_{3-6}$ cycloalkyl)-$C_{1-4}$ alkyl-, optionally substituted -$C_{1-4}$ alkyl-phenyl-$C_{1-4}$ alkyl-, optionally substituted -$C_{1-4}$ alkyl-(4-6 membered heterocycloalkyl)-$C_{1-4}$ alkyl-, or optionally substituted -$C_{1-4}$ alkyl-(5-6 membered heteroaryl)-$C_{1-4}$ alkyl-; wherein the alkyl, alkenyl, or alkynyl moieties of said optionally substituted $C_{1-10}$ alkyl, optionally substituted $C_{2-10}$ alkenyl, optionally substituted $C_{2-10}$ alkynyl, optionally substituted -$C_{1-6}$ alkyl-O-$C_{1-6}$ alkyl-, optionally substituted -$C_{1-6}$ alkyl-$NR^{a}$-$C_{1-6}$ alkyl-, optionally substituted -$C_{1-4}$ alkyl-($C_{3-6}$ cycloalkyl)-$C_{1-4}$ alkyl-, optionally substituted -$C_{1-4}$ alkyl-phenyl-$C_{1-4}$ alkyl-, optionally substituted -$C_{1-4}$ alkyl-(4-6 membered heterocycloalkyl)-$C_{1-4}$ alkyl-, and optionally substituted -$C_{1-4}$ alkyl-(5-6 membered heteroaryl)-$C_{1-4}$ alkyl- are each optionally substituted by 1 or 2 substituents independently selected from halo, $C_{1-6}$ haloalkyl, OH, O—P(O)(OH)$_2$, O—P(O)($R^I R^{II}$)$_2$, $OR^{c1}$, $NH_2$, $NR^{c1}R^{d1}$, $OC(O)R^{c1}$, $C(O)OH$, $C(O)OR^{c1}$, $S(O)R^{c1}$, $S(O)_2R^{c1}$, $C(O)NH_2$, $C(O)NR^{c1}R^{d1}$, $S(O)_2NH_2$, $S(O)_2NR^{c1}R^{d1}$, $OC(O)NH_2$, $OC(O)NR^{c1}R^{d1}$, $NR^{d1}C(O)R^{c1}$, $NR^{d1}S(O)R^{c1}$, $NR^{d1}C(O)OR^{c1}$, and $NR^{d1}S(O)_2R^{c1}$; and wherein the $C_{3-6}$ cycloalkyl, phenyl, 4-6 membered heterocycloalkyl and 5-6 membered heteroaryl moieties of optionally substituted -$C_{1-6}$ alkyl-($C_{3-6}$ cycloalkyl)-$C_{1-6}$ alkyl-, optionally substituted -$C_{1-6}$ alkyl-phenyl-$C_{1-6}$ alkyl-, optionally substituted -$C_{1-6}$ alkyl-(4-6 membered heterocycloalkyl)-$C_{1-6}$ alkyl-, and optionally substituted -$C_{1-6}$ alkyl-(5-6 membered heteroaryl)-$C_{1-6}$ alkyl- are each optionally substituted by 1, 2, 3, or 4 substituents independently selected from halo, OH, OP(O)(OH)$_2$, OP(O)($R^I R^{II}$)$_2$, amino, ($C_{1-4}$ alkyl)amino-, di-($C_{1-4}$ alkyl)amino-, $C_{1-4}$ alkyl, $C_{1-4}$ haloalkyl, $C_{1-4}$ haloalkoxy, $C_{1-4}$ alkoxy, OH-($C_{1-4}$ alkoxy), -($C_{1-4}$ alkoxyl)-O—P(O)(OH)$_2$, -($C_{1-4}$ alkoxyl)—OP(O)($R^I R^{II}$)$_2$, and $C_{1-4}$ alkoxy-($C_{1-4}$ alkoxy)-;

$R^5$ and $R^{5\prime\prime\prime}$ are each independently $C(O)NR^{d1}R^{f1}$, or one of $R^5$ and $R^{5\prime\prime\prime}$ is $C(O)NR^{d1}R^{f1}$, and the other of $R^5$ and $R^{5\prime\prime\prime}$ is H, C(O)OH or $C(O)OR^{c1}$;

$R^6$ and $R^{6\prime\prime\prime}$ are each independently selected from H, halo, $C_{1-6}$ haloalkyl, $C_{1-6}$ haloalkoxy, OH, OP(O)(OH)$_2$, OP(O)($R^I R^{II}$)$_2$, $NH_2$, $NR^{c1}R^{d1}$, $NR^{c1}R^{d1}$, $C(O)OR^{c1}$, $N(R^{d1})C(O)R^{c1}$, $NR^{d1}S(O)_2R^{c1}$, $NR^{g1}S(O)_2(C_{1-2}alkyl)-NR^{h1}R^{f1}$, $NR^{g1}C(O)(C_{1-2}alkyl)-NR^{h1}R^{f1}$, optionally substituted $C_{1-6}$ alkyl, optionally substituted 5-6 membered heterocycloalkyl, optionally substituted $C_{1-6}$ alkoxy, optionally substituted $C_{1-6}$ alkylamino, and optionally substituted di-($C_{1-6}$ alkyl)amino-; wherein the $C_{1-6}$ alkyl moiety of said optionally substituted $C_{1-6}$ alkyl, optionally substituted $C_{1-6}$ alkoxy, optionally substituted $C_{1-6}$ alkylamino, and optionally substituted di-($C_{1-6}$ alkyl)amino- are each optionally substituted by 1, 2, 3, or 4 substituents independently selected from $C_{1-3}$ alkyl, OH, CN, OP(O)(OH)$_2$, OP(O)($R^I R^{II}$)$_2$, $OR^{c1}$, $NH_2$, $NR^{c1}R^{c1}$, $NR^{c1}R^{d1}$, $C(O)OH$, $C(O)OR^{c1}$, $OC(O)R^{c1}$, $C(O)OH$, $C(O)OR^{c1}$, $S(O)R^{c1}$, $S(O)_2R^{c1}$, $C(O)NH_2$, $C(O)NR^{c1}R^{d1}$, $S(O)_2NH_2$, $S(O)_2NR^{c1}R^{d1}$, $OC(O)NH_2$, $OC(O)NR^{c1}R^{d1}$, $NR^{d1}C(O)R^{c1}$, $NR^{d1}S(O)R^{c1}$, $NR^{d1}C(O)OR^{c1}$, $NR^{d1}S(O)_2R^{c1}$, optionally substituted phenyl, optionally substituted 5-6 membered heterocycloalkyl and optionally substituted 5-6 membered heteroaryl group; wherein said optionally substituted phenyl, 5-6 membered heterocycloalkyl and 5-6 membered heteroaryl are each optionally substituted by 1, 2, 3, or 4 substituents independently selected from halo, OH, OP(O)(OH)$_2$, OP(O)($R^I R^{II}$)$_2$, amino, ($C_{1-4}$ alkyl)amino-, di-($C_{1-4}$ alkyl)amino-, $C_{1-4}$ alkyl, $C_{1-4}$ haloalkyl, OH-($C_{1-4}$ alkyl)-, -($C_{1-4}$ alkyl)-O—P(O)(OH)$_2$, -($C_{1-4}$ alkyl)-O—P(O)($R^I R^{II}$)$_2$, $C_{1-4}$ haloalkoxy)-, $C_{1-4}$ alkoxy-, OH-($C_{2-4}$ alkoxy)-, -($C_{2-4}$ alkoxy)-O—P(O)(OH)$_2$, -($C_{2-4}$ alkoxy)-O—P(O)($R^I R^{II}$)$_2$, $C_{1-4}$ alkoxy-($C_{1-4}$ alkoxy)-, —$C(O)R^{d1}$, —$C(O)N(R^{d1})(R^{f1})$, and $C(O)OR^{d1}$;

$R^{Z3}$ is optionally substituted $C_{1-4}$ alkyl, wherein said optionally substituted $C_{1-4}$ alkyl is optionally substituted by a substituent selected from $OR^{c1}$, $NR^{c1}R^{d1}$, $C(O)OR^{c1}$, $C(O)NR^{c1}R^{d1}$, $S(O)_2NR^{c1}R^{d1}$, and $OC(O)NR^{c1}R^{d1}$;

$R^{Z5}$ is H, halo, or $C_{1-4}$ alkyl;

$R^{Z2}$ and $R^{Z6}$ are each independently H, cyclopropyl, or $C_{1-4}$ alkyl;

each $R^{a1}$ is independently selected from H, $R^{c1}$, $C(O)R^{c1}$, $C(O)OH$, $C(O)OR^{c1}$, $S(O)R^{c1}$, $S(O)_2R^{c1}$, $C(O)NH_2$, $C(O)NR^{c1}R^{d1}$, $S(O)_2NH_2$, and $S(O)_2NR^{c1}R^{d1}$;

each $R^{b1}$ is independently selected from $C_{1-4}$ alkyl, $C_{1-4}$ haloalkyl, -($C_{1-4}$ alkyl)-OH, -($C_{1-4}$ alkyl)-O—P(O)(OH)$_2$, -($C_{1-4}$ alkyl)-O—P(O)($R^I R^{II}$)$_2$, -($C_{1-4}$ alkyl)-O-($C_{1-4}$ alkyl), -($C_{1-4}$ alkyl)$NR^{e1}R^{f1}$, -($C_{1-4}$ alkyl)-O—C(O)($C_{1-4}$ alkyl), and -($C_{1-4}$ alkyl)-C(O)—O-($C_{1-4}$ alkyl);

each $R^{c1}$ is independently selected from $C_{1-4}$ alkyl, $C_{1-4}$ haloalkyl, -($C_{1-4}$ alkyl)-OH, -($C_{1-4}$ alkyl)-O—P(O)(OH)$_2$, -($C_{1-4}$ alkyl)-O—P(O)($R^I R^{II}$)$_2$, -($C_{1-4}$ alkyl)-O-($C_{1-4}$ alkyl), -($C_{1-4}$ alkyl)-N($R^{e1}$)($R^{f1}$), -($C_{1-4}$ alkyl)-O—C(O)($C_{1-4}$ alkyl), -($C_{1-4}$ alkyl)-C(O)—O-($C_{1-4}$ alkyl), optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted -$C_{1-4}$ alkyl-$C_{3-6}$ cycloalkyl, optionally substituted -$C_{1-4}$ alkyl-phenyl, optionally substituted -$C_{1-4}$ alkyl-4-6 membered heterocycloalkyl, optionally substituted -$C_{1-4}$ alkyl-5-6 membered heteroaryl, and optionally substituted -$C_{1-4}$ alkyl-9-10 membered heteroaryl; wherein the $C_{3-6}$ cycloalkyl, phenyl, 4-6 membered heterocycloalkyl, 5-6 membered heteroaryl and 9-10 membered heteroaryl moieties of said optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted -$C_{1-4}$ alkyl-$C_{3-6}$ cycloalkyl, optionally substituted -$C_{1-4}$ alkyl-phenyl, optionally substituted -$C_{1-4}$ alkyl-4-6 membered heterocycloalkyl, optionally substituted -$C_{1-4}$ alkyl-5-6 membered heteroaryl, and optionally substituted -$C_{1-4}$ alkyl-9-10 membered heteroaryl are each optionally substituted by 1, 2, 3, or 4 substituents independently selected from halo, OH, OP(O)(OH)$_2$, OP(O)($R^I R^{II}$)$_2$, amino, ($C_{1-4}$ alkyl)NH$_2$, ($C_{1-4}$ alkyl)amino, di-($C_{1-4}$ alkyl)amino, $C_{1-4}$ alkyl, $C_{1-4}$ haloalkyl, $C_{1-4}$ haloalkoxy, $C_{1-6}$ alkoxy-, OH-($C_{2-4}$ alkoxy)-, -($C_{1-4}$ alkyl)-O—P(O)(OH)$_2$, -($C_{1-4}$ alkyl)-O—P(O)($R^I R^{II}$)$_2$, $C_{1-4}$ alkoxy-($C_{1-4}$ alkoxy)-, C(O)$R^{d1}$, C(O)N$R^{d1}R^{f1}$, and C(O)O$R^{d1}$;

each $R^{d1}$ is independently selected from H and $C_{1-4}$ alkyl;

each $R^{e1}$ is independently selected from H, $C_{1-4}$ alkyl, —C(O)($C_{1-4}$ alkyl), —OC(O)($C_{1-4}$ alkyl), —C(O)O($C_{1-4}$ alkyl), -($C_{1-4}$ alkyl)NH$_2$, -($C_{1-4}$ alkyl)-$C_{1-4}$ alkoxy, —C(O)-(optionally substituted 5-6 membered heterocycloalkyl), —C(O)($C_{1-4}$ alkyl)-(optionally substituted 5-6 membered heterocycloalkyl), —C(O) (optionally substituted 5-6 membered heteroaryl), and —C(O)($C_{1-4}$ alkyl)-(optionally substituted 5-6 membered heteroaryl), wherein the optionally substituted 5-6 membered heterocycloalkyl and optionally substituted 5-6 membered heteroaryl are each optionally substituted 1, 2, 3, or 4 substituents independently selected from halo, OH, —OP(O)(OH)$_2$, OP(O)($R^I R^{II}$)$_2$, amino, ($C_{1-4}$ alkyl)NH$_2$, ($C_{1-4}$ alkyl)amino-, di-($C_{1-4}$ alkyl)amino-, $C_{1-4}$ alkyl, $C_{1-4}$ haloalkyl, $C_{1-4}$ haloalkoxy, $C_{1-4}$ alkoxy-, OH-($C_{2-4}$ alkoxy)-, -($C_{1-4}$ alkyl)-O—P(O)(OH)$_2$, -($C_{1-4}$ alkyl)-O—P(O)($R^I R^{II}$)$_2$, $C_{1-4}$ alkoxy-($C_{1-4}$ alkoxy)-, $C_{1-4}$ alkoxy-($C_{1-4}$ alkoxy)-, C(O)$R^{d1}$, C(O)N$R^{d1}R^{f1}$, and C(O)O$R^{d1}$;

each $R^{f1}$ is independently selected from H and $C_{1-4}$ alkyl;

$R^{g1}$ and $R^{h1}$ are each independently selected from H and $C_{1-4}$ alkyl;

or $R^{g1}$ and $R^{h1}$, taken together with the atom or atoms through which they are connected form a 5-6 membered heterocycloalkyl ring; and each occurrence of $R^I$ and $R^{II}$ are independently $C_{1-6}$ alkoxy.

In some embodiments, S has Formula (S-1a):

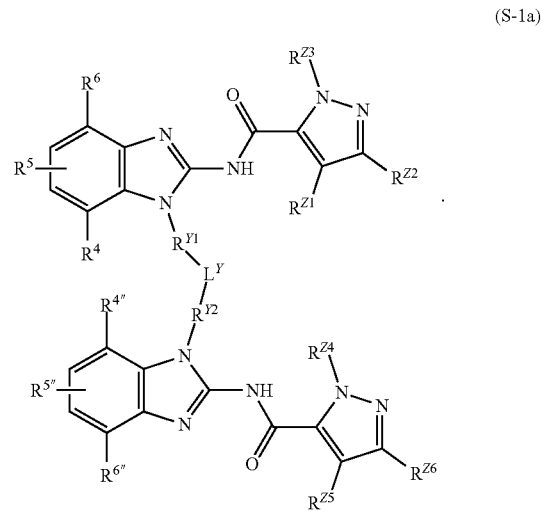

(S-1a)

In some embodiments, S has Formula (S-1a), wherein L is attached to $R^4$ or $R^{4'''}$.

In some embodiments, S has Formula (S-1a), wherein L is attached to $R^4$.

In some embodiments, S has Formula (S-1a), wherein L is attached to $R^{4'''}$.

In some embodiments, S has Formula (S-1a), wherein:
$R^4$ and $R^{4'''}$ are each independently H, halo, OH, N$R^{e1}R^{f1}$, optionally substituted $C_{1-6}$ alkyl, optionally substituted $C_{1-6}$ alkoxy, optionally substituted ($C_{1-6}$ alkyl)amino-, and optionally substituted ($C_{1-6}$ alkyl)($C_{1-4}$ alkyl)amino; wherein the $C_{1-6}$ alkyl moieties of said optionally substituted $C_{1-6}$ alkyl, optionally substituted $C_{1-6}$ alkoxy, optionally substituted ($C_{1-6}$ alkyl)amino, and optionally substituted ($C_{1-6}$ alkyl)($C_{1-4}$ alkyl)amino are each optionally substituted by 1-2 substituents independently selected from OH, OP(O)(OH)$_2$, OP(O)($R^I R^{II}$)$_2$, $C_{1-4}$ alkoxy, N$R^{e1}R^{f1}$, C(O)O$R^{f1}$, C(O)N$R^{e1}R^{f1}$, optionally substituted phenyl, and optionally substituted 5-6 membered heterocycloalkyl; wherein said optionally substituted phenyl and optionally substituted 5-6 membered heterocycloalkyl are each optionally substituted by 1-2 substituents independently selected from halo, OH, amino, ($C_{1-6}$ alkyl)amino, di-($C_{1-6}$ alkyl)($C_{1-6}$ alkyl)amino, NH$_2$-$C_{1-6}$ alkyl-, $C_{1-6}$ haloalkyl, HO-$C_{1-4}$ alkylene, $C_{1-4}$ haloalkoxy, $C_{1-4}$ alkoxy, HO-$C_{2-4}$ alkoxy-, $C_{1-4}$ alkoxy-$C_{1-4}$ alkyl-, and $C_{1-4}$ alkoxy-$C_{1-4}$ alkoxy-;
$R^{Z1}$ is H, halo, or $C_{1-3}$ alkyl;
$R^{Z4}$ is $C_{1-3}$ alkyl;
$R^{Y1}$ and $R^{Y2}$ are each independently a bond or —CH$_2$—, and $L^Y$, taken together with $R^{Y1}$ and $R^{Y2}$, forms a linking group, wherein $L^Y$ is a bond or $L^Y$ is $C_{1-4}$ haloalkyl, optionally substituted $C_{1-4}$ alkyl, optionally substituted $C_{2-4}$ alkenyl, optionally substituted -$C_{1-4}$ alkyl-O—$C_{1-4}$ alkyl-, optionally substituted -$C_{1-4}$ alkyl-N$R^{a1}$-$C_{1-4}$ alkyl-, optionally substituted $C_{3-6}$ cycloalkyl, optionally substituted phenyl, optionally substituted 4-6 membered heterocycloalkyl, optionally substituted -$C_{1-3}$ alkyl-($C_{3-6}$ cycloalkyl)-$C_{1-3}$ alkyl-, optionally substituted -$C_{1-3}$ alkyl-phenyl-$C_{1-3}$ alkyl-, and optionally substituted -$C_{1-3}$ alkyl-(4-6 membered heterocycloalkyl)-$C_{1-3}$ alkyl-; wherein the alkyl and alkenyl moieties of said optionally substituted $C_{1-4}$ alkyl, optionally substituted $C_{2-4}$ alkenyl, optionally substituted -$C_{1-4}$ alkyl-O—$C_{1-4}$ alkyl-, optionally substituted -$C_{1-4}$ alkyl-N$R^{a1}$-$C_{1-4}$ alkyl-, optionally substituted -$C_{1-3}$ alkyl-($C_{3-6}$ cycloalkyl)-$C_{1-3}$ alkyl-, optionally substituted -$C_{1-3}$ alkyl-phenyl-$C_{1-3}$ alkyl-, and optionally substituted -$C_{1-3}$ alkyl-(4-6 membered heterocycloalkyl)-$C_{1-3}$ alkyl- are each optionally substituted by 1, 2, 3, or 4 substituents independently selected from halo, OH, and $OR^{c1}$;

$R^5$ and $R^{5\prime\prime}$ are each independently $C(O)NR^{d1}R^{f1}$, or one of $R^5$ and $R^{5\prime\prime}$ is $C(O)NH_2$ and the other of $R^5$ and $R^{5\prime\prime}$ is H, $C(O)OH$ or $C(O)O$-$C_{1-4}$ alkyl;

$R^6$ and $R^{6\prime\prime}$ are each independently selected from H, halo, $C_{1-6}$ haloalkyl, $C_{1-6}$ haloalkoxy, OH, $NH_2$, $NR^{c1}R^{d1}$, $N(R^{d1})C(O)R^{c1}$, $NR^{d1}S(O)_2R^{c1}$, optionally substituted $C_{1-6}$ alkyl, optionally substituted $C_{1-6}$ alkoxy, optionally substituted $C_{1-6}$ alkylamino, optionally substituted di-($C_{1-6}$ alkyl)amino-, and optionally substituted 5-6 membered heterocycloalkyl; wherein the alkyl moiety of said optionally substituted $C_{1-6}$ alkyl, optionally substituted $C_{1-6}$ alkoxy, optionally substituted $C_{1-6}$ alkylamino, and optionally substituted di-($C_{1-6}$ alkyl)amino- are each optionally substituted by 1-2 substituents independently selected from $C_{1-3}$ alkyl, OH, CN, $OR^{c1}$, $NH_2$, $NR^{c1}R^{c1}$, $NR^{c1}R^{d1}$, $C(O)OR^{c1}$, $OC(O)R^{c1}$, $C(O)NH_2$, $C(O)NR^{c1}R^{d1}$, $NR^{d1}C(O)R^{c1}$, $NR^{d1}C(O)OR^{c1}$, and optionally substituted 5-6 membered heterocycloalkyl; wherein said optionally substituted 5-6 membered heterocycloalkyl is optionally substituted by 1, 2, 3, or 4 substituents independently selected from halo, OH, amino, ($C_{1-4}$ alkyl)amino-, di-($C_{1-4}$ alkyl)amino-, $C_{1-4}$ alkyl, and $C_{1-4}$ haloalkyl;

$R^{Z3}$ is $C_{1-3}$ alkyl;

$R^{Z5}$ is H, halo, or $C_{1-3}$ alkyl;

$R^{Z2}$ and $R^{Z6}$ are each independently H, cyclopropyl, or $C_{1-3}$ alkyl;

each $R^{a1}$ is independently selected from H, $C_{1-4}$ alkyl, and $C(O)R^{c1}$;

each $R^{b1}$ is independently selected from $C_{1-4}$ alkyl, $C_{1-4}$ haloalkyl, -($C_{1-4}$ alkyl)-OH, -($C_{1-4}$ alkyl)-O—P(O)(OH)$_2$, -($C_{1-4}$ alkyl)-O—P(O)($R^IR^{II}$)$_2$, -($C_{1-4}$ alkyl)-O—($C_{1-4}$ alkyl), -($C_{1-4}$ alkyl)$NR^{e1}R^{f1}$, -($C_{1-4}$ alkyl)-O—C(O)($C_{1-4}$ alkyl), and -($C_{1-4}$ alkyl)-C(O)—O—($C_{1-4}$ alkyl);

each $R^{c1}$ is independently selected from $C_{1-4}$ alkyl, $C_{1-4}$ haloalkyl, -($C_{1-4}$ alkyl)-OH, -($C_{1-4}$ alkyl)-O—P(O)(OH)$_2$, -($C_{1-4}$ alkyl)-O—P(O)($R^IR^{II}$)$_2$, -($C_{1-4}$ alkyl)-O—($C_{1-4}$ alkyl), -($C_{1-4}$ alkyl)-N($R^{e1}$)($R^{f1}$), -($C_{1-4}$ alkyl)-O—C(O)($C_{1-4}$ alkyl), and -($C_{1-4}$ alkyl)-C(O)—O—($C_{1-4}$ alkyl);

each $R^{d1}$ is independently selected from H and $C_{1-4}$ alkyl;

each $R^{e1}$ is independently selected from H, $C_{1-4}$ alkyl, —C(O)($C_{1-4}$ alkyl), —OC(O)($C_{1-4}$ alkyl), —C(O)O($C_{1-4}$ alkyl), -($C_{1-4}$ alkyl)$NH_2$, -($C_{1-4}$ alkyl) $C_{1-4}$ alkoxy, —C(O)-(optionally substituted 5-6 membered heterocycloalkyl), —C(O)($C_{1-4}$ alkyl)-(optionally substituted 5-6 membered heterocycloalkyl), —C(O)(optionally substituted 5-6 membered heteroaryl), and —C(O)($C_{1-4}$ alkyl)-(optionally substituted 5-6 membered heteroaryl), wherein the optionally substituted 5-6 membered heterocycloalkyl and optionally substituted 5-6 membered heteroaryl are each optionally substituted 1, 2, 3, or 4 substituents independently selected from halo, OH, amino, ($C_{1-4}$ alkyl)$NH_2$, ($C_{1-4}$ alkyl)amino-, di-($C_{1-4}$ alkyl)amino-, $C_{1-4}$ alkyl, $C_{1-4}$ haloalkyl, $C_{1-4}$ haloalkoxy, and $C_{1-6}$ alkoxy-;

each $R^{f1}$ is independently selected from H and $C_{1-4}$ alkyl;

$R^{g1}$ and $R^{h1}$ are each independently selected from H and $C_{1-4}$ alkyl;

or $R^{g1}$ and $R^{h1}$, taken together with the atom or atoms through which they are connected form a 5-6 membered ring; and each occurrence of $R^I$ and $R^{II}$ are independently $C_{1-6}$ alkoxy.

In some embodiments, S is a compound selected from any of the compounds in US Patent Publ. No. 20180105514, which is incorporated herein by reference in its entirety, wherein L is attached directly to any position of the one of the two bicyclic rings or through a substituent attached to a bicyclic ring. E.g., in Example 6 of US Patent Publ. No. 20180105514, L can be attached to one of the benzo[d]imidazole rings or to a substituent on the benzo[d]imidazole ring such as the $OCH_2CH_2CH_2OH$ substituent. Alternatively, L is attached directly to the one of the two pyrazole rings; or through a substituent attached to a pyrazole ring. E.g., in Example 6 of US Patent Publ. No. 20180105514, L can be attached to one of pyrazole rings or to the methyl or ethyl substituents on the pyrazole ring. In the context of L being attached to any position of the one of the two bicyclic rings, one of the two pyrazole rings, or through a substituent attached to a bicyclic rings or pyrazole rings of the compounds in US Patent Publ. No. 20180105514, L can replace any atom or acyclic moiety on the bicyclic or pyrazole ring; or any any atom or acyclic moiety on a substituent on the bicyclic or pyrazole rings.

With respect to L being attached directly to $R^4$, $R^5$, $R^6$, $R^{4\prime\prime}$, $R^{5\prime\prime}$, $R^{6\prime\prime}$, $R^{Z1}$, $R^{Z2}$, $R^{Z3}$, $R^{Z4}$, $R^{Z5}$, or $R^{Z6}$, a hydrogen atom on Ring A or Ring B or on a $R^A$ or $R^B$ is replaced by L.

In some embodiments, S has Formula (S-1b):

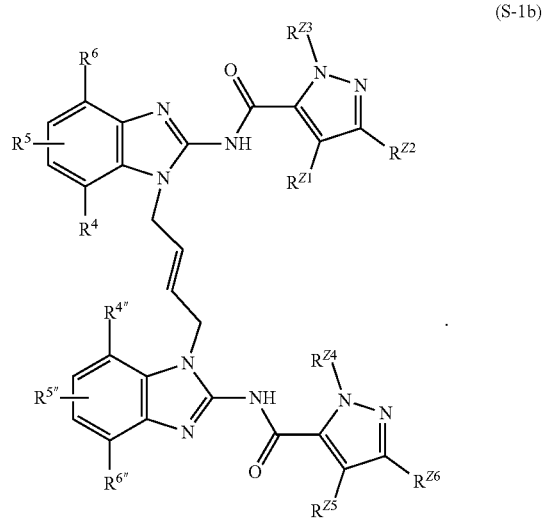

(S-1b)

In some embodiments, S has Formula (S-1b), wherein L is attached to $R^4$ or $R^{4\prime\prime}$.

In some embodiments, S has Formula (S-1b), wherein L is attached to $R^4$.

In some embodiments, S has Formula (S-1b), wherein L is attached to $R^{4\prime\prime}$.

In some embodiments, S has Formula (S-1c):

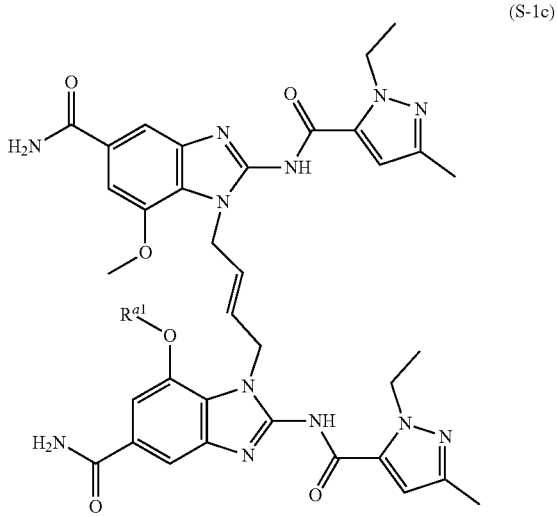

(S-1c)

wherein L is attached to $R^{a1}$.

In some embodiments, S has Formula (S-2):

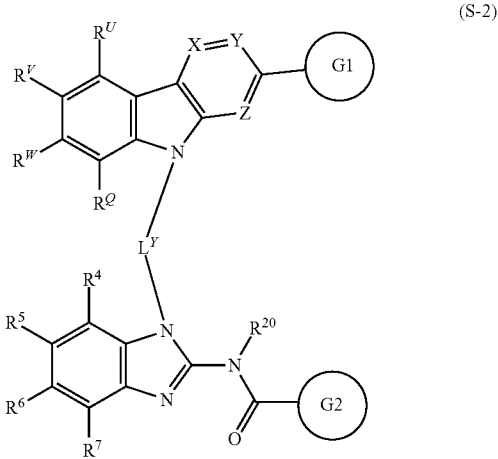

(S-2)

wherein:

L is attached to any $R^4$, $R^5$, $R^6$, $R^7$, $R^u$, $R^v$, $R^w$, RQ, $R^{G1}$ or $R^{G2}$, provided when L is attached to any of $R^4$, $R^5$, $R^6$, $R^7$, $R^u$, $R^v$, $R^w$, RQ, $R^{G1}$ or $R^{G2}$, then that $R^4$, $R^5$, $R^6$, $R^7$, $R^u$, $R^v$, $R^w$, RQ, $R^{G1}$ or $R^{G2}$ can additionally be a bond;

$R^U$, $R^V$, $R^W$, and $R^Q$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aU}$, $SR^{aU}$, $C(=O)R^{bU}$, $C(=O)NR^{cU}R^{dU}$, $C(=O)OR^{aU}$, $OC(=O)R^{bU}$, $OC(=O)NR^{cU}R^{dU}$, $NR^{cU}R^{dU}$, $NR^{cU}C(=O)R^{bU}$, $NR^{cU}C(=O)OR^{bU}$, $NR^{cU}C(=O)NR^{cU}R^{dU}$, $C(=NR^{eU})R^{bU}$, $C(=NR^{eU})NR^{cU}R^{dU}$, $NR^{cU}C(=NR^{eU})NR^{cU}R^{dU}$, $NR^{cU}S(=O)_2R^{bU}$, $NR^{cU}S(=O)_2NR^{cU}R^{dU}$, $S(=O)_2R^{bU}$, $S(=O)_2NR^{cU}R^{dU}$, $NR^{cU}S(=O)R^{bU}$, $NR^{cU}S(=O)NR^{cU}R^{dU}$, $S(=O)R^{bU}$, $S(=O)NR^{cU}R^{dU}$, and $OP(O)(OR^{fU})$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{U1}$ groups;

each $R^{aU}$, $R^{cU}$, and $R^{dU}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{U1}$ groups;

each $R^{bU}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{U1}$ groups;

each $R^{eU}$ is independently selected from H, $C_{1-4}$ alkyl, $C_{1-4}$ alkoxy, $C_{1-4}$ haloalkyl, and $C_{1-4}$ haloalkoxy;

each $R^{fU}$ is independently OH or $C_{1-6}$ alkoxy;

each $R^{U1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aU1}$, $SR^{aU1}$, $C(=O)R^{bU1}$, $C(=O)NR^{cU1}R^{dU1}$, $C(=O)OR^{aU1}$, $OC(=O)R^{bU1}$, $OC(=O)NR^{cU1}R^{dU1}$, $NR^{cU1}R^{dU1}$, $NR^{cU1}C(=O)R^{bU1}$, $NR^{cU1}C(=O)OR^{bU1}$, $NR^{cU1}C(=O)NR^{cU1}R^{dU1}$, $C(=NR^{eU1})R^{bU1}$, $C(=NR^{eU1})NR^{cU1}R^{dU1}$, $NR^{cU1}C(=NR^{eU1})NR^{cU1}R^{dU1}$, $NR^{cU1}S(=O)_2NR^{bU1}$, $NR^{cU1}S(=O)_2NR^{cU1}R^{dU1}$, $S(=O)_2R^{bU1}$, $S(=O)_2NR^{cU1}R^{dU1}$, $NR^{cU1}S(=O)R^{bU1}$, $NR^{cU1}S(=O)NR^{cU1}R^{dU1}$, $S(=O)R^{bU1}$, $S(=O)NR^{cU1}R^{dU1}$, and $OP(O)(OR^{fU1})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{aU1}$, $R^{cU1}$, and $R^{dU1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-2}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-2}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{bU1}$ is independently selected from $C_{1-6}$ alkyl, $C_{1-6}$ haloalkyl, $C_{2-6}$ alkenyl, $C_{2-6}$ alkynyl, $C_{3-2}$ cycloalkyl, phenyl, 4-7 membered heterocycloalkyl, 5-6 membered heteroaryl, $C_{3-2}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ groups;

each $R^{eU1}$ is independently selected from H, $C_{1-4}$ alkyl, $C_{1-4}$ alkoxy, $C_{1-4}$ haloalkyl, and $C_{1-4}$ haloalkoxy;

each $R^{fU1}$ is independently OH or $C_{1-6}$ alkoxy;

X is N or $CR^X$;

Y is N or $CR^Y$;

Z is N or $CR^Z$;

wherein i) X, Y and Z are $CR^X$, $CR^Y$, and $CR^Z$ respectively, or ii) only one of X, Y and Z is N, or iii) only two of X, Y and Z are N;

$R^X$, $R^Y$, and $R^Z$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a0}$, $SR^{a0}$, $C(=O)R^{b0}$, $C(=O)NR^{c0}R^{d0}$, $C(=O)OR^{a0}$, $OC(=O)R^{b0}$, $OC(=O)NR^{c0}R^{d0}$, $NR^{c0}R^{d0}$, $NR^{c0}C(=O)R^{b0}$, $NR^{c0}C(=O)OR^{b0}$, $NR^{c0}C(=O)NR^{c0}R^{d0}$, $C(=NR^{e0})R^{b0}$, $C(=NR^{e0})NR^{c0}R^{d0}$, $NR^{c0}C(=NR^{e0})NR^{c0}R^{d0}$, $NR^{c0}R^{d0}$, $NR^{c0}S(O)_2R^{b0}$, $NR^{e0}S(=O)_2NR^{c0}{}_S(=O)_2R^{b0}$, and $S(=O)_2NR^{c0}R^{d1}$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ groups;

each $R^{a0}$, $R^{c0}$, and $R^{d0}$ is independently selected from H, $C_{1-6}$ alkyl, and $C_{1-6}$ haloalkyl;

each $R^{b0}$ is independently selected from $C_{1-6}$ alkyl and $C_{1-6}$ haloalkyl;

each $R^{e0}$ is independently selected from H, $C_{1-4}$ alkyl, $C_{1-4}$ alkoxy, $C_{1-4}$ haloalkyl, and $C_{1-4}$ haloalkoxy;

Ring moiety G1 is 5-6 membered heteroaryl, which is optionally substituted by 1, 2, 3, or 4 independently selected $R^{G1}$ groups;

Ring moiety G2 is 5-6 membered heteroaryl, which is optionally substituted by 1, 2, 3, or 4 independently selected $R^{G2}$ groups;

each $R^{G1}$ and $R^{G2}$ is independently selected from halo, CN, $NO_2$, $C_{1-6}$ alkyl, $C_{2-6}$ alkenyl, $C_{2-6}$ alkynyl, $C_{1-6}$ haloalkyl, and $C_{3-7}$ cycloalkyl, wherein said $C_{1-6}$ alkyl, $C_{2-6}$ alkenyl, $C_{2-6}$ alkynyl, and $C_{3-7}$ cycloalkyl are each optionally substituted by 1, 2, 3, or 4 independently selected $R^G$ groups.

$L^Y$ is selected from -R-R-, -R-R-R-, -Cy-, -R-Cy-, -Cy-R-, and -R-Cy-R-;

each R is independently M, $C_{1-6}$ alkylene, $C_{2-6}$ alkenylene, $C_{2-6}$ alkynylene, $C_{1-6}$ alkylene-M, or M-$C_{1-6}$ alkylene, wherein each of said $C_{1-6}$ alkylene, $C_{2-6}$ alkenylene, and $C_{2-6}$ alkynylene is optionally substituted by 1, 2, 3, or 4 groups independently selected $R^G$ groups;

each Cy is independently selected from $C_{3-4}$ cycloalkyl, phenyl, 4-14 membered heterocycloalkyl, and 5-6 membered heteroaryl, each of which is optionally substituted by 1, 2, 3, or 4 independently selected $R^G$ groups;

each M is independently —O—, —S—, —C(O)—, —C(O)$NR^L$—, —C(O)O—, —OC(O)—, —OC(O)$NR^L$—, —$NR^L$—, —$NR^L$C(O)O—, —$NR^L$C(O)$NR^L$—, —$NR^L$S(O)$_2$—, —S(O)$_2$—, —S(O)$_2NR^L$—, or —$NR^L$S(O)$_2NR^L$—; provided that when M is attached to a nitrogen atom, then M is selected from —C(O)—, —C(O)$NR^L$—, —C(O)O—, —S(O)$_2$—, or —S(O)$_2NWR^L$—;

each $R^L$ is independently H or $C_{1-3}$ alkyl;

$R^{20}$ is H, $C_{1-4}$ alkyl, or $C_{1-4}$ haloalkyl;

$R^4$, $R^5$, $R^6$, and $R^7$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)OR^{b4}$, $NR^{c4}C(=O)NR^{c4}R^{d4}$, $C(=NR^{c4})NR^{c4}R^{d4}$, $NR^{c4}C(=NR^{e4})NR^{c4}R^{d4}$, $NR^{c4}S(=O)_2R^{b4}$, $NR^{c4}C(=O)_2NR^{c4}R^{d4}$, $S(=O)_2R^{b4}$, $S(=O)_2NR^{c4}R^{d4}$, and $OP(O)(OR^{f4})$, wherein said $C_{1-6}$ alkyl, $C_{2-6}$ alkenyl, $C_{2-6}$ alkynyl $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{4A}$ groups;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{4A}$ groups;

each $R^{b4}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{4A}$ groups;

each $R^{e4}$ is independently selected from H, $C_{1-4}$ alkyl, $C_{1-4}$ alkoxy, $C_{1-4}$ haloalkyl, and $C_{1-4}$ haloalkoxy;

each $R^{f4}$ is independently OH or $C_{1-6}$ alkoxy;

each $R^{4A}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a41}$, $SR^{a41}$, $C(=O)R^{b41}$, $C(=O)NR^{c41}R^{d41}$, $C(=O)OR^{a41}$, $OC(=O)R^{b41}$, $OC(=O)NR^{c41}R^{d41}$, $NR^{c41}R^{d41}$, $NR^{c41}C(=O)R^{b41}$, $NR^{c1}C(=O)OR^{b41}$, $NR^{c1}C(=O)NR^{c41}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}S(=O)_2R^{b41}$, $NR^{c41}S(=O)_2NR^{c41}R^{d41}$, $S(=O)_2R^{b41}$, $S(=O)_2NR^{c41}R^{d41}$, and $OP(O)(OR^{f41})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{4B}$ groups;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ groups;

each $R^{b41}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4B}$ groups;

each $R^{e41}$ is independently selected from H, $C_{1-4}$ alkyl, $C_{1-4}$ alkoxy, $C_{1-4}$ haloalkyl, and $C_{1-4}$ haloalkoxy;

each $R^{f41}$ is independently OH or $C_{1-6}$ alkoxy;

each $R^{4B}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a42}$, $SR^{a42}$, $C(=O)R^{b42}$, $C(=O)NR^{c42}d^{d42}$, $C(=O)OR^{a42}$, $OC(=O)R^{b42}$, $OC(=O)NR^{c42}R^{d42}$, $NR^{c42}R^{d42}$, $NR^{c42}C(=O)R^{b42}$, $NR^{c42}C(=O)OR^{b42}$, $NR^{c42}C(=O)NR^{c42}R^{d42}$, $C(=NR^{e42})R^{b42}$, $C(=NR^{e42})NR^{c42}R^{d42}$, $NR^{c42}C(=NR^{e42})NR^{c42}R^{d42}$, $NR^{c42}S(=O)_{2l\ R}^{b42}$, $NR^{c42}S(=O)_2NR^{c42}R^{d42}$, $S(=O)_2R^{b42}$, $S(=O)_2NR^{c42}R^{d42}$, and $OP(O)(OR^{f42})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b42}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ groups;

each $R^{e42}$ is independently selected from H, $C_{1-4}$ alkyl, $C_{1-4}$ alkoxy, $C_{1-4}$ haloalkyl, and $C_{1-4}$ haloalkoxy;

each $R^{f42}$ is independently OH or $C_{1-6}$ alkoxy; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments:

$R^U$ is H, halo, CN, $C_{1-6}$ alkyl, $C_{1-6}$ haloalkyl, $OR^{aU}$, or $C(=O)NR^{cU}R^{dU}$;

$R^V$ is H, halo, CN, $C_{1-6}$ alkyl, $C_{1-6}$ haloalkyl, $OR^{aU}$, or $C(=O)NR^{cU}R^{dU}$;

$R^W$ is H, halo, CN, $C_{1-6}$ alkyl, $C_{1-6}$ haloalkyl, $OR^{aU}$, or $C(=O)NR^{cU}R^{dU}$;

$R^Q$ is H, halo, CN, $C_{1-6}$ alkyl, $C_{1-6}$ haloalkyl, $OR^{aU}$, or $C(=O)NR^{cU}R^{dU}$;

$R^{aU}$ is selected from H, $C_{1-6}$ alkyl, $C_{1-6}$ haloalkyl, $C_{2-6}$ alkenyl, and $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{U1}$ groups;

$R^{cU}$ and $R^{dU}$ are each independently selected from H, $C_{1-6}$ alkyl, and $C_{1-6}$ haloalkyl;

each $R^{U1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $OR^{aU1}$, $SR^{aU1}$, $C(=O)R^{bU1}$, $C(=O)NR^{cU1}R^{dU1}$, $C(=O)OR^{aU1}$, $OC(=O)R^{bU1}$, $OC(=O)NR^{cU1}R^{du1}$, $NR^{cU1}R^{dU1}$, $NR^{cU1}C(=O)R^{bU1}$, $NR^{cU1}C(=O)OR^{bU1}$, $NR^{cU1}C(=O)NR^{cU1}R^{dU1}$, $NR^{cU1}S(=O)_2R^{bU1}$, $NR^{cU1}S(=O)_2NR^{cU1}R^{dU1}$, $S(=O)_2R^{bU1}$, $S(=O)^2NR^{cU1}R^{dU1}$, and $OP(O)(OR^{fU1})$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ groups;

each $R^{aU1}$, $R^{cU1}$, and $R^{dU1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^G$ groups;

each $R^{bU1}$ is independently selected from $C_{1-6}$ alkyl and $C_{1-6}$ haloalkyl, which are each optionally substituted with 1, 2, 3, or 4 independently selected $R^G$ groups;

each $R^{fU1}$ is independently OH or $C_{1-6}$ alkoxy;

X is $CR^X$;

Y is $CR^Y$ or N;

Z is $CR^Z$ or N;

$R^X$, $R^Y$, and $R^Z$ are each independently selected from H, D, halo, CN, $C_{1-6}$ alkyl, and $C_{1-6}$ haloalkyl;

$R^{20}$ is H;

each $R^4$, $R^5$, $R^6$, and $R^7$ are independently selected from H, halo, CN, $C_{1-6}$ alkyl, $C_{1-6}$ haloalkyl, $OR^{a4}$, amino, $C_{1-6}$ alkylamino, di($C_{1-6}$ alkyl)amino, carbamyl, $C_{1-6}$ alkylcarbamyl, and di($C_{1-6}$ alkyl)carbamyl;

$R^{a4}$ is selected from H, $C_{1-6}$ alkyl, $C_{1-6}$ haloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1 or 2 independently selected $R^{4A}$ groups;

each $R^{4A}$ is independently selected from CN, halo, $C_{1-6}$ alkyl, $C_{2-6}$ alkenyl, $C_{2-6}$ alkynyl, $C_{1-6}$ haloalkyl, $OR^{a41}$, $C(=O)R^{b41}$, $C(=O)NR^{c41}R^{d41}$, $C(=O)OR^{a41}$, $OC(=O)R^{b41}$, $OC(=O)NR^{c41}R^{d41}$, $NR^{c41}R^{d41}$, $NR^{c41}C(=O)R^{b41}$, $NR^{c41}C(=O)OR^{b41}$, $NR^{c41}C(=O)NR^{c41}R^{d41}$, $NR^{c41}S(=O)_2R^{b41}$, $NR^{c41}S(=O)_2NR^{c41}R^{d41}$, and $S(=O)_2R^{b41}$;

each $R^{a41}$, $R^{c41}$, and $R^{d41}$ independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1 or 2 independently selected $R^{4B}$ groups;

each $R^{b41}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, 3, or 4 independently selected $R^{4B}$ groups;

each $R^{4B}$ is independently selected from $C_{1-3}$ alkyl and $C_{1-3}$ haloalkyl;

Ring moiety G1 is a pyrazole ring, which is optionally substituted by 1, 2, 3, or 4 independently selected $R^{G1}$ groups;

Ring moiety G2 is a pyrazole ring, which is optionally substituted by 1, 2, 3, or 4 independently selected $R^{G2}$ groups;

each $R^{G1}$ is independently selected from halo, CN, $C_{1-6}$ alkyl, and $C_{1-6}$ haloalkyl;

each $R^{G2}$ is independently selected from halo, CN, $C_{1-6}$ alkyl, and $C_{1-6}$ haloalkyl; and $L^Y$ is —$CH_2$—CH=CH—$CH_2$—.

In some embodiments:

$R^U$ is H, halo, CN, $C_{1-6}$ alkyl, $C_{1-6}$ haloalkyl, $OR^{aU}$, or $C(=O)NR^{cU}R^{dU}$;

$R^V$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^W$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^Q$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^{aU}$ is selected from H, $C_{1-6}$ alkyl, $C_{1-6}$ haloalkyl, $C_{2-6}$ alkenyl, and $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{U1}$ groups;

each $R^{U1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $OR^{aU1}$, $SR^{aU1}$, $C(=O)R^{bU1}$, $C(=O)NR^{cU1}R^{dU1}$, $C(=O)OR^{aU1}$, $OC(=O)R^{bU1}$, $OC(=O)NR^{cU1}R^{dU1}$, $NR^{cU1}R^{dU1}$, $NR^{cU1}C(=O)R^{bU1}$, $NR^{cU1}C(=O)OR^{bU1}$, $NR^{cU1}C(=O)NR^{cU1}R^{dU1}$, $NR^{cU1}S(=O)_2R^{bU1}$, $NR^{cU1}S(=O)_2NR^{cU1}R^{dU1}$, $S(=O)_2R^{bU1}$, $S(=O)_{2N}R^{cU1}R^{dU1}$, and $OP(O)(OR^{fU1})$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ groups;

each $R^{aU1}$, $R^{cU1}$, and $R^{dU1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^G$ groups;

each $R^{bU1}$ is independently selected from $C_{1-6}$ alkyl and $C_{1-6}$ haloalkyl, which are each optionally substituted with 1, 2, 3, or 4 independently selected $R^G$ groups;

each $R^{fU1}$ is independently OH or $C_{1-6}$ alkoxy;

X is $CR^X$;

Y is N;

Z is N;

$R^X$ is selected from H, $C_{1-6}$ alkyl, and $C_{1-6}$ haloalkyl;

$R^{20}$ is H;

$R^4$ is H, halo, CN, $C_{1-6}$ alkyl, $C_{1-6}$ haloalkyl, $OR^{a4}$, carbamyl, $C_{1-6}$ alkylcarbamyl, and di($C_{1-6}$ alkyl)carbamyl;

$R^5$, $R^6$, and $R^7$ are independently selected from H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^{a4}$ is selected from H, $C_{1-6}$ alkyl, $C_{1-6}$ haloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1 or 2 independently selected $R^{4A}$ groups;

each $R^{4A}$ is independently selected from CN, halo, $C_{1-6}$ alkyl, $C_{2-6}$ alkenyl, $C_{2-6}$ alkynyl, $C_{1-6}$ haloalkyl, $OR^{a41}$, $C(=O)R^{b41}$, $C(=O)NR^{c41}R^{d41}$, $C(=O)OR^{a41}$, $OC(=O)R^{b41}$, $OC(=O)NR^{c41}R^{d41}$, $NR^{c41}R^{d41}$, $NR^{c41}C(=O)R^{b41}$, $NR^{c41}C(=O)OR^{b41}$, $NR^{c41}C(=O)NR^{c41}R^{d41}$, $NR^{c41}S(=O)_2R^{b41}$, $NR^{c41}S(=O)_2NR^{c41}R^{d41}$, and $S(=O)_2R^{b41}$;

each $R^{a41}$, $R^{c41}$, and $R^{d41}$ independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1 or 2 independently selected $R^{4B}$ groups;

each $R^{b41}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, 3, or 4 independently selected $R^{4B}$ groups;

each $R^{4B}$ is independently selected from $C_{1-3}$ alkyl and $C_{1-3}$ haloalkyl;

Ring moiety G1 is a pyrazole ring, which is optionally substituted by 1 or 2 independently selected $R^{G1}$ groups;

Ring moiety G2 is a pyrazole ring, which is optionally substituted by 1 or 2 independently selected $R^{G2}$ groups;

each $R^{G1}$ is independently selected from $C_{1-6}$ alkyl and $C_{1-6}$ haloalkyl;

each $R^{G2}$ is independently selected from $C_{1-6}$ alkyl and $C_{1-6}$ haloalkyl; and $L^Y$ is $C_{2-8}$ alkenylene;

In some embodiments:

$R^U$ is $OR^{aU}$;

$R^V$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^W$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^Q$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^{aU}$ is $C_{1-6}$ alkyl, wherein said $C_{1-6}$ alkyl is optionally substituted with 1 or 2 independently selected $R^{U1}$ groups;

each $R^{U1}$ is independently selected from H, halo, CN, and $OR^{aU1}$;

each $R^{aU1}$ is independently selected from H and $C_{1-6}$ alkyl;

X is $CR^X$;

Y is N;

Z is N;

$R^X$ is selected from H, $C_{1-3}$ alkyl, and $C_{1-3}$ haloalkyl;

$R^{20}$ is H;

$R^4$ is $OR^{a4}$;

$R^5$, $R^6$, and $R^7$ are independently selected from H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^{a4}$ is selected from $C_{1-6}$ alkyl, wherein said $C_{1-6}$ alkyl is optionally substituted with 1 or 2 independently selected $R^{4A}$ groups;

each $R^{4A}$ is independently selected from CN, halo, and $OR^{a41}$;

each $R^{a41}$ is independently selected from H and $C_{1-6}$ alkyl;

Ring moiety G1 is a pyrazole ring, which is optionally substituted by 1 or 2 independently selected $R^{G1}$ groups;

Ring moiety G2 is a pyrazole ring, which is optionally substituted by 1 or 2 independently selected $R^{G2}$ groups;

each $R^{G1}$ is independently selected from $C_{1-3}$ alkyl and $C_{1-3}$ haloalkyl;

each $R^{G2}$ is independently selected from $C_{1-3}$ alkyl and $C_{1-3}$ haloalkyl; and $L^Y$ is —$CH_2$—CH=CH—$CH_2$—.

In some embodiments, at least one of $R^4$, $R^5$, $R^6$, $R^7$, $R^U$, $R^V$, $R^W$, or $R^Q$ is $C(O)NH_2$.

In some embodiments, G1 is 5-membered heteroaryl, which is optionally substituted by 1 or 2 independently selected $R^{G1}$ groups. In some embodiments, G1 is a pyrazole ring, which is optionally substituted by 1, 2, 3, or 4 independently selected $R^{G1}$ substituents. In some embodiments, G1 is a pyrazole ring, which is optionally substituted by 1 or 2 independently selected $R^{G1}$ substituents. In some embodiments, each $R^{G1}$ is independently selected from halo, CN, $C_{1-6}$ alkyl, and $C_{1-6}$ haloalkyl.

In some embodiments, G2 is 5-membered heteroaryl, which is optionally substituted by 1 or 2 independently selected $R^{G2}$ groups. In some embodiments, G2 is a pyrazole ring, which is optionally substituted by 1, 2, 3, or 4 independently selected $R^{G2}$ substituents. In some embodiments, G2 is a pyrazole ring, which is optionally substituted by 1 or 2 independently selected $R^{G2}$ substituents. In some embodiments, each $R^{G2}$ is independently selected from halo, CN, $C_{1-6}$ alkyl, and $C_{1-6}$ haloalkyl.

In some embodiments, $R^{20}$ is H.

In some embodiments, $L^Y$ is $C_{1-4}$ alkylene-$NR^L$-$C_{1-4}$ alkylene, $C_{1-4}$ alkylene-O-$C_{1-4}$ alkylene, $C_{1-6}$ alkylene or $C_{2-6}$ alkenylene, wherein said $C_{1-6}$ alkylene or $C_{2-4}$ alkylene groups are substituted with 1, 2, 3, or 4 substituents independently selected from halo, OH, and $C_{1-4}$ alkoxy.

In some embodiments, $L^Y$ is $C_{1-6}$ alkylene or $C_{2-6}$ alkenylene.

In some embodiments, $L^Y$ is $C_{2-8}$ alkenylene.

In some embodiments, $L^Y$ is $C_{2-6}$ alkenylene.

In some embodiments, $L^Y$ is —CH$_2$—CH=CH—CH$_2$—.

In some embodiments:
$R^U$ is H, halo, CN, $C_{1-6}$ alkyl, $C_{1-6}$ haloalkyl, $OR^{aU}$, or $C(=O)NR^{cU}R^{dU}$;

$R^V$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^W$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^Q$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^{aU}$ is selected from H, $C_{1-6}$ alkyl, $C_{1-6}$ haloalkyl, $C_{2-6}$ alkenyl, and $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{U1}$ groups;

each $R^{U1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $OR^{aU1}$, $SR^{aU1}$, $C(=O)R^{bU1}$, $C(=O)NR^{cU1}R^{dU1}$, $C(=O)OR^{aU1}$, $OC(=O)R^{bU1}$, $OC(=O)NR^{cU1}R^{dU1}$, $NR^{cU1}R^{dU1}$, $NR^{cU1}C(=O)R^{bU1}$, $NR^{cU1}C(=O)OR^{bU1}$, $NR^{cU1}C(=O)NR^{cU1}R^{dU1}$, $NR^{cU1}S(=O)_2R^{bU1}$, $NR^{cU1}S(=O)_2NR^{cU1}R^{dU1}$, $S(=O)_2R^{bU1}$, $S(=O)_{2N}R^{cU1}R^{dU1}$, and $OP(O)(OR^{fU1})$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ groups;

each $R^{aU1}$, $R^{cU1}$, and $R^{dU1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^G$ groups;

each $R^{bU1}$ is independently selected from $C_{1-6}$ alkyl and $C_{1-6}$ haloalkyl, which are each optionally substituted with 1, 2, 3, or 4 independently selected $R^G$ groups;

each $R^{fU1}$ is independently OH or $C_{1-6}$ alkoxy.

In some embodiments:
$R^U$ is $OR^{aU}$;

$R^V$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^W$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^Q$ is H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^{aU}$ is $C_{1-6}$ alkyl, wherein said $C_{1-6}$ alkyl is optionally substituted with 1 or 2 independently selected $R^{U1}$ groups;

each $R^{U1}$ is independently selected from H, halo, CN, and $OR^{aU1}$; and each $R^{aU1}$ is independently selected from H and $C_{1-6}$ alkyl.

In some embodiments:
$R^4$ is H, halo, CN, $C_{1-6}$ alkyl, $C_{1-6}$ haloalkyl, $OR^{a4}$, carbamyl, $C_{1-6}$ alkylcarbamyl, and di($C_{1-6}$ alkyl)carbamyl;

$R^5$, $R^6$, and $R^7$ are independently selected from H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^{a4}$ is selected from H, $C_{1-6}$ alkyl, $C_{1-6}$ haloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1 or 2 independently selected $R^{44}$ groups;

each $R^{44}$ is independently selected from CN, halo, $C_{1-6}$ alkyl, $C_{2-6}$ alkenyl, $C_{2-6}$ alkynyl, $C_{1-6}$ haloalkyl, $OR^{a41}$, $C(=O)R^{b41}$, $C(=O)NR^{c41}R^{d41}$, $C(=O)OR^{a41}$, $OC(=O)R^{b41}$, $OC(=O)NR^{c41}R^{d41}$, $NR^{c41}R^{d41}$, $NR^{c41}C(=O)R^{b41}$, $NR^{c41}C(=O)OR^{b41}$, $NR^{c41}C(=O)NR^{c41}R^{d41}$, $NR^{c41}S(=O)_2R^{b41}$, $NR^{c41}S(=O)_2NR^{c41}R^{d41}$, and $S(=O)_2R^{b41}$;

each $R^{a41}$, $R^{c41}$, and $R^{d41}$ independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1 or 2 independently selected $R^{4B}$ groups;

each $R^{b41}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, 3, or 4 independently selected $R^{4B}$ groups; and each $R^{4B}$ is independently selected from $C_{1-3}$ alkyl and $C_{1-3}$ haloalkyl.

In some embodiments:
$R^4$ is $OR^{a4}$;

$R^5$, $R^6$, and $R^7$ are independently selected from H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

$R^{a4}$ is selected from $C_{1-6}$ alkyl, wherein said $C_{1-6}$ alkyl is optionally substituted with 1 or 2 independently selected $R^{44}$ groups;

each $R^{44}$ is independently selected from CN, halo, and $OR^{a41}$; and each $R^{a41}$ is independently selected from H and $C_{1-6}$ alkyl.

In the context of L being attached to any $R^4$, $R^5$, $R^6$, $R^7$, $R^U$, $R^V$, $R^W$, $R^Q$, $R^{G1}$, or $R^{G2}$, a hydrogen atom on $R^4$, $R^5$, $R^6$, $R^7$, $R^U$, $R^V$, $R^W$, $R^Q$, $R^{G1}$ or $R^{G2}$ is removed and replaced by L.

In some embodiments, L is attached to $R^4$ or $R^Q$.

In some embodiments, L is attached to $R^4$.

In some embodiments, L is attached to $R^Q$.

53

In some embodiments, S has Formula (S-2aa):

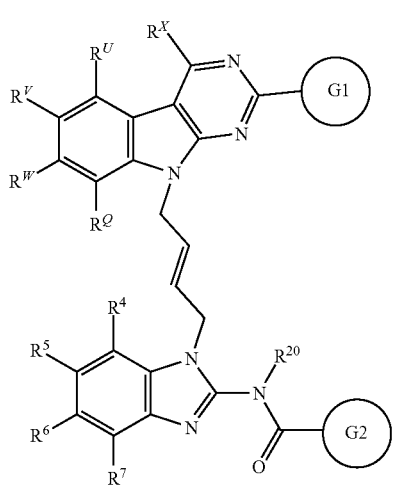

(S-2aa)

or a pharmaceutically acceptable salt thereof.

In some embodiments, S has Formula (S-2aa), wherein L is attached to $R^4$ or $R^Q$.

In some embodiments, S has Formula (S-2aa), wherein L is attached to $R^4$.

In some embodiments, S has Formula (S-2aa), wherein L is attached to $R^Q$.

In some embodiments, S has Formula (S-2a):

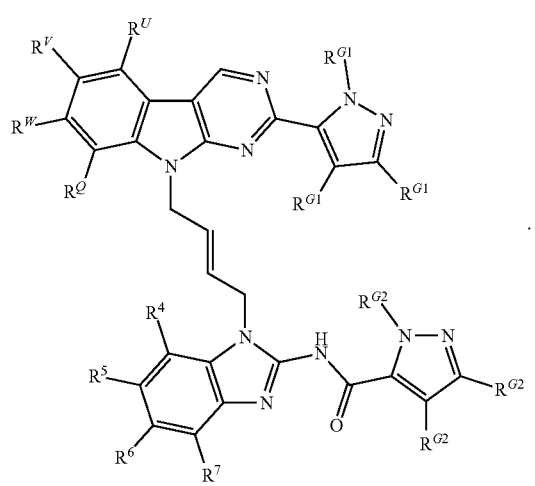

(S-2a)

In some embodiments, S has Formula (S-2a), wherein L is attached to $R^4$ or $R^Q$.

In some embodiments, S has Formula (S-2a), wherein L is attached to $R^4$.

In some embodiments, S has Formula (S-2a), wherein L is attached to $R^Q$.

54

In some embodiments, S has Formula (S-2b):

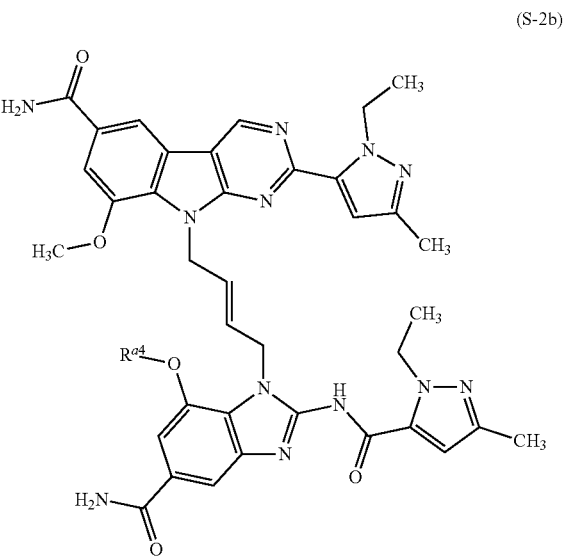

(S-2b)

wherein L is attached to $R^{a4}$.

In some embodiments, S is a compound selected from any of the compounds or formulae in U.S. application Ser. No. 16/421,881, which is incorporated herein by reference in its entirety, wherein L is attached directly to any position of the tricyclic ring or the bicyclic ring; or through a substituent attached to the tricyclic ring or the bicyclic ring. In some embodiments, S is a compound of the Examples S1-S28 and S32-S64, wherein L is attached directly to any position of the tricyclic ring or the bicyclic ring; or through a substituent attached to the tricyclic ring or the bicyclic ring. Alternatively, L is attached directly to the one of two pyrazole rings; or through a substituent attached to one of the pyrazole rings. In attaching L to the S moiety in Examples S1-S28 and S32-S64, L replaces any atom or acyclic moiety on the tricyclic ring, the bicyclic or the pyrazole ring; or any atom or acyclic moiety on a substituent on the tricyclic ring, the bicyclic or the pyrazole ring.

In another embodiment, S has Formula (S-3):

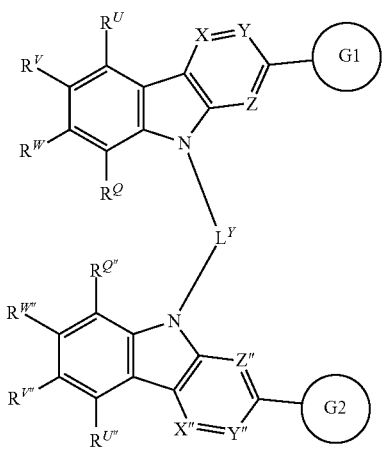

(S-3)

wherein:

L is attached to any $R^U$, $R^V$, $R^W$, $R^Q$, $R^{U''}$, $R^{V''}$, $R^{W''}$, $R^{Q''}$, $R^{G1}$ or $R^{G2}$, provided that when L is attached to any of $R^U$, $R^V$, $R^W$, $R^Q$, $R^{U''}$, $R^{V''}$, $R^{W''}$, $R^{Q''}$, $R^{G1}$ or $R^{G2}$, then the corresponding position can additionally be a bond;

$R^U$, $R^V$, $R^W$, and $R^Q$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aU}$, $SR^{aU}$, $C(=O)R^{bU}$, $C(=O)NR^{cU}R^{dU}$, $C(=O)OR^{aU}$, $OC(=O)R^{bU}$, $OC(=O)NR^{cU}R^{dU}$, $NR^{cU}R^{dU}$, $NR^{cU}C(=O)R^{bU}$, $NR^{cU}C(=O)OR^{bU}$, $NR^{cU}C(=O)NR^{cU}R^{dU}$, $C(=NR^{eU})R^{bU}$, $C(=NR^{eU})NR^{cU}R^{dU}$, $NR^{cU}C(=NR^{eU})NR^{cU}R^{dU}$, $NR^{cU}S(=O)_2R^{bU}$, $NR^{cU}S(=O)_2NR^{cU}R^{dU}$, $S(=O)_2R^{bU}$, $S(=O)_2NR^{cU}R^{dU}$, $NR^{cU}S(=O)R^{bU}$, $NR^{cU}S(=O)NR^{cU}R^{dU}$, $S(=O)R^{bU}$, $S(=O)NR^{cU}R^{dU}$, and $OP(O)(OR^{fU})$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{U1}$ groups;

$R^{U''}$, $R^{V''}$, $R^{W''}$, and $R^{Q''}$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aQ}$, $SR^{aQ}$, $C(=O)R^{bQ}$, $C(=O)NR^{cQ}R^{dQ}$, $C(=O)OR^{aQ}$, $OC(=O)R^{bQ}$, $OC(=O)NR^{cQ}R^{dQ}$, $NR^{cQ}R^{dQ}$, $NR^{cQ}C(=O)R^{bQ}$, $NR^{cQ}C(=O)OR^{bQ}$, $NR^{cQ}C(=O)NR^{cQ}R^{dQ}$, $C(=NR^{eQ})R^{bQ}$, $C(=NR^{eQ})NR^{cQ}R^{dQ}$, $NR^{cQ}C(=NR^{eQ})NR^{cQ}R^{dQ}$, $NR^{cQ}S(=O)_2R^{bQ}$, $NR^{cQ}S(=O)_2NR^{cQ}R^{dQ}$, $S(=O)_2R^{bQ}$, $S(=O)_2NR^{eQ}R^{dQ}$, $NR^{cQ}S(=O)R^{bQ}$, $NR^{cQ}S(=O)NR^{cQ}R^{dQ}$, $S(=O)R^{bQ}$, $S(=O)NR^{cQ}R^{dQ}$, and $OP(O)(OR^{fQ})$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{Q1}$ groups;

each $R^{aU}$, $R^{cU}$, and $R^{dU}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{U1}$ groups;

each $R^{bU}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{U1}$ groups;

each $R^{eU}$ is independently selected from H, $C_{1-4}$ alkyl, $C_{1-4}$ alkoxy, $C_{1-4}$ haloalkyl, and $C_{1-4}$ haloalkoxy;

each $R^{fU}$ is independently OH or $C_{1-6}$ alkoxy;

each $R^{aQ}$, $R^{cQ}$, and $R^{dQ}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{Q1}$ groups;

each $R^{bQ}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{Q1}$ groups;

each $R^{eQ}$ is independently selected from H, $C_{1-4}$ alkyl, $C_{1-4}$ alkoxy, $C_{1-4}$ haloalkyl, and $C_{1-4}$ haloalkoxy;

each $R^{fQ}$ is independently OH or $C_{1-6}$ alkoxy;

each $R^{U1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aU1}$, $SR^{aU1}$, $C(=O)R^{bU1}$, $C(=O)NR^{eU1}R^{dU1}$, $C(=O)OR^{aU1}$, $OC(=O)R^{bU1}$, $OC(=O)NR^{eU1}R^{dU1}$, $NR^{eU1}R^{dU1}$, $NR^{eU1}C(=O)R^{bU1}$, $NR^{eU1}C(=O)OR^{bU1}$, $NR^{eU1}C(=O)NR^{eU1}R^{dU1}$, $C(=NR^{eU1})R^{bU1}$, $C(=NR^{eU1})NR^{eU1}R^{dU1}$, $NR^{eU1}C(=NR^{eU1})NR^{eU1}R^{dU1}$, $NR^{eU1}S(=O)_2R^{bU1}$, $NR^{eU1}S(=O)_2NR^{eU1}R^{dU1}$, $S(=O)_2R^{bU1}$, $S(=O)_2NR^{eU1}R^{dU1}$, $NR^{eU1}S(=O)R^{bU1}$, $NR^{eU1}S(=O)NR^{eU1}R^{dU1}$, $S(=O)R^{bU1}$, $S(=O)NR^{eU1}R^{dU1}$, and $OP(O)(OR^{fU1})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{U2}$ groups;

each $R^{Q1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aQ1}$, $SR^{aQ1}$, $C(=O)R^{bQ1}$, $C(=O)NR^{cQ1}R^{dQ1}$, $C(=O)OR^{aQ1}$, $OC(=O)R^{bQ1}$, $OC(=O)NR^{cQ1}R^{dQ1}$, $NR^{cQ1}R^{dQ1}$, $NR^{cQ1}C(=O)R^{bQ1}$, $NR^{cQ1}C(=O)OR^{bQ1}$, $NR^{cQ1}C(=O)NR^{cQ1}R^{dQ1}$, $C(=NR^{eQ1})R^{bQ1}$, $C(=NR^{eQ1})NR^{cQ1}R^{dQ1}$, $NR^{cQ1}C(=NR^{eQ1})NR^{cQ1}R^{dQ1}$, $NR^{cQ1}S(=O)_2R^{bQ1}$, $NR^{cQ1}S(=O)_2NR^{cQ1}R^{dQ1}$, $S(=O)_2R^{bQ1}$, $S(=O)_2NR^{cQ1}R^{dQ1}$, $NR^{cQ11}S(=O)R^{bQ1}$, $NR^{cQ1}S(=O)NR^{cQ1}R^{dQ1}$, $S(=O)R^{bQ1}$, $S(=O)NR^{cQ1}R^{dQ1}$, and $OP(O)(OR^{fQ1})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{Q2}$ groups;

each $R^{aU1}$, $R^{cU1}$, and $R^{dU1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{U2}$ groups;

each $R^{bU1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein which are each optionally substituted with 1, 2, 3, or 4 independently selected $R^{U2}$ groups;

each $R^{eU1}$ is independently selected from H, $C_{1-4}$ alkyl, $C_{1-4}$ alkoxy, $C_{1-4}$ haloalkyl, and $C_{1-4}$ haloalkoxy;

each $R^{fU1}$ is independently OH or $C_{1-6}$ alkoxy;

each $R^{aQ1}$, $R^{cQ1}$, and $R^{dQ1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{Q2}$ groups;

each $R^{bQ1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{Q2}$ groups;

each $R^{eQ1}$ is independently selected from H, $C_{1-4}$ alkyl, $C_{1-4}$ alkoxy, $C_{1-4}$ haloalkyl, and $C_{1-4}$ haloalkoxy;

each $R^{fQ1}$ is independently OH or $C_{1-6}$ alkoxy;

each $R^{U2}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-2}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aU2}$, $SR^{aU2}$, $C(=O)R^{bU2}$, $C(=O)NR^{cU2}R^{dU2}$, $C(=O)OR^{aU2}$, $OC(=O)R^{bU2}$, $OC(=O)NR^{cU2}R^{dU2}$, $NR^{cU2}R^{dU2}$, $NR^{cU2}C(=O)R^{bU2}$, $NR^{cU2}C(=O)OR^{bU2}$, $NR^{cU2}C(=O)NR^{cU2}R^{dU2}$, $C(=NR^{eU2})R^{bU2}$, $C(=NR^{eU2})NR^{cU2}R^{dU2}$, $NR^{cU2}C(=NR^{eU2})NR^{cU2}R^{dU2}$, $NR^{cU1}S(=O)_2R^{bU2}$, $NR^{eU1}S(=O)_2NR^{cU2}R^{dU2}$, $S(=O)_2R^{bU2}$, $S(=O)_2NR^{cU2}R^{dU2}$, $NR^{cU2}S(=O)R^{bU2}$, $NR^{cu2}S(=O)NR^{cU2}R^{dU2}$, $S(=O)R^{bU2}$, $S(=O)NR^{cU2}R^{dU2}$, and $OP(O)(OR^{fU2})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-2}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{Q2}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aQ2}$, $SR^{aQ2}$, $C(=O)R^{bQ2}$, $C(=O)NR^{cQ2}R^{dQ2}$, $C(=O)OR^{aQ2}$, $OC(=O)R^{bQ2}$, $OC(=O)NR^{cQ2}R^{dQ2}$, $NR^{cQ2}R^{dQ2}$, $NR^{cQ2}C(=O)R^{bQ2}$, $NR^{cQ2}C(=O)OR^{bQ2}$, $NR^{cQ2}C(=O)NR^{cQ2}R^{dQ2}$, $C(=NR^{eQ2})R^{bQ2}$, $C(=NR^{eQ2})NR^{cQ2}R^{dQ2}$, $NR^{cQ2}C(=NR^{eQ2})NR^{cQ2}R^{dQ2}$, $NR^{cQ2}S(=O)_2R^{bQ2}$, $NR^{eQ2}S(=O)_2NR^{cQ2}R^{dQ2}$, $S(=O)_2R^{bQ2}$, $S(=O)_2NR^{cQ2}R^{dQ2}$, $NR^{eQ2}S(=O)R^{bQ2}$, $NR^{cQ2}S(=O)NR^{cQ2}R^{dQ2}$, $S(=O)R^{bQ2}$, $S(=O)NR^{cQ2}R^{dQ2}$, and $OP(O)(OR^{fQ2})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{aU2}$, $R^{cU2}$, and $R^{dU2}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-2}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{bU2}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ groups;

each $R^{eU2}$ is independently selected from H, $C_{1-4}$ alkyl, $C_{1-4}$ alkoxy, $C_{1-4}$ haloalkyl, and $C_{1-4}$ haloalkoxy;

each $R^{fU2}$ is independently OH or $C_{1-6}$ alkoxy;

each $R^{aQ2}$, $R^{eQ2}$, and $R^{dQ2}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{bQ2}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ groups;

each $R^{eQ2}$ is independently selected from H, $C_{1-4}$ alkyl, $C_{1-4}$ alkoxy, $C_{1-4}$ haloalkyl, and $C_{1-4}$ haloalkoxy;

each $R^{fQ2}$ is independently OH or $C_{1-6}$ alkoxy;

X is N or $CR^X$;

Y is N or $CR^Y$;

Z is N or $CR^Z$;

wherein i) X, Y and Z are $CR^X$, $CR^Y$, and $CR^Z$ respectively, or ii) only one of X, Y and Z is N, or iii) only two of X, Y and Z are N;

X" is N or $CR^{X"}$;

Y" is N or $CR^{Y"}$;

Z" is N or $CR^{Z"}$;

wherein i) X", Y" and Z" are $CR^{X"}$, $CR^{Y"}$, and $CR^{Z"}$ respectively, or ii) only one of X", Y" and Z" is N, or iii) only two of X", Y" and Z" are N;

$R^X$, $R^Y$, $R^Z$, $R^{X''}$, $R^{Y''}$, and $R^{Z''}$ are each independently selected from H, D, halo, CN, NO$_2$, C$_{1-6}$ alkyl, C$_{2-6}$ alkenyl, C$_{2-6}$ alkynyl, C$_{1-6}$ haloalkyl, OR$^{a0}$, SR$^{a0}$, C(=O)R$^{b0}$, C(=O)NR$^{c0}$R$^{d0}$, C(=O)OR$^{a0}$, OC(=O)R$^{b0}$, OC(=O)NR$^{c0}$R$^{d0}$, NR$^{c0}$R$^{d0}$, NR$^{c0}$C(=O)R$^{b0}$, NR$^{c0}$C(=O)OR$^{b0}$, NR$^{c0}$C(=O)NR$^{c0}$R$^{d0}$, C(=NR$^{e0}$)R$^{b0}$, C(=NR$^{e0}$)NR$^{c0}$R$^{d0}$, NR$^{c0}$C(=NR$^{e0}$)NR$^{c0}$R$^{d0}$, NR$^{c0}$S(=O)$_2$R$^{b0}$, NR$^{c0}$S(=O)$_2$NR$^{c0}$R$^{d0}$, S(=O)$_2$R$^{b0}$, and S(=O)$_2$NR$^{c0}$R$^{d0}$, wherein said C$_{1-6}$ alkyl, C$_{2-6}$ alkenyl, C$_{2-6}$ alkynyl, and C$_{1-6}$ haloalkyl are each optionally substituted by 1, 2, 3, or 4 independently selected R$^G$ groups;

each $R^{a0}$, $R^{c0}$, and $R^{d0}$ is independently selected from H, C$_{1-6}$ alkyl, and C$_{1-6}$ haloalkyl;

each $R^{b0}$ is independently selected from C$_{1-6}$ alkyl and C$_{1-6}$ haloalkyl;

each $R^{e0}$ is independently selected from H, C$_{1-4}$ alkyl, C$_{1-4}$ alkoxy, C$_{1-4}$ haloalkyl, and C$_{1-4}$ haloalkoxy;

Ring moiety G1 is 5-6 membered heteroaryl, which is optionally substituted by 1, 2, 3, or 4 independently selected R$^{G1}$ groups;

Ring moiety G2 is 5-6 membered heteroaryl, which is optionally substituted by 1, 2, 3, or 4 independently selected R$^{G2}$ groups;

each $R^{G1}$ and $R^{G2}$ is independently selected from halo, CN, NO$_2$, C$_{1-6}$ alkyl, C$_{2-6}$ alkenyl, C$_{2-6}$ alkynyl, C$_{1-6}$ haloalkyl, and C$_{3-7}$ cycloalkyl, wherein said C$_{1-6}$ alkyl, C$_{2-6}$ alkenyl, C$_{2-6}$ alkynyl, and C$_{3-7}$ cycloalkyl are each optionally substituted by 1, 2, 3, or 4 independently selected R$^G$ groups.

$L^Y$ is selected from -R-R-, -R-R-R-, -Cy-, -R-Cy-, -Cy-R-, and -R-Cy-R-;

each R is independently M, C$_{1-6}$ alkylene, C$_{2-6}$ alkenylene, C$_{2-6}$ alkynylene, C$_{1-6}$ alkylene-M, or M-C$_{1-6}$ alkylene, wherein each of said C$_{1-6}$ alkylene, C$_{2-6}$ alkenylene, and C$_{2-6}$ alkynylene is optionally substituted by 1, 2, 3, or 4 groups independently selected R$^G$ groups;

each Cy is independently selected from C$_{3-14}$ cycloalkyl, phenyl, 4-14 membered heterocycloalkyl, and 5-6 membered heteroaryl, each of which is optionally substituted by 1, 2, 3, or 4 independently selected R$^G$ groups;

each M is independently —O—, —S—, —C(O)—, —C(O)NR$^L$—, —C(O)O—, —OC(O)—, —OC(O)NR$^L$—, —NR$^L$—, —NR$^L$C(O)O—, —NR$^L$C(O)NR$^L$—, —NR$^L$S(O)$_2$—, —S(O)$_2$—, —S(O)$_2$NR$^L$—, or —NR$^L$S(O)$_2$NR$^L$—; provided that when M is attached to a nitrogen atom, then M is selected from —C(O)—, —C(O)NR$^L$—, —C(O)O—, —S(O)$_2$—, or —S(O)$_2$NR$^L$—;

each $R^L$ is independently H or C$_{1-3}$alkyl; and each $R^G$ is independently selected from OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO-C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-3}$ alkoxycarbonyl, C$_{1-3}$ alkylcarbonyloxy, C$_{1-3}$ alkylcarbonylamino, C$_{1-3}$ alkoxycarbonylamino, C$_{1-3}$ alkylaminocarbonyloxy, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino In some embodiments:

$R^U$ is H, halo, CN, C$_{1-6}$ alkyl, C$_{1-6}$ haloalkyl, OR$^{aU}$, or C(=O)NR$^{cU}$R$^{dU}$;

$R^V$ is H, halo, CN, C$_{1-6}$ alkyl, C$_{1-6}$ haloalkyl, OR$^{aU}$, or C(=O)NR$^{cU}$R$^{dU}$;

$R^W$ is H, halo, CN, C$_{1-6}$ alkyl, C$_{1-6}$ haloalkyl, OR$^{aU}$, or C(=O)NR$^{cU}$R$^{dU}$;

$R^Q$ is H, halo, CN, C$_{1-6}$ alkyl, C$_{1-6}$ haloalkyl, OR$^{aU}$, or C(=O)NR$^{cU}$R$^{dU}$;

$R^{U''}$ is H, halo, CN, C$_{1-6}$ alkyl, C$_{1-6}$ haloalkyl, OR$^{aQ}$, or C(=O)NR$^{cQ}$R$^{dQ}$;

$R^{V''}$ is H, halo, CN, C$_{1-6}$ alkyl, C$_{1-6}$ haloalkyl, OR$^{aQ}$, or C(=O)NR$^{cQ}$R$^{dQ}$;

$R^{W''}$ is H, halo, CN, C$_{1-6}$ alkyl, C$_{1-6}$ haloalkyl, OR$^{aQ}$, or C(=O)NR$^{cQ}$R$^{dQ}$;

$R^{Q''}$ is H, halo, CN, C$_{1-6}$ alkyl, C$_{1-6}$ haloalkyl, OR$^{aQ}$, or C(=O)NR$^{cQ}$R$^{dQ}$;

$R^{aU}$ is selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{U1}$ groups;

$R^{cU}$ and $R^{dU}$ are each independently selected from H, C$_{1-6}$ alkyl, and C$_{1-6}$ haloalkyl;

$R^{aQ}$ is selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{Q1}$ groups;

$R^{cQ}$ and $R^{dQ}$ are each independently selected from H, C$_{1-6}$ alkyl, and C$_{1-6}$ haloalkyl;

each $R^{U1}$ is independently selected from CN, halo, C$_{1-6}$ alkyl, C$_{2-6}$ alkenyl, C$_{2-6}$ alkynyl, C$_{1-6}$ haloalkyl, OR$^{aU1}$, C(=O)R$^{bU1}$, C(=O)NR$^{cU1}$R$^{dU1}$, C(=O)OR$^{aU1}$, OC(=O)R$^{bU1}$, OC(=O)NR$^{cU1}$R$^{dU1}$, NR$^{cU1}$R$^{dU1}$, NR$^{cU1}$C(=O)R$^{bU1}$, NR$^{cU1}$C(=O)OR$^{bU1}$, NR$^{cU1}$C(=O)NR$^{cU1}$R$^{dU1}$, NR$^{cU1}$S(=O)$_2$R$^{bU1}$, NR$^{cU1}$S(=O)$_2$NR$^{cU1}$R$^{dU1}$, and S(=O)$_2$R$^{bU1}$;

each $R^{Q1}$ is independently selected from CN, halo, C$_{1-6}$ alkyl, C$_{2-6}$ alkenyl, C$_{2-6}$ alkynyl, C$_{1-6}$ haloalkyl, OR$^{aQ1}$, C(=O)R$^{bQ1}$, C(=O)NR$^{cQ1}$R$^{dQ1}$, C(=O)OR$^{aQ1}$, OC(=O)R$^{bQ1}$, OC(=O)NR$^{cQ1}$R$^{dQ1}$, NR$^{cQ1}$R$^{dQ1}$, NR$^{cQ1}$C(=O)R$^{bQ1}$, NR$^{cQ1}$C(=O)OR$^{bQ1}$, NR$^{cQ1}$C(=O)NR$^{cQ1}$R$^{dQ1}$, NR$^{cQ1}$S(=O)$_2$R$^{bQ1}$, NR$^{cQ1}$S(=O)$_2$NR$^{cQ1}$R$^{dQ1}$, and S(=O)$_2$R$^{bQ1}$;

each $R^{aU1}$, $R^{cU1}$, and $R^{dU1}$ independently selected from H, C$_{1-6}$ alkyl, C$_{1-6}$ haloalkyl, C$_{3-7}$ cycloalkyl, phenyl, 4-7 membered heterocycloalkyl, and 5-6 membered heteroaryl, wherein said C$_{1-6}$ alkyl, C$_{1-6}$ haloalkyl, C$_{3-7}$ cycloalkyl, phenyl, 4-7 membered heterocycloalkyl, and 5-6 membered heteroaryl are each optionally substituted by 1 or 2 independently selected R$^{U2}$ groups;

each $R^{bU1}$ is independently selected from C$_{1-6}$ alkyl, C$_{1-6}$ haloalkyl, C$_{3-7}$ cycloalkyl, phenyl, 4-7 membered heterocycloalkyl, and 5-6 membered heteroaryl, each of which is optionally substituted by 1, 2, 3, or 4 independently selected $R^{U2}$ groups;

each $R^{U2}$ is independently selected from $C_{1-3}$ alkyl and $C_{1-3}$ haloalkyl;

each $R^{aQ1}$, $R^{cQ1}$, and $R^{dQ1}$ independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1 or 2 independently selected $R^{Q2}$ groups;

each $R^{bQ1}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, 3, or 4 independently selected $R^{Q2}$ groups;

each $R^{Q2}$ is independently selected from $C_{1-3}$ alkyl and $C_{1-3}$ haloalkyl;

X is $CR^X$;
Y is $CR^Y$ or N;
Z is $CR^Z$ or N;
X" is $CR^{X''}$;
Y is $CR^{Y''}$ or N;
Z is $CR^{Z''}$ or N;

$R^X$, $R^Y$, $R^Z$, $R^{X''}$, $R^{Y''}$, and $R^{Z''}$ are each independently selected from H, D, halo, CN, $C_{1-6}$ alkyl, and $C_{1-6}$ haloalkyl;

Ring moiety G1 is a pyrazole ring, which is optionally substituted by 1, 2, 3, or 4 independently selected $R^{G1}$ groups;

Ring moiety G2 is a pyrazole ring, which is optionally substituted by 1, 2, 3, or 4 independently selected $R^{G2}$ groups;

each $R^{G1}$ is independently selected from halo, CN, $C_{1-6}$ alkyl, and $C_{1-6}$ haloalkyl;

each $R^{G2}$ is independently selected from halo, CN, $C_{1-6}$ alkyl, and $C_{1-6}$ haloalkyl; and $L^Y$ is —$CH_2$—CH=CH—$CH_2$—.

In some embodiments:

$R^Q$, $R^U$, $R^V$, and $R^W$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;

$R^{Q''}$, $R^{W''}$, $R^{V''}$, and $R^{U''}$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;

$R^X$ is selected from H, D, halo, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;

$R^{X''}$ is selected from H, D, halo, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;

Ring moiety G1 is a pyrazole ring, which is optionally substituted with 1, 2, or 3 independently selected $R^{G1}$ substituents;

each $R^{G1}$ is independently selected from H, $C_{1-6}$ alkyl, $C_{2-6}$ alkenyl, $C_{2-6}$ alkynyl, CN, and $C_{1-6}$ haloalkyl;

Ring moiety G2 is a pyrazole ring, which is optionally substituted with 1, 2, or 3 independently selected $R^{G2}$ substituents;

each $R^{G2}$ is independently selected from H, $C_{1-6}$ alkyl, $C_{2-6}$ alkenyl, $C_{2-6}$ alkynyl, CN, and $C_{1-6}$ haloalkyl; and $L^Y$ is —$CH_2$—CH=CH—$CH_2$—.

In some embodiments, S has Formula (S-3aa):

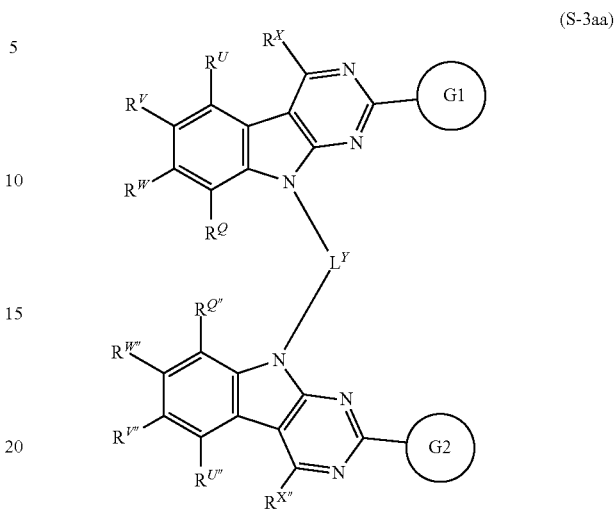

(S-3aa)

In some embodiments, at least one of $R^U$, $R^V$, $R^W$, $R^Q$, $R^{U''}$, $R^{V''}$, $R^{W''}$, and $R^{Q''}$ is $C(O)NH_2$.

In some embodiments, $R^Q$, $R^U$, $R^V$, and $R^W$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl.

In some embodiments, $R^{Q''}$, $R^{W''}$, $R^{V''}$, and $R^{U''}$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl.

In some embodiments, $R^X$ is selected from H, D, halo, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl.

In some embodiments, $R^X$ is selected from H and $C_{1-6}$ alkyl.

In some embodiments, $R^{X''}$ is selected from H, D, halo, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl.

In some embodiments, $R^{X''}$ is selected from H and $C_{1-6}$ alkyl.

In some embodiments, G1 is 5-membered heteroaryl, which is optionally substituted with 1 or 2 independently selected $R^{G1}$ substituents. In some embodiments, G1 is a pyrazole ring, which are optionally substituted by 1, 2, 3, or 4 independently selected $R^{G1}$ substituents. In some embodiments, each $R^{G1}$ is independently selected from H and $C_{1-6}$ alkyl.

In some embodiments, G2 is a 5-membered heteroaryl ring, which is optionally substituted with 1 or 2 independently selected $R^{G2}$ substituents. In some embodiments, G2 is a pyrazole ring, which are optionally substituted by 1, 2, 3, or 4 independently selected $R^{G2}$ substituents. In some embodiments, each $R^{G2}$ is independently selected from H and $C_{1-6}$ alkyl.

In some embodiments, $L^Y$ is $C_{1-4}$ alkylene-$NR^L$-$C_{1-4}$ alkylene, $C_{1-4}$ alkylene-O-$C_{1-4}$ alkylene, $C_{1-6}$ alkylene or $C_{2-6}$ alkenylene, wherein said $C_{1-6}$ alkylene or $C_{1-4}$ alkylene groups are substituted with 1, 2, 3, or 4 substituents independently selected from halo, OH, and $C_{1-4}$ alkoxy.

In some embodiments, $L^Y$ is $C_{1-6}$ alkylene or $C_{2-6}$ alkenylene.

In some embodiments, $L^Y$ is $C_{2-6}$ alkenylene.

In some embodiments, $L^Y$ is —CH$_2$—CH=CH—CH$_2$—.

In some embodiments, $R^X$, $R^Y$, $R^Z$, $R^{X\prime\prime\prime}$, $R^{Y\prime\prime\prime}$, and $R^{Z\prime\prime\prime}$ are each independently selected from H, halo, methyl, and ethyl.

In the context of L being attached to any $R^U$, $R^V$, $R^W$, $R^Q$, $R^{U\prime\prime\prime}$, $R^{V\prime\prime\prime}$, $R^{W\prime\prime\prime}$, $R^{Q\prime\prime\prime}$, $R^{G1}$ or $R^{G2}$, a hydrogen atom on $R^U$, $R^V$, $R^W$, $R^Q$, $R^{U\prime\prime\prime}$, $R^{V\prime\prime\prime}$, $R^{W\prime\prime\prime}$, $R^{Q\prime\prime\prime}$, $R^{G1}$ or $R^{G2}$ is removed and replaced with L.

In some embodiments, L is attached to $R^Q$ or $R^{Q\prime\prime\prime}$.

In some embodiments, L is attached to $R^Q$.

In some embodiments, L is attached to $R^{Q\prime\prime\prime}$.

In some embodiments, S is a compound selected from any of the compounds or formulae in U.S. application Ser. No. 16/528,181, which is incorporated herein by reference in its entirety, wherein L is attached directly to any position of the tricyclic ring; or through a substituent attached to the tricyclic ring. In some embodiments, S is the compound of Examples S29 and 65, wherein L is attached directly to any position of the tricyclic ring; or through a substituent attached to the tricyclic ring. Alternatively, L is attached directly to the one of two pyrazole rings; or through a substituent attached to one of the pyrazole rings. In attaching L to the S moiety in Examples S29 or S65, L replaces any atom or acyclic moiety on the tricyclic ring or the pyrazole ring; or any atom or acyclic moiety on a substituent on the tricyclic ring or the pyrazole ring.

In a further embodiment, S has Formula (S-4):

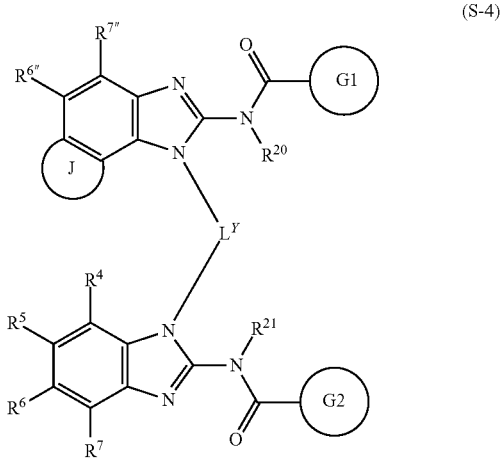

(S-4)

wherein:

L is attached to any $R^4$, $R^5$, $R^6$, $R^7$, $R^{6\prime\prime\prime}$, $R^{7\prime\prime\prime}$, $R^J$, $R^{G1}$ or $R^{G2}$, provided that when L is attached to any of $R^4$, $R^5$, $R^6$, $R^7$, $R^{6\prime\prime\prime}$, $R^{7\prime\prime\prime}$, $R^J$, $R^{G1}$ or $R^{G2}$, then the corresponding position can additionally be a bond;

$R^{20}$ and $R^{21}$ are each independently selected from H, $C_{1-4}$ alkyl, and $C_{1-4}$ haloalkyl;

Ring J is selected from a phenyl ring, a 5-6 membered heteroaryl ring, a $C_{5-7}$ cycloalkyl ring, and a 5-7 membered heterocycloalkyl ring, which is optionally substituted with 1, 2, 3, 4, or 5 independently selected $R^J$ substituents;

$R^4$, $R^5$, $R^6$, and $R^7$ are each independently selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)OR^{b4}$, $NR^{c4}C(=O)NR^{c4}R^{d4}$, $C(=NR^{e4})R^{b4}$, $C(=NR^{e4})NR^{c4}R^{d4}$, $NR^{c4}C(=NR^{e4})R^{b4}$, $NR^{c4}C(=NR^{e4})_2R^{b4}$, $NR^{c4}S(=O)_2NR^{c4}R^{d4}$, $S(=O)_2R^{b4}$, $S(=O)_2NR^{c4}R^{d4}$, $NR^{c4}S(=O)R^{b4}$, $NR^{c4}S(O)NR^{c4}R^{d4}$, $S(=O)R^{b4}$, $S(=O)NR^{c4}R^{d4}$, and $OP(O)(OR^{f4})$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted by 1, 2, 3, or 4 independently selected $R^{4A}$ groups;

each $R^J$, $R^{6\prime\prime\prime}$ and $R^{7\prime\prime\prime}$ are each independently selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-2}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(=O)_2R^{b5}$, $NR^{c5}S(=O)_2NR^{c5}R^{d5}$, $S(=O)_2 R^{b5}$, $S(=O)_2NR^{c5}R^{d5}$, $NR^{c5}S(=O)R^{b5}$, $NR^{c5}S(=O)NR^{c5}R^{d5}$, $S(=O)R^{b5}$, $S(=O)NR^{c5}R^{d5}$, and $OP(O)(OR^{f5})$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5A}$ groups;

each $R^{a4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-2}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4A}$ groups;

each $R^{b4}$ is independently selected from $C_{1-6}$ alkyl, $C_{1-6}$ haloalkyl, $C_{2-6}$ alkenyl, $C_{2-6}$ alkynyl, $C_{3-2}$ cycloalkyl, phenyl, 4-7 membered heterocycloalkyl, 5-6 membered heteroaryl, $C_{3-2}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4A}$ groups;

each $R^{e4}$ is independently selected from H, $C_{1-4}$ alkyl, $C_{1-4}$ alkoxy, $C_{1-4}$ haloalkyl, and $C_{1-4}$ haloalkoxy;

each $R^{g4}$ is independently OH or $C_{1-6}$ alkoxy;

each $R^{a5}$, $RC^{c5}$, and $R^{d5}$ is independently selected from H, $C_{1-6}$ alkyl, $C_{1-6}$ haloalkyl, $C_{2-6}$ alkenyl, and $C_{2-6}$ alkynyl, $C_{3-7}$ cycloalkyl, phenyl, 4-7 membered heterocycloalkyl, 5-6 membered heteroaryl, $C_{3-2}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-2}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ groups;

each $R^{b5}$ is independently selected from $C_{1-6}$ alkyl, $C_{1-6}$ haloalkyl, $C_{2-6}$ alkenyl, $C_{2-6}$ alkynyl, $C_{3-2}$ cycloalkyl, phenyl, 4-7 membered heterocycloalkyl, 5-6 membered heteroaryl, $C_{3-2}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5A}$ groups;

each $R^{e5}$ is independently selected from H, $C_{1-4}$ alkyl, $C_{1-4}$ alkoxy, $C_{1-4}$ haloalkyl, and $C_{1-4}$ haloalkoxy;

each $R^{f5}$ is independently OH or $C_{1-6}$ alkoxy;

each $R^{4A}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a41}$, $SR^{a41}$, $C(=O)R^{b41}$, $C(=O)NR^{c41}R^{d41}$, $C(=O)OR^{a41}$, $OC(=O)R^{b41}$, $OC(=O)NR^{c41}R^{d41}$, $NR^{c41}R^{d41}$, $NR^{c41}C(=O)R^{b41}$, $NR^{c41}C(=O)OR^{b41}$, $NR^{c41}C(=O)NR^{c41}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}S(=O)_2R^{b41}$, $NR^{c41}S(=O)_2NR^{c41}R^{d41}$, $S(=O)_2R^{b41}$, $S(=O)_2NR^{c41}R^{d41}$, $NR^{c41}S(=O)R^{b41}$, $NR^{c41}S(=O)NR^{c41}R^{d41}$, $S(=O)R^{b41}$, $S(=O)NR^{c41}R^{d41}$, and $OP(O)(OR^{f41})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{4B}$ groups;

each $R^{5A}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $C(=O)R^{b51}$, $C(=O)NR^{c51}R^{d51}$, $C(=O)OR^{a51}$, $OC(=O)R^{b51}$, $OC(=O)NR^{c51}R^{d51}$, $NR^{c51}R^{d51}$, $NR^{c51}C(=O)R^{b51}$, $NR^{c51}C(=O)OR^{b51}$, $NR^{c51}C(=O)NR^{c51}R^{d51}$, $C(=NR^{e51})R^{b51}$, $C(=NR^{e51})NR^{c51}R^{d51}$, $NR^{c51}C(=NR^{e51})NR^{c51}R^{d51}$, $NR^{c51}S(=O)_2R^{b51}$, $NR^{c51}S(=O)_2NR^{c51}R^{d51}$, $S(=O)_2R^{b51}$, $S(=O)_2NR^{c51}R^{d51}$, $NR^{c51}S(=O)R^{b51}$, $NR^{c51}S(O)NR^{c51}R^{d51}$, $S(=O)R^{b51}$, $S(=O)NR^{c51}R^{d51}$, and $OP(O)(OR^{f51})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5B}$ groups;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ groups;

each $R^{b41}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4B}$ groups;

each $R^{e41}$ is independently selected from H, $C_{1-4}$ alkyl, $C_{1-4}$ alkoxy, $C_{1-4}$ haloalkyl, and $C_{1-4}$ haloalkoxy;

each $R^{f41}$ is independently OH or $C_{1-6}$ alkoxy;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ groups;

each $R^{b51}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5B}$ groups;

each $R^{e51}$ is independently selected from H, $C_{1-4}$ alkyl, $C_{1-4}$ alkoxy, $C_{1-4}$ haloalkyl, and $C_{1-4}$ haloalkoxy;

each $R^{f51}$ is independently OH or $C_{1-6}$ alkoxy;

each $R^{4B}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a42}$, $SR^{a42}$, $C(=O)R^{b42}$, $C(=O)NR^{c42}R^{d42}$, $C(=O)OR^{a42}$, $OC(=O)R^{b42}$, $OC(=O)NR^{c42}R^{d42}$, $NR^{c42}R^{d42}$, $NR^{c42}C(=O)R^{b42}$, $NR^{c42}C(=O)OR^{b42}$, $NR^{c42}C(=O)NR^{c42}R^{d42}$, $C(=NR^{e42})R^{b42}$, $C(=NR^{e42})NR^{c42}R^{d42}$, $NR^{c42}C(=NR^{e42})NR^{c42}R^{d42}$, $NR^{c42}S(=O)_2R^{b42}$, $NR^{c42}S(=O)_2NR^{c42}R^{d42}$, $S(=O)_2R^{b42}$, $S(=O)_2NR^{c42}R^{d42}$, $NR^{c42}S(=O)R^{b42}$, $NR^{c42}S(=O)NR^{c42}R^{d42}$, $S(=O)R^{b42}$, $S(=O)NR^{c42}R^{d42}$, and $OP(O)(OR^{f42})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{5B}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $C(=O)R^{b52}$, $C(=O)NR^{c52}R^{d52}$, $C(=O)OR^{a52}$, $OC(=O)R^{b52}$, $OC(=O)NR^{c52}R^{d52}$, $NR^{c52}R^{d52}$, $NR^{c52}C(=O)R^{b52}$, $NR^{c52}C(=O)OR^{b52}$, $NR^{c52}C(=O)NR^{c52}R^{d52}$, $C(=NR^{e52})R^{b52}$, $C(=NR^{e52})NR^{c52}Rd^{52}$, $NR^{c52}C(=NR^{e52})NR^{c52}R^{d52}$, $NR^{c52}S(=O)_2R^{b52}$, $NR^{c52}S(=O)_2NR^{c52}R^{d52}$, $S(=O)_2R^{b52}$, $S(=O)_2NR^{c52}R^{d52}$, $NR^{c52}S(=O)R^{b52}$, $NR^{c52}S(=O)NR^{a52}R^{d52}$, $S(=O)R^{b52}$, $S(=O)NR^{c52}R^{d52}$, and $OP(O)(OR^{f52})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b42}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ groups;

each $R^{e42}$ is independently selected from H, $C_{1-4}$ alkyl, $C_{1-4}$ alkoxy, $C_{1-4}$ haloalkyl, and $C_{1-4}$ haloalkoxy;

each $R^{f42}$ is independently OH or $C_{1-6}$ alkoxy;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ groups;

each $R^{e52}$ is independently selected from H, $C_{1-4}$ alkyl, $C_{1-4}$ alkoxy, $C_{1-4}$ haloalkyl, and $C_{1-4}$ haloalkoxy;

each $R^{f52}$ is independently OH or $C_{1-6}$ alkoxy;

Ring moiety G1 is 5-6 membered heteroaryl, which is optionally substituted by 1, 2, 3, or 4 independently selected $R^{G1}$ groups;

Ring moiety G2 is 5-6 membered heteroaryl, which is optionally substituted by 1, 2, 3, or 4 independently selected $R^{G2}$ groups;

each $R^{G1}$ and $R^{G2}$ is independently selected from halo, CN, $NO_2$, $C_{1-6}$ alkyl, $C_{2-6}$ alkenyl, $C_{2-6}$ alkynyl, $C_{1-6}$ haloalkyl, and $C_{3-7}$ cycloalkyl, wherein said $C_{1-6}$ alkyl, $C_{2-6}$ alkenyl, $C_{2-6}$ alkynyl, and $C_{3-7}$ cycloalkyl are each optionally substituted by 1, 2, 3, or 4 independently selected $R^G$ groups.

$L^Y$ is selected from -R-R-, -R-R-R-, -Cy-, -R-Cy-, -Cy-R-, and -R-Cy-R-;

each R is independently M, $C_{1-6}$ alkylene, $C_{2-6}$ alkenylene, $C_{2-6}$ alkynylene, $C_{1-6}$ alkylene-M, or M-$C_{1-6}$ alkylene, wherein each of said $C_{1-6}$ alkylene, $C_{2-6}$ alkenylene, and $C_{2-6}$ alkynylene is optionally substituted by 1, 2, 3, or 4 groups independently selected $R^G$ groups;

each Cy is independently selected from $C_{3-14}$ cycloalkyl, phenyl, 4-14 membered heterocycloalkyl, and 5-6 membered heteroaryl, each of which is optionally substituted by 1, 2, 3, or 4 independently selected $R^G$ groups;

each M is independently —O—, —S—, —C(O)—, —C(O)NR$^L$—, —C(O)O—, —OC(O)—, —OC(O)NR$^L$—, —NR$^L$—, —NR$^C$C(O)—, —NR$^L$C(O)O—, —NR$^L$C(O)NR$^L$—, —NR$^L$S(O)$_2$—, —S(O)$_2$—, —S(O)$_2$NR$^L$—, or —NR$^L$S(O)$_2$NR$^L$—; provided that when M is attached to a nitrogen atom, then M is selected from —C(O)—, —C(O)NR$^L$—, —C(O)O—, —S(O)$_2$—, or —S(O)$_2$NR$^L$—;

each $R^L$ is independently H or $C_{1-3}$ alkyl;

each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino In some embodiments:

$R^{20}$ and $R^{21}$ are each H;

$R^4$ is H, halo, CN, $C_{1-6}$ alkyl, $C_{1-6}$ haloalkyl, OR$^{a4}$, or C(=O)NR$^{c4}$R$^{d4}$;

$R^5$ is H, halo, CN, $C_{1-6}$ alkyl, $C_{1-6}$ haloalkyl, OR$^{a4}$, or C(=O)NR$^{c4}$R$^{d4}$;

$R^6$ is H, halo, CN, $C_{1-6}$ alkyl, $C_{1-6}$ haloalkyl, OR$^{a4}$, or C(=O)NR$^{c4}$R$^{d4}$;

$R^7$ is H, halo, CN, $C_{1-6}$ alkyl, $C_{1-6}$ haloalkyl, OR$^{a4}$, or C(=O)NR$^{c4}$R$^{d4}$;

$R^{6''}$ is H, halo, CN, $C_{1-6}$ alkyl, $C_{1-6}$ haloalkyl, OR$^{a5}$, or C(=O)NR$^{c5}$R$^{d5}$;

$R^{7''}$ is H, halo, CN, $C_{1-6}$ alkyl, $C_{1-6}$ haloalkyl, OR$^{a5}$, or C(=O)NR$^{c5}$R$^{d5}$;

$R^J$ is H, halo, CN, $C_{1-6}$ alkyl, and $C_{1-6}$ haloalkyl;

$R^{a4}$ is selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4A}$ groups;

$R^{c4}$ and $R^{d4}$ are each independently selected from H, $C_{1-6}$ alkyl, and $C_{1-6}$ haloalkyl;

$R^{a5}$ is selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ groups;

$R^{c5}$ and $R^{d5}$ are each independently selected from H, $C_{1-6}$ alkyl, and $C_{1-6}$ haloalkyl;

each $R^{4A}$ is independently selected from CN, halo, $C_{1-6}$ alkyl, $C_{2-6}$ alkenyl, $C_{2-6}$ alkynyl, $C_{1-6}$ haloalkyl, OR$^{a41}$, C(=O)R$^{b41}$, C(=O)NR$^{c41}$R$^{d41}$, C(=O)OR$^{a41}$, OC(=O)

$R^{b41}$, $OC(=O)NR^{c41}R^{d41}$, $NR^{c41}R^{d41}$, $NR^{c41}C(=O)R^{b41}$, $NR^{c41}C(=O)OR^{b41}$, $NR^{c41}C(=O)NR^{c41}R^{d41}$, $NR^{c41}S(=O)_2R^{b41}$, $NR^{c41}S(=O)_2NR^{c41}R^{d41}$, and $S(=O)_2R^{b41}$;

each $R^{5A}$ is independently selected from CN, halo, $C_{1-6}$ alkyl, $C_{2-6}$ alkenyl, $C_{2-6}$ alkynyl, $C_{1-6}$ haloalkyl, $OR^{a51}$, $C(=O)R^{b51}$, $C(=O)NR^{c51}R^{d51}$, $C(=O)OR^{a51}$, $OC(=O)R^{b51}$, $OC(=O)NR^{c51}R^{d51}$, $NR^{c51}R^{d51}$, $NR^{c51}C(=O)R^{b51}$, $NR^{c51}C(=O)OR^{b51}$, $NR^{c51}C(=O)NR^{c51}R^{d51}$, $NR^{c51}S(=O)_2R^{b51}$, $NR^{c51}S(=O)_2NR^{c51}R^{d51}$, and $S(=O)_2R^{b51}$;

each $R^{a41}$, $R^{c41}$, and $R^{d41}$ independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1 or 2 independently selected $R^{4B}$ groups;

each $R^{b41}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, 3, or 4 independently selected $R^{4B}$ groups;

each $R^{4B}$ is independently selected from $C_{1-3}$ alkyl and $C_{1-3}$ haloalkyl;

each $R^{a51}$, $R^{c51}$, and $R^{d51}$ independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1 or 2 independently selected $R^{5B}$ groups;

each $R^{b51}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, 3, or 4 independently selected $R^{5B}$ groups;

each $R^{5B}$ is independently selected from $C_{1-3}$ alkyl and $C_{1-3}$ haloalkyl;

Ring moiety G1 is a pyrazole ring, which is optionally substituted by 1, 2, 3, or 4 independently selected $R^{G1}$ groups;

Ring moiety G2 is a pyrazole ring, which is optionally substituted by 1, 2, 3, or 4 independently selected $R^{G2}$ groups;

each $R^{G1}$ is independently selected from halo, CN, $C_{1-6}$ alkyl, and $C_{1-6}$ haloalkyl;

each $R^{G2}$ is independently selected from halo, CN, $C_{1-6}$ alkyl, and $C_{1-6}$ haloalkyl; and $L^Y$ is —$CH_2$—CH=CH—$CH_2$—.

In some embodiments:

$R^{6'''}$ and $R^{7'''}$ are each independently selected from H, halo, CN, OH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;

Ring J is a moiety selected from:

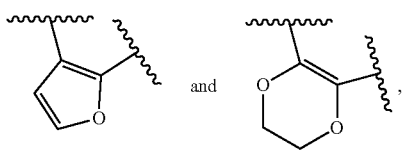 [SMILES: *c1ccoc1* ; *C1=C(*)OCCO1]

each of which are optionally substituted with 1 or 2 independently selected $R^J$ substituents;

each $R^J$ is independently selected from H and $C_{1-6}$ alkyl;

$R^4$, $R^5$, $R^6$, and $R^7$ are each independently selected H, halo, CN, OH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;

Ring moiety G1 is a pyrazole ring, which is optionally substituted with 1, 2, or 3 independently selected $R^{G1}$ substituents;

Ring moiety G2 is a pyrazole ring, which is optionally substituted with 1, 2, or 3 independently selected $R^{G2}$ substituents;

each $R^{G1}$ is independently selected from H and $C_{1-6}$ alkyl;

each $R^{G2}$ is independently selected from H and $C_{1-6}$ alkyl; and $L^Y$ is —$CH_2$—CH=CH—$CH_2$—.

In some embodiments, S has Formula (S-4aa) or (S-4bb):

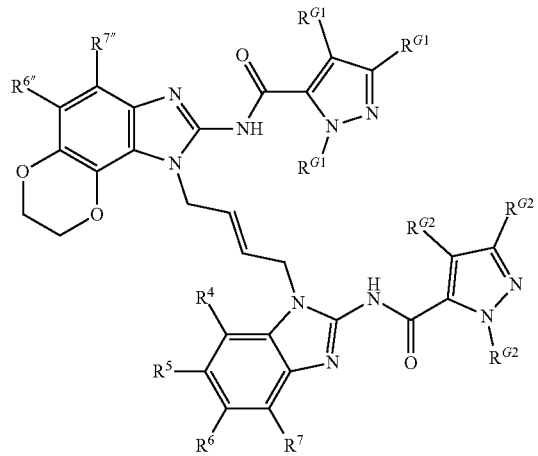

(S-4aa)

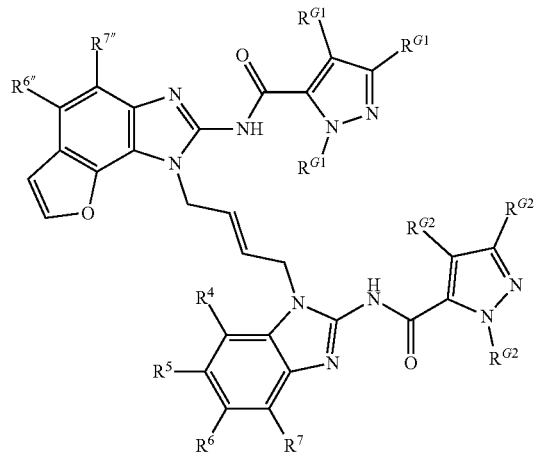

(S-4bb)

or a pharmaceutically acceptable salt thereof.

In some embodiments, at least one of $R^4$, $R^5$, $R^6$, $R^7$, $R^{6'''}$, $R^{7'''}$, and $R^J$ is $C(O)NH_2$. In some embodiments, $R^{6'''}$ and $R^{7'''}$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl.

In some embodiments, Ring J is a 5-membered heteroaryl ring or a 6-membered heterocycloalkyl ring, each of which is optionally substituted with 1, 2, 3, or 4 independently selected $R^J$ substituents.

In some embodiments, Ring J is a moiety selected from:

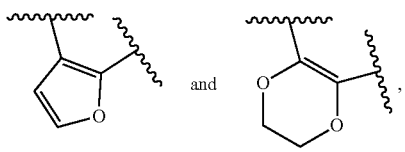 [SMILES: *c1ccoc1* ; *C1=C(*)OCCO1]

and

In some embodiments, $R^4$, $R^5$, $R^6$, and $R^7$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkypcarbamyl.

In some embodiemnts, G1 is 5-membered heteroaryl, which is optionally substituted by 1 or 2 independently selected $R^{G1}$ groups. In some embodiments, G1 is a pyrazole ring, which is optionally substituted by 1, 2, 3, or 4 independently selected $R^{G1}$ substituents. In some embodiments, each $R^{G1}$ is independently selected from halo, CN, $C_{1-6}$ alkyl, and $C_{1-6}$ haloalkyl.

In some embodiemnts, G2 is 5-membered heteroaryl, which is optionally substituted by 1 or 2 independently selected $R^{G2}$ groups. In some embodiments, G2 is a pyrazole ring, which is optionally substituted by 1, 2, 3, or 4 independently selected $R^{G2}$ substituents. In some embodiments, each $R^{G2}$ is independently selected from halo, CN, $C_{1-6}$ alkyl, and $C_{1-6}$ haloalkyl.

In some embodiments, $L^Y$ is $C_{1-4}$ alkylene-$NR^L$-$C_{1-4}$ alkylene, $C_{1-4}$ alkylene—O—$C_{1-4}$ alkylene, $C_{1-6}$ alkylene or $C_{2-6}$ alkenylene, wherein said $C_{1-6}$ alkylene and $C_{1-4}$ alkylene groups are substituted with 1, 2, 3, or 4 substituents independently selected from halo, OH, and $C_{1-4}$ alkoxy.

In some embodiments, $L^Y$ is $C_{1-6}$ alkylene or $C_{2-6}$ alkenylene.

In some embodiments, $L^Y$ is $C_{2-6}$ alkenylene.

In some embodiments, $L^Y$ is —$CH_2$—CH=CH—$CH_2$—.

In some embodiments, $R^{20}$ and $R^{21}$ are each H.

In the context of L being attached to any $R^4$, $R^5$, $R^6$, $R^7$, $R^{6''}$, $R^{7''}$, $R^J$, $R^{G1}$ or $R^{G2}$, a hydrogen atom on $R^4$, $R^5$, $R^6$, $R^7$, $R^{6''}$, $R^{7''}$, $R^J$, $R^{G1}$ or $R^{G2}$ is removed and replaced by L.

In some embodiments, S is a compound selected from any of the compounds in U.S. application Ser. No. 16/528,062, which is incorporated herein by reference in its entirety, wherein L is attached directly to any position of the tricyclic ring or bicyclic ring; or through a substituent attached to the tricyclic ring or bicyclic ring. In some embodiments, S is a compound of the Examples S30-S31 and S66, wherein L is attached directly to any position of the tricyclic ring or the bicyclic ring; or through a substituent attached to the tricyclic ring or the bicyclic ring. Alternatively, L is attached directly to the one of two pyrazole rings; or through a substituent attached to one of the pyrazole rings. In attaching L to the S moiety in Examples S30-S31 or S66, L replaces any atom or acyclic moiety on the tricyclic ring, the bicyclic or the pyrazole ring; or any atom or acyclic moiety on a substituent on the tricyclic ring, the bicyclic or the pyrazole ring.

In another aspect, S is a cyclic dinucleotide.
In some embodiments, S has Formula (S-5):

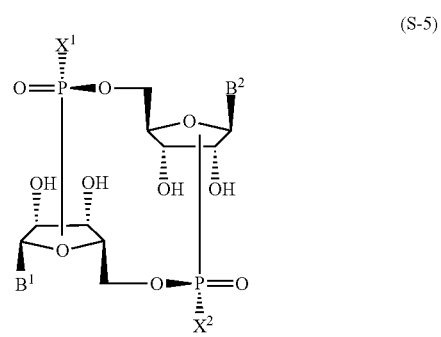

(S-5)

wherein:
wherein L is attached to $B^1$ or $B^2$, to any $R^{30}$, or to one of the OH substiutents on the ribose, or to $X^1$ or $X^2$;
each phosphorous, P, forms a P—O bond with one of the two OH groups of the ribose;
$X^1$ and $X^2$ are independently OH or SH;
$B^1$ and $B^2$ are each 5-10 membered heteroaryl or 4-10 membered heterocycloalkyl each of which has 1, 2, 3, or 4 heteroatom ring members selected from N, S, and O, wherein at least one ring member is N; wherein said 5-10 membered heteroaryl and 4-10 membered heterocycloalkyl are each optionally substituted with 1, 2, 3, 4, 5, or 6 independently selected $R^{30}$ substituents; and wherein $B^1$ and $B^2$ are attached to the ribose moiety through a N ring member on the 5-10 membered heteroaryl or 4-10 membered heterocycloalkyl;

each $R^{30}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a30}$, $SR^{a30}$, C(=O)$R^{b30}$, C(=O)$NR^{c30}R^{d30}$, C(=O)$OR^{a30}$, OC(=O)$R^{b30}$, OC(=O)$NR^{c30}R^{d30}$, $NR^{c30}R^{d30}$, $NR^{c30}$C(=O)$R^{b30}$, $NR^{c30}$C(=O)$OR^{b30}$, $NR^{c30}$C(=O)$NR^{c30}R^{d30}$, C(=$NR^{e30}$)$R^{b30}$, C(=$NR^{e30}$)$NR^{c30}R^{d30}$, $NR^{c30}$C(=$NR^{e30}$)$NR^{c30}R^{d30}$, $NR^{c30}$S(=O)$_2R^{b30}$, $NR^{c30}$S(=O)$_2NR^{c30}R^{d30}$, S(=O)$_2R^{b30}$, S(=O)$_2NR^{c30}R^{d30}$, $NR^{c30}$S(=O)$R^{b30}$, $NR^{c30}$S(=O)$NR^{c30}R^{d30}$, S(=O)$R^{b30}$, S(=O)$NR^{c30}R^{d30}$, and OP(O)(OR$^{f30}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{30A}$ groups;

or any two $R^{30}$ attached to a single carbon atom form a C(O) or C(S) group;

each $R^{a30}$, $R^{c30}$, and $R^{d30}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, and 4-10 membered heterocycloalkyl-$C_{1-4}$ alkyl, 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{30A}$ groups;

each $R^{b30}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{30A}$ groups;

each $R^{e30}$ is independently selected from H, $C_{1-4}$ alkyl, $C_{1-4}$ alkoxy, $C_{1-4}$ haloalkyl, and $C_{1-4}$ haloalkoxy;

each $R^{f30}$ is independently OH or $C_{1-6}$ alkoxy; and each $R^{30A}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino In some embodiments, $B^1$ and $B^2$ are independently selected from 9-purine, 9-adenine, 9-guanine, 9-hypoxanthine, 9-xanthine, 9-uric acid, and 9-isoguanine;

In some embodiments, S has Formula (S-5a):

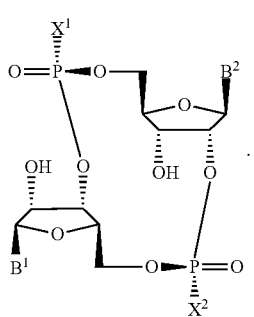

(S-5a)

In some embodiments, S is a compound based on ADU-S100 (Aduro Biotech) having Formula (S-5b):

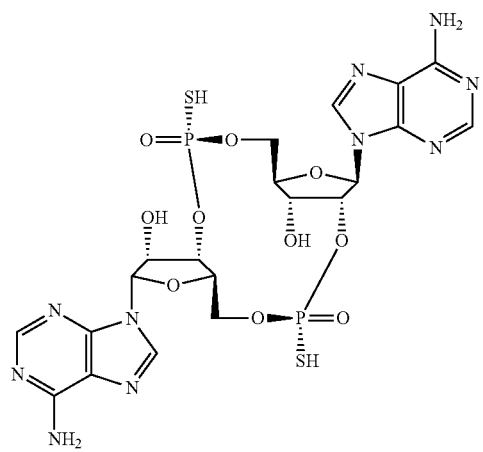

(S-5b)

wherein L is attached to one of the purine rings or through one of the OH, SH, or $NH_2$ substituents. In some embodiments, S has Formula (S-6):

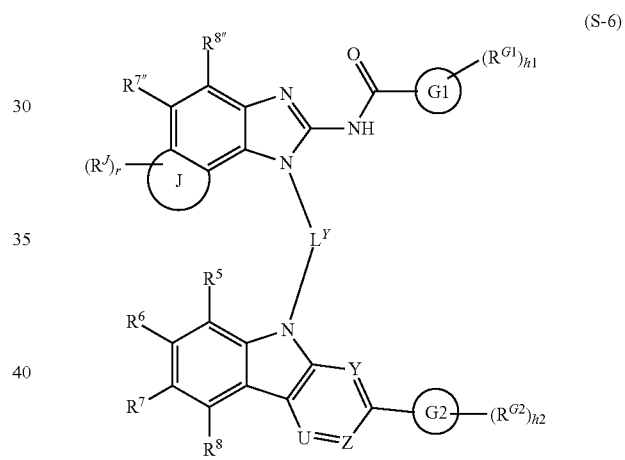

(S-6)

wherein:
L is attached to any $R^5$, $R^6$, $R^7$, $R^8$, $R^{7"}$, $R^{8"}$, $R^J$, $R^{G1}$ or $R^{G2}$, provided that when L is attached to any of $R^5$, $R^6$, $R^7$, $R^8$, $R^{7"}$, $R^{8"}$, $R^J$, $R^{G1}$ or $R^{G2}$, then the corresponding position can additionally be a bond;
r is 0, 1, or 2;
h1 is 0, 1, 2, 3, or 4;
h2 is 0, 1, 2, 3, or 4;
U is N or $CR^U$;
Y is N or $CR^Y$;
Z is N or $CR^Z$;
wherein (i) Z is $CR^Z$, U is $CR^U$, and Y is $CR^Y$; or (ii) Z is N, U is $CR^U$, and Y is $CR^Y$; or (iii) Z is $CR^Z$, U is N, and Y is $CR^Y$; or (iv) Z is $CR^Z$, U is $CR^U$, and Y is N; or (v) Z is N, U is N, and Y is $CR^Y$; or (vi) Z is $CR^Z$, U is N, and Y is N; or (vii) Z is N, U is $CR^U$, and Y is N;
$R^U$, $R^Y$, and $R^Z$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a0}$, $SR^{a0}$, $NHOR^{a0}$, $C(O)R^{b0}$, $C(O)NR^{c0}R^{d0}$, $C(O)NR^{c0}$ $(OR^{a0})$, $C(O)OR^{a0}$, $OC(O)R^{b0}$, $OC(O)NR^{c0}R^{d0}$, $NR^{c0}R^{d0}$, $NR^{c0}NR^{c0}R^{d0}$, $NR^{c0}C(O)R^{b0}$, $NR^{c0}C(O)OR^{a0}$, $NR^{c0}C(O)$ $NR^{c0}R^{d0}$, $C(=NR^{e0})R^{b0}$, $C(=NR^{e0})NR^{c0}R^{d0}$, $NR^{c0}C(=NR^{e0})NR^{c0}R^{d0}$, $NR^{c0}C(NR^{e0})R^{b0}$, $NR^{c0}S(O)NR^{c0}R^{d0}$, $NR^{c0}S(O)R^{b0}$, $NR^{c0}S(O)_2R^{b0}$, $NR^{c0}S(O)(=NR^{e0})R^{b0}$, $NR^{c0}S(O)_2NR^{c0}R^{d0}$, $S(O)R^{b0}$, $S(O)NR^{c0}R^{d0}$, $S(O)_2{}^{b0}$, $S(O)_2 NR^{c0}R^{d0}$, $OS(O)(=NR^{e0})R^{b0}$, $OS(O)_2R^{b0}$, $SF_5$, $P(O)$ $R^{f0}R^{g0}$, $OP(O)(OR^{h0})(OR^{i0})$, $P(O)(OR^{h0})(OR^{i0})$, and $BR^{j0}R^{k0}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^S$ substituents;

each $R^{a0}$, $R^{c0}$, and $R^{d0}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^S$ substituents;

or, any $R^{c0}$ and $R^{d0}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^S$ substituents;

each $R^{b0}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^S$ substituents;

each $R^{e0}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl;

each $R^{f0}$ and $R^{g0}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl;

each $R^{h0}$ and $R^{i0}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl;

each $R^{j0}$ and $R^{k0}$ is independently selected from OH, $C_{1-6}$ alkoxy, and $C_{1-6}$ haloalkoxy;

or any $R^{j0}$ and $R^{k0}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^{7''}$, $R^{8''}$, $R^5$, $R^6$, $R^7$, $R^8$ and each $R^J$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a4}$, $SR^{a4}$, $C(O)R^{b4}$, $C(O)NR^{a4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, $S(O)_2NR^{c4}R^{d4}$, and $OP(O)(OR^{h4})(OR^{i4})$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4A}$ substituents;

or, any $R^{c4}$ and $R^{d4}$ attached to the same N atom, together with the N atom to which they are attached, form a 5- or 6-membered heteroaryl or a 4-7 membered heterocycloalkyl group, wherein the 5- or 6-membered heteroaryl or 4-7 membered heterocycloalkyl group is optionally substituted with 1, 2, 3, or 4 independently selected $R^{4A}$ substituents;

each $R^{b4}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4A}$ substituents;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{4A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $NR^{c41}S(O)_2R^{b41}$, $NR^{c41}S(O)_2NR^{c41}R^{d41}$, $S(O)_2R^{b41}$, $S(O)_2NR^{c41}R^{d41}$, and $OP(O)(OR^{h41})(OR^{i41})$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ substituents;

each $R^{a41}$, $R^{c41}$, and $R^{d41}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{4B}$ substituents;

each $R^{b41}$ is independently selected from $C_{1-6}$ alkyl and $C_{1-6}$ haloalkyl, which are each optionally substituted with 1, 2, 3, or 4 independently selected $R^{4B}$ substituents;

each $R^{h41}$ and $R^{i41}$ is independently selected from H and $C_{1-6}$ alkyl;

each $R^{4B}$ is independently selected from H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

Ring moiety G1 is 5-6 membered heteroaryl;

Ring moiety G2 is 5-6 membered heteroaryl;

each $R^{G1}$ and $R^{G2}$ is independently selected from H, halo, CN, $C_{1-6}$ alkyl, $C_{2-6}$ alkenyl, $C_{2-6}$ alkynyl, and $C_{1-6}$ haloalkyl;

$L^Y$ is selected from -R-R-, -R-R-R-, -Cy-, -R-Cy-, -Cy-R-, and -R-Cy-R-;

each R is independently selected from M, $C_{1-6}$ alkylene, $C_{2-6}$ alkenylene, $C_{2-6}$ alkynylene, $C_{1-6}$ alkylene-M, and M-$C_{1-6}$ alkylene, wherein each of said $C_{1-6}$ alkylene, $C_{2-6}$ alkenylene, and $C_{2-6}$ alkynylene is optionally substituted with 1, 2, 3, or 4 substituents independently selected $R^S$ substituents;

each Cy is independently selected from $C_{3-7}$ cycloalkyl, phenyl, 4-7 membered heterocycloalkyl, and 5-6 membered heteroaryl, each of which is optionally substituted with 1, 2, 3, or 4 independently selected $R^S$ substituents;

each M is independently selected from —O—, —C(O)—, —C(O)$NR^L$—, —$NR^L$—, —$NR^L$C(O)—, —$NR^L$C(O)O—, —$NR^L$S(O)$_2$—, —S(O)$_2$—, and —S(O)$_2NR^L$—, provided that when M is attached to a nitrogen atom, then M is selected from —C(O)—, —C(O)$NR^L$—, —S(O)$_2$—, and —S(O)$_2NR^L$—;

each $R^L$ is independently selected from H and $C_{1-3}$ alkyl; and each $R^S$ is independently selected from H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, r is 0;

h1 is 0, 1, or 2;

h2 is 0, 1, or 2;

U is $CR^U$;

Y is N;

Z is N;

$R^U$ is selected from H, halo, CN, $C_{1-6}$ alkyl, $C_{1-6}$ haloalkyl, $OR^{a0}$, and $NR^{c0}R^{d0}$, wherein said $C_{1-6}$ alkyl and $C_{1-6}$ haloalkyl are each optionally substituted with 1, 2, 3, or 4 independently selected $R^S$ substituents;

each $R^{a0}$, $R^{c0}$, and $R^{d0}$ is independently selected from H, $C_{1-6}$ alkyl, and $C_{1-6}$ haloalkyl;

$R^{7''}$, $R^{8''}$, $R^5$, $R^6$, $R^7$, $R^8$ and each $R^J$ are each independently selected from H, halo, CN, $C_{1-6}$ alkyl, $C_{1-6}$ haloalkyl, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$; wherein said $C_{1-6}$ alkyl and $C_{1-6}$ haloalkyl are each optionally substituted with 1, 2, or 3 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4A}$ substituents;

each $R^{b4}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4A}$ substituents;

each $R^{4A}$ is independently selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a41}$, $C(O)R^{b41}$, $C(O)NR^{c41}R^{d41}$, $(O)OR^{a41}$, $NR^{c41}R^{d41}$, $NR^{c41}C(O)R^{b41}$, $NR^{c41}S(O)_2R^{b41}$, $NR^{c41}S(O)_2NR^{c41}R^{d41}$, $S(O)_2R^{b41}$, and $S(O)_2NR^{c41}R^{d41}$;

each $R^{a41}$, $R^{c41}$, and $R^{d41}$ is independently selected from H, $C_{1-6}$ alkyl, and $C_{1-6}$ haloalkyl;

each $R^{b41}$ is independently selected from $C_{1-6}$ alkyl and $C_{1-6}$ haloalkyl;

Ring moiety G1 is 5-membered heteroaryl;

Ring moiety G2 is 5-membered heteroaryl;

each $R^{G1}$ and $R^{G2}$ is independently selected from H, $C_{1-6}$ alkyl, and $C_{1-6}$ haloalkyl;

$L^Y$ is selected from -R-R- and -R-R-R-;

each R is independently selected from $C_{1-6}$ alkylene, $C_{2-6}$ alkenylene, $C_{2-6}$ alkynylene, wherein each of said $C_{1-6}$ alkylene, $C_{2-6}$ alkenylene, and $C_{2-6}$ alkynylene is optionally substituted with 1, 2, 3, or 4 substituents independently selected $R^S$ substituents; and each $R^S$ is independently selected from H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, r is 0;

h1 is 0, 1, or 2;

h2 is 0, 1, or 2;

U is $CR^U$;

Y is N;

Z is N;

$R^U$ is selected from H, halo, CN, $C_{1-6}$ alkyl, and $C_{1-6}$ haloalkyl;

$R^5$ is H, halo, CN, $C_{1-6}$ alkyl, $C_{1-6}$ haloalkyl, $OR^{a4}$, carbamyl, $C_{1-6}$ alkylcarbamyl, and di($C_{1-6}$ alkyl)carbamyl;

$R^{7''}$, $R^{8''}$, $R^5$, $R^6$, $R^7$, and $R^8$ are each independently selected from H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl;

each $R^{a4}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{44}$ substituents;

each $R^{44}$ is independently selected from H, halo, CN, $C_{1-6}$ alkyl, $C_{1-6}$ haloalkyl, $C_{3-4}$ cycloalkyl, $OR^{a41}$, C(O)NR$^{c41}$R$^{d41}$, C(O)OR$^{a41}$, and NR$^{c41}$R$^{d41}$;

each $R^{a41}$, $R^{c41}$, and $R^{d41}$ is independently selected from H, $C_{1-6}$ alkyl, and $C_{1-6}$ haloalkyl;

Ring moiety G1 is pyrazole;

Ring moiety G2 is pyrazole;

each $R^{G1}$ and $R^{G2}$ is independently selected from H and $C_{1-6}$ alkyl; and $L^Y$ is $C_{2-8}$ alkenylene.

In some embodiments, U is $CR^U$.

In some embodiments, Y is N.

In some embodiments, Z is N.

In some embodiments, $R^U$ is selected from H, halo, CN, $C_{1-6}$ alkyl, and $C_{1-6}$ haloalkyl.

In some embodiments, $R^{7''}$, $R^{8''}$, $R^6$, $R^7$, and $R^8$ are each independently selected from H, halo, CN, $C_{1-6}$ alkyl, and $C_{1-6}$ haloalkyl.

In some embodiments, $R^5$ is H, halo, CN, $C_{1-6}$ alkyl, $C_{1-6}$ haloalkyl, $OR^{a4}$, carbamyl, $C_{1-6}$ alkylcarbamyl, and di($C_{1-6}$ alkyl)carbamyl;

each $R^{a4}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{44}$ substituents;

each $R^{44}$ is independently selected from H, halo, CN, $C_{1-6}$ alkyl, $C_{1-6}$ haloalkyl, $C_{3-4}$ cycloalkyl, $OR^{a41}$, C(O)NR$^{c41}$R$^{d41}$, C(O)OR$^{a41}$, and NR$^{c41}$R$^{d41}$; and each $R^{a41}$, $R^{c41}$, and $R^{d41}$ is independently selected from H, $C_{1-6}$ alkyl, and $C_{1-6}$ haloalkyl.

In some embodiments, $R^5$ is $OR^{a4}$;

each $R^{a4}$ is independently selected from $C_{1-6}$ alkyl, which is optionally substituted with 1 or 2 independently selected $R^{44}$ substituents;

each $R^{44}$ is independently selected from H, halo, CN, $C_{1-6}$ alkyl, $C_{1-6}$ haloalkyl, and $OR^{a41}$; and each $R^{a41}$, $R^{c41}$, and $R^{d41}$ is independently selected from H and $C_{1-6}$ alkyl.

In some embodiments, $R^{7''}$, $R^{8''}$, $R^5$, $R^6$, $R^7$, and $R^8$ are each independently selected from H, halo, CN, $C_{1-6}$ alkyl, $C_{1-6}$ haloalkyl, $C_{1-6}$ alkoxy, $C_{1-6}$ haloalkoxy, carbamyl, $C_{1-6}$ alkylcarbamyl, and di($C_{1-6}$ alkyl)carbamyl.

In some embodiments, G1 is a pyrazole ring, which is optionally substituted by 1 or 2 independently selected $R^{G1}$ substituents. In some embodiments, each $R^{G1}$ is independently selected from H and $C_{1-6}$ alkyl. In some embodiments, each $R^{G1}$ is independently selected from H, methyl, and ethyl.

In some embodiments, G2 is a pyrazole ring, which is optionally substituted by 1 or 2 independently selected $R^{G2}$ substituents. In some embodiments, each $R^{G2}$ is independently selected from H and $C_{1-6}$ alkyl. In some embodiments, each $R^{G2}$ is independently selected from H, methyl, and ethyl.

In some embodiments, $L^Y$ is $C_{1-4}$ alkylene—NR$^L$-$C_{1-4}$ alkylene, $C_{1-4}$ alkylene-O—$C_{1-4}$ alkylene, $C_{1-6}$ alkylene or $C_{2-6}$ alkenylene, wherein said $C_{1-6}$ alkylene or $C_{1-4}$ alkylene groups are substituted with 1, 2, 3, or 4 substituents independently selected from halo, OH, and $C_{1-4}$ alkoxy.

In some embodiments, $L^Y$ is $C_{1-6}$ alkylene or $C_{2-6}$ alkenylene.

In some embodiments, $L^Y$ is $C_{2-6}$ alkenylene.

In some embodiments, $L^Y$ is —CH$_2$—CH=CH—CH$_2$—.

In the context of L being attached to any $R^2$, $R^3$, $R^4$, $R^5$, $R^6$, $R^7$, $R^8$, $R^U$, $R^{G1}$ or $R^{G2}$, a hydrogen atom on $R^2$, $R^3$, $R^4$, $R^5$, $R^6$, $R^7$, $R^8$, $R^U$, $R^{G1}$ or $R^{G2}$ is removed and replaced by L.

In some embodiments, L is attached to $R^J$ or $R^5$.

In some embodiments, L is attached to $R^5$.

In some embodiments, S has Formula (S-6a):

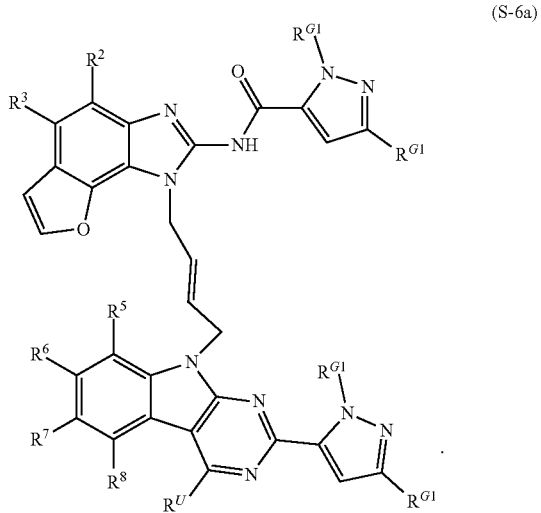

In some embodiments, S has Formula (S-6a), wherein L is attached to $R^5$.

In some embodiments, S is a compound selected from any of the compounds in US Provisional Application No. 62/789,101, which is incorporated herein by reference in its entirety, wherein L is attached directly to any position of the tricyclic ring; or through a substituent attached to the tricyclic ring. In some embodiments, S is a compound of the Examples S66-S69, wherein L is attached directly to any position of the tricyclic ring; or through a substituent attached to the tricyclic ring. Alternatively, L is attached directly to the one of two pyrazole rings; or through a substituent attached to one of the pyrazole rings. In attaching L to the S moiety in Examples S66-S69, L replaces any atom or acyclic moiety on the tricyclic ring or the pyrazole ring; or any atom or acyclic moiety on a substituent on the tricyclic ring or the pyrazole ring.

Linker L

In some embodiments, L is sufficiently polar to avoid the compound or salt to penetrate a cell membrane, e.g., through the incorporation of a polar backbone, such as a water-soluble or water-dispersible polymer, or through incorporation of highly polar substituents that can form anions or cations.

For example, in some embodiments, L comprises (or alternatively, consists of) a water-soluble or water-dispersible polymer such as a polyalkylene glycol, such as polypropylene glycol or polyethylene glycol. In some embodiments, L comprises (or alternatively, consists of) poly($C_{1-6}$ alkyl)ene glycol. In some embodiments, L comprises (or alternatively, consists of) polyethylene glycol. In some embodiments, L comprises (or alternatively, consists of) polyethylene glycol having from 2 to 20 ethylene glycol units. In some embodiments, L comprises (or alternatively, consists of) polyethylene glycol having from 5 to 10 ethylene glycol units. In some embodiments, L comprises (or alternatively, consists of) polyethylene glycol having 8 ethylene glycol units.

In other embodiments, L has one or more highly polar substituents, such as a carboxylic acid or guanidine moiety. In some embodiments, L is substituted by 1, 2, 3, 4, 5, or 6 substituents independently selected from —NHC(=NH)NH$_2$ and —C(O)OH substituent. In some embodiments, L is substituted by 1, 2, 3, 4, 5, or 6 substituents independently selected from —NHC(=O)NH$_2$, —NHC(=NH)NH$_2$ and —C(O)OH substituent.

In other embodiments, L comprises (or alternatively, consists of) a peptide.

In some embodiments, L comprises (or alternatively, consists of) a peptide comprising one or more amino acids independently selected from aspartic acid, glutamic acid, asparagine, proline, arginine, lysine, glycine, and valine.

In some embodiments, L comprises (or alternatively, consists of) a peptide comprising one or more amino acids independently selected from aspartic acid and arginine.

In some embodiments, L comprises (or alternatively, consists of) a -Asp-Arg-Asp-Asp- linking group.

In some embodiments, L comprises (or alternatively, consists of) a linking group selected from -Asp-Asp-, -Asp-Asp-Asp-, -Asp-Asp-Asp-Asp-, -Asp-Asp-Asp-Asp-Asp-, and -(Asp)$_7$-.

In some embodiments, L comprises (or alternatively, consists of) a linking group selected from -Asp-Arg-Asp-Asp-Asp-Arg-Asp-Asp-, Asp-Asp-Arg-Asp-, -Arg-Asp-Asp-Asp-, -Asp-Lys-Asp-Asp-, and -Glu-Asp-Glu-Glu-.

In some embodiments, L comprises (or alternatively, consists of) a -Asp-{NH—CH(CH$_2$CH$_2$CH$_2$NHC(O)NH$_2$)C(O)}-Asp-Asp- linking group.

In some embodiments, L comprises (or alternatively, consists of) a dipeptide.

In some embodiments, L has a length along the shortest path of 6 atoms to 50 atoms.

In some embodiments, L comprises (or alternatively, consists of) a —CH2—(triazol-1,4-diyl)—CH$_2$— linking group.

In some embodiments, L is a non-cleavable linker.

In some embodiments, L is an in vivo cleavable linker. For example, in some embodiments, the linker comprises (or alternatively, consists of) a cleavage disulfide linker or p-aminobenzyloxycarbonyl linker. In some embodiments, L further comprises (or alternatively, consists of) a peptide sequence which is enzymatically cleaved in vivo, e.g., a valine-arginine, valine-lysine, valine-citrulline, or valine-alanine dipeptide. In some embodiments, the dipeptide is bonded to the amino group of a p-aminobenzyloxycarbonyl linking moiety through the carbon end group of the arginine, lysine, citrulline, or alanine amino acid.

In some embodiments, L comprises (or alternatively, consists of) a disulfide linking group.

In some embodiments, L comprises (or alternatively, consists of) a linking group of formula:

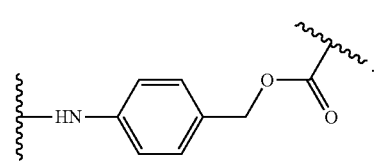 [SMILES: *Nc1ccc(COC(*)=O)cc1]

In some embodiments, L comprises a linking group of formula:

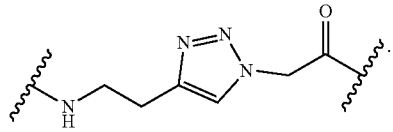 [SMILES: *NCCc1cn(CC(*)=O)nn1]

In some embodiments, L comprises (or alternatively, consists of) a dipeptide. In some embodiments, the dipeptide is valine-arginine. In some embodiments, the dipeptide is valine-lysine. In some embodiments, the dipeptide is valine-citrulline. In some embodiments, the dipeptide is valine-alanine.

In some embodiments, L comprises (or alternatively, consists of) a linking group of formula:

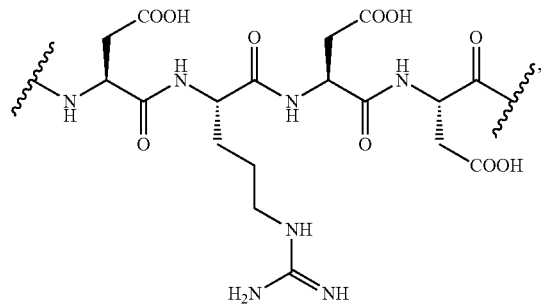

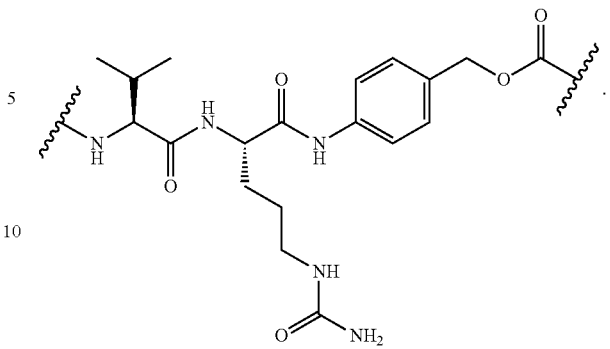

In some embodiments, L comprises (or alternatively, consists of) a linking group of a formula selected from:

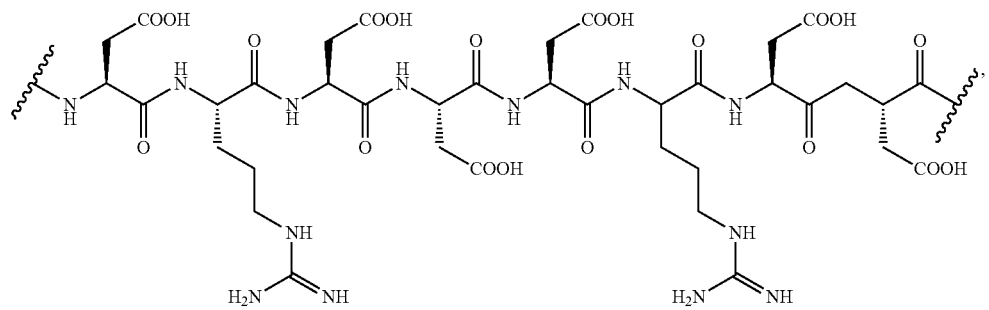

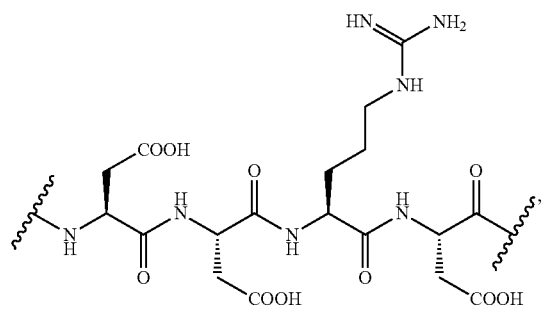

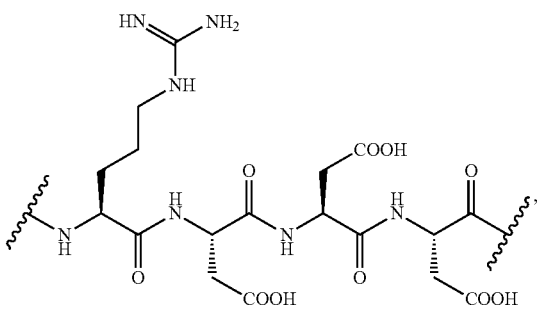

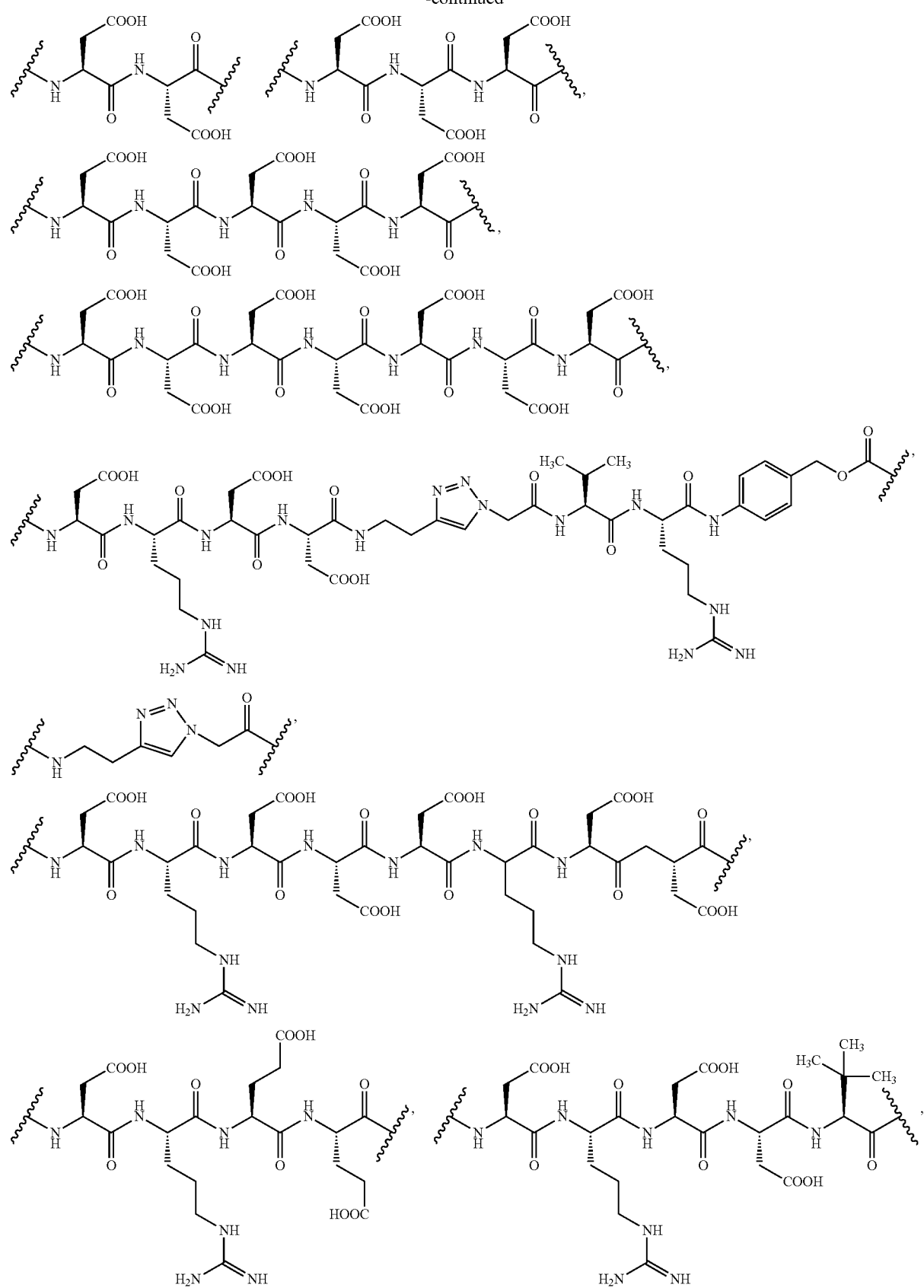

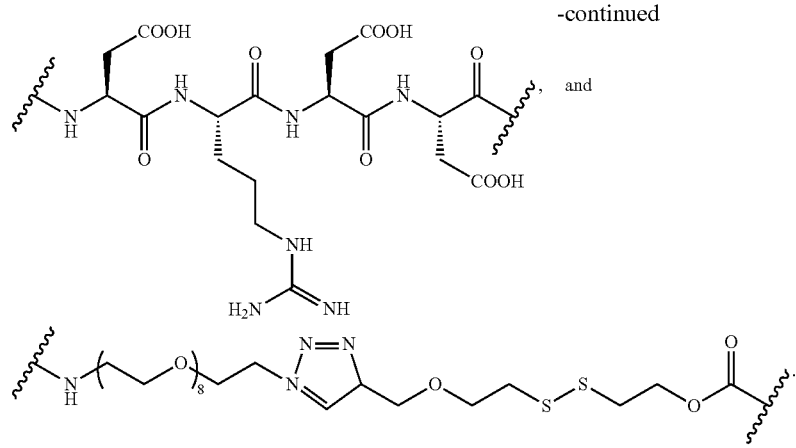

, and

In some embodiments, L is

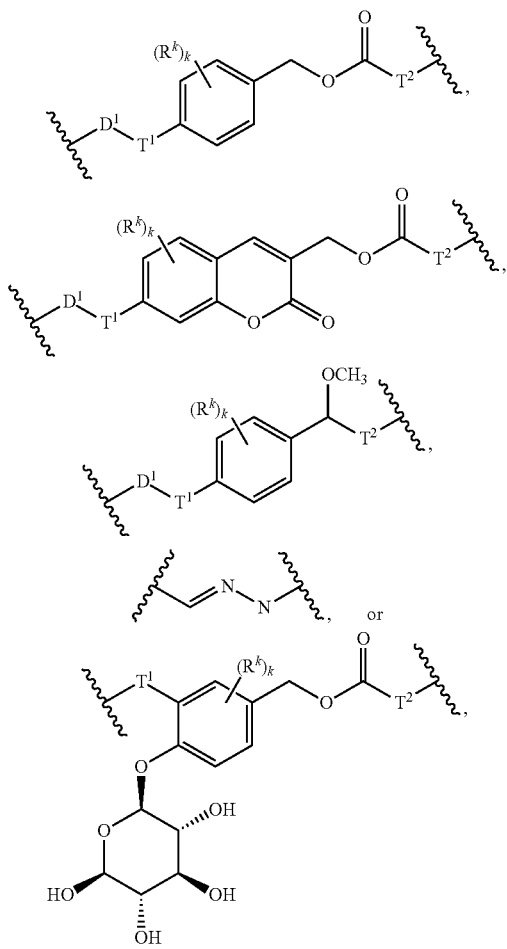

wherein:
$D^1$ is a peptide;
$T^1$ is S, O, or $NR^r$;
$T^2$ is S, O, or $NR^r$;
$R^r$ is H or $C_{1-6}$ alkyl;
k is an integer of 0, 1, 2, 3 or 4;
each $R^k$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, amino-$C_{1-3}$ alkyl, $C_{1-3}$ alkylamino-$C_{1-3}$ alkyl, di($C_{1-3}$ alkyl)amino-$C_{1-3}$ alkyl, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carbamyl-$C_{1-3}$ alkyl, $C_{1-3}$ alkylcarbamyl-$C_{1-3}$ alkyl, di($C_{1-3}$ alkyl)carbamyl-$C_{1-3}$ alkyl, carboxy, carboxy-$C_{1-3}$ alkyl, $C_{1-3}$ alkylcarbonyl, $C_{1-3}$ alkoxycarbonyl, $C_{1-3}$ alkylcarbonyl-$C_{1-3}$ alkyl, $C_{1-3}$ alkoxycarbonyl-$C_{1-3}$ alkyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, $D^1$ is a dipeptide. In some embodiments, $D^1$ is a valine-arginine, valine-lysine, valine-citrulline, or valine-alanine dipeptide.

In some embodiments, k is 0. In some embodiments, k is 1 and $R^k$ is carboxy-$C_{1-3}$ alkyl.

In some embodiments, $T^1$ is O, S, or NH. In some embodiments, $T^1$ is O. In some embodiments, $T^1$ is S. In some embodiments, $T^1$ is NH. In some embodiments, $T^2$ is O, S, or NH. In some embodiments, $T^2$ is O. In some embodiments, $T^2$ is S. In some embodiments, $T^2$ is NH.

In some embodiments, L is -$(A^1)_{a1}$-$(C^1)_{a2}$-$(A^1)_{a3}$-, -$(A^1)_{a1}$-$(C^1)_{a2}$-$(C^1)_{a3}$-, -$(A^1)_{a1}$-$(D^1)_{a2}$-$(A^1)_{a3}$-, -$(A^1)_{a1}$-$(D^1)_{a2}$-$(C^1)_{a3}$-, -$(A^1)_{a1}$-$(D^2)_{a2}$-$(A^1)_{a3}$-, -$(A^1)_{a1}$-$(D^2)_{a2}$-$(C^1)_{a3}$-, -$(A^1)_{a1}$-$(D^2)_{a2}$-$(C^1)_{a3}$-$(C^1)_{a3}$-, -$(C^1)_{a1}$-$(D^2)_{a2}$-$(C^1)_{a3}$-$(A^1)_{a1}$-$(D^1)_{a2}$-$(A^1)_{a3}$-$(D^2)_{a4}$-$(A^1)_{a5}$-, -$(A^1)_{a1}$-$(D^1)_{a2}$-$(C^1)_{a3}$-$(D^2)_{a4}$-$(A^1)_{a5}$-, -$(C^1)_{a1}$-$(D^1)_{a2}$-$(A^1)_{a3}$-$(D^2)_{a4}$-$(A^1)_{a5}$-, -$(C^1)_{a1}$-$(D^2)_{a2}$-$(A^1)_{a3}$-$(D^1)_{a4}$-$(A^1)_{a5}$-, -$(A^1)_{a1}$-$(D^1)_{a2}$-$(C^1)_{a3}$-$(D^2)_{a4}$-$(C^1)_{a5}$-, -$(A^1)_{a1}$-$(D^2)_{a2}$-$(C^1)_{a3}$-$(D^1)_{a4}$-$(C^1)_{a5}$-, -$(C^1)_{a1}$-$(D^1)_{a2}$-$(A^1)_{a3}$-$(D^2)_{a4}$-$(C^1)_{a5}$-, -$(C^1)_{a1}$-$(C^1)_{a2}$-$(D^1)_{a3}$-$(A^1)_{a4}$-$(D^2)_{a5}$-, -$(A^1)_{a1}$-$(D^1)_{a2}$-$(A^1)_{a3}$-$(D^1)_{a4}$-$(A^1)_{a5}$-, -$(C^1)_{a1}$-$(D^1)_{a2}$-$(A^1)_{a3}$-$(D^1)_{a4}$-$(A^1)_{a5}$-, -$(A^1)_{a1}$-$(D^1)_{a2}$-$(C^1)_{a3}$-$(D^1)_{a4}$-$(A^1)_{a5}$-, -$(C^1)_{a1}$-$(D^1)_{a2}$-$(A^1)_{a3}$-$(D^1)_{a4}$-$(C^1)_{a5}$-, -$(C^1)_{a1}$-$(D^1)_{a2}$-$(C^1)_{a3}$-$(D^1)_{a4}$-$(A^1)_{a5}$-, -$(C^1)_{a1}$-$(C^1)_{a2}$-$(D^1)_{a3}$-$(A^1)_{a4}$-$(D^1)_{a5}$-$(A^1)_{a6}$-, -$(A^1)_{a1}$-$(D^2)_{a2}$-$(A^1)_{a3}$-$(D^2)_{a4}$-$(A^1)_{a5}$-, -$(C^1)_{a1}$-$(D^2)_{a2}$-$(A^1)_{a3}$-$(D^2)_{a4}$-$(A^1)_{a5}$-, -$(A^1)_{a1}$-$(D^2)_{a2}$-$(C^1)_{a3}$-$(D^2)_{a4}$-$(A^1)_{a5}$-, -$(C^1)_{a1}$-$(D^2)_{a2}$-$(A^1)_{a3}$-$(D^2)_{a4}$-$(C^1)_{a5}$-, -$(C^1)_{a1}$-$(D^2)_{a2}$-$(C^1)_{a3}$-$(D^2)_{a4}$-$(A^1)_{a5}$-, or -$(C^1)_{a1}$-$(C^1)_{a2}$-$(D^2)_{a3}$-$(A^1)_{a4}$-$(D^2)_{a5}$-$(A^1)_{a6}$-, wherein the right side of the linking groups can be linked to either P or S; wherein:

subscript a1 is 0 or 1;
subscript a2 is 0 or 1;
subscript a3 is 0 or 1;
subscript a4 is 0 or 1;
subscript a5 is 0 or 1;
subscript a6 is 0 or 1;
wherein a1+a2+a3+a4+a5+a6 is 1, 2, 3, 4, 5, or 6;

each $A^1$ is independently $C_{1-20}$ alkylene or $C_{1-20}$ heteroalkylene, each of which is optionally substituted with 1, 2, 3, or 4 independently selected $R^k$ substituents;

each $C^1$ is independently $-Cy^1-$, $-C_{1-20}$ alkylene-$Cy^1-$, $-Cy^1-C_{1-20}$ alkylene-, $-C_{1-20}$ alkylene-$Cy^1-C_{1-20}$ alkylene-, $-C_{1-20}$ heteroalkylene-$Cy^1-$, $-Cy^1-C_{1-20}$ heteroalkylene-, $-C_{1-20}$ heteroalkylene-$Cy^1-C_{1-20}$ heteroalkylene-, $-C_{1-20}$ alkylene-$Cy^1-C_{1-20}$ heteroalkylene-, or $-C_{1-20}$ heteroalkylene-$Cy^1-C_{1-20}$ alkylene-, wherein said alkylene or heteroalkylene is optionally substituted with 1, 2, 3, or 4 independently selected $R^k$ substituents;

$D^1$ is a peptide comprising from 1 to 20 amino acid repeat units;

$D^2$ is polyethylene glycol having from 1 to 20 ethylene glycol repeat units;

wherein $C_{1-20}$ heteroalkylene is a $C_{1-20}$ alkylene group wherein 1, 2, 3, 4, 5, or 6 non-adjacent $C_1$ alkylene chain members are replaced with a group independently selected from —O—, —S—, —S—S—, —C(O)—, —S(O)—, —S(O)$_2$—, —NR$^{L1}$—, —C(O)NR$^{L1}$—, —NR$^{L1}$C(O)—, —C(=S)NR$^{L1}$—, —NR$^{L1}$C(=S)—, —C(=NR$^{L3}$)NR$^{L1}$—, —NR$^{L1}$C(=NR$^{L1}$)—, —C(=NOR$^{L1}$)NR$^{L1}$—, —NR$^{L1}$C(=NOR$^{L1}$)—, —S(O)NR$^{L1}$—, —NR$^{L1}$S(O)—, —NR$^{L1}$S(O)NR$^{L1}$—, —S(O)$_2$NR$^{L1}$—, —NR$^{L1}$S(O)$_2$—, —NR$^{L1}$S(O)$_2$NR$^{L1}$—, —NR$^{L1}$C(O)O—, —OC(O)NR$^{L1}$—, —NR$^{L1}$C(O)NR$^{L1}$—, —P(O)(OR$^{L1}$)O—, and —OP(O)(OR$^{L1}$)—;

each $Cy^1$ is independently $C_{6-10}$ aryl, $C_{3-14}$ cycloalkyl, 5-10 membered heteroaryl, and 4-14 membered heterocycloalkyl, each of which is optionally substituted with 1, 2, 3, or 4 independently selected $R^k$ substituents;

each $R^{L1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^k$ substituents; and each $R^k$ is independently selected from OH, NO$_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, amino- $C_{1-3}$ alkyl, $C_{1-3}$ alkylamino-$C_{1-3}$ alkyl, di($C_{1-3}$ alkyl)amino-$C_{1-3}$ alkyl, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carbamyl-$C_{1-3}$ alkyl, $C_{1-3}$ alkylcarbamyl-$C_{1-3}$ alkyl, di($C_{1-3}$ alkyl)carbamyl-$C_{1-3}$ alkyl, carboxy, carboxy-$C_{1-3}$ alkyl, $C_{1-3}$ alkylcarbonyl, $C_{1-3}$ alkoxycarbonyl, $C_{1-3}$ alkylcarbonyl-$C_{1-3}$ alkyl, $C_{1-3}$ alkoxycarbonyl-$C_{1-3}$ alkyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, a1, a2, a3, a4, a5, and a6 are each 1.

In some embodiments, L is -($A^1$)-($D^1$)-($A^1$)-.
In some embodiments, L is -($A^1$)-($D^1$)-($C^1$)-.
In some embodiments, L is -($A^1$)-($D^2$)-($C^1$)-.
In some embodiments, L is -($A^1$)-($D^1$)-($C^1$)-($D^1$)-($A^1$)-.

In some embodiments, $D^1$ is a peptide comprising from 1 to 6 amino acid repeat units. In some embodiments, $D^1$ is a peptide comprising from 1 to 4 amino acid repeat units. In some embodiments, $D^1$ is a dipeptide. In some embodiments, $D^1$ is a tetrapeptide. In some embodiments, the amino acids are independently selected from aspartic acid, glutamic acid, asparagine, proline, arginine, lysine, glycine, and valine. In some embodiments, the amino acids are independently selected from aspartic acid and arginine In some embodiments, the peptide is valine-arginine, valine-lysine, valine-citrulline, or valine-alanine dipeptide.

In some embodiments, $D^2$ is polyethylene glycol having from 1 to 10 ethylene glycol repeat units. In some embodiments, $D^2$ is polyethylene glycol having from 1 to 8 ethylene glycol repeat units. In some embodiments, $D^2$ is polyethylene glycol having from 6 to 10 ethylene glycol repeat units.

In some embodiments, each $A^1$ is $C_{1-10}$ alkylene or $C_{1-15}$ heteroalkylene, each of which is optionally substituted with 1, 2, 3, or 4 independently selected $R^k$ substituents, wherein $C_{1-15}$ heteroalkylene is a $C_{1-15}$ alkylene group wherein 1, 2, 3, or 4 non-adjacent $C_1$ alkylene chain members are replaced with a group independently selected from —O—, —S—S—, —C(O)—, —NH—, —C(O)NH—, —NHC(O)—, —NHC(O)O—, and —OC(O)NH—. In some embodiments, each $A^1$ is $C_{1-15}$ heteroalkylene, which is optionally substituted with 1, 2, 3, or 4 independently selected $R^k$ substituents, wherein $C_{1-15}$ heteroalkylene is a $C_{1-15}$ alkylene group wherein 1, 2, 3, or 4 non-adjacent $C_1$ alkylene chain members are replaced with a group independently selected from —O—, —S—S—, —C(O)—, —NH—, —C(O)NH—, —NHC(O)—, —NHC(O)O—, and —OC(O)NH—, wherein $A^1$ has one —S—S— group.

In some embodiments, each $C^1$ is independently -$C_{1-20}$ heteroalkylene-$Cy^1$-$C_{1-20}$ heteroalkylene- or -$C_{1-20}$ alkylene-$Cy^1$-$C_{1-20}$ heteroalkylene-, wherein said alkylene or heteroalkylene is optionally substituted with 1, 2, 3, or 4 independently selected $R^k$ substituents, wherein "$C_{1-15}$ heteroalkylene" is a $C_{1-15}$ alkylene group wherein 1, 2, 3, or 4 non-adjacent $C_1$ alkylene chain members are replaced with a group independently selected from —O—, —S—S—, —C(O)—, —NH—, —C(O)NH—, —NHC(O)—, —NHC(O)O—, and —OC(O)NH—. In some embodiments, each $C^1$ is independently -$C_{1-20}$ heteroalkylene-$Cy^1$-$C_{1-20}$ heteroalkylene- or -$C_{1-20}$ alkylene-$Cy^1$-$C_{1-20}$ heteroalkylene-, wherein said alkylene or heteroalkylene is optionally substituted with 1, 2, 3, or 4 independently selected $R^k$ substituents, wherein "$C_{1-15}$ heteroalkylene" is a $C_{1-150}$ alkylene group wherein 1, 2, 3, or 4 non-adjacent $C_1$ alkylene chain members are replaced with a group independently selected from —O—, —S—S—, —C(O)—, —NH—, —C(O)NH—, —NHC(O)—, —NHC(O)O—, and —OC(O)NH—, wherein $C^1$ has one —S—S— group.

In some embodiments, each $Cy^1$ is independently phenyl, 5-10 membered heteroaryl, or 4-10 membered heterocycloalkyl, each of which is optionally substituted with 1 or 2 independently selected $R^k$ substituents. In some embodiments, each Cy is independently phenyl or 5-6 membered heteroaryl.

In some embodiments, each $R^k$ is independently selected from carboxy and carboxy-$C_{1-3}$ alkyl.

In some embodiments, L is selected from $C_{4-50}$ alkylene, $C_{4-50}$ alkenylene, and $C_{4-50}$ alkynylene, wherein one or more C, CH or CH$_2$ groups in said $C_{4-50}$ alkylene, $C_{4-50}$ alkenylene, and $C_{4-50}$ alkynylene are optionally replaced by a linking group independently selected from $Cy^1$, —O—, —S—, —C(O)—, —S(O)—, —S(O)2—, —C(O)NR$^{L1}$—, —NR$^{L1}$C(O)—, —C(=S)NR$^{L1}$—, —NR$^{L1}$C(=S)—, —C(=NR$^{L3}$)NR$^{L1}$—, —NR$^{L1}$C(=NR$^{L1}$)—, —C(=NOR$^{L1}$)NR$^{L1}$—, —NR$^{L1}$C(=NOR$^{L1}$)—, —S(O)NR$^{L1}$—, —NR$^{L1}$S(O)—, —NR$^{L1}$S(O)NR$^{L1}$—, —S(O)$_2$NR$^{L1}$—, —NR$^{L1}$S(O)$_2$—, —NR$^{L1}$S(O)$_2$NR$^{L1}$—, —NR$^{L1}$C(O)O—, —OC(O)NR$^{L1}$—, —NR$^{L1}$C(O)NR$^{L1}$—, —P(O)(OR$^{L1}$)O—, and —OP(O)(OR$^{L1}$)—; and wherein said C$_{4-50}$ alkylene, C$_{4-50}$ alkenylene, and C$_{4-50}$ alkynylene is optionally substituted by one or more independently selected R$^{L2}$ substituents;

each R$^{L3}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each Cy$^1$ is independently C$_{6-10}$ aryl, C$_{3-14}$ cycloalkyl, 5-10 membered heteroaryl, and 4-14 membered heterocycloalkyl, each of which is optionally substituted with 1-4 independently selected R$^{L2}$ substituents;

each R$^{L1}$ is independently selected from H, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-4}$ alkyl-, C$_{3-7}$ cycloalkyl-C$_{1-4}$ alkyl-, (5-6 membered heteroaryl)-C$_{1-4}$ alkyl-, and (4-7 membered heterocycloalkyl)-C$_{1-4}$ alkyl-; wherein said C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-4}$ alkyl-, C$_{3-7}$ cycloalkyl-C$_{1-4}$ alkyl-, (5-6 membered heteroaryl)-C$_{1-4}$ alkyl-, and (4-7 membered heterocycloalkyl)-C$_{1-4}$ alkyl- are each optionally substituted with 1-4 independently selected R$^{L2}$ substituents;

each R$^{L2}$ is independently selected from D, C$_{1-6}$ alkyl, C$_{2-6}$ alkenyl, C$_{2-6}$ alkynyl, C$_{1-6}$ haloalkyl, CN, NO$_2$, CN, NO$_2$, OR$^{aL4}$, SR$^{aL4}$, NHOR$^{aL4}$, C(O)R$^{bL4}$, C(O)NR$^{cL4}$R$^{dL4}$, C(O)NR$^{cL4}$(OR$^{aL4}$), C(O)OR$^{aL4}$, OC(O)R$^{bL4}$, OC(O)NR$^{cL4}$R$^{aL4}$, NR$^{cL4}$R$^{dL4}$, NR$^{cL4}$NR$^{cL4}$R$^{aL4}$, NR$^{cL4}$C(O)R$^{bL4}$, NR$^{cL4}$C(O)OR$^{aL4}$, NR$^{cL4}$C(O)NR$^{cL4}$R$^{aL4}$, C(=NR$^{eL4}$)R$^{bL4}$, C(=NOH)R$^{bL4}$, C(=NCN)R$^{bL4}$, C(=NR$^{eL4}$)NR$^{cL4}$R$^{dL4}$, NR$^{cL4}$C(=NR$^{eL4}$)NR$^{cL4}$R$^{dL4}$, NR$^{cL4}$C(=NOH)NR$^{cL4}$R$^{dL4}$, NR$^{cL4}$C(=NCN)NR$^{cL4}$R$^{dL4}$, NR$^{cL4}$C(=NR$^{eL4}$)R$^{bL4}$, NR$^{cL4}$S(O)NR$^{cL4}$R$^{dL4}$, NR$^{cL4}$S(O)R$^{bL4}$, NR$^{cL4}$S(O)$_2$R$^{bL4}$, NR$^{cL4}$S(O)(=NR$^{eL4}$)R$^{bL4}$, NR$^{cL4}$S(O)$_2$NR$^{Cl4}$R$^{dL4}$, S(O)R$^{bL4}$, S(O)NR$^{cL4}$R$^{dL4}$, S(O)$_2$R$^{bL4}$, S(O)$_2$NR$^{cL4}$R$^{dL4}$, OS(O)(=NR$^{eL4}$)R$^{bL4}$, OS(O)$_2$R$^{bL4}$, SF$_5$, P(O)R$^{fL4}$R$^{gL4}$, OP(O)(OR$^{hL4}$)(OR$^{iL4}$), P(O)(OR$^{hL4}$)(OR$^{iL4}$), and BR$^{jL4}$R$^{kL4}$, wherein the C$_{1-6}$ alkyl, C$_{2-6}$ alkenyl, and C$_{2-6}$ alkynyl are each optionally substituted with 1-4 independently selected R$^{L5}$ substituents;

each R$^{aL4}$, R$^{bL4}$, R$^{cL4}$, and R$^{dL4}$ is independently selected from H, C$_{1-6}$ alkyl, and C$_{1-6}$ haloalkyl, wherein said C$_{1-6}$ alkyl, and C$_{1-6}$ haloalkyl are each optionally substituted with 1, 2, 3, or 4 independently selected R$^{L5}$ substituents;

or, any R$^{cL4}$ and R$^{dL4}$, attached to the same N atom, together with the N atom to which they are attached, form a 4-10 membered heterocycloalkyl group, wherein the 4-10 membered heterocycloalkyl group is optionally substituted with 1-4 independently selected R$^{L5}$ substituents;

each R$^{eL4}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^{fL4}$ and R$^{gL4}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-14}$ cycloalkyl, 5-14 membered heteroaryl, 4-14 membered heterocycloalkyl, C$_{6-10}$ aryl-C$_{1-6}$ alkyl, C$_{3-14}$ cycloalkyl-C$_{1-6}$ alkyl, (5-14 membered heteroaryl)-C$_{1-6}$ alkyl, and (4-14 membered heterocycloalkyl)-C$_{1-6}$ alkyl;

each R$^{hL4}$ and R$^{iL4}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered hetereocycloalkyl, C$_{6-10}$ aryl-C$_{1-6}$ alkyl, C$_{3-10}$ cycloalkyl-C$_{1-6}$ alkyl, (5-10 membered heteroaryl)-C$_{1-6}$ alkyl, and (4-10 membered hetereocycloalkyl)-C$_{1-6}$ alkyl-;

each R$^{jL4}$ and R$^{kL4}$ is independently selected from OH, C$_{1-6}$ alkoxy, and C$_{1-6}$ haloalkoxy;

or any R$^{jL4}$ and R$^{kL4}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl; and each R$^{L5}$ is independently selected from OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO-C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-3}$ alkoxycarbonyl, C$_{1-3}$ alkylcarbonyloxy, C$_{1-3}$ alkylcarbonylamino, C$_{1-3}$ alkoxycarbonylamino, C$_{1-3}$ alkylaminocarbonyloxy, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino.

In some embodiments, L is -(A$^1$)$_{a1}$-(B$^1$)$_{a2}$-(C$^1$)$_{a3}$-(D$^1$)$_{a4}$-(E$^1$)$_{a5}$-(F$^1$)$_{a6}$-(G$^1$)$_{a7}$-(H$^1$)$_{a8}$-;

subscript a1 is 0 or 1;
subscript a2 is 0 or 1;
subscript a3 is 0 or 1;
subscript a4 is 0 or 1;
subscript a5 is 0 or 1;
subscript a6 is 0 or 1;
subscript a7 is 0 or 1;
subscript a8 is 0 or 1;
wherein a1+a2+a3+a4+a5+a6 is 1, 2, 3, 4, 5, 6, 7, or 8;

A$^1$, B$^1$, C$^1$, D$^1$, E$^1$, F$^1$, G$^1$, and H$^1$ are each independently selected from M$^1$, C$_{1-6}$ alkylene, C$_{2-8}$ heteroalkylene, Cy$^1$, Cy$^1$-C$_{1-6}$ alkylene, C$_{1-6}$ alkylene-Cy$^1$, a peptide of 1-8 amino acids, and polyethylene glycol having from 1 to 10 ethylene glycol repeat units, wherein said C$_{1-6}$ alkylene and C$_{2-8}$ heteroalkylene are optionally substituted with 1 or 2 independently selected R$^{k1}$ substituents;

M$^1$ is O—, —S—, —S—S—, —C(O)—, —S(O)—, —S(O)$_2$—, —NR$^{L1}$—, —NR$^{L1}$C(O)—, —C(=S)NR$^{L1}$—, —NR$^{L1}$C(=S)—, —C(=NR$^{L1}$)NR$^{L1}$—, —NR$^{L1}$C(=NR$^{L1}$)—, —C(=NOR$^{L1}$)NR$^{L1}$—, —NR$^{L1}$C(=NOR$^{L1}$)—, —S(O)NR$^{L1}$—, —NR$^{L1}$S(O)—, —NR$^{L1}$S(O)NR$^{L1}$—, —S(O)2NR$^{L1}$—, —NR$^{L1}$S(O)$_2$—, —NR$^{L1}$S(O)$_2$NR$^{L1}$—, —NR$^{L1}$C(O)O—, —OC(O)NR$^{L1}$—, —NR$^{L1}$C(O)NR$^{L1}$—, —P(O)(OR$^{L1}$)O—, and —OP(O)(OR$^{L1}$)—;

C$_{2-8}$ heteroalkylene is a straight-chain alkylene chain, wherein wherein 1, 2, or 3 non-adjacent C$_1$ alkylene chain members are replaced with a group independently selected from O—, —S—, —S—S—, —C(O)—, —S(O)—, —S(O)$_2$—, —NR$^{L1}$—, —C(=S)NR$^{L1}$—, —NR$^{L1}$C(=S)—, —C(=NR$^{L3}$)NR$^{L1}$—, —NR$^{L1}$C(=NR$^{L1}$)—, —C(=NOR$^{L1}$)NR$^{L1}$—, —NR$^{L1}$C(=NOR$^{L1}$)—, —S(O)NR$^{L1}$—, —NR$^{L1}$S(O)—, —NR$^{L1}$S(O)NR$^{L1}$—, —S(O)$_2$NR$^{L1}$—, —NR$^{L1}$S(O)$_2$—, —NR$^{L1}$S(O)$_2$NR$^{L1}$—, —NR$^{L1}$C(O)O—, —OC(O)NR$^{L1}$—, and —NR$^{L1}$C(O)NR$^{L1}$—, provided that said C$_{2-8}$ heteroalkylene retains at least one C$_1$ alkylene chain member;

each Cy$^1$ is independently phenyl, C$_{3-7}$ cycloalkyl, 5-6 membered heteroaryl, and 4-7 membered heterocycloalkyl, each of which is optionally substituted with 1, 2, or 3 independently selected $R^{k1}$ substituents;

each $R^{L1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{k1}$ substituents; and each $R^{k1}$ is independently selected from —NHC(=NH)NH$_2$, OH, NO$_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, amino-$C_{1-6}$ alkyl, $C_{1-6}$ alkylamino-$C_{1-6}$ alkyl, di($C_{1-6}$ alkyl)amino-$C_{1-6}$ alkyl, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carbamyl-$C_{1-6}$ alkyl, $C_{1-6}$ alkylcarbamyl-$C_{1-6}$ alkyl, di($C_{1-6}$ alkyl)carbamyl-$C_{1-6}$ alkyl, carboxy, carboxy-$C_{1-6}$ alkyl, $C_{1-6}$ alkylcarbonyl, $C_{1-6}$ alkoxycarbonyl, $C_{1-6}$ alkylcarbonyl-$C_{1-6}$ alkyl, $C_{1-6}$ alkoxycarbonyl-$C_{1-6}$ alkyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^{L1}$ is H.

In some embodiments, L is -(A$^1$)$_{a1}$-(B$^1$)$_{a2}$-(C$^1$)$_{a3}$-(D$^1$)$_{a4}$-(E$^1$)$_{a5}$-(F$^1$)$_{a6}$-(G$^1$)$_{a7}$-(H$^1$)$_{a8}$-;

subscript a1 is 0 or 1;
subscript a2 is 0 or 1;
subscript a3 is 0 or 1;
subscript a4 is 0 or 1;
subscript a5 is 0 or 1;
subscript a6 is 0 or 1;
subscript a7 is 0 or 1;
subscript a8 is 0 or 1;

wherein a1+a2+a3+a4+a5+a6 is 1, 2, 3, 4, 5, 6, 7, or 8;

A$^1$, B$^1$, C$^1$, D$^1$, E$^1$, F$^1$, G$^1$, and H$^1$ are each independently selected from M$^1$, $C_{3-6}$ alkylene, $C_{2-8}$ heteroalkylene, Cy$^1$, Cy$^1$-$C_{1-6}$ alkylene, $C_{1-6}$ alkylene-Cy$^1$, a peptide of 1-8 amino acids, and polyethylene glycol having from 1 to 10 ethylene glycol repeat units, wherein said $C_{1-6}$ alkylene and $C_{2-8}$ heteroalkylene are optionally substituted with 1 or 2 independently selected $R^{k1}$ substituents;

M$^1$ is —O—, —S—, —S—S—, —C(O)—, —NH—, —C(O)NH—, —NHC(O)—, NHC(O)O—, —OC(O)NH—, and —NHC(O)NH—;

$C_{2-8}$ heteroalkylene is a straight-chain alkylene chain, wherein wherein 1, 2, or 3 non-adjacent C$_1$ alkylene chain members are replaced with a group independently selected from —O—, —S—, —S—S—, —C(O)—, —NH—, —C(O)NH—, —NHC(O)—, NHC(O)O—, —OC(O)NH—, and —NHC(O)NH—, provided that said $C_{2-8}$ heteroalkylene retains at least one C$_1$ alkylene chain member;

each Cy$^1$ is independently phenyl, $C_{3-7}$ cycloalkyl, 5-6 membered heteroaryl, and 4-7 membered heterocycloalkyl, each of which is optionally substituted with 1, 2, or 3 independently selected $R^{k1}$ substituents;

each $R^{L1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{k1}$ substituents; and each $R^{k1}$ is independently selected from —NHC(=NH)NH$_2$, OH, NO$_2$, CN, halo, $C_{1-6}$ alkyl, $C_{2-6}$ alkenyl, $C_{2-6}$ alkynyl, $C_{3-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, amino-$C_{1-6}$ alkyl, $C_{1-6}$ alkylamino-$C_{1-6}$ alkyl, di($C_{1-6}$ alkyl)amino-$C_{1-6}$ alkyl, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carbamyl-$C_{1-6}$ alkyl, $C_{1-6}$ alkylcarbamyl-$C_{1-6}$ alkyl, di($C_{1-6}$ alkyl)carbamyl-$C_{1-6}$ alkyl, carboxy, carboxy-$C_{1-6}$ alkyl, $C_{1-6}$ alkylcarbonyl, $C_{1-6}$ alkoxycarbonyl, $C_{1-6}$ alkylcarbonyl-$C_{1-6}$ alkyl, $C_{1-6}$ alkoxycarbonyl-$C_{1-6}$ alkyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino wherein a1+a2+a3+a4+a5+a6 is 1, 2, 3, 4, 5, or 6;

In some embodiments, the peptide comprises 1-8 amino acids independently selected from aspartic acid, glutamic acid, asparagine, proline, arginine, lysine, glycine, and valine.

In some embodiments, 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "-$C_{1-4}$ alkyl-", "alkylene", "alkenylene" and "alkynylene" linking groups, in any of the compounds described herein, are optionally replaced by deuterium atoms.

Definitions

It is further appreciated that certain features of the disclosure, which are, for clarity, described in the context of separate embodiments, can also be provided in combination in a single embodiment (i.e., as if the embodiments are multiply dependent claims). Conversely, various features of the disclosure which are, for brevity, described in the context of a single embodiment, can also be provided separately or in any suitable subcombination. This disclosure is intended to include all combinations of embodiments for each variable described hereinabove including salts thereof. In particular, the S, P, and L embodiments can be combined as if they were written in multiply dependent claims.

At various places in the present specification, divalent linking substituents are described. It is specifically intended that each divalent linking substituent include both the forward and backward forms of the linking substituent. For example, —NR(CR'R'')$_n$— includes both —NR(CR'R'')$_n$— and —(CR'R'')$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency, that the designated atom's normal valency is not exceeded, and that the substitution results in a stable compound.

As used herein, the phrase "each 'variable' is independently selected from" means substantially the same as wherein "at each occurrence 'variable' is selected from."

When any variable (e.g., $R^S$) occurs more than one time in any constituent or formula for a compound, its definition at each occurrence is independent of its definition at every other occurrence. Thus, for example, if a group is shown to be substituted with 1, 2, 3, or 4 $R^S$, then said group may optionally be substituted with up to four $R^S$ groups and $R^S$ at each occurrence is selected independently from the definition of $R^S$. Also, combinations of substituents and/or variables are permissible only if such combinations result in stable compounds; for example the combination of a first M group and second M group in the combination of two R groups are permissible only if such combinations of M-M result in stable compounds (e.g., M-M is not permissible if it will form highly reactive compounds such as peroxides having O—Obonds).

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, "peptide" refers to a sequence of one or more amino acids, wherein, when there are more than one amino acid, the bonds between the amino acids are amide bonds.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms. As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms. As used herein, the term "$C_{n-m}$ alkoxy", employed alone or in combination with other terms, refers to a group of formula-0-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —$NH_2$.

As used herein, the term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, the aryl group has from 6 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include $OCF_3$ and $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, the term "thio" refers to a group of formula —SH.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonylamino" refers to a group of formula —NHC(O)O($C_{n-m}$ alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfmyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "cyano-$C_{1-6}$ alkyl" refers to a group of formula -($C_{1-6}$ alkylene)—CN. As used herein, the term "cyano-$C_{1-3}$ alkyl" refers to a group of formula -($C_{1-3}$ alkylene)—CN.

As used herein, the term "HO-$C_{1-6}$ alkyl" refers to a group of formula -($C_{1-6}$ alkylene)—OH. As used herein, the term "HO-$C_{1-3}$ alkyl" refers to a group of formula -($C_{1-3}$ alkylene)—OH.

As used herein, the term "$C_{1-6}$ alkoxy-$C_{1-6}$ alkyl" refers to a group of formula -($C_{1-6}$ alkylene)—O($C_{1-6}$ alkyl). As used herein, the term "$C_{1-3}$ alkoxy-$C_{1-3}$ alkyl" refers to a group of formula -($C_{1-3}$ alkylene)—O($C_{1-3}$ alkyl).

As used herein, the term "carboxy" refers to a group of formula —C(O)OH.

As used herein, the term "di($C_{n-m}$ alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$ alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkylcarbonyloxy" is a group of formula —OC(O)-alkyl, wherein the alkyl group has n to m carbon atoms. In some embodiments, the alkyl group has 1 to 6, 1 to 4, or 1 to 3 carbon atoms.

As used herein, "aminocarbonyloxy" is a group of formula —OC(O)—NH$_2$.

As used herein, "$C_{n-m}$ alkylaminocarbonyloxy" is a group of formula —OC(O)—NH-alkyl, wherein the alkyl group has n to m carbon atoms. In some embodiments, the alkyl group has 1 to 6, 1 to 4, or 1 to 3 carbon atoms.

As used herein, "di($C_{n-m}$ alkyl)aminocarbonyloxy" is a group of formula —OC(O)—N(alkyl)$_2$, wherein each alkyl group has, independently, n to m carbon atoms. In some embodiments, each alkyl group independently has 1 to 6, 1 to 4, or 1 to 3 carbon atoms.

As used herein $C_{n-m}$ alkoxycarbonylamino refers to a group of formula —NHC(O)—O-alkyl, wherein the alkyl group has n to m carbon atoms.

As used herein, the term "carbamyl" to a group of formula —C(O)NH$_2$.

As used herein, the term "carbonyl", employed alone or in combination with other terms, refers to a —C(O)— group.

As used herein, "cycloalkyl" refers to non-aromatic cyclic hydrocarbons including cyclized alkyl and alkenyl groups. Cycloalkyl groups can include mono- or polycyclic (e.g., having 2, 3 or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, 12, 13 or 14 ring-forming carbons (i.e., $C_{3-14}$). In some embodiments, the cycloalkyl is a $C_{3-14}$ monocyclic or bicyclic cycloalkyl which is optionally substituted by $CH_2F$, $CHF_2$, $CF_3$, and $CF_2CF_3$. In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-14}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 or 3 fused rings) aromatic heterocycle having at least one heteroatom ring member selected from N, O, S and B. In some embodiments, the heteroaryl ring has 1, 2, 3, or 4 heteroatom ring members independently selected from N, O, S and B, wherein any ring forming N is optionally an N-oxide group. In some embodiments, the heteroaryl is a 5-14 membered monocyclic, bicyclic, or tricyclic heteroaryl having 1, 2, 3, or 4 heteroatom ring members independently selected from N, O, and S. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-6 monocyclic heteroaryl having 1 or 2 heteroatom ring members independently selected from N, O, S and B. In some embodiments, the heteroaryl is a 5-6 monocyclic heteroaryl having 1 or 2 heteroatom ring members independently selected from from N, O, S, and B. In some embodiments, the heteroaryl group contains 3 to 14, 3 to 10, 4 to 14, 4 to 10, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, isoxazole, thiophene, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine, thieno[3,2-b]pyridine, imidazo[1,2-a]pyridine, 1,5-naphthyridine, 1H-pyrazolo[4,3-b]pyridine, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, and 1,2-dihydro-1,2-azaborine. 6p As used herein, "heterocycloalkyl" or "heterocycyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S and B, and wherein the ring-forming carbon atoms and heteroatoms of the heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2 fused rings) systems. Included in heterocycloalkyl are monocyclic and polycyclic 4-14-, 4-10-, 4-7-, and 5-6 membered heterocycloalkyl groups. Heterocycloalkyl groups can also include spirocycles and bridged rings (e.g., a 5-10 membered bridged biheterocycloalkyl ring having one or more of the ring-forming carbon atoms replaced by a heteroatom independently selected from N, O, S and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 4 to 14 ring-forming atoms, 4 to 10 ring-forming atoms, 4 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidaolidinyl, azepanyl, benzazapene, 1.2.3.4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "alkylene" refers a divalent straight chain or branched alkyl linking group. Examples of "alkylene groups" include methylene, ethan-1,1-diyl, ethan-1,2-diyl, propan-1,3-dilyl, propan-1,2-diyl, propan-1,1-diyl and the like.

As used herein, the term "alkenylene" refers a divalent straight chain or branched alkenyl linking group. Examples of "alkenylene groups" include ethen-1,1-diyl, ethen-1,2-diyl, propen-1,3-diyl, 2-buten-1,4-diyl, 3-penten-1,5-diyl, 3-hexen-1,6-diyl, 3-hexen-1,5-diyl, and the like.

As used herein, the term "alkynylene" refers a divalent straight chain or branched alkynyl linking group. Examples of "alkynylene groups" include propyn-1,3-diyl, 2-butyn-1,4-diyl, 3-pentyn-1,5-diyl, 3-hexyn-1,6-diyl, 3-hexyn-1,5-diyl, and the like.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, a dashed bond ($=$) represents a single or double bond depending on the nature of the atoms in each ring and as required to complete the valencies of the atoms being linked by the bond.

As used herein, the term "independently selected from" means that each occurrence of a variable or substituent are independently selected at each occurrence from the applicable list.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

In some embodiments, the compounds of the present disclosure, or salts thereof, are substantially isolated. By "substantially isolated" is meant that the compound is at least partially or substantially separated from the environment in which it was formed or detected. Partial separation can include, e.g., a composition enriched in the compounds of the present disclosure. Substantial separation can include compositions containing at least about 50%, at least about 60%, at least about 70%, at least about 80%, at least about 90%, at least about 95%, at least about 97%, or at least about 99% by weight of the compounds of the present disclosure, or salt thereof.

Methods

Compounds of the present disclosure can activate STING-mediated IRF3 and NFκB signaling pathways to produce type I interferons and proinflammatory chemokines and cytokines and, thus, are useful in treating infectious diseases and cancer. The activation of STING, results in IRF3 and NFκB upregulation and production of IFNs and other cytokines. The production of those interferons and proinflammatory cytokines can enhance the immune response to cancerous cells and infectious diseases in mammals, including humans. In certain embodiments, the compounds of the present disclosure, or pharmaceutically acceptable salts or stereoisomers thereof, are useful for therapeutic administration to enhance, stimulate and/or increase immunity in cancer, chronic infection or sepsis, including enhancement of response to vaccination.

In addition, compounds of the present disclosure can reduce PD-1/PD-L1 protein/protein interaction, resulting in resulting in a PD-1 pathway blockade. Accordingly, the compounds are useful in treating diseases and disorders associated with activity of PD-1 and the diseases and disorders associated with PD-L1 including its interaction with other proteins such as PD-1 and B7-1 (CD80). The blockade of PD-1 can enhance the immune response to cancerous cells and infectious diseases in mammals, including humans.

Accordingly, the present disclosure provides a method of treating cancer in a patient, comprising administering to the patient a compound as described herein, or a pharmaceutically acceptable salt thereof. In some embodiments, the present disclosure provides treatment of an individual or a patient in vivo using a compound of Formula (I) or a salt or stereoisomer thereof such that growth of cancerous tumors is inhibited. A compound of Formula (I) or of any of the formulas as described herein, or a compound as recited in any of the claims and described herein, or a salt or stereoisomer thereof, can be used to inhibit the growth of cancerous tumors. Alternatively, a compound of Formula (I) or of any of the formulas as described herein, or a compound as recited in any of the claims and described herein, or a salt or stereoisomer thereof, can be used in conjunction with other agents or standard cancer treatments, as described below. In one embodiment, the present disclosure provides a method for inhibiting growth of tumor cells in vitro. The method includes contacting the tumor cells in vitro with a compound of Formula (I) or of any of the formulas as described herein, or of a compound as recited in any of the claims and described herein, or of a salt or stereoisomer thereof. In another embodiment, the present disclosure provides a method for inhibiting growth of tumor cells in an individual or a patient. The method includes administering to the individual or patient in need thereof a therapeutically effective amount of a compound of Formula (I) or of any of the formulas as described herein, or of a compound as recited in any of the claims and described herein, or a salt or a stereoisomer thereof.

The present disclosure also provides a method of activating STING, comprising contacting a cell with a compound of Formula (I), or a pharmaceutically acceptable salt thereof. The present disclosure further provides a method of agonizing STING, comprising contacting a cell with a compound of Formula (I), or a pharmaceutically acceptable salt thereof.

In some embodiments, the compound or salt selectively agonizes STING in high PD-L1 expressing cells as compared to low PD-L1 expressing cells, wherein the high PD-L1 expressing cells have 200-fold more surface PD-L1 expression than a negative control and the low PD-L1 expressing cells have about 10-fold more surface PD-L1 expression than a negative control. In some embodiments, the high PD-L1 and low PD-L1 expression are determined by measuring the mean fluorescence intensity of PD-L1 expression of high PD-L1 expressing cells and low PD-L1 expressing HEK-293T cell lines stained with phycoerythrin-conjugated anti-PD-L1 antibody (e.g., as described in Example 8B).

In some embodiments, the compound or salt is at least 5-fold more selective for the high PD-L1 expressing cells as compared to the low PD-L1 expressing cells.

In some embodiments, the compound or salt is at least 10-fold more selective for the high PD-L1 expressing cells as compared to the low PD-L1 expressing cells. 6p In some embodiments, the compound or salt is at least 50-fold more selective for the high PD-L1 expressing cells as compared to the low PD-L1 expressing cells.

In some embodiments, the compound or salt is at least 100-fold more selective for the high PD-L1 expressing cells as compared to the low PD-L1 expressing cells.

In some embodiments, the compound or salt is at least 200-fold more selective for the high PD-L1 expressing cells as compared to the low PD-L1 expressing cells.

In some embodiments, provided herein is a method for treating cancer. The method includes administering to a patient in need thereof, a therapeutically effective amount of a compound described herein or a salt thereof. Examples of cancers include those whose growth may be inhibited using compounds of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a compound described herein or a salt thereof.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers, especially metastatic cancers that express PD-L1.

In some embodiments, cancers treatable with compounds of the present disclosure include melanoma (e.g., metastatic malignant melanoma), renal cancer (e.g., clear cell carcinoma), prostate cancer (e.g. hormone refractory prostate adenocarcinoma), breast cancer, triple-negative breast cancer, colon cancer, lung cancer (e.g., non-small cell lung cancer and small cell lung cancer), squamous cell head and neck cancer, urothelial cancer (e.g., bladder) and cancers with high microsatellite instability ($MSI^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

PD-1 pathway blockade and STING activation with compounds of the present disclosure can also be used for treating infections such as viral, bacteria, fungus and parasite infections. See Rao M et al., International Journal of Infectious Diseases, 56 (2017) 221-228. The present disclosure provides a method for treating infections such as viral infections. The method includes administering to a patient in need thereof, a therapeutically effective amount of a compound described herein or a salt thereof. Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

The present disclosure provides a method for treating bacterial infections. The method includes administering to a patient in need thereof, a therapeutically effective amount of a compound described herein or a salt thereof. Non-limiting examples of pathogenic bacteria causing infections treatable by methods of the disclosure include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a compound described herein or a salt thereof. Non-limiting examples of pathogenic fungi causing infections treatable by methods of the disclosure include Candida (albicans, krusei, glabrata, tropicalis, etc.), *Cryptococcus neoformans, Aspergillus* (fumigatus, niger, etc.), Genus Mucorales (mucor, absidia, rhizophus), *Sporothrix schenkii, Blastomyces dermatitidis, Paracoccidioides brasiliensis, Coccidioides immitis* and *Histoplasma capsulatum*.

The present disclosure provides a method for treating parasite infections. The method includes administering to a patient in need thereof, a therapeutically effective amount of a compound described herein or a salt thereof. Non-limiting examples of pathogenic parasites causing infections treatable by methods of the disclosure include *Entamoeba histolytica, Balantidium coli, Naegleriafowleri, Acanthamoeba sp., Giardia lambia, Cryptosporidium sp., Pneumocystis carinii, Plasmodium vivax, Babesia microti, Trypanosoma brucei, Trypanosoma cruzi, Leishmania donovani, Toxoplasma gondi,* and *Nippostrongylus brasiliensis*.

The present disclosure provides a method for treating sepsis. The method includes treating sepsis by administering to a patient in need thereof, a therapeutically effective amount of a compound described herein or a salt thereof.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the present disclosure are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anticancer agent(s) include antibody therapeutics such as 4-1BB (e.g. urelumab, utomilumab)

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736. In some embodiments, the inhibitor of an immune checkpoint molecule is an inhibitor of PD-1 and PD-L1, e.g., an anti-PD-1/PD-L1 bispecific antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX4OL fusion protein. In some embodiments, the anti-OX40 antibody is MEDI0562, MOXR-0916, PF-04518600, GSK3174998, or BMS-986178. In some embodiments, the OX40L fusion protein is MED16383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions.

Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, and FAK kinase inhibitors such as, for example, those described in WO 2006/056399. Other agents such as therapeutic antibodies can be used in combination with the compounds of the present disclosure for treatment of PI3K-associated diseases, disorders or conditions. The one or more additional pharmaceutical agents can be administered to a patient simultaneously or sequentially.

The compounds as disclosed herein can be used in combination with one or more other enzyme/protein/receptor inhibitors therapies for the treatment of diseases, such as cancer and other diseases or disorders described herein. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, BCL2, CDK, TGF-☐R, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFEXR, PDGF☐R, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCY54828), INCB62079), an EGFR inhibitor (also known as ErB-1 or HER-1; e.g. erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g. olaparib, rucaparib, veliparib or niraparib), a JAK inhibitor (JAK1 and/or JAK2, e.g., ruxolitinib, baricitinib, itacitinib (INCB39110), an IDO inhibitor (e.g., epacadostat, NLG919, or BMS-986205, MK7162), an LSD1 inhibitor (e.g., INCB59872 and INCB60003), a TDO inhibitor, a PI3K-delta inhibitor (e.g., INCB50465 and INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a chemokine receptor inhibitor (e.g. CCR2 or CCR5 inhibitor), a PD-L1 inhibitor (e.g., INCB086550), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), and an adenosine receptor antagonist, or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-I agonists, STING agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib, rucaparib, bortezombi, olaparib, and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethas one, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present disclosure with an additional agent.

In some embodiments, the compounds of the disclosure can be used in combination with an inhibitor of JAK or PI3Kδ.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, Leishmania, *Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, Candida (albicans, krusei, glabrata, tropicalis, etc.), *Cryptococcus neoformans, Aspergillus* (fumigatus, niger, etc.), Genus Mucorales (mucor, absidia, rhizophus), *Sporothrix schenkii, Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli, Naegleriafowleri, Acanthamoeba sp., Giardia lambia, Cryptosporidium sp., Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

The reactions for preparing compounds of the disclosure can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry or by chromatographic methods such as high performance liquid chromatography (HPLC) or thin layer chromatography (TLC).

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The Schemes below provide general guidance in connection with preparing the compounds of the disclosure. One skilled in the art would understand that the preparations shown in the Schemes can be modified or optimized using general knowledge of organic chemistry to prepare various compounds of the disclosure.

The P ligands of Formula (P-1), (P-1a), and (P-1b) (and embodiments thereof) can be synthesized as described in US Patent Publ. Nos. 20180179201, 20180179197, 20180179179, 20180179202, 20180177784, 20180177870, 20190300524, and 20190345170, each of which is incorporated herein by reference in its entirety.

The P ligands of Formula (P-3) (and embodiments thereof) can be synthesized as described in WO 2018195321, which is incorporated herein by reference in its entirety.

The S moieties of Formula (S-1) can be synthesized by methods analogous to those described in US Patent Publ. No. 20180105514, which is incorporated herein by reference in its entirety.

The S moieties of Formula (S-5) can be synthesized by methods analogous to those described in US Patent Publ. No. 20150056224 and 20140205653, each of which is incorporated herein by reference in its entirety.

The S moieties of Formula (S-2) can be synthesized according to Schemes 1-3. Accordingly, intermediates of formula 1-10 can be synthesized using a process shown in Scheme 1. Nucleophilic aromatic substitution of an appropriately functionalized nitro-halo-phenyl compound 1-1 with an amine containing a linker group $L^Y$ 1-2 can afford compound 1-3. Reduction of the aromatic nitro group followed by ring closing reaction with cyanogen bromide can provide the aminobenzimidazole 1-5. Amide coupling of compound 1-5 with carboxylic acid 1-6 can generate the aminobenzimidazole 1-7. Removal of the Boc protecting group in 1-7 can afford the amine 1-8 which can be converted to the alcohol 1-9 under Sandmeyer conditions. The compound 1-10 could be achieved by reacting the alcohol 1-9 with phosphorus (III) bromide.

Scheme 1

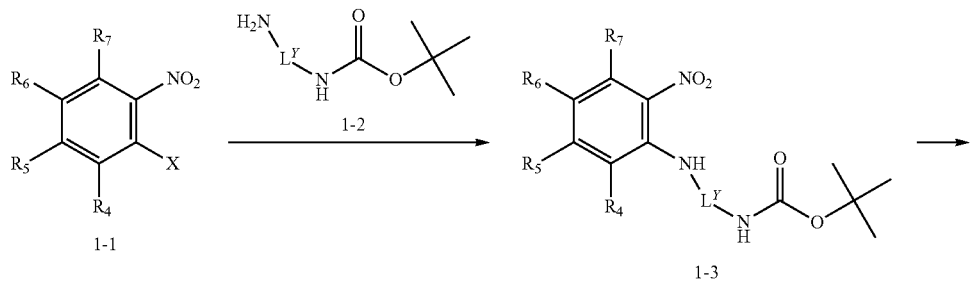

-continued

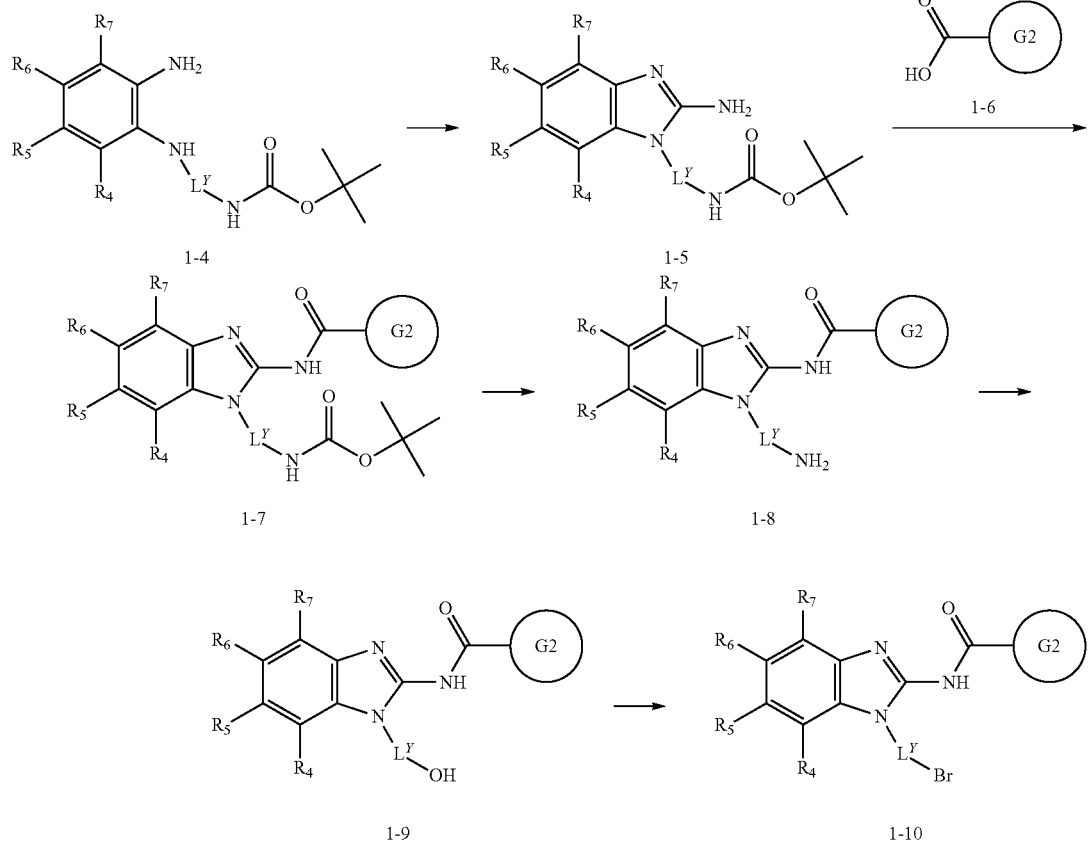

Compounds of formula 2-8 can be synthesized using a process shown in Scheme 2. Palladium-catalyzed cross-coupling reactions of the appropriate aryl halides and boronic acids/esters can produce the biaryl compounds of formula 2-5. Under deoxygenation conditions, the in-situ generated nitrene from compound 2-5 can insert into the adjacent aromatic C-H bond and afford the tricyclic compound 2-6. Suzuki coupling of the aryl-Cl 2-6 with aromatic boronic ester 2-7 can furnish the compounds of formula 2-8.

Scheme 2

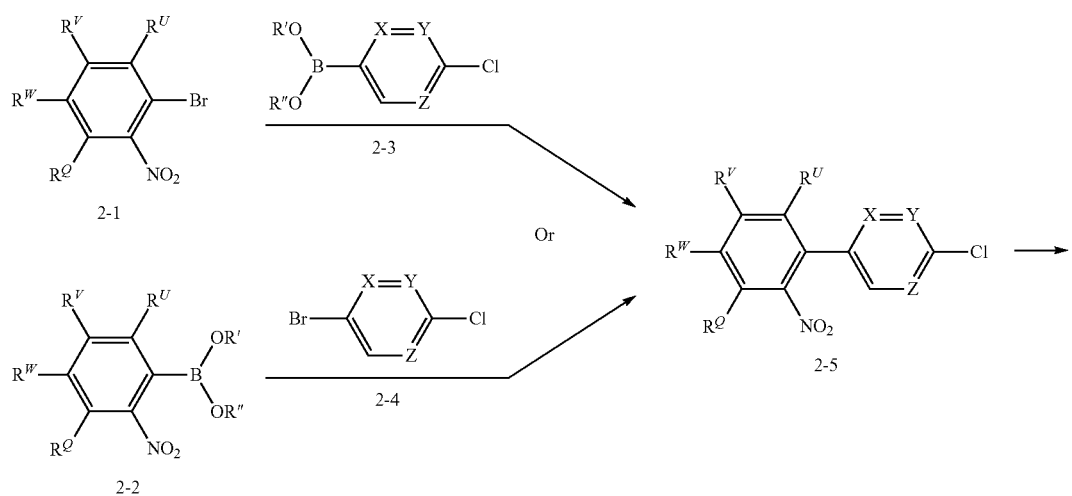

-continued

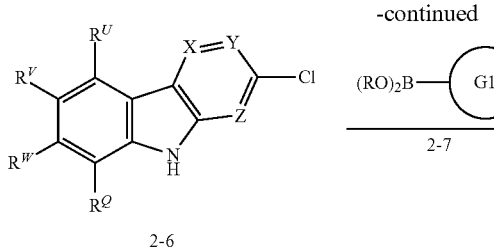

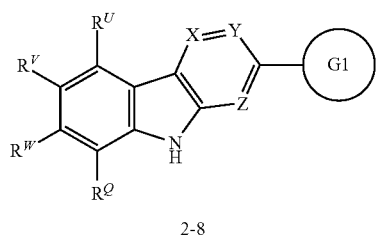

As shown in Scheme 3, reactions of compounds 3-1 and 3-2 under basic conditions can afford the compound of Formula (S-2).

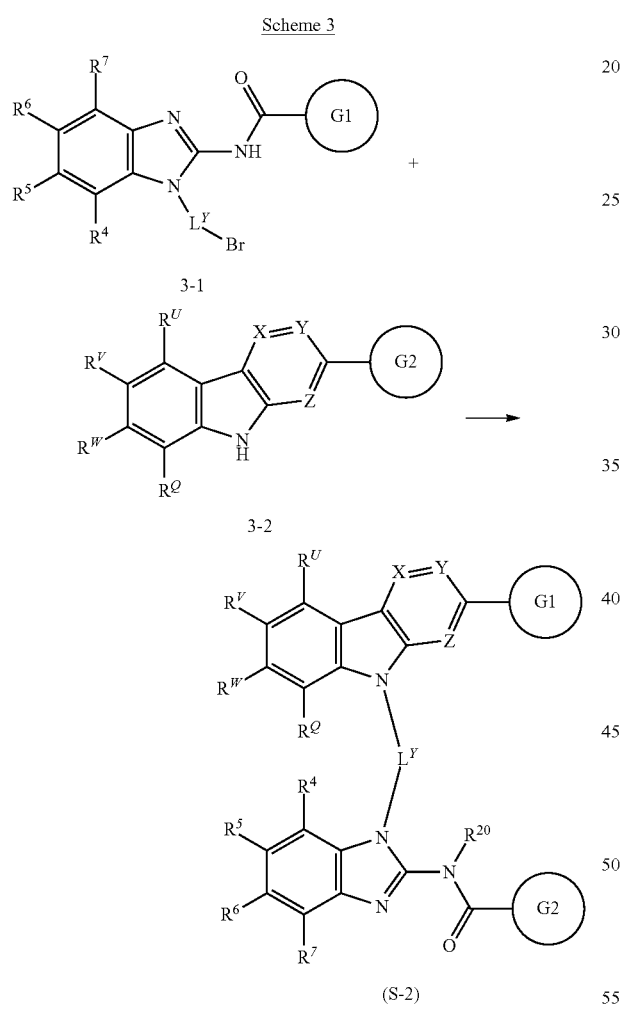

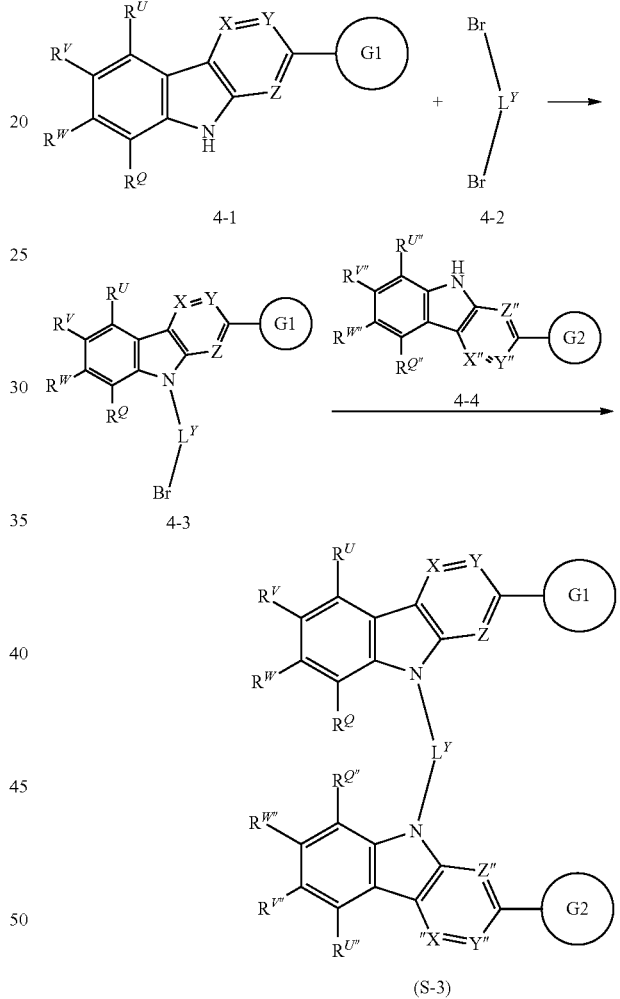

The S moieties of Formula (S-3) can be synthesized according to Scheme 4. First, intermediates 4-1 and 4-4 are synthesized by methods analogous to those in Scheme 2. Then, as shown in Scheme 4, reactions of compounds 4-1 and excess 4-2 under basic conditions can afford the compound of formula 4-3. Further reaction of compounds 4-3 and 4-4 under alkylation conditions such as in the presence of suitable base and a polar solvent can generate the target moiety of Formula (S-3).

The S moieties of Formula (S-4) can be synthesized according to Schemes 5-6. Accordingly, intermediates 5-8 can be synthesized using a process shown in Scheme 5. Nucleophilic aromatic substitution of an appropriately functionalized nitro-halo-phenyl compound 5-1 with an amine containing a linker group $L^Y$ of formula 5-2 can afford compound 5-3. Alternatively, transition metal (including, but not limited to, Pd and Cu) catalyzed C—N bond forming reactions may also be used to provide compound 5-3. Reduction of the aromatic nitro group followed by ring closing reaction with cyanogen bromide can provide the aminobenzimidazole 5-5. Amide coupling of compound 5-5 with carboxylic acid 5-6 can generate the aminobenzimidazole 5-7. Removal of the Boc protecting group in 5-7 can then afford the amine 5-8.

Scheme 5.

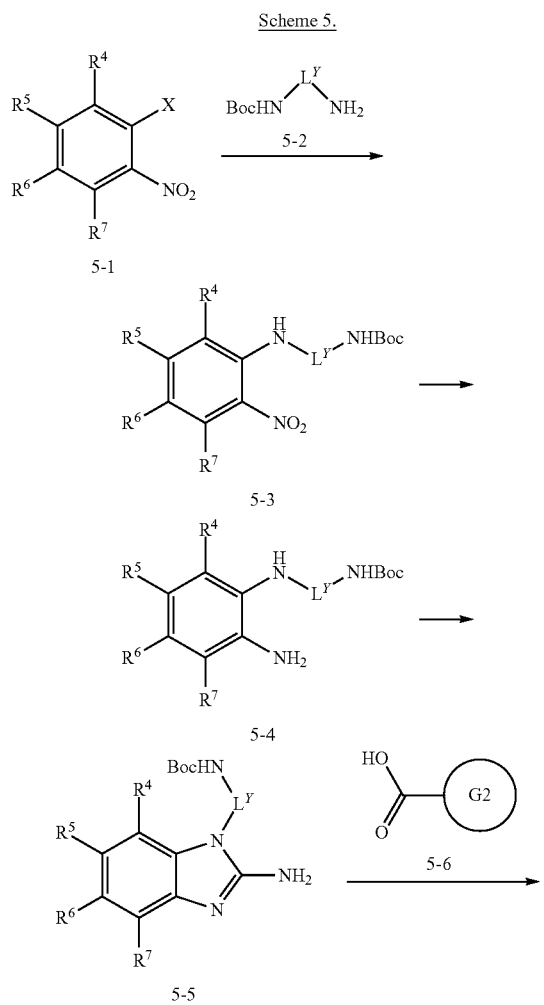

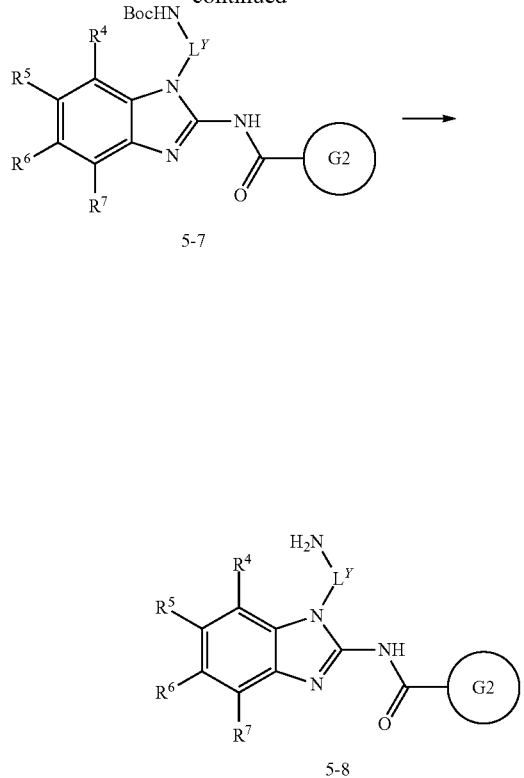

Compounds of Formula (S-4) can be synthesized using a process shown in Scheme 6. Cyclization of halo-benzene compound 6-1 in one or more steps provides an appropriately functionalized bicyclic nitro-halo-phenyl compound 6-2. Nucleophilic aromatic substitution of compound 6-2 with amine 5-8 can afford compound 6-4. Alternatively, transition metal (e.g. Pd, Cu, etc.) catalyzed C—N bond forming reactions may also be used to provide compound 6-4. Reduction of the aromatic nitro group followed by ring closing reaction with cyanogen bromide can provide the aminobenzimidazole 6-6. Amide coupling of compound 6-6 with carboxylic acid 6-7 can generate the amide 6-8.

Scheme 6.

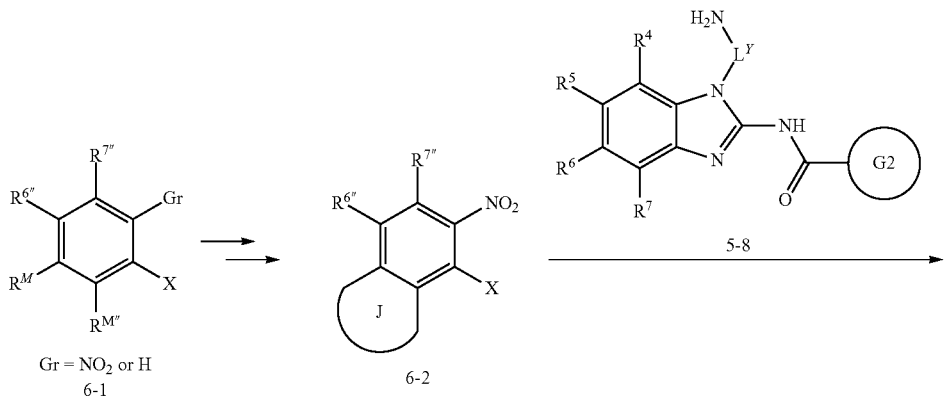

-continued

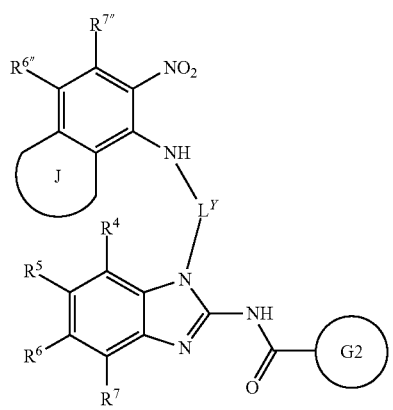

6-4

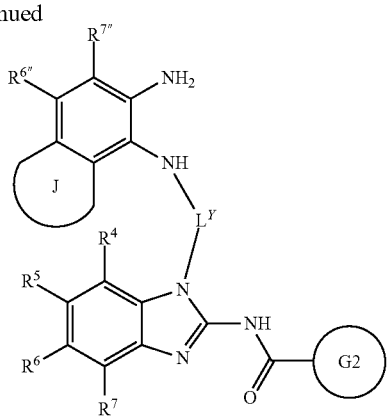

6-5

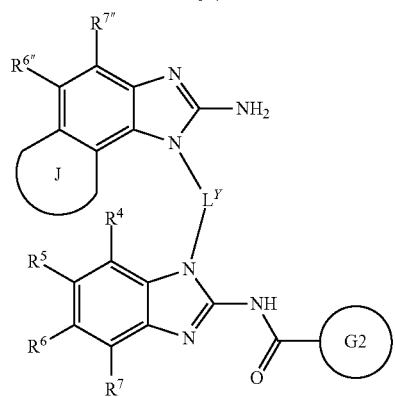

6-6

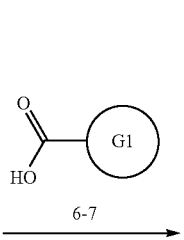

6-7

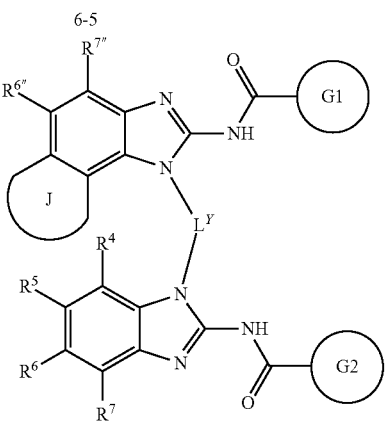

(S-4)

Conjugates of formula 7-5 can be synthesized using a process shown in Scheme 7. The S moiety 7-1 with unprotected amine and an appropriate linker 7-2 (e.g. peptide, polyethylene glycol, and etc.), with an Fmoc protected amine capped at one end and a naked carboxylic acid capped at the other end, are linked together under standard amide coupling conditions (e.g. BOP, HATU, etc.). After a same pot Fmoc removal, free amine 7-3 can be obtained. Following another amide coupling with PD-L1 protein ligand moiety containing carboxylic acid 7-4, which can be synthesized following the method we published previously, under standard conditions, the desired conjugate 7-5 can be obtained.

Scheme 7.

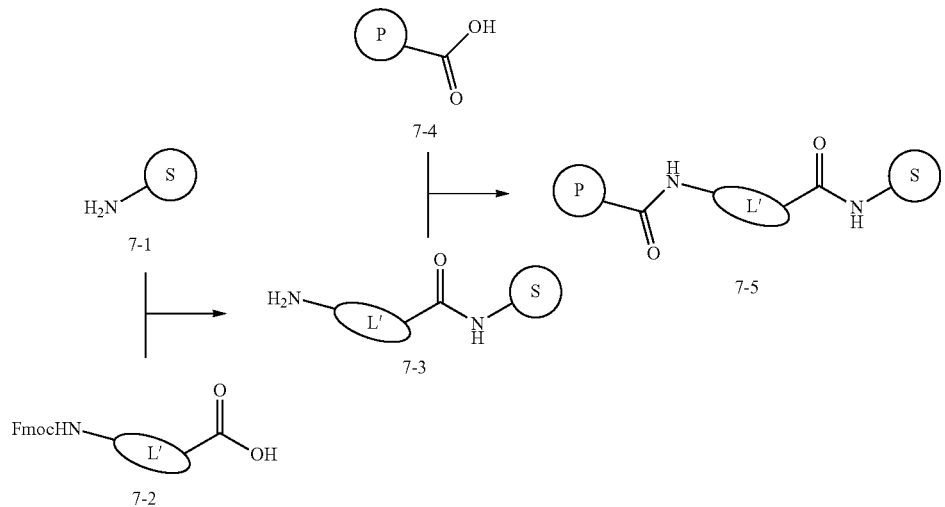

A conjugate of formula 8-4 with a cleavable dipeptide linker can be synthesized using a process shown in Scheme 8. The S moiety 7-1 with un-protected amine is coupled with commercially available 8-1 under standard carbamate formation conditions (e.g. DMAP and etc). After removal of Fmoc protection, free amine 8-2 can be obtained. After a sequence of amide coupling with an appropriate linker 7-2 and Fmoc deprotection will arrive at free amine 2-3. The desired conjugate 8-4 can be obtained by coupling the thus obtained amine 8-3 and PD-L1 protein ligand 7-4 under standard amide coupling conditions.

Scheme 8.

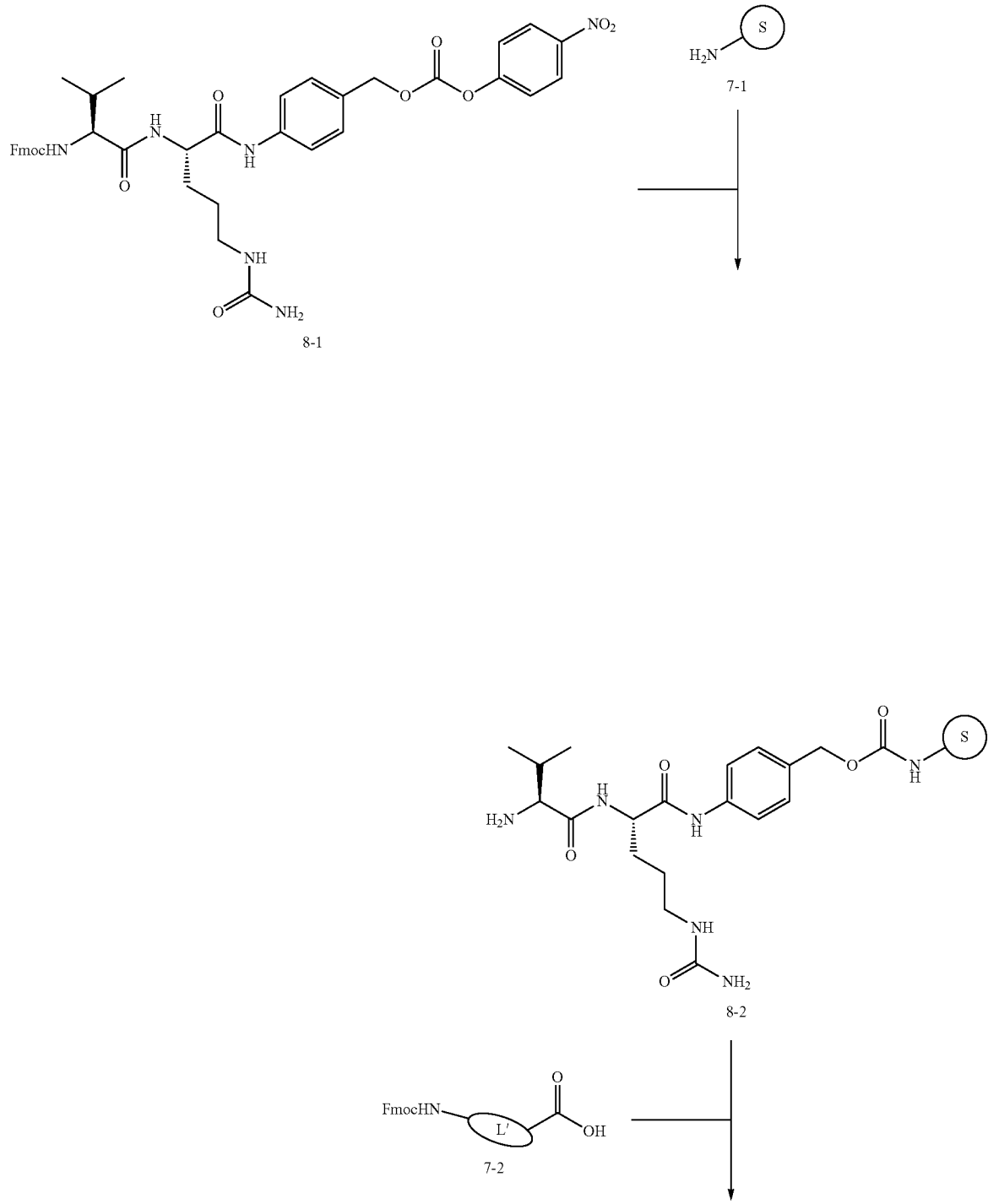

-continued

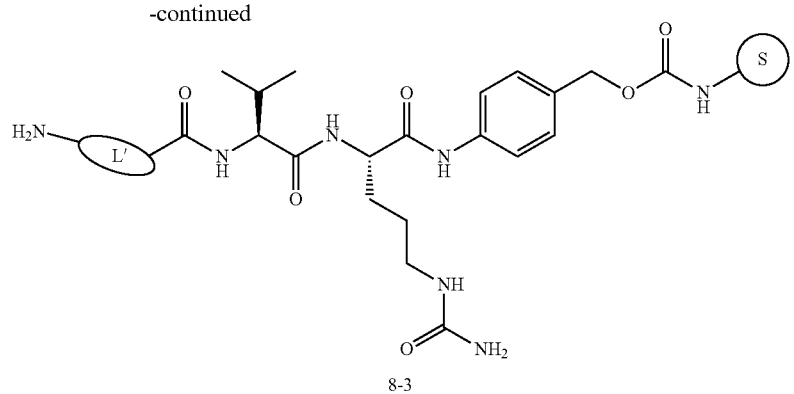

8-3

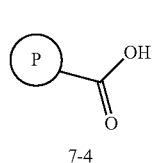

7-4

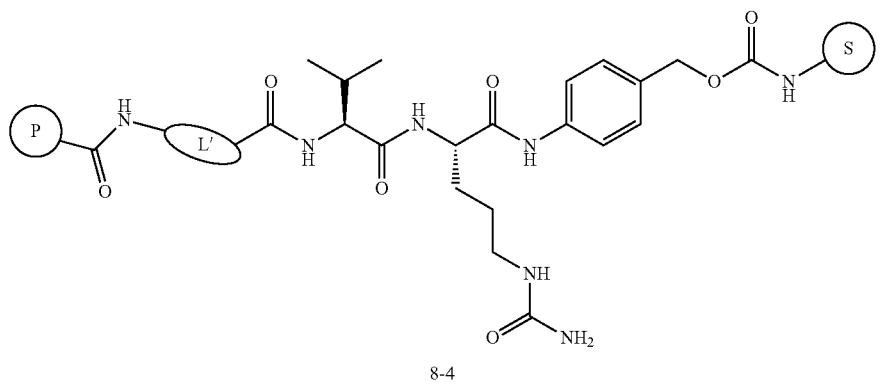

8-4

Conjugates having a disulfide linkage 9-5 can be prepared according to Scheme 9. Trityl protected thioamine 9-1 can be coupled to the PD-L1 ligand 7-4 under standard amide coupling conditions. After deprotection of trityl, thiol 9-2 can be obtained. On the other hand, STING agonist moiety 7-1 with un-protected amine is coupled with disulfide 9-3 under DMAP mediated carbamate formation condition to generate disulfide 9-4. Thus obtained thiol 9-2 and disulfide 9-4 can do disulfide exchange to afford the desired conjugate 9-5.

Scheme 9.

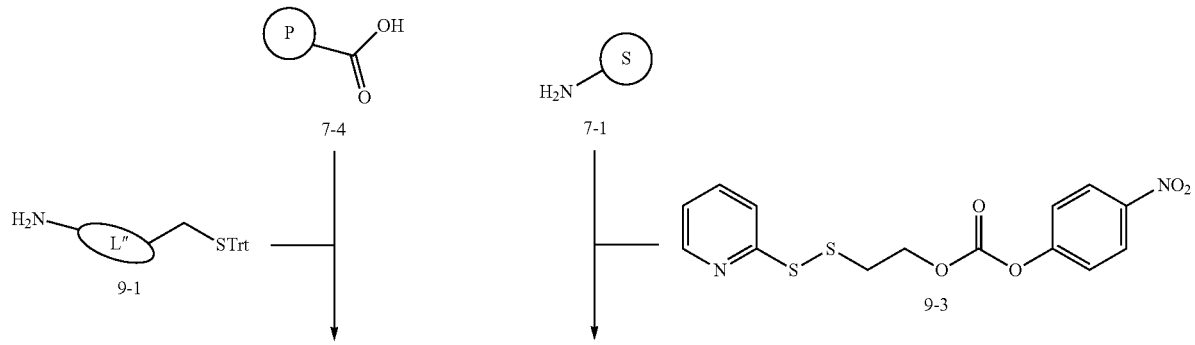

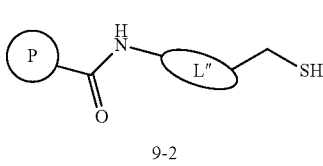
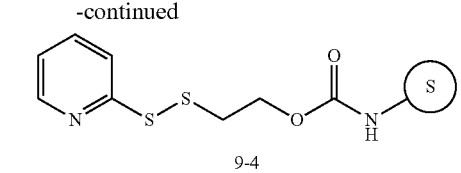
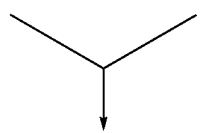
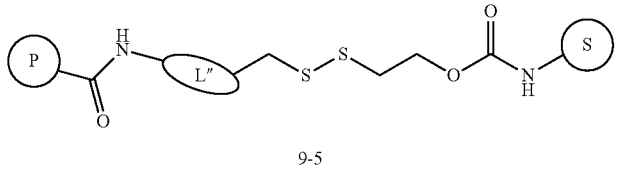

Alternatively, disulfide linkage containing conjugate 10-5 can be prepared according to Scheme 10. Azido amine 10-1 can be coupled to the PD-L1 ligand 7-4 under standard amide coupling conditions to provide azide 10-2. On the other hand, S moiety 7-1 with un-protected amine is coupled with 2-((2-(prop-2-yn-1-yloxy)ethyl)disulfanyl)ethan-1-ol 10-3 under CDI mediated carbamate formation condition to generate alkyne 10-4. Thus obtained azide 10-2 and alkyne 10-4 can be tethered together under standard click chemistry conditions (e.g. CuSO$_4$) to afford the desired conjugate 10-5.

Scheme 10.

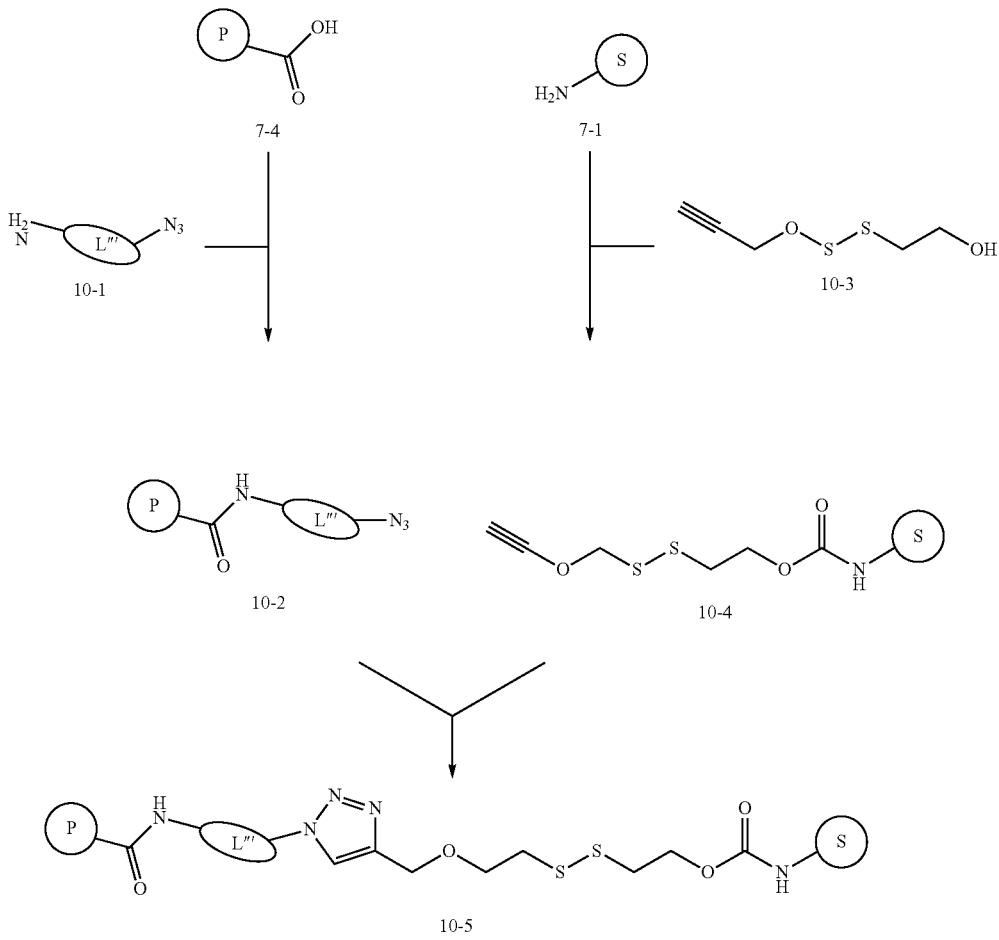

Formulation, Dosage Forms and Administration

When employed as pharmaceuticals, the compounds of the present disclosure can be administered in the form of pharmaceutical compositions. Thus the present disclosure provides a composition comprising a compound described herein or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This present disclosure also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the present disclosure, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the present disclosure may be milled using known milling procedures such as wet milling to obtain a particle size appropriate for tablet formation and for other formulation types. Finely divided (nanoparticulate) preparations of the compounds of the present disclosure can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the present disclosure can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 0.5 to about 1,000 mg, or from about 5 to about 1,000 mg (1 g), or from about 100 mg to about 500 mg, of the active ingredient. In some embodiments, each dosage contains about 1 mg of the active ingredient. In some embodiments, each dosage contains about 5 mg of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present disclosure can vary according to, e.g., the particular use for which the treatment is made, the manner of administration of the compound, the health and condition of the patient, and the judgment of the prescribing physician. The proportion or concentration of a compound of the present disclosure in a pharmaceutical composition can vary depending upon a number of factors including dosage, chemical characteristics (e.g., hydrophobicity), and the route of administration. For example, the compounds of the present disclosure can be provided in an aqueous physiological buffer solution containing from about 0.01 to about 10% w/v, or from about 0.1 to about 10% w/v, of the compound for parenteral administration. Some typical dose ranges are from about 0.1 µg/kg to about 1 g/kg, or from about 1 µg/kg to about 1 g/kg, of body weight per day. In some embodiments, the dose range is from about 0.001 mg/kg to about 100 mg/kg, or from about 0.01 mg/kg to about 100 mg/kg, of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.01 to about 1000 mg, or about 0.1 to about 1000 mg, of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.01, at least about 0.05, at least about 0.1, at least about 0.25, at least about 0.5, at least about 1, at least about 2 or at least about 5 wt % of the compound of the present disclosure. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present disclosure can vary according to, e.g., the particular use for which the treatment is made, the manner of administration of the compound, the health and condition of the patient, and the judgment of the prescribing physician. The proportion or concentration of a compound of the present disclosure in a pharmaceutical composition can vary depending upon a number of factors including dosage, chemical characteristics (e.g., hydrophobicity), and the route of administration. For example, the compounds of the present disclosure can be provided in an aqueous physiological buffer solution containing about 0.01 to about 10% w/v, or from about 0.1 to about 10% w/v of the compound for parenteral administration. Some typical dose ranges are from about 0.1 µg/kg to about 1 g/kg, or from about 1 µg/kg to about 1 g/kg, of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

The compounds of the present disclosure can further be useful in investigations of biological processes in normal and abnormal tissues. Thus, another aspect of the present disclosure relates to labeled compounds of the disclosure (radio-labeled, fluorescent-labeled, etc.) that would be useful not only in imaging techniques but also in assays, both in vitro and in vivo, for localizing and quantitating PD-1 or PD-L1 or STING protein in tissue samples, including human, and for identifying PD-L1 or STING ligands by inhibition binding of a labeled compound. Substitution of one or more of the atoms of the compounds of the present disclosure can also be useful in generating differentiated ADME (Adsorption, Distribution, Metabolism and Excretion). Accordingly, the present disclosure includes PD-1/PD-L1 or STING binding assays that contain such labeled compounds.

The present disclosure further includes isotopically-substituted compounds of the disclosure. An "isotopically-substituted" compound is a compound of the disclosure where one or more atoms are replaced or substituted by an atom having an atomic mass or mass number from the atomic mass or mass number typically found in nature (i.e., naturally occurring). Suitable radionuclides that may be incorporated in compounds of the present disclosure include but are not limited to $^2$H, $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —CD$_3$ being substituted for —CH$_3$). In some embodiments, alkyl groups of the disclosed Formulas (e.g., Formula (I), (II), etc.), can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —CD$_3$ being substituted for —CH$_3$). In some embodiments, the compound includes two or more deuterium atoms. In some embodiments, the compound includes 1, 1-2, 1-3, 1-4, 1-5, 1-6, 1-7, 1-8, or 1-9 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et.al. J. Med. Chem. 2011, 54, 201-210; R. Xu et.al. J. Label Compd. Radiopharm. 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro PD-L1 protein labeling and competition assays, compounds that incorporate $^3$H, $^{14}$C, $^{82}$Br, $^{125}$I, $^{131}$I, or $^{35}$S or can generally be useful.

It is understood that a "radio-labeled" or "labeled compound" is a compound that has incorporated at least one radionuclide. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. In some embodiments the radionuclide is selected from the group consisting of $^3$H, $^{14}$C, $^{125}$I, $^{35}$5 and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify and/or evaluate compounds. For example, a newly synthesized or identified compound (i.e., test compound) which is labeled can be evaluated for its ability to bind a PD-L1 protein by monitoring its concentration variation when contacting with the PD-L1 protein, through tracking of the labeling. For example, a test compound (labeled) can be evaluated for its ability to reduce binding of another compound which is known to bind to a PD-L1 protein (i.e., standard compound). Accordingly, the ability of a test compound to compete with the standard compound for binding to the PD-L1 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of PD-L1 or STING including its interaction with other proteins such as PD-1 and B7-1 (CD80), such as cancer or infections, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner Those of skill in the art will readily recognize a variety of non-critical parameters which can be changed or modified to yield essentially the same results.

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 30×100 mm or Waters XBridge™ $C_{18}$ 5 µm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ $C_{18}$ 5 µm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

Example S1. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-9H-pyrimido[4,5-b]indole-6-carboxamide

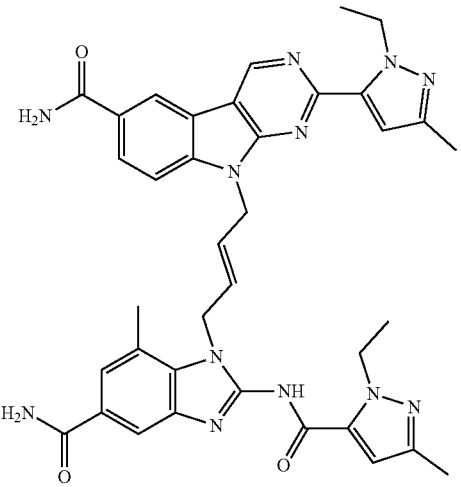 [SMILES: CCn1nc(C)cc1C(=O)Nc1nc2cc(C(N)=O)cc(C)c2n1C/C=C/Cn1c2ccc(C(N)=O)cc2c2cnc(-c3cc(C)nn3CC)nc21]

Step 1: 4-fluoro-3-methyl-5-nitrobenzamide

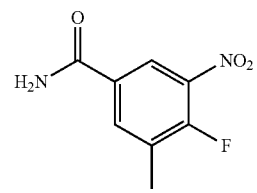

At 0° C., a mixture of nitric acid (2.51 ml, 39.2 mmol) and sulfuric acid (2.173 ml, 40.8 mmol) was added dropwise over 10 min into a solution of 4-fluoro-3-methylbenzamide (4.46 g, 29.1 mmol) in sulfuric acid (13.97 ml, 262 mmol). The mixture was stirred for 1.5 h while slowly warming up to room temperature. The mixture was slowly poured into ice water (50 mL), and the precipitated solid was filtered and then washed with water (50 mL). The resulting solid residue was dried to provide the desired product as a white solid. LC-MS calculated for $C_8H_8FN_2O_3$ $(M+H)^+$: m/z=199.04; found 199.2

Step 2: (E)-tert-butyl 4-(4-carbamoyl-2-methyl-6-nitrophenylamino)but-2-enylcarbamate

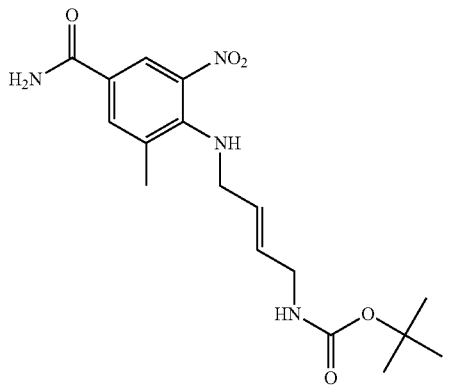

To a solution of 4-fluoro-3-methyl-5-nitrobenzamide (0.400 g, 2.019 mmol) and tert-butyl (E)-(4-aminobut-2-en-1-yl)carbamate (0.376 g, 2.019 mmol) (Ark Pharm, cat #AK308564) in dry DMSO (2.019 ml) was added $K_2CO_3$ (0.614 g, 4.44 mmol). The resulting yellow solution was stirred at room temperature for 1 h. The reaction mixture was diluted with water (15 mL) dropwise. The precipitated solid was filtered and then washed with water (10 mL). The resulting solid residue was dried to provide the desired product as a yellow solid. LC-MS calculated for $C_{17}H_{24}N_4NaO_5$ (M+Na)$^+$: m/z=387.2; found 387.2.

Step 3: (E)-tert-butyl 4-(2-amino-4-carbamoyl-6-methylphenylamino)but-2-enylcarbamate

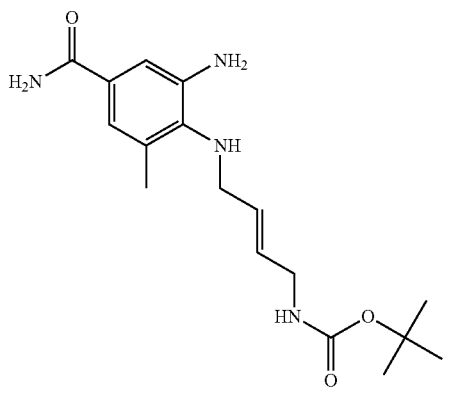

To a solution of tert-butyl (E)-(4-((4-carbamoyl-2-methyl-6-nitrophenyl)amino)but-2-en-1-yl)carbamate (220 mg, 0.604 mmol) in dioxane (1509 µl) and water (503 µl) was added ammonium chloride (226 mg, 4.23 mmol) and zinc (276 mg, 4.23 mmol) at 0° C. The reaction mixture was stirred at room temperature for 1 h, after which time it was filtered through a Celite bed. The filtrate was partitioned between DCM and water. The organic layer was separated, dried over $MgSO_4$, filtered, and concentrated to provide the product. LC-MS calculated for $Ci7H26N4NaO3$ (M+Na)$^+$: m/z=357.2 ; found 357.3.

Step 4: (E)-tert-butyl 4-(2-amino-5-carbamoyl-7-methyl-1H-benzo[d]imidazol-1-yl)but-2-enylcarbamate

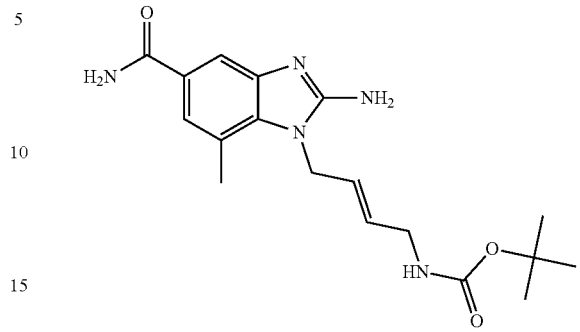

To a solution of tert-butyl (E)-(4-((2-amino-4-carbamoyl-6-methylphenyl)amino)but-2-en-1-yl)carbamate (0.201 g, 0.60 mmol) in MeOH (2.000 ml) was added cyanogen bromide (0.047 ml, 0.900 mmol). The reaction mixture was stirred at room temperature for 1 h. The mixture was diluted with DCM, and washed with water and brine. The organic phase was dried over $MgSO_4$ before filtering. The filtrate was concentrated and purified by flash chromatography on a silica gel column eluting with 0 to 8% MeOH in DCM to afford the desired product. LC-MS calculated for $C_{18}H_{26}N_5O_3$ (M+H)$^+$: m/z=360.2; found 360.3.

Step 5: (E)-tert-butyl 4-(5-carbamoyl-2-(1-ethyl-3-methyl-1H-pyrazole-5-carboxamido)-7-methyl-1H-benzo[d]imidazol-1-yl)but-2-enylcarbamate

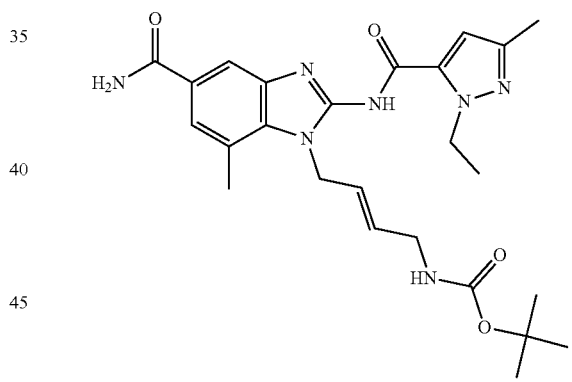

A mixture of 1-ethyl-3-methyl-1H-pyrazole-5-carboxylic acid (Combi-Blocks, cat #QB-0979: 93 mg, 0.60 mmol), tert-butyl (E)-(4-(2-amino-5-carbamoyl-7-methyl-1H-benzo[d]imidazol-1-yl)but-2-en-1-yl)carbamate (216 mg, 0.600 mmol), 2-(3H-[1,2,3]triazolo[4,5-b]pyridin-3-yl)-1,1,3,3-tetramethylisouronium hexafluorophosphate(V) (274 mg, 0.720 mmol), and N,N-Diisopropylethylamine (209 µl, 1.200 mmol) in DMF (2000 µl) was stirred at room temperature for 2 h. The mixture was concentrated under reduced pressure. The mixture was then diluted with DCM and water, and the layers were separated. The aqeous layer was further extracted with DCM and the combined organic layers were washed with brine, dried over $Na_2SO_4$, filtered, and concentrated in vacuo. The crude residue was purified by flash chromatography on a silica gel column eluting with 0 to 8% MeOH in DCM to afford the desired product. LC-MS calculated for $C_{25}H_{34}N_7O_4$ (M+H)$^+$: m/z=496.3 ; found 496.3.

Step 6: (E)-1-(4-aminobut-2-enyl)-2-(1-ethyl-3-methyl-1H-pyrazole-5-carboxamido)-7-methyl-1H-benzo[d]imidazole-5-carboxamide

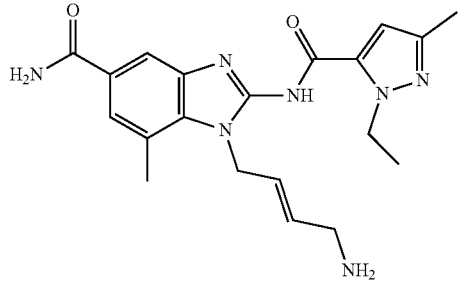 [SMILES: CCn1nc(C)cc1C(=O)Nc1nc2cc(C(N)=O)cc(C)c2n1C/C=C/CN]

To a solution of tert-butyl (E)-(4-(5-carbamoyl-2-(1-ethyl-3-methyl-1H-pyrazole-5-carboxamido)-7-methyl-1H-benzo[d]imidazol-1-yl)but-2-en-1-yl)carbamate (180.0 mg, 0.363 mmol) in DCM (2.0 mL) was added TFA (0.2 mL). The resulting solution was stirred at room temperature for 0.5 h. The reaction mixture was quenched by NaHCO$_3$ aqueous solution then extracted with DCM. The organic phases were combined and dried over MgSO$_4$, then filtered. The filtrate was concentrated and used directly in the next step without further purification. For characterization purposes, the crude material was purified by prep HPLC (pH=2, water+TFA) to provide the desired compound as its TFA salt. LC-MS calculated for $C_{20}H_{26}N_7O_2$ (M+H)$^+$: m/z=396.2; found 396.3. $^1$H NMR (400 MHz, DMSO) δ 12.91 (s, 1H), 7.87 (m, 2H), 7.69 (br s, 2H), 7.57 (s, 1H), 7.30 (s, 1H), 6.64 (s, 1H), 6.10 (dt, J=16.0, 4.8 Hz, 1H), 5.33 (dt, J=16.0, 6.4 Hz, 1H), 5.06 (brs, 2H), 4.59 (q, J=6.8 Hz, 2H), 3.42 (dt, J=6.4 Hz, 4.8 Hz, 2H), 2.63 (s, 3H), 2.16 (s, 3H), 1.34 (t, J=6.8 Hz, 3H).

Step 7: (E)-2-(1-ethyl-3-methyl-1H-pyrazole-5-carboxamido)-1-(4-hydroxybut-2-enyl)-7-methyl-1H-benzo[d]imidazole-5-carboxamide

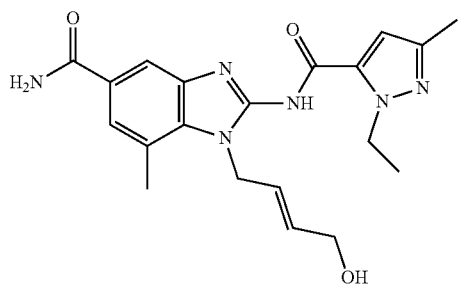 [SMILES: CCn1nc(C)cc1C(=O)Nc1nc2cc(C(N)=O)cc(C)c2n1C/C=C/CBr]

To a mixture of (E)-1-(4-aminobut-2-en-1-yl)-2-(1-ethyl-3-methyl-1H-pyrazole-5-carboxamido)-7-methyl-1H-benzo[d]imidazole-5-carboxamide (180.0 mg, 0.455 mmol) and KBr (108 mg, 0.910 mmol) in water (228 μl) was added sodium nitrite (62.8 mg, 0.910 mmol). The mixture was stirred at 70° C. for 2 h. After cooling to rt, the mixture was diluted with DCM, and washed with water and brine. The organic phase was dried over MgSO$_4$ before filtering. The filtrate was concentrated to afford the desired product. LC-MS calculated for $C_{20}H_{25}N_6O_3$ (M+H)$^+$: m/z=397.2; found 397.2.

Step 8: (E)-1-(4-bromobut-2-enyl)-2-(1-ethyl-3-methyl-1H-pyrazole-5-carboxamido)-7-methyl-1H-benzo[d]imidazole-5-carboxamide

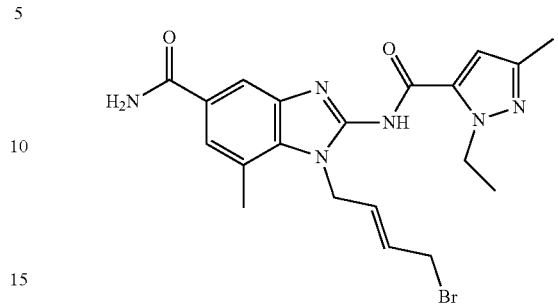

To a solution of (E)-2-(1-ethyl-3-methyl-1H-pyrazole-5-carboxamido)-1-(4-hydroxybut-2-enyl)-7-methyl-1H-benzo[d]imidazole-5-carboxamide (180.0 mg, 0.455 mmol) in THF (2.0 mL) was added PBr$_3$ (86 μl, 0.910 mmol) dropwise. The resulting solution was stirred at room temperature for 10 h. The reaction mixture was quenched by NaHCO$_3$ aqueous solution then extracted with DCM. The organic phases were combined and dried over MgSO$_4$, then filtered. The crude residue was purified by flash chromatography on a silica gel column eluting with 0 to 10% MeOH in DCM to afford the desired product. LC-MS calculated for C2oH24BrN6O2 (M+H)$^+$: m/z=459.1, 461.1; found 459.1, 461.1.

Step 9: 3-(2-chloropyrimidin-5-yl)-4-nitrobenzamide

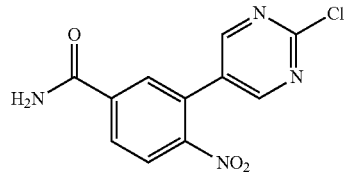 [SMILES: NC(=O)c1ccc([N+](=O)[O-])c(-c2cnc(Cl)nc2)c1]

To a solution of 3-bromo-4-nitrobenzamide (Matrix Scientific, cat #184225: 600.0 mg, 2.449 mmol), (2-chloropyrimidin-5-yl)boronic acid (Combi-Blocks, cat #BB-5457: 388 mg, 2.449 mmol), and sodium carbonate (519 mg, 4.90 mmol) in dioxane (2 mL) and water (0.4 mL) was added dichloro[1,1'-bis(diphenylphosphino)ferrocene]palladium (II) dichloromethane adduct (120 mg, 0.147 mmol). The vial was flushed with nitrogen, and the reaction was stirred at 100° C. for 1 h. The reaction mixture was quenched by NH$_4$OH aqueous solution then extracted with DCM. The organic phases were combined and dried over MgSO$_4$, then filtered. The crude residue was purified by flash chromatography on a silica gel column eluting with 0 to 8% MeOH in DCM to afford the desired product. LC-MS calculated for $C_{11}H_8ClN_4O_3$ (M+H)$^+$: m/z=279.0; found 279.0.

Step 10: 2-chloro-9H-pyrimido[4,5-b]indole-6-carboxamide

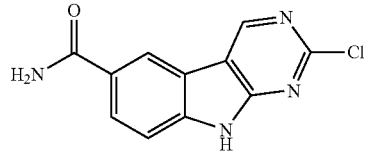 [SMILES: NC(=O)c1ccc2[nH]c3nc(Cl)ncc3c2c1]

A mixture of 3-(2-chloropyrimidin-5-yl)-4-nitrobenzamide (320.0 mg, 1.148 mmol) and 1,2-bis(diphenylphosphino)ethane (572 mg, 1.435 mmol) was dissolved in 1,2-dichlorobenzene (3828 µl). The vial was flushed with nitrogen before heating at 160° C. for 1 h. After removal of the solvent under vacuum, the reaction mixture was extracted with DCM and water. The organic phases were combined and dried over MgSO$_4$, filtered, then concentrated under reduced pressure. The crude residue was purified by flash chromatography on a silica gel column eluting with 0 to 8% MeOH in DCM to afford the desired product. LC-MS calculated for CiiH8C1N4O (M+H)$^+$: m/z=247.0; found 247.0.

Step 11: 2-(1-ethyl-3-methyl-1H-pyrazol-5-yl)-9H-pyrimiclo[4,5-b]indole-6-carboxamide

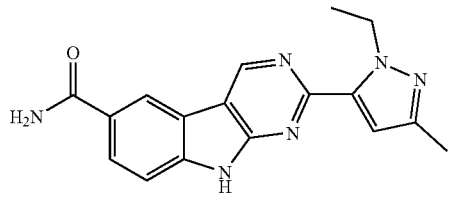 [SMILES: CCn1nc(C)cc1-c1ncc2c(n1)[nH]c1ccc(C(N)=O)cc12]

To a solution of 2-chloro-9H-pyrimido[4,5-b]indole-6-carboxamide (60.0 mg, 0.243 mmol), 1-ethyl-3-methyl-5-(4,4,5,5-tetramethyl-1,3,2-dioxaborolan-2-yl)-1H-pyrazole (Enamine, cat #EN300-207291: 57.4 mg, 0.243 mmol), and sodium carbonate (51.6 mg, 0.487 mmol) in dioxane (676 µl) and water (135 µl) was added dichloro[1,1'-bis(diphenylphosphino)ferrocene]palladium (II) dichloromethane adduct (11.92 mg, 0.015 mmol). The vial was flushed with nitrogen, and the reaction was stirred at 100° C. for 1 h. The reaction mixture was quenched by NH$_4$OH aqueous solution then extracted with DCM. The organic phases were combined and dried over MgSO$_4$, then filtered. The crude residue was purified by flash chromatography on a silica gel column eluting with 0 to 8% MeOH in DCM to afford the desired product. LC-MS calculated for C$_{17}$H$_{17}$N6O (M+H)$^+$: m/z=321.1; found 321.1.

Step 12: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1- ethyl-3-methyl-1H-pyrazol-5-yl)-9H-pyrimido[4,5-b]indole-6-carboxamide A mixture of 2-(1-ethyl-3-methyl-1H-pyrazol-5-yl)-9H-pyrimido[4,5-b]indole-6-carboxamide (5.0 mg, 0.016 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (7.17 mg, 0.016 mmol), and cesium carbonate (11.19 mg, 0.034 mmol) was stirred in DMF (156 µl) at 50° C. for 1 h. The reaction mixture was diluted with MeOH and purified by prep-HPLC (pH=2, acetonitrile/water+TFA) to give the desired product as its TFA salt. LC-MS calculated for C$_{37}$H$_{39}$N$_{12}$O$_3$ (M+H)$^+$: m/z=699.3; found 699.3.

Example S2. (E)-1-(4-(2-(1-ethyl-3-methyl-1H-pyrazol-5-yl)-9H-pyrimido[4,5-b]indol-9-yl)but-2-enyl)-2-(1-ethyl-3-methyl-1H-pyrazole-5-carboxamido)-7-methyl-1H-benzo[d]imidazole-5-carboxamide

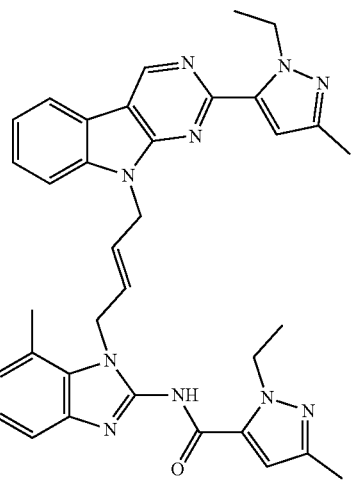

Step 1: 2-(1-ethyl-3-methyl-1H-pyrazol-5-yl)-9H-pyrimido[4,5-b]indole

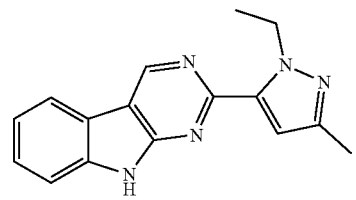 [SMILES: CCn1nc(C)cc1-c1ncc2c(n1)[nH]c1ccccc12]

This compound was prepared using similar procedures as described for Example S1, Step 9 to Step 11 with 1-bromo-2-nitrobenzene (Aldrich, cat #365424) replacing 3-bromo-4-nitrobenzamide LC-MS calculated for C$_{16}$H$_{16}$N$_5$ (M+H)$^+$: m/z=278.2; found 278.2.

Step 2: (E)-1-(4-(2-(1-ethyl-3-methyl-1H-pyrazol-5-yl)-9H-pyrimido[4,5-b]indol-9-yl)but-2-enyl)-2-(1-ethyl-3-methyl-1H-pyrazole-5-carboxamido)-7-methyl-1H-benzo[d]imidazole-5-carboxamide A mixture of 2-(1-ethyl-3-methyl-1H-pyrazol-5-yl)-9H-pyrimido[4,5-b]indole (5.0 mg, 0.018 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (8.28 mg, 0.018 mmol), and cesium carbonate (12.92 mg, 0.040 mmol) was stirred in DMF (60.1 µl) at 50° C. for 1 h. The reaction mixture was diluted with MeOH and purified by prep-HPLC (pH=2, acetonitrile/water+TFA) to give the desired product as its TFA salt. LC-MS calculated for C$_{36}$H$_{38}$N$_{11}$O$_2$ (M+H)$^+$: m/z=656.3; found 656.3.

Example S3. (E)-9-(4-(5-carbamoyl-2-(1-ethyl-3-methyl-1H-pyrazole-5-carb oxamido)-7-methyl-1H-benzo[d]imidazol-1-yl)but-2-enyl)-2-(1,3-dimethyl-1H-pyrazol-5-yl)-9H-pyrimido[4,5-b]indole-6-carboxamide

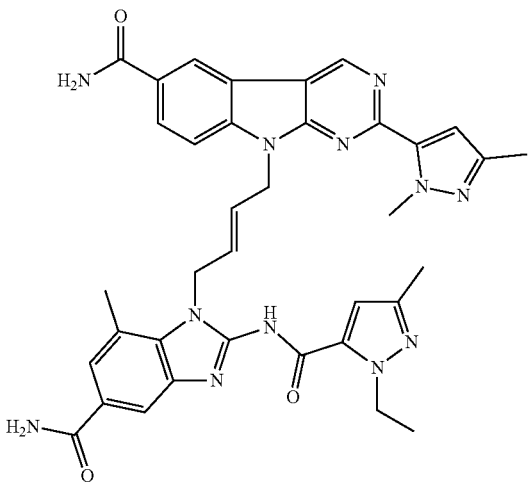 [SMILES: CCn1nc(C)cc1C(=O)Nc1nc2cc(C(N)=O)cc(C)c2n1C/C=C/Cn1c2ccc(C(N)=O)cc2c2cnc(-c3cc(C)nn3C)nc21]

Step 1: 2-(1,3-dimethyl-1H-pyrazol-5-yl)-9H-pyrimido[4,5-b]indole-6-carboxamide

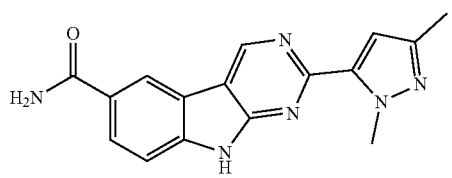 [SMILES: Cc1cc(-c2ncc3c(n2)[nH]c2ccc(C(N)=O)cc23)n(C)n1]

This compound was prepared using similar procedures as described for Example S1, Step 11 with 1,3-dimethyl-5-(4,4,5,5-tetramethyl-1,3,2-dioxaborolan-2-yl)-1H-pyrazole (Combi-Blocks, cat #PN-6021) replacing 1-ethyl-3-methyl-5-(4,4,5,5-tetramethyl-1,3,2-dioxaborolan-2-yl)-1H-pyrazole. LC-MS calculated for $C_{16}H_{15}N_6O$ $(M+H)^+$: m/z=307.2; found 307.2.

Step 2: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1,3-dimethyl-1H-pyrazol-5-yl)-9H-pyrimido[4,5-b]indole-6-carboxamide A mixture of 2-(1,3-dimethyl-1H-pyrazol-5-yl)-9H-pyrimido[4,5-b]indole-6-carboxamide (5.0 mg, 0.016 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (7.50 mg, 0.016 mmol), and cesium carbonate (11.70 mg, 0.036 mmol) was stirred in DMF (54.4 μl) at 50° C. for 1 h. The reaction mixture was diluted with MeOH and purified by prep-HPLC (pH=2, acetonitrile/water+TFA) to give the desired product as its TFA salt. LC-MS calculated for $C_{36}H_{37}N_{12}O_3$ $(M+H)^+$: m/z=685.3; found 685.3. $^1$H NMR (600 MHz, DMSO) δ 9.50 (s, 1H), 8.81 (s, 1H), 8.05 (d, J=8.6 Hz, 1H), 7.83 (s, 1H), 7.71 (d, J=8.6 Hz, 1H), 7.46 (s, 1H), 6.79 (s, 1H), 6.45 (s, 1H), 5.91 (dt, J=15.6, 4.8 Hz, 1H), 5.66 (dt, J=15.6, 4.8 Hz, 1H), 5.13 (d, J=4.8 Hz, 2H), 4.95 (d, J=4.8 Hz, 2H), 4.49 (q, J=7.0 Hz, 3H), 4.17 (s, 3H), 2.46 (s, 3H), 2.20 (s, 3H), 2.10 (s, 3H), 1.24 (t, J=7.0 Hz, 2H).

Example S4. (E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-d]indole-6-carboxamide

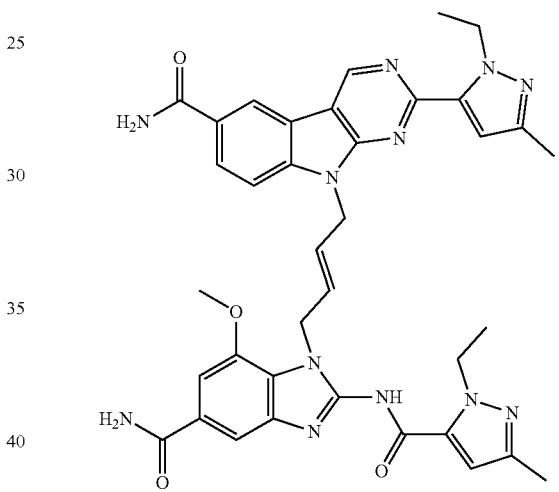

Step 1: 4-fluoro-3-methoxy-5-nitrobenzamide

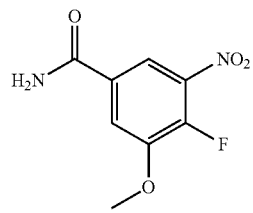

Methyl 4-fluoro-3-methoxy-5-nitrobenzoate (4.0 g, 17.45 mmol) was stirred in ammonium hydroxide (42.8 ml, 1100 mmol) at room temperature for 10 h. The solid was filtered and rinsed with cold water. The resulting solid residue was dried to provide the desired product as a light yellow solid. LC-MS calculated for $C_8H_8FN_2O_4$ $(M+H)^+$: m/z=215.04; found 215.2

Step 2: (E)-tert-butyl 4-(4-carbamoyl-2-methoxy-6-nitrophenylamino)but-2-enylcarbamate

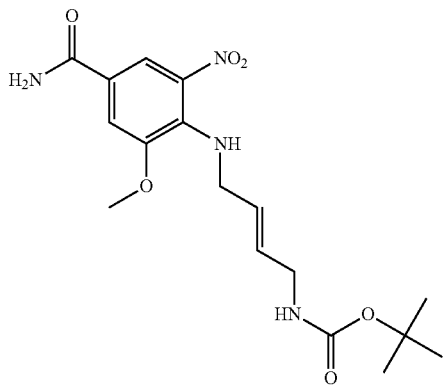 [SMILES: COc1cc(C(N)=O)cc([N+](=O)[O-])c1NC/C=C/CNC(=O)OC(C)(C)C]

To a solution of 4-fluoro-3-methoxy-5-nitrobenzamide (300.0 mg, 1.401 mmol), tert-butyl (E)-(4-aminobut-2-en-1-yl)carbamate (391 mg, 2.101 mmol) in dry DMSO (2335 µl) was added $K_2CO_3$ (387 mg, 2.80 mmol). The resulting solution was heated at 70° C. for 12 h. The mixture was concentrated under reduced pressure, and then extracted with DCM and water. The combined organic layers were dried, filtered, and concentrated in vacuo. The crude residue was purified by flash chromatography on a silica gel column to afford the desired product. LC-MS calculated for $C_{17}H_{24}N_4NaO_6$ (M+Na)$^+$: m/z=403.2; found 403.2.

Step 3: (E)-1-(4-bromobut-2-en-1-yl)-2-(1-ethyl-3-methyl-1H-pyrazole-5-carboxamido)-7-methoxy-1H-benzo[d]imidazole-5-carboxamide

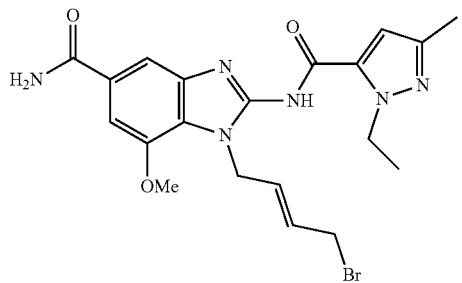 [SMILES: CCn1nc(C)cc1C(=O)Nc1nc2cc(C(N)=O)cc(OC)c2n1C/C=C/CBr]

This compound was prepared using similar procedures as described for Example S1, Step 3-8 with (E)-tert-butyl 4-(4-carbamoyl-2-methoxy-6-nitrophenylamino)but-2-enylcarbamate replacing (E)-(4-((4-carbamoyl-2-methyl-6-nitrophenyl)amino)but-2-en-1-yl)carbamate. LC-MS calculated for $C_{20}H_{24}BrN_6O_3$ (M+H)$^+$: m/z=475.1, 477.1; found 475.1, 477.1.

Step 4: (E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide A mixture of 2-(1-ethyl-3-methyl-1H-pyrazol-5-yl)-9H-pyrimido[4,5-b]indole-6-carboxamide (5.0 mg, 0.016 mmol), (E)-1-(4-bromobut-2-en-1-yl)-2-(1-ethyl-3-methyl-1H-pyrazole-5-carboxamido)-7-methoxy-1H-benzo[d]imidazole-5-carboxamide (7.42 mg, 0.016 mmol), and cesium carbonate (11.19 mg, 0.034 mmol) was stirred in DMF (52.0 µl) at 50° C. for 1 h. The reaction mixture was diluted with MeOH and purified by prep-HPLC (pH=2, acetonitrile/water+TFA) to give the desired product as its TFA salt. LC-MS calculated for $C_{37}H_{39}N_{12}O_4$ (M+H)$^+$: m/z=715.3; found 715.3.

Example S5. (E)-9-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazol-5-yl)-9H-pyrido[2,3-b]indole-6-carboxamide

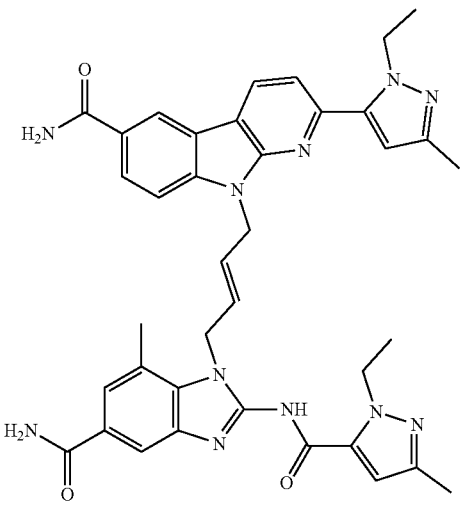 [SMILES: CCn1nc(C)cc1C(=O)Nc1nc2cc(C(N)=O)cc(C)c2n1C/C=C/Cn1c2ccc(C(N)=O)cc2c2ccc(-c3cc(C)nn3CC)nc21]

Step 1: 3-(6-(1-ethyl-3-methyl-1H-pyrazol-5-yl)pyridin-3-yl)-4-nitrobenzonitrile

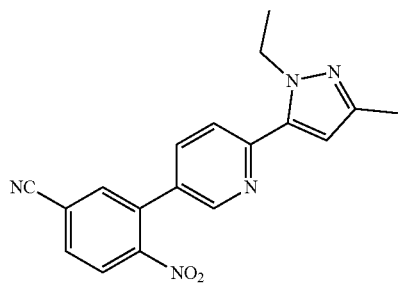 [SMILES: CCn1nc(C)cc1-c1ccc(-c2cc(C#N)ccc2[N+](=O)[O-])cn1]

To a degasseed solution of 3-bromo-4-nitrobenzonitrile (J&W PharmLab, cat #05R0293: 50 mg, 0.220 mmol) and 2-chloro-5-(4,4,5,5-tetramethyl-1,3,2-dioxaborolan-2-yl)pyridine (Aldrich, cat #659843: 52.8 mg, 0.220 mmol) in dioxane (587 µl) and water (147 µl) was added dichloro[1, 1'-bis(diphenylphosphino)ferrocene]palladium (II) dichloromethane adduct (8.99 mg, 0.011 mmol) and sodium carbonate (46.7 mg, 0.440 mmol). The reaction was stirred at 100° C. for 2 h. 1-Ethyl-3-methyl-5-(4,4,5,5-tetramethyl-1,3,2-dioxaborolan-2-yl)-1H-pyrazole (Enamine Ltd, cat #EN300-207291: 52.0 mg, 0.220 mmol) was added. The reaction mixture was heated to 100° C. for another 1 h. $H_2O$ (2 mL) was added to the reaction mixture, followed by extraction with ethyl acetate (2 mL×5). The combined organic layers were dried with $Na_2SO_4$, filtered and concentrated. The crude product was used directly without further purification. LC-MS calculated for $C_{18}H_{16}N_5O_2$ (M+H)$^+$: m/z=334.1; found 334.2.

149

Step 2: 2-(1-ethyl-3-methyl-1H-pyrazol-5-yl)-9H-pyrido[2,3-b]indole-6-carbonitrile

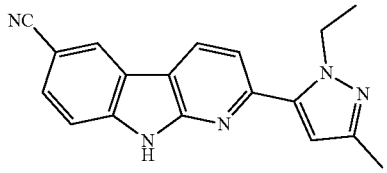 [SMILES: CCn1nc(C)cc1-c1ccc2c(n1)[nH]c1ccc(C#N)cc12]

To a solution of above crude 3-(6-(1-ethyl-3-methyl-1H-pyrazol-5-yl)pyridin-3-yl)-4-nitrobenzonitrile in 1,2-dichlorobenzene (1 mL) was added dppe (132 mg, 0.330 mmol). The reaction mixture was heated to 160° C. for 3 h, then the solvent was removed under vacuum. The crude product was used directly without further purification. LC-MS calculated for $C_{18}H_{16}N_5$ (M+H)$^+$: m/z=302.1; found 302.2.

Step 3: 2-(1-ethyl-3-methyl-1H-pyrazol-5-yl)-9H-pyrido[2,3-b]indole-6-carboxamide

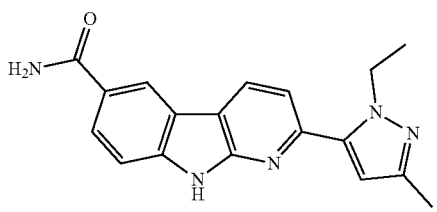 [SMILES: CCn1nc(C)cc1-c1ccc2c(n1)[nH]c1ccc(C(N)=O)cc12]

The above crude 2-(1-ethyl-3-methyl-1H-pyrazol-5-yl)-9H-pyrido[2,3-b]indole-6-carbonitrile was dissolved in EtOH (0.8 mL) and water (0.2 mL). Ghaffar-Parkins cat. (5 mg) was added and the resulting mixture was heated at 95° C. for 4 h to afford 2-(1-ethyl-3-methyl-1H-pyrazol-5-yl)-9H-pyrido[2,3-b]indole-6-carboxamide as the major regioselective isomer. The reaction mixture was diluted with MeOH then purified by prep-HPLC (pH=2, acetonitrile/water+TFA) to give the desired product as the TFA salt. LC-MS calculated for $C_{18}H_{18}N_5O$ (M+H)$^+$: m/z=320.1; found 320.2. $^1$H NMR (500 MHz, DMSO-d$_6$) δ 12.13 (s, 1H), 8.75 (s, 1H), 8.57 (d, J=8.0 Hz, 1H), 8.01 (dd, J=8.5, 1.6 Hz, 2H), 7.97-7.93 (m, 1H), 7.60 (d, J=8.0 Hz, 1H), 7.52 (d, J=8.5 Hz, 1H), 7.37-7.15 (m, 1H), 6.58 (s, 1H), 4.64 (q, J=7.1 Hz, 2H), 2.21 (s, 3H), 1.37 (t, J=7.1 Hz, 3H).

Step 4: (E)-9-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazol-5-yl)-9H-pyrido[2,3-b]indole-6-carboxamide A mixture of 2-(1-ethyl-3-methyl-1H-pyrazol-5-yl)-9H-pyrido[2,3-b]indole-6-carboxamide (3.5 mg, 0.011 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (5.0 mg, 0.011 mmol), and cesium carbonate (12.92 mg, 0.040 mmol) was stirred in DMF (60.1 µl) at r.t. for 1 h. The reaction mixture was diluted with MeOH and purified by prep-HPLC (pH=2, acetonitrile/water+TFA) to give the desired product as its TFA salt. LC-MS calculated for $C_{38}H_{40}N_{11}O_3$ (M+H)$^+$: m/z=698.3; found 698.3.

150

Example S6. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(3-methyl-1-propyl-1H-pyrazol-5-yl)-9 H-pyrimido[4,5-b]indole-6-carboxamide

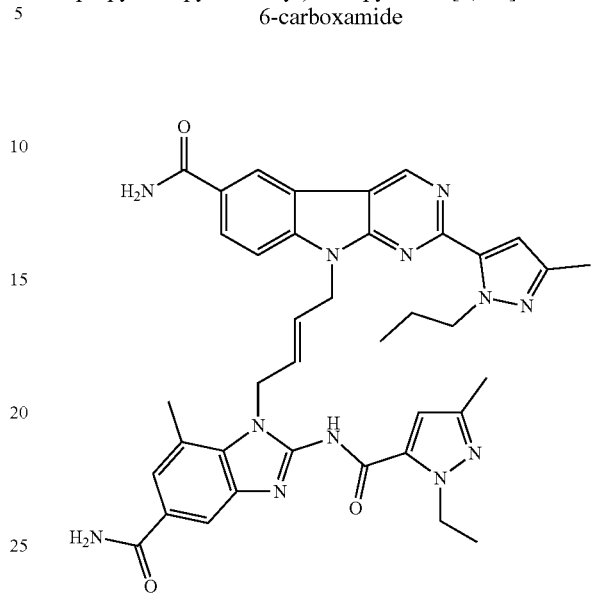

Step 1: 2-(3-methyl-1-propyl-1H-pyrazol-5-yl)-9H-pyrimido[4,5-b]indole-6-carboxamide

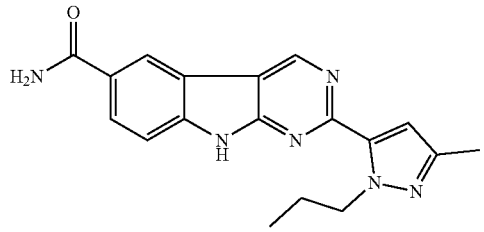 [SMILES: CCCn1nc(C)cc1-c1ncc2c(n1)[nH]c1ccc(C(N)=O)cc12]

This compound was prepared using similar procedures as described for Example S1, Step 11 with 3-methyl-1-propyl-5-(4,4,5,5-tetramethyl-1,3,2-dioxaborolan-2-yl)-1H-pyrazole (Combi-Blocks, cat # FM-3989) replacing 1-ethyl-3-methyl-5-(4,4,5,5-tetramethyl-1,3,2-dioxaborolan-2-yl)-1H-pyrazole. LC-MS calculated for $C_{18}H_{19}N_6O$ (M+H)$^+$: m/z=335.2; found 335.2.

Step 2: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(3-methyl-1-propyl-1H-pyrazol-5-yl)-9H-pyrimido[4,5-b]indole-6-carboxamide A mixture of 2-(3-methyl-1-propyl-1H-pyrazol-5-yl)-9H-pyrimido[4,5-b]indole-6-carboxamide (6.68 mg, 0.02 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example S1, Step 8; 9.18 mg, 0.02 mmol), and cesium carbonate (14.32 mg, 0.044 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{38}H_{41}N_{12}O_3$ (M+H)$^+$: m/z=713.3; found 713.4.

Example S7. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-1H-pyrazol-5-yl)-9H-pyrimido[4,5-b]indole-6-carboxamide Example S8. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(3-ethyl-1-methyl-1H-pyrazol-4-yl)-9H-pyrimido[4,5-b]indole-6-carboxamide

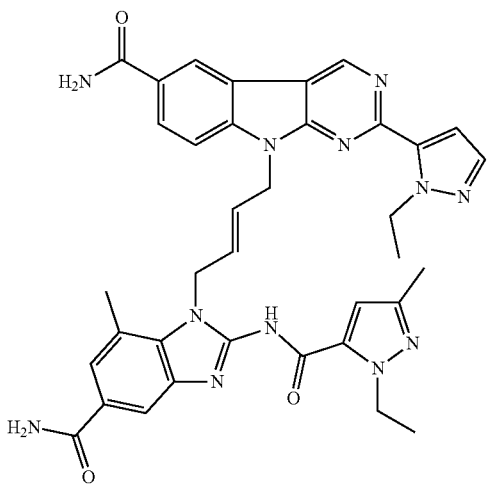 [SMILES: CCn1nc(C)cc1C(=O)Nc1nc2cc(C(N)=O)cc(C)c2n1C/C=C/Cn1c2ccc(C(N)=O)cc2c2cnc(-c3ccnn3CC)nc21]

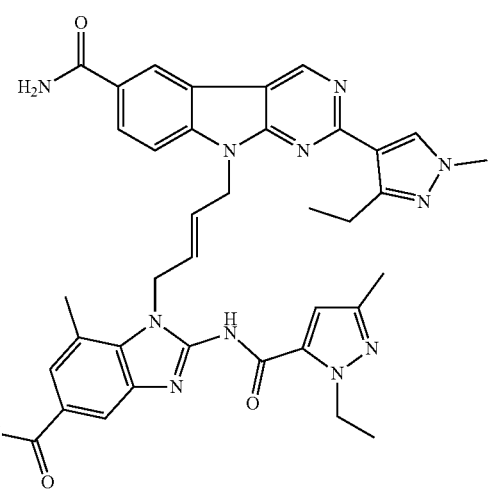

Step 1: 2-(1-ethyl-1H-pyrazol-5-yl)-9H-pyrimido[4,5-b]indole-6-carboxamide

Step 1: 2-(3-ethyl-1-methyl-1H-pyrazol-4-yl)-9H-pyrimido[4,5-b]indole-6-carboxamide

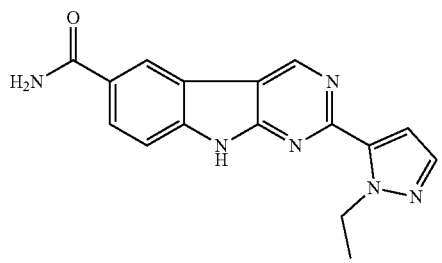 [SMILES: CCn1nccc1-c1ncc2c(n1)[nH]c1ccc(C(N)=O)cc12]

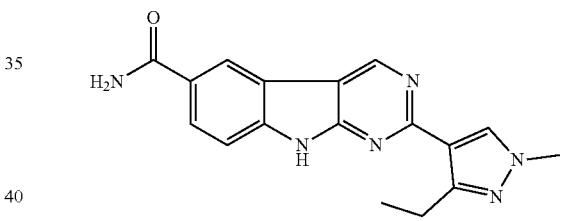

This compound was prepared using similar procedures as described for Example S1, Step 11 with 1-ethyl-5-(4,4,5,5-tetramethyl-1,3,2-dioxaborolan-2-yl)-1H-pyrazole (Combi-Blocks, cat # PN-6476) replacing 1-ethyl-3-methyl-5-(4,4,5,5-tetramethyl-1,3,2-dioxaborolan-2-yl)-1H-pyrazole. LC-MS calculated for $C_{16}H_{15}N_6O$ (M+H)$^+$: m/z=307.1; found 307.1.

Step 2: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-1H-pyrazol-5-yl)-9H-pyrimido[4,5-b]indole-6-carboxamide A mixture of 2-(1-ethyl-1H-pyrazol-5-yl)-9H-pyrimido[4,5-b]indole-6-carboxamide (6.12 mg, 0.02 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example S1, Step 8: 9.18 mg, 0.02 mmol), and cesium carbonate (14.32 mg, 0.044 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{36}H_{37}N_{12}O_3$ (M+H)$^+$: m/z=685.3; found 685.4.

This compound was prepared using similar procedures as described for Example S1, Step 11 with 3-ethyl-1-methyl-4-(4,4,5,5-tetramethyl-1,3,2-dioxaborolan-2-yl)-1H-pyrazole (AstaTech, cat #P17340) replacing 1-ethyl-3-methyl-5-(4,4,5,5-tetramethyl-1,3,2-dioxaborolan-2-yl)-1H-pyrazole. LC-MS calculated for $C_{17}H_{17}N_6O$ (M+H)$^+$: m/z=321.1; found 321.1.

Step 2: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(3-ethyl-1-methyl-1H-pyrazol-4-yl)-9H-pyrimido[4,5-b]indole-6-carboxamide A mixture of 2-(3-ethyl-1-methyl-1H-pyrazol-4-yl)-9H-pyrimido[4,5-b]indole-6-carboxamide (6.4 mg, 0.02 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example S1, Step 8: 9.18 mg, 0.02 mmol), and cesium carbonate (14.32 mg, 0.044 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{37}H_{39}N_{12}O_3$ (M+H)$^+$: m/z=699.3; found 699.4.

Example S9. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-(trifluoromethyl)-1H-pyrazol-5-yl)-9H-pyrimido[4,5-b]indole-6-carboxamide

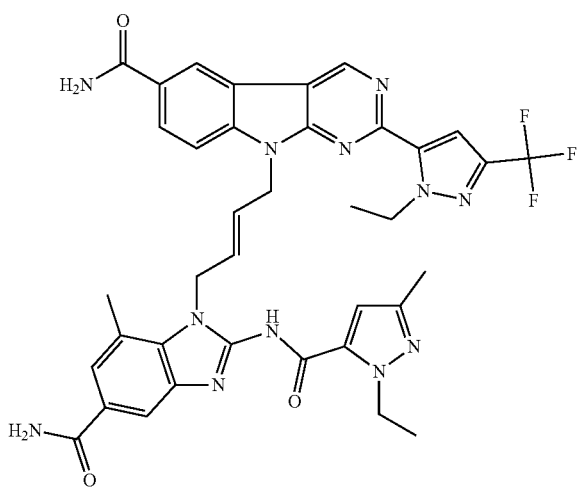 [SMILES: CCn1nc(C)cc1C(=O)Nc1nc2cc(C(N)=O)cc(C)c2n1C/C=C/Cn1c2ccc(C(N)=O)cc2c2cnc(-c3cc(C(F)(F)F)nn3CC)nc21]

Step 1: 2-(1-ethyl-3-(trifluoromethy0-1H-pyrazol-5-yl)-9H-pyrimido[4,5-b]indole-6-carboxamide

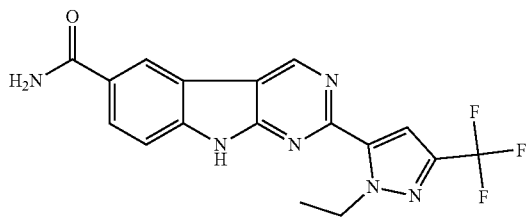 [SMILES: CCn1nc(C(F)(F)F)cc1-c1ncc2c(n1)[nH]c1ccc(C(N)=O)cc12]

This compound was prepared using similar procedures as described for Example S1, Step 11 with 1-ethyl-5-(4,4,5,5-tetramethyl-1,3,2-dioxaborolan-2-yl)-3-(trifluoromethyl)-1H-pyrazole replacing 1-ethyl-3-methyl-5-(4,4,5,5-tetramethyl-1,3,2-dioxaborolan-2-yl)-1H-pyrazole. LC-MS calculated for $C_{17}H_{14}F_3N_6O$ $(M+H)^+$: m/z=375.1; found 375.1.

Step 2: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-(trifluoromethyl)-1H-pyrazol-5-yl)-9H-pyrimido[4,5-b]indole-6-carboxamide A mixture of 2-(1-ethyl-3-(trifluoromethyl)-1H-pyrazol-5-yl)-9H-pyrimido[4,5-b]indole-6-carboxamide (8.96 mg, 0.024 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example S1, Step 8: 11 mg, 0.024 mmol), and cesium carbonate (17.2 mg, 0.053 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{37}H_{36}F_3N_{12}O_3$ $(M+H)^+$: m/z=753.3; found 753.4.

Example S10. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-methoxy-9H-pyrimido[4,5-b]indole-6-carboxamide

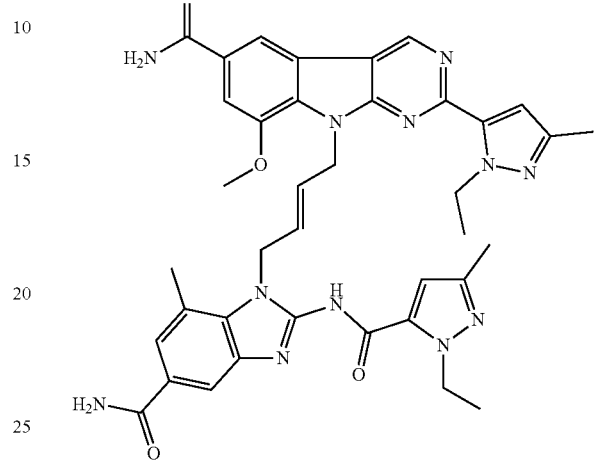

Step 1: 3-bromo-5-fluoro-4-nitrobenzamide

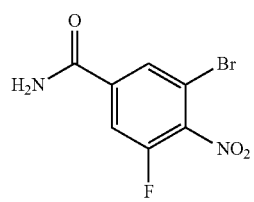 [SMILES: NC(=O)c1cc(F)c([N+](=O)[O-])c(Br)c1]

Methyl 3-bromo-5-fluoro-4-nitrobenzoate (AstaTech, cat #AB9640: 5.0 g, 17.98 mmol) was stirred in ammonium hydroxide (44.1 ml, 1133 mmol) at room temperature for 10 h. The solid was filtered and rinsed with cold water. The resulting solid residue was dried to provide the desired product as a light yellow solid.

Step 2: 3-bromo-5-methoxy-4-nitrobenzamide

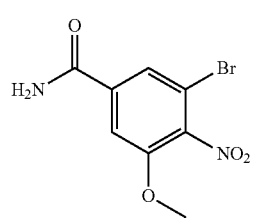

To a stirred solution of 3-bromo-5-fluoro-4-nitrobenzamide (1.0 g, 3.80 mmol) in MeOH (19.01 ml) was added sodium methoxide (1.232 g, 5.70 mmol). The reaction mixture was stirred at 60° C. for 0.5 h. The reaction mixture was concentrated under reduced pressure. The residue was dissolved in water, and then extracted with DCM. The combined organic layers were dried, filtered, and concentrated in vacuo. The crude product was used directly without further purification. LC-MS calculated for $C_8H_8BrN_2O_4$ $(M+H)^+$: m/z=275.0, 277.0; found 275.0, 277.0.

Step 3: 3-(2-(1-ethyl-3-methyl-1H-pyrazol-5-yl)pyrimidin-5-yl)-5-methoxy-4-nitrobenzamide

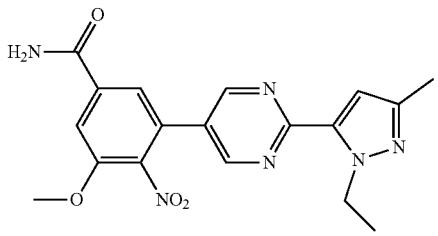

To a degassed solution of (2-chloropyrimidin-5-yl)boronic acid (Combi-Blocks, cat #BB-5457: 82 mg, 0.52 mmol) and 3-bromo-5-methoxy-4-nitrobenzamide (143 mg, 0.520 mmol) in dioxane (1733 µl) and water (347 µl) was added dichloro[1,1'-bis(diphenylphosphino)ferrocene]palladium (II) dichloromethane adduct (25.5 mg, 0.031 mmol) and sodium carbonate (110 mg, 1.040 mmol). The reaction was stirred at 100° C. for 2 h. Then, 1-ethyl-3-methyl-5-(4,4,5,5-tetramethyl-1,3,2-dioxaborolan-2-yl)-1H-pyrazole (Enamine Ltd, cat #EN300-207291; 123.0 mg, 0.520 mmol) was added. The reaction mixture was heated to 100° C. for another 1 h. H$_2$O was added to the reaction mixture, and the reaction was extracted with DCM. The combined organic layers were dried with Na$_2$SO$_4$, filtered and concentrated. The crude residue was purified by flash chromatography on a silica gel column eluting with 0 to 8% MeOH in DCM to afford the desired product. LC-MS calculated for C$_{18}$H$_{19}$N$_6$O$_4$ (M+H)$^+$: m/z=383.1; found 383.2.

Step 4: 2-(1-ethyl-3-methyl-1H-pyrazol-5-yl)-8-methoxy-9H-pyrimido[4,5-b]indole-6-carboxamide

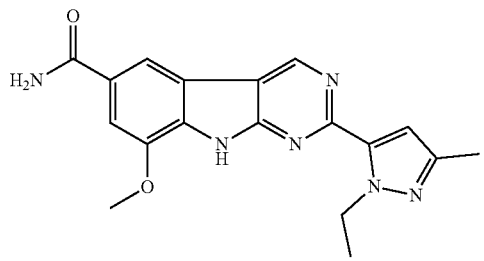 [SMILES: CCn1nc(C)cc1-c1ncc2c(n1)[nH]c1c(OC)cc(C(N)=O)cc12]

A mixture of 3-(2-(1-ethyl-3-methyl-1H-pyrazol-5-yppyrimidin-5-yl)-5-methoxy-4-nitrobenzamide (280.0 mg, 0.732 mmol) and 1,2-bis(diphenylphosphino)ethane (365 mg, 0.915 mmol) was dissolved in 1,2-dichlorobenzene (2.4 mL). The vial was flushed with nitrogen before heating at 160° C. for 1 h. After removal of the solvent under vacuum, the reaction mixture was extracted with DCM and water. The organic phases were combined and dried over MgSO$_4$, filtered, then concentrated under reduced pressure. The crude residue was purified by flash chromatography on a silica gel column eluting with 0 to 8% MeOH in DCM to afford the desired product. LC-MS calculated for C$_{188}$H$_{19}$N$_6$O$_2$ (M+H)$^+$: m/z=351.1; found 351.1.

Step 5: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-methoxy-9H-pyrimido[4,5-b]indole-6-carboxamide A mixture of 2-(1-ethyl-3-methyl-1H-pyrazol-5-yl)-8-methoxy-9H-pyrimido[4,5-b]indole-6-carboxamide (7.0 mg, 0.02 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example S1, Step 8; 9.18 mg, 0.02 mmol), and cesium carbonate (14.32 mg, 0.044 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for C$_{38}$H$_{41}$N$_{12}$O$_4$ (M+H)$^+$: m/z=729.3; found 729.4.

Example S11. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-morpholinopropoxy)-9H-pyrimido[4,5-b]indole-6-carboxamide

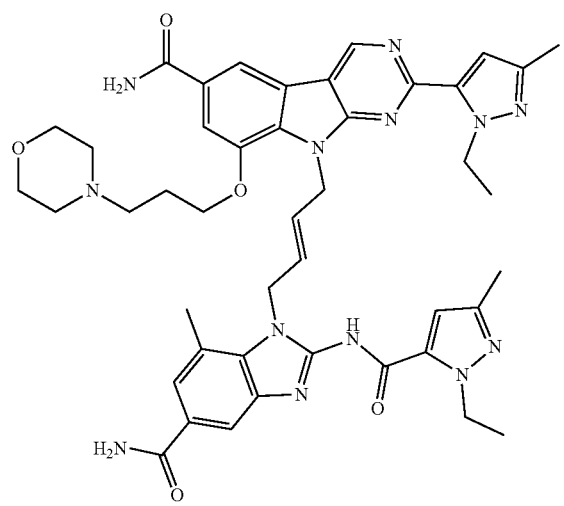 [SMILES: CCn1nc(C)cc1C(=O)Nc1nc2cc(C(N)=O)cc(C)c2n1C/C=C/Cn1c2nc(-c3cc(C)nn3CC)ncc2c2cc(C(N)=O)cc(OCCCN3CCOCC3)c21]

Step 1: 3-bromo-5-(3-morpholinopropoxy)-4-nitrobenzamide

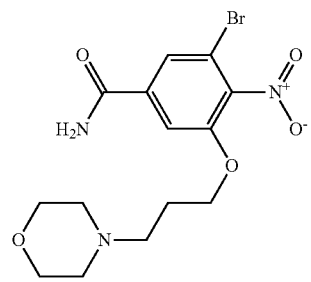 [SMILES: NC(=O)c1cc(Br)c([N+](=O)[O-])c(OCCCN2CCOCC2)c1]

To a stirred solution of 3-morpholinopropan-1-ol (Combi-Blocks, cat #OR-5079: 0.121 g, 0.836 mmol) in THF (2.79 ml) was added sodium hydride (0.067 g, 1.673 mmol). The reaction mixture was stirred at room temperature for 10 min. To the solution of sodium alkoxide was then added 3-bromo-5-fluoro-4-nitrobenzamide (0.220 g, 0.836 mmol). The mixture was heated at 60° C. for 0.5 h. The reaction mixture was concentrated under reduced pressure, and then extracted with DCM and water. The combined organic layers were dried, filtered, and concentrated in vacuo. The crude product was used directly without further purification. LC-MS calculated for C$_{14}$H$_{19}$BrN$_3$O$_5$ (M+H)$^+$: m/z=388.0, 390.0; found 388.1, 390.1.

Step 2: 3-(2-(1-ethyl-3-methyl-1H-pyrazol-5-yl)pyrimidin-5-yl)-5-(3-morpholinopropoxy)-4-nitrobenzamide

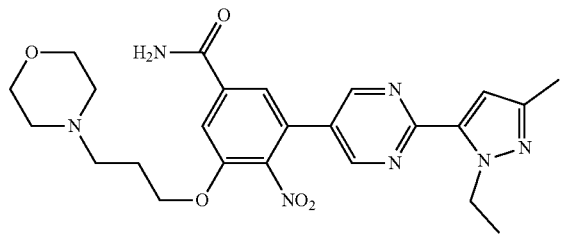 [SMILES: CCn1nc(C)cc1-c1ncc(-c2cc(C(N)=O)cc(OCCCN3CCOCC3)c2[N+](=O)[O-])cn1]

This compound was prepared using similar procedures as described for Example S10, Step 3 with 3-bromo-5-(3-morpholinopropoxy)-4-nitrobenzamide replacing 3-bromo-5-methoxy-4-nitrobenzamide. LC-MS calculated for $C_{24}H_{30}N_7O_5$ (M+H)⁺: m/z=496.2; found 496.3.

Step 3: 2-(1-ethyl-3-methyl-1H-pyrazol-5-yl)-8-(3-morpholinopropoxy)-9H-pyrimido[4,5-b]indole-6-carboxamide

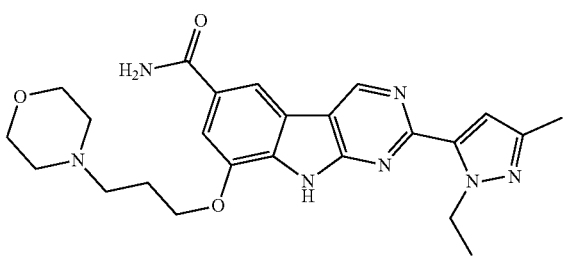 [SMILES: CCn1nc(C)cc1-c1ncc2c(n1)[nH]c1c(OCCCN3CCOCC3)cc(C(N)=O)cc12]

This compound was prepared using similar procedures as described for Example S10, Step 4 with 3-(2-(1-ethyl-3-methyl-1H-pyrazol-5-yl)pyrimidin-5-yl)-5-(3-morpholinopropoxy)-4-nitrobenzamide replacing 3-(2-(1-ethyl-3-methyl-1H-pyrazol-5-yl)pyrimidin-5-yl)-5-methoxy-4-nitrobenzamide LC-MS calculated for C24H30N7O3 (M+H)⁺: m/z=464.2; found 464.3.

Step 4: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-morpholinopropoxy)-9H-pyrimido[4,5-b]indole-6-carboxamide A mixture of 2-(1-ethyl-3-methyl-1H-pyrazol-5-yl)-8-(3-morpholinopropoxy)-9H-pyrimido[4,5-b]indole-6-carboxamide (7.0 mg, 0.015 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example S1, Step 8; 6.94 mg, 0.015 mmol), and cesium carbonate (10.82 mg, 0.033 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{44}H_{52}N_{13}O_5$ (M+H)⁺: m/z=842.4; found 842.4.

Example S12. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-methoxypropoxy)-9H-pyrimido[4,5-b]indole-6-carboxamide

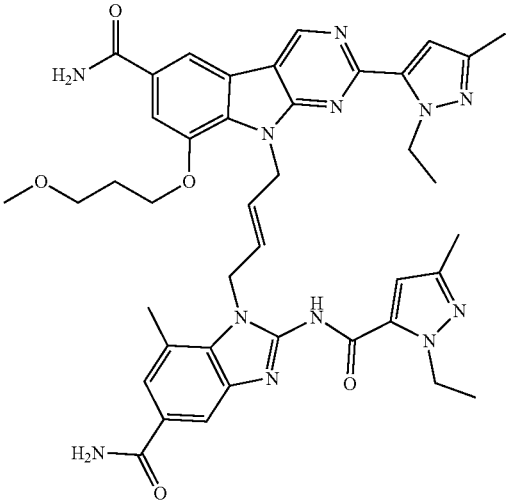

Step 1: 3-bromo-5-(3-methoxypropoxy)-4-nitrobenzamide

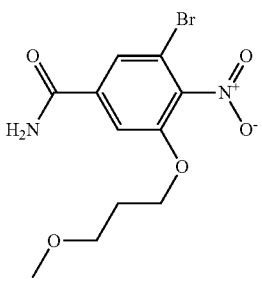 [SMILES: COCCCOc1cc(C(N)=O)cc(Br)c1[N+](=O)[O-]]

This compound was prepared using similar procedures as described for Example S11, Step 1 with 3-methoxypropan-1-ol (Aldrich, cat #38457) replacing 3-morpholinopropan-1-ol. LC-MS calculated for $C_{11}H_{14}BrN_2O_5$ (M+H)⁺: m/z=333.0, 335.0; found 333.0, 335.0.

Step 2: 3-(2-(1-ethyl-3-methyl-1H-pyrazol-5-yl)pyrimidin-5-yl)-5-(3-methoxypropoxy)-4-nitrobenzamide

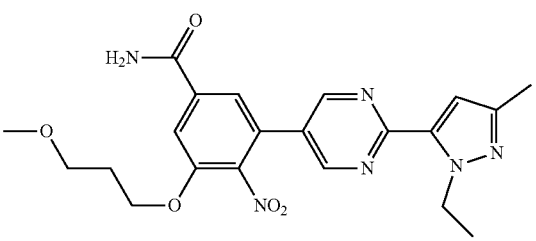

This compound was prepared using similar procedures as described for Example S10, Step 3 with 3-bromo-5-(3-methoxypropoxy)-4-nitrobenzamide replacing 3-bromo-5-methoxy-4-nitrobenzamide. LC-MS calculated for $C_{21}H_{25}N_6O_5$ (M+H)⁺: m/z=441.2; found 441.3.

Step 3: 2-(1-ethyl-3-methyl-1H-pyrazol-5-yl)-8-(3-methoxypropoxy)-9H-pyrimido[4,5-b]indole-6-carboxamide

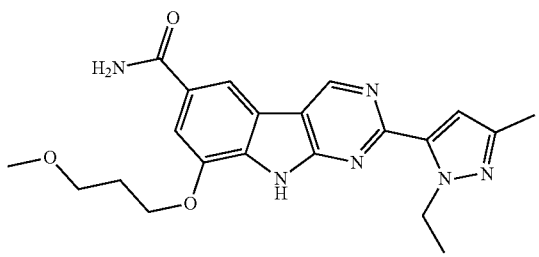

This compound was prepared using similar procedures as described for Example S10, Step 4 with 3-(2-(1-ethyl-3-methyl-1H-pyrazol-5-yl)pyrimidin-5-yl)-5-(3-methoxypropoxy)-4-nitrobenzamide replacing 3-(2-(1-ethyl-3-methyl-1H-pyrazol-5-yl)pyrimidin-5-yl)-5-methoxy-4-nitrobenzamide. LC-MS calculated for $C_{21}H_{25}N_6O_3$ (M+H)$^+$: m/z=409.2; found 409.2.

Step 4: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-methoxypropoxy)-9H-pyrimido[4,5-b]indole-6-carboxamide A mixture of 2-(1-ethyl-3-methyl-1H-pyrazol-5-yl)-8-(3-methoxypropoxy)-9H-pyrimido[4,5-b]indole-6-carboxamide (7.0 mg, 0.015 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example S1, Step 8: 6.94 mg, 0.015 mmol), and cesium carbonate (10.82 mg, 0.033 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{41}H_{47}N_{12}O_5$ (M+H)$^+$: m/z=787.4; found 787.4.

Example S13. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-hydroxypropoxy)-9H-pyrimido[4,5-b]indole-6-carboxamide

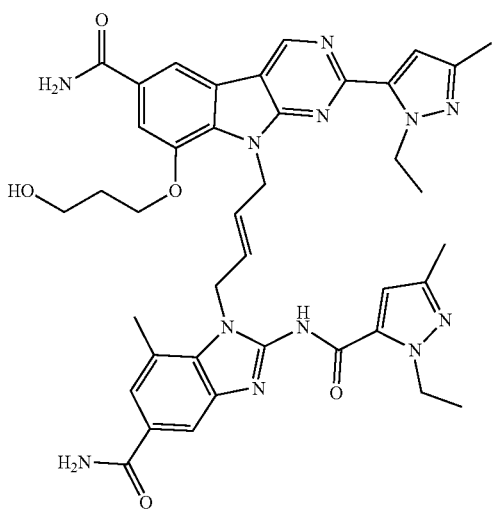 [SMILES: CCn1nc(C)cc1C(=O)Nc1nc2cc(C(N)=O)cc(C)c2n1C/C=C/Cn1c2nc(-c3cc(C)nn3CC)ncc2c2cc(C(N)=O)cc(OCCCO)c21]

Step 1: 3-bromo-5-(3-(tert-butyldimethylsilyloxy)propoxy)-4-nitrobenzamide

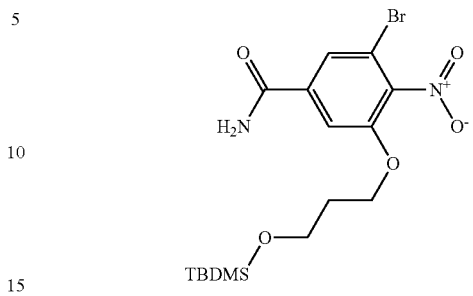

This compound was prepared using similar procedures as described for Example S11, Step 1 with 3-((tert-butyldimethylsilyl)oxy)propan-1-ol (Combi-Blocks, cat #QH-3826) replacing 3-morpholinopropan-1-ol. LC-MS calculated for $C_{16}H_{26}BrN_2O_5Si$ (M+H)$^+$: m/z=433.1, 435.1; found 433.2, 435.2.

Step 2: 3-(3-(tert-butyldimethylsilyloxy)propoxy)-5-(2-(1-ethyl-3-methyl-1H-pyrazol-5-yl)pyrimidin-5-yl)-4-nitrobenzamide

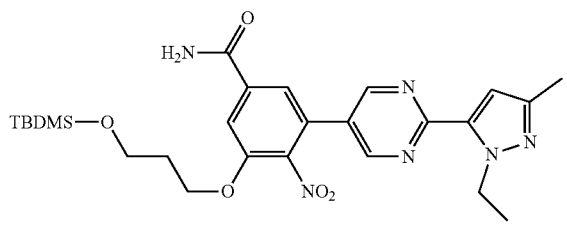

This compound was prepared using similar procedures as described for Example S10, Step 3 with 3-bromo-5-(3-(tert-butyldimethylsilyloxy)propoxy)-4-nitrobenzamide replacing 3-bromo-5-methoxy-4-nitrobenzamide. LC-MS calculated for $C_{26}H_{37}N_6O_5Si$ (M+H)$^+$: m/z=541.3; found 541.3.

Step 3: 8-(3-(tert-butyldimethylsilyloxy)propoxy)-2-(1-ethyl-3-methyl-1H-pyrazol-5-yl)-9H-pyrimido[4,5-b]indole-6-carboxamide

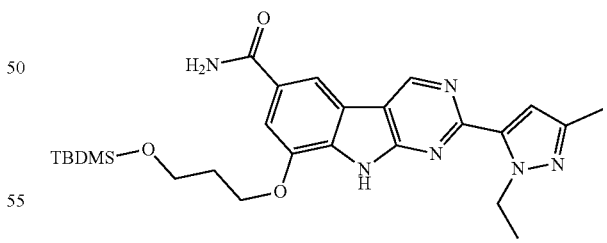

This compound was prepared using similar procedures as described for Example S10, Step 4 with 3-(3-(tert-butyldimethylsilyloxy)propoxy)-5-(2-(1-ethyl-3-methyl-1H-pyrazol-5-yl)pyrimidin-5-yl)-4-nitrobenzamide replacing 3-(2-(1-ethyl-3-methyl-1H-pyrazol-5-yl)pyrimidin-5-yl)-5-methoxy-4-nitrobenzamide. LC-MS calculated for $C_{26}H_{37}N_6O_3Si$ (M+H)$^+$: m/z=509.3; found 509.3.

Step 4: (E)-9-(4-(5-carbamoyl-2-(1-ethyl-3-methyl-1H-pyrazole-5-carboxamido)-7-methyl-1H-benzo[d]imidazol- 1-yl)but-2-enyl)-2-(1-ethyl-3-methyl-1H-pyrazol-5-yl)-8-(3-hydroxypropoxy)-9H-pyrimido[4,5-b]indole-6-carboxamide A mixture of 28-(3-(tert-butyldimethylsilyloxy)propoxy)-2-(1-ethyl-3-methyl-1H-pyrazol-5-yl)-9H-pyrimido[4,5-b]indole-6-carboxamide (7.63 mg, 0.015 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (6.89 mg, 0.015 mmol), and cesium carbonate (10.75 mg, 0.033 mmol) was stirred in DMF (0.2 mL) at 50° C. for 1 h. The primary alcohol was deprotected during the process. Otherwise, the TBS group could be removed with the addition of 4 equivalents of HCl (0.015 mL of 4 M HCl in dioxane), followed by stirring at room temperature for 1 h. The reaction mixture was diluted with MeOH and purified by prep-HPLC (pH=2, acetonitrile/water+TFA) to give the desired product as its TFA salt. LC-MS calculated for $C_{40}H_{45}N_{12}O_5$ (M+H)$^+$: m/z=773.4; found 773.4.

Example S14. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-methoxy-9H-pyrido[2,3-b]indole-6-carboxamide

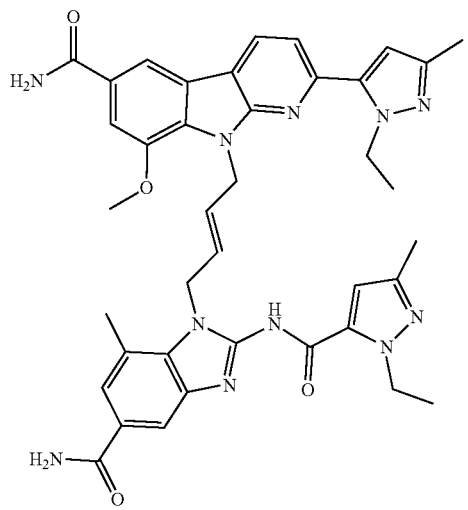 [SMILES: CCn1nc(C)cc1C(=O)Nc1nc2cc(C(N)=O)cc(C)c2n1C/C=C/Cn1c2nc(-c3cc(C)nn3CC)ccc2c2cc(C(N)=O)cc(OC)c21]

Step 1: 3-(6-(1-ethyl-3-methyl-1H-pyrazol-5-yl)pyridin-3-yl)-5-methoxy-4-nitrobenzamide

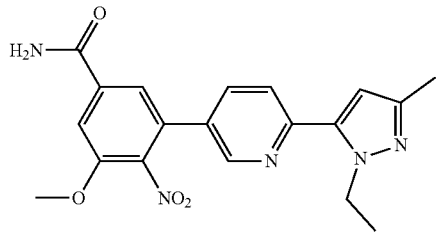 [SMILES: CCn1nc(C)cc1-c1ccc(-c2cc(C(N)=O)cc(OC)c2[N+](=O)[O-])cn1]

This compound was prepared using similar procedures as described for Example S10, Step 3 with 2-chloro-5-(4,4,5,5-tetramethyl-1,3,2-dioxaborolan-2-yl)pyridine replacing (2-chloropyrimidin-5-yl)boronic acid. LC-MS calculated for $C_{19}H_{20}N_5O_4$ (M+H)$^+$: m/z=382.1; found 382.3.

Step 2: 2-(1-ethyl-3-methyl-1H-pyrazol-5-yl)-8-methoxy-9H-pyrido[2,3-b]indole-6-carboxamide

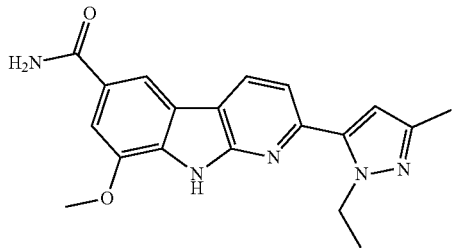 [SMILES: CCn1nc(C)cc1-c1ccc2c(n1)[nH]c1c(OC)cc(C(N)=O)cc12]

This compound was prepared using similar procedures as described for Example S10, Step 4 with 3-(6-(1-ethyl-3-methyl-1H-pyrazol-5-yl)pyridin-3-yl)-5-methoxy-4-nitrobenzamide replacing 3-(2-(1-ethyl-3-methyl-1H-pyrazol-5-yl)pyrimidin-5-yl)-5-methoxy-4-nitrobenzamide. Two isomers were formed. The reaction mixture was diluted with MeOH and purified by prep-HPLC (pH=2, acetonitrile/water+TFA) to give the desired product as its TFA salt. LC-MS calculated for $C_{19}H_{20}N_5O_2$ (M+H)$^+$: m/z=350.2; found 350.2. $^1$H NMR (500 MHz, DMSO) δ 12.26 (s, 1H), 8.53 (d, J=8.1 Hz, 1H), 8.39 (s, 1H), 7.59 (s, 1H), 7.57 (d, J=8.1 Hz, 1H), 6.58 (s, 1H), 4.65 (q, J=7.1 Hz, 2H), 4.04 (s, 3H), 2.21 (s, 3H), 1.36 (t, J=7.1 Hz, 3H).

Step 3: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-methoxy-9H-pyrido[2,3-b]indole-6-carboxamide A mixture of 2-(1-ethyl-3-methyl-1H-pyrazol-5-yl)-8-methoxy-9H-pyrido[2,3-b]indole-6-carboxamide (7.0 mg, 0.02 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (9.18 mg, 0.02 mmol), and cesium carbonate (14.32 mg, 0.044 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{39}H_{42}N_{11}O_4$ (M+H)$^+$: m/z=728.3; found 728.4.

Example S15. (E)-3-((5-carbamoyl-1-(4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

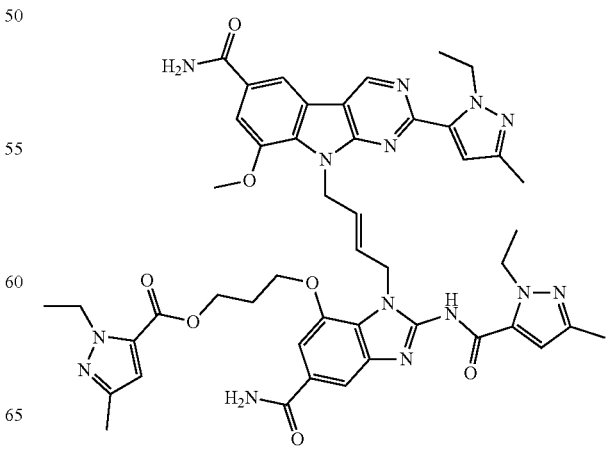

Step 1: 4-chloro-3-hydroxy-5-nitrobenzamide

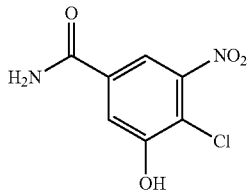 [SMILES: NC(=O)c1cc(O)c(Cl)c([N+](=O)[O-])c1]

In a round-bottomed flask, 4-chloro-3-methoxy-5-nitrobenzamide (Astatech, cat #97780: 1.0 g, 4.34 mmol) was dissolved in DCM. 1M BBr$_3$ in DCM (13.01 ml, 13.01 mmol) was added to the reaction mixture dropwise, then was refluxed for 12 h. The reaction mixture was cooled and then was poured into ice water. After stirring for 30 min, the reaction mixture was filtered and the filter cake was rinsed with water and dried to provide the desired compound as a white solid. LC-MS calculated for $C_7H_6ClN_2O_4$ (M+H)$^+$: m/z=217.0; found 216.9.

Step 2: 3-(3-((tert-butyldimethylsilyl)oxy)propoxy)-4-chloro-5-nitrobenzamide

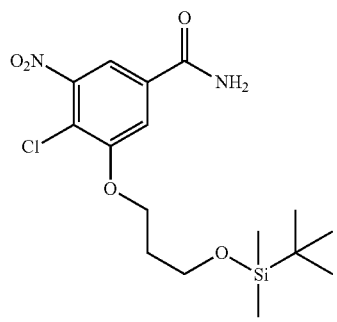 [SMILES: CC(C)(C)[Si](C)(C)OCCCOc1cc(C(N)=O)cc([N+](=O)[O-])c1Cl]

To a suspension of 4-chloro-3-hydroxy-5-nitrobenzamide (211.0 mg, 0.974 mmol), and cesium carbonate (476 mg, 1.461 mmol) in DMF (3247 μl) was added (3-bromopropoxy)(tert-butyl)dimethylsilane (Aldrich, cat #429066: 271 μl, 1.169 mmol). The reaction was then sealed and heated to 50° C. with stirring for 12 h. After cooling with an ice bath, the product was triturated with cold water, filtered, and dried to provide the desired product as a yellow solid. LC-MS calculated for $C_{16}H_{26}ClN_2O_5Si$ (M+H)+: m/z=389.1; found 389.1.

Step 3: tert-butyl (E)-(4-((2-(3-((tert-butyldimethylsilyl)oxy)propoxy)-4-carbamoyl-6-nitrophenyl(amino)but-2-en-1-yl)carbamate

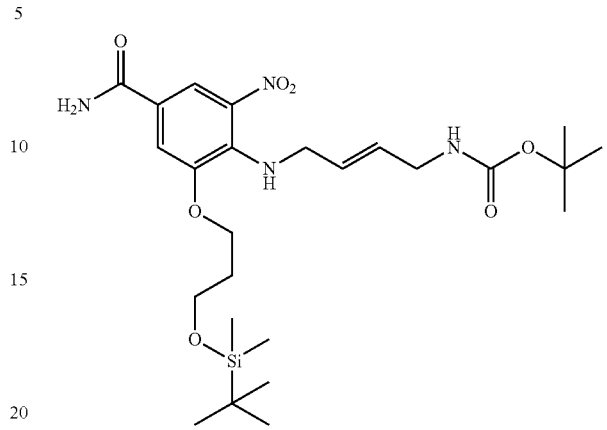

To a vial was added 3-(3-((tert-butyldimethylsilyl)oxy) propoxy)-4-chloro-5-nitrobenzamide (1.004 g, 2.58 mmol), tert-butyl (E)-(4-aminobut-2-en-1-yl)carbamate (Ark Pharm, cat #AK308564: 0.481 g, 2.58 mmol), DMSO (12.91 ml), and DIPEA (2.254 ml, 12.91 mmol). The mixture was sealed, then heated at 100° C. overnight with stirring. After cooling to rt, the mixture was diluted with water and extracted with CHCl$_3$/IPA (3:1). The combined organic extracts were dried over MgSO$_4$, filtered, and concentrated in vacuo to provide the desired product as a brown oil. LC-MS calculated for $C_{25}H_{43}N_4O_7Si$ (M+Na)$^+$: m/z=561.3; found 561.3.

Step 4: tert-butyl (E)-(4-((2-amino-6-(3-((tert-butyldimethylsilyl)oxy)propoxy)-4-carbamoylphenyl)amino)but-2-en-1-yl)carbamate

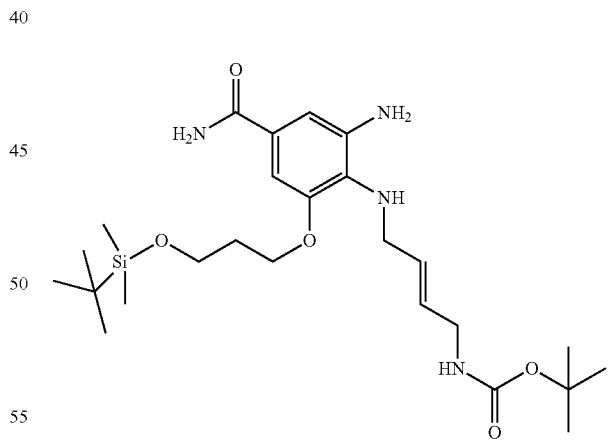

This compound was prepared using similar procedures as described for Example S1, Step 3 with tert-butyl (E)-(4-((2-(3-((tert-butyldimethylsilyl)oxy)propoxy)-4-carbamoyl-6-nitrophenyl)amino)but-2-en-1-yl)carbamate replacing tert-butyl (E)-(4-((4-carbamoyl-2-methyl-6-nitrophenyl)amino) but-2-en-1-yl)carbamate. LC-MS calculated for $C_{25}H_{45}N_4O_5Si$ (M+H)$^+$: m/z=509.3; found 509.3.

Step 5: tert-butyl (E)-(4-(2-amino-5-carbamoyl-7-(3-hydroxypropoxy)-1H-benzo[d]imidazol-1-yl)but-2-en-1-yl)carbamate

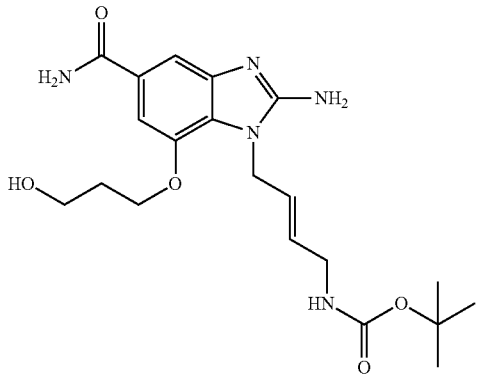 [SMILES: CC(C)(C)OC(=O)NC/C=C/Cn1c(N)nc2cc(C(N)=O)cc(OCCCO)c21]

This compound was prepared using similar procedures as described for Example S1, Step 4 with tert-butyl (E)-(4-((2-amino-6-(3-((tert-butyldimethylsilyl)oxy)propoxy)-4-carbamoylphenyl)amino)but-2-en-1-yl)carbamate replacing tert-butyl (E)-(4-((2-amino-4-carbamoyl-6-methylphenyl)amino)but-2-en-1-yl)carbamate. LC-MS calculated for $C_{20}H_{30}N_5O_5$ $(M+H)^+$: m/z=420.2; found 420.3.

Step 6: (E)-3-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

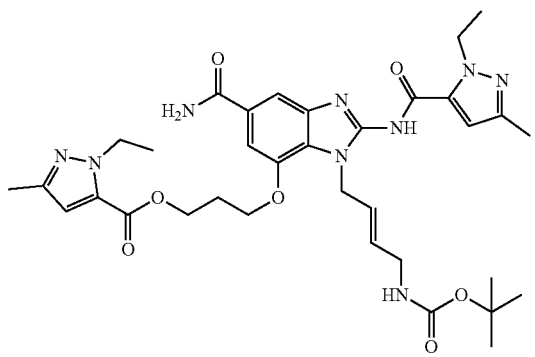

To a solution of 1-ethyl-3-methyl-1H-pyrazole-5-carboxylic acid (Combi-Blocks, cat #QB-0979: 0.336 g, 2.179 mmol) in DMF (4.95 ml) at rt was added HATU (0.911 g, 2.397 mmol) and DIPEA (0.951 ml, 5.45 mmol). The mixture was stirred for 15 min, then a solution of tert-butyl (E)-(4-(2-amino-5-carbamoyl-7-(3-hydroxypropoxy)-1H-benzo[d]imidazol-1-yl)but-2-en-1-yl)carbamate (0.457 g, 1.089 mmol) in DMF (0.495 ml) was added and stirred overnight. The reaction was concentrated, and was diluted with water. The aqueous mixture was extracted with DCM (3×20 mL). The combined organic layers were washed with brine, dried over MgSO$_4$, filtered, and concentrated. The product was purified by column chromatography (15% MeOH/DCM) to provide the desired product as a white solid. LC-MS calculated for $C_{34}H_{46}N_9O_7$ $(M+H)^+$: m/z=692.3; found 692.4.

Step 7: (E)-3-((1-(4-aminobut-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

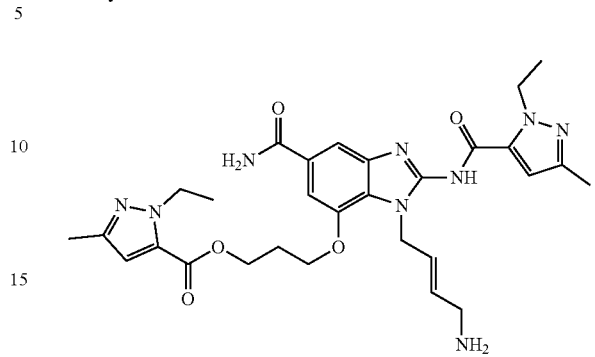

This compound was prepared using similar procedures as described for Example S1, Step 6 with (E)-3-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate replacing tert-butyl (E)-(4-(5-carbamoyl-2-(1-ethyl-3-methyl-1H-pyrazole-5-carboxamido)-7-methyl-1H-benzo[d]imidazol-1-yl)but-2-en-1-yl)carbamate. LC-MS calculated for $C_{29}H_{38}N_9O_5$ $(M+H)^+$: m/z=592.3; found 592.4.

Step 8: (E)-3-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)propyl 1-ethyl-3-methyl-1H-pyrazole-5-carboxylate

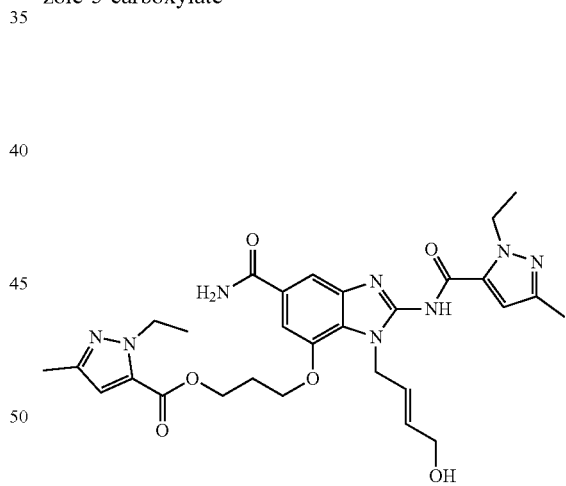

This compound was prepared using similar procedures as described for Example S1, Step 7 with (E)-3-((1-(4-aminobut-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate replacing (E)-1-(4-aminobut-2-en-1-yl)-2-(1-ethyl-3-methyl-1H-pyrazole-5-carboxamido)-7-methyl-1H-benzo[d]imidazole-5-carboxamide. LC-MS calculated for $C_{29}H_{37}N_8O_6$ $(M+H)^+$: m/z=593.3; found 593.4.

Step 9: (E)-3-((1-(4-bromobut-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

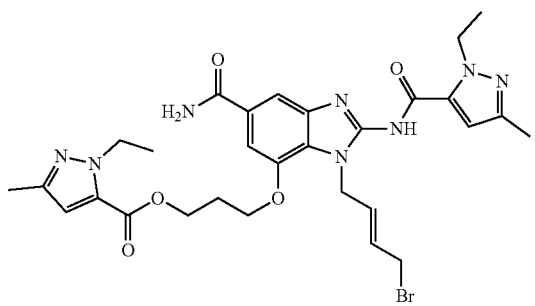

This compound was prepared using similar procedures as described for Example S1, Step 8 with (E)-3-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)propyl 1-ethyl-3-methyl-1H-pyrazole-5-carboxylate replacing (E)-2-(1-ethyl-3-methyl-1H-pyrazole-5-carboxamido)-1-(4-hydroxybut-2-enyl)-7-methyl-1H-benzo[d]imidazole-5-carboxamide. LC-MS calculated for $C_{29}H_{36}BrN_8O_5$ $(M+H)^+$: m/z=655.2/657.2; found 655.3/657.3.

Step 10: (E)-3-((5-carbamoyl-1-(4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate To a mixture of (E)-3-((1-(4-bromobut-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate (24 mg, 0.037 mmol) and 2-(1-ethyl-3-methyl-1H-pyrazol-5-yl)-8-methoxy-9H-pyrimido[4,5-b]indole-6-carboxamide (Example S10, Step 4: 12.83 mg, 0.037 mmol) in DMF (366 µl) was added DIPEA (19.18 µl, 0.110 mmol). After stirring for 20 min, $Cs_2CO_3$ (35.8 mg, 0.110 mmol) was added. The mixture was stirred at rt overnight. 180 uL of the reaction mixture was removed and diluted with TFA/water, then purified by prep-HPLC (pH=2, acetonitrile/water+TFA) to give the desired product as the TFA salt. LC-MS calculated for $C_{47}H_{54}N_{14}O_7$ $(M+2H)^{2+}$: m/z=463.2; found 463.3.

Example S16. (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-8-methoxy-9H-pyrimido[4,5-b]indole-6-carboxamide

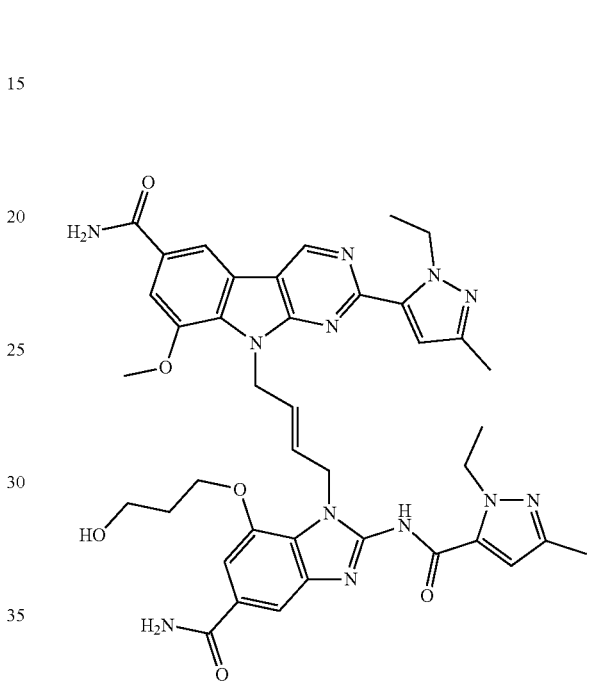

To a mixture of (E)-3-((1-(4-bromobut-2-en-1-yl)-5-carbamoyl-2-(1-ethyl-3-methyl-1H-pyrazole-5-carboxamido)-1H-benzo[d]imidazol-7-ypoxy)propyl 1-ethyl-3-methyl-1H-pyrazole-5-carboxylate (Example S15, Step 9: 24 mg, 0.037 mmol) and 2-(1-ethyl-3-methyl-1H-pyrazol-5-yl)-8-methoxy-9H-pyrimido[4,5-b]indole-6-carboxamide (Example S10, Step 4: 12.83 mg, 0.037 mmol) in DMF (366 µl) was added DIPEA (19.18 µl, 0.110 mmol). After 20 min, $Cs_2CO_3$ (35.8 mg, 0.110 mmol) was added. The mixture was stirred at rt overnight. 180 uL of the reaction mixture was removed and purified to provide Example S15. To the remaining reaction mixture was added aqueous 1 N sodium hydroxide (36.6 µl, 0.037 mmol). The mixture was stirred for 15 min, then was diluted with MeCN, TFA, then water. The resulting solution was purified by prep-HPLC (pH=2, acetonitrile/water+TFA) to give the desired product as the TFA salt. LC-MS calculated for $C_{40}H_{45}N_{12}O_6$ $(M+H)^+$: m/z=789.4; found 789.3.

Example S17. (E)-3-((5-carbamoyl-1-(4-(6-carbam-
oyl-2-(1-ethyl-3-methyl-1H-pyrazol-5-yl)-9H-py-
rimido[4,5-b]indol-9-yl)but-2-en-1-yl)-2-(1-ethyl-3-
methyl-1H-pyrazole-5-carboxamido)-1H-benzo[d]
imidazol-7-yl)oxy)propyl 1-ethyl-3-methyl-1H-
pyrazole-5-carboxylate

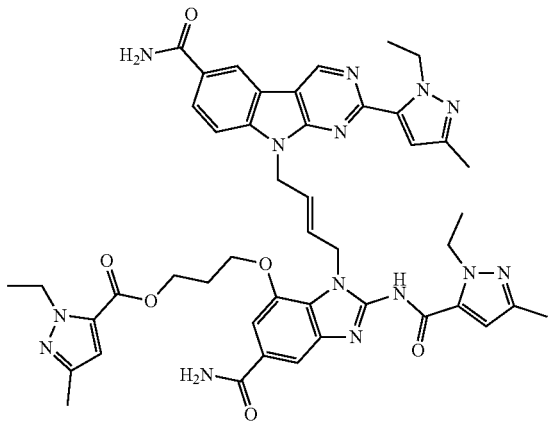 [SMILES: CCn1nc(C)cc1C(=O)Nc1nc2cc(C(N)=O)cc(OCCCOC(=O)c3cc(C)nn3CC)c2n1C/C=C/Cn1c2ccc(C(N)=O)cc2c2cnc(-c3cc(C)nn3CC)nc21]

This compound was prepared using similar procedures as described for Example S15, Step 10 with 2-(1-ethyl-3-methyl-1H-pyrazol-5-yl)-9H-pyrimido[4,5-b]indole-6-carboxamide (Example S1, Step 11) replacing 2-(1-ethyl-3-methyl-1H-pyrazol-5-yl)-8-methoxy-9H-pyrimido[4,5-b]indole-6-carboxamide. An aliquot of the reaction mixture was diluted with TFA/water, then purified by prep-HPLC (pH 32 2, acetonitrile/water+TFA) to give the desired product as the TFA salt. LC-MS calculated for $C_{46}H_{51}N_{14}O_6$ $(M+H)^+$: m/z=895.4; found 895.4.

Example S18. (E)-9-(4-(5-carbamoyl-2-(1-ethyl-3-
methyl-1H-pyrazole-5-carboxamido)-7-(3-hydroxy-
propoxy)-1H-benzo[d]imidazol-1-yl)but-2-en-1-yl)-
2-(1-ethyl-3-methyl-1H-pyrazol-5-yl)-9H-pyrimido
[4,5-b]indole-6-carboxamide

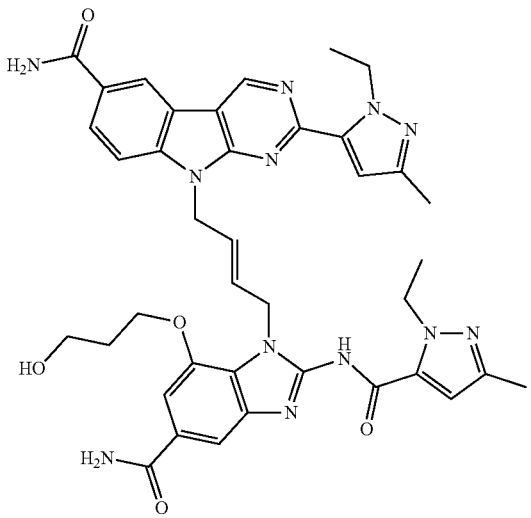 [SMILES: CCn1nc(C)cc1C(=O)Nc1nc2cc(C(N)=O)cc(OCCCO)c2n1C/C=C/Cn1c2ccc(C(N)=O)cc2c2cnc(-c3cc(C)nn3CC)nc21]

This compound was prepared using similar procedures as described for Example S16 with 2-(1-ethyl-3-methyl-1H-pyrazol-5-yl)-9H-pyrimido[4,5-b]indole-6-carboxamide (Example S1, Step 11) replacing 2-(1-ethyl-3-methyl-1H-pyrazol-5-yl)-8-methoxy-9H-pyrimido[4,5-b]indole-6-carboxamide. The reaction mixture was diluted with TFA/water, then purified by prep-HPLC (pH=2, acetonitrile/water+TFA) to give the desired product as the TFA salt. LC-MS calculated for $C_{39}H_{43}N_{12}O_5$ $(M+H)^+$: m/z=759.3; found 759.3.

Example S19. (E)-3-((5-carbamoyl-1-(4-(6-carbam-
oyl-2-(1-ethyl-3-methyl-1H-pyrazol-5-yl)-8-(3-mor-
pholinopropoxy)-9H-pyrimido[4,5-b]indol-9-yl)but-
2-en-1-yl)-2-(1-ethyl-3-methyl-1H-pyrazole-5-
carboxamido)-1H-benzo[d]imidazol-7-yl)oxy)propyl
1-ethyl-3-methyl-1H-pyrazole-5-carboxylate

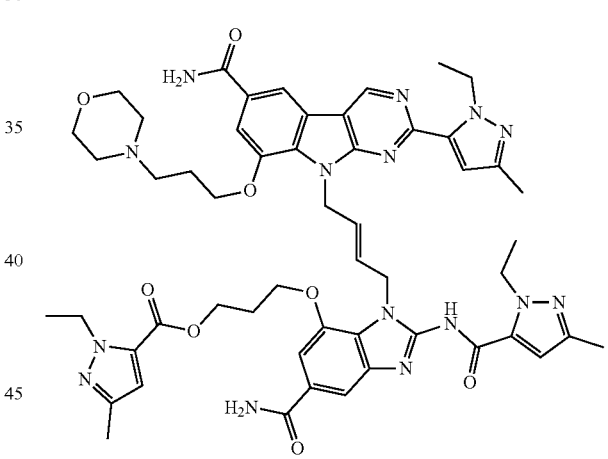

This compound was prepared using similar procedures as described for Example S15, Step 10 with 2-(1-ethyl-3-methyl-1H-pyrazol-5-yl)-8-(3-morpholinopropoxy)-9H-pyrimido[4,5-b]indole-6-carboxamide (Example S11, Step 3) replacing 2-(1-ethyl-3-methyl-1H-pyrazol-5-yl)-8-methoxy-9H-pyrimido[4,5-b]indole-6-carboxamide. An aliquot of the reaction mixture was diluted with TFA/water, then purified by prep-HPLC (pH=2, acetonitrile/water+TFA) to give the desired product as the TFA salt. LC-MS calculated for $C_{53}H_{65}N_{15}O_8$ $(M+2H)^{2+}$: m/z=519.8; found 519.9.

Example S20. (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-8-(3-morpholinopropoxy)-9H-pyrimido[4,5-b]indole-6-carboxamide

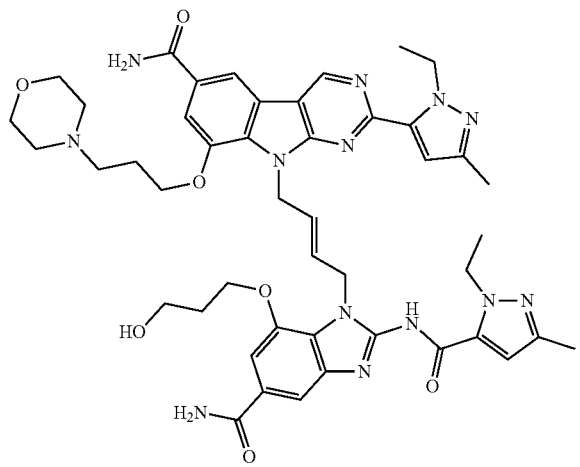 [SMILES: CCn1nc(C)cc1C(=O)Nc1nc2cc(C(N)=O)cc(OCCCO)c2n1C/C=C/Cn1c2nc(-c3cc(C)nn3CC)ncc2c2cc(C(N)=O)cc(OCCCN3CCOCC3)c21]

This compound was prepared using similar procedures as described for Example S16 with 2-(1-ethyl-3-methyl-1H-pyrazol-5-yl)-8-(3-morpholinopropoxy)-9H-pyrimido[4,5-b]indole-6-carboxamide (Example S11, Step 3) replacing 2-(1-ethyl-3-methyl-1H-pyrazol-5-yl)-8-methoxy-9H-pyrimido[4,5-b]indole-6-carboxamide. The reaction mixture was diluted with TFA/water, then purified by prep-HPLC (pH=2, acetonitrile/water+TFA) to give the desired product as the TFA salt. LC-MS calculated for $C_{46}H_{57}N_{13}O_7$ $(M+H)^{2+}$: m/z=451.7; found 451.8.

Example S21. (E)-3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

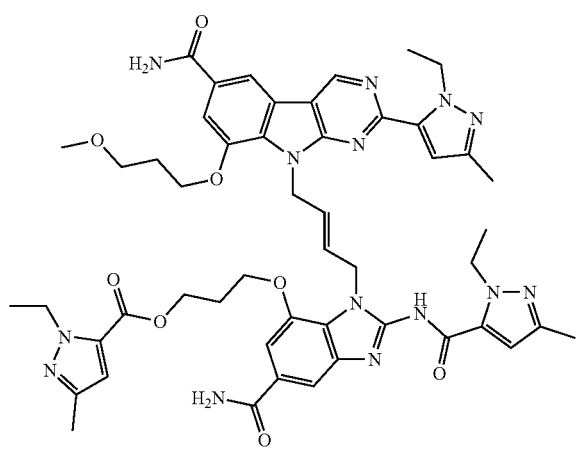 [SMILES: CCn1nc(C)cc1C(=O)Nc1nc2cc(C(N)=O)cc(OCCCOC(=O)c3cc(C)nn3CC)c2n1C/C=C/Cn1c2nc(-c3cc(C)nn3CC)ncc2c2cc(C(N)=O)cc(OCCCOC)c21]

This compound was prepared using similar procedures as described for Example S15, Step 10 with 2-(1-ethyl-3-methyl-1H-pyrazol-5-yl)-8-(3-methoxypropoxy)-9H-pyrimido[4,5-b]indole-6-carboxamide (Example S12, Step 3) replacing 2-(1-ethyl-3-methyl-1H-pyrazol-5-yl)-8-methoxy-9H-pyrimido[4,5-b]indole-6-carboxamide. An aliquot of the reaction mixture was diluted with TFA/water, then purified by prep-HPLC (pH=2, acetonitrile/water+TFA) to give the desired product as the TFA salt. LC-MS calculated for $C_{50}H_{60}N_{14}O_8$ $(M+2H)^{2+}$: m/z=492.2; found 492.3.

Example S22. (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

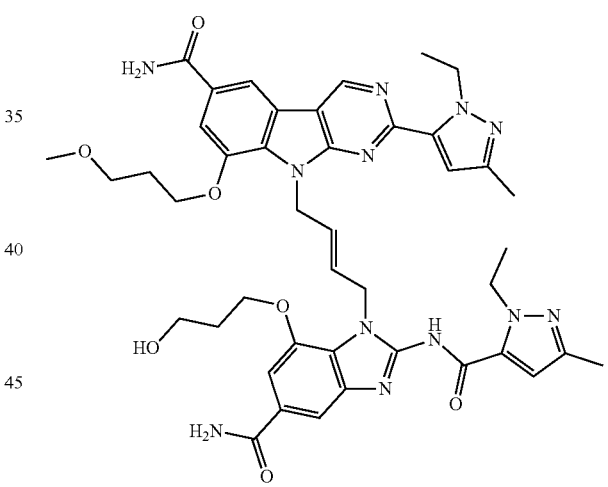

This compound was prepared using similar procedures as described for Example S16 with 2-(1-ethyl-3-methyl-1H-pyrazol-5-yl)-8-(3-methoxypropoxy)-9H-pyrimido[4,5-b]indole-6-carboxamide (Example S12, Step 3) replacing 2-(1-ethyl-3-methyl-1H-pyrazol-5-yl)-8-methoxy-9H-pyrimido[4,5-b]indole-6-carboxamide. The remaining reaction mixture was diluted with TFA/water, then purified by prep-HPLC (pH=2, acetonitrile/water+TFA) to give the desired product as the TFA salt. LC-MS calculated for $C_{43}H_{51}N_{12}O_7$ $(M+H)^+$: m/z=847.4; found 847.4.

Example S23. (E)-5-(4-(5-carbamoyl-2-(1-ethyl-3-methyl-1H-pyrazole-5-carboxamido)-7-methyl-1H-benzo[d]imidazol-1-yl)but-2-en-1-yl)-3-(1-ethyl-3-methyl-1H-pyrazol-5-yl)-4-fluoro-5H-pyrido[4,3-b]indole-8-carboxamide

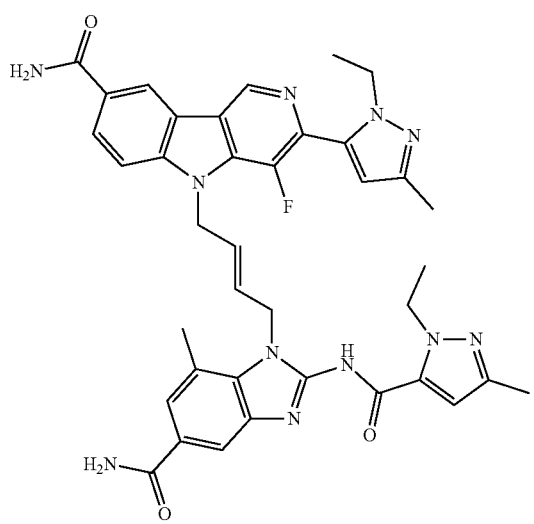 [SMILES: CCn1nc(C)cc1C(=O)Nc1nc2cc(C(N)=O)cc(C)c2n1C/C=C/Cn1c2ccc(C(N)=O)cc2c2cnc(-c3cc(C)nn3CC)c(F)c21]

Step 1: 3-(6-chloro-5-fluoropyridin-3-yl)-4-nitrobenzamide

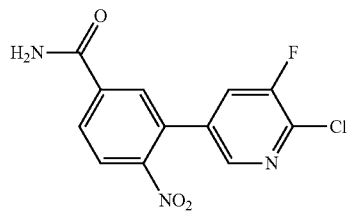 [SMILES: NC(=O)c1ccc([N+](=O)[O-])c(-c2cnc(Cl)c(F)c2)c1]

This compound was prepared using similar procedures as described for Example S1, Step 9 with 2-chloro-3-fluoro-5-(4,4,5,5-tetramethyl-1,3,2-dioxaborolan-2-yl)pyridine (Astatech, cat #33955) replacing (2-chloropyrimidin-5-yl)boronic acid. LC-MS calculated for $C_{12}H_8ClFN_3O_3$ (M+H)$^+$: m/z=296.0; found 296.1.

Step 2: 3-(6-(1-ethyl-3-methyl-1H-pyrazol-5-yl)-5-fluoropyridin-3-yl)-4-nitrobenzamide

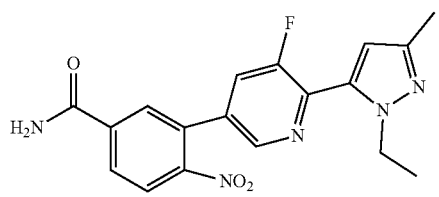 [SMILES: CCn1nc(C)cc1-c1ncc(-c2cc(C(N)=O)ccc2[N+](=O)[O-])cc1F]

This compound was prepared using similar procedures as described for Example S1, Step 11 with 3-(6-chloro-5-fluoropyridin-3-yl)-4-nitrobenzamide replacing 2-chloro-9H-pyrimido[4,5-b]indole-6-carboxamide. LC-MS calculated for $C_{18}H_{37}FN_5O_3$ (M+H)$^+$: m/z=370.1; found 370.1.

Step 3: 3-(1-ethyl-3-methyl-1H-pyrazol-5-yl)-4-fluoro-5H-pyrido[4,3-b]indole-8-carboxamide and 2-(1-ethyl-3-methyl-1H-pyrazol-5-yl)-3-fluoro-9H-pyrido[2,3-b]indole-6-carboxamide

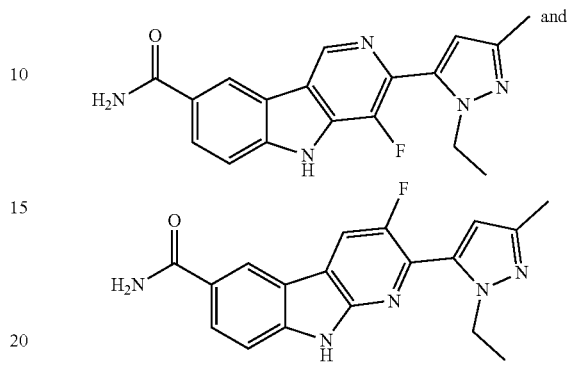

This compound was prepared using similar procedures as described for Example S1, Step 10 with 3-(6-(1-ethyl-3-methyl-1H-pyrazol-5-yl)-5-fluoropyridin-3-yl)-4-nitrobenzamide replacing 3-(2-chloropyrimidin-5-yl)-4-nitrobenzamide. After cooling to rt, the reaction was concentrated under reduced pressure and purified by flash chromatography (15% MeOH/DCM) with 2-(1-ethyl-3-methyl-1H-pyrazol-5-yl)-3-fluoro-9H-pyrido[2,3-b]indole-6-carboxamide eluting first (major product) and 3-(1-ethyl-3-methyl-1H-pyrazol-5-yl)-4-fluoro-5H-pyrido[4,3-b]indole-8-carboxamide eluting second (minor product). LC-MS calculated for $C_{18}H_{17}FN_5O$ (M+H)$^+$: m/z=338.1; found 338.2. Major product: $^1$H NMR (400 MHz, MeOD) δ 8.69 (s, 1H), 8.37 (d, J=10.5 Hz, 1H), 8.05 (dd, J=8.6, 1.6 Hz, 1H), 7.56 (d, J=8.6 Hz, 1H), 6.56 (d, J=4.0 Hz, 1H), 4.56 (q, J=7.1 Hz, 2H), 3.35 (s, 2H), 2.32 (s, 3H), 1.44 (t, J=7.1 Hz, 3H). Minor product: $^1$H NMR (400 MHz, MeOD) δ 9.22 (s, 1H), 8.81 (s, 1H), 8.11 (dd, J=8.6, 1.4 Hz, 1H), 7.65 (d, J=8.6 Hz, 1H), 6.48 (d, J=2.3 Hz, 1H), 4.40 (q, J=7.1 Hz, 2H), 2.33 (s, 3H), 1.36 (t, J=7.1 Hz, 3H).

Step 4: (E)-5-(4-(5-carbamoyl-2-(1-ethyl-3-methyl-1H-pyrazole-5-carboxamido)-7-methyl-1H-benzo[d]imidazol-1-yl)but-2-en-1-yl)-3-(1-ethyl-3-methyl-1H-pyrazol-5-yl)-4-fluoro-5H-pyrido[4,3-b]indole-8-carboxamide To a mixture of (E)-1-(4-bromobut-2-en-1-yl)-2-(1-ethyl-3-methyl-1H-pyrazole-5-carboxamido)-7-methyl-1H-benzo[d]imidazole-5-carboxamide (Example S1, Step 8:10 mg, 0.022 mmol) and 3-(1-ethyl-3-methyl-1H-pyrazol-5-yl)-4-fluoro-5H-pyrido[4,3-b]indole-8-carboxamide (7.34 mg, 0.022 mmol) in DMF (218 µl) was added DIPEA (11.41 µl, 0.065 mmol). After 20 min, Cs$_2$CO$_3$ (21.28 mg, 0.065 mmol) was added. The mixture was stirred at rt overnight. The reaction was diluted with TFA/water, then purified by prep-HPLC (pH=2, acetonitrile/water+TFA) to give the desired product as the TFA salt. LC-MS calculated for $C_{38}H_{39}FN_{11}O_3$ (M+H)$^+$: m/z=716.3; found 716.3.

Example S24. (E)-9-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazol-5-yl)-3-fluoro-9H-pyrido[2,3-b]indole-6-carboxamide

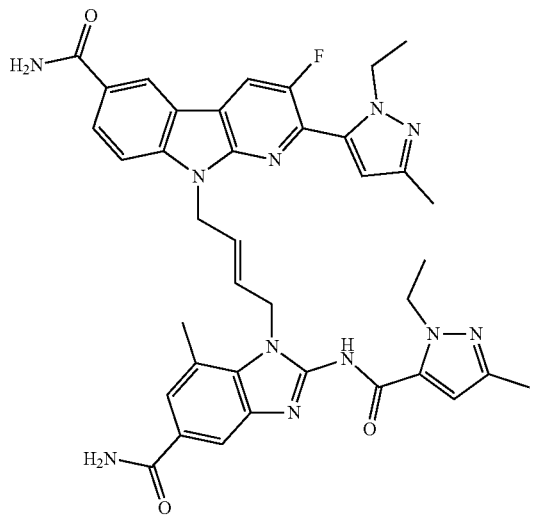 [SMILES: CCn1nc(C)cc1C(=O)Nc1nc2cc(C(N)=O)cc(C)c2n1C/C=C/Cn1c2ccc(C(N)=O)cc2c2cc(F)c(-c3cc(C)nn3CC)nc21]

This compound was prepared using similar procedures as described for Example S23, Step 4 with 2-(1-ethyl-3-methyl-1H-pyrazol-5-yl)-3-fluoro-9H-pyrido[2,3-b]indole-6-carboxamide (Example S23, Step 3) replacing 3-(1-ethyl-3-methyl-1H-pyrazol-5-yl)-4-fluoro-5H-pyrido[4,3-b]indole-8-carboxamide. LC-MS calculated for $C_{38}H_{39}FN_{11}O_3$ (M+H)$^+$: m/z=716.3; found 716.3.

Example S25. (E)-9-(4-(5-carbamoyl-2-(1-ethyl-3-methyl-1H-pyrazole-5-carboxamido)-7-methyl-1H-benzo[d]imidazol-1-yl)but-2-en-1-yl)-3-cyano-2-(1-ethyl-3-methyl-1H-pyrazol-5-yl)-9H-pyrido[2,3-b]indole-6-carboxamide

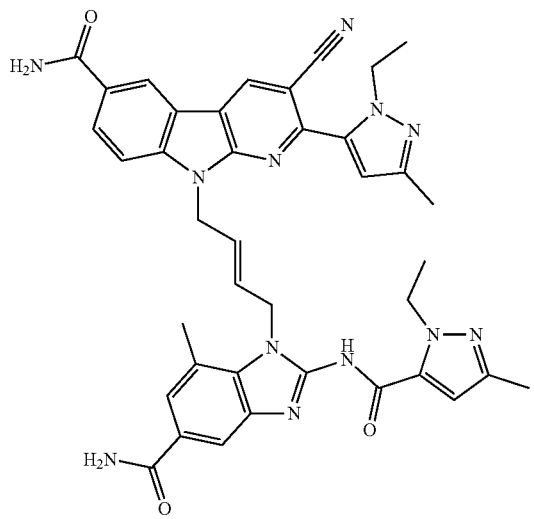 [SMILES: CCn1nc(C)cc1C(=O)Nc1nc2cc(C(N)=O)cc(C)c2n1C/C=C/Cn1c2ccc(C(N)=O)cc2c2cc(C#N)c(-c3cc(C)nn3CC)nc21]

Step 1: (6-chloro-5-cyanopyridin-3-yl)boronic acid

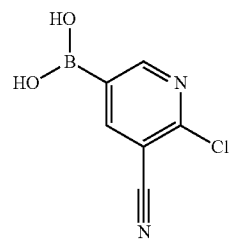 [SMILES: N#Cc1cc(B(O)O)cnc1Cl]

To a vial was added 5-bromo-2-chloronicotinonitrile (Aldrich, cat #759716: 0.500 g, 2.299 mmol), bis(pinacolato)diboron (0.701 g, 2.76 mmol), potassium acetate (0.564 g, 5.75 mmol), dichloro[1,1'-bis(diphenylphosphino)ferrocene]palladium (II) dichloromethane adduct (0.188 g, 0.230 mmol), 1,4-dioxane (5.75 ml), and a stir bar. The mixture was sparged with nitrogen for 2 min, then was sealed and heated at 110° C. for 1 h with stirring. After cooling, the mixture was filtered through Celite® and purified using flash chromatography (5% MeOH/DCM). LC-MS calculated for $C_6H_5BClN_2O_2$ (M+H)$^+$: m/z=183.0; found 183.0.

Step 2: 3-(6-chloro-5-cyanopyridin-3-yl)-4-nitrobenzamide

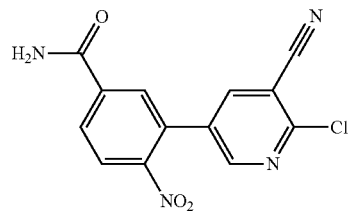 [SMILES: N#Cc1cc(-c2cc(C(N)=O)ccc2[N+](=O)[O-])cnc1Cl]

This compound was prepared using similar procedures as described for Example S1, Step 9 with (6-chloro-5-cyanopyridin-3-yl)boronic acid replacing (2-chloropyrimidin-5-yl)boronic acid. LC-MS calculated for $C_{13}H_8ClN_4O_3$ (M+H)$^+$: m/z=303.0; found 302.8.

Step 3: 3-(5-cyano-6-(1-ethyl-3-methyl-1H-pyrazol-5-yl)pyridin-3-yl)-4-nitrobenzamide

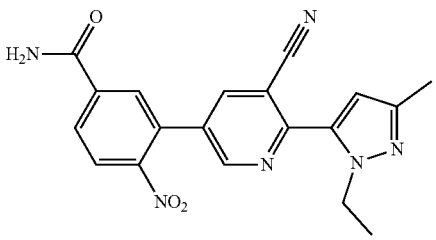 [SMILES: CCn1nc(C)cc1-c1ncc(-c2cc(C(N)=O)ccc2[N+](=O)[O-])cc1C#N]

This compound was prepared using similar procedures as described for Example S1, Step 11 with 3-(6-chloro-5-cyanopyridin-3-yl)-4-nitrobenzamide replacing 2-chloro-9H-pyrimido[4,5-b]indole-6-carboxamide. LC-MS calculated for $C_{19}H_{17}N_6O_3$ (M+H)+: m/z=377.1; found 377.1.

Step 4: 3-cyano-2-(1-ethyl-3-methyl-1H-pyrazol-5-yl)-9H-pyrido[2,3-b]indole-6-carboxamide and 4-cyano-3-(1-ethyl-3-methyl-1H-pyrazol-5-yl)-5H-pyrido[4,3-b]indole-8-carboxamide

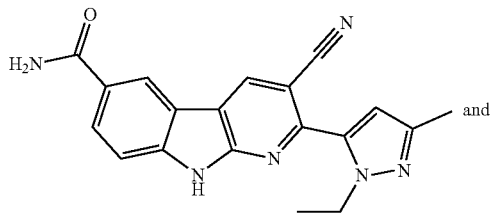

and

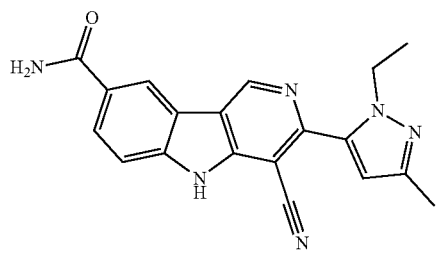

Example S26. (E)-5-(4-(5-carbamoyl-2-(1-ethyl-3-methyl-1H-pyrazole-5-carboxamido)-7-methyl-1H-benzo[d]imidazol-1-yl)but-2-en-1-yl)-4-cyano-3-(1-ethyl-3-methyl-1H-pyrazol-5-yl)-5H-pyrido[4,3-b]indole-8-carboxamide

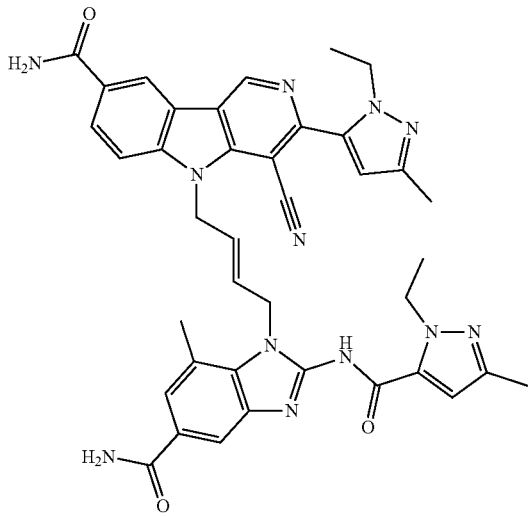 [SMILES: CCn1nc(C)cc1C(=O)Nc1nc2cc(C(N)=O)cc(C)c2n1C/C=C/Cn1c2ccc(C(N)=O)cc2c2cnc(-c3cc(C)nn3CC)c(C#N)c21]

This compound was prepared using similar procedures as described for Example S1, Step 10 with 3-(5-cyano-6-(1-ethyl-3-methyl-1H-pyrazol-5-yl)pyridin-3-yl)-4-nitrobenzamide replacing 3-(2-chloropyrimidin-5-yl)-4-nitrobenzamide. After cooling to rt, the reaction was concentrated under reduced pressure and purified by flash chromatography (15% MeOH/DCM) with 3-cyano-2-(1-ethyl-3-methyl-1H-pyrazol-5-yl)-9H-pyrido[2,3-b]indole-6-carboxamide eluting first (major product) and 4-cyano-3-(1-ethyl-3-methyl-1H-pyrazol-5-yl)-5H-pyrido[4,3-b]indole-8-carboxamide eluting second (minor product). LC-MS calculated for $C_{19}H_{17}N_6O$ (M+H)$^+$: m/z=345.1; found 345.2.

Step 5: (E)-9-(4-(5-carbamoyl-2-(1-ethyl-3-methyl-1H-pyrazole-5-carboxamido)-7-methyl-1H-benzo[d]imidazol-1-yl)but-2-en-1-yl)-3-cyano-2-(1-ethyl-3-methyl-1H-pyrazol-5-yl)-9H-pyrido[2,3-b]indole-6-carboxamide This compound was prepared using similar procedures as described for Example S23, Step 4 with 3-cyano-2-(1-ethyl-3-methyl-1H-pyrazol-5-yl)-9H-pyrido[2,3-b]indole-6-carboxamide replacing 3-(1-ethyl-3-methyl-1H-pyrazol-5-yl)-4-fluoro-5H-pyrido[4,3-b]indole-8-carboxamide. $^1$H NMR (600 MHz, DMSO) δ 12.82 (s, 1H), 9.18 (s, 1H), 8.87 (s, 1H), 8.15-8.07 (m, 1H), 8.02 (s, 1H), 7.86 (s, 1H), 7.82 (s, 1H), 7.77 (d, J=8.6 Hz, 1H), 7.46 (s, 1H), 7.39 (s, 1H), 7.27 (s, 1H), 6.65 (s, 1H), 6.41 (s, 1H), 5.84 (dt, J=15.6, 4.8 Hz, 1H), 5.55 (dt, J=15.6, 5.4 Hz, 1H), 5.14 (d, J=4.8 Hz, 2H), 4.91 (brs, 2H), 4.46 (q, J=6.6 Hz, 2H), 4.11 (q, J=7.2 Hz, 2H), 2.42 (s, 3H), 2.24 (s, 3H), 2.10 (s, 3H), 1.21 (t, J=7.2 Hz, 3H), 1.17 (t, J=6.6 Hz, 3H). LC-MS calculated for $C_{39}H_{39}N_{12}O_3$ (M+H)$^+$: m/z=723.3; found 723.3.

Example S26. (E)-5-(4-(5-carbamoyl-2-(1-ethyl-3-methyl-1H-pyrazole-5-carboxamido)-7-methyl-1H-benzo[d]imidazol-1-yl)but-2-en-1-yl)-4-cyano-3-(1-ethyl-3-methyl-1H-pyrazol-5-yl)-5H-pyrido[4,3-b]indole-8-carboxamide This compound was prepared using similar procedures as described for Example S23, Step 4 with 4-cyano-3-(1-ethyl-3-methyl-1H-pyrazol-5-yl)-5H-pyrido[4,3-b]indole-8-carboxamide (Example S25, Step 4) replacing 3-(1-ethyl-3-methyl-1H-pyrazol-5-yl)-4-fluoro-5H-pyrido[4,3-b]indole-8-carboxamide. LC-MS calculated for $C_{39}H_{39}N_{12}O_3$ (M+H)$^+$: m/z=723.3; found 723.3.

Example S27. (E)-9-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

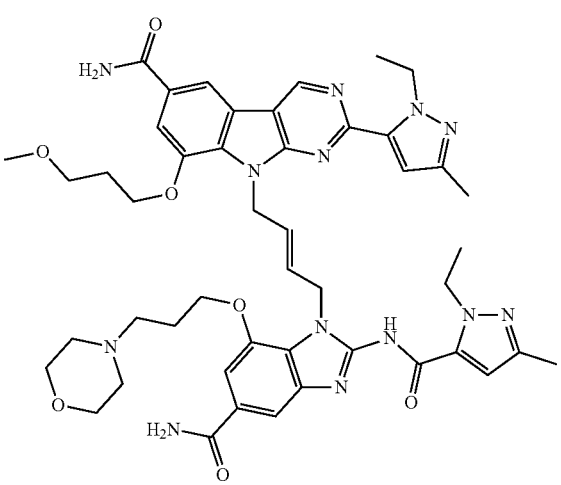

Step 1: (E)-9-(4-(5-carbamoyl-2-(1-ethyl-3-methyl-1H-pyrazole-5-carboxamido)-7-(3-oxopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

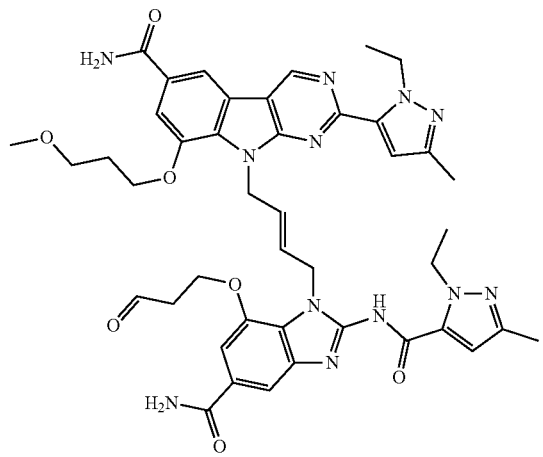

To a vial was added (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example S22: 0.025 g, 0.030 mmol), DMF (0.295 ml), and a stir bar. The mixture was cooled to 0° C., and DMP (0.025 g, 0.059 mmol) and water (4.25 µl, 0.236 mmol) were added. The reaction was gradually warmed up to rt, stirring overnight. After cooling to 0° C., ice and sodium bicarbonate were added, followed by saturated aqueous sodium thiosulfate. The reaction was extracted with chloroform/ipa (3:1), dried over MgSO$_4$, filtered, and concentrated under reduced pressure. The crude product was used directly in the next step without further purification. LC-MS calculated for $C_{43}H_{49}N_{12}O_7$ (M+H)$^+$: m/z=845.4; found 845.3.

Step 2: (E)-9-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide To a vial was added (E)-9-(4-(5-carbamoyl-2-(1-ethyl-3-methyl-1H-pyrazole-5-carboxamido)-7-(3-oxopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (0.025 g, 0.030 mmol), DMF (0.592 ml), DIPEA (0.016 ml, 0.089 mmol), and morpholine (7.73 µl, 0.089 mmol). Sodium cyanoborohydride (5.58 mg, 0.089 mmol) was then added and the reaction was stirred for 1 h. The reaction was diluted with TFA/water, then purified by prep-HPLC (pH=2, acetonitrile/water+TFA) to give the desired product as the TFA salt. LC-MS calculated for $C_{47}H_{59}N_{13}O_7$ (M+2H)$^{2+}$: m/z=458.7; found 458.7.

Example S28. (E)-9-(4-(5-carbamoyl-2-(1-ethyl-3-methyl-1H-pyrazole-5-carboxamido)-7-hydroxy-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

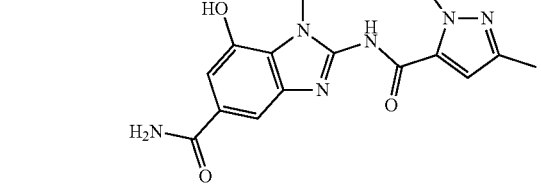

This compound was prepared as a by-product from Example S27, Step 2, where-in (E)-9-(4-(5-carbamoyl-2-(1-ethyl-3-methyl-1H-pyrazole-5-carboxamido)-7-(3-oxopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide undergoes a retro-Michael reaction. The reaction was diluted with TFA/water, then purified by prep-HPLC (pH=2, acetonitrile/water+TFA) to give the desired product as the TFA salt. $^1$H NMR (600 MHz, DMSO) δ 12.67 (s, 1H), 10.34 (s, 1H), 9.48 (s, 1H), 8.42 (d, J=1.2 Hz, 1H), 8.04 (s, 1H), 7.78 (s, 1H), 7.60 (d, J=1.2 Hz, 1H), 7.41 (s, 1H), 7.36 (s, 1H), 7.19 (s, 1H), 7.10 (s, 1H), 6.79 (s, 1H), 6.37 (s, 1H), 5.94 (m, 1H), 5.85-5.68 (m, 1H), 5.27 (d, J=4.8 Hz, 2H), 4.89 (d, J=6.0 Hz, 2H), 4.60 (q, J=7.2 Hz, 2H), 4.44 (q, J=6.9 Hz, 2H), 4.12 (t, J=6.3 Hz, 2H), 3.35 (t, J=6.3 Hz, 2H), 3.16 (s, 3H), 2.19 (s, 3H), 2.05 (s, 3H), 1.86 (tt, J=6.3, 6.3 Hz, 2H), 1.26 (t, J=6.9 Hz, 3H), 1.18 (t, J=7.2 Hz, 3H). LC-MS calculated for $C_{40}H_{45}N_{12}O_6$ (M+H)$^+$: m/z=789.4; found 789.3.

Example S29. (E)-9,9'-(but-2-ene-1,4-diyl)bis(2-(1-ethyl-3-methyl-1H-pyrazol-5-yl)-8-methoxy-9H-pyrimido[4,5-b]inclole-6-carboxamide)

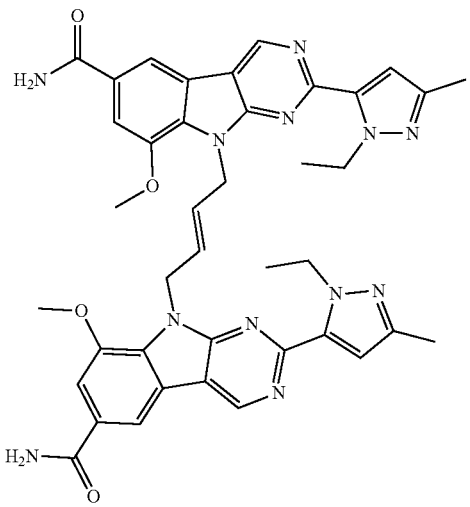 [SMILES: CCn1nc(C)cc1-c1ncc2c3cc(C(N)=O)cc(OC)c3n(C/C=C/Cn3c4nc(-c5cc(C)nn5CC)ncc4c4cc(C(N)=O)cc(OC)c43)c2n1]

Step 1: 4-fluoro-3-methyl-5-nitrobenzamide

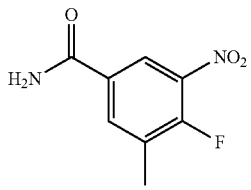

At 0° C., a mixture of nitric acid (2.51 mL, 39.2 mmol) and sulfuric acid (2.173 mL, 40.8 mmol) was added dropwise over 10 min into a solution of 4-fluoro-3-methylbenzamide (4.46 g, 29.1 mmol) in sulfuric acid (13.97 mL, 262 mmol). The mixture was stirred for 1.5 h while slowly warming up to room temperature. The mixture was slowly poured into ice water (50 mL), and the precipitated solid was filtered and then washed with water (50 mL). The resulting solid residue was dried to provide the desired product as a white solid. LC-MS calculated for $C_8H_8FN_2O_3$ $(M+H)^+$: m/z=199.04; found 199.2

Step 2: (E)-tert-butyl 4-(4-carbamoyl-2-methyl-6-nitrophenylamino)but-2-enylcarbamate

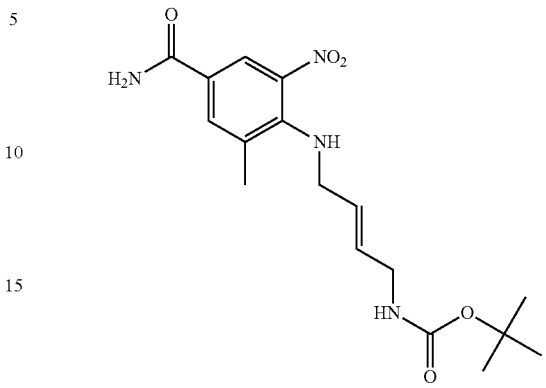

To a solution of 4-fluoro-3-methyl-5-nitrobenzamide (0.400 g, 2.019 mmol) and tert-butyl (E)-(4-aminobut-2-en-1-yl)carbamate (0.376 g, 2.019 mmol) (Ark Pharm, cat #AK308564) in dry DMSO (2.019 mL) was added $K_2CO_3$ (0.614 g, 4.44 mmol). The resulting yellow solution was stirred at room temperature for 1 h. The reaction mixture was diluted with water (15 mL) dropwise. The precipitated solid was filtered and then washed with water (10 mL). The resulting solid residue was dried to provide the desired product as a yellow solid. LC-MS calculated for $C_{17}H_{24}N_4NaO_5$ $(M+Na)^+$: m/z=387.2; found 387.2.

Step 3: (E)-tert-butyl 4-(2-amino-4-carbamoyl-6-methylphenylamino)but-2-enylcarbamate

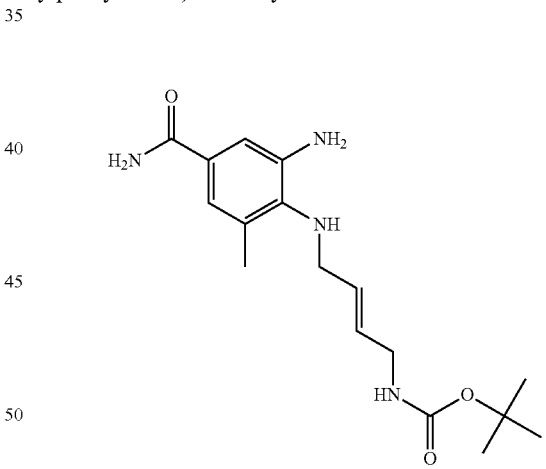

To a solution of tert-butyl (E)-(4-((4-carbamoyl-2-methyl-6-nitrophenyl)amino)but-2-en-1-yl)carbamate (220 mg, 0.604 mmol) in dioxane (1509 μL) and water (503 μL) was added ammonium chloride (226 mg, 4.23 mmol) and zinc (276 mg, 4.23 mmol) at 0° C. The reaction mixture was stirred at room temperature for 1 h, after which time it was filtered through a Celite® bed. The filtrate was partitioned between DCM and water. The organic layer was separated, dried over $MgSO_4$, filtered, and concentrated to provide the product. LC-MS calculated for $C_{17}H_{26}N_4NaO_3$ $(M+Na)^+$: m/z=357.2 ; found 357.3.

Step 4: (E)-tert-butyl 4-(2-amino-5-carbamoyl-7-methyl-1H-benzo[d]imidazol-1-yl)but-2-enylcarbamate

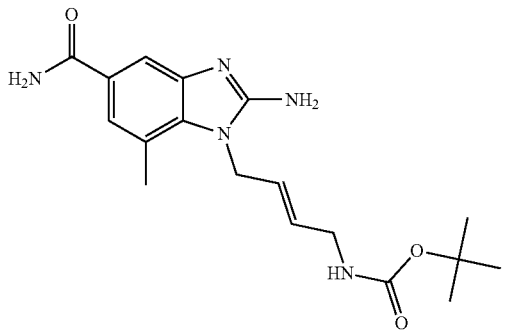 [SMILES: Cc1cc(C(N)=O)cc2nc(N)n(C/C=C/CNC(=O)OC(C)(C)C)c12]

To a solution of tert-butyl (E)-(4-((2-amino-4-carbamoyl-6-methylphenyl)amino)but-2-en-1-yl)carbamate (0.201 g, 0.60 mmol) in MeOH (2.000 mL) was added cyanogen bromide (0.047 mL, 0.900 mmol). The reaction mixture was stirred at room temperature for 1 h. The mixture was diluted with DCM, and washed with water and brine. The organic phase was dried over MgSO$_4$ before filtering. The filtrate was concentrated and purified by flash chromatography on a silica gel column eluting with 0 to 8% MeOH in DCM to afford the desired product. LC-MS calculated for C$_{18}$H$_{26}$N$_5$O$_3$ (M+H)$^+$: m/z=360.2; found 360.3.

Step 5: (E)-tert-butyl 4-(5-carbamoyl-2-(1-ethyl-3-methyl-1H-pyrazole-5-carboxamido)-7-methyl-1H-benzo[d]imidazol-1-yl)but-2-enylcarbamate

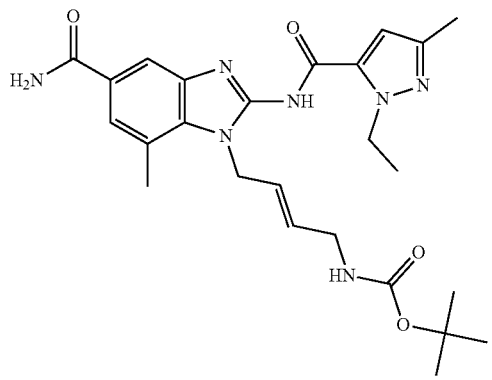

A mixture of 1-ethyl-3-methyl-1H-pyrazole-5-carboxylic acid (Combi-Blocks, cat #QB-0979: 93 mg, 0.60 mmol), tert-butyl (E)-(4-(2-amino-5-carbamoyl-7-methyl-1H-benzo[d]imidazol-1-yl)but-2-en-1-yl)carbamate (216 mg, 0.600 mmol), 2-(3H-[1,2,3]triazolo[4,5-b]pyridin-3-yl)-1,1,3,3-tetramethylisouronium hexafluorophosphate(V) (274 mg, 0.720 mmol), and N,N-Diisopropylethylamine (209 μL, 1.200 mmol) in DMF (2000 μL) was stirred at room temperature for 2 h. The mixture was concentrated under reduced pressure. The mixture was then diluted with DCM and water, and the layers were separated. The aqeous layer was further extracted with DCM and the combined organic layers were washed with brine, dried over Na2SO$_4$, filtered, and concentrated in vacuo. The crude residue was purified by flash chromatography on a silica gel column eluting with 0 to 8% MeOH in DCM to afford the desired product. LC-MS calculated for C$_{25}$H$_{34}$N$_7$O$_4$ (M+H)$^+$: m/z=496.3 ; found 496.3.

Step 6: (E)-1-(4-aminobut-2-enyl)-2-(1-ethyl-3-methyl-1H-pyrazole-5-carboxamido)-7-methyl-1H-benzo[d]imidazole-5-carboxamide

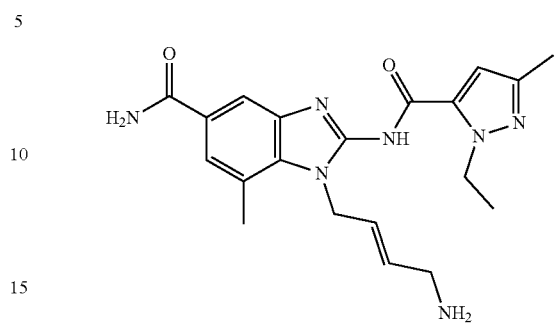

To a solution of tert-butyl (E)-(4-(5-carbamoyl-2-(1-ethyl-3-methyl-1H-pyrazole-5-carboxamido)-7-methyl-1H-benzo[d]imidazol-1-yl)but-2-en-1-yl)carbamate (180.0 mg, 0.363 mmol) in DCM (2.0 mL) was added TFA (0.2 mL). The resulting solution was stirred at room temperature for 0.5 h. The reaction mixture was quenched by NaHCO$_3$ aqueous solution then extracted with DCM. The organic phases were combined and dried over MgSO$_4$, then filtered. The filtrate was concentrated and used directly in the next step without further purification. For characterization purposes, the crude material was purified by prep HPLC (pH=2, water+TFA) to provide the desired compound as its TFA salt. LC-MS calculated for C$_{20}$H$_{26}$N$_7$O$_2$ (M+H)$^+$: m/z=396.2; found 396.3. $^1$H NMR (400 MHz, DMSO) δ 12.91 (s, 1H), 7.87 (m, 2H), 7.69 (br s, 2H), 7.57 (s, 1H), 7.30 (s, 1H), 6.64 (s, 1H), 6.10 (dt, J=16.0, 4.8 Hz, 1 H), 5.33 (dt, J=16.0, 6.4 Hz, 1 H), 5.06 (brs, 2H), 4.59 (q, J=6.8 Hz, 2H), 3.42 (dt, J=6.4 Hz, 4.8 Hz, 2H), 2.63 (s, 3H), 2.16 (s, 3H), 1.34 (t, J=6.8 Hz, 3H).

Step 7: (E)-2-(1-ethyl-3-methyl-1H-pyrazole-5-carboxamido)-1-(4-hydroxybut-2-enyl)-7-methyl-1H-benzo[d]imidazole-5-carboxamide

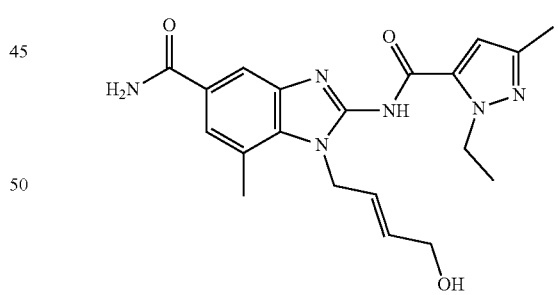

To a mixture of (E)-1-(4-aminobut-2-en-1-yl)-2-(1-ethyl-3-methyl-1H-pyrazole-5-carboxamido)-7-methyl-1H-benzo[d]imidazole-5-carboxamide (180.0 mg, 0.455 mmol) and KBr (108 mg, 0.910 mmol) in water (228 μL) was added sodium nitrite (62.8 mg, 0.910 mmol). The mixture was stirred at 70° C. for 2 h. After cooling to rt, the mixture was diluted with DCM, and washed with water and brine. The organic phase was dried over MgSO$_4$ before filtering. The filtrate was concentrated to afford the desired product. LC-MS calculated for C$_{20}$H$_{25}$N$_6$O$_3$ (M+H)$^+$: m/z=397.2; found 397.2.

Step 8: (E)-1-(4-bromobut-2-enyl)-2-(1-ethyl-3-methyl-1H-pyrazole-5-carboxamido)-7-methyl-1H-benzo[d]imidazole-5-carboxamide

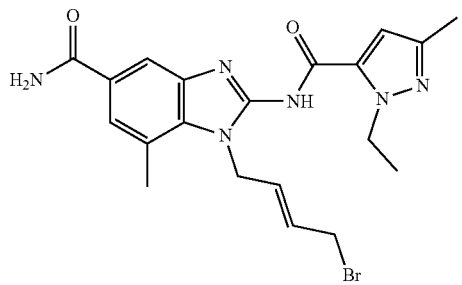 [SMILES: CCn1nc(C)cc1C(=O)Nc1nc2cc(C(N)=O)cc(C)c2n1C/C=C/CBr]

To a solution of (E)-2-(1-ethyl-3-methyl-1H-pyrazole-5-carboxamido)-1-(4-hydroxybut-2-enyl)-7-methyl-1H-benzo[d]imidazole-5-carboxamide (180.0 mg, 0.455 mmol) in THF (2.0 mL) was added PBr$_3$ (86 μL, 0.910 mmol) dropwise. The resulting solution was stirred at room temperature for 10 h. The reaction mixture was quenched by NaHCO$_3$ aqueous solution then extracted with DCM. The organic phases were combined and dried over MgSO$_4$, then filtered. The crude residue was purified by flash chromatography on a silica gel column eluting with 0 to 10% MeOH in DCM to afford the desired product. LC-MS calculated for C$_{20}$H$_{24}$BrN$_6$O$_2$ (M+H)$^+$: m/z=459.1, 461.1; found 459.1, 461.1.

Step 9: 3-bromo-5-fluoro-4-nitrobenzamide

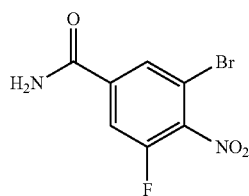 [SMILES: NC(=O)c1cc(F)c([N+](=O)[O-])c(Br)c1]

Methyl 3-bromo-5-fluoro-4-nitrobenzoate (Ark Pharm, cat # AK139034: 650.0 mg, 2.338 mmol) was stirred in ammonium hydroxide (5735 μL, 147 mmol) at room temperature for 10 h. The solid was filtered and rinsed with cold water. The resulting solid residue was dried to provide the desired product. LC-MS calculated for C$_7$H$_5$BrFN$_2$O$_3$ (M+H)$^+$: m/z=262.94. While the UV signal of the desired product was observed, the expected molecular weight was not shown due to the presence of the nitro group.

Step 10: 3-bromo-5-methoxy-4-nitrobenzamide

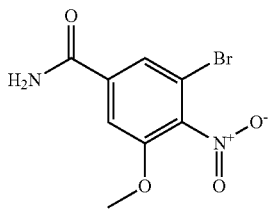

To a stirred solution of 3-bromo-5-fluoro-4-nitrobenzamide (0.400 g, 1.521 mmol) in MeOH (15.21 mL) was added sodium methoxide (0.493 g, 2.281 mmol). After stirring at 60° C. for 3 h, the mixture was concentrated under reduced pressure, and then extracted with water and a solution of 25% isopropyl alcohol in CHCl$_3$. The combined organic layers were dried, filtered, and concentrated in vacuo. The crude residue was purified by flash chromatography on a silica gel column to afford the desired product. LC-MS calculated for C$_8$H$_8$BrN$_2$O$_4$ (M+H)$^+$: m/z=275.0, 277.0; found 275.0, 277.0.

Step 11: 3-(2-(1-ethyl-3-methyl-1H-pyrazol-5-yl)pyrimidin-5-yl)-5-methoxy-4-nitrobenzamide

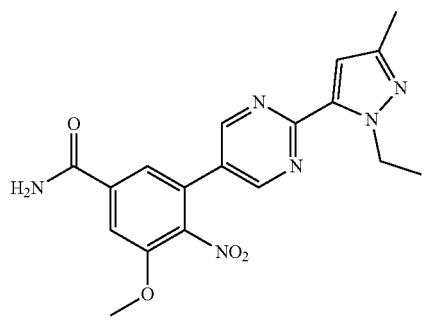 [SMILES: CCn1nc(C)cc1-c1ncc(-c2cc(C(N)=O)cc(OC)c2[N+](=O)[O-])cn1]

To a solution of (2-chloropyrimidin-5-yl)boronic acid (82 mg, 0.52 mmol), 3-bromo-5-methoxy-4-nitrobenzamide (143 mg, 0.520 mmol), and sodium carbonate (110 mg, 1.040 mmol) in dioxane (2 mL) and water (0.4 mL) was added dichloro[1,1'-bis(diphenylphosphino)ferrocene]palladium (II) dichloromethane adduct (25.5 mg, 0.031 mmol). The vial was flushed with nitrogen, and the reaction was stirred at 100° C. for 1 h. The reaction mixture was cooled to room temperature, and 1-ethyl-3-methyl-5-(4,4,5,5-tetramethyl-1,3,2-dioxaborolan-2-yl)-1H-pyrazole (Enamine Ltd, cat #EN300-207291: 123 mg, 0.520 mmol) was added. The reaction mixture was flushed with nitrogen, and heated to 100° C. for another 1 h. The reaction mixture was quenched by NH$_4$OH aqueous solution, and extracted with DCM. The organic phases were combined and dried over MgSO$_4$, then filtered. The crude residue was purified by flash chromatography on a silica gel column eluting with 0 to 8% MeOH in DCM to afford the desired product. LC-MS calculated for C$_{18}$H$_{19}$N$_6$O$_4$ (M+H)+: m/z=383.1; found 383.2.

Step 12: 2-(1-ethyl-3-methyl-1H-pyrazol-5-yl)-8-methoxy-9H-pyrimido[4,5-b]indole-6-carboxamide

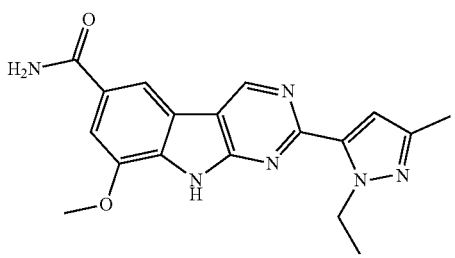 [SMILES: CCn1nc(C)cc1-c1ncc2c(n1)[nH]c1c(OC)cc(C(N)=O)cc12]

A mixture of 3-(2-(1-ethyl-3-methyl-1H-pyrazol-5-yppyrimidin-5-yl)-5-methoxy-4-nitrobenzamide (87.0 mg, 0.228 mmol) and 1,2-bis(diphenylphosphino)ethane (113 mg, 0.284 mmol) was dissolved in 1,2-dichlorobenzene (758 μL). The vial was flushed with nitrogen before heating at 160° C. for 1 h. After removal of the solvent under vacuum, the reaction mixture was extracted with DCM and water. The organic phases were combined and dried over MgSO$_4$, filtered, then concentrated under reduced pressure. The crude residue was purified by flash chromatography on a silica gel column eluting with 0 to 8% MeOH in DCM to afford the desired product. LC-MS calculated for $C_{18}H_{19}N_6O_2$ (M+H)$^+$: m/z=351.1; found 351.1.

Step 13: (E)-9,9'-(but-2-ene-1,4-diyl)bis(2-(1-ethyl-3-methyl-1H-pyrazol-5-yl)-8-methoxy-9H-pyrimido[4,5-b]indole-6-carboxamide)

A mixture of 2-(1-ethyl-3-methyl-1H-pyrazol-5-yl)-8-methoxy-9H-pyrimido[4,5-b]indole-6-carboxamide (12.0 mg, 0.034 mmol), (E)-1,4-dibromobut-2-ene (2.93 mg, 0.014 mmol), and cesium carbonate (24.55 mg, 0.075 mmol) was stirred in DMF (114 µL) at 50° C. for 1 h. The reaction mixture was diluted with MeOH and purified by prep-HPLC (pH=2, acetonitrile/water+TFA) to give the desired product as its TFA salt. LC-MS calculated for $C_{40}H_{41}N_{12}O_4$ (M+H)$^+$: m/z=753.3; found 753.3.

Example S30. (E)-1-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazole-5-carboxamido)-7,8-dihydro-1H-[1,4]dioxino[2',3':3,4]benzo[1,2-d]imidazole-5-carboxamide

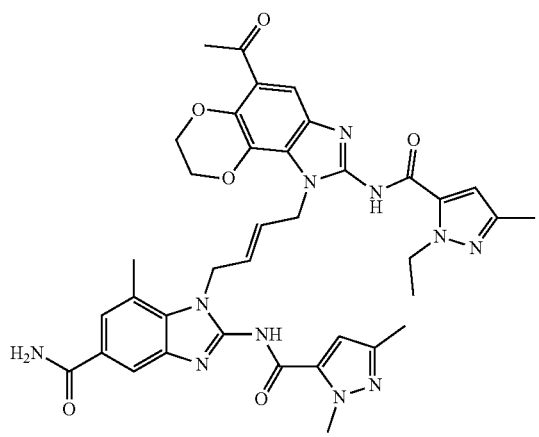 [SMILES: CCn1nc(C)cc1C(=O)Nc1nc2cc(C(C)=O)c3c(c2n1C/C=C/Cn1c(NC(=O)c2cc(C)nn2C)nc2cc(C(N)=O)cc(C)c21)OCCO3]

Step 1: 4-fluoro-3-methyl-5-nitrobenzamide

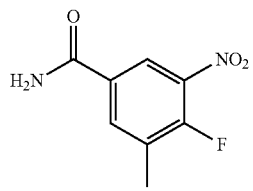

At 0° C., a mixture of nitric acid (2.51 mL, 39.2 mmol) and sulfuric acid (2.173 mL, 40.8 mmol) was added dropwise over 10 min into a solution of 4-fluoro-3-methylbenzamide (4.46 g, 29.1 mmol) in sulfuric acid (13.97 mL, 262 mmol). The mixture was stirred for 1.5 h while slowly warming up to room temperature (rt). The mixture was slowly poured into ice water (50 mL), and the precipitated solid was filtered and then washed with water (50 mL). The resulting solid residue was dried to provide the desired product as a white solid. LC-MS calculated for $C_8H_8FN_2O_3$ (M+H)$^+$: m/z=199.04; found 199.2

Step 2: (E)-tert-butyl 4-(4-carbamoyl-2-methyl-6-nitrophenylamino)but-2-enylcarbamate

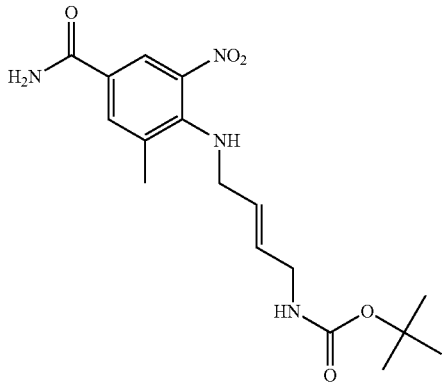 [SMILES: Cc1cc(C(N)=O)cc([N+](=O)[O-])c1NC/C=C/CNC(=O)OC(C)(C)C]

To a solution of 4-fluoro-3-methyl-5-nitrobenzamide (0.400 g, 2.019 mmol) and tert-butyl (E)-(4-aminobut-2-en-1-yl)carbamate (0.376 g, 2.019 mmol) (Ark Pharm, cat #AK308564) in dry DMSO (2.019 mL) was added $K_2CO_3$ (0.614 g, 4.44 mmol). The resulting yellow solution was stirred at room temperature for 1 h. The reaction mixture was diluted with water (15 mL) dropwise. The precipitated solid was filtered and then washed with water (10 mL). The resulting solid residue was dried to provide the desired product as a yellow solid. LC-MS calculated for $C_{17}H_{24}N_4NaO_5$ (M+Na)$^+$: m/z=387.2; found 387.2.

Step 3: (E)-tert-butyl 4-(2-amino-4-carbamoyl-6-methylphenylamino)but-2-enylcarbamate

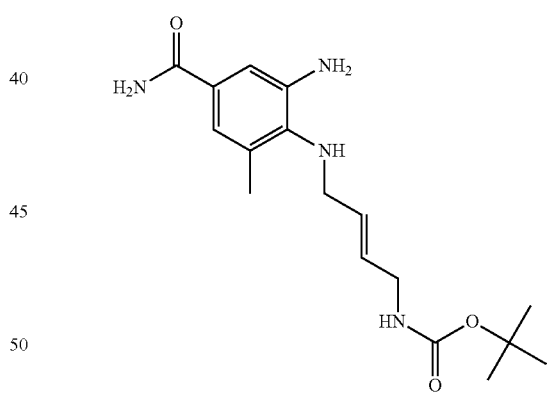

To a solution of tert-butyl (E)-(4-((4-carbamoyl-2-methyl-6-nitrophenyl)amino)but-2-en-1-yl)carbamate (220 mg, 0.604 mmol) in dioxane (1509 µL) and water (503 µL) was added ammonium chloride (226 mg, 4.23 mmol) and zinc (276 mg, 4.23 mmol) at 0° C. The reaction mixture was stirred at room temperature for 1 h, after which time it was filtered through a Celite® bed. The filtrate was partitioned between DCM and water. The organic layer was separated, dried over MgSO$_4$, filtered, and concentrated to provide the product. LC-MS calculated for $C_{17}H_{26}N_4NaO_3$ (M+Na)$^+$: m/z=357.2 ; found 357.3.

Step 4: (E)-tert-butyl 4-(2-amino-5-carbamoyl-7-methyl-1H-benzo[d]imidazol-1-yl)but-2-enylcarbamate

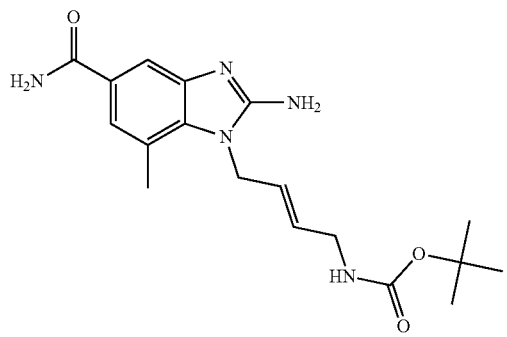 [SMILES: Cc1cc(C(N)=O)cc2nc(N)n(C/C=C/CNC(=O)OC(C)(C)C)c12]

To a solution of tert-butyl (E)-(4-((2-amino-4-carbamoyl-6-methylphenyl)amino)but-2-en-1-yl)carbamate (0.201 g, 0.60 mmol) in MeOH (2.000 mL) was added cyanogen bromide (0.047 mL, 0.900 mmol). The reaction mixture was stirred at room temperature for 1 h. The mixture was diluted with DCM, and washed with water and brine. The organic phase was dried over MgSO$_4$ before filtering. The filtrate was concentrated and purified by flash chromatography on a silica gel column eluting with 0 to 8% MeOH in DCM to afford the desired product. LC-MS calculated for C$_{18}$H$_{26}$N$_5$O$_3$ (M+H)$^+$: m/z=360.2; found 360.3.

Step 5: tert-butyl (E)-4-(5-carbamoyl-2-(1-ethyl-3-methyl-1H-pyrazole-5-carboxamido)-7-methyl-1H-benzo[d]imidazol-1-yl)but-2-enylcarbamate

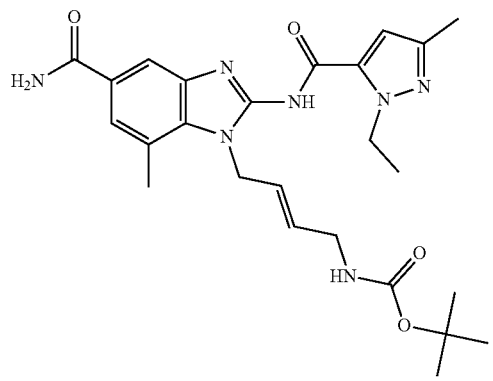 [SMILES: CCn1nc(C)cc1C(=O)Nc1nc2cc(C(N)=O)cc(C)c2n1C/C=C/CNC(=O)OC(C)(C)C]

A mixture of 1-ethyl-3-methyl-1H-pyrazole-5-carboxylic acid (Combi-Blocks, cat #QB-0979: 93 mg, 0.60 mmol), tert-butyl (E)-(4-(2-amino-5-carbamoyl-7-methyl-1H-benzo[d]imidazol-1-yl)but-2-en-1-yl)carbamate (216 mg, 0.600 mmol), 2-(3H-[1,2,3]triazolo[4,5-b]pyridin-3-yl)-1,1,3,3-tetramethylisouronium hexafluorophosphate(V) (274 mg, 0.720 mmol), and N,N-diisopropylethylamine (209 µL, 1.200 mmol) in DMF (2000 µL) was stirred at room temperature for 2 h. The mixture was concentrated under reduced pressure. The mixture was then diluted with DCM and water, and the layers were separated. The aqueous layer was further extracted with DCM and the combined organic layers were washed with brine, dried over Na$_2$SO$_4$, filtered, and concentrated in vacuo. The crude residue was purified by flash chromatography on a silica gel column eluting with 0 to 8% MeOH in DCM to afford the desired product. LC-MS calculated for C$_{25}$H$_{34}$N$_7$O$_4$ (M+H)$^+$: m/z=496.3 ; found 496.3.

Step 6: (E)-1-(4-aminobut-2-enyl)-2-(1-ethyl-3-methyl-1H-pyrazole-5-carboxamido)-7-methyl-1H-benzo[d]imidazole-5-carboxamide

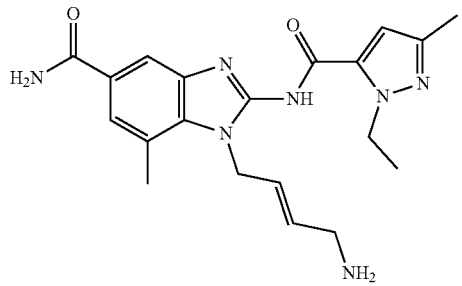

To a solution of tert-butyl (E)-(4-(5-carbamoyl-2-(1-ethyl-3-methyl-1H-pyrazole-5-carboxamido)-7-methyl-1H-benzo[d]imidazol-1-yl)but-2-en-1-yl)carbamate (180.0 mg, 0.363 mmol) in DCM (2.0 mL) was added TFA (0.2 mL). The resulting solution was stirred at room temperature for 0.5 h. The reaction mixture was quenched by NaHCO$_3$ aqueous solution then extracted with DCM. The organic phases were combined and dried over MgSO$_4$, then filtered. The filtrate was concentrated and used directly in the next step without further purification. For characterization purposes, the crude material was purified by prep HPLC (pH=2, water+TFA) to provide the desired compound as its TFA salt. LC-MS calculated for C$_{20}$H$_{26}$N$_7$O$_2$ (M+H)$^+$: m/z=396.2; found 396.3. $^1$H NMR (400 MHz, DMSO) 7.87 (m, 2H), 7.69 (br s, 2H), 7.57 (s, 1H), 7.30 (s, 1H), 6.64 (s, 1H), 6.10 (dt, J=16.0, 4.8 Hz, 1 H), 5.33 (dt, J=16.0, 6.4 Hz, 1 H), 5.06 (brs, 2H), 4.59 (q, J=6.8 Hz, 2H), 3.42 (dt, J=6.4 Hz, 4.8 Hz, 2H), 2.63 (s, 3H), 2.16 (s, 3H), 1.34 (t, J=6.8 Hz, 3H).

Step 7: ethyl 8-bromo-2,3-dihydrobenzo[b][1,4]dioxine-5-carboxylate

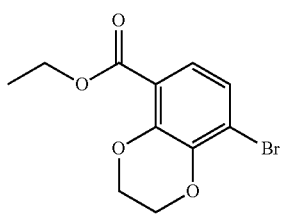 [SMILES: CCOC(=O)c1ccc(Br)c2c1OCCO2]

To a vial was added ethyl 4-bromo-2,3-dihydroxybenzoate (AstaTech, cat #53231: 0.950 g, 3.64 mmol), DMF (36.4 mL), 1,2-dibromoethane (0.408 mL, 4.73 mmol), a stir bar, and potassium carbonate (1.106 g, 8.01 mmol). The mixture was sealed and heated at 50° C. overnight with stirring. After cooling to rt, the mixture was concentrated in vacuo and the resulting residue was diluted with water and CHCl$_3$/IPA (3:1). The layers were separated, and the aqueous layer was further extracted. The combined organic extracts were dried over MgSO$_4$, filtered, and concentrated in vacuo to provide the desired product as a brown oil. LC-MS calculated for C$_{11}$H$_{12}$BrO$_4$ (M+H)$^+$: m/z=287.0/289.0; found 287.0/289.0.

Step 8: 8-bromo-2,3-dihydrobenzo[b][1,4]dioxine-5-carboxamide

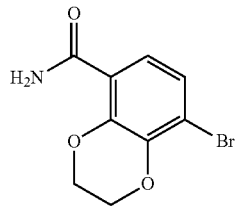 [SMILES: NC(=O)c1ccc(Br)c2c1OCCO2]

To a vial was added ethyl 8-bromo-2,3-dihydrobenzo[b][1,4]dioxine-5-carboxylate (1.08 g, 3.76 mmol) and 30% ammonium hydroxide (9.23 mL, 237 mmol). The reaction was stirred at 50° C. for 2 d. At this time, the solid was filtered and washed with water to provide the desired compound as a yellow solid. LC-MS calculated for $C_9H_9BrNO_3$ (M+H)$^+$: m/z=258.0/260.0; found 258.0/260.0.

Step 9: 8-bromo-7-nitro-2,3-dihydrobenzo[b][1,4]dioxine-5-carboxamide

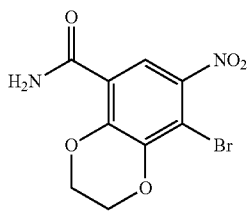 [SMILES: NC(=O)c1cc([N+](=O)[O-])c(Br)c2c1OCCO2]

A flask was charged with 8-bromo-2,3-dihydrobenzo[b][1,4]dioxine-5-carboxamide (0.540 g, 2.092 mmol) and a stir bar, then the flask was cooled to 0° C. Sulfuric acid (13.95 mL) was added dropwise with stirring. To a separate flask containing sulfuric acid (6.97 mL), cooled to 0° C., was added 70% nitric acid (0.181 mL, 2.82 mmol) dropwise. The resulting nitrite solution was transferred to an addition funnel, and added to the sulfuric acid/aryl amide mixture, dropwise, over a period of 10 min. After the addition, the mixture was warmed to rt, and stirred for 5 min. The mixture was poured over ice, and diluted with DCM. The layers were separated and the aqueous layer was further extracted with DCM. The combined organic extracts were dried over $MgSO_4$, filtered, and concentrated under reduced pressure. The resulting solid was a mixture of regioisomers, which was then washed with water, then 1:1 DCM/MeOH. The remaining solid was the desired regioisomer, and the filtrate was a mixture of both isomers. The filtrate was concentrated and purified by column chromatography (60% EtOAc/DCM) with the desired regioisomer eluting second. LC-MS calculated for $C_9H_8BrN_2O_5$ (M+H)$^+$: m/z=303.0/305.0; found 303.0/305.0.

Step 10: (E)-1-(4-(8-carbamoyl-6-nitro-2,3-dihydrobenzo[b][1,4]dioxin-5-ylaminotbut-2-enyl)-2-(1-ethyl-3-methyl-1H-pyrazole-5-carboxamido)-7-methyl-1H-benzo[d]imidazole-5-carboxamide

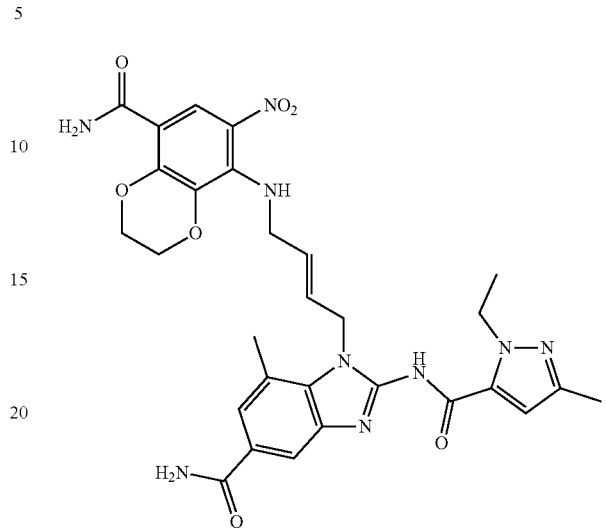

To a vial was added (E)-1-(4-aminobut-2-en-1-yl)-2-(1-ethyl-3-methyl-1H-pyrazole-5-carboxamido)-7-methyl-1H-benzo[d]imidazole-5-carboxamide (0.126 g, 0.269 mmol), 8-bromo-7-nitro-2,3-dihydrobenzo[b][1,4]dioxine-5-carboxamide (0.082 g, 0.269 mmol), BINAP (0.020 g, 0.032 mmol), tris(dibenzylideneacetone)dipalladium(0) (0.025 g, 0.027 mmol), cesium carbonate (0.438 g, 1.345 mmol), and a stir bar. The vial was then evacuated and flushed with nitrogen (3×). Dioxane (5.4 mL) was then added under nitrogen, and the reaction vial was then heated to 90° C. with stirring overnight. After cooling to rt, the mixture was filtered over Celite, and concentrated under reduced pressure. The crude residue was used directly in the next step without further purification. LC-MS calculated for $C_{29}H_{32}N_9O_7$ (M+H)$^+$: m/z=618.2; found 618.3.

Step 11: (E)-1-(4-(6-amino-8-carbamoyl-2,3-dihydrobenzo[b][1,4]dioxin-5-ylamino)but-2-enyl)-2-(1-ethyl-3-methyl-1H-pyrazole-5-carboxamido)-7-methyl-1H-benzo[d]imidazole-5-carboxamide

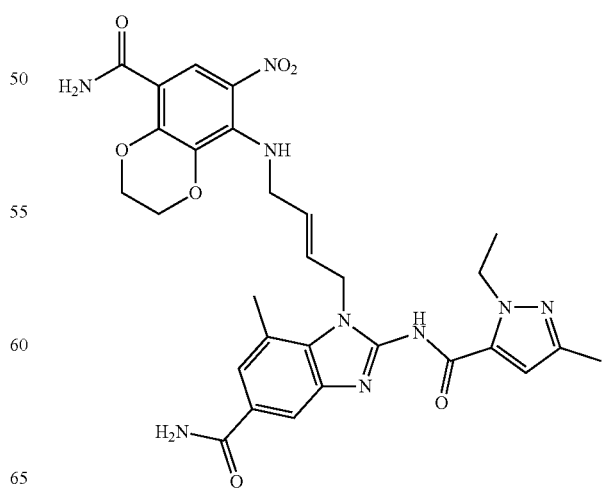

To a solution of (E)-1-(4-(8-carbamoyl-6-nitro-2,3-dihydrobenzo[b][1,4]dioxin-5-ylamino)but-2-enyl)-2-(1-ethyl-3-methyl-1H-pyrazole-5-carboxamido)-7-methyl-1H-benzo[d]imidazole-5-carboxamide (0.165 g, 0.267 mmol) in dioxane (4 mL)/water (1.3 mL) was added ammonium chloride (0.107 g, 2.0 mmol) and zinc (0.131 g, 2.0 mmol) at 0° C. The reaction mixture was stirred at rt for 10 min, then it was filtered. The filtrate was partitioned between $H_2O$ (10 mL) and 3:1 $CHCl_3$/IPA (30 mL). The organic layer was separated, dried over $MgSO_4$, concentrated, and dried under high vacuum to provide the desired product as an orange foam. LC-MS calculated for $C_{29}H_{34}N_9O_5$ $(M+H)^+$: m/z=588.3; found 588.3.

Step 12: (E)-2-amino-1-(4-(5-carbamoyl-2-(1-ethyl-3-methyl-1H-pyrazole-5-carboxamido)-7-methyl-1H-benzo[d]imidazol-1-yl)but-2-en-1-yl)-7,8-dihydro-1H-[1,4]dioxino[2',3':3,4]benzo[1,2-d]imidazole-carboxamide

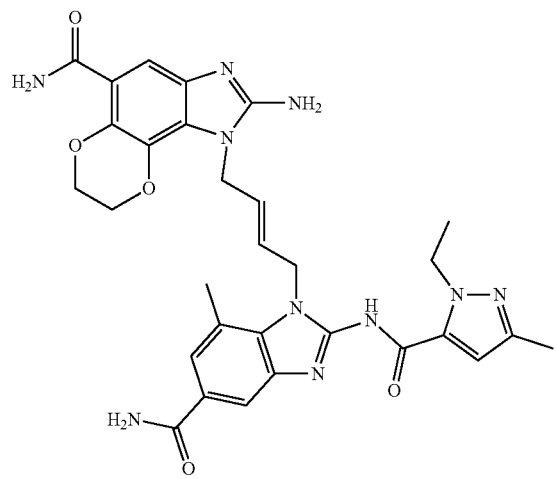 [SMILES: CCn1nc(C)cc1C(=O)Nc1nc2cc(C(N)=O)cc(C)c2n1C/C=C/Cn1c(N)nc2cc(C(N)=O)c3c(c21)OCCO3]

To a vial was added (E)-1-(4-((6-amino-8-carbamoyl-2,3-dihydrobenzo[b][1,4]dioxin-5-yl)amino)but-2-en-1-yl)-2-(1-ethyl-3-methyl-1H-pyrazole-5-carboxamido)-7-methyl-1H-benzo[d]imidazole-5-carboxamide (0.158 g, 0.269 mmol) and MeOH (2.69 mL). Cyanogen bromide (0.085 g, 0.807 mmol) was added and the reaction was stirred for 30 min at rt. The product was then triturated using EtOAc (5 mL), which was then filtered, washed with EtOAc, and dried. LC-MS calculated for $C_{30}H_{33}N_{10}O_5$ $(M+H)^+$: m/z=613.3; found 613.2.

Step 13: (E)-1-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazole-5-carboxamido)-7,8-dihydro-1H-[1,4]dioxino[2',3':3,4]benzo[1,2-d]imidazole-5-carboxamide To a solution of 1-Ethyl-3-methyl-1H-pyrazole-5-carboxylic acid (Combi-Blocks, cat #QB-0979: 0.070 g, 0.457 mmol) in DMF (2.285 mL) was added HATU (0.174 g, 0.457 mmol) and triethylamine (0.159 mL, 1.143 mmol). The mixture was stirred for 5 min then (E)-2-amino-1-(4-(5-carbamoyl-2-(1-ethyl-3-methyl-1H-pyrazole-5-carboxamido)-7-methyl-1H-benzo[d]imidazol-1-yl)but-2-en-1-yl)-7,8-dihydro-1H-[1,4]dioxino[2',3':3,4]benzo[1,2-d]imidazole-5-carboxamide (0.140 g, 0.229 mmol) was added and stirred overnight. The reaction mixture was diluted with MeCN and was then purified by prep-HPLC (pH=2, acetonitrile/water+TFA) to provide the desired compound as its TFA salt. LC-MS calculated for $C_{37}H_{41}N_{12}O_6$ $(M+H)+$: m/z=749.3; found 749.3.

Example S31. (E)-1-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide

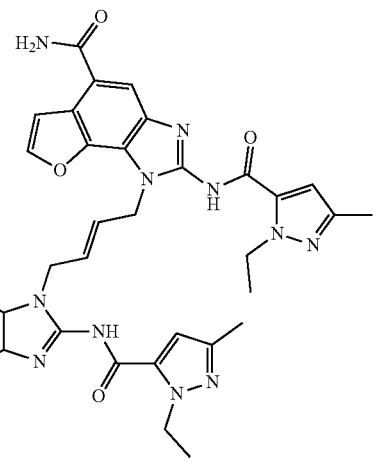

Step 1: methyl 2-bromo-4-chloro-3-hydroxy-5-nitrobenzoate

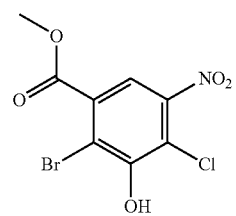 [SMILES: COC(=O)c1cc([N+](=O)[O-])c(Cl)c(O)c1Br]

To a solution of t-butylamine (1.774 mL, 16.88 mmol) in dry toluene (11.25 mL) was added bromine (0.319 mL, 6.19 mmol) dropwise at −3 ° C. (~10 min) under nitrogen. The mixture was cooled to −78° C., and a solution of methyl 4-chloro-3-hydroxy-5-nitrobenzoate (Combi-Blocks, cat #CA-5786: 1.3030 g, 5.63 mmol) in DCM (45.0 mL) was added dropwise under nitrogen (~30 min). The mixture was warmed to rt gradually and stirred overnight. The reaction was diluted with EtOAc and the organic phase washed with 1.0 M HCl (2×) and brine (1×). The organic phase was dried over anhydrous $MgSO_4$, filtered, and the filtrate evaporated under reduced pressure. The residue was purified by flash chromatography (10% EtOAc/hexanes) to give the desired product as a white solid. LC-MS calculated for $C_8H_6BrClNO_5$ $(M+H)^+$: m/z=309.9/311.9; found 309.8/312.0.

Step 2: methyl 3-acetoxy-2-bromo-4-chloro-5-nitrobenzoate

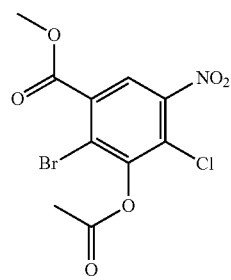 [SMILES: COC(=O)c1cc([N+](=O)[O-])c(Cl)c(OC(C)=O)c1Br]

To a solution of methyl 2-bromo-4-chloro-3-hydroxy-5-nitrobenzoate (1.37 g, 4.41 mmol) and triethylamine (1.845 mL, 13.24 mmol) in CH$_2$Cl$_2$ (12.98 mL) was added Ac$_2$O (0.541 mL, 5.74 mmol) at 0° C. After stirring for 18 h at rt, the mixture was diluted with HCl (1 M, 10 mL). The resulting mixture was extracted with CH$_2$Cl$_2$ (3×10 mL). The combined organic layers were washed with brine, dried over MgSO$_4$ and concentrated in vacuo. The crude residue was then purified by flash chromatography (10% EtOAc/hexanes) to provide the desired product as a white solid. LC-MS calculated for C$_{10}$H$_8$BrClNO$_6$ (M+H)$^+$: m/z=351.9/353.9; found 351.9/353.8. $^1$H NMR (500 MHz, DMSO) δ 8.48 (s, 1H), 3.92 (s, 3H), 2.49 (s, 3H). $^{13}$C NMR (125 MHz, DMSO) δ 167.0, 163.6, 147.0, 146.8, 132.8, 124.4, 124.1, 122.1, 53.4, 20.0.

Step 3: methyl 3-acetoxy-4-chloro-5-nitro-2-((trimethylsilyl)ethynyl)benzoate

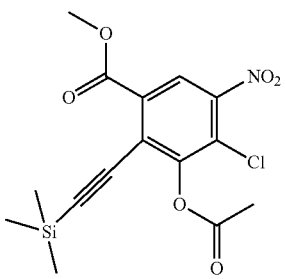 [SMILES: COC(=O)c1cc([N+](=O)[O-])c(Cl)c(OC(C)=O)c1C#C[Si](C)(C)C]

Methyl 3-acetoxy-2-bromo-4-chloro-5-nitrobenzoate (0.503 g, 1.427 mmol), cuprous iodide (0.027 g, 0.143 mmol) and dichlorobis(triphenylphosphine)-palladium(II) (0.050 g, 0.071 mmol) were added in a vial and the vial was sealed, evacuated and flushed with nitrogen (3×). Then DMF (3.57 mL) and DIPEA (1.189 mL) were added under nitrogen. After this ethynyltrimethylsilane (0.605 mL, 4.28 mmol) was added and reaction was stirred at 35° C. overnight. After cooling to rt, the mixture was diluted with DCM and 1 N HCl. The layers were separated, and the aqueous layer was further extracted. The combined organic layers were dried over MgSO$_4$, filtered, and concentrated in vacuo. The crude residue was then purified by flash chromatography (10% EtOAc/hexanes) to provide the desired product as a clear solid. LC-MS calculated for C$_{15}$H$_{17}$ClNO$_6$Si (M+H)$^+$: m/z=370.0; found 370.0.

Step 4: methyl 4-chloro-2-ethynyl-3-hydroxy-5-nitrobenzoate

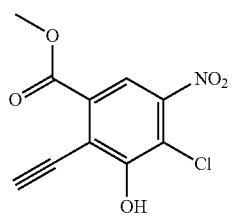 [SMILES: C#Cc1c(C(=O)OC)cc([N+](=O)[O-])c(Cl)c1O]

To a solution of methyl 3-acetoxy-4-chloro-5-nitro-2-((trimethylsilyl)ethynyl)benzoate (0.331 g, 0.895 mmol) in MeOH (8.95 mL) was added potassium carbonate (0.124 g, 0.895 mmol). The reaction was stirred for 15 min, and was then diluted with DCM and 1 N HCl. The layers were separated, and the aqueous layer was further extracted with DCM. The combined organic layers were dried over MgSO$_4$, filtered, and concentrated in vacuo. The resulting residue was then used directly in the next step without further purification. LC-MS calculated for C$_{10}$H$_7$ClNO$_5$ (M+H)$^+$: m/z=256.0; found 256.1.

Step 5: 7-chloro-6-nitrobenzofuran-4-carboxamide

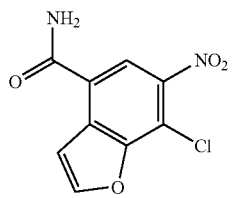 [SMILES: NC(=O)c1cc([N+](=O)[O-])c(Cl)c2occc12]

To a vial was added methyl 4-chloro-2-ethynyl-3-hydroxy-5-nitrobenzoate (201 mg, 0.786 mmol) and ammonium hydroxide (9186 μL, 236 mmol). The mixture was stirred at rt for 20 h, and was then filtered. The resulting solid was washed with water, dried, and used directly in the next step without further purification. LC-MS calculated for C$_9$H$_6$ClN$_2$O$_4$ (M+H)$^+$: m/z=241.0; found 241.0. $^1$H NMR (500 MHz, DMSO) δ 8.53 (s, 1H), 8.51 (d, J=2.25 Hz, 1H), 8.35 (s, 1H), 7.76 (s, 1H), 7.54 (d, J=2.25 Hz, 1H). $^{13}$C NMR (125 MHz, DMSO) δ 165.6, 152.7, 150.6, 142.6, 131.5, 126.0, 120.0, 113.5, 108.8.

Step 6: (E)-1-(4-(4-carbamoyl-6-nitrobenzofuran-7-ylamino)but-2-enyl)-2-(1-ethyl-3-methyl-1H-pyrazole-5-carboxamido)-7-methyl-1H-benzo[d]imidazole-5-carboxamide

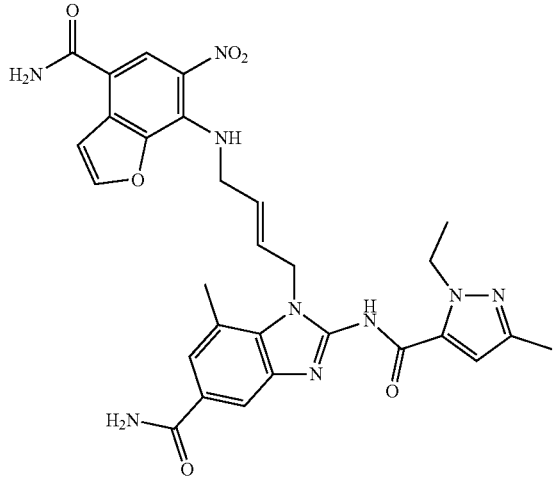 [SMILES: CCn1nc(C)cc1C(=O)Nc1nc2cc(C(N)=O)cc(C)c2n1C/C=C/CNc1c([N+](=O)[O-])cc(C(N)=O)c2ccoc12]

To a vial was added (E)-1-(4-aminobut-2-en-1-yl)-2-(1-ethyl-3-methyl-1H-pyrazole-5-carboxamido)-7-methyl-1H-benzo[d]imidazole-5-carboxamide (Example S1, Step 6: 0.1 g, 0.213 mmol), 7-chloro-6-nitrobenzofuran-4-carboxamide (0.051 g, 0.213 mmol), a stir bar, DMSO (1.067 mL), and DIPEA (0.186 mL, 1.067 mmol). The resulting mixture was sealed and heated at 80° C. overnight, then 100° C. for 8 h. After cooling to rt, the product was triturated with water, filtered, washed with cold water, and dried to provide the desired product as a beige solid. LC-MS calculated for $C_{29}H_{30}N_9O_6$ $(M+H)^+$: m/z=600.2; found 600.2.

Step 7: (E)-1-(4-(6-amino-4-carbamoylbenzofuran-7-ylamino)but-2-enyl)-2-(1-ethyl-3-methyl-1H-pyrazole-5-carboxamido)-7-methyl-1H-benzo[d]imidazole-5-carboxamide

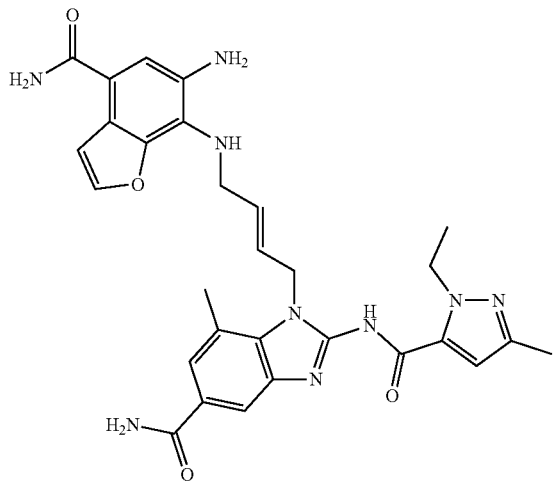 [SMILES: CCn1nc(C)cc1C(=O)Nc1nc2cc(C(N)=O)cc(C)c2n1C/C=C/CNc1c(N)cc(C(N)=O)c2ccoc12]

This compound was prepared using similar procedures as described for Example S1, Step 11 with (E)-1-(4-(4-carbamoyl-6-nitrobenzofuran-7-ylamino)but-2-enyl)-2-(1-ethyl-3-methyl-1H-pyrazole-5-carboxamido)-7-methyl-1H-benzo[d]imidazole-5-carboxamide replacing (E)-1-(4-(8-carbamoyl-6-nitro-2,3-dihydrobenzo[b][1,4]dioxin-5-ylamino)but-2-enyl)-2-(1-ethyl-3-methyl-1H-pyrazole-5-carboxamido)-7-methyl-1H-benzo[d]imidazole-5-carboxamide. LC-MS calculated for $C_{29}H_{32}N_9O_4$ $(M+H)^+$: m/z=570.3; found 570.3.

Step 8: (E)-2-amino-1-(4-(5-carbamoyl-2-(1-ethyl-3-methyl-1H-pyrazole-5-carboxamido)-7-methyl-1H-benzo[d]imidazol-1-yl)but-2-enyl)-1H-benzofuro[6,7-d]imidazole-5-carboxamide

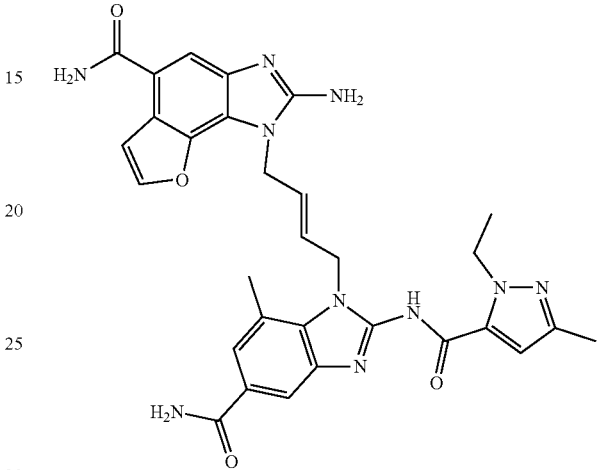

This compound was prepared using similar procedures as described for Example S1, Step 12 with (E)-1-(4-(6-amino-4-carbamoylbenzofuran-7-ylamino)but-2-enyl)-2-(1-ethyl-3-methyl-1H-pyrazole-5-carboxamido)-7-methyl-1H-benzo[d]imidazole-5-carboxamide replacing (E)-1-(4-((6-amino-8-carbamoyl-2,3-dihydrobenzo[b][1,4]dioxin-5-yl)amino)but-2-en-1-yl)-2-(1-ethyl-3-methyl-1H-pyrazole-5-carboxamido)-7-methyl-1H-benzo[d]imidazole-5-carboxamide. LC-MS calculated for $C_{30}H_{31}N_{10}O_4$ $(M+H)^+$: m/z=595.3; found 595.3.

Step 9: (E)-1-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide This compound was prepared using similar procedures as described for Example S1, Step 13 with (E)-2-amino-1-(4-(5-carbamoyl-2-(1-ethyl-3-methyl-1H-pyrazole-5-carboxamido)-7-methyl-1H-benzo[d]imidazol-1-yl)but-2-enyl)-1H-benzofuro[6,7-d]imidazole-5-carboxamide replacing (E)-2-amino-1-(4-(5-carbamoyl-2-(1-ethyl-3-methyl-1H-pyrazole-5-carboxamido)-7-methyl-1H-benzo[d]imidazol-1-yl)but-2-en-1-yl)-7,8-dihydro-1H-[1,4]dioxino[2',3':3,4]benzo[1,2-d]imidazole-5-carboxamide. The reaction mixture was diluted with MeCN, acidified with a few drops of TFA, and purified by prep-HPLC (pH=2, acetonitrile/water+TFA) to give the desired product as its TFA salt. LC-MS calculated for $C_{37}H_{39}N_{12}O_5$ $(M+H)^+$: m/z=731.3; found 731.3. $^1$H NMR (500 MHz, DMSO) δ 7.94 (d, J=2.0 Hz, 1H), 7.88 (br s, 1H), 7.85 (s, 1H), 7.84 (s, 1H), 7.45 (s, 1H), 7.39 (br s, 1H), 7.35 (d, J=2.0 Hz, 1H), 7.26 (br s, 1H), 6.55 (s, 1H), 6.47 (s, 1H), 5.81 (m, 1H), 5.65-5.55 (m, 1H), 4.98 (br s, 2H), 4.93 (br s, 2H), 4.54-4.50 (m, 2H), 4.49-4.44 (m, 2H), 2.39 (s, 3H), 2.12 (s, 3H), 2.09 (s, 3H), 1.26 (t, J=7.0 Hz, 3H), 1.22 (t, J=7.0 Hz, 3H).

Example S32. (E)-7-(3-(3-aminopropanamido)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide

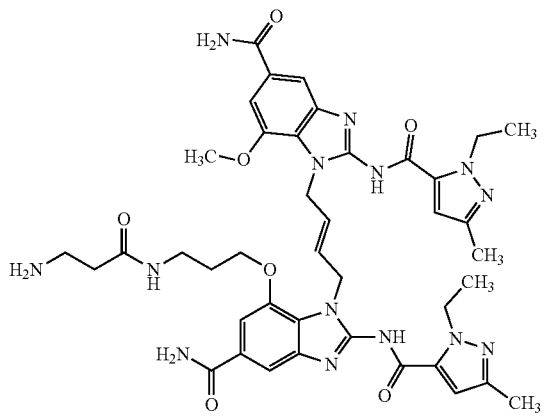 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(=O)CCN)c21]

In a 1 dram vial (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (Example 1, Step 17: 43 mg, 0.049 mmol) was dissolved in DMF (489 μL) to give a color solution. Boc-beta-alanine (Chem-Impex, cat #01323: 27.7 mg, 0.147 mmol), DIPEA (25.6 μL, 0.147 mmol) and BOP (64.8 mg, 0.147 mmol) were added to the reaction mixture in one portion. After 30 min, the reaction mixture was concentrated to dryness and dissolved in DCM (0.5 mL). Trifluoroacetic acid (0.5 mL) was added to the reaction mixture. After 30 min, the reaction mixture was concentrated to dryness and diluted with MeOH then purified by prep-HPLC (pH=2, acetonitrile/water+TFA) to give the desired product as the TFA salt. LC-MS calculated for $C_{41}H_{51}N_{14}O_7$ (M+H)$^+$: m/z=851.4; found 851.3.

Example S33. (E)-7-(3-acetamidopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide

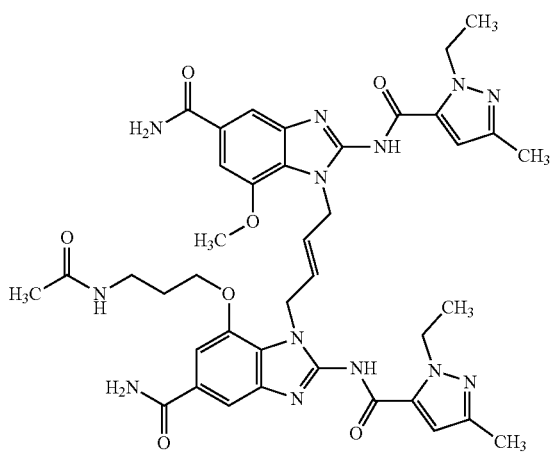 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(C)=O)c21]

In a 1 dram vial (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (Example 1, Step 17: 43 mg, 0.049 mmol) was dissolved in DMF (489 82 L) to give a color solution. Acetic anhydride (13.9 μL, 0.147 mmol) and DIPEA (11.6 μL, 0.147 mmol) were added to the reaction mixture in one portion. After 30 min, the reaction mixture was concentrated to dryness and diluted with MeOH then purified by prep-HPLC (pH=2, acetonitrile/water+TFA) to give the desired product as the TFA salt. LC-MS calculated for $C_{40}H_{48}N_{13}O_7$ (M+H)$^+$: m/z=822.4; found 822.3.

Example S34. (E)-9-(4-(5-carbamoyl-7-(3-cyanopropoxy)-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

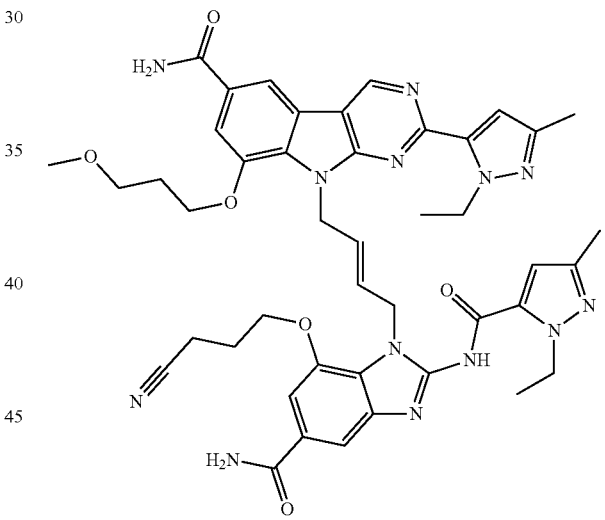

To a vial was added (E)-9-(4-(5-carbamoyl-2-(1-ethyl-3-methyl-1H-pyrazole-5-carboxamido)-7-hydroxy-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example S28: 1.9 mg, 2.409 μmol), DMF (0.241 ml), cesium carbonate (1.726 mg, 5.30 μmol), 4-bromobutanenitrile (Combi-Blocks, cat #QE-2324: 0.239 μl, 2.409 μmol) and a stir bar. The mixture was stirred at rt for 15 min, then heated at 50° C. for 10 min. After cooling to rt, the mixture was diluted with MeCN, and purified by prep HPLC (pH=2, MeCN/water+TFA) to provide the desired compound as the TFA salt. LC-MS calculated for $C_{44}H_{50}N_{13}O_6$ (M+H)+: m/z=856.4; found 856.4.

Example S35. (E)-9-(4-(5-carbamoyl-2-(1-ethyl-3-methyl-1H-pyrazole-5-carboxamido)-7-isopropoxy-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

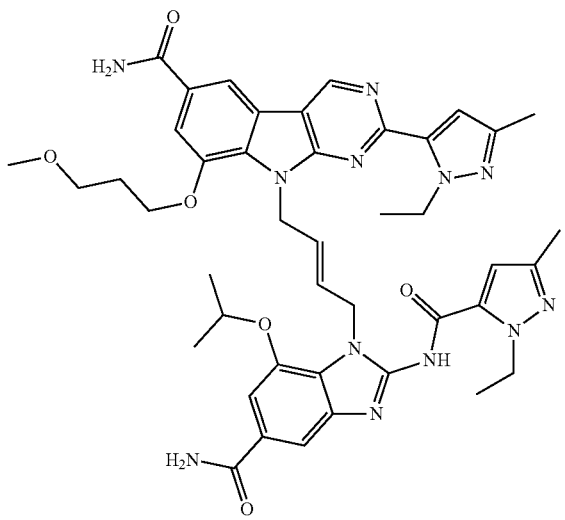

This compound was prepared using similar procedures as described for Example S34 with 2-bromopropane (Aldrich, cat #B78114) replacing 4-bromobutanenitrile. After cooling to rt, the mixture was diluted with MeCN, and purified by prep HPLC (pH=2, MeCN/water+TFA) to provide the desired compound as the TFA salt. LC-MS calculated for $C_{43}H_{51}N_{12}O_6$ (M+H)$^+$: m/z=831.4; found 831.3.

Example S36. (E)-9-(4-(5-carbamoyl-2-(1-ethyl-3-methyl-1H-pyrazole-5-carboxamido)-7-(3-(4-methylpiperazin-1-yl)propoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

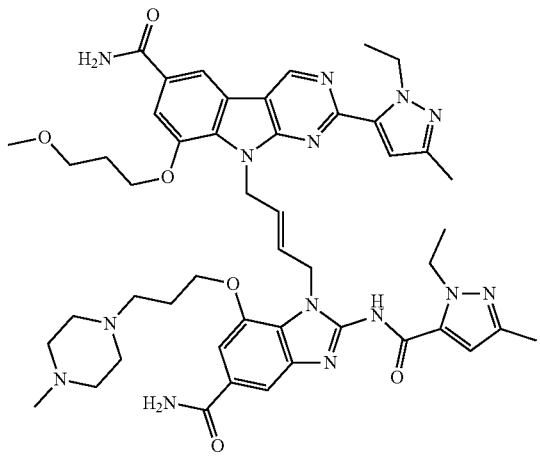

This compound was prepared using similar procedures as described for Example S27, Step 2 with 1-methylpiperazine (Aldrich, cat #130001) replacing morpholine. The reaction was diluted with MeCN, and purified by prep HPLC (pH=2, MeCN/water+TFA) to provide the desired compound as the TFA salt. LC-MS calculated for $C_{48}H_{62}N_{14}O_6$ (M+2H)$^{2+}$: m/z=465.2; found 465.5.

Example S37. (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-3-fluoro-9H-pyrido[2,3-b]indole-6-carboxamide

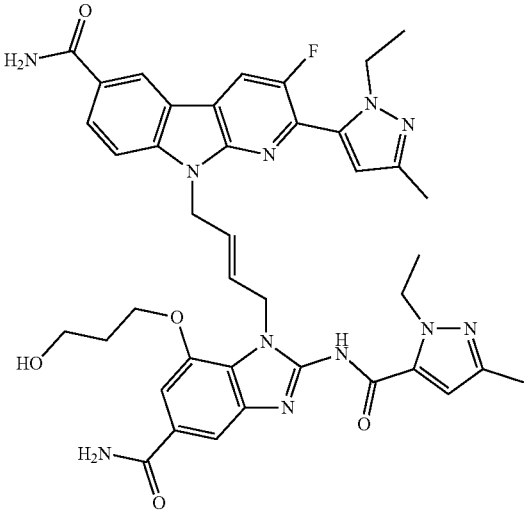 [SMILES: CCn1nc(C)cc1C(=O)Nc1nc2cc(C(N)=O)cc(OCCCO)c2n1C/C=C/Cn1c2ccc(C(N)=O)cc2c2cc(F)c(-c3cc(C)nn3CC)nc21]

Step 1: (E)-3-((5-carbamoyl-1-(4-(6-carbamoyl-2-(1-ethyl-3-methyl-1H-pyrazol-5-yl)-3-fluoro-9H-pyrido[2,3-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

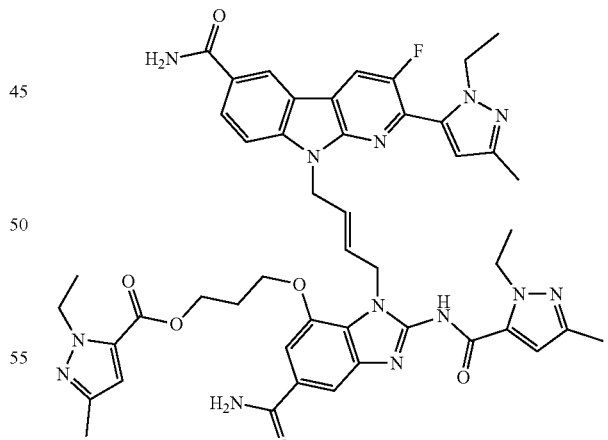

This compound was prepared using similar procedures as described for Example S15, Step 10 with 2-(1-ethyl-3-methyl-1H-pyrazol-5-yl)-3-fluoro-9H-pyrido[2,3-b]indole-6-carboxamide (Example S23, Step 3) replacing 2-(1-ethyl-3-methyl-1H-pyrazol-5-yl)-8-methoxy-9H-pyrimido[4,5-b]indole-6-carboxamide. LC-MS calculated for $C_{47}H_{52}FN_{13}O_6$ (M+2H)$^{2+}$: m/z=456.7; found 457.0.

Step 2: (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-3-fluoro-9H-pyrido[2,3-b]indole-6-carboxamide To a solution of (E)-3-((5-carbamoyl-1-(4-(6-carbamoyl-2-(1-ethyl-3-methyl-1H-pyrazol-5-yl)-3-fluoro-9H-pyrido[2,3-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate (15.3 mg, 0.017 mmol) in DMF (0.168 ml) was added 1 N aqueous sodium hydroxide (0.0336 ml, 0.034 mmol). The mixture was stirred for 15 min at rt and was diluted with MeCN and water, and purified by prep HPLC (pH=2, MeCN/water+TFA) to provide the desired product as the TFA salt. LC-MS calculated for $C_{40}H_{43}FN_{11}O_5$ $(M+H)^+$: m/z=776.3; found 776.3.

Example S38. (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

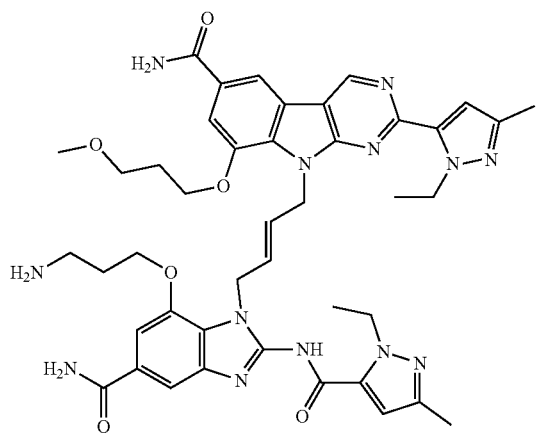 [SMILES: CCn1nc(C)cc1C(=O)Nc1nc2cc(C(N)=O)cc(OCCCN)c2n1C/C=C/Cn1c2nc(-c3cc(C)nn3CC)ncc2c2cc(C(N)=O)cc(OCCCOC)c21]

Step 1: tert-butyl (3-(5-carbamoyl-2-chloro-3-nitrophenoxy)propyl)carbamate

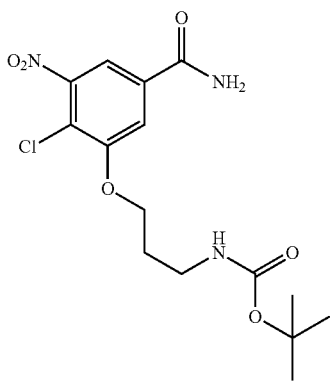 [SMILES: CC(C)(C)OC(=O)NCCCOc1cc(C(N)=O)cc([N+](=O)[O-])c1Cl]

This compound was prepared using similar procedures as described for Example S15, Step 2 with tert-butyl (3-bromopropyl)carbamate (Aldrich, cat #17356) replacing (3-bromopropoxy)(tert-butyl)dimethylsilane. LC-MS calculated for $C_{11}H_{13}ClN_3O_6$ $(M-C_4H_7)^+$: m/z=318.0; found 318.0.

Step 2: (E)-2-(4-bromobut-2-en-1-yl)isoindoline-1,3-dione

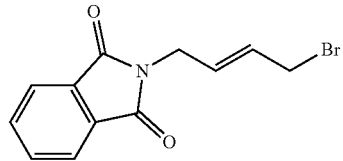 [SMILES: O=C1c2ccccc2C(=O)N1C/C=C/CBr]

A solution of (E)-1,4-dibromobut-2-ene (Aldrich, cat #D39207: 23.10 g, 108 mmol) and potassium carbonate (16.42 g, 119 mmol) in DMF (50.0 ml) at room temperature was treated with phthalimide, potassium salt (Aldrich, cat #160385: 10 g, 54.0 mmol). The reaction mixture was stirred at rt for 24 h, filtered, and concentrated in vacuo. The resulting oil was diluted with ethyl acetate (200 mL), washed with PBS buffer (2×100 mL), dried over MgSO$_4$, filtered and concentrated in vacuo. The crude oil was purified by column chromatography (0-20% ethyl acetate/hexanes). LC-MS calculated for $C_{12}H_{11}BrNO_2$ $(M+H)^+$: m/z=280.0/282.0; found 280.1/282.1.

Step 3: (E)-9-(4-(1,3-dioxoisoindolin-2-yl)but-2-en-1-yl)-2-(1-ethyl-3-methyl-1H-pyrazol-5-yl)-8-(3-methoxypropoxy)-9H-pyrimido[4,5-b]indole-6-carboxamide

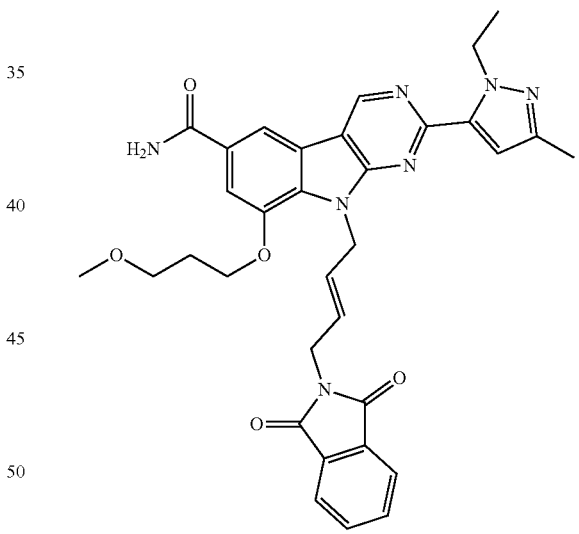

To a solution of (E)-2-(4-bromobut-2-en-1-yl)isoindoline-1,3-dione (0.034 g, 0.122 mmol) and 2-(1-ethyl-3-methyl-1H-pyrazol-5-yl)-8-(3-methoxypropoxy)-9H-pyrimido[4,5-b]indole-6-carboxamide (Example S12, Step 3: 0.05 g, 0.122 mmol) in DMF (0.769 ml) was added DIPEA (0.064 ml, 0.367 mmol) and cesium carbonate (0.120 g, 0.367 mmol). The mixture was stirred at rt overnight. After cooling with an ice bath, water was added, and the reaction was extracted with 3:1 CHCl$_3$/IPA. The combined organic extracts were dried over MgSO$_4$, filtered, and purified by silica gel chromatography (0-10% MeOH/DCM) to provide the desired product as a white solid. LC-MS calculated for $C_{33}H_{34}N_7O_5$ $(M+H)^+$: m/z=608.3; found 608.3.

Step 4: (E)-9-(4-aminobut-2-en-1-yl)-2-(1-ethyl-3-methyl-1H-pyrazol-5-yl)-8-(3-methoxypropoxy)-9H-pyrimido[4,5-b]indole-6-carboxamide

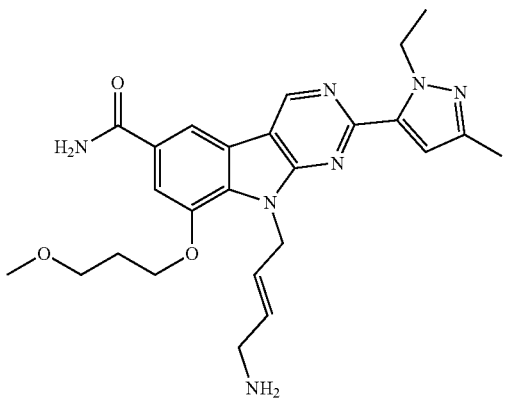

To a solution of (E)-9-(4-(1,3-dioxoisoindolin-2-yl)but-2-en-1-yl)-2-(1-ethyl-3-methyl-1H-pyrazol-5-yl)-8-(3-methoxypropoxy)-9H-pyrimido[4,5-b]indole-6-carboxamide (0.036 g, 0.059 mmol) in ethanol (0.846 ml) at room temperature was added hydrazine monohydrate (0.029 ml, 0.592 mmol). After 10 min of stirring at rt, the reaction mixture was warmed to 60° C. for 2 h, then cooled to 0° C. in an ice bath. The resulting slurry was filtered, and the filtrate was concentrated in vacuo. The resulting solid was purified by flash chromatography (6% NH$_4$OH in methanol). LC-MS calculated for C$_{25}$H$_{32}$N$_7$O$_3$ (M+H)$^+$: m/z=478.2; found 478.3.

Step 5: tert-butyl (E)-(3-(5-carbamoyl-2-((4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)amino)-3-nitrophenoxy)propyl)carbamate

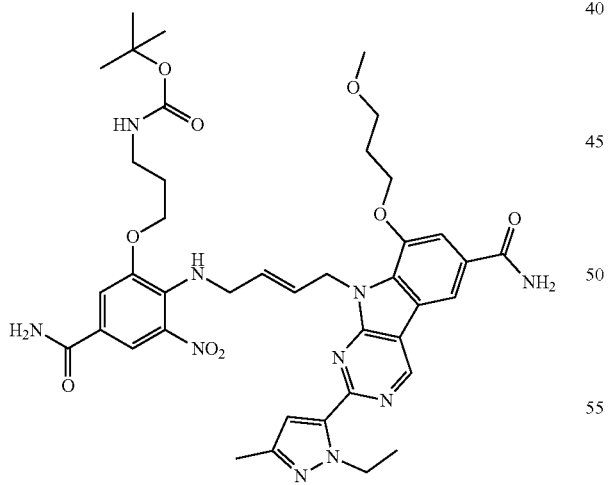

To a vial was added tert-butyl (3-(5-carbamoyl-2-chloro-3-nitrophenoxy)propyl)carbamate (0.121 g, 0.324 mmol), (E)-9-(4-aminobut-2-en-1-yl)-2-(1-ethyl-3-methyl-1H-pyrazol-5-yl)-8-(3-methoxypropoxy)-9H-pyrimido[4,5-b]indole-6-carboxamide (0.155 g, 0.324 mmol), EtOH (1.619 ml), and DIPEA (0.283 ml, 1.619 mmol). The mixture was sealed, then heated at 120° C. overnight with stirring. After cooling to rt, the mixture was concentrated under reduced pressure and purified by silica gel chromatography (15% MeOH/DCM). LC-MS calculated for C$_{40}$H$_{51}$N$_{10}$O$_9$ (M+H)$^+$: m/z=815.4; found 815.5.

Step 6: tert-butyl (E)-(3-(3-amino-5-carbamoyl-2-((4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)amino)phenoxy)propyl)carbamate

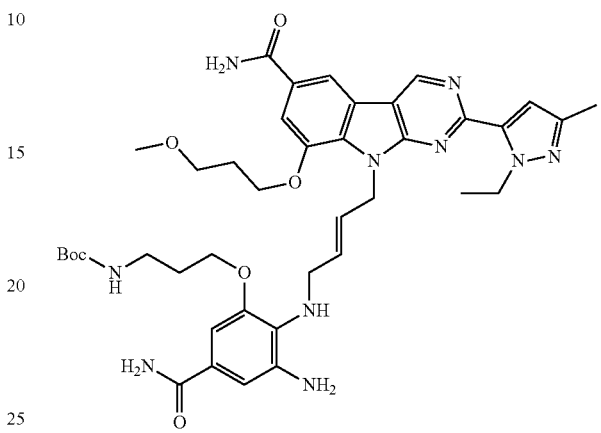

To a vial was added a stir bar, tert-butyl (E)-(3-(5-carbamoyl-2-((4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)amino)-3-nitrophenoxy)propyl)carbamate (0.040 g, 0.049 mmol), ammonium chloride (0.018 g, 0.344 mmol), and zinc (0.022 g, 0.344 mmol). 1,4-Dioxane (0.736 ml) and water (0.245 ml) were added and the mixture was stirred at rt for 10 min. The resulting mixture was filtered and extracted with CHCl$_3$/IPA (3:1). The combined organic extracts were dried over MgSO$_4$, filtered, and concentrated in vacuo. The crude product was used directly in the next step without further purification. LC-MS calculated for C$_{40}$H$_{53}$N$_{10}$O$_7$ (M+H)$^+$: m/z=785.4; found 785.5.

Step 7: tert-butyl (E)-(3-((2-amino-5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-1H-benzo[d]imidazol-7-yl)oxy)propyl)carbamate

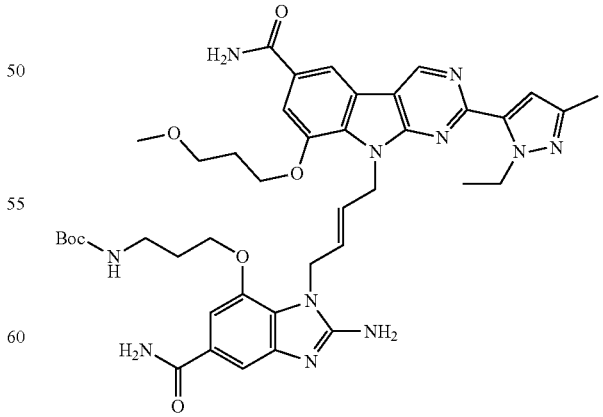

This compound was prepared using similar procedures as described for Example S1, Step 4 with tert-butyl (E)-(3-(3-amino-5-carbamoyl-2-((4-(6-carbamoyl-2-(1-ethyl-3- methyl-1H-pyrazol-5-yl)-8-(3-methoxypropoxy)-9H-pyrimido[4,5-b]indol-9-yl)but-2-en-1-yl)amino)phenoxy)propyl)carbamate replacing tert-butyl (E)-(4-((2-amino-4-carbamoyl-6-methylphenyl)amino)but-2-en-1-yl)carbamate. LC-MS calculated for $C_{41}H_{52}N_{11}O_7$ (M+H)$^+$: m/z=810.4; found 810.4.

Step 8: tert-butyl (E)-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate

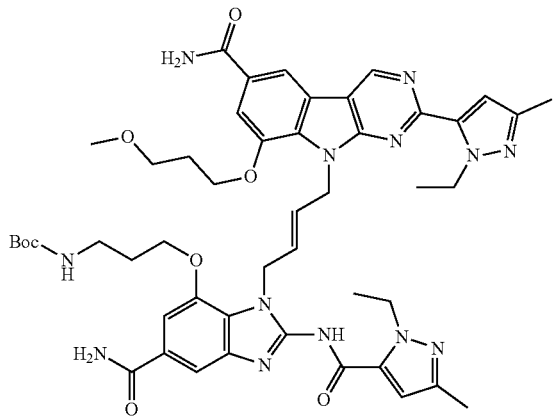 [SMILES: CCn1nc(C)cc1C(=O)Nc1nc2cc(C(N)=O)cc(OCCCNC(=O)OC(C)(C)C)c2n1C/C=C/Cn1c2nc(-c3cc(C)nn3CC)ncc2c2cc(C(N)=O)cc(OCCCOC)c21]

This compound was prepared using similar procedures as described for Example S15, Step 6 with tert-butyl (E)-(3-((2-amino-5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-1H-benzo[d]imidazol-7-yl)oxy)propyl)carbamate replacing tert-butyl (E)-(4-(2-amino-5-carbamoyl-7-(3-hydroxypropoxy)-1H-benzo[d]imidazol-1-yl)but-2-en-1-yl)carbamate. LC-MS calculated for $C_{48}H_{60}N_{13}O_8$ (M+H)$^+$: m/z=946.5; found 946.6.

Step 9: (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide To a solution of tert-butyl (E)-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate (0.050 g, 0.053 mmol) in 1,4-dioxane (0.528 ml) was added 4.0 M HCl in dioxane (0.132 ml, 0.528 mmol). The mixture was stirred for 15 min, then was diluted with MeCN/water and purified by prep HPLC (pH=2, MeCN/water+TFA) to provide the desired compound as the TFA salt. LC-MS calculated for $C_{43}H_{52}N_{13}O_6$ (M+H)$^+$: m/z=846.4; found 846.4.

Example S39. (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoic acid

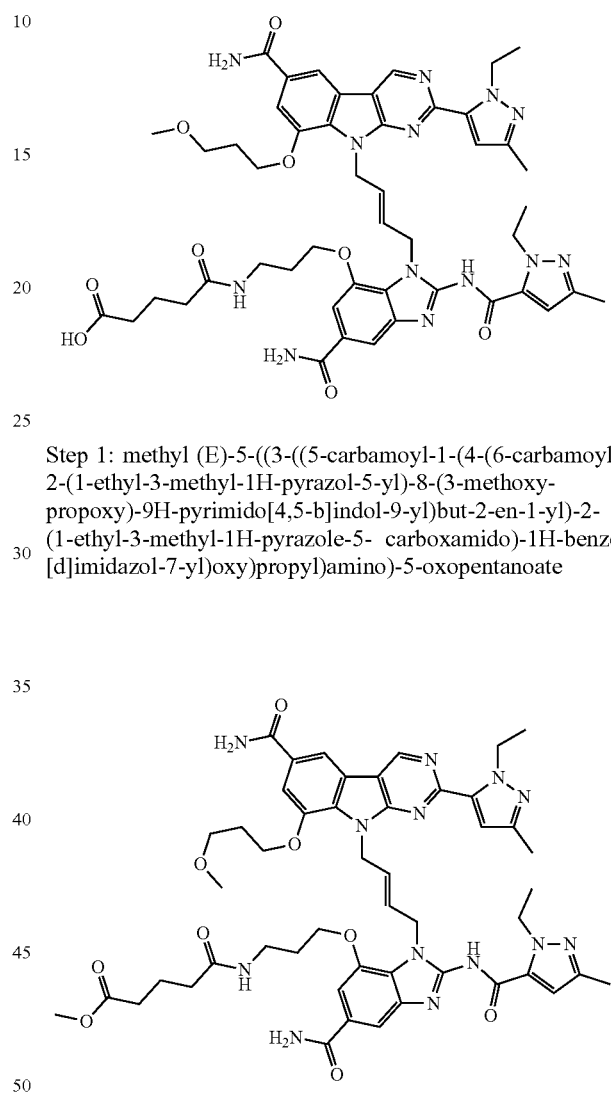

Step 1: methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5- carboxamido)-1H-benzo[d]imidazol-7-yl)oxy)propyl)amino)-5-oxopentanoate In a 1 dram vial, (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (6 mg, 7.09 μmol) was dissolved in DMF (709 μl). Mono-methyl glutarate (Aldrich, cat #M47353: 2.67 μl, 0.021 mmol), DIPEA (3.72 μl, 0.021 mmol) and BOP (9.41 mg, 0.021 mmol) were added to the reaction mixture sequentially. After 15 min, the reaction mixture was concentrated to dryness and used directly in the next step without further purification. LC-MS calculated for $C_{49}H_{60}N_{13}O_9$ (M+H)$^+$: m/z=974.5; found 974.6.

Step 2: (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoic acid In a 1 dram vial, methyl (E)-5-((3-((5-carbamoyl-1-(4-(6-carbamoyl-2-(1-ethyl-3-methyl-1H-pyrazol-5-yl)-8-(3-methoxypropoxy)-9H- pyrimido[4,5-b]indol-9-yl)but-2-en-1-yl)-2-(1-ethyl-3-methyl-1H-pyrazole-5-carboxamido)-1H-benzo[d]imidazol-7-ypoxy)propypamino)-5-oxopentanoate (6.91 mg, 7.09 µmol) was dissolved in THF (0.140 ml), MeOH (0.071 ml), and 2.0 N LiOH (70.9 µl, 0.142 mmol). The mixture was stirred at rt for 15 min, then the reaction was diluted in MeCN/water and purified by prep HPLC (pH=2, MeCN/water+TFA) to provide the desired compound as the TFA salt. $^1$H NMR (600 MHz, DMSO) δ 12.78 (s, 1H), 9.48 (s, 1H), 8.41 (d, J=1.2 Hz, 1H), 8.04 (s, 1H), 7.92 (s, 1H), 7.79-7.64 (m, 1H), 7.61 (s, 1H), 7.56 (s, 1H), 7.35 (s, 1H), 7.31 (s, 1H), 7.23 (s, 1H), 6.79 (s, 1H), 6.41 (s, 1H), 5.86 (m, 1H), 5.74-5.68 (m, 1H), 5.27-5.24 (m, 2H), 4.89-4.87 (m, 2H), 4.63-4.58 (m, 2H), 4.46 (m, 2H), 4.04 (t, J=6.4 Hz, 2H), 3.89-3.84 (m, 2H), 3.31 (t, J=6.3 Hz, 2H), 3.15 (s, 3H), 2.97-2.93 (m, 2H), 2.19 (s, 3H), 2.15 (t, J=7.4 Hz, 2H), 2.07 (s, 3H), 2.02-1.97 (m, 2H), 1.78 (dt, J=12.3, 6.4 Hz, 2H), 1.63 (dt, J=14.8, 7.5 Hz, 2H), 1.53-1.45 (m, 2H), 1.27 (t, J=7.1 Hz, 3H), 1.20 (t, J=7.1 Hz, 3H). LC-MS calculated for $C_{48}H_{59}N_{13}O_9$ $(M+2H)^{2+}$: m/z=480.7; found 480.9.

Example S40. (E)-2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate

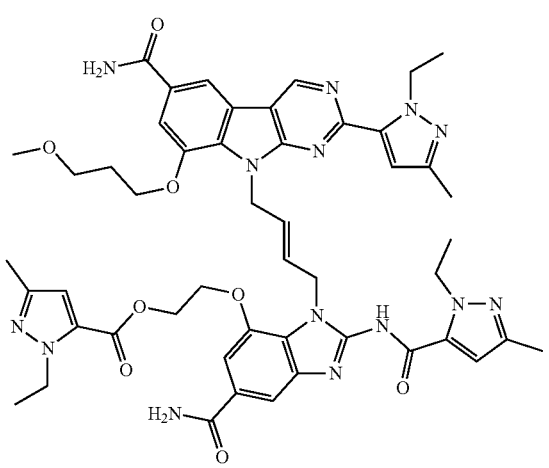

Step 1: 3-(2-((tert-butyldimethylsilyl)oxy)ethoxy)-4-chloro-5-nitrobenzamide

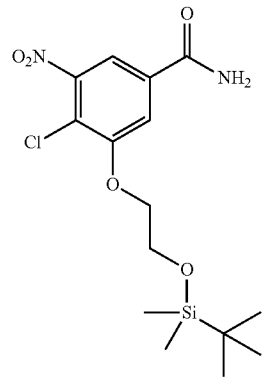 [SMILES: CC(C)(C)[Si](C)(C)OCCOc1cc(C(N)=O)cc([N+](=O)[O-])c1Cl]

This compound was prepared using similar procedures as described for Example S15, Step 2 with (2-bromoethoxy)(tert-butyl)dimethylsilane (Aldrich, cat #428426) replacing (3-bromopropoxy)(tert-butyl)dimethylsilane. LC-MS calculated for $C_{15}H_{24}ClN_2O_5Si$ (M+H)+: m/z=375.1; found 375.3.

Step 2: tert-butyl (E)-(4-((2-(2-((tert-butyldimethylsilyl)oxy)ethoxy)-4-carbamoyl-6-nitrophenyl)amino)but-2-en-1-yl)carbamate

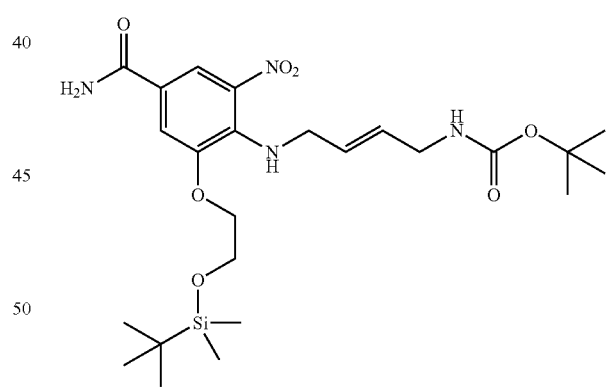

This compound was prepared using similar procedures as described for Example S15, Step 3 with 3-(2-((tert-butyldimethylsilypoxy)ethoxy)-4-chloro-5-nitrobenzamide replacing 3-(3-((tert-butyldimethylsilyl)oxy)propoxy)-4-chloro-5-nitrobenzamide. LC-MS calculated for $C_{24}H_{40}N_4NaO_7Si$ $(M+Na)^+$: m/z=547.3; found 547.3.

211

Step 3: tert-butyl (E)-(4-((2-amino-6-(2-((tert-butyldimethylsilyl)oxy)ethoxy)-4-carbamoylphenyl)amino)but-2-en-1-yl)carbamate

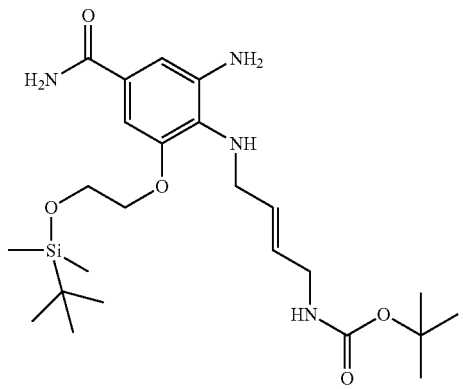 [SMILES: CC(C)(C)OC(=O)NC/C=C/CNc1c(N)cc(C(N)=O)cc1OCCO[Si](C)(C)C(C)(C)C]

This compound was prepared using similar procedures as described for Example S1, Step 3 with tert-butyl (E)-(4-((2-(2-((tert-butyldimethylsilyl)oxy)ethoxy)-4-carbamoyl-6-nitrophenyl)amino)but-2-en-1-yl)carbamate replacing tert-butyl (E)-(4-((4-carbamoyl-2-methyl-6-nitrophenyl)amino)but-2-en-1-yl)carbamate. LC-MS calculated for $C_{24}H_{43}N_4O_5Si$ (M+H)$^+$: m/z=495.3; found 495.4.

Step 4: tert-butyl (E)-(4-(2-amino-5-carbamoyl-7-(2-hydroxyethoxy)-1H-benzo[d]imidazol-1-yl)but-2-en-1-yl)carbamate

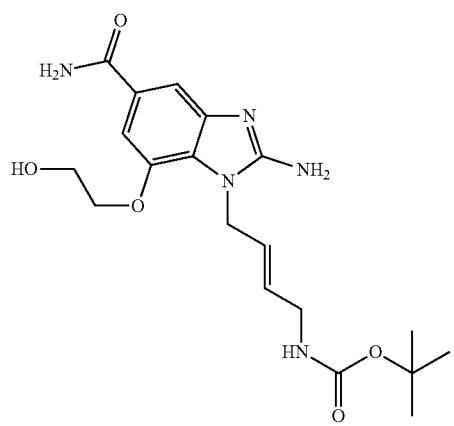 [SMILES: CC(C)(C)OC(=O)NC/C=C/Cn1c(N)nc2cc(C(N)=O)cc(OCCO)c21]

This compound was prepared using similar procedures as described for Example S1i, Step 4 with tert-butyl (E)-(4-((2-amino-6-(2-((tert-butyldimethylsilyl)oxy)ethoxy)-4-carbamoylphenyl)amino)but-2-en-1-yl)carbamate replacing tert-butyl (E)-(4-((2-amino-4-carbamoyl-6-methylphenyl)amino)but-2-en-1-yl)carbamate. LC-MS calculated for $C_{19}H_{28}N_5O_5$ (M+H)$^+$: m/z=406.2; found 406.2.

212

Step 5: (E)-2-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate

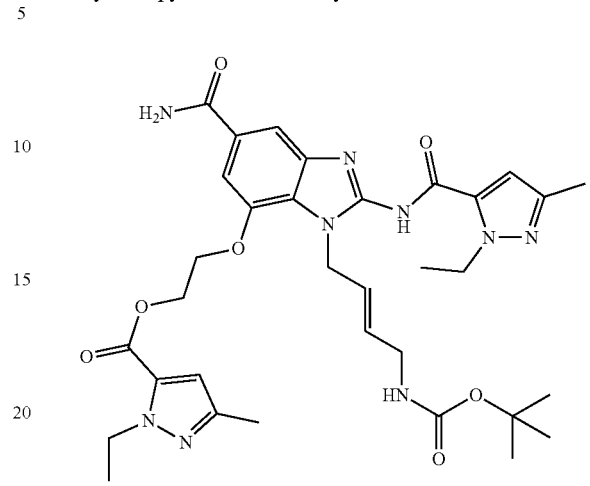

This compound was prepared using similar procedures as described for Example S15, Step 6 with tert-butyl (E)-(4-(2-amino-5-carbamoyl-7-(2-hydroxyethoxy)-1H-benzo[d]imidazol-1-yl)but-2-en-1-yl)carbamate replacing tert-butyl (E)-(4-(2-amino-5-carbamoyl-7-(3-hydroxypropoxy)-1H-benzo[d]imidazol-1-yl)but-2-en-1-yl)carbamate. LC-MS calculated for $C_{33}H_{44}N_9O_7$ (M+H)+: m/z=678.3; found 678.4.

Step 6: (E)-2-((1-(4-aminobut-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate

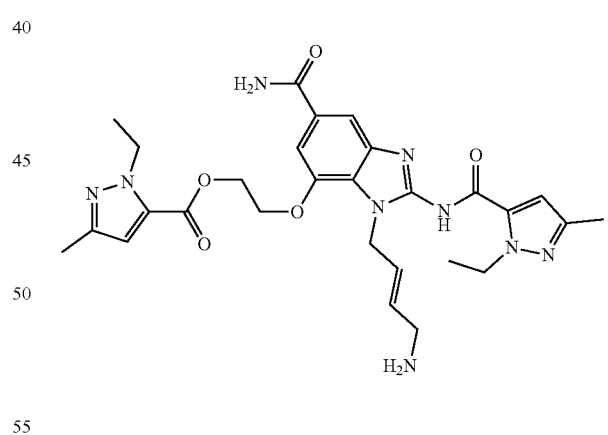

This compound was prepared using similar procedures as described for Example S1, Step 6 with (E)-2-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate replacing tert-butyl (E)-(4-(5-carbamoyl-2-(1-ethyl-3-methyl-1H-pyrazole-5-carboxamido)-7-methyl-1H-benzo[d]imidazol-1-yl)but-2-en-1-yl)carbamate. LC-MS calculated for $C_{28}H_{36}N_9O_5$ (M+H)$^+$: m/z=578.3; found 578.2.

Step 7: (E)-2-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)ethyl 1-ethyl-3-methyl-1H-pyrazole-5-carboxylate

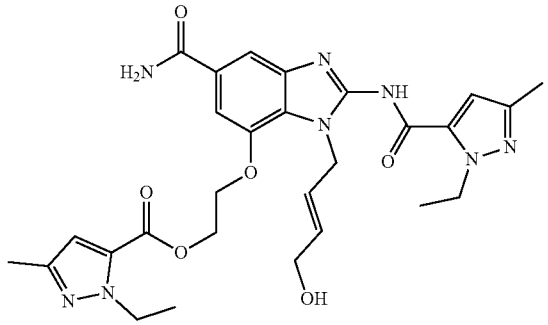

This compound was prepared using similar procedures as described for Example S1, Step 7 with (E)-2-((1-(4-aminobut-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate replacing (E)-1-(4-aminobut-2-en-1-yl)-2-(1-ethyl-3-methyl-1H-pyrazole-5-carboxamido)-7-methyl-1H-benzo[d]imidazole-5-carboxamide. LC-MS calculated for $C_{28}H_{35}N_8O_6$ $(M+H)^+$: m/z=579.3; found 579.3.

Step 8: (E)-2-((1-(4-bromobut-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate

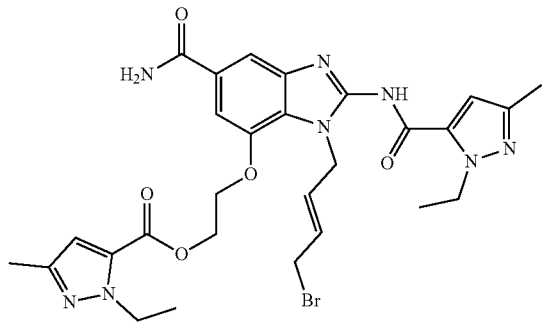

This compound was prepared using similar procedures as described for Example S1, Step 8 with (E)-2-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)ethyl 1-ethyl-3-methyl-1H-pyrazole-5-carboxylate replacing (E)-2-(1-ethyl-3-methyl-1H-pyrazole-5-carboxamido)-1-(4-hydroxybut-2-enyl)-7-methyl-1H-benzo[d]imidazole-5-carboxamide. LC-MS calculated for $C_{28}H_{34}BrN_8O_5$ $(M+H)^+$: m/z=641.2/643.2; found 641.3/643.3.

Step 9: (E)-2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzoimidazol-7-yl)oxy)ethyl 1-ethyl-3-methyl-1H-pyrazole-5-carboxylate To a mixture of (E)-2-((1-(4-bromobut-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate (120 mg, 0.187 mmol) and 2-(1-ethyl-3-methyl-1H-pyrazol-5-yl)-8-(3-methoxypropoxy)-9H-pyrimido[4,5-b]indole-6-carboxamide (76 mg, 0.187 mmol) in DMF (1871 µl) was added DIPEA (98 µl, 0.561 mmol). After 5 min, $Cs_2CO_3$ (183 mg, 0.561 mmol) was added. The mixture was stirred at rt overnight. The reaction mixture was diluted with TFA/water, then purified by prep-HPLC (pH=2, acetonitrile/water+TFA) to give the desired product as the TFA salt. LC-MS calculated for $C_{49}H_{57}N_{34}O_8$ $(M+H)^+$: m/z=969.4; found 969.4.

Example S41. (E)-9-(4-(5-carbamoyl-2-(1-ethyl-3-methyl-1H-pyrazole-5-carboxamido)-7-(2-hydroxyethoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

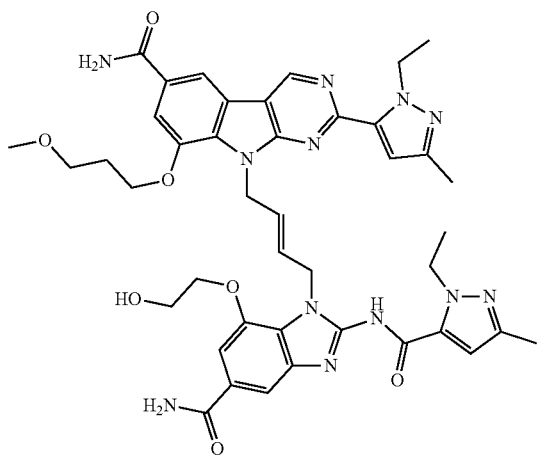

This compound was prepared using similar procedures as described for Example S37, Step 2 with (E)-2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate (Example S40, Step 9) replacing (E)-3-((5-carbamoyl-1-(4-(6-carbamoyl-2-(1-ethyl-3-methyl-1H-pyrazol-5-yl)-3-fluoro-9H-pyrido[2,3-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate. $^1$H NMR (600 MHz, DMSO) δ 12.77 (s, 1H), 9.49 (s, 1H), 8.42 (m, 1H), 8.04 (s, 1H), 7.93 (s, 1H), 7.62 (s, 1H), 7.57 (s, 1H), 7.35 (s, 1H), 7.31 (s, 1H), 7.26 (s, 1H), 6.79 (s, 1H), 6.40 (s, 1H), 5.94 (m, 1H), 5.75-5.67 (m, 1H), 5.26 (d, J=4.8 Hz, 2H), 4.90 (d, J=5.6 Hz, 2H), 4.61 (dd, J=14.1, 7.0 Hz, 2H), 4.46 (d, J=6.5 Hz, 2H), 4.10-4.01 (m, 2H), 3.95-3.86 (m, 2H), 3.35 (m, 2H), 3.30 (m, 2H), 3.15 (d, J=4.9 Hz, 3H), 2.19 (s, 3H), 2.07 (s, 3H), 1.85-1.77 (m, 2H), 1.32 — 1.24 (m, 3H), 1.20 (t, J=7.1 Hz, 3H). LC-MS calculated for $C_{42}H_{49}N_{32}O_7$ $(M+H)^+$: m/z=833.4; found 833.4.

Example S42. (6S,9S,12S,15S)-15-amino-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yloxy)-6,9-bis(carboxymethyl)-12-(3-guanidinopropyl)-5,8,11,14-tetraoxo-4,7,10,13-tetraazaheptadecan-17-oic acid

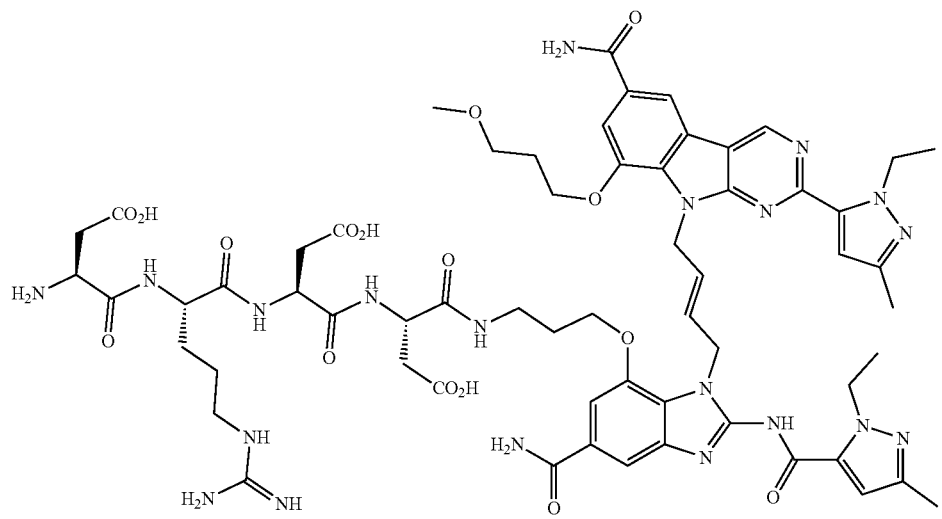 [SMILES: CCn1nc(C)cc1C(=O)Nc1nc2cc(C(N)=O)cc(OCCCNC(=O)[C@H](CC(=O)O)NC(=O)[C@H](CC(=O)O)NC(=O)[C@H](CCCNC(=N)N)NC(=O)[C@@H](N)CC(=O)O)c2n1C/C=C/Cn1c2nc(-c3cc(C)nn3CC)ncc2c2cc(C(N)=O)cc(OCCCOC)c21]

Step 1: tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate

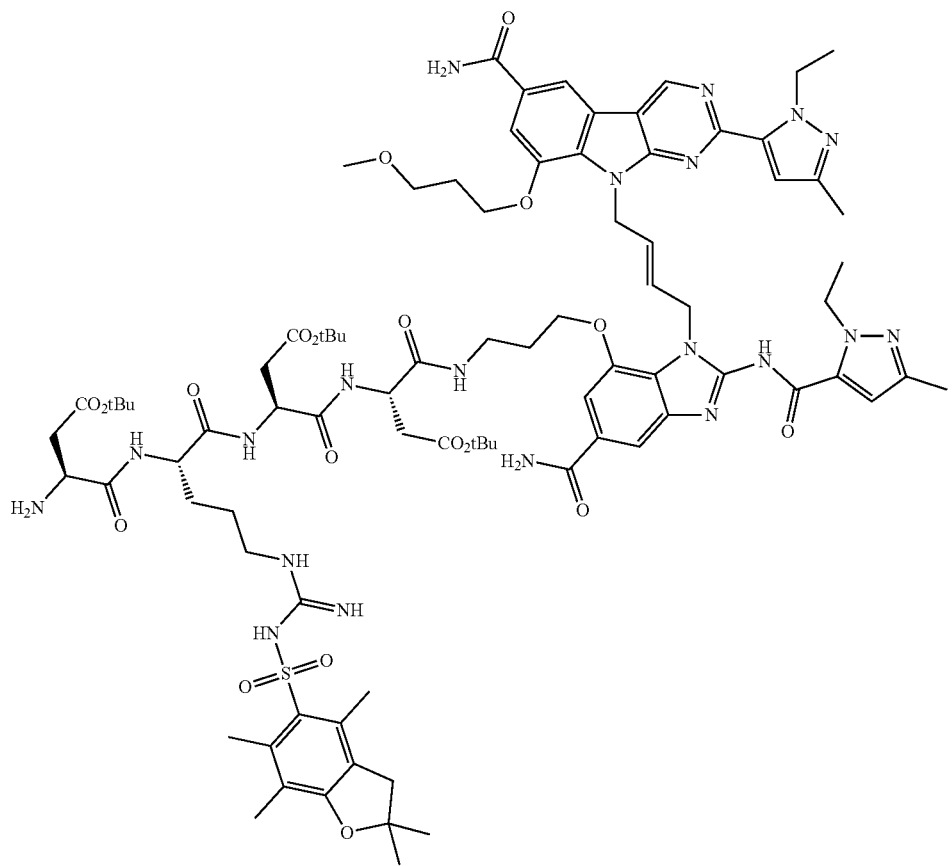 [SMILES: CCn1nc(C)cc1C(=O)Nc1nc2cc(C(N)=O)cc(OCCCNC(=O)[C@H](CC(=O)OC(C)(C)C)NC(=O)[C@H](CC(=O)OC(C)(C)C)NC(=O)[C@H](CCCNC(=N)NS(=O)(=O)c3c(C)c(C)c4c(c3C)CC(C)(C)O4)NC(=O)[C@@H](N)CC(=O)OC(C)(C)C)c2n1C/C=C/Cn1c2nc(-c3cc(C)nn3CC)ncc2c2cc(C(N)=O)cc(OCCCOC)c21]

In a 1 dram vial, (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example S38, Step 9: 37 mg, 0.044 mmol) was dissolved in DMF (875 µl). Fmoc-Asp(OtBu)-Arg(Pbf)-Asp(OtBu)-Asp(OtBu)-OH (Peptides International, cat #PCS-33379-PI : 73.5 mg, 0.066 mmol), DIPEA (38.2 µl, 0.219 mmol) and BOP (38.7 mg, 0.087 mmol) were added to the reaction mixture sequentially. After stirring for 15 min, piperidine (0.1 mL) was added. After 30 min, the reaction mixture was diluted with MeOH then purified by prep-HPLC (pH=2, acetonitrile/water+TFA) to give the desired product as the TFA salt. LC-MS calculated for $C_{86}H_{120}N_{20}O_{19}S$ $(M+2H)^{2+}$: m/z=884.4; found 884.5.

Step 2: (6S,9S,12S,15S)-15-amino-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-6,9-bis(carboxymethyl)-12-(3-guanidinopropyl)-5,8,11,14-tetraoxo-4,7,10,13-tetraazaheptadecan-17-oic acid Tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate (5 mg, 2.83 µmol) was stirred in TFA (0.5 mL) for 5 min. The reaction was diluted with MeCN then purified by prep HPLC (pH=2, MeCN/water+TFA) to provide the desired compound as the TFA salt. $^1$H NMR (600 MHz, DMSO) δ 12.78 (s, 1H), 9.48 (s, 1H), 8.59 (d, J=7.2 Hz, 1H), 8.41 (s, 1H), 8.26 (d, J=7.2 Hz, 1H), 8.18-8.06 (ovrlp m, 3H), 8.05 (s, 1H), 7.93 (s, 1H), 7.72 (m, 1H), 7.60 (s, 1H), 7.57 (s, 1H), 7.45 (s, 1H), 7.36 (s, 1H), 7.34 (s, 1H), 7.23 (s, 1H), 6.79 (s, 1H), 6.37 (s, 1H), 5.85 (m, 1H), 5.69 (m, 1H), 5.26 (s, 2H), 4.87 (s, 2H), 4.61 (m, 2H), 4.52 (dd, J=13.6, 7.4 Hz, 1H), 4.43 (ovrlp m, 4H), 4.27 (dd, J=13.6, 7.4 Hz, 1H), 4.12 (s, 1H), 4.09-4.00 (m, 2H), 3.89 (m, 2H), 3.31 (dd, J=6.3, 6.3 Hz, 2H), 3.15 (s, 3H), 3.10-3.00 (ovrlp m, 3H), 2.96 (m, 1H), 2.83 (dd, J=17.8, 3.3 Hz, 1H), 2.76-2.62 (ovrlp m, 2H), 2.567-2.50 (m, 3H), 2.20 (s, 3H), 2.06 (s, 3H), 1.83-1.73 (m, 2H), 1.65 (m, 1H), 1.55-1.42 (m, 4H), 1.33-1.24 (m, 3H), 1.21-1.16 (m, 3H). LC-MS calculated for $C_{61}H_{80}N_{20}O_{16}$ $(M+2H)^{2+}$: m/z=674.3; found 674.5.

Example S43. (E)-9-(4-(5-carbamoyl-2-(1-ethyl-3-methyl-1H-pyrazole-5-carboxamido)-7-(2-morpholinoethoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide To a vial was added (E)-9-(4-(5-carbamoyl-2-(1-ethyl-3-methyl-1H-pyrazole-5-carboxamido)-7-(2-hydroxyethoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example S41: 0.003 g, 3.60 µmol), DMF (0.360 ml), and a stir bar. The mixture was cooled to 0° C., and DMP (3.06 mg, 7.20 µmol) and water (0.519 µl, 0.029 mmol) were added. The mixture was warmed to rt and stirred overnight. To this mixture was then added morpholine (0.941 µl, 10.81 µmol), acetic acid (3.09 µl, 0.054 mmol), then sodium cyanoborohydride (0.453 mg, 7.20 µmop. After stirring for 15 min, the reaction was diluted with water/MeCN and purified by prep HPLC (pH=2, MeCN/water+TFA) to provide the desired compound as the TFA salt. LC-MS calculated for $C_{46}H_{57}N_{13}O_7$ $(M+2H)^{2+}$: m/z=451.7; found 451.7.

Example S44. (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)propanoic acid

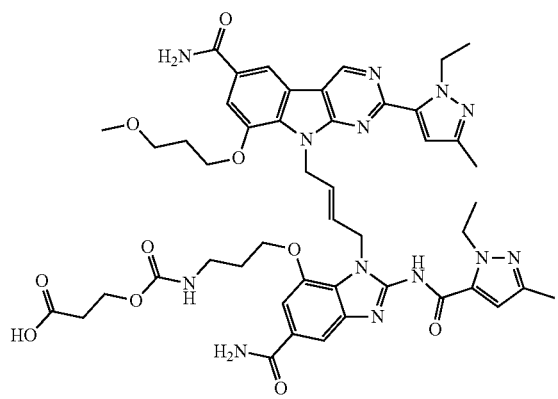

Step 1: tert-butyl 3-(((4-nitrophenoxy)carbonyl)oxy)propanoate

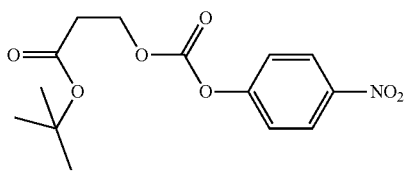 [SMILES: CC(C)(C)OC(=O)CCOC(=O)Oc1ccc([N+](=O)[O-])cc1]

To a solution of tert-butyl 3-hydroxypropanoate (Aldrich, cat #90218: 0.247 g, 1.69 mmol) and N-methylmorpholine (0.539 ml, 4.90 mmol) in dry THF (8.5 ml) was added 4-nitrophenyl carbonochloridate (Aldrich, cat #160210: 0.681 g, 3.38 mmol) at 0° C. and the resulting mixture was stirred at rt for 1 h. After completion of the reaction, the reaction was cooled to 0° C. and water was added. The aqueous phase was extracted with $CH_2Cl_2$. The organic extracts were dried over $MgSO_4$, filtered, and the solvent was removed. The crude mixture was purified by flash-chromatography (1:8 EtOAc/hexanes) to afford the desired product as an oil. LC-MS calculated for $C_{14}H_{17}NNaO_7$ $(M+Na)^+$: m/z=334.1; found 334.0.

Step 2: tert-butyl (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)propanoate

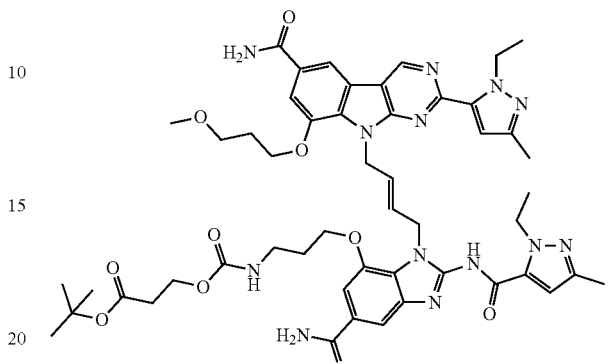

To a solution of (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example S38, Step 9: 0.015 g, 0.018 mmol) in DMF (0.177 ml) was added DIPEA (9.29 µl, 0.053 mmol). After cooling to 0° C., tert-butyl 3-(((4-nitrophenoxy)carbonyl)oxy)propanoate (5.52 mg, 0.018 mmol) was added and the mixture was warmed to rt and stirred for 1 h. The mixture was cooled to 0° C. and quenched with water. The reaction was extracted with $CHCl_3$/IPA (3:1) and the combined organic layers were dried over $MgSO_4$, filtered, and concentrated under reduced pressure. The crude product was used directly in the next step without further purification. LC-MS calculated for $C_{51}H_{64}N_{13}O_{10}$ $(M+H)^+$: m/z=1018.5; found 1018.6.

Step 3: (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)propanoic acid This compound was prepared using similar procedures as described for Example S42, Step 2 with tert-butyl (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)propanoate replacing tert-butyl (6S,9S,12S,15S)-15-amino-6,9-bis(2-(tert-butoxy)-2-oxoethyl)-1-((5-carbamoyl-1-((E)-4-(6-carbamoyl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate.
$^1$H NMR (600 MHz, DMSO) δ 12.78 (s, 1H), 9.47 (s, 1H), 8.41 (d, J=1.2 Hz, 1H), 8.03 (s, 1H), 7.93 (s, 1H), 7.62 (s, 1H), 7.56 (d, J=1.2 Hz, 1H), 7.35 (s, 1H), 7.31 (s, 1H), 7.24

(d, J=0.6 Hz, 1H), 7.10 (t, J=5.7 Hz, 1H), 6.79 (s, 1H), 6.40 (s, 1H), 5.85 (m, 1H), 5.72 (dt, J=15.6, 5.4 Hz, 1H), 5.25 (d, J=4.8 Hz, 2H), 4.87 (d, J=5.4 Hz, 2H), 4.61 (q, J=6.9 Hz, 2H), 4.45 (1, J=6.9 Hz, 2H), 4.03 (ovrlp dt, J=11.4, 6.6 Hz, 4H), 3.88 (t, J=6.3 Hz, 2H), 3.31 (t, J=6.0 Hz, 2H), 3.15 (s, 3H), 2.89 (m, 2H), 2.46 (t, J=6.0 Hz, 2H), 2.19 (s, 3H), 2.07 (s, 3H), 1.78 (dt, J=12.6, 6.3 Hz, 2H), 1.52 (dt, J=12.6, 6.3 Hz, 2H), 1.27 (t, J=6.9 Hz, 3H), 1.20 (t, J=6.9 Hz, 3H). LC-MS calculated for $C_{47}H_{57}N_{13}O_{10}$ $(M+2H)^{2+}$: m/z=481.7; found 481.5.

Example S45. (E)-2-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)acetic acid

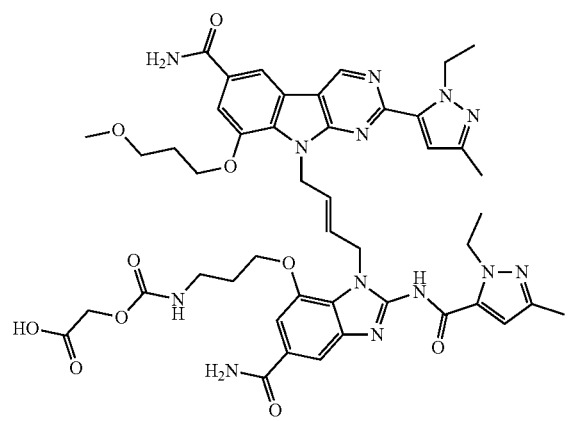 [SMILES: CCn1nc(C)cc1C(=O)Nc1nc2cc(C(N)=O)cc(OCCCNC(=O)OCC(=O)O)c2n1C/C=C/Cn1c2nc(-c3cc(C)nn3CC)ncc2c2cc(C(N)=O)cc(OCCCOC)c21]

Step 1: methyl 2(((4-nitrophenoxy)carbonyhoxy)acetate

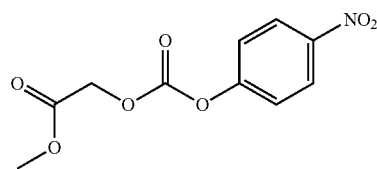 [SMILES: COC(=O)COC(=O)Oc1ccc([N+](=O)[O-])cc1]

This compound was prepared using similar procedures as described for Example S44, Step 1 with methyl 2-hydroxyacetate (Aldrich, cat #325260) replacing 3-hydroxypropanoate. The crude product was purified using silica gel chromatography (0-24% EtOAc/hexanes) to provide the desired compound as an oil. LC-MS calculated for $C_{10}H_{10}NO_7$ $(M+H)^+$: m/z=256.0; found 256.1.

Step 2: methyl (E)-2-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)acetate

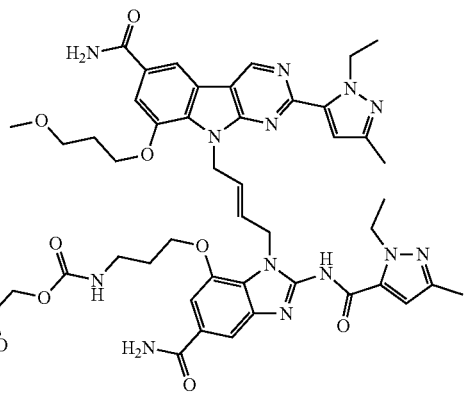

This compound was prepared using similar procedures as described for Example S44, Step 2 with methyl 2-(((4-nitrophenoxy)carbonyl)oxy)acetate replacing tert-butyl 3-(((4-nitrophenoxy)carbonyl)oxy)propanoate. LC-MS calculated for $C_{47}H_{56}N_{13}O_{10}$ $(M+H)^+$: m/z=962.4; found 962.5.

Step 3: (E)-2-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)acetic acid This compound was prepared using similar procedures as described for Example S39, Step 2 with methyl (E)-2-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)acetate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. $^1$H NMR (600 MHz, DMSO) δ 12.77 (s, 1H), 9.47 (s, 1H), 8.41 (d, J=1.2 Hz, 1H), 8.02 (s, 1H), 7.93 (s, 1H), 7.61 (s, 1H), 7.57 (s, 1H), 7.37-7.29 (ovrlp m, 2H), 7.24 (s, 1H), 6.79 (s, 1H), 6.39 (s, 1H), 5.85 (m, 1H), 5.74-5.67 (m, 1H), 5.25 (d, J=4.2 Hz, 2H), 4.87 (d, J=4.2 Hz, 2H), 4.61 (q, J=7.2 Hz, 2H), 4.48-4.41 (m, 2H), 4.36 (s, 2H), 4.05 (t, J=5.7 Hz, 2H), 3.90 (t, J=5.7 Hz, 2H), 3.31 (t, J=5.7 Hz, 2H), 3.15 (s, 3H), 2.92 (m, 3H), 2.19 (s, 3H), 2.07 (s, 2H), 1.78 (tt, J=5.7, 5.7 Hz, 2H), 1.56-1.50 (m, 2H), 1.26 (t, J=7.2 Hz, 3H), 1.19 (t, J=7.2 Hz, 3H). LC-MS calculated for $C_{46}H_{55}N_{13}O_{10}$ $(M+2H)^{2+}$: m/z=474.7; found 474.8.

Example S46. (E)-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)glycine

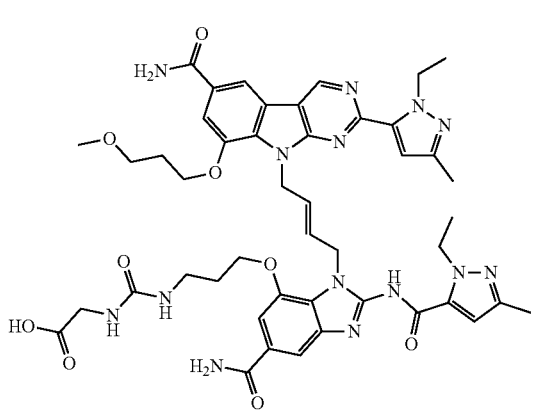

To a vial was added (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example S38, Step 9: 0.015 g, 0.018 mmol), DIPEA (9.29 0, 0.053 mmol), then ethyl 2-isocyanatoacetate (Aldrich, cat #238627: 2.98 0, 0.027 mmol). The mixture was stirred at rt overnight, and then was concentrated under reduced pressure. To the resulting crude mixture was added THF (0.180 ml, 2.199 mmol), MeOH (0.089 ml, 2.199 mmol), and aqueous 2 M LiOH (0.089 ml, 0.177 mmol). The mixture was stirred for 15 min at rt and was then diluted with water and purified by prep HPLC (pH=2, MeCN/water+TFA) to provide the desired product as the TFA salt. $^1$H NMR (600 MHz, DMSO) δ 12.77 (s, 1H), 9.48 (s, 1H), 8.41 (d, J=1.5 Hz, 1H), 8.04 (s, 1H), 7.93 (s, 1H), 7.61 (s, 1H), 7.57 (d, J=1.5 Hz, 1H), 7.35 (s, 1H), 7.31 (s, 1H), 7.25 (s, 1H), 6.79 (s, 1H), 6.39 (s, 1H), 6.13 (t, J=6.0 Hz, 1H), 5.99 (t, J=5.4 Hz, 1H), 5.86 (m, 1H), 5.73-5.67 (m, 1H), 5.26 (d, J=4.8 Hz, 2H), 4.87 (d, J=4.8 Hz, 2H), 4.60 (q, J=7.2 Hz, 2H), 4.45 (br q, J=6.9 Hz, 2H), 4.05 (t, J=6.6 Hz, 2H), 3.88 (t, J=6.0 Hz, 2H), 3.64 (d, J=5.4 Hz, 11H), 3.27 (t, J=6.0 Hz, 2H), 3.15 (s, 3H), 2.94 (m, 2H), 2.19 (s, 3H), 2.07 (s, 3H), 1.78 (tt, J=6.6, 6.0 Hz, 2H), 1.49 (tt, J=6.0, 6.0 Hz, 2H), 1.26 (t, J=7.2 Hz, 3H), 1.19 (t, J=6.9 Hz, 3H). LC-MS calculated for $C_{46}H_{55}N_{14}O_9$ (M+H)$^+$: m/z=947.4; found 947.4.

Example S47

(S,E)-3-amino-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoic acid

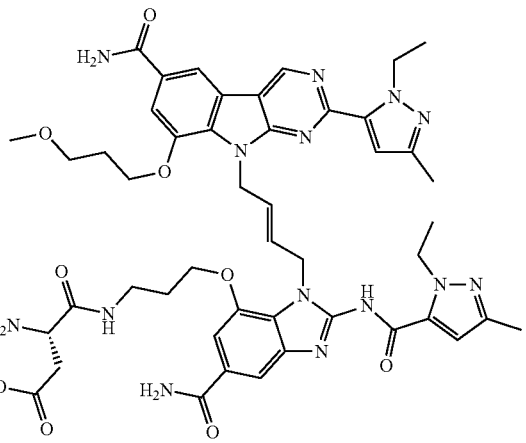

Step 1: methyl (S,E)-3-amino-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoate

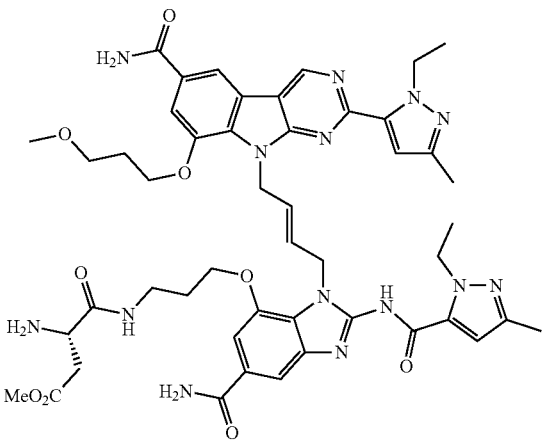

In a 1 dram vial, (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example S38, Step 9: 10 mg, 0.012 mmol) was dissolved in DMF (236 μl). (S)-2-((((9H-fluoren-9-yl)methoxy)carbonyl)amino)-4-methoxy-4-oxobutanoic acid (Aurum Pharmatech, cat #B-7268: 8.73 mg, 0.024 mmol), DIPEA (10.32 μl, 0.059 mmol) and BOP (10.46 mg, 0.024 mmol) were added to the reaction mixture sequentially. After 15 min, piperidine (0.1 mL) was added. After 1 h, the reaction mixture was diluted with MeOH then purified by prep-HPLC (pH=2, acetonitrile/water+TFA) to give the desired product as the TFA salt. LC-MS calculated for $C_{48}H_{60}N_{14}O_9$ $(M+2H)^{2+}$: m/z=488.2; found 488.5.

Step 2: (S,E)-3-amino-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoic acid This compound was prepared using similar procedures as described for Example S39, Step 2 with methyl (S,E)-3-amino-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. LC-MS calculated for $C_{47}H_{58}N_{14}O_9$ $(M+2H)^{2+}$: m/z=481.2; found 481.3.

Example S48. (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid

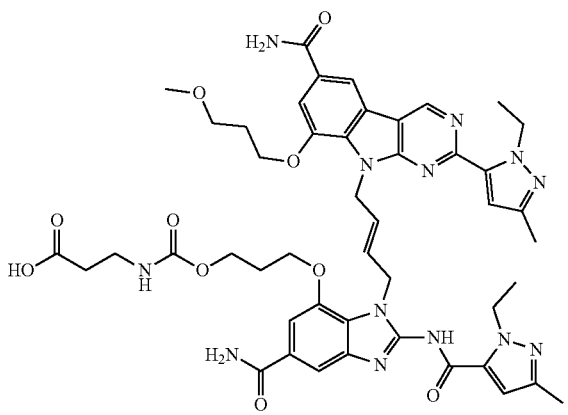 [SMILES: CCn1nc(C)cc1C(=O)Nc1nc2cc(C(N)=O)cc(OCCCOC(=O)NCCC(=O)O)c2n1C/C=C/Cn1c2nc(-c3cc(C)nn3CC)ncc2c2cc(C(N)=O)cc(OCCCOC)c21]

Step 1: tert-butyl (E)-(4-(5-carbamoyl-2-(1-ethyl-3-methyl-1H-pyrazole-5-carboxamido)-7-(3-hydroxypropoxy)-1H-benzo[s]imidazol-1-yl)but-2-en-1-yl)carbamate

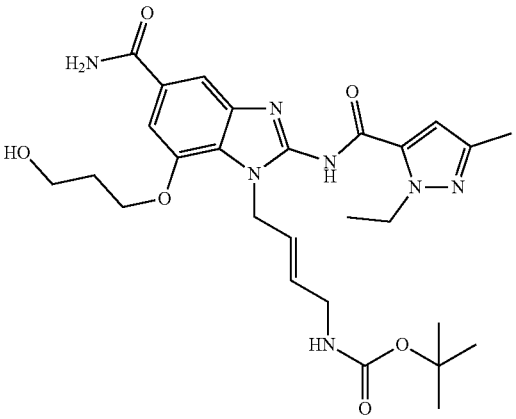 [SMILES: CCn1nc(C)cc1C(=O)Nc1nc2cc(C(N)=O)cc(OCCCO)c2n1C/C=C/CNC(=O)OC(C)(C)C]

To a solution of (E)-3-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate (Example S15, Step 6: 0.406 g, 0.587 mmol) in THF (1.956 ml) and MeOH (0.978 ml) was added 2 M LiOH (0.880 ml, 1.761 mmol). The reaction was stirred at rt for 15 min, then water and DCM were added and the layers were separated. The aqueous layer was further extracted with DCM, and the combined organic layers were dried over MgSO₄, filtered, and concentrated under reduced pressure. The crude product was used directly in the next step without further purification. LC-MS calculated for $C_{27}H_{38}N_7O_6$ $(M+H)^+$: m/z=556.3; found 556.5.

Step 2: ethyl (E)-3-(((3-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)propoxy)carbonyl)amino)propanoate

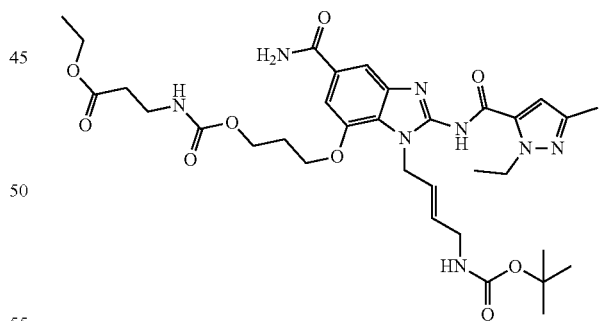

To a solution of tert-butyl (E)-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)carbamate (0.050 g, 0.090 mmol) and DIPEA (0.024 ml, 0.135 mmol) in THF (0.900 ml) was added ethyl 3-isocyanatopropionate (Aldrich, cat #479012: 0.012 ml, 0.090 mmol). The reaction was stirred at 70° C. overnight. After cooling to rt, the reaction was diulted with water and CHCl₃/IPA (3:1), and the layers were separated. The aqueous layer was further extracted and the combined organic extracts were dried over MgSO₄, filtered, and concentrated under reduced

227 pressure. The crude product was purified by silica gel chromatography (30% MeOH/DCM). LC-MS calculated for $C_{33}H_{47}N_8O_9$ (M+H)$^+$: m/z=699.3; found 699.7.

Step 3: ethyl (E)-3-(((3-((1-(4-aminobut-2-en-1-yl)-5-carbamoyl-2-(1-ethyl-3-methyl-1H-pyrazole-5-carboxamido)-1H-benzo[d]imidazol-7-yl)oxy)propoxy)carbonyl)amino)propanoate

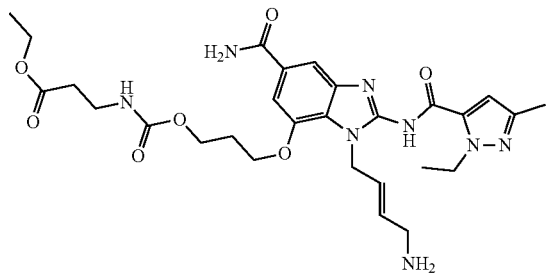 [SMILES: CCOC(=O)CCNC(=O)OCCCOc1cc(C(N)=O)cc2nc(NC(=O)c3cc(C)nn3CC)n(C/C=C/CN)c12]

To a solution of ethyl (E)-3-(((3-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)propoxy)carbonyl)amino)propanoate (0.066 g, 0.094 mmol) in dioxane (0.945 ml) was added 4 M HCl in dioxane (0.236 ml, 0.945 mmol). The reaction was stirred for 1 h, then was concentrated under reduced pressure and used directly in the next step without further purification. LC-MS calculated for $C_{28}H_{39}N_8O_7$ (M+H)$^+$: m/z=599.3; found 599.3.

Step 4: ethyl (E)-3-(((3-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)propoxy)carbonyl)amino)propanoate

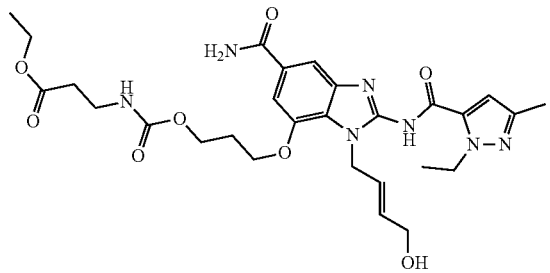 [SMILES: CCOC(=O)CCNC(=O)OCCCOc1cc(C(N)=O)cc2nc(NC(=O)c3cc(C)nn3CC)n(C/C=C/CO)c12]

This compound was prepared using similar procedures as described for Example S1, Step 7 with ethyl (E)-3-(((3-((1-(4-aminobut-2-en-1-yl)-5-carbamoyl-2-(1-ethyl-3-methyl-1H-pyrazole-5-carboxamido)-1H-benzo[d]imidazol-7-yl)oxy)propoxy)carbonyl)amino)propanoate replacing (E)-1-(4-aminobut-2-en-1-yl)-2-(1-ethyl-3-methyl-1H-pyrazole-5-carboxamido)-7-methyl-1H-benzo[d]imidazole-5-carboxamide. The crude product was purified using silica gel chromatography (20% MeOH/DCM). LC-MS calculated for $C_{28}H_{38}N_7O_8$ (M+H)$^+$: m/z=600.3; found 600.3.

228

Step 5: ethyl (E)-3-(((3-((5-carbamoyl-2-(1-ethyl-3-methyl-1H-pyrazole-5-carboxamido)-1-(4-((methylsulfonyhoxy)but-2-en-1-yl)-1H-benzo[d]imidazol-7-yl)oxy)propoxy)carbonyl)amino)propanoate

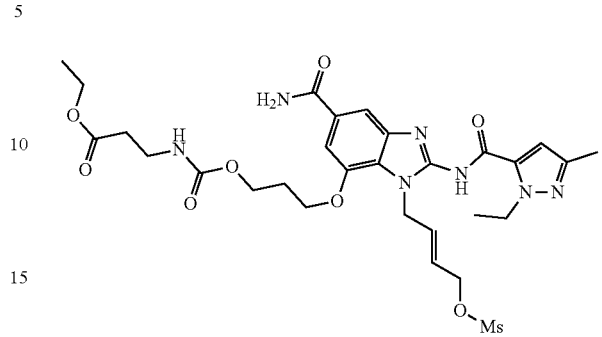

To a vial was added ethyl (E)-3-(((3-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)propoxy)carbonyl)amino)propanoate (0.028 g, 0.047 mmol), THF (0.467 ml), Et$_3$N (9.76 µl, 0.070 mmol), then Ms-Cl (4.37 µl, 0.056 mmol). After stirring at rt for 1 h, the reaction was quenched with aqueous saturated sodium bicarbonate, and extracted with CHCl$_3$/IPA (3:1). The combined organic layers were dried over MgSO$_4$, filtered, and concentrated under reduced pressure. The crude product was used directly in the next step without further purification. LC-MS calculated for $C_{29}H_{40}N_7O_{10}S$ (M+H)$^+$: m/z=678.3; found 678.3.

Step 6: ethyl (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoate

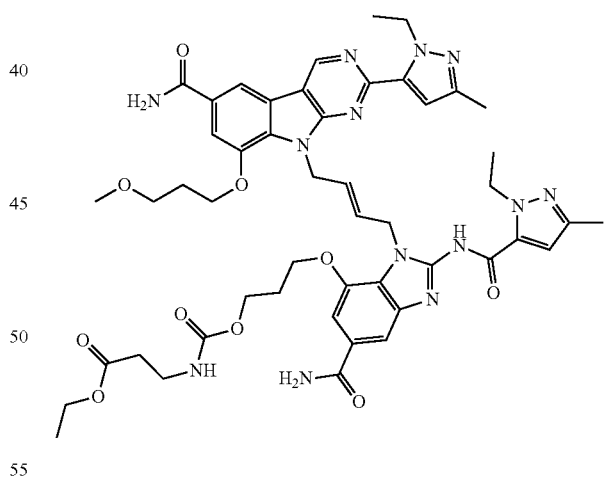

To a solution of ethyl (E)-3-(((3-((5-carbamoyl-2-(1-ethyl-3-methyl-1H-pyrazole-5-carboxamido)-1-(4-((methylsulfonyl)oxy)but-2-en-1-yl)-1H-benzo[d]imidazol-7-yl)oxy)propoxy)carbonyl)amino)propanoate (0.030 g, 0.044 mmol) in DMF (0.443 ml) was added 2-(1-ethyl-3-methyl-1H-pyrazol-5-yl)-8-(3-methoxypropoxy)-9H-pyrimido[4,5-b]indole-6-carboxamide (Example S12, Step 3: 0.018 g, 0.044 mmol) and cesium carbonate (0.043 g, 0.133 mmol). The mixture was stirred for 3 h at rt, and was then diluted with water. The mixture was extracted with CHCl$_3$/IPA (3:1) and the combined organic extracts were dried over MgSO$_4$, filtered, and concentrated under reduced pressure. The crude product was used directly in the next step without further purification. LC-MS calculated for $C_{49}H_{60}N_{13}O_{10}$ (M+H)⁺: m/z=990.4; found 990.0.

Step 7: (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid To a solution of ethyl (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonypamino) propanoate was added THF (0.440 mL), MeOH (0.221 mL) and aqueous 2 M LiOH (0.221 ml, 0.443 mmol). After stirring 15 min at rt, the mixture was diluted with water, and purified by prep HPLC (pH=2, MeCN/water+TFA) to provide the desired compound as the TFA salt. LC-MS calculated for $C_{47}H_{56}N_{13}O_{10}$ (M+H)⁺: m/z=962.4; found 962.4.

Example S49. (E)-3-(2-(2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethoxy)ethoxy)propanoic acid

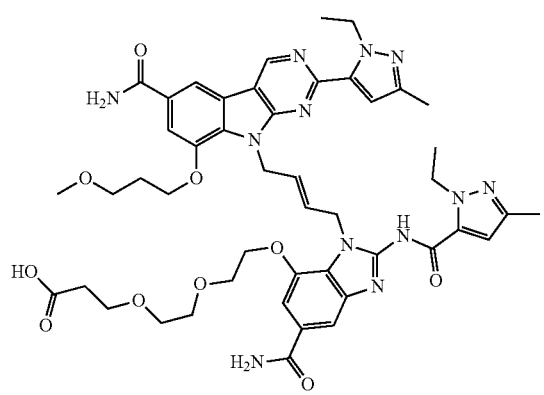 [SMILES: CCn1nc(C)cc1C(=O)Nc1nc2cc(C(N)=O)cc(OCCOCCOCCC(=O)O)c2n1C/C=C/Cn1c2nc(-c3cc(C)nn3CC)ncc2c2cc(C(N)=O)cc(OCCCOC)c21]

Step 1: tert-butyl 3-(2-(2-(5-carbamoyl-2-chloro-3-nitrophenoxy)ethoxy)ethoxy)propanoate

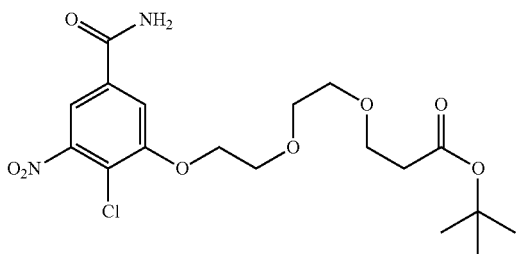 [SMILES: CC(C)(C)OC(=O)CCOCCOCCOc1cc(C(N)=O)cc([N+](=O)[O-])c1Cl]

To a suspension of 4-chloro-3-hydroxy-5-nitrobenzamide (0.200 g, 0.923 mmol), and cesium carbonate (0.451 g, 1.385 mmol) in DMF (2.309 ml) was added tert-butyl 3-(2-(2-bromoethoxy)ethoxy)propanoate (Combi-Blocks, cat #QD-1308: 0.329 g, 1.108 mmol). After stirring at 50° C. for 4 h, the reaction was diluted with water and DCM, and the layers were separated. The aqueous layer was further extracted with DCM, and the combined organic layers were dried over MgSO₄, filtered, and concentrated under reduced pressure. The resulting crude oil was purified by silica gel chromatography (5% MeOH/DCM). LC-MS calculated for $C_{18}H_{25}ClN_2NaO_8$ (M+Na)⁺: m/z=455.1; found 455.1.

Step 2: (E)-2-(4-hydroxybut-2-en-1-yl)isoindoline-1,3-dione

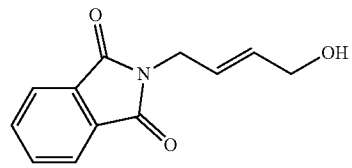 [SMILES: O=C1c2ccccc2C(=O)N1C/C=C/CO]

To a solution of (E)-but-2-ene-1,4-diol (Astatech, cat #70835: 1.198 g, 13.59 mmol) in tetrahydrofuran (34.0 ml) was added triphenylphosphine (3.57 g, 13.59 mmol). After cooling to 0° C., isoindoline-1,3-dione (1.0 g, 6.80 mmol) was added. A 40% wt/v solution of DEAD (5.92 ml, 13.59 mmol) in toluene was added dropwise and the reaction was warmed up to rt with stirring for 1 h. The reaction was concentrated and purified by silica gel column to provide the desired product (0–>5% MeOH/DCM). LC-MS calculated for $C_{12}H_{32}NO_3$ (M+H)⁺: m/z=218.1; found 218.1.

Step 3: (E)-2-(4-((tert-butyldimethylsilyl)oxy)but-2-en-1-yl)isoindoline-1,3-dione

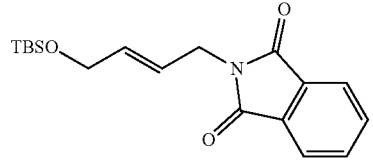 [SMILES: CC(C)(C)[Si](C)(C)OC/C=C/CN1C(=O)c2ccccc2C1=O]

To a mixture of (E)-2-(4-hydroxybut-2-en-1-yl)isoindoline-1,3-dione (1.5 g, 6.91 mmol) and Et₃N (1.444 ml, 10.36 mmol) in DCM (69.1 ml) was added TBS-Cl (1.249 g, 8.29 mmol). The mixture was stirred at rt for 16 h and was then concentrated under reduced pressure. Saturated aqueous NaHCO₃ was added to the reaction mixture followed by extraction with dichloromethane (3 times). The combined organic layers were dried over Na2SO4, filtered and concentrated. The crude product was added to a silica gel column and was eluted with ethyl acetate/hexane from 0% to 40% to give (E)-2-(4-((tert-butyldimethylsilypoxy)but-2-en-1-yl)isoindoline-1,3-dione (2.03 g, 6.12 mmol, 89% yield) as a colorless oil. LC-MS calculated for $C_{18}H_{27}NO_4Si$ (M+NH₄)⁺: m/z=349.2; found 349.3.

Step 4: (E)-4-((tert-butyldimethylsilyl)oxy)but-2-en-1-amine

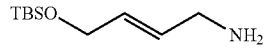

To a solution of (E)-2-(4-((tert-butyldimethylsilypoxy)but-2-en-1-yl)isoindoline-1,3-dione (2.02 g, 6.09 mmol) in DCM (30.5 ml) and MeOH (30.5 ml) was added hydrazine monohydrate (4.43 ml, 91 mmol). After heating for 2 h at 40° C., the mixture was filtered to remove the precipitated phthalhydrazide. The filtrate was washed with aqueous saturated NaHCO₃ and dried over MgSO₄, filtered and concentrated under reduced pressure. The crude product was used without further purification. LC-MS calculated for $C_{10}H_{24}NOSi$ (M+H)$^+$: m/z=202.2; found 202.2.

Step 5: tert-butyl (E)-3-(2-(2-(2-((4-((tert-butyldimethylsilyl)oxy)but-2-en-1-yl)amino)-5-carbamoyl-3-nitrophenoxy)ethoxy)ethovy)propanoate

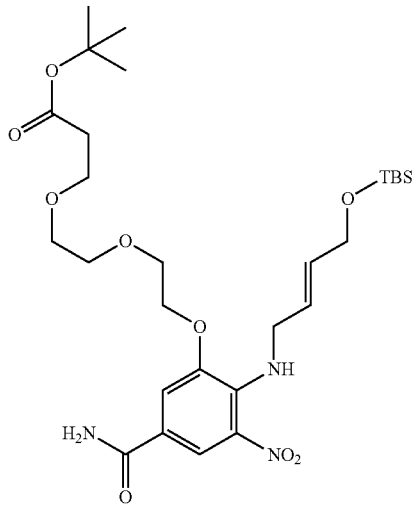

To a solution of tert-butyl 3-(2-(2-(5-carbamoyl-2-chloro-3-nitrophenoxy)ethoxy)ethoxy)propanoate (0.400 g, 0.924 mmol) in ethanol (4.62 ml) was added DIPEA (0.807 ml, 4.62 mmol) and (E)-4-((tert-butyldimethylsilypoxy)but-2-en-1-amine (0.186 g, 0.924 mmol). The resulting mixture was heated at 120° C. overnight. After cooling, the reaction was concentrated, and purified by silica gel column (10% MeOH/DCM). LC-MS calculated for $C_{28}H_{48}N_3O_9Si$ (M+H)$^+$: m/z=598.3; found 598.3.

Step 6: tert-butyl (E)-3-(2-(2-(3-amino-2-((4-((tert-butyldimethylsilyl)oxy)but-2-en-1-yl)amino)-5-carbamoylphenoxy)ethoxy)ethoxy)propanoate

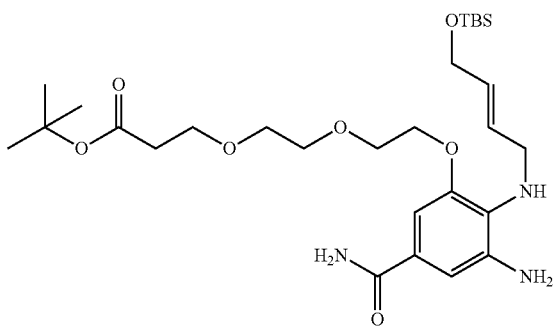 [SMILES: CC(C)(C)OC(=O)CCOCCOCCOc1cc(C(N)=O)cc(N)c1NC/C=C/CO[Si](C)(C)C(C)(C)C]

To a solution of tert-butyl (E)-3-(2-(2-(2-((4-((tert-butyldimethylsilypoxy)but-2-en-1-yl)amino)-5-carbamoyl-3-nitrophenoxy)ethoxy)ethoxy)propanoate (0.480 g, 0.803 mmol) in MeOH (12.04 ml) was added sodium hydrosulfite (0.699 g, 4.01 mmol) in water (2.53 ml, 141 mmol) and 30% aq. ammonium hydroxide (1.303 ml, 10.04 mmol) at 0° C. The reaction mixture was warmed to room temperature. After 10 min, H$_2$O was added to the reaction mixture followed by extraction with DCM. The combined organic layers were dried over MgSO$_4$, filtered and concentrated under reduced pressure. The crude product was used directly in the next step without further purification. LC-MS calculated for $C_{28}H_{50}N_3O_7Si$ (M+H)$^+$: m/z=568.3; found 568.4.

Step 7: tert-butyl (E)-3-(2-(2-((2-amino-5-carbamoyl-1-(4-hydroxybut-2-en-1-yl)-1H-benzo[d]imidazol-7-yl)oxy)ethoxy)ethoxy)propanoate

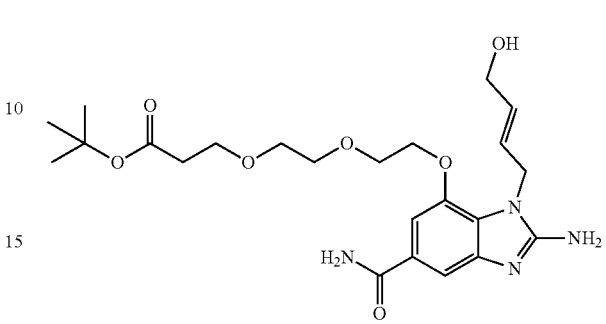

To a solution of tert-butyl (E)-3-(2-(2-(3-amino-2-((4-((tert-butyldimethylsilypoxy)but-2-en-1-yl)amino)-5-carbamoylphenoxy)ethoxy)ethoxy)propanoate (0.312 g, 0.549 mmol) in MeOH (2.75 ml) was added cyanogen bromide (0.144 ml, 2.75 mmol). The mixture was stirred for 2 d, and was then concentrated under reduced pressure. The resulting oil was used directly in the next step without further purification. LC-MS calculated for $C_{23}H_{35}N_4O_7$ (M+H)$^+$: m/z=479.2; found 479.4.

Step 8: (E)-4-(7-(2-(2-(3-(tert-butoxy)-3-oxopropoxy)ethoxy)ethoxy)-5-carbamoyl-2-(1-ethyl-3-methyl-1H-pyrazole-5-carboxamido)-1H-benzo[d]imidazol-1-yl)but-2-en-1-yl 1-ethyl-3-methyl-1H-pyrazole-5-carboxylate

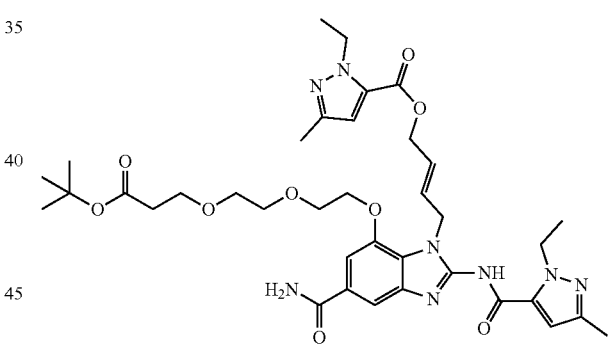

To a solution of tert-butyl (E)-3-(2-(2-((2-amino-5-carbamoyl-1-(4-hydroxybut-2-en-1-yl)-1H-benzo[d]imidazol-7-yl)oxy)ethoxy)ethoxy)propanoate (0.263 g, 0.549) in DMF (5 mL) was added DIPEA (0.768 ml, 4.40 mmol), 1-ethyl-3-methyl-1H-pyrazole-5-carboxylic acid (Combi-Blocks, cat #QB-0979: 0.254 g, 1.648 mmol) and benzotriazol-1-yloxytris(dimethylamino)-phosphonium hexafluorophosphate (0.729 g, 1.648 mmol). After 1 h, H$_2$O was added to the reaction mixture followed by extraction with ethyl acetate (5 mL×3). The combined organic layers were dried over MgSO$_4$, filtered and concentrated under reduced pressure. The crude product was added to a silica gel column and was eluted with methanol/dichloromethane from 0% to 10% to give (E)-4-(7-(2-(2-(3-(tert-butoxy)-3-oxopropoxy)ethoxy)ethoxy)-5-carbamoyl-2-(1-ethyl-3-methyl-1H-pyrazole-5-carboxamido)-1H-benzo[d]imidazol-1-yl)but-2-en-1-yl 1-ethyl-3-methyl-1H-pyrazole-5-carboxylate as a brown foam. LC-MS calculated for $C_{37}H_{51}N_8O_9$ (M+H)+: m/z=751.4; found 751.3.

Step 9: tert-butyl (E)-3-(2-(2-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)ethoxy)ethoxy)propanoate Step 11: tert-butyl (E)-3-(2-(2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethoxy)ethoxy)propanoate

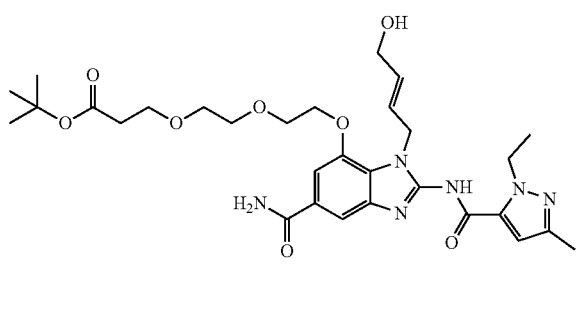 [SMILES: CCn1nc(C)cc1C(=O)Nc1nc2cc(C(N)=O)cc(OCCOCCOCCC(=O)OC(C)(C)C)c2n1C/C=C/CO]

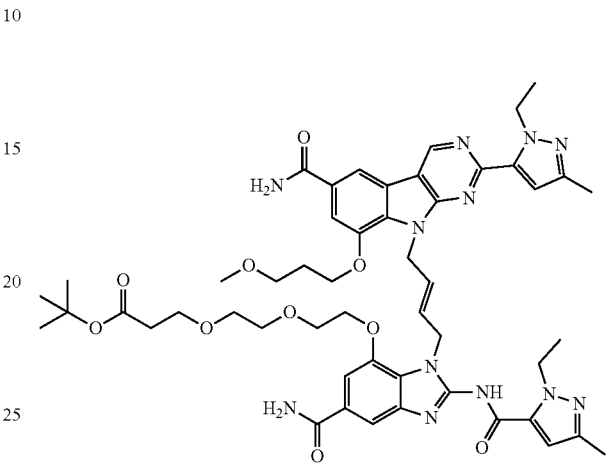

To a solution of (E)-4-(7-(2-(2-(3-(tert-butoxy)-3-oxopropoxy)ethoxy)ethoxy)-5-carbamoyl-2-(1-ethyl-3-methyl-1H-pyrazole-5-carboxamido)-1H-benzo[d]imidazol-1-yl)but-2-en-1-yl 1-ethyl-3-methyl-1H-pyrazole-5-carboxylate (0.413 g, 0.550 mmol) in THF (1.833 ml) and MeOH (0.917 ml) was added 2 N LiOH (1.375 ml, 2.75 mmol). After stirring for 2 h at rt, the reaction was extracted with $CHCl_3$/IPA (3:1). The combined organic extracts were dried over $MgSO_4$, filtered, and concentrated under reduced pressure. The resulting oil was purified by silica gel chromatography (15% MeOH/DCM) to provide the desired product as a beige foam. LC-MS calculated for $C_{30}H_{43}N_6O_8$ $(M+H)^+$: m/z=615.3; found 615.3.

Step 10: tert-butyl (E)-3-(2-(2-((1-(4-bromobut-2-en-1-yl)-5-carbamoyl-2-(1-ethyl-3-methyl-1H-pyrazole-5-carboxamido)-1H-benzo[d]imidazol-7-yl)oxy)ethoxy)ethoxy)propanoate

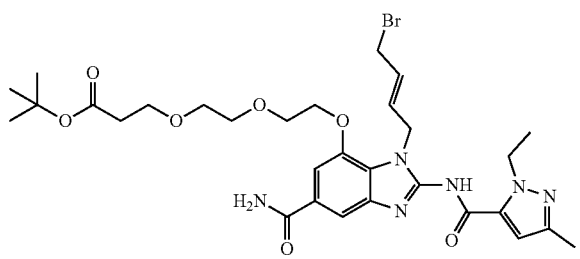 [SMILES: CCn1nc(C)cc1C(=O)Nc1nc2cc(C(N)=O)cc(OCCOCCOCCC(=O)OC(C)(C)C)c2n1C/C=C/CBr]

To a solution of tert-butyl (E)-3-(2-(2-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)ethoxy)ethoxy)propanoate (0.153 g, 0.249 mmol) in THF (1.833 ml) was added $PBr_3$ (0.052 ml, 0.550 mmol) at 0° C. The reaction was warmed to rt and stirred for 15 min. After cooling to 0° C. the reaciton was quenched with aqueous saturated sodium bicarbonate. The reaction was extracted with DCM, and the combined organic extracts were dried over $MgSO_4$, filtered, and concentrated. The resulting brown oil was then used directly in the next step. LC-MS calculated for $C_{30}H_{42}BrN_6O_7$ $(M+H)^+$: m/z=677.2/679.2; found 677.2/679.2.

To a solution of tert-butyl (E)-3-(2-(2-((1-(4-bromobut-2-en-1-yl)-5-carbamoyl-2-(1-ethyl-3-methyl-1H-pyrazole-5-carboxamido)-1H-benzo[d]imidazol-7-yl)oxy)ethoxy)propanoate (0.020 g, 0.030 mmol) and 2-(1-ethyl-3-methyl-1H-pyrazol-5-yl)-8-(3-methoxypropoxy)-9H-pyrimido[4,5-b]indole-6-carboxamide (Example S12, Step 3: 0.012 g, 0.030 mmol) in DMF (0.295 mL) was added $Cs_2CO_3$ (0.029 g, 0.089 mmol). The mixture was stirred at rt for 30 min. The mixture was diluted with water and EtOAc. The layers were separated, and the organic layer was washed with 10% brine (2×), brine, then dried over $MgSO_4$. The combined organic layers were filtered and concentrated under reduced pressure. The resulting crude oil was used directly in the next step without further purification. LC-MS calculated for $C_{51}H_{66}N_{12}O_{10}$ $(M+2H)^{2+}$: m/z=503.2; found 503.5.

Step 12: (E)-3-(2-(2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxytethoxy)ethoxy)propanoic acid To a vial was added tert-butyl (E)-3-(2-(2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethoxy)ethoxy)propanoate (0.030 mg, 0.030 mmol) and TFA (0.2 mL, 2.60 mmol). The mixture was stirred for 15 min, and was then diluted with MeCN and water and purified by prep HPLC (pH=2, MeCN/water+TFA) to provide the desired product as the TFA salt. LC-MS calculated for $C_{47}H_{57}N_{12}O_{10}$ $(M+H)^+$: m/z=949.4; found 949.4.

Example S50. (E)-4-(N-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)sulfamoyl)butanoic acid

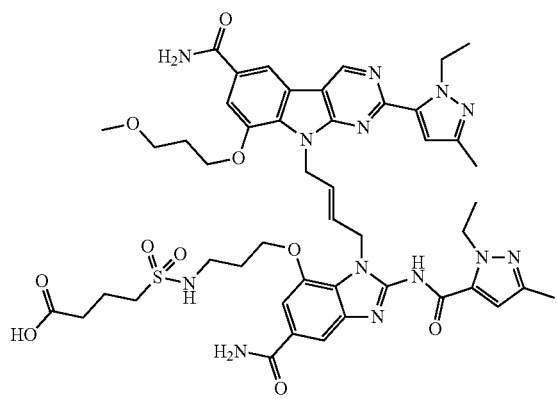 [SMILES: CCn1nc(C)cc1C(=O)Nc1nc2cc(C(N)=O)cc(OCCCNS(=O)(=O)CCCC(=O)O)c2n1C/C=C/Cn1c2nc(-c3cc(C)nn3CC)ncc2c2cc(C(N)=O)cc(OCCCOC)c21]

Step 1: methyl (E)-4-(N-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl(oxy)propyl)sulfamoyl)butanoate

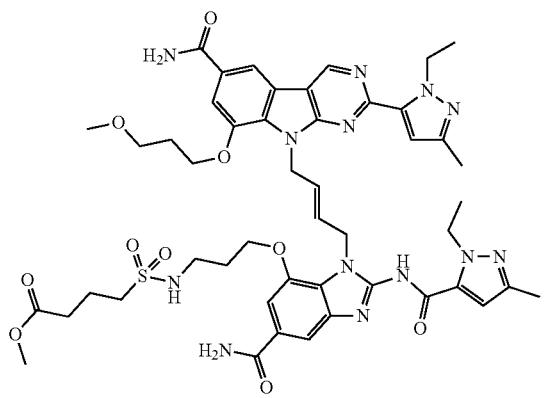 [SMILES: CCn1nc(C)cc1C(=O)Nc1nc2cc(C(N)=O)cc(OCCCNS(=O)(=O)CCCC(=O)OC)c2n1C/C=C/Cn1c2nc(-c3cc(C)nn3CC)ncc2c2cc(C(N)=O)cc(OCCCOC)c21]

To a solution of (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example S38, Step 9: 0.020 g, 0.024 mmol) in THF (0.236 ml)/DMF (0.236 ml) was added Et$_3$N (9.89 µl, 0.071 mmol) then methyl 4-(chlorosulfonyl)butanoate (Enamine, cat #EN300-31554: 4.74 mg, 0.024 mmol) dropwise. After stirring for 1 h at rt, the reaction was quenched with aqueous saturated sodium bicarbonate, and was extracted with 3:1 CHCl$_3$/IPA. The combined organic layers were dried over MgSO$_4$, filtered, and concentrated under reduced pressure, and the crude product was used directly in the next step without further purification. LC-MS calculated for C$_{48}$H$_{60}$N$_{13}$O$_{10}$S (M+H)$^+$: m/z=1010.4; found 1010.2.

Step 2: (E)-4-(N-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl(oxy)propyltsulfamoyl)butanoic acid To a solution of methyl (E)-4-(N-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)sulfamoyl)butanoate (0.024 g, 0.024 mmol) in THF (0.572 mL) and MeOH (0.236) was added aqueous 2 N LiOH (0.236 ml, 0.473 mmol). After stirring for 15 min, the mixture was diulted with water and MeCN and was purified by prep HPLC (pH=2, MeCN/water+TFA) to provide the desired compound as the TFA salt. LC-MS calculated for C$_{47}$H$_{58}$N$_{13}$O$_{10}$S (M+H)$^+$: m/z=996.4; found 996.2.

Example S51. (E)-5-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid

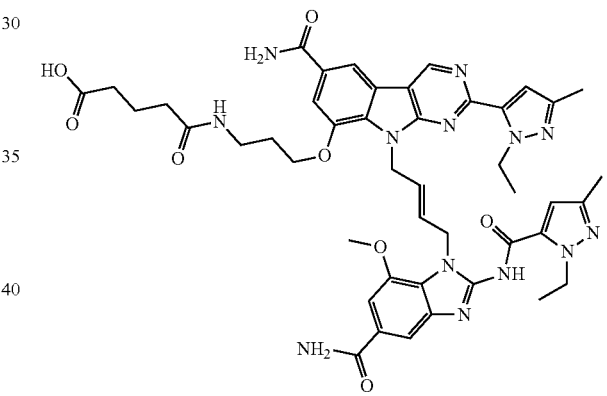

Step 1: tert-butyl 3-(3-bromo-5-carbamoyl-2-nitrophenoxy)propylcarbamate

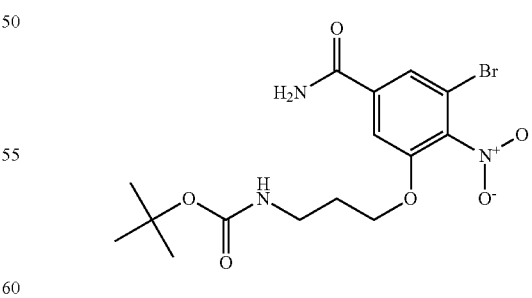

This compound was prepared using similar procedures as described for Example S11, Step 1 with tert-butyl 3-hydroxypropylcarbamate (Aldrich, cat #416444) replacing 3-morpholinopropan-1-ol. LC-MS calculated for C$_{15}$H$_{21}$BrN$_3$O$_6$ (M+H)$^+$: m/z=418.1, 420.1; found 318.1, 320.1.

Step 2: tert-butyl (3-(5-carbamoyl-3-(2-(1-ethyl-3-methyl-1H-pyrazol-5-yl)pyrimidin-5-yl)-2-nitrophenoxy)propyh-carbamate

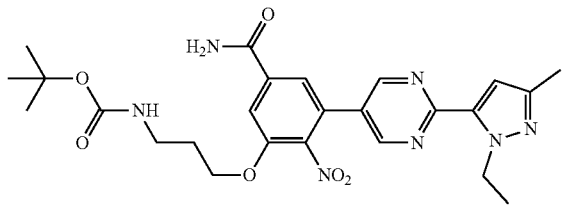 [SMILES: CCn1nc(C)cc1-c1ncc(-c2cc(C(N)=O)cc(OCCCNC(=O)OC(C)(C)C)c2[N+](=O)[O-])cn1]

This compound was prepared using similar procedures as described for Example S10, Step 3 with tert-butyl 3-(3-bromo-5-carbamoyl-2-nitrophenoxy)propylcarbamate replacing 3-bromo-5-methoxy-4-nitrobenzamide. LC-MS calculated for $C_{25}H_{32}N_7O_6$ (M+H)+: m/z=526.2; found 526.2.

Step 3: tert-butyl 3-(6-carbamoyl-2-(1-ethyl-3-methyl-1H-pyrazol-5-yl)-9H-pyrimido[4,5-b]indol-8-yloxy)propylcarbamate

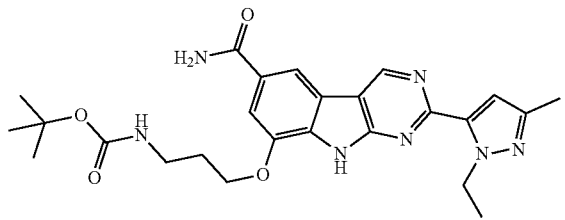 [SMILES: CCn1nc(C)cc1-c1ncc2c(n1)[nH]c1c(OCCCNC(=O)OC(C)(C)C)cc(C(N)=O)cc12]

This compound was prepared using similar procedures as described for Example S10, Step 4 with tert-butyl (3-(5-carbamoyl-3-(2-(1-ethyl-3-methyl-1H-pyrazol-5-yl)pyrimidin-5-yl)-2-nitrophenoxy)propyl)carbamate replacing 3-(2-(1-ethyl-3-methyl-1H-pyrazol-5-yl)pyrimidin-5-yl)-5-methoxy-4-nitrobenzamide. LC-MS calculated for $C_{25}H_{32}N_7O_4$ (M+H)+: m/z=494.2; found 494.3.

Step 4: (E)-tert-butyl 3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamate

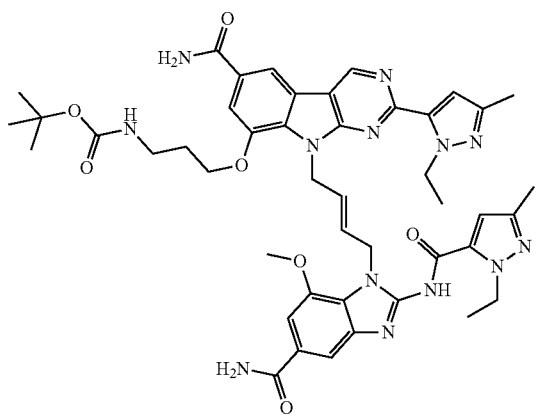 [SMILES: CCn1nc(C)cc1C(=O)Nc1nc2cc(C(N)=O)cc(OC)c2n1C/C=C/Cn1c2nc(-c3cc(C)nn3CC)ncc2c2cc(C(N)=O)cc(OCCCNC(=O)OC(C)(C)C)c21]

This compound was prepared using similar procedures as described for Example S4, Step 4 with tert-butyl 3-(6-carbamoyl-2-(1-ethyl-3-methyl-1H-pyrazol-5-yl)-9H-pyrimido[4,5-b]indo1-8-yloxy)propylcarbamate replacing 2-(1-ethyl-3-methyl-1H-pyrazol-5-yl)-9H-pyrimido[4,5-b]indole-6-carboxamide. The mixture was diluted with DCM, and was washed with water and brine. The organic phase was dried over MgSO₄ before filtering. The filtrate was concentrated and purified by flash chromatography on a silica gel column eluting with 0 to 20% MeOH in DCM to afford the desired product. LC-MS calculated for $C_{45}H_{54}N_{13}O_7$ (M+H)+: m/z=888.4; found 888.4.

Step 5: (E)-8-(3-aminopropoxy)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide

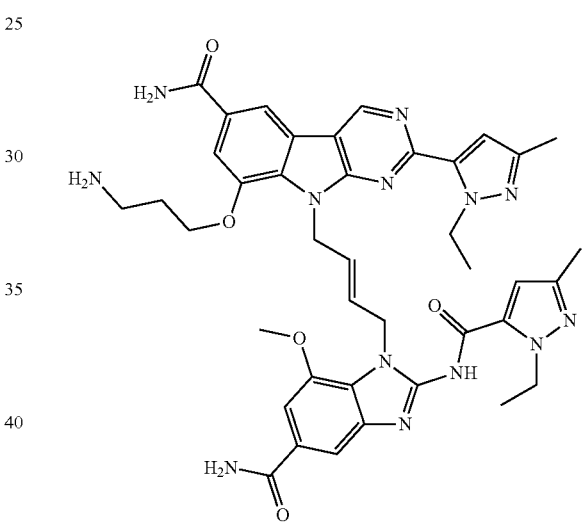

This compound was prepared using similar procedures as described for Example S38, Step 9 with (E)-tert-butyl 3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamate replacing tert-butyl (E)-(3-((5-carbamoyl-1-(4-(6-carbamoyl-2-(1-ethyl-3-methyl-1H-pyrazol-5-yl)-8-(3-methoxy-propoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate. The reaction mixture was concentrated and used in the next step without further purification. LC-MS calculated for $C_{40}H_{46}N_{13}O_5$ (M+H)+: m/z=788.4; found 788.4.

Step 6: (E)-methyl 5-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoate Example S52. (E)-3-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid

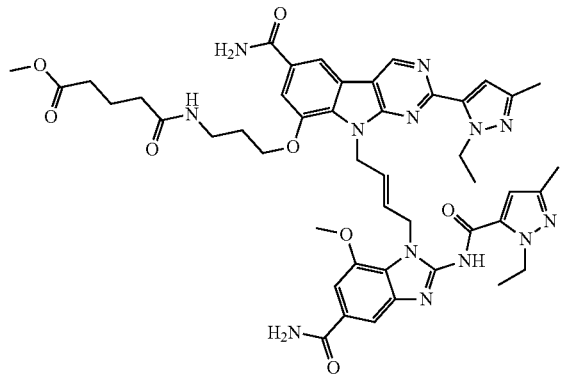

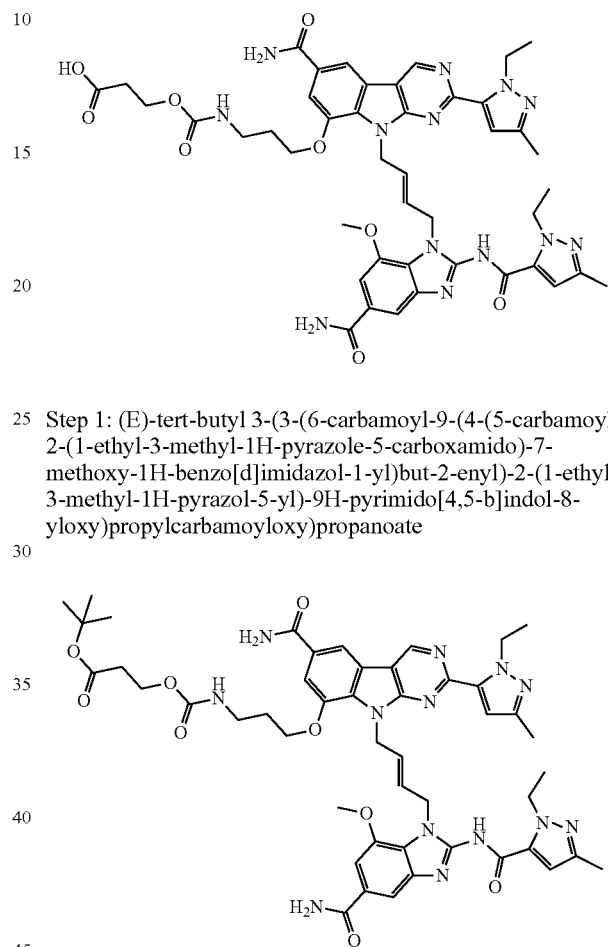

This compound was prepared using similar procedures as described for Example S39, Step 1 with (E)-8-(3-aminopropoxy)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{46}H_{54}N_{13}O_8$ $(M+H)^+$: m/z=916.4; found 916.4.

Step 7: (E)-5-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid This compound was prepared using similar procedures as described for Example S39, Step 2 with (E)-methyl 5-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. The reaction mixture was diluted with MeOH and purified by prep-HPLC (pH=2, acetonitrile/water+TFA) to give the desired product as its TFA salt. LC-MS calculated for $C_{45}H_{52}N_{13}O_8$ $(M+H)^+$: m/z=902.4; found 902.4.

Step 1: (E)-tert-butyl 3-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoate

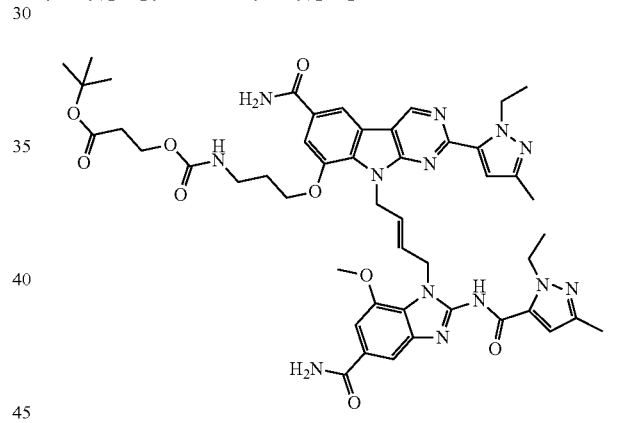

This compound was prepared using similar procedures as described for Example S44, Step 2 with (E)-8-(3-aminopropoxy)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide (Example 46, Step 5) replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{48}H_{58}N_{13}O_9$ $(M+H)^+$: m/z=960.4; found 960.5.

Step 2: (E)-3-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid This compound was prepared using similar procedures as described for Example S42, Step 2 with (E)-tert-butyl 3-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoate replacing tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate. The reaction mixture was diluted with MeOH and purified by prep-HPLC (pH=2, acetonitrile/water+TFA) to give the desired product as its TFA salt. LC-MS calculated for $C_{44}H_{50}N_{13}O_9$ $(M+H)^+$: m/z=904.4; found 904.5.

Example S53. (E)-5-(3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid This compound was prepared using similar procedures as described for Example S15, Step 10 with tert-butyl 3-(6-carbamoyl-2-(1-ethyl-3-methyl-1H-pyrazol-5-yl)-9H-pyrimido[4,5-b]indol-8-yloxy)propylcarbamate (Example S51, Step 3) replacing 2-(1-ethyl-3-methyl-1H-pyrazol-5-yl)-8-methoxy-9H-pyrimido[4,5-b]indole-6-carboxamide. LC-MS calculated for $C_{54}H_{66}N_{15}O_9$ $(M+H)^+$: m/z=1068.5; found 1068.8.

Step 2: (E)-3-(1-(4-(8-(3-aminopropoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate

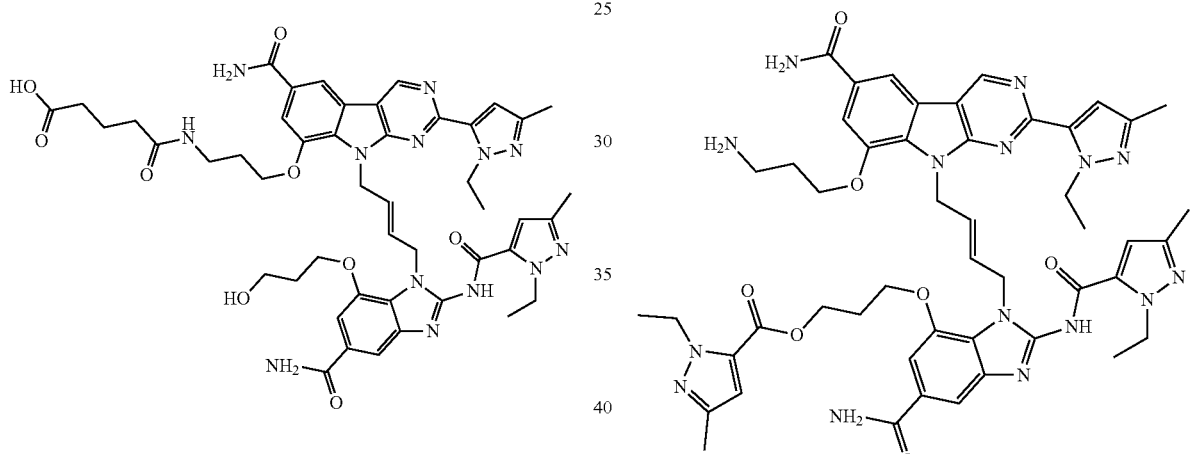

Step 1: (E)-3-(1-(4-(8-(3-(tert-butoxycarbonylamino)propoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate

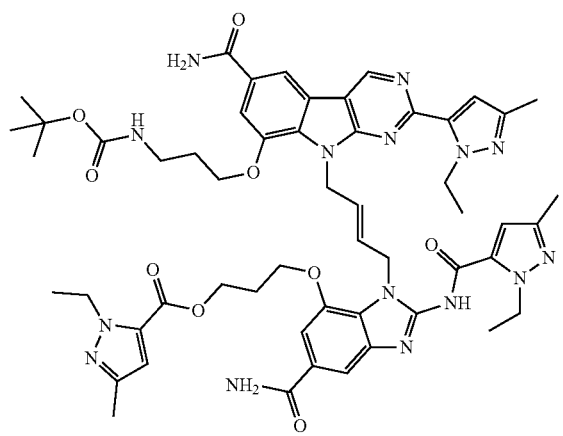 [SMILES: CCn1nc(C)cc1C(=O)Nc1nc2cc(C(N)=O)cc(OCCCOC(=O)c3cc(C)nn3CC)c2n1C/C=C/Cn1c2nc(-c3cc(C)nn3CC)ncc2c2cc(C(N)=O)cc(OCCCNC(=O)OC(C)(C)C)c21]

This compound was prepared using similar procedures as described for Example S38, Step 9 with (E)-3-(1-(4-(8-(3-(tert-butoxycarbonylamino)propoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate replacing tert-butyl (E)-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate. The reaction mixture was concentrated and used in the next step without further purification. LC-MS calculated for $C_{49}H_{58}N_{15}O_7$ $(M+H)^+$: m/z=968.5; found 968.6.

Step 3: (E)-3-(5-carbamoyl-1-(4-(6-carbamoyl-2-(1-ethyl-3-methyl-1H-pyrazol-5-yl)-8-(3-(5-methoxy-5-oxopentanamido)propoxy)-9H-pyrimido[4,5-b]indol-9-yl)but-2-enyl)-2-(1-ethyl-3-methyl-1H-pyrazole-5-carboxamido)-1H-benzo[d]imidazol-7-yloxy)propyl 1-ethyl-3-methyl-1H-pyrazole-5-carboxylate

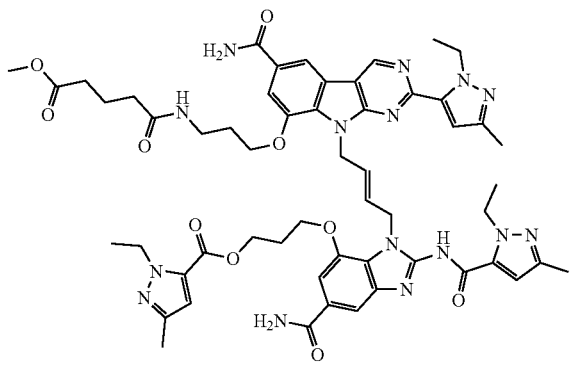

This compound was prepared using similar procedures as described for Example S39, Step 1 with (E)-3-(1-(4-(8-(3-aminopropoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{55}H_{66}N_{15}O_{10}$ $(M+H)^+$: m/z=1096.5; found 1096.8.

Step 4: (E)-5-(3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid This compound was prepared using similar procedures as described for Example S39, Step 2 with (E)-3-(5-carbamoyl-1-(4-(6-carbamoyl-2-(1-ethyl-3-methyl-1H-pyrazol-5-yl)-8-(3-(5-methoxy-5-oxopentanamido)propoxy)-9H-pyrimido[4,5-b]indol-9-yl)but-2-enyl)-2-(1-ethyl-3-methyl-1H-pyrazole-5-carboxamido)-1H-benzo[d]imidazol-7-yloxy)propyl 1-ethyl-3-methyl-1H-pyrazole-5-carboxylate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. The reaction mixture was diluted with MeOH and purified by prep-HPLC (pH=2, acetonitrile/water+TFA) to give the desired product as its TFA salt. LC-MS calculated for $C_{47}H_{56}N_{13}O_9$ $(M+H)^+$: m/z=946.4; found 946.6.

Example S54. (E)-3-(3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid

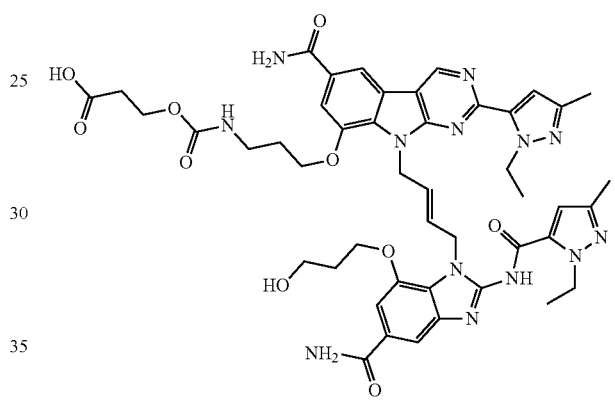

Step 1: (E)-3-(1-(4-(8-(3-((3-tert-butoxy-3-oxopropoxy)carbonylamino)propoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate

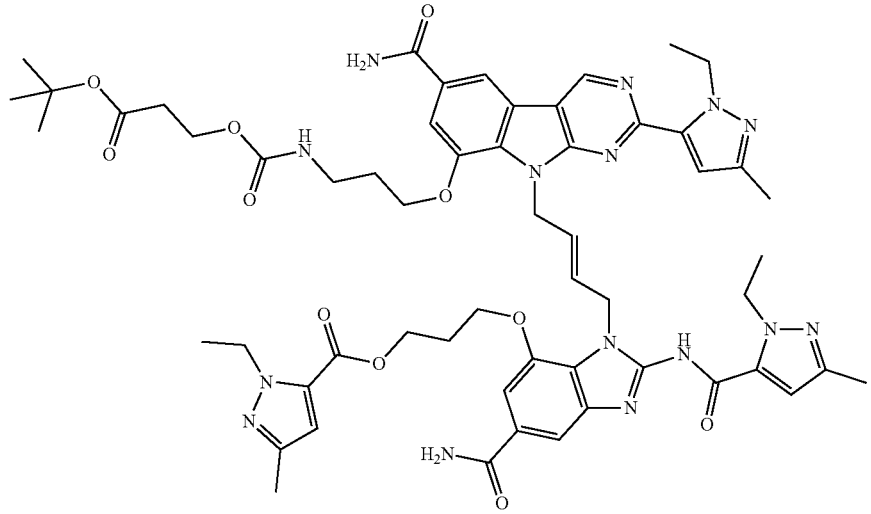 [SMILES: CCn1nc(C)cc1C(=O)Nc1nc2cc(C(N)=O)cc(OCCCOC(=O)c3cc(C)nn3CC)c2n1C/C=C/Cn1c2nc(-c3cc(C)nn3CC)ncc2c2cc(C(N)=O)cc(OCCCNC(=O)OCCC(=O)OC(C)(C)C)c21]

This compound was prepared using similar procedures as described for Example S44, Step 2 with (E)-3-(1-(4-(8-(3-aminopropoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate (Example S53, Step 2) replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{57}H_{70}N_{15}O_{11}$ (M+H)$^+$: m/z=1140.5; found 1140.6.

Step 2: (E)-3-(3-(6-carbamoyl-9-(4-(5-carbamoyl-7-(3-(1-ethyl-3-methyl-1H-pyrazole-5-carbonyloxy)propoxy)-2-(1-ethyl-3-methyl-1H-pyrazole-5-carboxamido)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid

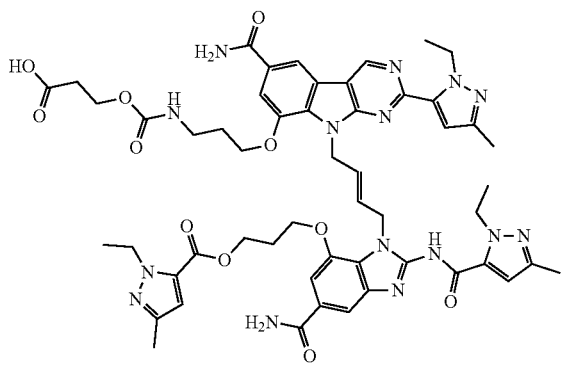 [SMILES: CCn1nc(C)cc1C(=O)Nc1nc2cc(C(N)=O)cc(OCCCOC(=O)c3cc(C)nn3CC)c2n1C/C=C/Cn1c2nc(-c3cc(C)nn3CC)ncc2c2cc(C(N)=O)cc(OCCCNC(=O)OCCC(=O)O)c21]

This compound was prepared using similar procedures as described for Example S42, Step 2 with (E)-3-(1-(4-(8-(3-((3-tert-butoxy-3-oxopropoxy)carbonylamino)propoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate replacing tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-ypoxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate. The reaction mixture was concentrated and used in the next step without further purification. LC-MS calculated for $C_{53}H_{62}N_{15}O_{11}$ (M+H)$^+$: m/z=1084.5; found 1084.7.

Step 3: (E)-3-(3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid This compound was prepared using similar procedures as described for Example S39, Step 2 with (E)-3-(3-(6-carbamoyl-9-(4-(5-carbamoyl-7-(3-(1-ethyl-3-methyl-1H-pyrazole-5-carbonyloxy)propoxy)-2-(1-ethyl-3-methyl-1H-pyrazole-5-carboxamido)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propypamino)-5-oxopentanoate. The reaction mixture was diluted with MeOH and purified by prep-HPLC (pH=2, acetonitrile/water+TFA) to give the desired product as its TFA salt. LC-MS calculated for $C_{46}H_{54}N_{13}O_{10}$ (M+H)$^+$: m/z=948.4; found 948.5.

Example S55. (E)-5-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid

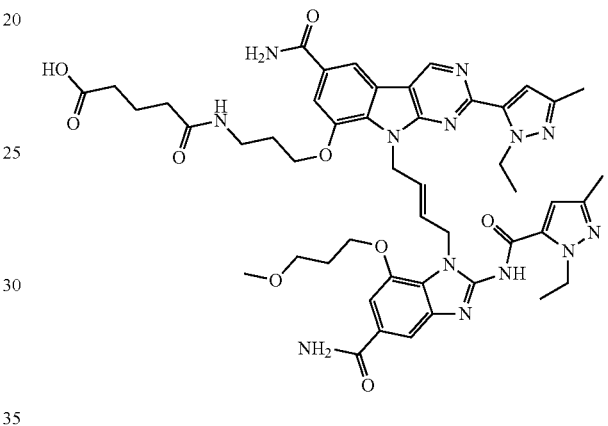

Step 1: 4-chloro-3-(3-methoxypropoxy)-5-nitrobenzamide

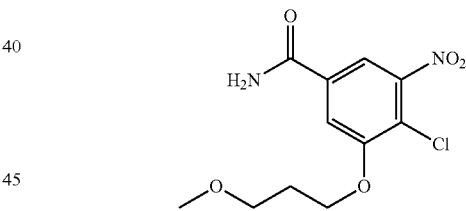

This compound was prepared using similar procedures as described for Example S15, Step 2 with 3-methoxypropan-1-ol (Aldrich, cat #38457) replacing (3-bromopropoxy)(tert-butyl)dimethylsilane. LC-MS calculated for $C_{11}H_{14}ClN_2O_5$ (M+H)$^+$: m/z=289.1; found 289.0.

Step 2: (E)-tert-butyl 4-(4-carbamoyl-2-(3-methoxypropoxy)-6-nitrophenylamino)but-2-enylcarbamate

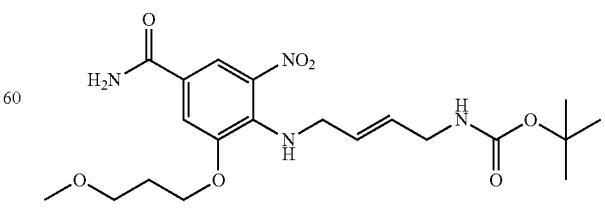

This compound was prepared using similar procedures as described for Example S15, Step 3 with 4-chloro-3-(3- methoxypropoxy)-5-nitrobenzamide replacing 3-(3-((tert-butyldimethylsilypoxy)propoxy)-4-chloro-5-nitrobenzamide. LC-MS calculated for $C_{20}H_{30}N_4NaO_7$ $(M+Na)^+$: m/z=461.2; found 461.2.

Step 3: (E)-tert-butyl 4-(2-amino-4-carbamoyl-6-(3-methoxypropoxy)phenylamino)but-2-enylcarbamate

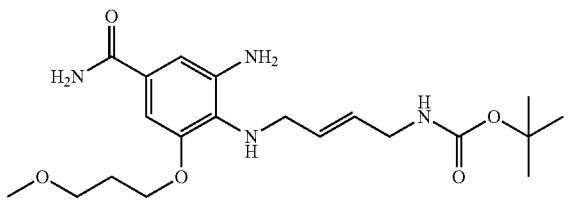 [SMILES: COCCCOc1cc(C(N)=O)cc([N+](=O)[O-])c1NC/C=C/CNC(=O)OC(C)(C)C]

This compound was prepared using similar procedures as described for Example S1, Step 3 with tert-butyl (E)-tert-butyl 4-(4-carbamoyl-2-(3-methoxypropoxy)-6-nitrophenylamino)but-2-enylcarbamate replacing tert-butyl (E)-(4-((4-carbamoyl-2-methyl-6-nitrophenyl)amino)but-2-en-1-yl)carbamate. LC-MS calculated for $C_{20}H_{33}N_4O_5$ $(M+H)+$: m/z=409.2; found 409.2.

Step 4: (E)-tert-butyl 4-(2-amino-5-carbamoyl-7-(3-methoxypropoxy)-1H-benzo[c]imidazol-1-yl)but-2-enylcarbamate

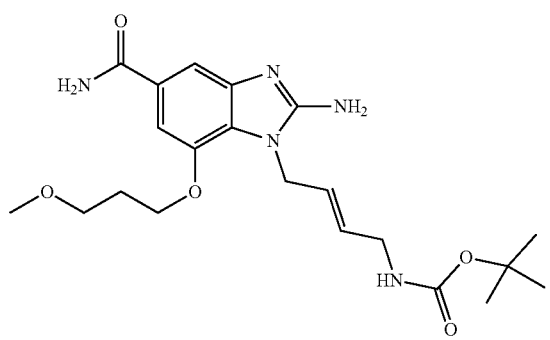 [SMILES: COCCCOc1cc(C(N)=O)cc2nc(N)n(C/C=C/CNC(=O)OC(C)(C)C)c12]

This compound was prepared using similar procedures as described for Example S1, Step 4 with (E)-tert-butyl 4-(2-amino-4-carbamoyl-6-(3-methoxypropoxy)phenylamino)but-2-enylcarbamate replacing tert-butyl (E)-(4-((2-amino-4-carbamoyl-6-methylphenyl)amino)but-2-en-1-yl)carbamate. LC-MS calculated for $C_{21}H_{32}N_5O_5$ $(M+H)^+$: m/z=434.2; found 434.5.

Step 5: (E)-tert-butyl 4-(5-carbamoyl-2-(1-ethyl-3-methyl-1H-pyrazole-5-carboxamido)-7-(3-methoxypropoxy)-1H-benzo[d]imidazol-1-yl)but-2-enylcarbamate

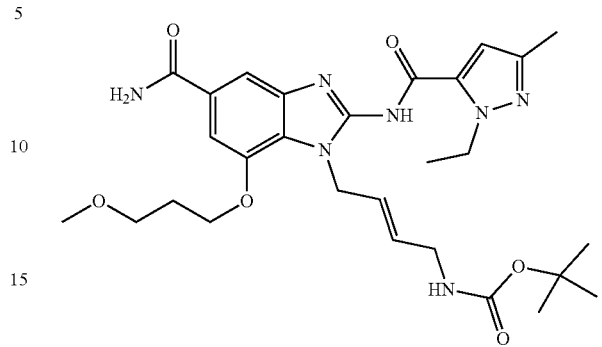

This compound was prepared using similar procedures as described for Example S1, Step 5 with (E)-tert-butyl 4-(2-amino-5-carbamoyl-7-(3-methoxypropoxy)-1H-benzo[d]imidazol-1-yl)but-2-enylcarbamate replacing (E)-tert-butyl 4-(2-amino-5-carbamoyl-7-methyl-1H-benzo[d]imidazol-1-yl)but-2-enylcarbamate. LC-MS calculated for $C_{28}H_{40}N_7O_6$ $(M+H)+$: m/z=570.3; found 570.4.

Step 6: (E)-1-(4-aminobut-2-enyl)-2-(1-ethyl-3-methyl-1H-pyrazole-5-carboxamido)-7-(3-methoxypropoxy)-1H-benzo[d]imidazole-5-carboxamide

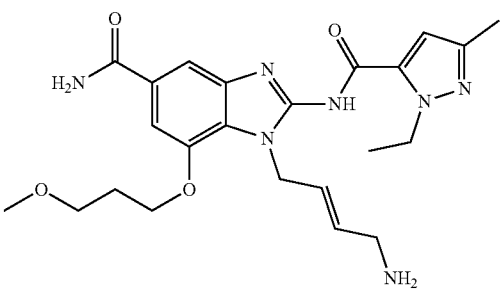

This compound was prepared using similar procedures as described for Example S1, Step 6 with (E)-tert-butyl 4-(5-carbamoyl-2-(1-ethyl-3-methyl-1H-pyrazole-5-carboxamido)-7-(3-methoxypropoxy)-1H-benzo[d]imidazol-1-yl)but-2-enylcarbamate replacing tert-butyl (E)-(4-(5-carbamoyl-2-(1-ethyl-3-methyl-1H-pyrazole-5-carboxamido)-7-methyl-1H-benzo[d]imidazol-1-yl)but-2-en-1-yl)carbamate. LC-MS calculated for $C_{23}H_{32}N_7O_4$ $(M+H)^+$: m/z=470.2; found 470.3.

Step 7: (E)-2-(1-ethyl-3-methyl-1H-pyrazole-5-carboxamido)-1-(4-hydroxybut-2-enyl)-7-(3-methoxypropoxy)-1H-benzo[d]imidazole-5-carboxamide

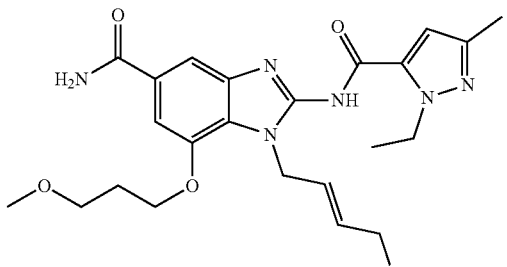

This compound was prepared using similar procedures as described for Example S1, Step 7 with (E)-1-(4-aminobut-2-enyl)-2-(1-ethyl-3-methyl-1H-pyrazole-5-carboxamido)-7-(3-methoxypropoxy)-1H-benzo[d]imidazole-5-carboxamide replacing (E)-1-(4-aminobut-2-en-1-yl)-2-(1-ethyl-3-methyl-1H-pyrazole-5-carboxamido)-7-methyl-1H-benzo[d]imidazole-5 -carboxamide. LC-MS calculated for $C_{23}H_{31}N_6O_5$ (M+H)$^+$: m/z=471.2; found 471.3.

Step 8: (E)-1-(4-bromobut-2-enyl)-2-(1-ethyl-3-methyl-1H-pyrazole-5-carboxamido)-7-(3-methoxypropoxy)-1H-benzo[d]imidazole-5-carboxamide

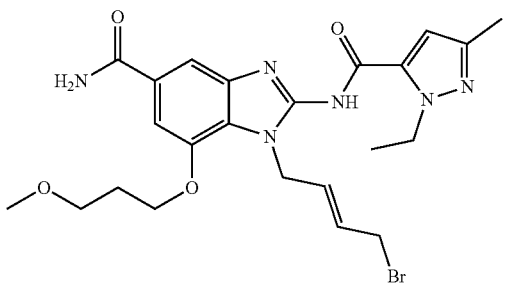

This compound was prepared using similar procedures as described for Example S1, Step 8 with (E)-2-(1-ethyl-3-methyl-1H-pyrazole-5-carboxamido)-1-(4-hydroxybut-2-enyl)-7-(3-methoxypropoxy)-1H-benzo[d]imidazole-5-carboxamide replacing (E)-2-(1-ethyl-3-methyl-1H-pyrazole-5-carboxamido)-1-(4-hydroxybut-2-enyl)-7-methyl-1H-benzo[d]imidazole-5-carboxamide. LC-MS calculated for $C_{23}H_{30}BrN_6O_4$ (M+H)$^+$: m/z=533.1/535.1; found 533.1/535.1.

Step 9: (E)-tert-butyl 3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamate

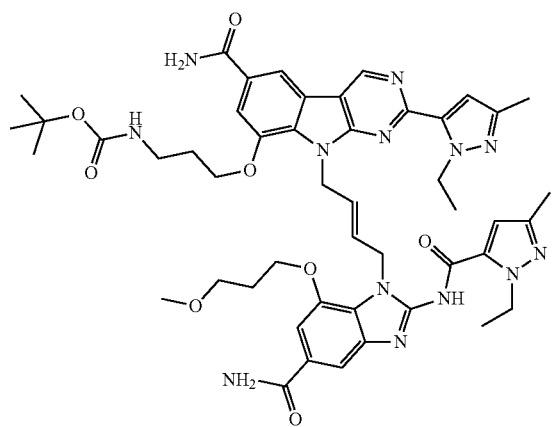 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCCNC(=O)OC(C)(C)C)c21]

To a mixture of tert-butyl (3-(((6-carbamoyl-2-(1-ethyl-3-methyl-1H-pyrazol-5-yl)-9H-pyrimido[4,5-b]indol-8-yl)oxy)propyl)carbamate (Example S51, Step 3, 35.0 mg, 0.071 mmol), and (E)-1-(4-bromobut-2-en-1-yl)-2-(1-ethyl-3-methyl-1H-pyrazole-5-carboxamido)-7-(3-methoxypropoxy)-1H-benzo[d]imidazole-5-carboxamide (37.8 mg, 0.071 mmol) in DMF (0.4 mL) was added $Cs_2CO_3$ (50.8 mg, 0.156 mmol). The mixture was stirred at 50° C. for 1 hour. The reaction mixture was concentrated and purified by flash chromatography on a silica gel column eluting with 0 to 20% MeOH in DCM to afford the desired product. LC-MS calculated for $C_{48}H_{60}N_{13}O_8$ (M+H)$^+$: m/z=946.5; found 946.5.

Step 10: (E)-8-(3-aminopropoxy)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indole-6-carboxamide

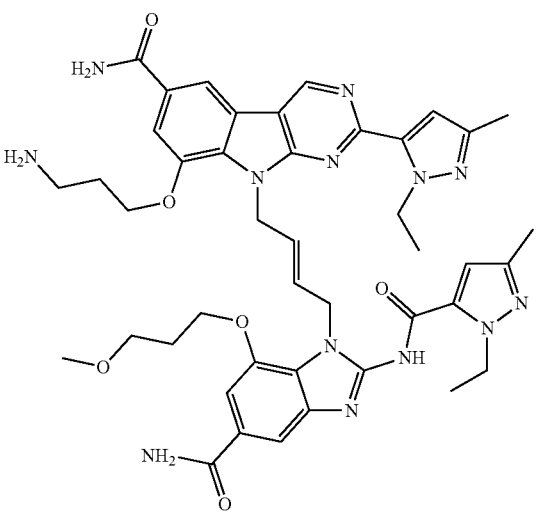 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCCN)c21]

This compound was prepared using similar procedures as described for Example S38, Step 9 with (E)-tert-butyl 3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamate replacing tert-butyl (E)-(3-((5-carbamoyl-1-(4-(6-carbamoyl-2-(1-ethyl-3-methyl-1H-pyrazol-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate. The reaction mixture was concentrated and used in the next step without further purification. LC-MS calculated for $C_{43}H_{52}N_{13}O_6$ (M+H)$^+$: m/z=846.4; found 846.5.

Step 11: (E)-methyl 5-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoate

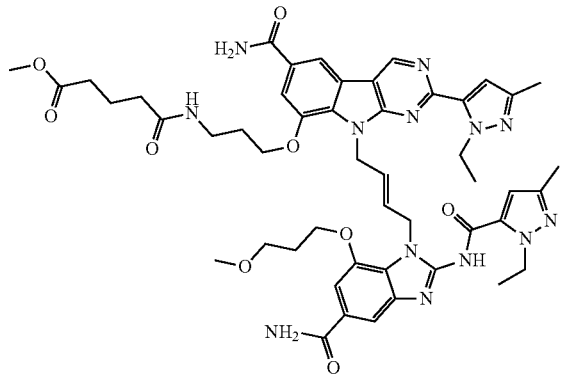

This compound was prepared using similar procedures as described for Example S39, Step 1 with (E)-8-(3-aminopropoxy)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indole-6-carboxamide replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{49}H_{60}N_{13}O_9$ (M+H)$^+$: m/z=974.5; found 974.8.

Step 12: (E)-5-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid This compound was prepared using similar procedures as described for Example S39, Step 2 with (E)-methyl 5-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. The reaction mixture was diluted with MeOH and purified by prep-HPLC (pH=2, acetonitrile/water+TFA) to give the desired product as its TFA salt. LC-MS calculated for $C_{48}H_{58}N_{13}O_9$ (M+H)$^+$: m/z=960.4; found 960.5.

Example S56. (E)-3-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid

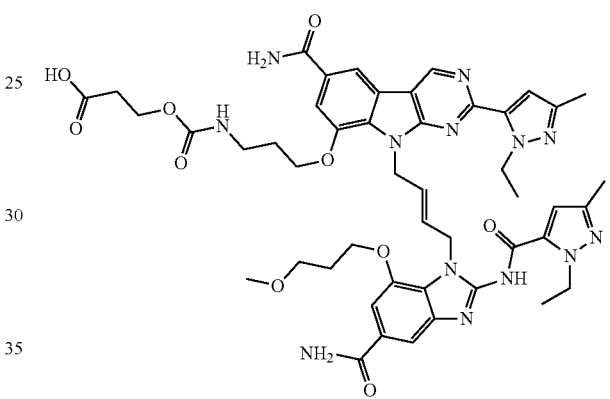

Step 1: (E)-tert-butyl 3-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoate

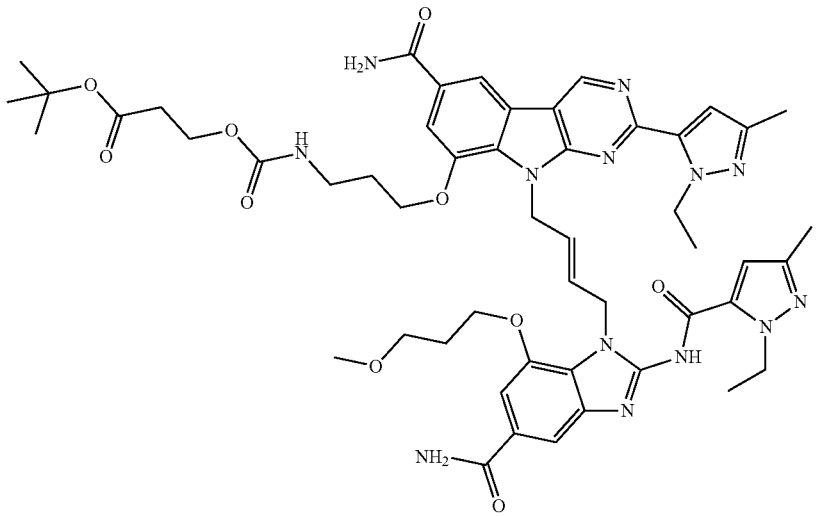 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCCNC(=O)OCCC(=O)OC(C)(C)C)c21]

This compound was prepared using similar procedures as described for Example S44, Step 2 with (E)-8-(3-aminopropoxy)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indole-6-carboxamide (Example S55, Step 10) replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{51}H_{64}N_{13}O_{10}$ (M+H)⁺: m/z=1018.5; found 1018.4.

Step 2: (E)-3-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-yl)-ethyl-3-methyl-1H-pyrazol-5-yl)-9H-pyrimido[4,5-b]indol-8-yloxy)propylcarbamoyloxy)propanoic acid This compound was prepared using similar procedures as described for Example S42, Step 2 with (E)-tert-butyl 3-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy) propylcarbamoyloxy)propanoate replacing tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3 4(2,2,4,6,7-pentamethyl-2,3-dihydrobenzofuran-5-yl)sulfonyl)guanidino)propyl)-4,7,10,13-tetraazaheptadecan-17-oate. The reaction mixture was diluted with MeOH and purified by prep-HPLC (pH=2, acetonitrile/water+TFA) to give the desired product as its TFA salt. LC-MS calculated for $C_{47}H_{56}N_{13}O_{10}$ (M+H)⁺: m/z=962.4; found 962.4.

Example S57. (E)-3-((3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoic acid

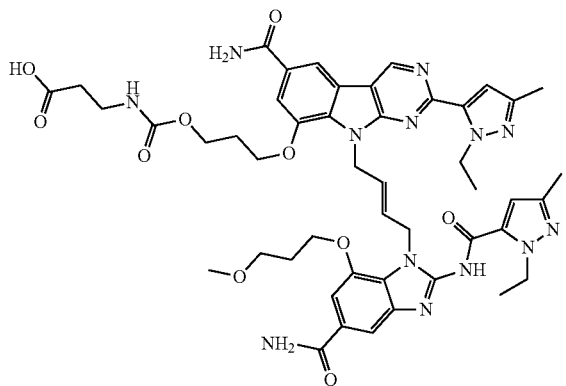 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCCOC(=O)NCCC(=O)O)c21]

Step 1: (E)-8-(3-(tert-butyldimethylsilyloxy)propoxy)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indole-6-carboxamide

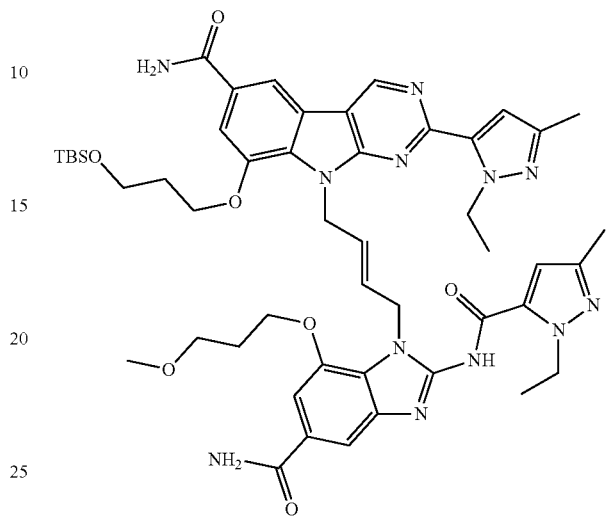

This compound was prepared using similar procedures as described for Example S55, Step 9 with 8-(3-(tert-butyldimethylsilyloxy)propoxy)-2-(1-ethyl-3-methyl-1H-pyrazol-5-yl)-9H-pyrimido[4,5-b]indole-6-carboxamide (Example S13, Step 3) replacing tert-butyl (3-((6-carbamoyl-2-(1-ethyl-3-methyl-1H-pyrazol-5-yl)-9H-pyrimido[4,5-b]indol-8-yl)oxy)propyl)carbamate. LC-MS calculated for $C_{49}H_{65}N_{12}O_7Si$ (M+H)⁺: m/z=961.5; found 961.6.

Step 2: (E)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-8-(3-hydroxypropoxy)-9H-pyrimido[4,5-b]indole-6-carboxamide

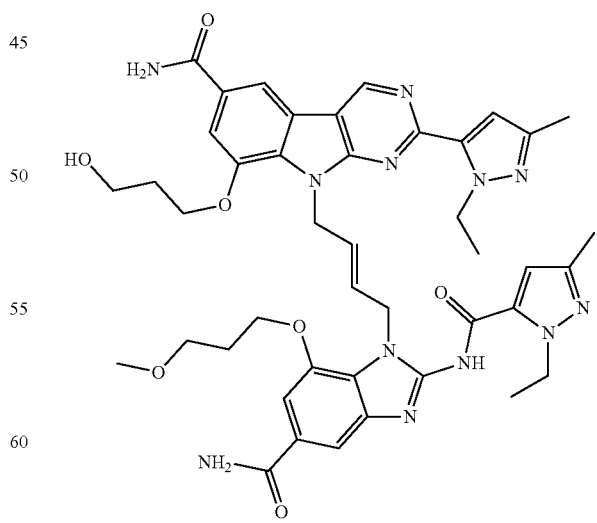

This compound was prepared using similar procedures as described for Example S38, Step 9 with (E)-8-(3-(tert-butyldimethylsilyloxy)propoxy)-9-(4-(5-carbamoyl-2-(1- ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indole-6-carboxamide replacing tert-butyl (E)-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate. The reaction mixture was concentrated and used in the next step without further purification. LC-MS calculated for $C_{43}H_{51}N_{12}O_7$ $(M+H)^+$: m/z=847.4; found 847.4.

Step 3: (E)-ethyl 3-((3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoate

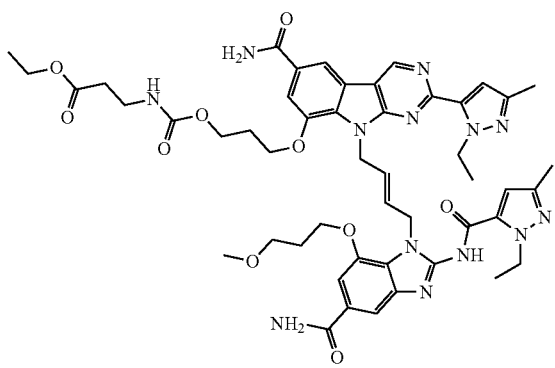 [SMILES: CCOC(=O)CCNC(=O)OCCCOc1cc(C(N)=O)cc2c3cnc(-c4cc(C)nn4CC)nc3n(C/C=C/Cn3c(NC(=O)c4cc(C)nn4CC)nc4cc(C(N)=O)cc(OCCCOC)c43)c12]

This compound was prepared using similar procedures as described for Example S48, Step 2 with (E)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-8-(3-hydroxypropoxy)-9H-pyrimido[4,5-b]indole-6-carboxamide replacing tert-butyl (E)-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl) carbamate. The reaction mixture was concentrated and used in the next step without further purification. LC-MS calculated for $C_{49}H_{60}N_{13}O_{10}$ $(M+H)^+$: m/z=990.5; found 990.7.

Step 4: (E)-3-((3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoic acid This compound was prepared using similar procedures as described for Example S39, Step 2 with (E)-ethyl 3-((3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. The reaction mixture was diluted with MeOH and purified by prep-HPLC (pH=2, acetonitrile/water+TFA) to give the desired product as its TFA salt. LC-MS calculated for $C_{47}H_{56}N_{13}O_{10}$ $(M+H)^+$: m/z=962.4; found 962.6.

Example S58. (E)-3-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)propanoic acid

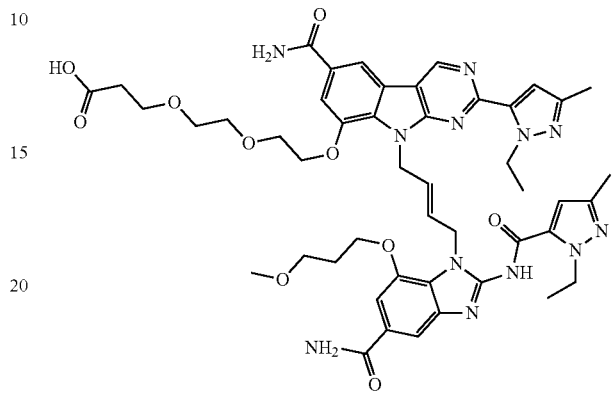

Step 1: tert-butyl 3-(2-(2-(3-bromo-5-carbamoyl-2-nitrophenoxy)ethoxy)ethoxy)propanoate

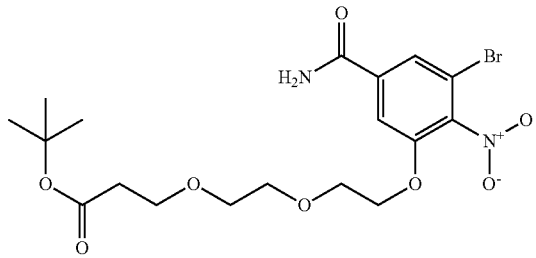 [SMILES: CC(C)(C)OC(=O)CCOCCOCCOc1cc(C(N)=O)cc(Br)c1[NH+]([O-])O]

This compound was prepared using similar procedures as described for Example S11, Step 1 with tert-butyl 3-(2-(2-hydroxyethoxy)ethoxy)propanoate (Aldrich, cat # ANV00316) replacing 3-morpholinopropan-1-ol. LC-MS calculated for $C_{18}H_{25}BrN_2NaO_8$ $(M+H)^+$: m/z=499.1, 501.1; found 499.2, 501.2.

Step 2: tert-butyl 3-(2-(2-(5-carbamoyl-3-(2-(1-ethyl-3-methyl-1H-pyrazol-5-yl)pyrimidin-5-yl)-2-nitrophenoxy)ethoxy)ethoxy)propanoate

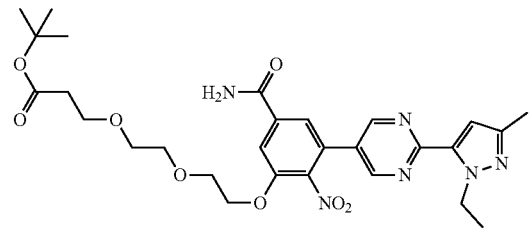 [SMILES: CCn1nc(C)cc1-c1ncc(-c2cc(C(N)=O)cc(OCCOCCOCCC(=O)OC(C)(C)C)c2[N+](=O)[O-])cn1]

This compound was prepared using similar procedures as described for Example S10, Step 3 with tert-butyl 3-(2-(2-(3-bromo-5-carbamoyl-2-nitrophenoxy)ethoxy)ethoxy)propanoate replacing 3-bromo-5-methoxy-4-nitrobenzamide. LC-MS calculated for $C_{28}H_{37}N_6O_8$ $(M+H)^+$: m/z=585.3; found 585.2.

Step 3: tert-butyl 3-(2-(2-((6-carbamoyl-2-(1-ethyl-3-methyl-1H-pyrazol-5-yl)-9H-pyrimido[4,5-b]indol-8-yl)oxy)ethoxy)ethoxy)propanoate

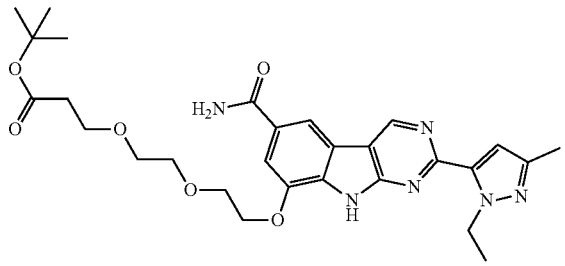 [SMILES: CCn1nc(C)cc1-c1ncc2c(n1)[nH]c1c(OCCOCCOCCC(=O)OC(C)(C)C)cc(C(N)=O)cc12]

This compound was prepared using similar procedures as described for Example S10, Step 4 with tert-butyl 3-(2-(2-(5-carbamoyl-3-(2-(1-ethyl-3-methyl-1H-pyrazol-5-yl)pyrimidin-5-yl)-2-nitrophenoxy)ethoxy)ethoxy)propanoate replacing 3-(2-(1-ethyl-3-methyl-1H-pyrazol-5-yl)pyrimidin-5-yl)-5-methoxy-4-nitrobenzamide. LC-MS calculated for $C_{28}H_{37}N_6O_6$ (M+H)$^+$: m/z=553.3; found 553.3.

Step 4: (E)-tert-butyl 3-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)propanoate

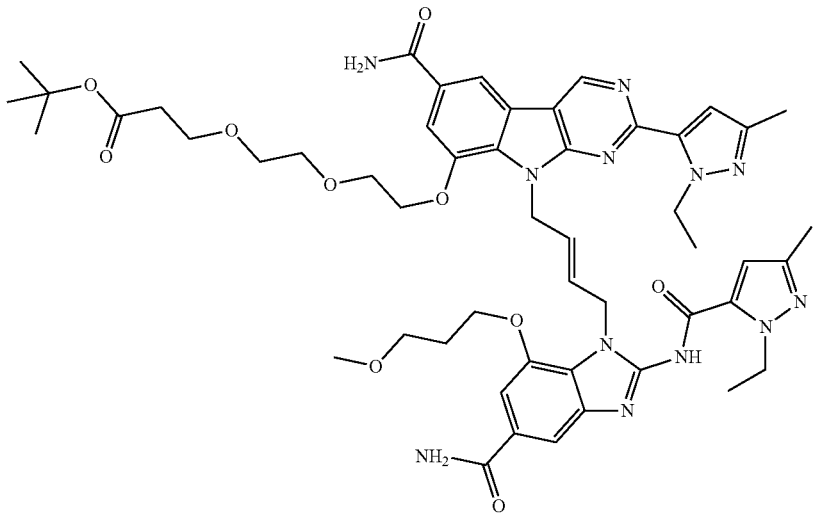 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCOCCOCCC(=O)OC(C)(C)C)c21]

This compound was prepared using similar procedures as described for Example S55, Step 9 with tert-butyl 3-(2-(2-((6-carbamoyl-2-(1-ethyl-3-methyl-1H-pyrazol-5-yl)-9H-pyrimido[4,5-b]indol-8-yl)oxy)ethoxy)ethoxy)propanoate replacing tert-butyl (3-((6-carbamoyl-2-(1-ethyl-3-methyl-1H-pyrazol-5-yl)-9H-pyrimido[4,5-b]indol-8-yl)oxy)propyl)carbamate. LC-MS calculated for $C_{51}H_{65}N_{12}O_{10}$ (M+H)$^+$: m/z=1005.5; found 1005.7.

Step 5: (E)-3-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)propanoic acid This compound was prepared using similar procedures as described for Example S42, Step 2 with (E)-tert-butyl 3-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)propanoate replacing tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate. The reaction mixture was diluted with MeOH and purified by prep-HPLC (pH=2, acetonitrile/water+TFA) to give the desired product as its TFA salt. LC-MS calculated for $C_{47}H_{57}N_{12}O_{10}$ (M+H)$^+$: m/z=949.4; found 949.6.

Example S59. (E)-3-(2-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)ethoxy)propanoic acid

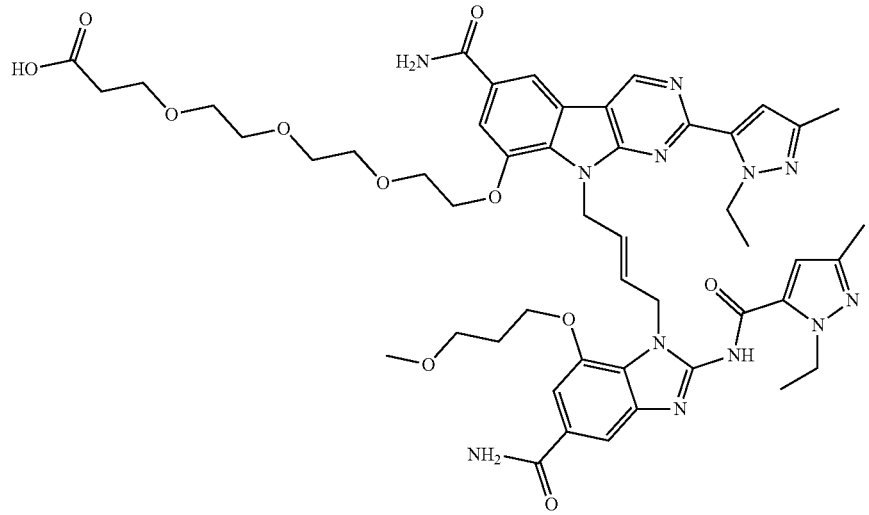 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCOCCOCCOCCC(=O)O)c21]

This compound was prepared using similar procedures as described for Example S58, with tert-butyl 3-(2-(2-(2-hydroxyethoxy)ethoxy)ethoxy)propanoate (AURUM pharmatech, cat # U37808) replacing tert-butyl 3-(2-(2-hydroxyethoxy)ethoxy)propanoate in Step 1. After finishing the final step, the reaction mixture was diluted with MeOH and purified by prep-HPLC (pH=2, acetonitrile/water+TFA) to give the desired product as its TFA salt. LC-MS calculated for $C_{49}H_{61}N_{12}O_{11}$ $(M+H)^+$: m/z=993.5; found 993.6.

Example S60. (E)-4-(4-(2-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)ethyl)piperidin-1-yl)butanoic acid

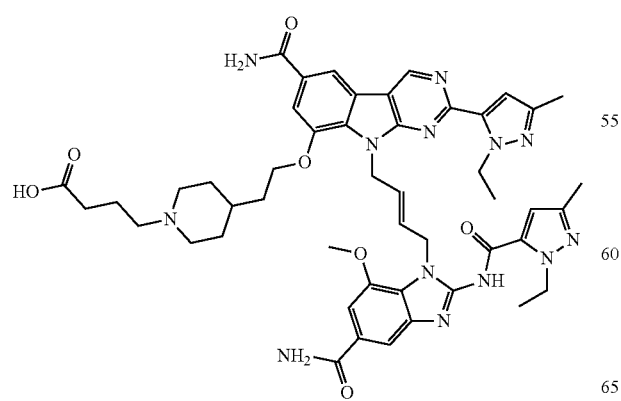

Step 1: (E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-8-(2-(piperidin-4-yl)ethoxy)-9H-pyrimido[4,5-b]indole-6-carboxamide

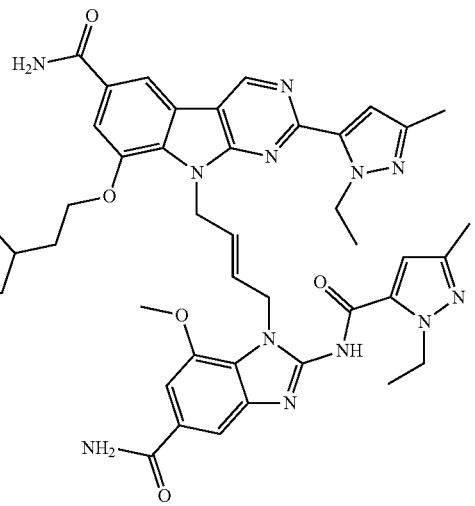

This compound was prepared using similar procedures as described for Example S51, Steps 1 to 5 with tert-butyl 4-(2-hydroxyethyl)piperidine-1-carboxylate (Matrix Scientific, cat # 069039) replacing tert-butyl 3-hydroxypropylcarbamate in Step 1. LC-MS calculated for $C_{44}H_{52}N_{13}O_5$ $(M+H)^+$: m/z=842.4; found 842.6.

Step 2: (E)-4-(4-(2-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)ethyl)piperidin-1-yl)butanoic acid This compound was prepared using similar procedures as described for Example S51, Steps 6 and 7 with (E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5 yl)-8-(2-(piperidin-4-yl)ethoxy)-9H-pyrimido[4,5-b]indole-6-carboxamide replacing (E)-8-(3-aminopropoxy)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide in Step 6. After finishing the final step, the reaction mixture was diluted with MeOH and purified by prep-HPLC (pH=2, acetonitrile/water+TFA) to give the desired product as its TFA salt. LC-MS calculated for $C_{48}H_{58}N_{13}O_7$ $(M+H)^+$: m/z=928.5; found 928.5.

Example S61. (E)-2-(4-(2-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)ethyl)piperidine-1-carbonyloxy)acetic acid

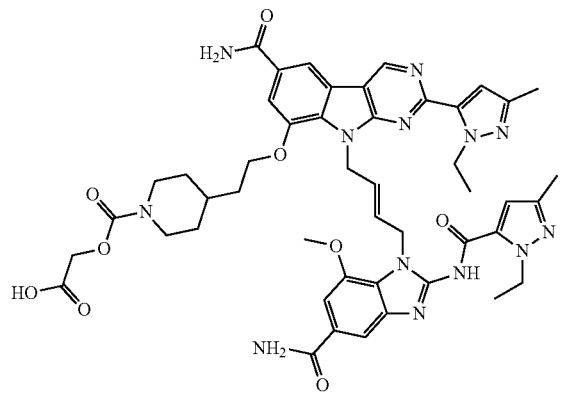 [SMILES: CCn1nc(C)cc1C(=O)Nc1nc2cc(C(N)=O)cc(OC)c2n1C/C=C/Cn1c2nc(-c3cc(C)nn3CC)ncc2c2cc(C(N)=O)cc(OCCC3CCN(C(=O)OCC(=O)O)CC3)c21]

This compound was prepared using similar procedures as described for Example S45, Steps 2 and 3, with (E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-8-(2-(piperidin-4-yl)ethoxy)-9H-pyrimido[4,5-b]indole-6-carboxamide (Example S60, Step 1) replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide in Step 2. After finishing the final step, the reaction mixture was diluted with MeOH and purified by prep-HPLC (pH=2, acetonitrile/water+TFA) to give the desired product as its TFA salt. LC-MS calculated for $C_{47}H_{54}N_{13}O_9$ $(M+H)^+$: m/z=944.4; found 944.5.

Example S62. (E)-3-((3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoic acid

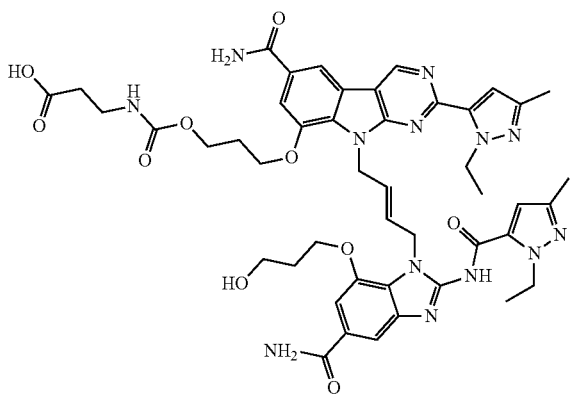

Step 1: (E)-3-(5-carbamoyl-1-(4-(6-carbamoyl-8-(3-(3-ethoxy-3-oxopropylcarbamoyloxy)propoxy)-2-(1-ethyl-3-methyl-1H-pyrazol-5-yl)-9H-pyrimido[4,5-b]indol-9-yl)but-2-enyl)-2-(1-ethyl-3-methyl-1H-pyrazole-5-carboxamido)-1H-benzo[d]imidazol-7-yloxy)propyl 1-ethyl-3-methyl-1H-pyrazole-5-carboxylate

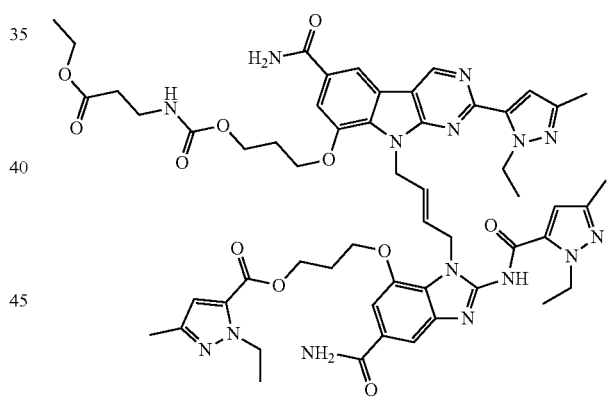

This compound was prepared using similar procedures as described for Example S57, Steps 1 to 3 with (E)-3-(1-(4-bromobut-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate (Example S15, Step 9) replacing (E)-1-(4-bromobut-2-enyl)-2-(1-ethyl-3-methyl-1H-pyrazole-5-carboxamido)-7-(3-methoxypropoxy)-1H-benzo[d]imidazole-5-carboxamide in Step 1.

Step 2: (E)-3-((3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoic acid This compound was prepared using similar procedures as described for Example S39, Step 2 with (E)-3-(5-carbamoyl-1-(4-(6-carbamoyl-8-(3-(3-ethoxy-3-oxopropylcarbamoyloxy)propoxy)-2-(1-ethyl-3-methyl-1H-pyrazol-5-yl)-9H-pyrimido[4,5-b]indol-9-yl)but-2-enyl)-2-(1-ethyl-3-methyl-1H-pyrazole-5-carboxamido)-1H-benzo[d]imidazol-7-yloxy)propyl 1-ethyl-3-methyl-1H-pyrazole-5-carboxylate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propypamino)-5-oxopentanoate. The reaction mixture was diluted with MeOH and purified by prep-HPLC (pH=2, acetonitrile/water+TFA) to give the desired product as its TFA salt. LC-MS calculated for $C_{46}H_{54}N_{13}O_{10}$ (M+H)$^+$: m/z=948.4; found 948.5.

Example S63. (E)-3-(((3-((5-carbamoyl-1-(4-(6-carbamoyl-8-(2-(2-(2-carboxyethoxy)ethoxy)ethoxy)-2-(1-ethyl-3-methyl-1H-pyrazol-5-yl)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid

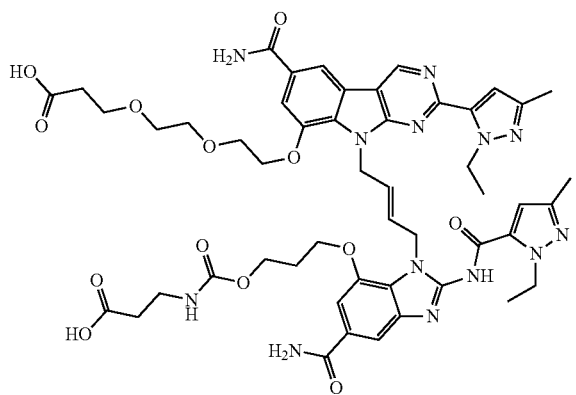 [SMILES: CCn1nc(C)cc1C(=O)Nc1nc2cc(C(N)=O)cc(OCCCOC(=O)NCCC(=O)O)c2n1C/C=C/Cn1c2nc(-c3cc(C)nn3CC)ncc2c2cc(C(N)=O)cc(OCCOCCOCCC(=O)O)c21]

Step 1: (E)-3-((1-(4-(8-(2-(2-(3-(tert-butoxy)-3-oxopropoxy)ethoxy)ethoxy)-6-carbamoyl-2-(1-ethyl-3-methyl-1H-pyrazol-5-yl)-9H-pyrimido[4,5-b]indo1-9-yl)but-2-en-1-yl)-5-carbamoyl-2-(1-ethyl-3-methyl-1H-pyrazole-5-carboxamido)-1H-benzo[c]imidazol-7-yl)oxy)propyl 1-ethyl-3-methyl-1H-pyrazole-5-carboxylate

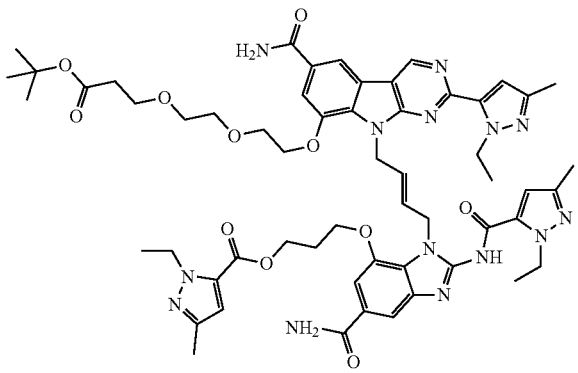 [SMILES: CCn1nc(C)cc1C(=O)Nc1nc2cc(C(N)=O)cc(OCCCOC(=O)c3cc(C)nn3CC)c2n1C/C=C/Cn1c2nc(-c3cc(C)nn3CC)ncc2c2cc(C(N)=O)cc(OCCOCCOCCC(=O)OC(C)(C)C)c21]

This compound was prepared using similar procedures as described for Example S58, Steps 1 to 3 with (E)-3-(1-(4-bromobut-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate (Example S15, Step 9) replacing (E)-1-(4-bromobut-2-enyl)-2-(1-ethyl-3-methyl-1H-pyrazole-5-carboxamido)-7-(3-methoxypropoxy)-1H-benzo[d]imidazole-5-carboxamide in Step 1. LC-MS calculated for $C_{57}H_{71}N_{14}O_{11}$ (M+H)$^+$: m/z=1127.5; found 1127.2.

Step 2: tert-butyl (E)-3-(2-(2-(4(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-9H-pyrimido[4,5-b]indol-8-yl)oxy)ethoxy)ethoxy)propanoate

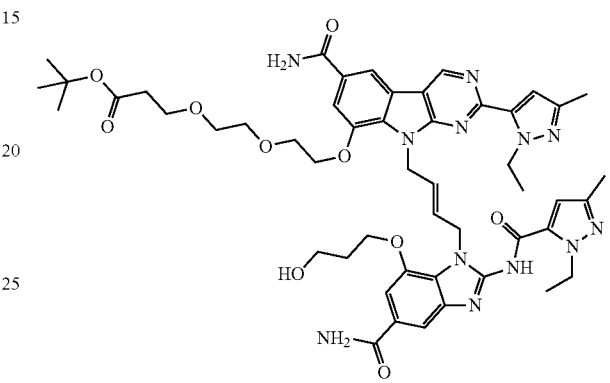

This compound was prepared using similar procedures as described for Example S39, Step 2 with (E)-3-((1-(4-(8-(2-(2-(3-(tert-butoxy)-3-oxopropoxy)ethoxy)ethoxy)-6-carbamoyl-2-(1-ethyl-3-methyl-1H-pyrazol-5-yl)-9H-pyrimido[4,5-b]indol-9-yl)but-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. LC-MS calculated for $C_{50}H_{63}N_{12}O_{10}$ (M+H)$^+$: m/z=991.5; found 991.4.

Step 3: tert-butyl (E)-3-(2-(2-((6-carbamoyl-9-(4-(5-carbamoyl-7-(3-(((3-ethoxy-3-oxopropyl)carbamoyl)oxy)propoxy)-2-(1-ethyl-3-methyl-1H-pyrazole-5-carboxamido)-1H-benzo[c]imidazol-1-yl)but-2-en-1-yl)-2-(1-ethyl-3-methyl-1H-pyrazol-5-yl)-9H-pyrimido[4,5-b]indol-8-yl)oxy)ethoxy)ethoxy)propanoate

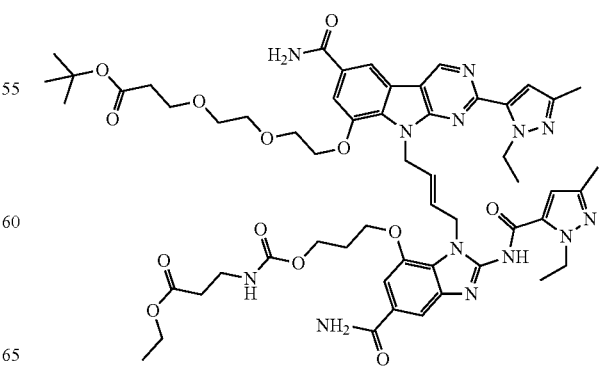

This compound was prepared using similar procedures as described for Example S48, Step 2 with tert-butyl (E)-3-(2-(2-((6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-9H-pyrimido[4,5-b]indol-8-yl)oxy)ethoxy)ethoxy)propanoate replacing tert-butyl (E)-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)carbamate. The reaction mixture was concentrated and used in the next step without further purification. LC-MS calculated for $C_{56}H_{72}H_{13}O_{13}$ $(M+H)^+$: m/z=1134.5; found 1134.6.

Step 4: (E)-3-(((3-((1-(4-(8-(2-(2-(3-(tert-butoxy)-3-oxopropoxy)ethoxy)ethoxy)-6-carbamoyl-2-(1-ethyl-3-methyl-1H-pyrazol-5-yl)-9H-pyrimido[4,5-b]indol-9-yl)but-2-en-1-yl)-5-carbamoyl-2-(1-ethyl-3-methyl-1H-pyrazole-5-carboxamido)-1H-benzo[d]imidazol-7-yl)oxy)propoxy)carbonyl)amino)propanoic acid

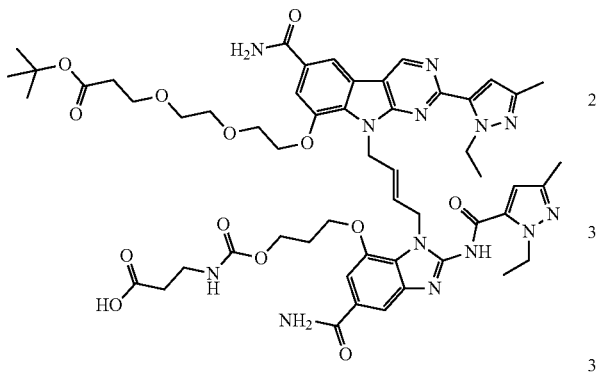

This compound was prepared using similar procedures as described for Example S39, Step 2 with tert-butyl (E)-3-(2-(2-((6-carbamoyl-9-(4-(5-carbamoyl-7-(3-(((3-ethoxy-3-oxopropyl)carbamoyl)oxy)propoxy)-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-9H-pyrimido[4,5-b]indol-8-yl)oxy)ethoxy)ethoxy)propanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. LC-MS calculated for $C_{54}H_{68}N_{13}O_{13}$ $(M+H)^+$: m/z=1106.5; found 1106.7.

Step 5: (E)-3-(((3-((5-carbamoyl-1-(4-(6-carbamoyl-8-(2-(2-(2-carboxyethoxy)ethoxy)ethoxy)-2-(1-ethyl-3-methyl-1H-pyrazol-5-yl)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino) propanoic acid This compound was prepared using similar procedures as described for Example S42, Step 2 with (E)-3-(((3-((1-(4-(8-(2-(2-(3-(tert-butoxy)-3-oxopropoxy)ethoxy)ethoxy)-6-carbamoyl-2-(1-ethyl-3-methyl-1H-pyrazol-5-yl)-9H-pyrimido[4,5-b]indol-9-yl)but-2-en-1-yl)-5-carbamoyl-2-(1-ethyl-3-methyl-1H-pyrazole-5-carboxamido)-1H-benzo[d]imidazol-7-yl)oxy)propoxy)carbonypamino)propanoic acid replacing tert-butyl (6S,9S,12S,15S)-15-amino-6,9-bis(2-(tert-butoxy)-2-oxoethyl)-14(5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate. The reaction mixture was diluted with MeOH and purified by prep-HPLC (pH=2, acetonitrile/water+TFA) to give the desired product as its TFA salt. LC-MS calculated for $C_{50}H_{60}N_{13}O_{13}$ $(M+H)^+$: m/z=1050.4; found 1050.5.

Example S64. (E)-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoic acid Step 1: methyl (E)-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoate

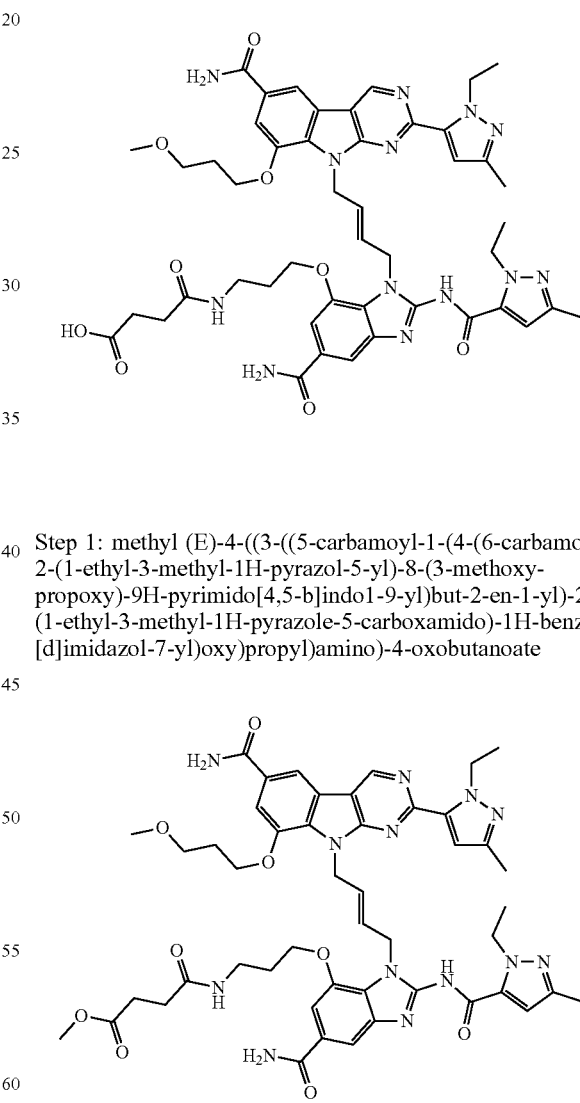

This compound was prepared using similar procedures as described for Example S39, Step 1 with mono-methyl hydrogen succinate replacing mono-methyl glutarate. LC-MS calculated for $C_{48}H_{58}N_{13}O_9$ $(M+H)^+$: m/z=960.4; found 960.5.

Step 2: (E)-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoic acid This compound was prepared using similar procedures as described for Example S39, Step 2 with methyl (E)-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. LC-MS calculated for $C_{47}H_{56}N_{13}O_9$ (M+H)$^+$: m/z=946.4; found 946.5.

Example S65. (E)-9,9'-(but-2-ene-1,4-diyl)bis(2-(1-ethyl-3-methyl-1H-pyrazol-5-yl)-8-(3-hydroxypropoxy)-9H-pyrimido[4,5-b]indole-6-carboxamide)

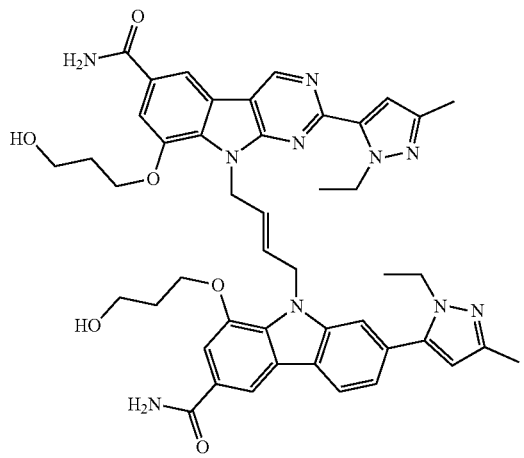 [SMILES: CCn1nc(C)cc1-c1ccc2c3cc(C(N)=O)cc(OCCCO)c3n(C/C=C/Cn3c4nc(-c5cc(C)nn5CC)ncc4c4cc(C(N)=O)cc(OCCCO)c43)c2c1]

Step 1: 3-bromo-5-(3-(tert-butyldimethylsilyloxy)propoxy)-4-nitrobenzamide

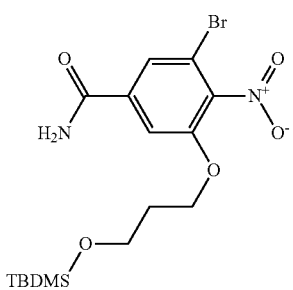

This compound was prepared using similar procedures as described for Example S29, Step 2, with 3-((tert-butyldimethylsilypoxy)propan-1-ol (Combi-Blocks, cat #QH-3826) replacing sodium methoxide. LC-MS calculated for $C_{16}H_{26}BrN_2O_5Si$ (M+H)+: m/z=433.1, 435.1; found 433.2, 435.2.

Step 2: 3-(3-(tert-butyldimethylsilyloxy)propoxy)-5-(2-(1-ethyl-3-methyl-1H-pyrazol-5-yl)pyrimidin-5-yl)-4-nitrobenzamide

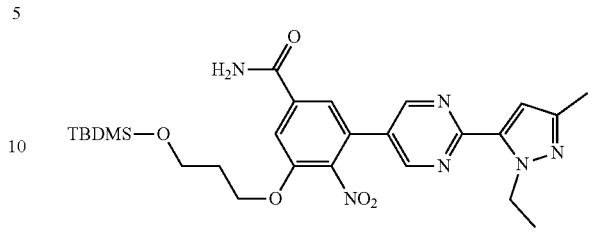

This compound was prepared using similar procedures as described for Example S29, Step 3, with 3-bromo-5-(3-(tert-butyldimethylsilyloxy)propoxy)-4-nitrobenzamide replacing 3-bromo-5-methoxy-4-nitrobenzamide. LC-MS calculated for $C_{26}H_{37}N_6O_5Si$ (M+H)$^+$: m/z=541.3; found 541.3.

Step 3: 8-(3-(tert-butyldimethylsilyloxy)propoxy)-2-(1-ethyl-3-methyl-1H-pyrazol-5-yl)-9H-pyrimido[4,5-b]indole-6-carboxamide

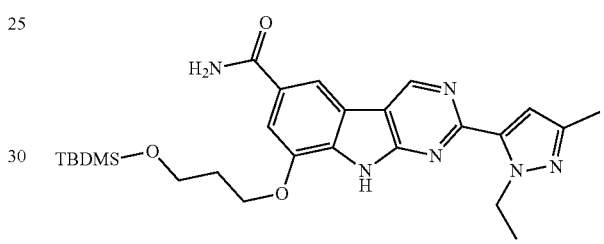

This compound was prepared using similar procedures as described for Example S29, Step 4, with 3-(3-(tert-butyldimethylsilyloxy)propoxy)-5-(2-(1-ethyl-3-methyl-1H-pyrazol-5-yl)pyrimidin-5-yl)-4-nitrobenzamide replacing 3-(2-(1-ethyl-3-methyl-1H-pyrazol-5-yl)pyrimidin-5-yl)-5-methoxy-4-nitrobenzamide. LC-MS calculated for $C_{26}H_{37}N_6O_3Si$ (M+H)$^+$: m/z=509.3; found 509.3.

Step 4: 2-(1-ethyl-3-methyl-1H-pyrazol-5-yl)-8-(3-hydroxypropoxy)-9H-pyrimido[4,5-b]indole-6-carboxamide

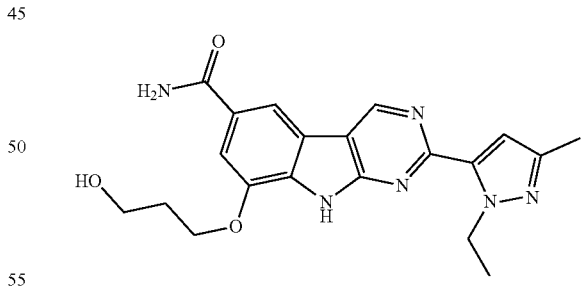

To a stirred solution of 8-(3-(tert-butyldimethylsilyloxy)propoxy)-2-(1-ethyl-3-methyl-1H-pyrazol-5-yl)-9H-pyrimido[4,5-b]indole-6-carboxamide (35 mg, 0.069 mmol) in 1,4-dioxane (1.5 mL) was added 4N HCl in 1,4-dioxane (0.069 ml, 0.274 mmol). After stirring at room temperature for 2 h, the mixture was concentrated under reduced pressure, and then extracted with water and a solution of 25% isopropyl alcohol in CHCl$_3$. The combined organic layers were dried, filtered, and concentrated in vacuo. LC-MS calculated for $C_{20}H_{23}N_6O_3$ (M+H)$^+$: m/z=395.2; found 395.2.

Step 5: (E)-9,9'-(but-2-ene-1,4-diyl)bis(2-(1-ethyl-3-methyl-1H-pyrazol-5-yl)-8-(3-hydroxypropoxy)-9H-pyrimido[4,5-b]indole-6-carboxamide)

A mixture of 2-(1-ethyl-3-methyl-1H-pyrazol-5-yl)-8-(3-hydroxypropoxy)-9H-pyrimido[4,5-b]indole-6-carboxamide (5.0 mg, 0.013 mmol), (E)-1,4-dibromobut-2-ene (1.085 mg, 0.005 mmol), and cesium carbonate (9.09 mg, 0.028 mmol) was stirred in DMF (114 μL) at 50° C. for 1 h. The reaction mixture was diluted with MeOH and purified by prep-HPLC (pH=2, acetonitrile/water+TFA) to give the desired product as its TFA salt. LC-MS calculated for $C_{44}H_{49}N_{12}O_6$ (M+H)$^+$: m/z=841.4; found 841.4.

Example S66. (E)-3-(((3-((5-carbamoyl-1-(4-(5-carbamoyl-2-(1-ethyl-3-methyl-1H-pyrazole-5-carboxamido)-1H-benzofuro[6,7-d]imidazol-1-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid

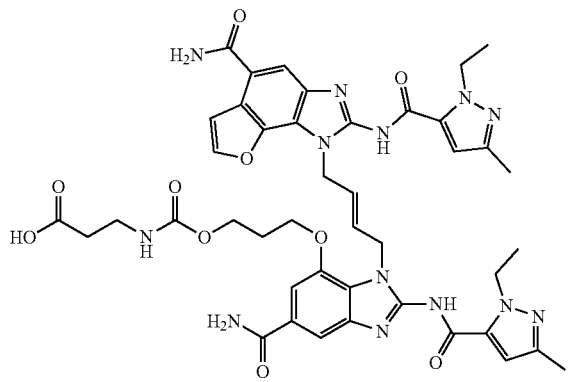 [SMILES: CCn1nc(C)cc1C(=O)Nc1nc2cc(C(N)=O)cc(OCCCOC(=O)NCCC(=O)O)c2n1C/C=C/Cn1c(NC(=O)c2cc(C)nn2CC)nc2cc(C(N)=O)c3ccoc3c21]

Step 1: tert-butyl (E)-(4((4-carbamoyl-6-nitrobenzofuran-7-yl)amino)but-2-en-1-yl)carbamate

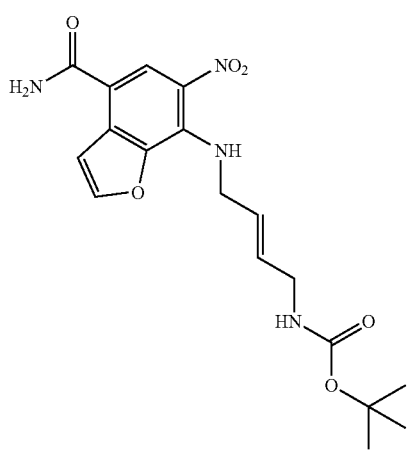 [SMILES: CC(C)(C)OC(=O)NC/C=C/CNc1c([N+](=O)[O-])cc(C(N)=O)c2ccoc12]

To a vial was added tert-butyl (E)-(4-aminobut-2-en-1-yl)carbamate (Ark Pharm, cat #AK308564: 0.140 g, 0.752 mmol), 7-chloro-6-nitrobenzofuran-4-carboxamide (Example S31, Step 5, 0.181 g, 0.752 mmol), a stir bar, EtOH (3.76 mL), and DIPEA (0.656 mL, 3.76 mmol). The resulting mixture was sealed and heated at 80° C. overnight, then 120° C. for 8 h. After cooling to rt, the mixture was concentrated and used directly in the next step. LC-MS calculated for $C_{18}H_{22}N_4O_6Na$ (M+Na)$^+$: m/z=413.2; found 413.2.

Step 2: tert-butyl (E)-(4-((6-amino-4-carbamoylbenzofuran-7-yl)amino)but-2-en-1-yl)carbamate

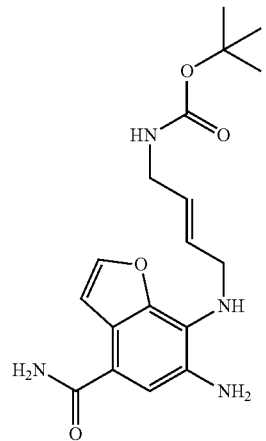 [SMILES: CC(C)(C)OC(=O)NC/C=C/CNc1c(N)cc(C(N)=O)c2ccoc12]

To a solution of tert-butyl (E)-(4-((4-carbamoyl-6-nitrobenzofuran-7-yl)amino)but-2-en-1-yl)carbamate (0.293 g, 0.751 mmol) in MeOH (11.25 mL) was added sodium hydrosulfite (0.653 g, 3.75 mmol) in water (2.364 mL, 131 mmol) and 30% aq ammonium hydroxide (1.218 mL, 9.38 mmol) at 0° C. The reaction mixture was warmed to room temperature. After 10 min, $H_2O$ was added to the reaction mixture followed by extraction with ethyl acetate. The combined organic layers were dried over $MgSO_4$, filtered and concentrated to provide the desired product. LC-MS calculated for $C_{18}H_{24}N_4O_4Na$ (M+Na)$^+$: m/z=383.2; found 383.1.

Step 3: tert-butyl (E)-(4-(2-amino-5-carbamoyl-1H-benzofuro[6,7-d]imidazol-1-yl)but-2-en-1-yl)carbamate

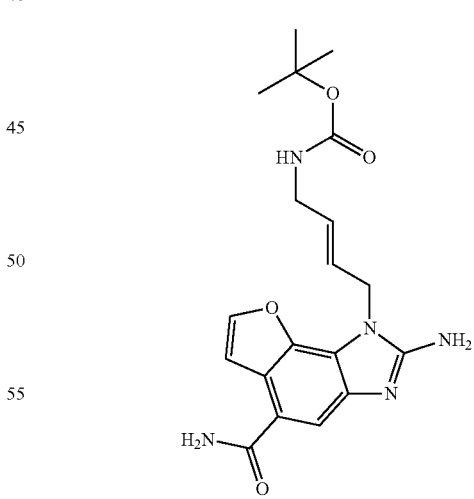

To a solution of tert-butyl (E)-(4-((6-amino-4-carbamoylbenzofuran-7-yl)amino)but-2-en-1-yl)carbamate (0.270 g, 0.751 mmol) in MeOH (11.25 mL) was added cyanogen bromide (0.238 g, 2.252 mmol). After 1 hr, the reaction mixture was concentrated to dryness and the crude residue was used directly in the next step. LC-MS calculated for $C_{19}H_{24}N_5O_4$ (M+H)$^+$: m/z=386.2; found 386.2.

Step 4: tert-butyl (E)-(4-(5-carbamoyl-2-(1-ethyl-3-methyl-1H-pyrazole-5-carboxamido)-1H-benzofuro[6,7-d]imidazol-1-yl)but-2-en-1-yl)carbamate

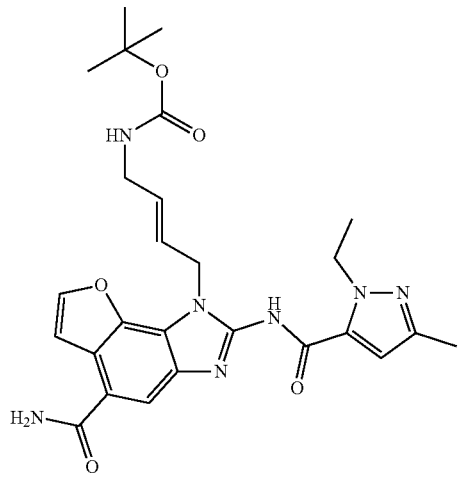 [SMILES: CCn1nc(C)cc1C(=O)Nc1nc2cc(C(N)=O)c3ccoc3c2n1C/C=C/CNC(=O)OC(C)(C)C]

To a solution of tert-butyl (E)-(4-(2-amino-5-carbamoyl-1H-benzofuro[6,7-d]imidazol-1-yl)but-2-en-1-yl)carbamate (289 mg, 0.751 mmol) in DMF (5 mL) was added DIPEA (1.049 mL, 6.00 mmol), 1-Ethyl-3-methyl-1H-pyrazole-5-carboxylic acid (Combi-Blocks, cat #QB-0979: 0.347 g, 2.252 mmol) and BOP (0.996 g, 2.252 mmol). After stirring overnight, H$_2$O was added to the reaction mixture followed by extraction with CHCl$_3$/IPA (3:1). The combined organic layers were dried over MgSO$_4$, filtered, and concentrated. The crude product was added to a silica gel column and was eluted with methanol/dichloromethane from 0% to 10%. LC-MS calculated for C$_{26}$H$_{32}$N$_7$O$_5$ (M+H)$^+$: m/z=522.2; found 522.2.

Step 5: (E)-1-(4-aminobut-2-en-1-yl)-2-(1-ethyl-3-methyl-1H-pyrazole-5-carboxamido)-1H-benzofuro[6,7-c]imidazole-5-carboxamide

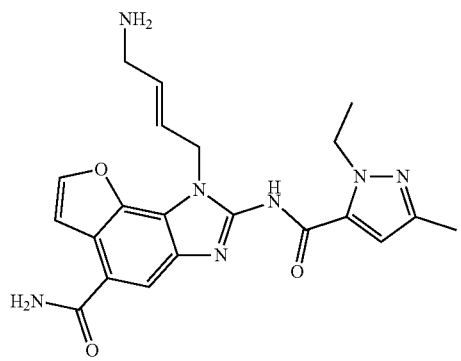 [SMILES: CCn1nc(C)cc1C(=O)Nc1nc2cc(C(N)=O)c3ccoc3c2n1C/C=C/CN]

To a solution of tert-butyl (E)-(4-(5-carbamoyl-2-(1-ethyl-3-methyl-1H-pyrazole-5-carboxamido)-1H-benzofuro[6,7-d]imidazol-1-yl)but-2-en-1-yl)carbamate (0.300 g, 0.575 mmol) in 1,4-dioxane (5.75 mL) was added 4 N HCl in dioxane (1.438 mL, 5.75 mmol). The resulting solution was stirred for 1 h, then was triturated with EtOAc and filtered to provide the HCl salt. LC-MS calculated for C$_{21}$H$_{24}$N$_7$O$_3$ (M+H)+: m/z=422.2; found 422.4.

Step 6: 4-chloro-3-hydroxy-5-nitrobenzamide

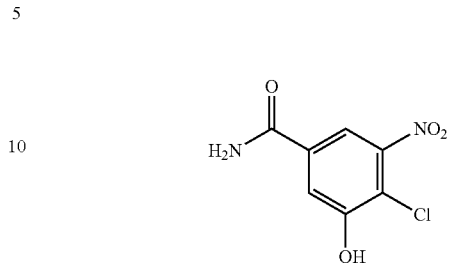

In a round-bottomed flask, 4-chloro-3-methoxy-5-nitrobenzamide (Astatech, cat # 97780: 1.0 g, 4.34 mmol) was dissolved in DCM. 1M BBr$_3$ in DCM (13.01 mL, 13.01 mmol) was added to the reaction mixture dropwise, then was refluxed for 12 h. The reaction mixture was cooled and then was poured into ice water. After stirring for 30 min, the reaction mixture was filtered and the filter cake was rinsed with water and dried to provide the desired compound as a white solid. LC-MS calculated for C$_7$H$_6$ClN$_2$O$_4$ (M+H)$^+$: m/z=217.0; found 216.9.

Step 7: 3-(3-(((tert-butyldimethylsilyl)oxy)propoxy)-4-chloro-5-nitrobenzamide

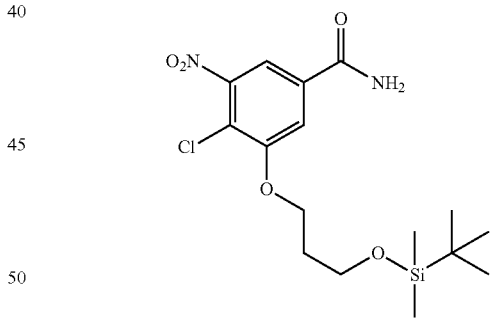

To a suspension of 4-chloro-3-hydroxy-5-nitrobenzamide (211.0 mg, 0.974 mmol), and cesium carbonate (476 mg, 1.461 mmol) in DMF (3247 µL) was added (3-bromopropoxy)(tert-butyl)dimethylsilane (Aldrich, cat #429066: 271 µL, 1.169 mmol). The reaction was then sealed and heated to 50° C. with stirring for 12 h. After cooling with an ice bath, the product was triturated with cold water, filtered, and dried to provide the desired product as a yellow solid. LC-MS calculated for C$_{16}$H$_{26}$ClN$_2$O$_5$Si (M+H)$^+$: m/z=389.1; found 389.1.

Step 8: (E)-1-(4-(2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzofuro[6,7-c]imidazole-5-carboxamide

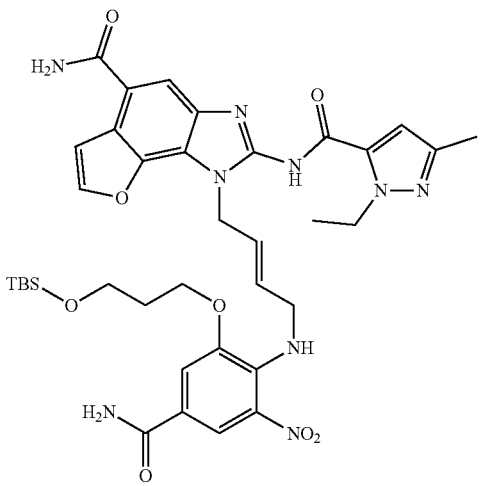

To a solution of 3-(3-((tert-butyldimethylsilypoxy)propoxy)-4-chloro-5-nitrobenzamide (0.150 g, 0.386 mmol) in EtOH (1.928 mL) was added DIPEA (0.337 mL, 1.928 mmol) and (E)-1-(4-aminobut-2-en-1-yl)-2-(1-ethyl-3-methyl-1H-pyrazole-5-carboxamido)-1H-benzofuro[6,7-d]imidazole-5-carboxamide, HCl (0.177 g, 0.386 mmol). The mixture was sealed and heated to 120° C. with stirring overnight. Reaction was cooled to rt and concentrated under reduced pressure. The crude product was then purified by column chromatography (15% MeOH/DCM). LC-MS calculated for $C_{37}H_{48}N_9O_8Si$ $(M+H)^+$: m/z=774.3; found 774.3.

Step 9: (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-1H-benzofuro[6,7-d]imidazole-5-carboxamide

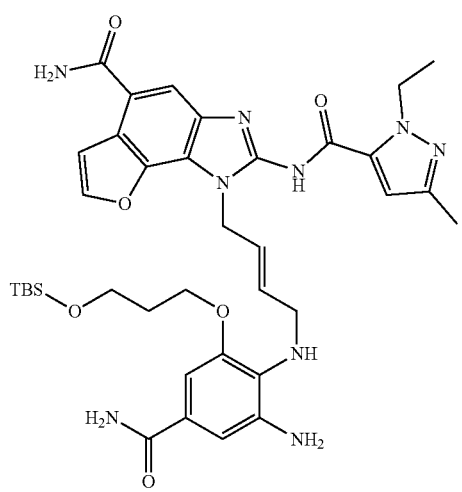

To a solution of (E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzofuro[6,7-d]imidazole-5-carboxamide (0.124 g, 0.160 mmol) in MeOH (3.47 mL) was added sodium hydrosulfite (0.201 g, 1.156 mmol) in water (0.729 mL, 40.5 mmol) and 30% aq ammonium hydroxide (0.375 mL, 2.89 mmol) at 0° C. The reaction mixture was warmed to room temperature. After 10 min, H₂O was added to the reaction mixture followed by extraction with DCM. The combined organic layers were dried over MgSO₄, filtered, and concentrated under reduced pressure. The resulting crude product was used directly in the next step. LC-MS calculated for $C_{37}H_{50}N_9O_6Si$ $(M+H)^+$: m/z=744.4; found 744.6.

Step 10: (E)-1-(4-(2-amino-7-(3-((tert-butyldimethylsilyl)oxy)propoxy)-5-carbamoyl-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide

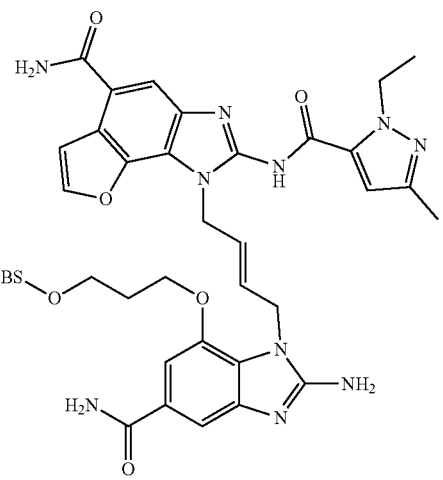

To a solution of (E)-1-(4-((2-amino-6-(3-((tert-butyldimethylsilypoxy)propoxy)-4-carbamoylphenyl)amino)but-2-en-1-yl)-2-(1-ethyl-3-methyl-1H-pyrazole-5-carboxamido)-1H-benzofuro[6,7-d]imidazole-5-carboxamide (0.124 g, 0.167 mmol) in MeOH (3.47 mL) was added cyanogen bromide (122 mg, 1.156 mmol). The mixture was stirred overnight, then concentrated to dryness. The crude residue was used directly in the next step without further purification. LC-MS calculated for $C_{38}H_{49}N_{10}O_6Si$ $(M+H)^+$: m/z=769.4; found &b 769.6.

Step 11: (E)-1-(4-(7-(3-((tert-butyldimethylsilyl)oxy)propoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide

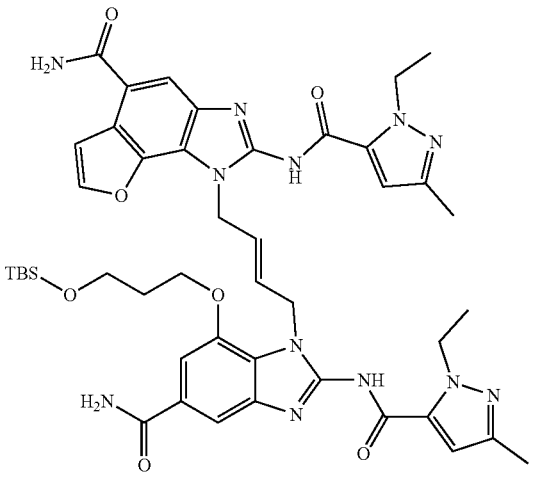

To a solution of (E)-1-(4-(2-amino-7-(3-((tert-butyldimethylsilyl)oxy)propoxy)-5-carbamoyl-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide (0.093 g, 0.121 mmol) in DMF (5 mL) was added DIPEA (0.169 mL, 0.968 mmol), 1-ethyl-3-methyl-1H-pyrazole-5-carboxylic acid (Combi-Blocks, cat #QB-0979: 0.056 g, 0.363 mmol) and BOP (0.160 g, 0.363 mmol). After stirring for 1 h, H₂O was added to the reaction mixture followed by extraction with EtOAc. The combined organic layers were dried over MgSO₄, filtered and concentrated under reduced pressure. The crude product was added to a silica gel column and was eluted with methanol/dichloromethane from 0% to 30%. LC-MS calculated for $C_{45}H_{58}N_{12}O_7Si$ (M+2H)²⁺: m/z=453.2; found 453.4.

Step 12: (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide

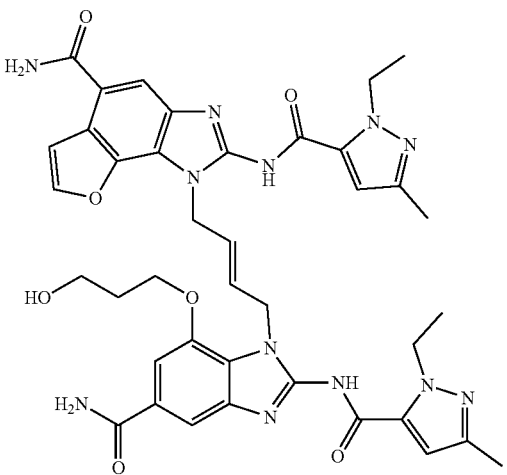 [SMILES: CCn1nc(C)cc1C(=O)Nc1nc2cc(C(N)=O)cc(OCCCO)c2n1C/C=C/Cn1c(NC(=O)c2cc(C)nn2CC)nc2cc(C(N)=O)c3ccoc3c21]

To a solution of (E)-1-(4-(7-(3-((tert-butyldimethylsilyl)oxy)propoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide (0.054 g, 0.060 mmol) in THF (0.597 mL) was added 1.0 M TBAF solution in THF (0.239 mL, 0.239 mmol). The mixture was stirred at rt overnight. The reaction was concentrated, then purified by column (MeOH/DCM from 0 to 30%). LC-MS calculated for $C_{39}H_{43}N_{12}O_7$ (M+H)⁺: m/z=791.3; found 791.3.

Step 13: Ethyl (E)-3-(((3-((5-carbamoyl-1-(4-(5-carbamoyl-2-(1-ethyl-3-methyl-1H-pyrazole-5-carboxamido)-1H-benzofuro[6,7-d]imidazol-1-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoate

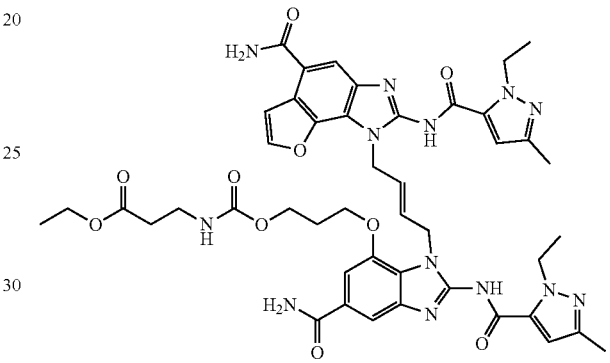

To a solution of (E)-1-(4-(5-carbamoyl-2-(1-ethyl-3-methyl-1H-pyrazole-5-carboxamido)-7-(3-hydroxypropoxy)-1H-benzo[di]imidazol-1-yl)but-2-en-1-yl)-2-(1-ethyl-3-methyl-1H-pyrazole-5-carboxamido)-1H-benzofuro[6,7-d]imidazole-5-carboxamide (0.047 g, 0.059 mmol) in THF (0.594 mL) was added DIPEA (0.125 mL, 0.713 mmol) and ethyl 3-isocyanatopropanoate (0.078 mL, 0.594 mmol). The mixture was heated at 70° C. overnight. The reaction was cooled and diluted with water. The reaction was extracted with CHCl₃/IPA (3:1), dried over MgSO₄, filtered, and concentrated under reduced pressure. The crude product was purified by column (30% MeOH/DCM). LC-MS calculated for $C_{45}H_{52}N_{13}O_{10}$ (M+H)⁺: m/z=934.4; found 934.5.

Step 14: (E)-3-(((3-((5-carbamoyl-1-(4-(5-carbamoyl-2-(1-ethyl-3-methyl-1H-pyrazole-5-carboxamido)-1H-benzofuro[6,7-d]imidazol-1-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid Ethyl (E)-3-(((3-((5-carbamoyl-1-(4-(5-carbamoyl-2-(1-ethyl-3-methyl-1H-pyrazole-5-carboxamido)-1H-benzofuro[6,7-d]imidazol-1-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoate (0.040 g, 0.0428 mmol) was dissolved in THF (0.6 mL) and MeOH (0.3 mL). To this was added 2 M LiOH (0.297 mL, 0.594 mmol). The reaction was stirred for 15 min, and was then dissolved in MeOH and purified by prep HPLC (pH=2, MeCN/water+TFA) to provide the desired compound as the TFA salt. LC-MS calculated for $C_{43}H_{48}N_{13}O_{10}$ (M+H)⁺: m/z=906.4; found 906.0.

Example S67. (E)-1-(4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzofuro[6,7-d]imidazole-5-carboxamide

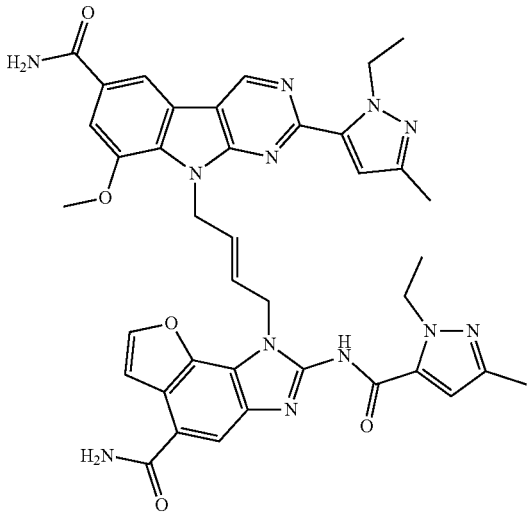 [SMILES: CCn1nc(C)cc1C(=O)Nc1nc2cc(C(N)=O)c3ccoc3c2n1C/C=C/Cn1c2nc(-c3cc(C)nn3CC)ncc2c2cc(C(N)=O)cc(OC)c21]

Step 1: methyl 2-bromo-4-chloro-3-hydroxy-5-nitrobenzoate

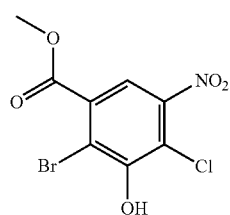 [SMILES: COC(=O)c1cc([N+](=O)[O-])c(Cl)c(O)c1Br]

To a solution of t-butylamine (1.774 mL, 16.88 mmol) in dry toluene (11.25 mL) was added bromine (0.319 mL, 6.19 mmol) dropwise at −30° C. (~10 min) under nitrogen. The mixture was cooled to −78° C., and a solution of methyl 4-chloro-3-hydroxy-5-nitrobenzoate (Combi-Blocks, cat #CA-5786: 1.3030 g, 5.63 mmol) in DCM (45.0 mL) was added dropwise under nitrogen (~30 min). The mixture was warmed to room temperature (rt) gradually and stirred overnight. The reaction was diluted with EtOAc and the organic phase washed with 1.0 M HCl (2×) and brine (1×). The organic phase was dried over anhydrous MgSO$_4$, filtered, and the filtrate evaporated under reduced pressure. The residue was purified by flash chromatography (10% EtOAc/hexanes) to give the desired product as a white solid. LC-MS calculated for $C_8H_6BrClNO_5$ (M+H)$^+$: m/z=309.9/311.9; found 309.8/312.0.

Step 2: methyl 3-acetoxy-2-bromo-4-chloro-5-nitrobenzoate

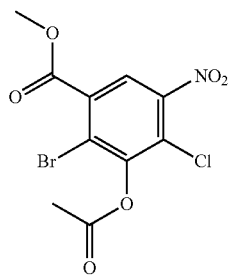 [SMILES: COC(=O)c1cc([N+](=O)[O-])c(Cl)c(OC(C)=O)c1Br]

To a solution of methyl 2-bromo-4-chloro-3-hydroxy-5-nitrobenzoate (1.37 g, 4.41 mmol) and triethylamine (1.845 mL, 13.24 mmol) in CH$_2$Cl$_2$ (12.98 mL) was added Ac$_2$O (0.541 mL, 5.74 mmol) at 0° C. After stirring for 18 h at rt, the mixture was diluted with HCl (1 M, 10 mL). The resulting mixture was extracted with CH$_2$Cl$_2$ (3×10 mL). The combined organic layers were washed with brine, dried over MgSO$_4$ and concentrated in vacuo. The crude residue was then purified by flash chromatography (10% EtOAc/hexanes) to provide the desired product as a white solid. LC-MS calculated for $C_{10}H_8BrClNO_6$ (M+H)$^+$: m/z=351.9/353.9; found 351.9/353.8. $^1$H NMR (500 MHz, DMSO) δ 8.48 (s, 1H), 3.92 (s, 3H), 2.49 (s, 3H). $^{13}$C NMR (125 MHz, DMSO) δ 167.0, 163.6, 147.0, 146.8, 132.8, 124.4, 124.1, 122.1, 53.4, 20.0.

Step 3: methyl 3-acetoxy-4-chloro-5-nitro-2-((trimethylsilyl)ethynyl)benzoate

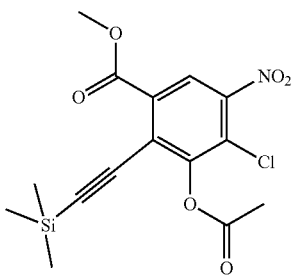 [SMILES: COC(=O)c1cc([N+](=O)[O-])c(Cl)c(OC(C)=O)c1C#C[Si](C)(C)C]

Methyl 3-acetoxy-2-bromo-4-chloro-5-nitrobenzoate (0.503 g, 1.427 mmol), cuprous iodide (0.027 g, 0.143 mmol) and dichlorobis(triphenylphosphine)-palladium(II) (0.050 g, 0.071 mmol) were added in a vial and the vial was sealed, evacuated and flushed with nitrogen (3×). Then DMF (3.57 mL) and DIPEA (1.189 mL) were added under nitrogen. Next, ethynyltrimethylsilane (0.605 mL, 4.28 mmol) was added and reaction mixture was stirred at 35° C. overnight. After cooling to rt, the mixture was diluted with DCM and 1 N HCl. The layers were separated, and the aqueous layer was further extracted. The combined organic layers were dried over MgSO$_4$, filtered, and concentrated in vacuo. The crude residue was then purified by flash chromatography (10% EtOAc/hexanes) to provide the desired product as a clear solid. LC-MS calculated for $C_{15}H_{17}ClNO_6Si$ (M+H)$^+$: m/z=370.0; found 370.0.

Step 4: methyl 4-chloro-2-ethynyl-3-hydroxy-5-nitrobenzoate

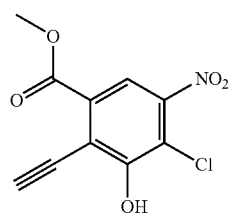 [SMILES: C#Cc1c(C(=O)OC)cc([N+](=O)[O-])c(Cl)c1O]

To a solution of methyl 3-acetoxy-4-chloro-5-nitro-2-((trimethylsilyl)ethynyl)benzoate (0.331 g, 0.895 mmol) in MeOH (8.95 mL) was added potassium carbonate (0.124 g, 0.895 mmol). The reaction mixture was stirred for 15 min, and was then diluted with DCM and 1 N HCl. The layers were separated, and the aqueous layer was further extracted with DCM. The combined organic layers were dried over $MgSO_4$, filtered, and concentrated in vacuo. The resulting residue was then used directly in the next step without further purification. LC-MS calculated for $C_{10}H_7ClNO_5$ $(M+H)^+$: m/z=256.0; found 256.1.

Step 5: 7-chloro-6-nitrobenzofuran-4-carboxamide

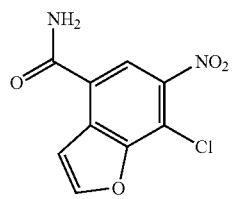 [SMILES: NC(=O)c1cc([N+](=O)[O-])c(Cl)c2occc12]

To a vial was added methyl 4-chloro-2-ethynyl-3-hydroxy-5-nitrobenzoate (201 mg, 0.786 mmol) and ammonium hydroxide (9186 µL, 236 mmol). The mixture was stirred at rt for 20 h, and was then filtered. The resulting solid was washed with water, dried, and used directly in the next step without further purification. LC-MS calculated for $C_9H_6ClN_2O_4$ $(M+H)^+$: m/z=241.0; found 241.0. $^1H$ NMR (500 MHz, DMSO) δ 8.53 (s, 1H), 8.51 (d, J=2.25 Hz, 1H), 8.35 (s, 1H), 7.76 (s, 1H), 7.54 (d, J=2.25 Hz, 1H). $^{13}C$ NMR (125 MHz, DMSO) δ 165.6, 152.7, 150.6, 142.6, 131.5, 126.0, 120.0, 113.5, 108.8.

Step 6: tert-butyl (E)-(4-((4-carbamoyl-6-nitrobenzofuran-7-yl)aminotbut-2-en-1-yl)carbamate

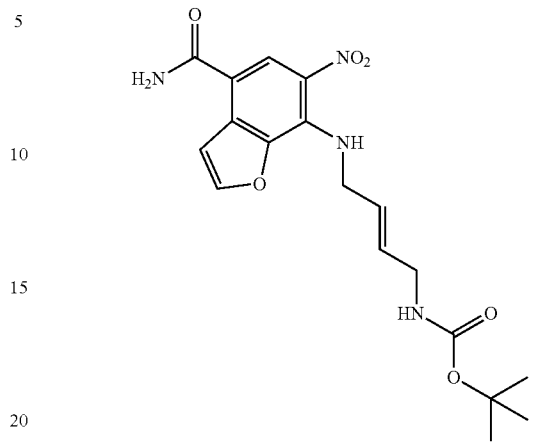

To a vial was added tert-butyl (E)-(4-aminobut-2-en-1-yl)carbamate (Enamine, cat #EN300-134337: 0.07 g, 0.376 mmol), 7-chloro-6-nitrobenzofuran-4-carboxamide (0.090 g, 0.376 mmol), a stir bar, DMSO (1.879 mL), and DIPEA (0.328 mL, 1.879 mmol). The resulting mixture was sealed and heated at 100° C. for 8 h. After cooling to rt, the mixture was concentrated and purified by column chromatography (10% MeOH/DCM). LC-MS calculated for $C_{18}H_{22}N_4O_6Na$ (M+Na)+: m/z=413.2; found 413.2.

Step 7: (tert-butyl (E)-(4-((6-amino-4-carbamoylbenzofuran-7-yl)amino)but-2-en-1-yl)carbamate

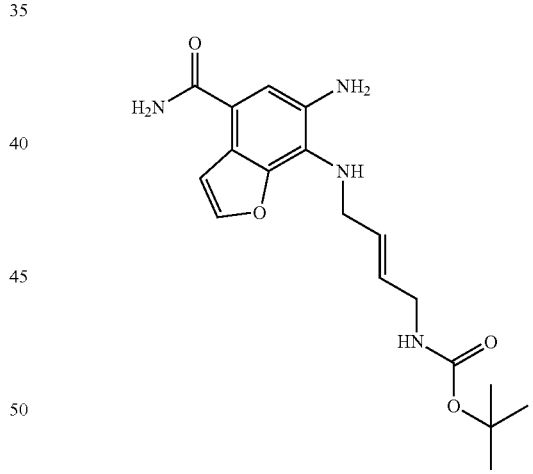

To a solution of tert-butyl (E)-(4-((4-carbamoyl-6-nitrobenzofuran-7-yl)amino)but-2-en-1-yl)carbamate (0.150 g, 0.384 mmol) in dioxane (2.88 mL))/water (0.961 mL) was added ammonium chloride (0.082 g, 1.537 mmol) and zinc (0.100 g, 1.537 mmol) at 0° C. The reaction mixture was stirred at rt for 10 min, after which time it was filtered. The filtrate was partitioned between water (10 mL) and EtOAc (30 mL). The organic layer was separated, dried over $MgSO_4$, concentrated, and dried under high vacuum to provide the product as an orange foam. The orange solid solid was washed with MeCN to provide the desired product as a yellow solid. LC-MS calculated for $C_{18}H_{24}N_4O_4Na$ $(M+Na)^+$: m/z=383.2; found 383.2.

Step 8: tert-butyl (E)-(4-(2-amino-5-carbamoyl-1H-benzo-furo[6,7-d]imidazol-1-yl)but-2-en-1-yl)carbamate

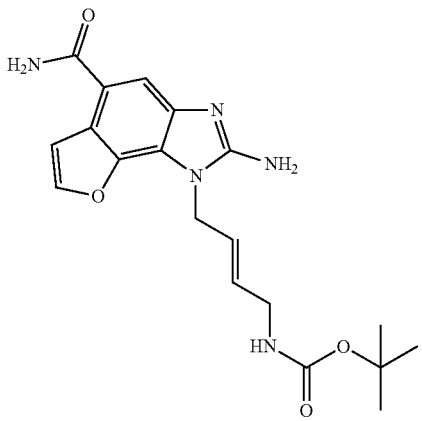 [SMILES: CC(C)(C)OC(=O)NC/C=C/Cn1c(N)nc2cc(C(N)=O)c3ccoc3c21]

To a solution of tert-butyl (E)-(4-((6-amino-4-carbamoyl-benzofuran-7-yl)amino)but-2-en-1-yl)carbamate (0.107g, 0.297 mmol) in MeOH (1.484 mL) was added cyanogen bromide (0.023 mL, 0.445 mmol). The mixture was stirred at rt for 20 min. The reaction was concentrated and triturated with EtOAc and filtered to provide the desired compound as an orange solid. LC-MS calculated for $C_{19}H_{24}N_5O_4$ $(M+H)^+$: m/z=386.2; found 386.2.

Step 9: tert-butyl (E)-(4-(5-carbamoyl-2-(1-ethyl-3-methyl-1H-pyrazole-5-carboxamido)-1H-benzofuro[6,7-d]imidazol-1-yl)but-2-en-1-yl)carbamate

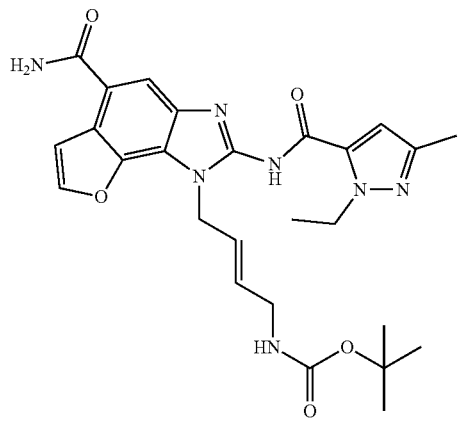 [SMILES: CCn1nc(C)cc1C(=O)Nc1nc2cc(C(N)=O)c3ccoc3c2n1C/C=C/CNC(=O)OC(C)(C)C]

To a solution of 1-ethyl-3-methyl-1H-pyrazole-5-carboxylic acid (Combi-Blocks, cat #QB-0979: 0.050 g, 0.325 mmol) in DMF (1.109 mL) at rt was added HATU (0.146 g, 0.385 mmol) and DIPEA (0.258 mL, 1.479 mmol). The mixture was stirred for 15 min, then a solution of tert-butyl (E)-(4-(2-amino-5-carbamoyl-1H-benzofuro[6,7-d]imidazol-1-yl)but-2-en-1-yl)carbamate (0.114 g, 0.296 mmol) in DMF (0.370 mL) was added and stirred overnight. The reaction was concentrated, and was diluted with water. The aqueous mixture was extracted with DCM (3×20 mL). The combined organic layers were washed with brine, dried over $MgSO_4$, filtered, and concentrated. The product was purified by column chromatography (15% MeOH/DCM) to provide the desired product as a white solid. LC-MS calculated for $C_{26}H_{32}N_7O_5$ $(M+H)^+$: m/z=522.2; found 522.3.

Step 10: (E)-1-(4-aminobut-2-en-1-yl)-2-(1-ethyl-3-methyl-1H-pyrazole-5-carboxamido)-1H-benzofuro[6,7-d]imidazole-5-carboxamide

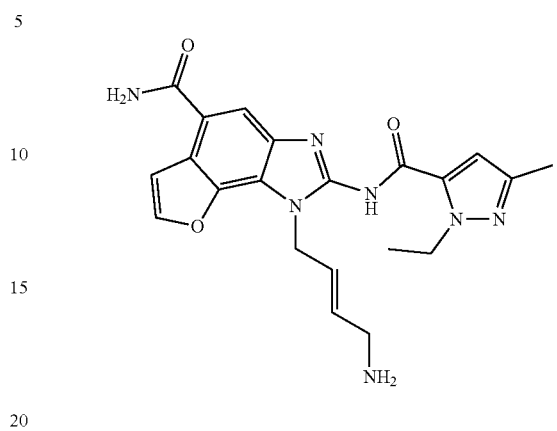

To a solution of tert-butyl (E)-(4-(5-carbamoyl-2-(1-ethyl-3-methyl-1H-pyrazole-5-carboxamido)-1H-benzofuro[6,7-d]imidazol-1-yl)but-2-en-1-yl)carbamate (0.124 g, 0.238 mmol) in 1,4-dioxane (2.377 mL) was added 1 N HCl in 1,4-dioxane (2.377 mL, 2.377 mmol). The resulting solution was stirred for 1 h, then concentrated to provide the desired product as its HCl salt. LCMS calculated for $C_{21}H_{24}N_7O_3$ $(M+H)^+$: m/z=422.2; found 422.3.

Step 11: (E)-2-(1-ethyl-3-methyl-1H-pyrazole-5-carboxamido)-1-(4-hydroxybut-2-en-1-yl)-1H-benzofuro[6,7-c]imidazole-5-carboxamide

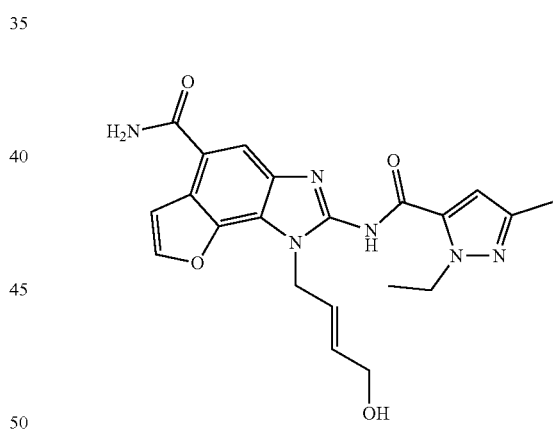

To a solution of (E)-1-(4-aminobut-2-en-1-yl)-2-(1-ethyl-3-methyl-1H-pyrazole-5-carboxamido)-1H-benzofuro[6,7-d]imidazole-5-carboxamide (0.058 g, 0.138 mmol) in THF (0.917 mL) and water (0.917 mL) was added potassium bromide (0.025 g, 0.206 mmol) and sodium nitrite (0.014 g, 0.206 mmol). The mixture was stirred 1 h at rt, and was diluted with 3:1 $CHCl_3$/IPA and water. The layers were separated and the aqueous layer was further extracted. The combined organic layers were dried over $MgSO_4$, filtered, and concentrated in vacuo. The crude product was used directly in the next step without further purification. LC-MS calculated for $C_{21}H_{21}N_6O_4$ $(M+H)^+$: m/z=423.2; found 423.1.

Step 12: (E)-1-(4-bromobut-2-en-1-yl)-2-(1-ethyl-3-methyl-1H-pyrazole-5-carboxamido)-1H-benzofuro[6,7-c]imidazole-5-carboxamide

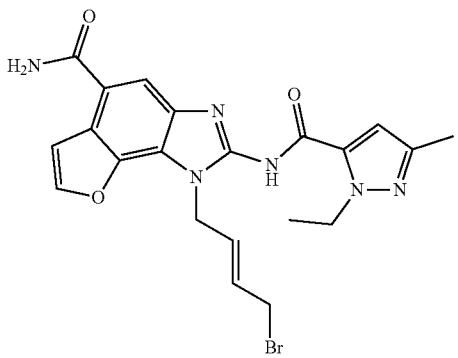 [SMILES: CCn1nc(C)cc1C(=O)Nc1nc2cc(C(N)=O)c3ccoc3c2n1C/C=C/CBr]

To a solution of (E)-2-(1-ethyl-3-methyl-1H-pyrazole-5-carboxamido)-1-(4-hydroxybut-2-en-1-yl)-1H-benzofuro[6,7-d]imidazole-5-carboxamide (0.058 g, 0.137 mmol) in THF (0.917 mL) was added PBr$_3$ (0.019 mL, 0.206 mmol). The reaction was stirred for 30 min at rt, then quenched with saturated aqueous sodium bicarbonate. The mixture was diluted with DCM and the layers were separated. The aqueous layer was further extracted, and the combined organic layers were dried over MgSO$_4$, filtered, and concentrated in vacuo. The crude product was used directly in the next step without further purification. LC-MS calculated for $C_{21}H_{22}BrN_6O_3$ (M+H)$^+$: m/z=485.1, 487.1; found 485.1, 487.1.

Step 13: 3-bromo-5-fluoro-4-nitrobenzamide

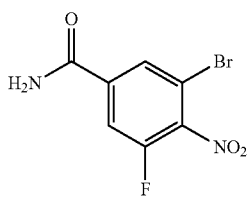 [SMILES: NC(=O)c1cc(F)c([N+](=O)[O-])c(Br)c1]

Methyl 3-bromo-5-fluoro-4-nitrobenzoate (AstaTech, cat #AB9640: 5.0 g, 17.98 mmol) was stirred in ammonium hydroxide (44.1 mL, 1133 mmol) at room temperature for 10 h. The solid was filtered and rinsed with cold water. The resulting solid residue was dried to provide the desired product as a light yellow solid.

Step 14: 3-bromo-5-methoxy-4-nitrobenzamide

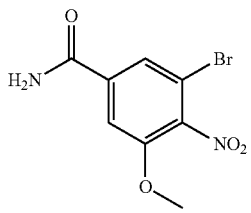

To a stirred solution of 3-bromo-5-fluoro-4-nitrobenzamide (1.0 g, 3.80 mmol) in MeOH (19.01 mL) was added sodium methoxide (1.232 g, 5.70 mmol). The reaction mixture was stirred at 60° C. for 0.5 h. The reaction mixture was concentrated under reduced pressure. The residue was dissolved in water, and then extracted with DCM. The combined organic layers were dried, filtered, and concentrated in vacuo. The crude product was used directly without further purification. LC-MS calculated for $C_8H_8BrN_2O_4$ (M+H)$^+$: m/z=275.0, 277.0; found 275.0, 277.0.

Step 15: 3-(2-(1-ethyl-3-methyl-1H-pyrazol-5-yl)pyrimidin-5-yl)-5-methoxy-4-nitrobenzamide

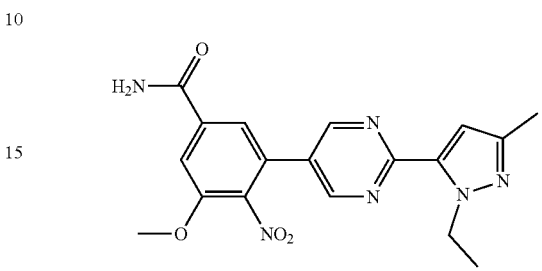

To a degassed solution of (2-chloropyrimidin-5-yl)boronic acid (Combi-Blocks, cat #BB-5457: 82 mg, 0.52 mmol) and 3-bromo-5-methoxy-4-nitrobenzamide (143 mg, 0.520 mmol) in dioxane (1733 µl) and water (347 µl) was added dichloro[1,1'-bis(diphenylphosphino)ferrocene]palladium (II) dichloromethane adduct (25.5 mg, 0.031 mmol) and sodium carbonate (110 mg, 1.040 mmol). The reaction was stirred at 100° C. for 2 h. Then, 1-ethyl-3-methyl-5-(4,4,5,5-tetramethyl-1,3,2-dioxaborolan-2-yl)-1H-pyrazole (Enamine Ltd, cat #EN300-207291: 123.0 mg, 0.520 mmol) was added. The reaction mixture was heated to 100° C. for another 1 h. H$_2$O was added to the reaction mixture, and the reaction was extracted with DCM. The combined organic layers were dried with Na$_2$SO$_4$, filtered, and concentrated. The crude residue was purified by flash chromatography on a silica gel column eluting with 0 to 8% MeOH in DCM to afford the desired product. LC-MS calculated for $C_{18}H_{19}N_6O_4$ (M+H)$^+$: m/z=383.1; found 383.2.

Step 16: 2-(1-ethyl-3-methyl-1H-pyrazol-5-yl)-8-methoxy-9H-pyrimido[4,5-b]indole-6-carboxamide

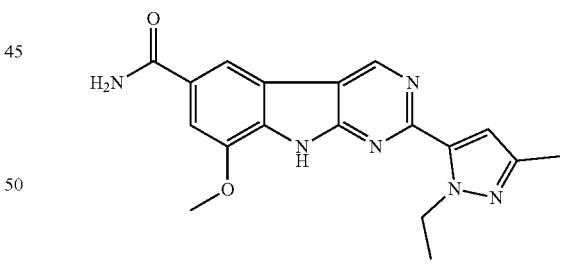

A mixture of 3-(2-(1-ethyl-3-methyl-1H-pyrazol-5-yl)pyrimidin-5-yl)-5-methoxy-4-nitrobenzamide (280.0 mg, 0.732 mmol) and 1,2-bis(diphenylphosphino)ethane (365 mg, 0.915 mmol) was dissolved in 1,2-dichlorobenzene (2.4 mL). The vial was flushed with nitrogen before heating at 160° C. for 1 h. After removal of the solvent under vacuum, the reaction mixture was extracted with DCM and water. The organic phases were combined and dried over MgSO$_4$, filtered, then concentrated under reduced pressure. The crude residue was purified by flash chromatography on a silica gel column eluting with 0 to 8% MeOH in DCM to afford the desired product. LC-MS calculated for $C_{18}H_{19}N_6O_2$ (M+H)$^+$: m/z=351.1; found 351.1.

Step 17: (E)-1-(4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzofuro[6,7-d]imidazole-5-carboxamide To a solution of (E)-1-(4-bromobut-2-en-1-yl)-2-(1-ethyl-3-methyl-1H-pyrazole-5-carboxamido)-1H-benzofuro[6,7-d]imidazole-5-carboxamide (5 mg, 10.30 µmol) and 2-(1-ethyl-3-methyl-1H-pyrazol-5-yl)-8-methoxy-9H-pyrimido[4,5-b]indole-6-carboxamide (3.97 mg, 0.011 mmol) in DMF (103 µL) was added DIPEA (5.40 µL, 0.031 mmol). After 20 min, Cs$_2$CO$_3$ (10.07 mg, 0.031 mmol) was added. The mixture was stirred at rt overnight. The mixture was diluted with MeCN and water, acidified with TFA, then purified by prep-HPLC (pH=2, acetonitrile/water+TFA) to give the desired product as the TFA salt. LC-MS calculated for C$_{39}$H$_{39}$N$_{12}$O$_5$ (M+H)$^+$: m/z=755.3; found 755.3.

Example S68. (E)-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzofuro[6,7-d]imidazole-5-carboxamide

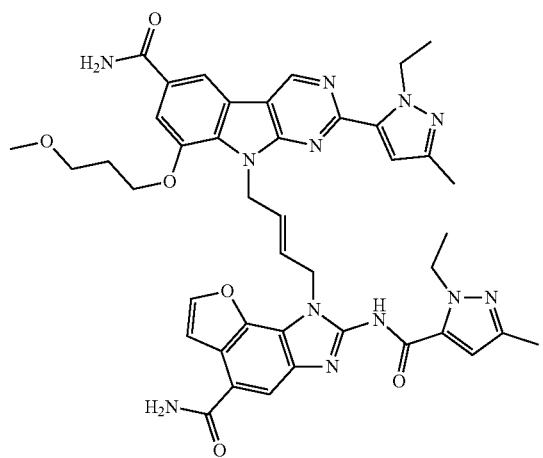

Step 1: 3-bromo-5-(3-methoxypropoxy)-4-nitrobenzamide

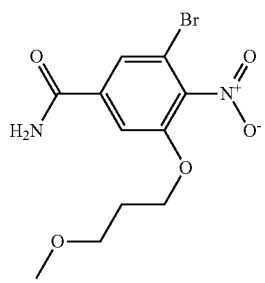 [SMILES: COCCCOc1cc(C(N)=O)cc(Br)c1[N+](=O)[O-]]

To dry THF (12.67 mL) was added 60% sodium hydride (0.304 g, 7.60 mmol). While stirring, 3-methoxypropan-1-ol (Aldrich, cat #38457: 0.364 mL, 3.80 mmol) was added slowly and the mixture was stirred at room temperature for 10 min. To the solution of sodium alkoxide was added 3-bromo-5-fluoro-4-nitrobenzamide (1.00 g, 3.80 mmol). The reaction mixture was heated to 60° C. for 0.5 h. The resulting mixture was carefully diulted with water, and extracted with DCM. The combined organic layers were dried over MgSO$_4$, filtered, concentrated in vacuo, and used directly in the next step without further purification. LC-MS calculated for C$_{11}$H$_{14}$BrN$_2$O$_5$ (M+H)$^+$: m/z=333.0, 335.0; found 333.0, 335.0.

Step 2: 3-(2-(1-ethyl-3-methyl-1H-pyrazol-5-yl)pyrimidin-5-yl)-5-(3-methoxypropoxy)-4-nitrobenzamide

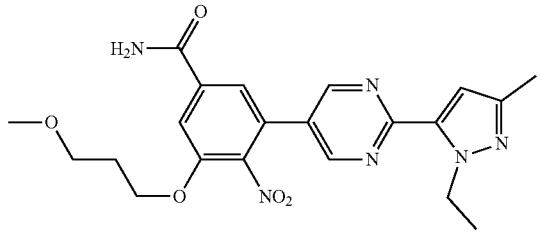

This compound was prepared using similar procedures as described for Example S67, Step 15 with 3-bromo-5-(3-methoxypropoxy)-4-nitrobenzamide replacing 3-bromo-5-methoxy-4-nitrobenzamide. LC-MS calculated for C$_{21}$H$_{25}$N$_6$O$_5$ (M+H)$^+$: m/z=441.2; found 441.3.

Step 3: 2-(1-ethyl-3-methyl-1H-pyrazol-5-yl)-8-(3-methoxypropoxy)-9H-pyrimido[4,5-b]indole-6-carboxamide

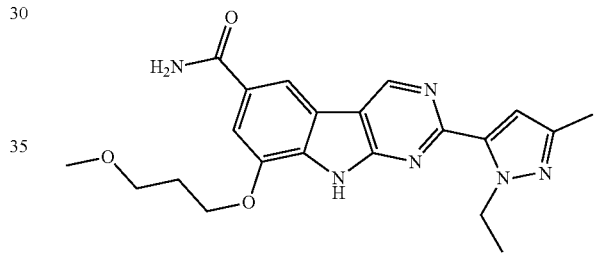

This compound was prepared using similar procedures as described for Example S67, Step 16 with 3-(2-(1-ethyl-3-methyl-1H-pyrazol-5-yl)pyrimidin-5-yl)-5-(3-methoxypropoxy)-4-nitrobenzamide replacing 3-(2-(1-ethyl-3-methyl-1H-pyrazol-5-yl)pyrimidin-5-yl)-5-methoxy-4-nitrobenzamide. LC-MS calculated for C$_{21}$H$_{25}$N$_6$O$_3$ (M+H)$^+$: m/z=409.2; found 409.2.

Step 4: (E)-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzofuro[6,7-c]imidazole-5-carboxamide This compound was prepared using similar procedures as described for Example S67, Step 17 with 2-(1-ethyl-3-methyl-1H-pyrazol-5-yl)-8-(3-methoxypropoxy)-9H-pyrimido[4,5-b]indole-6-carboxamide replacing 2-(1-ethyl-3-methyl-1H-pyrazol-5-yl)-8-methoxy-9H-pyrimido[4,5-b]indole-6-carboxamide. LC-MS calculated for C$_{42}$H$_{45}$N$_{12}$O$_6$ (M+H)$^+$: m/z=813.4; found 813.3. $^1$H NMR (600 MHz, DMSO) δ 12.97 (s, 1H), 9.48 (s, 1H), 8.41 (s, 1H), 8.04 (s, 1H), 7.85 (d, J=2.0 Hz, 1H), 7.81 (s, 1H), 7.56 (s, 1H), 7.36 (s, 1H), 7.31 (s, 1H), 6.77 (s, 1H), 6.44 (s, 1H), 5.97 (d, J=15.6 Hz, 1H), 5.79 (d, J=15.6 Hz, 1H), 5.35-5.17 (m, 2H), 5.07-4.80 (m, 2H), 4.58 (q, J=7.2 Hz, 2H), 4.48 (q, J=7.2 Hz, 2H), 4.12-3.98 (m, 2H), 3.26 (m, 2H), 3.13 (s, 3H), 2.19 (s, 3H), 2.08 (s, 3H), 1.76 (m, 2H), 1.27-1.07 (m, 6H).

287

Example S69. (E)-1-(4-(6-carbamoyl-2-(1-ethyl-3-methyl-1H-pyrazol-5-yl)-8-(3-hydroxypropoxy)-9H-pyrimido[4,5-b]indol-9-yl)but-2-en-1-yl)-2-(1-ethyl-3-methyl-1H-pyrazole-5-carboxamido)-1H-benzofuro[6,7-d]imidazole-5-carboxamide

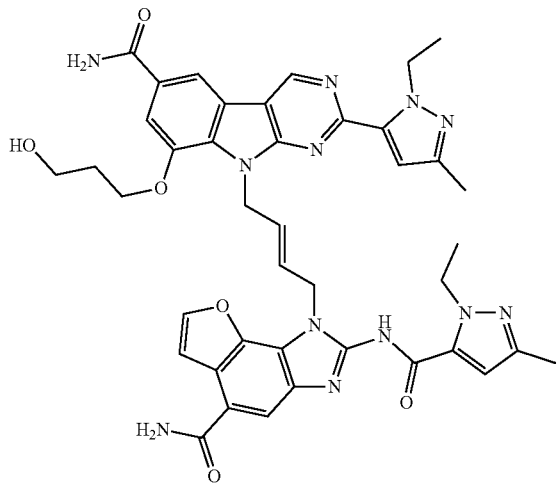 [SMILES: CCn1nc(C)cc1C(=O)Nc1nc2cc(C(N)=O)c3ccoc3c2n1C/C=C/Cn1c2nc(-c3cc(C)nn3CC)ncc2c2cc(C(N)=O)cc(OCCCO)c21]

Step 1: 3-bromo-5-(3-(tert-butyldimethylsilyloxy)propoxy)-4-nitrobenzamide

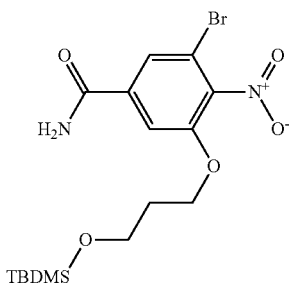

This compound was prepared using similar procedures as described for Example S68, Step 1 with 3-((tert-butyldimethylsilypoxy)propan-1-ol (Combi-Blocks, cat #QH-3826) replacing 3-morpholinopropan-1-ol. LC-MS calculated for $C_{16}H_{26}BrN_2O_5Si$ (M+H)⁺: m/z=433.1, 435.1; found 433.2, 435.2.

Step 2: 3-(3-(tert-butyldimethylsilyloxy)propoxy)-5-(2-(1-ethyl-3-methyl-1H-pyrazol-5-yl)pyrimidin-5-yl)-4-nitrobenzamide

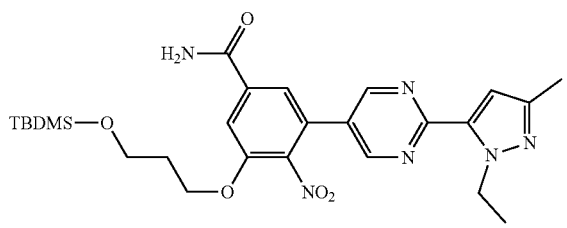

288

This compound was prepared using similar procedures as described for Example S67, Step 15 with 3-bromo-5-(3-(tert-butyldimethylsilyloxy)propoxy)-4-nitrobenzamide replacing 3-bromo-5-methoxy-4-nitrobenzamide. LC-MS calculated for $C_{26}H_{37}N_6O_5Si$ (M+H)⁺: m/z=541.3; found 541.3.

Step 3: 8-(3-(tert-butyldimethylsilyloxy)propoxy)-2-(1-ethyl-3-methyl-1H-pyrazol-5-yl)-9H-pyrimido[4,5-]indole-6-carboxamide

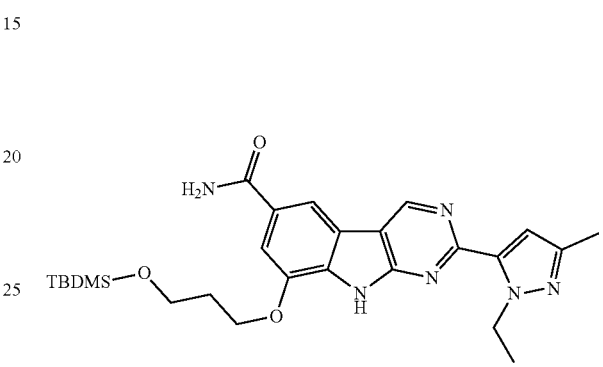

This compound was prepared using similar procedures as described for Example S67, Step 16 with 3-(3-(tert-butyldimethylsilyloxy)propoxy)-5-(2-(1-ethyl-3-methyl-1H-pyrazol-5-yl)pyrimidin-5-yl)-4-nitrobenzamide replacing 3-(2-(1-ethyl-3-methyl-1H-pyrazol-5-yl)pyrimidin-5-yl)-5-methoxy-4-nitrobenzamide. LC-MS calculated for $C_{26}H_{37}N_6O_3Si$ (M+H)⁺: m/z=509.3; found 509.3.

Step 4: (E)-1-(4-(6-carbamoyl-2-(1-ethyl-3-methyl-1H-pyrazol-5-yl)-8-(3-hydroxypropoxy)-9H-pyrimido[4,5-b]indol-9-yl)but-2-en-1-yl)-2-(1-ethyl-3-methyl-1H-pyrazole-5-carboxamido)-1H-benzofuro[6,7-c]imidazole-5-carboxamide This compound was prepared using similar procedures as described for Example S67, Step 17 with 8-(3-(tert-butyldimethylsilyloxy)propoxy)-2-(1-ethyl-3-methyl-1H-pyrazol-5-yl)-9H-pyrimido[4,5-b]indole-6-carboxamide replacing 2-(1-ethyl-3-methyl-1H-pyrazol-5-yl)-8-methoxy-9H-pyrimido[4,5-b]indole-6-carboxamide. The primary alcohol was deprotected during the process. Otherwise, the TBS group could be removed with the addition of 4 equivalents of HCl (0.015 mL of 4 M HCl in dioxane), followed by stirring at room temperature for 1 h. The reaction mixture was diluted with MeOH and purified by prep-HPLC (pH=2, acetonitrile/water+TFA) to give the desired product as its TFA salt. LC-MS calculated for $C_{41}H_{43}N_{12}O_6$ (M+H)+: m/z=799.3; found 799.4.

Example 1. (3S,6S,9S,12S)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-9-(3-guanidinopropyl)-5,8,11,14-tetraoxo-4,7,10,13-tetraazaheptadecanoic acid Step 2: 5-tert-butyl 2-methyl 1-methyl-6,7-dihydro-1H-imidazo[4,5-c]pyridine-2,5(4H)-dicarboxylate

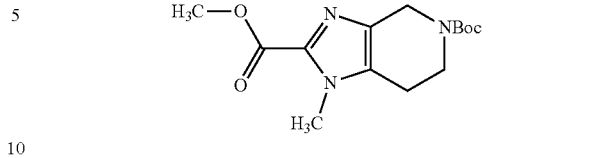

n-Butyllithium in hexanes (2.5 M, 7.00 mL, 17.49 mmol) was added to a cold (−78° C.) solution of tert-butyl 1-methyl-1,4,6,7-tetrahydro-5H-imidazo[4,5-c]pyridine-5-carboxylate (3.46 g, 14.6 mmol) in tetrahydrofuran (60 mL). The reaction mixture was stirred at −78 ° C. for 10 min prior to the addition of methyl chloroformate (1.69 mL, 21.87 mmol). After being stirred at −78 ° C. for 30 min, the reaction was then quenched with saturated aqueous NaHCO₃ solution, and extracted with ethyl acetate. The combined organic layers were washed with brine, dried over Na₂SO₄, filtered, and concentrated under reduced pressure. The residue was purified by flash chromatography on a silica gel column eluting with 80% ethyl acetate in hexanes to afford the desired product. LC-MS calculated for $C_{14}H_{22}N_3O_4$ (M+H)⁺: m/z=296.2; found 296.3.

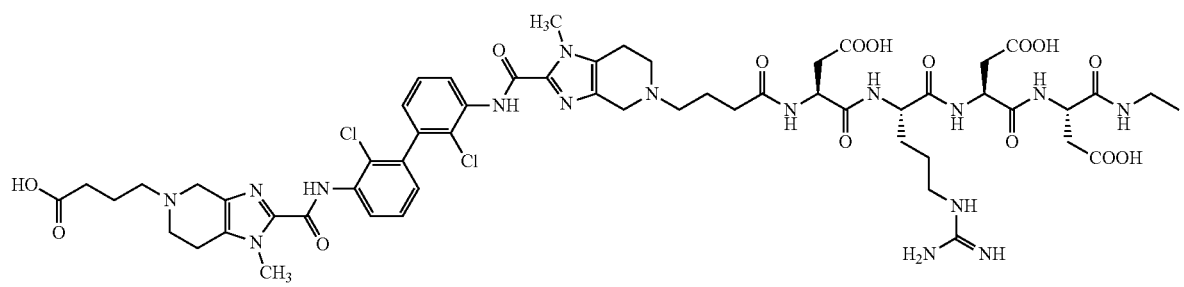

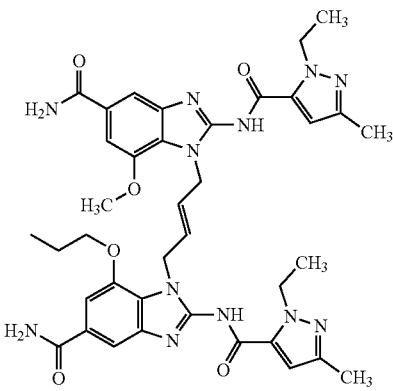

Step 1: tert-butyl 1-methyl-1,4,6,7-tetrahydro-5H-imidazo[4,5-c]pyridine-5-carboxylate

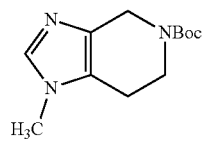 [SMILES: Cn1cnc2c1CCN(C(=O)OC(C)(C)C)C2]

A solution of 1-methyl-4,5,6,7-tetrahydro-1H-imidazo[4,5-c]pyridine (Accela, cat #SY032476: 2.0 g, 14.58 mmol) and (Boc)₂O (3.38 mL, 14.58 mmol) in dichloromethane (60 mL) was stirred at room temperature for 1 h. The reaction was quenched with saturated aqueous NaHCO₃ solution, and extracted with ethyl acetate. The combined organic layers were washed with brine, dried over Na₂SO₄, filtered, and concentrated under reduced pressure. The crude product was used directly in the next step without further purification. LC-MS calculated for $C_{12}H_{20}N_3O_2$ (M+H)⁺: m/z=238.2; found 238.2.

Step 3: tert-butyl 2-(3-bromo-2-chlorophenyl)carbamoyl)-1-methyl-1,4,6,7-tetrahydro-5H-imidazo[4,5-c]pyridine-5-carboxylate

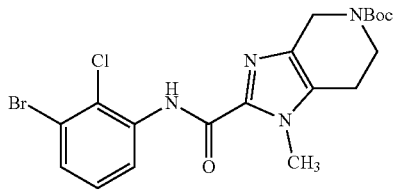 [SMILES: Cn1c(C(=O)Nc2cccc(Br)c2Cl)nc2c1CCN(C(=O)OC(C)(C)C)C2]

Potassium tert-butoxide in THF (1.0 M, 3.39 mL, 3.39 mmol) was added to a solution of 5-tert-butyl 2-methyl 1-methyl-6,7-dihydro-1H-imidazo[4,5-c]pyridine-2,5(4H)-dicarboxylate (500 mg, 1.69 mmol) and 3-bromo-2-chloroaniline (350 mg, 1.69 mmol) in tetrahydrofuran (12.0 mL). After being stirred at room temperature for 30 min, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 50% ethyl acetate in hexanes to afford the desired product. LC-MS calculated for C$_{19}$H$_{23}$BrClN$_4$O$_3$ (M+H)$^+$: m/z=469.1/471.1; found 469.1/471.1.

Step 4: tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate

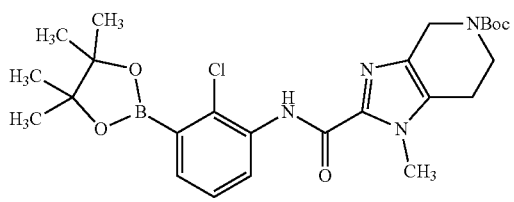 [SMILES: Cn1c(C(=O)Nc2cccc(B3OC(C)(C)C(C)(C)O3)c2Cl)nc2c1CCN(C(=O)OC(C)(C)C)C2]

A mixture of tert-butyl 2-((3-bromo-2-chlorophenyl)carbamoyl)-1-methyl-1,4,6,7-tetrahydro-5H-imidazo[4,5-c]pyridine-5-carboxylate (1.0 g, 2.13 mmol), 4,4,5,5,4',4',5',5'-octamethyl-[2,2]bi[[1,3,2]dioxaborolanyl] (0.649 g, 2.55 mmol), [1,1'-bis(diphenylphosphino)ferrocene]dichloropalladium(II) complexed with dichloromethane (1:1) (0.174 g, 0.213 mmol) and potassium acetate (0.522 g, 5.32 mmol) in 1,4-dioxane (24.0 mL) was purged with nitrogen and then stirred at 110° C. for 3 h. The reaction mixture was cooled to room temperature, diluted with dichloromethane, and then filtered through Celite. The filtrate was concentrated under reduced pressure, and the residue was purified by flash chromatography on a silica gel column eluting with 30% ethyl acetate in hexanes to afford the desired product. LC-MS calculated for C$_{25}$H$_{35}$BClN$_4$O$_5$ (M+H)$^+$: m/z=517.2; found 517.2.

Step 5: tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

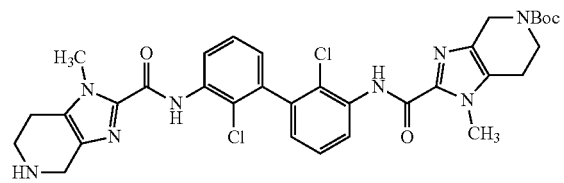 [SMILES: Cn1c(C(=O)Nc2cccc(-c3cccc(NC(=O)c4nc5c(n4C)CCN(C(=O)OC(C)(C)C)C5)c3Cl)c2Cl)nc2c1CCNC2]

A mixture of tert-butyl 2-((3-bromo-2-chlorophenyl)carbamoyl)-1-methyl-1,4,6,7-tetrahydro-5H-imidazo[4,5-c]pyridine-5-carboxylate (Step 3: 900 mg, 1.92 mmol) in trifluoroacetic acid (2 mL) and dichloromethane (4 mL) was stirred at room temperature for 1 h. The reaction mixture was concentrated under reduced pressure. A mixture of the above residue, tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Step 4: 1.19 g, 2.30 mmol), sodium carbonate (1.02 g, 9.58 mmol) and [1,1-bis(di-cyclohexylphosphino)ferrocene]dichloropalladium(II) (145 mg, 0.19 mmol) in 1,4-dioxane (12.0 mL) and water (6.0 mL) was purged with nitrogen and then stirred at 110° C. for 2 h. After being cooled to room temperature, the reaction mixture was diluted with water and extracted with dichloromethane. The combined organic layers were dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{33}$H$_{37}$Cl$_2$N$_8$O$_4$ (M+H)$^+$: m/z=679.2; found 679.2.

Step 6: 4,4'-(((((2,2'-dichloro-[1,1'-biphenyl]-3,3'-diyl)bis(azanediyl))bis(carbonyl)bis(1-methyl-1,4,6,7-tetrahydro-5H-imidazo[4,5-c]pyridine-2,5-diyl))dibutyric acid

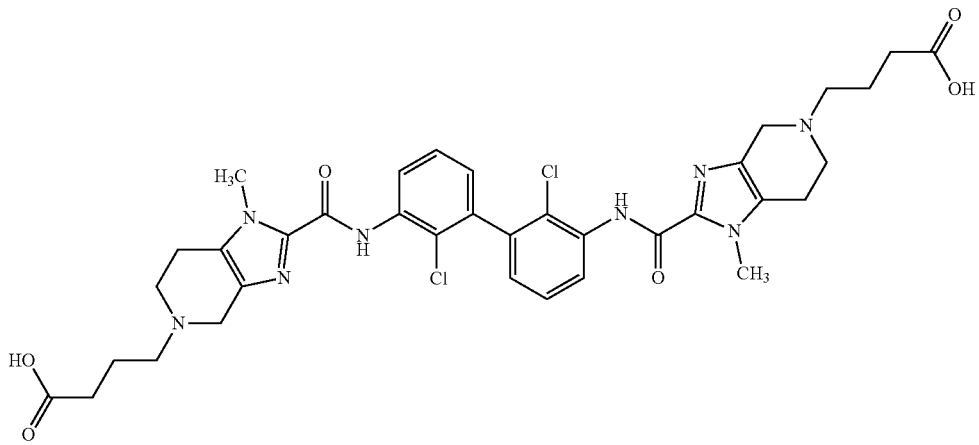 [SMILES: Cn1c(C(=O)Nc2cccc(-c3cccc(NC(=O)c4nc5c(n4C)CCN(CCCC(=O)O)C5)c3Cl)c2Cl)nc2c1CCN(CCCC(=O)O)C2]

A mixture of tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (300 mg, 0.385 mmol) in dichloromethane (10.0 mL) and trifluoroacetic acid (5.0 mL) was stirred at room temperature for 1 h. The mixture was concentrated under reduced pressure. The residue was sequentiantly treated with methyl 4-oxobutanoate (134 mg, 1.15 mmol), DIPEA (336 μL, 1.92 mmol) and sodium triacetoxyborohydride (326 mg, 1.54 mmol) in DCM (4.0 mL). The mixture was stirred at rt for 2 h. The reaction mixture was quenched with saturated aqueous NaHCO$_3$ solution, and extracted with dichloromethane. The organic layers were washed with brine, dried over Na$_2$SO$_4$, filtered and concentrated under reduced pressure. The residue was treated with LiOH (92 mg, 3.85 mmol) in a 1:1:1 mixture of THF, MeOH and water. After 12 h, the reaction mixture was diluted with MeOH then purified by prep-HPLC (pH=2, acetonitrile/water+TFA) to give the desired product as the TFA salt. LC-MS calculated for C$_{36}$H$_{41}$Cl$_2$N$_8$O$_6$ (M+H)$^+$: m/z=751.2; found 751.3.

Step 7: 4-chloro-3-methoxy-5-nitrobenzamide

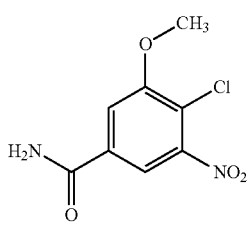

Methyl 4-chloro-3-methoxy-5-nitrobenzoate (Ark Pharm, cat #67521: 5.00 g, 20.36 mmol) was stirred in 30% ammonium hydroxide (49.9 ml, 385 mmol) at room temperature for 24 h. The solid was filtered and rinsed with cold water. The filter cake was then dried under vacuum to give 4-chloro-3-methoxy-5-nitrobenzamide (3.90 g, 16.9 mmol, 83% yield) as yellow powder. LC-MS calculated for C$_8$H$_8$ClN$_2$O$_4$ (M+H)$^+$: m/z=231.0; found 231.1.

Step 8: 4-chloro-3-hydroxy-5-nitrobenzamide

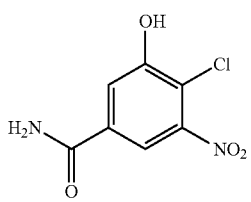 [SMILES: NC(=O)c1cc(O)c(Cl)c([N+](=O)[O-])c1]

In a 150 mL round-bottomed flask 4-chloro-3-methoxy-5-nitrobenzamide (1.50 g, 6.50 mmol) was dissolved in DCM (21 mL) to give a yellowish suspension. 1 M BBr$_3$ in DCM (19 mL, 19.5 mmol) was added to the reaction mixture dropwise. After the completion of the reaction, the reaction mixture was poured into ice water (200 mL). After stirred for 30 min, the reaction mixture was filtered through a Buchner funnel and the filter cake was rinsed with water to give 4-chloro-3-hydroxy-5-nitrobenzamide (1.22 g, 5.63 mmol, 87% yield) as yellow powder. LC-MS calculated for C$_7$H$_6$ClN$_2$O$_4$ (M+H)$^+$: m/z=217.0; found 217.1.

Step 9: tert-butyl (3-(5-carbamoyl-2-chloro-3-nitrophenoxy)propyl)carbamate

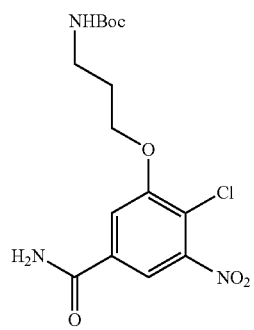 [SMILES: CC(C)(C)OC(=O)NCCCOc1cc(C(N)=O)cc([N+](=O)[O-])c1Cl]

To a solution of 4-chloro-3-hydroxy-5-nitrobenzamide (1319 mg, 6.09 mmol), tert-butyl (3-bromopropyl)carbamate (Ark Pharm, cat #AK-36511: 1.45 g, 6.09 mmol) in dry DMF (12 mL) was added Cs$_2$CO$_3$ (2.38 g, 7.31 mmol). The resulting yellow solution was stirred at 100° C. for 2 h. The reaction mixture was diluted with water (25 mL) dropwise. The reaction mixture was filtered through a Buchner funnel and the filter cake was rinsed with water to give tert-butyl (3-(5-carbamoyl-2-chloro-3-nitrophenoxy)propyl)carbamate (1.96 g, 5.24 mmol, 86% yield) as yellow powder. LC-MS calculated for C$_{15}$H$_{23}$ClN$_3$O$_6$ (M+H)$^+$: m/z=374.1; found 374.1.

Step 10: 4-chloro-3-methoxy-5-nitrobenzamide

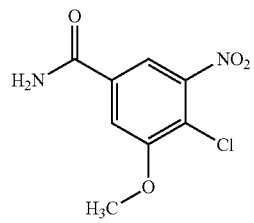

Methyl 4-chloro-3-methoxy-5-nitrobenzoate (Combi-blocks, cat #QB-0156: 10.0 g, 40.7 mmol) was stirred in 30% ammonium hydroxide (100 ml, 769 mmol) at room temperature for 24 h. The solid was filtered and rinsed with cold water. The solid was then dried under vacuum to give 4-chloro-3-methoxy-5-nitrobenzamide (9.00 g, 39.0 mmol, 96% yield) as yellow powder. LC-MS calculated for C$_8$H$_8$ClN$_2$O$_4$ (M+H)$^+$: m/z=231.0; found 231.0.

Step 11: tert-butyl (E)-(4-((4-carbamoyl-2-methoxy-6-nitrophenyl)amino)but-2-en-1-yl)carbamate

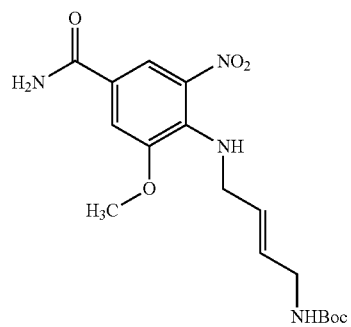 [SMILES: COc1cc(C(N)=O)cc([N+](=O)[O-])c1NC/C=C/CNC(=O)OC(C)(C)C]

To a solution of 4-chloro-3-methoxy-5-nitrobenzamide (3.00 g, 13.0 mmol), tert-butyl (E)-(4-aminobut-2-en-1-yl)carbamate hydrochloride (Ark Pharm, cat #AK308564: 3.48 g, 15.6 mmol) in dry EtOH (26 mL) was added DIPEA (6.82 mL, 39.0 mmol). The resulting yellow solution was microwaved at 120° C. with stirring for 4 h. The reaction mixture was diluted with water (18 mL) dropwise. The reaction mixture was filtered through a Buchner funnel and the filter cake was rinsed with water to give tert-butyl (E)-(4-((4-carbamoyl-2-methoxy-6-nitrophenyl)amino)but-2-en-1-yl)carbamate (3.60 g, 9.46 mmol, 72.7% yield) as yellow solid. LC-MS calculated for $C_{17}H_{25}N_4O_6$ $(M+H)^+$: m/z=381.2; found 381.3.

Step 12: (E)-4-((4-aminobut-2-en-1-yl)amino)-3-methoxy-5-nitrobenzamide

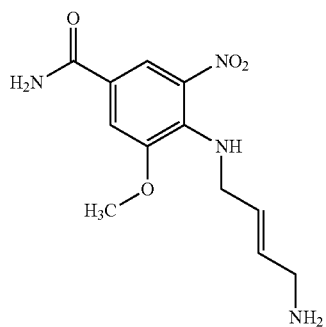 [SMILES: COc1cc(C(N)=O)cc([N+](=O)[O-])c1NC/C=C/CN]

In a 4 dram vial tert-butyl (E)-(4-((4-carbamoyl-2-methoxy-6-nitrophenyl)amino)but-2-en-1-yl)carbamate (4.96 g, 13.0 mmol) was dissolved in EtOH (26 mL) to give a yellow suspension. 4M HCl in 1,4-dioxane (16.3 mL, 65.0 mmol) was added. After 16 h, the reaction mixture was filtered through a Buchner funnel and the filter cake was rinsed with diethyl ether (3 mL×3) to give (E)-4-((4-aminobut-2-en-1-yl)amino)-3-methoxy-5-nitrobenzamide (3.24 g, 11.6 mmol, 89% yield) as bright orange solid. LC-MS calculated for $C_{12}H_{17}N_4O_4$ $(M+H)^+$: m/z=281.1; found 281.3.

Step 13: tert-butyl (E)-(3-(5-carbamoyl-2-((4-((4-carbamoyl-2-methoxy-6-nitrophenyl)amino)but-2-en-1-yl)amino)-3-nitrophenoxy)propyl)carbamate

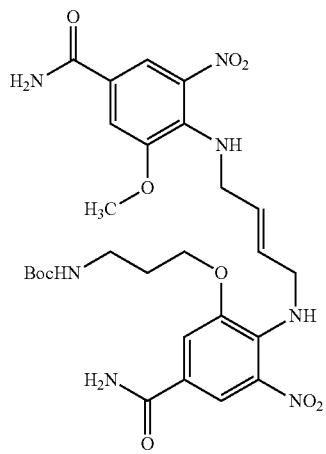

To a solution of tert-butyl (3-(5-carbamoyl-2-chloro-3-nitrophenoxy)propyl)carbamate (Step 9: 1.33 g, 3.55 mmol), (E)-4-((4-aminobut-2-en-1-yl)amino)-3-methoxy-5-nitrobenzamide (Step 12: 1.09 g, 3.90 mmol) in dry EtOH (18 mL) was added DIPEA (3.10 mL, 17.7 mmol). The resulting yellow solution was microwaved at 120° C. with stirring for 2 h. The reaction mixture was diluted with water (18 mL) dropwise. The reaction mixture was filtered through a Buchner funnel and the filter cake was rinsed with water. After dried under vacuum, tert-butyl (E)-(3-(5-carbamoyl-2-((4-((4-carbamoyl-2-methoxy-6-nitrophenyl)amino)but-2-en-1-yl)amino)-3-nitrophenoxy)propyl)carbamate was obtained as yellow solid (606 mg, 28% yield). LC-MS calculated for $C_{27}H_{36}N_7O_{10}$ $(M+H)^+$: m/z=618.2; found 618.3.

Step 14: tert-butyl (E)-(3-(3-amino-2-((4-((2-amino-4-carbamoyl-6-methoxyphenyl)amino)but-2-en-1-yl)amino)-5-carbamoylphenoxy)propyl)carbamate

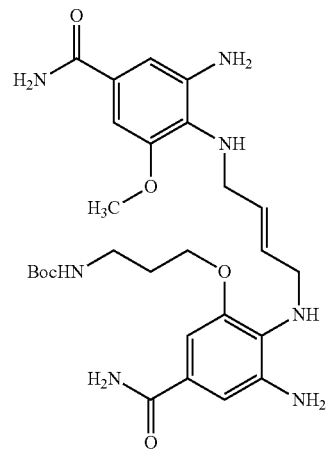 [SMILES: COc1cc(C(N)=O)cc(N)c1NC/C=C/CNc1c(N)cc(C(N)=O)cc1OCCCNC(=O)OC(C)(C)C]

To a solution of tert-butyl (E)-(3-(3-amino-2-((4-((2-amino-4-carbamoyl-6-methoxyphenyl)amino)but-2-en-1-yl)amino)-5-carbamoylphenoxy)propyl)carbamate (200 mg, 0.324 mmol) in MeOH (4.9 mL) was added sodium hydrosulfite (564 mg, 3.24 mmol) in water (2.0 mL) and 30% aq ammonium hydroxide (1.05 mL, 8.10 mmol) at 0° C. The reaction mixture was warmed to room temperature. After 10 min, water (15 mL) was added to the reaction mixture followed by extraction with ethyl acetate (10 mL×6). The combined organic layers were dried $Na_2SO_4$, filtered and concentrated to dryness and used for next step without further purification. LC-MS calculated for $C_{27}H_{40}N_7O_6$ $(M+H)^+$: m/z=558.3; found 558.3.

Step 15: tert-butyl (E)-(3-((2-amino-1-(4-(2-amino-5-carbamoyl-7-methoxy-1H-benzo[d]imidazol-1-yl)but-2-en-1-yl)-5-carbamoyl-1H-benzo[d]imidazol-7-yl)oxy)propyl)carbamate

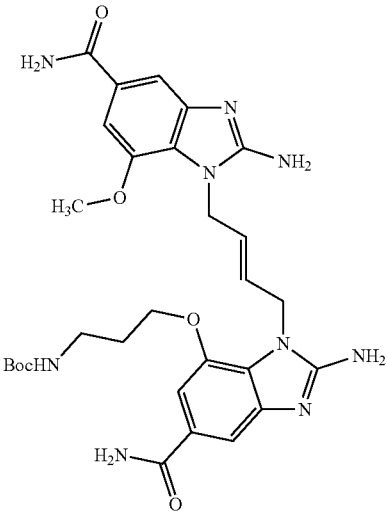 [SMILES: COc1cc(C(N)=O)cc2nc(N)n(C/C=C/Cn3c(N)nc4cc(C(N)=O)cc(OCCCNC(=O)OC(C)(C)C)c43)c12]

To a solution of above crude product in MeOH (4.9 mL) was added 3M BrCN in DCM (432 μL, 1.30 mmol). After 5 hr, the reaction mixture was concentrated to dryness and used for next step without further purification. LC-MS calculated for $C_{29}H_{38}N_9O_6$ (M+H)$^+$: m/z=608.3; found 608.4.

Step 16: tert-butyl (E)-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamate

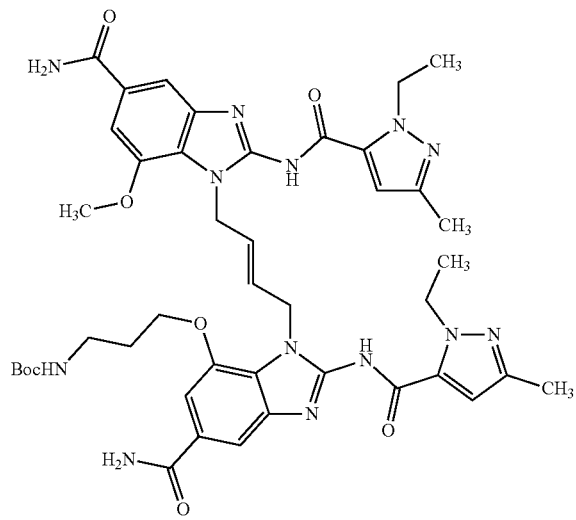 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(=O)OC(C)(C)C)c21]

To a solution of above crude product in DMF (5 mL) was added DIPEA (339 μL, 1.94 mmol), 1-ethyl-3-methyl-1H-pyrazole-5-carboxylic acid (200 mg, 1.30 mmol) and BOP (573 mg, 1.30 mmol). After 1 h, water (5 mL) was added to the reaction mixture followed by extraction with ethyl acetate (30 mL×6). The combined organic layers were dried Na$_2$SO$_4$, filtered and concentrated. The crude product was added to a silica gel column and was eluted with ethyl acetate/hexane from 50% to 100%, then methanol/dichloromethane from 0% to 10% to give tert-butyl (E)-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamate (158 mg, 0.180 mmol, 55.4% yield over three steps) as a yellow solid. LC-MS calculated for $C_{43}H_{54}N_{13}O_8$ (M+H)+: m/z=880.4; found 880.4.

Step 17: (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide

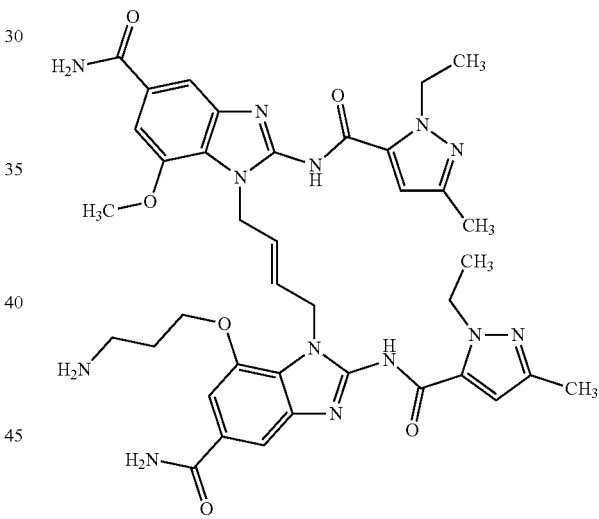

In a 1 dram vial tert-butyl (E)-(3-(5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamate (160 mg, 0.182 mmol) was dissolved in DCM (1.5 mL) to give a brownish suspension. Trifluoroacetic acid (0.5 mL) was added to the reaction mixture. After 1 h, the reaction mixture was concentrated to dryness and then diluted with MeOH then purified by prep-HPLC (pH 32 2, acetonitrile/water+ TFA) to give the desired product as the TFA salt. LC-MS calculated for $C_{38}H_{46}N_{13}O_6$ (M+H)$^+$: m/z=780.4; found 780.4.

Step 18: tert-butyl (6S,9S,12S,15S)-15-amino-6,9-bis(2-(tert-butoxy)-2-oxoethyl)-1-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate 4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)-9-(3-guanidinopropyl)-5,8,11,14-tetraoxo-4,7,10,13-tetraazaheptadecanoic acid In a 1 dram vial tert-butyl (6S,9S,12S,15S)-15-amino-6,9-bis(2-(tert-butoxy)-2-oxoethyl)-1-((5-carbamoyl-1-((E)-4-(5-carbamoyl-2-(1-ethyl-3-methyl-1H-pyrazole-5-car-

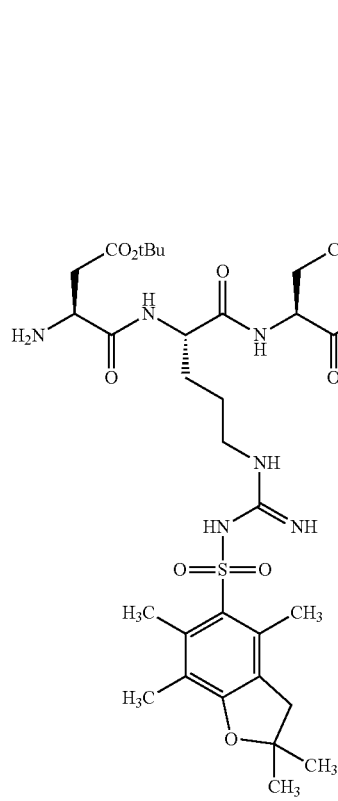
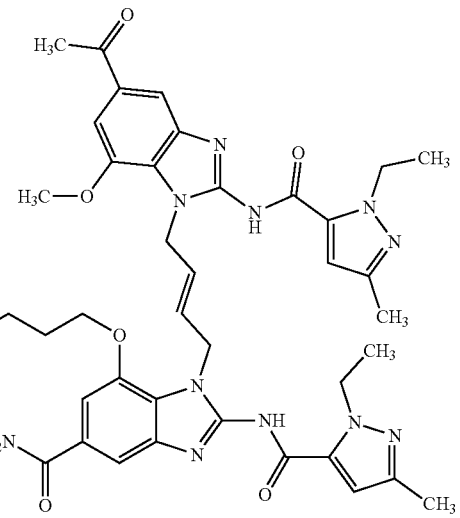

In a 1 dram vial (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (26.9 mg, 0.034 mmol) was dissolved in DMF (1.5 mL) to give a pale yellow solution. Fmoc-Asp(OtBu)-Arg(Pbf)-Asp(OtBu)-Asp(OtBu)-OH (Peptides International, cat #PCS-33379-PI: 48.1 mg, 0.041 mmol), DIPEA (30.1 μL, 0.172 mmol) and BOP (22.9 mg, 0.052 mmol) were added to the reaction mixture in one portion. After 1 h, piperidine (0.1 mL) was added. After 1 h, the reaction mixture was diluted with MeOH then purified by prep-HPLC (pH=2, acetonitrile/water+TFA) to give the desired product as the TFA salt. LC-MS calculated for $C_{81}H_{114}N_{20}O_{19}S$ $(M+2H)^{2+}$: m/z=851.9; found 851.7.

Step 19: (3S,6S,9S,12S)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-6,12-bis(carboxymethyl)-17-(2-((3'-(5-(3-carboxypropyl)-1-methylboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate (5 mg, 2.94 μmol) dissolved in DMF (294 μL) to give a colorless solution. 4,4'-((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))dibutyric acid (Step 6: 4.42 mg, 5.88 μmol), DIPEA (2.57 μL, 0.015 mmol) and BOP (3.90 mg, 8.81 μmol) were added to the reaction mixture in one portion. After 30 min, the reaction mixture was concentrated to dryness. Trifluoroacetic acid (0.5 mL) was added to the reaction mixture. After 20 min, the reaction mixture was diluted with water and MeOH then purified by prep-HPLC (pH=2, acetonitrile/water+TFA) to give the desired product as the TFA salt. LC-MS calculated for $C_{92}H_{113}Cl_2N_{28}O_{21}$ $(M+3H)^{3+}$: m/z=672.5; found 672.3.

Example 2. 4-(2-((3'-(5-(4-(((S)-1-(((S)-1-((4-((((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamoyl)oxy)methyl)phenyl)amino)-1-oxo-5-ureidopentan-2-yl)amino)-3-methyl-1-oxobutan-2-yl)amino)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl) butanoic acid

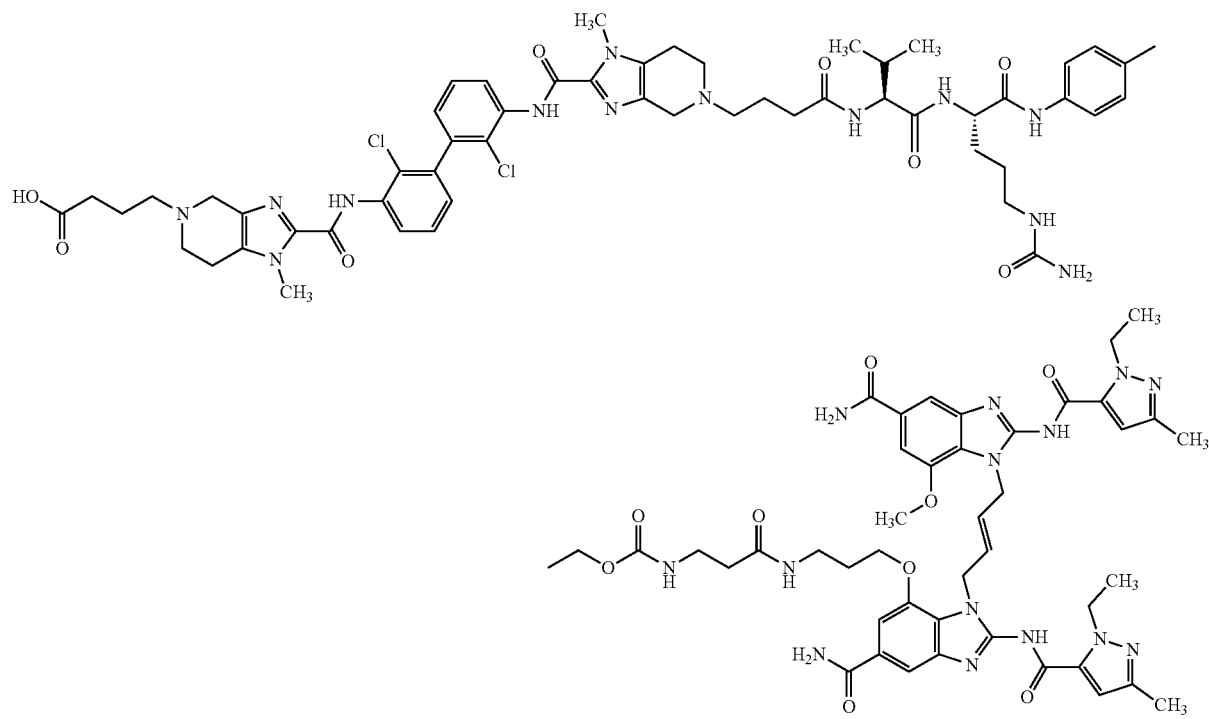

Step 1: (E)-7-(3-(3-aminopropanamido)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide

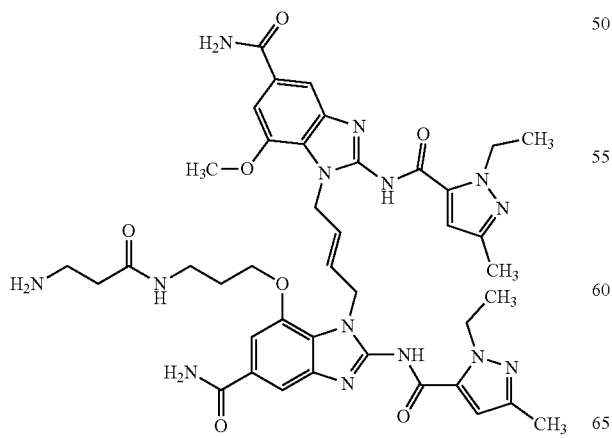

In a 1 dram vial (E)-7-(3-aminopropoxy)-1-(4-(5-carbamoyl-2 -(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (Example 1, Step 17: 43 mg, 0.049 mmol) was dissolved in DMF (489 μL) to give a color solution. Boc-beta-alanine (Chem-Impex, cat #01323: 27.7 mg, 0.147 mmol), DIPEA (25.6 μL, 0.147 mmol) and BOP (64.8 mg, 0.147 mmol) were added to the reaction mixture in one portion. After 30 min, the reaction mixture was concentrated to dryness and dissolved in DCM (0.5 mL). Trifluoroacetic acid (0.5 mL) was added to the reaction mixture. After 30 min, the reaction mixture was concentrated to dryness and diluted with MeOH then purified by prep-HPLC (pH=2, acetonitrile/water+TFA) to give the desired product as the TFA salt. LC-MS calculated for $C_{41}H_{51}N_{14}P_7$ (M+H)$^+$: m/z=851.4; found 851.3.

Step 2: 4-((S)-2-((S)-2-amino-3-methylbutanamido)-5-ureidopentanamido)benzyl (3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyltamino)-3-oxopropyl)carbamate (0.1 mL) was added. After 1 hr, the reaction mixture was diluted with MeOH then purified by prep-HPLC (pH=2, acetonitrile/water+TFA) to give the desired product as the TFA salt. LC-MS calculated for $C_{60}H_{79}N_{19}O_{12}$ (M+2H)$^{2+}$: m/z=628.8; found 628.7.

Step 3: 4-(2-((3'-(5-(4-(((S)-1-(((S)-1-((4-(((((3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamoyl)oxy)methyl)phenyl)amino)-1-oxo-5-ureidopentan-2-yl)amino)-3-methyl-1-oxobutan-2-yl)amino)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid In a 1 dram vial 4-((S)-2-((S)-2-amino-3-methylbutanamido)-5-ureidopentanamido)benzyl (3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamate (3.0 mg, 2.39 μmol) dissolved in DMF (239 μl) to give a colorless solution. 4,4'-((((2,2'-Dichloro-

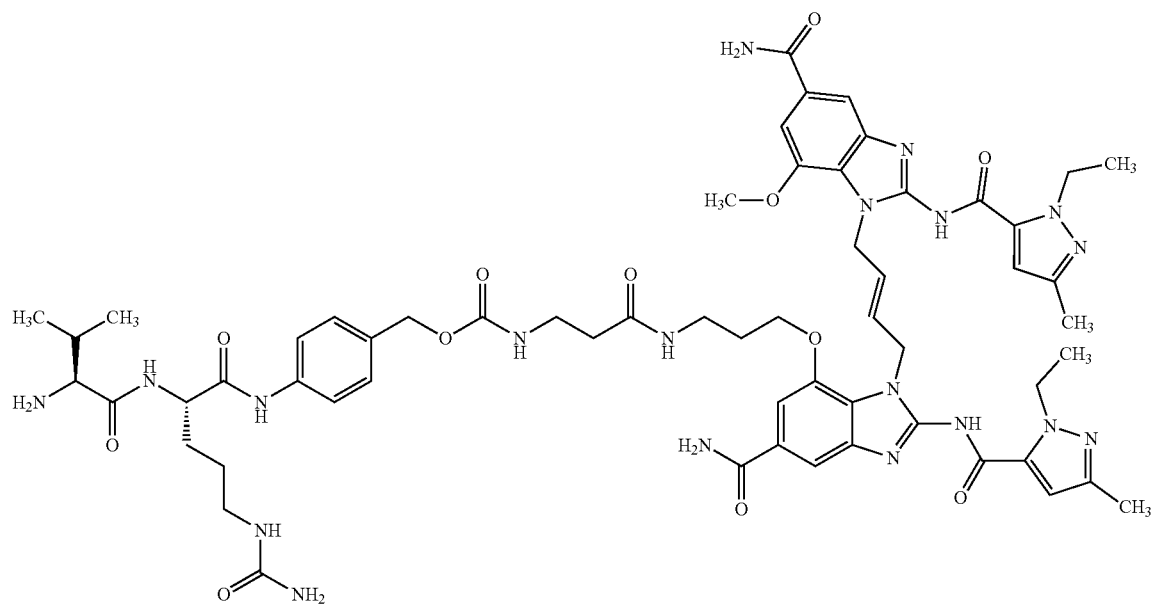 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(=O)CCNC(=O)OCc3ccc(NC(=O)[C@H](CCCNC(N)=O)NC(=O)[C@@H](N)C(C)C)cc3)c21]

In a 1 dram vial (E)-7-(3-(3-aminopropanamido)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (4.0 mg, 4.70 μmol) was dissolved in DMF (470 μL) to give a pale yellow solution. (9H-fluoren-9-yl)methyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate (BroadPharm, cat #BP-22309: 7.21 mg, 9.40 μmol) and DMAP (2.87 mg, 0.024 mmol) were added to the reaction mixture. After 30 min, piperidine

[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))dibutyric acid (Example 1, Step 6: 3.59 mg, 4.78 μmol), DIPEA (2.08 μL, 0.012 mmol) and BOP (3.17 mg, 7.16 μmol) were added to the reaction mixture in one portion. After 30 min, the reaction mixture was diluted with water and MeOH then purified by prep-HPLC (pH=2, acetonitrile/water+TFA) to give the desired product as the TFA salt. LC-MS calculated for $C_{96}H_{118}Cl_2N_{27}O_{17}$ (M+3H)$^{3+}$: m/z=664.2; found 664.0.

Example 3. (4-(2-((3'-(5-(4-(((S)-1-(((S)-1-((4-((((3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamoyl)oxy)methyl)phenyl)amino)-1-oxo-5-ureidopentan-2-yl)amino)-3-methyl-1-oxobutan-2-yl)amino)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoyl)-L-aspartic acid

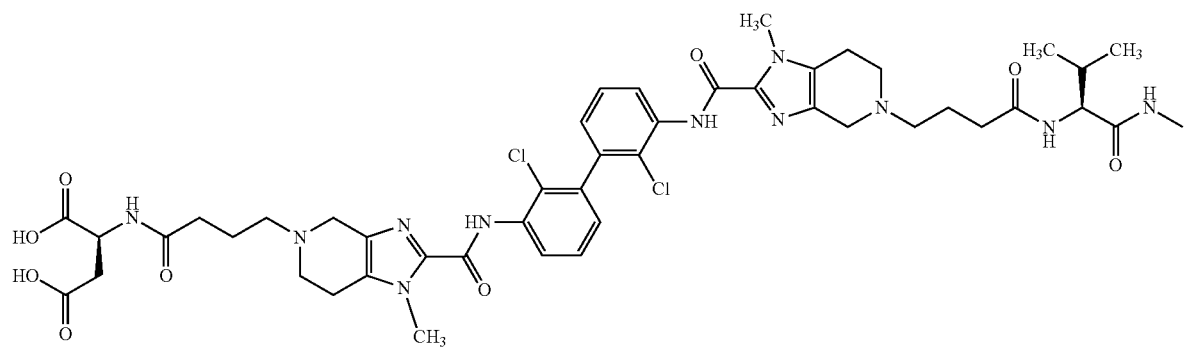

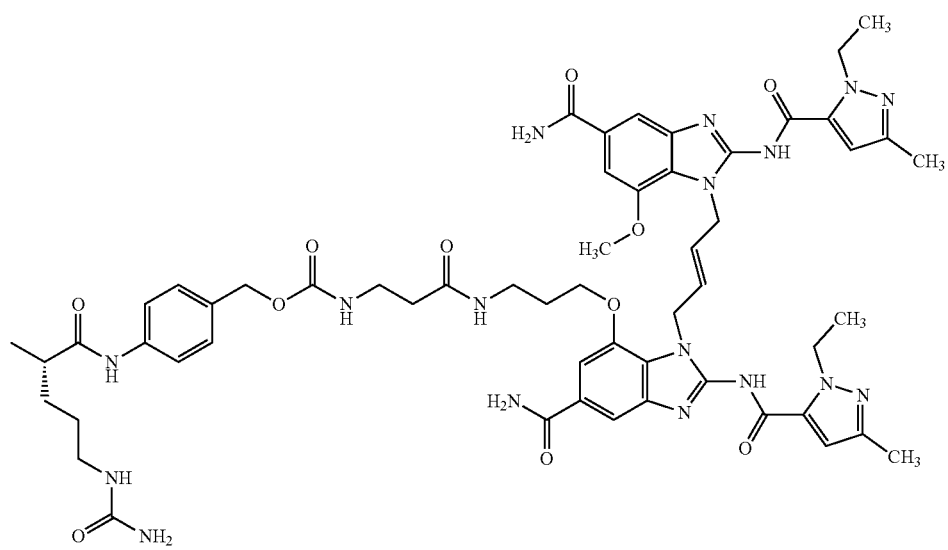

Step 1: (S)-4-(2-((2,2'-dichloro-3'-(5-(4-(((1,4-dibutoxy-1,4-dioxobutan-2-yl)amino)-4-oxobutyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)butanoic acid

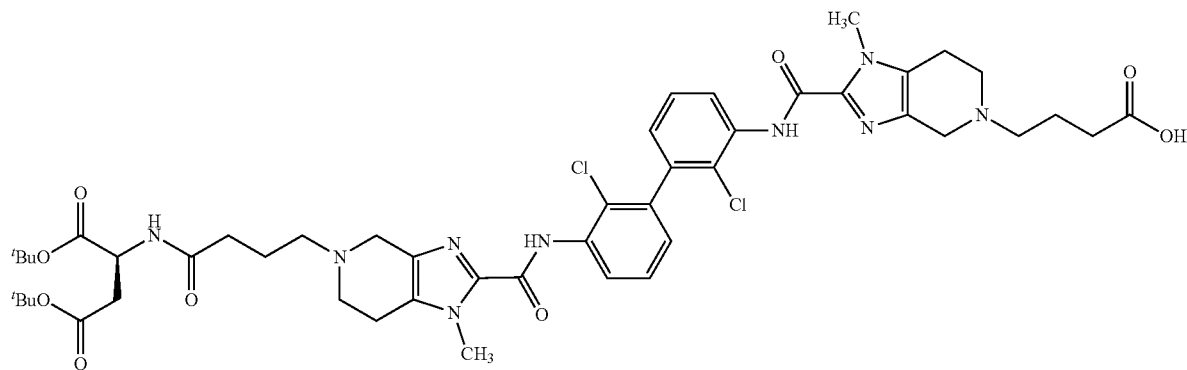 [SMILES: Cn1c(C(=O)Nc2cccc(-c3cccc(NC(=O)c4nc5c(n4C)CCN(CCCC(=O)N[C@@H](CC(=O)OC(C)(C)C)C(=O)OC(C)(C)C)C5)c3Cl)c2Cl)nc2c1CCN(CCCC(=O)O)C2]

In a 1 dram vial 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))dibutyric acid (Example 1, Step 6: 20 mg, 0.027 mmol) was dissolved in DMF (0.66 mL) to give a color solution. H-Asp(OtBu)-OtBu HCl (Combi-blocks, cat #SS-7947: 7.50 mg, 0.027 mmol), DIPEA (23.4 μL, 0.135 mmol) and BOP (23.5 mg, 0.053 mmol) were added to the reaction mixture in one portion. After 1 h, the reaction mixture was diluted with water and MeOH then purified by prep-HPLC (pH=2, acetonitrile/water+TFA) to give the desired product as the TFA salt. LC-MS calculated for $C_{48}H_{62}Cl_2N_9O_9$ $(M+H)^+$: m/z=978.4; found 978.6.

Step 2: (4-(2-((3'-(5-(4-(((S)-1-(((S)-1-((4-(((3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamoyl)oxy)methyl)phenyl)amino)-1-oxo-5-ureidopentan-2-yl)amino)-3-methyl-1-oxobutan-2-yl)amino)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoyl)-L-aspartic acid In a 1 dram vial (S)-4-(2-((2,2'-dichloro-3'-(5-(4-(((1,4-dibutoxy-1,4-dioxobutan-2-yl)amino)-4-oxobutyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)butanoic acid (4.1 mg, 4.19 μmol) was dissolved in DMF (419 μL) to give a colorless solution. 4-((S)-2-((S)-2-amino-3-methylbutanamido)-5-ureidopentanamido)benzyl (3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl) oxy) propyl)amino)-3-oxopropyl)carbamate (Example 2, Step 2: 5.26 mg, 4.19 μmol), DIPEA (3.66 μL, 0.021 mmol) and BOP (3.70 mg, 8.38 μmol) were added to the reaction mixture in one portion. After 1 h, the reaction mixture was concentrated to dryness and dissolved in DCM (0.5 mL). Trifluoroacetic acid (0.5 mL) was added to the reaction mixture. After 30 min, the reaction mixture was concentrated to dryness and diluted with MeOH then purified by prep-HPLC (pH=2, acetonitrile/water+TFA) to give the desired product as the TFA salt. LC-MS calculated for $C_{100}H_{123}Cl_2N_{28}O_{20}$ $(M+3H)^{3+}$: m/z=702.6; found 702.5.

Example 4. (3S,6S,9S,12S)-3-((2-(1-(2-(((S)-1-(((S)-1-((4-((((3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamoyl)oxy)methyl)phenyl)amino)-1-oxo-5-ureidopentan-2-yl)amino)-3-methyl-1-oxobutan-2-yl)amino)-2-oxoethyl)-1H-1,2,3-triazol-4-yl)ethyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-9-(3-guanidinopropyl)-5,8,11,14-tetraoxo-4,7,10,13-tetraazaheptadecanoic acid

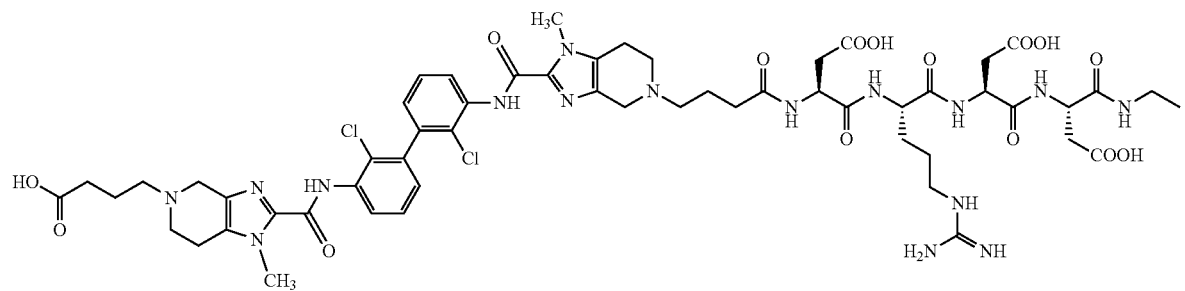

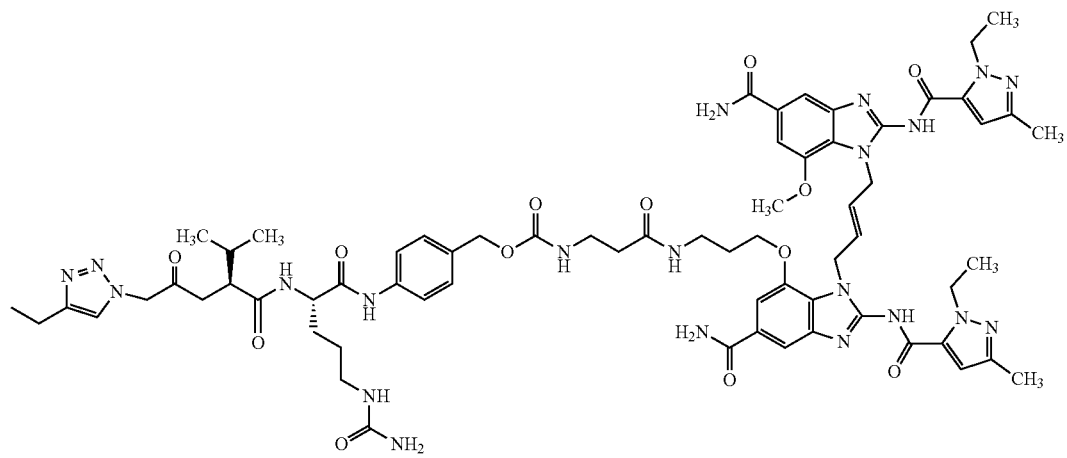

311

Step 1: tert-butyl (3S,6S,9S,12S)-3-amino-9,12-bis(2-(tert-butoxy)-2-oxoethyl)-4,7,10,13-tetraoxo-6-(3-(3-((2,2,4,6,7-pentamethyl-2,3-dihydrobenzofuran-5-yl)sulfonyl)guanidino)propyl)-5,8,11,14-tetraazaoctadec-17-ynoate

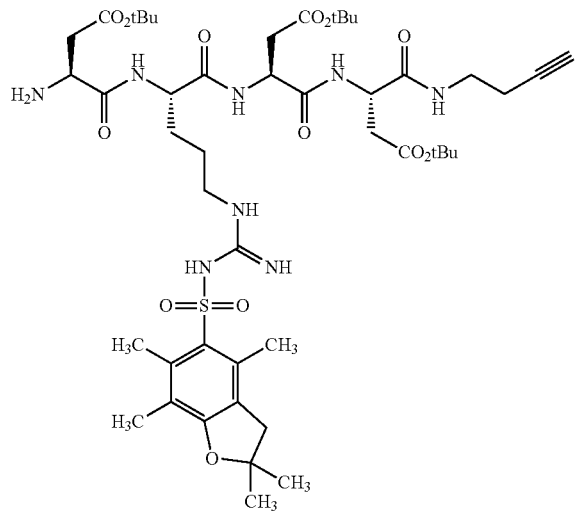 [SMILES: C#CCCNC(=O)[C@H](CC(=O)OC(C)(C)C)NC(=O)[C@H](CC(=O)OC(C)(C)C)NC(=O)[C@H](CCCNC(=N)NS(=O)(=O)c1c(C)c(C)c2c(c1C)CC(C)(C)O2)NC(=O)[C@@H](N)CC(=O)OC(C)(C)C]

312

In a 1 dram vial but-3-yn-1-amine (4.63 mg, 0.067 mmol) was dissolved in DMF (446 μL). Fmoc-Asp(OtBu)-Arg(Pbf)-Asp(OtBu)-Asp(OtBu)-OH (Peptides International, cat #PCS-33379-PI: 50 mg, 0.045 mmol), DIPEA (31.2 μL, 0.179 mmol) and HATU (33.9 mg, 0.089 mmol) were added to the reaction mixture in one portion. After 1 h, piperidine (0.1 mL) was added. After 1 h, the reaction mixture was diluted with MeOH then purified by prep-HPLC (pH=2, acetonitrile/water+TFA) to give the desired product as the TFA salt. LC-MS calculated for $C_{47}H_{75}N_8O_{13}S$ $(M+H)^+$: m/z=991.5; found 991.5.

Step 2: 4-(2-((2,2'-dichloro-3'-(1-methyl-5-(((6S,9S,12S,15S)-6,12,15-tris(2-(tert-butoxy)-2-oxoethyl)-4,7,10,13,16-pentaoxo-9-(3-(3-((2,2,4,6,7-pentamethyl-2,3-dihydrobenzofuran-5-yl)sulfonyl)gnanidino)propyl)-5,8,11,14,17-pentaazahenicos-20-yn-1-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)butanoic acid

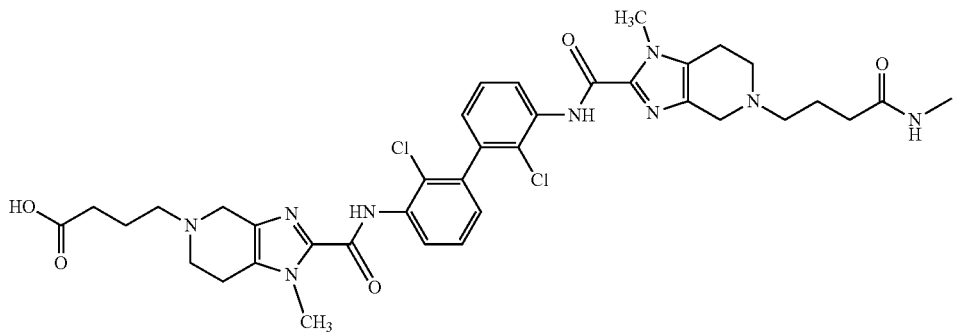

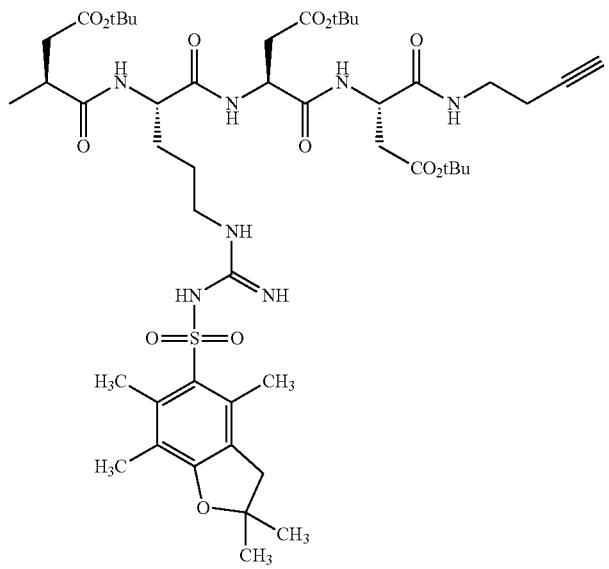

313

In a 1 dram vial tert-butyl (3S,6S,9S,12S)-3-amino-9,12-bis(2-(tert-butoxy)-2-oxoethyl)-4,7,10,13-tetraoxo-6-(3-(3-((2,2,4,6,7-pentamethyl-2,3-dihydrobenzofuran-5-yl)sulfonyl)guanidino)propyl)-5,8,11,14-tetraazaoctadec-17-ynoate (18 mg, 0.018 mmol) was dissolved in DMF (1.8 mL). 4,4'-((((2,2'-Dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))dibutyric acid (Example 1, Step 6: 27.3 mg, 0.036 mmol), DIPEA (15.9 µL, 0.091 mmol) and HATU (13.8 mg, 0.036 mmol) were added to the reaction mixture in one portion. After 1 h, the reaction mixture was diluted with MeOH then purified by prep-HPLC (pH=2, acetonitrile/water+TFA) to give the desired product as the TFA salt. LC-MS calculated for $C_{83}H_{114}Cl_2N_{16}O_{18}S$ $(M+2H)^{2+}$: m/z=863.4; found 863.2.

Step 3: (3S,6S,9S,12S)-9,12-bis(carboxymethyl)-3-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-6-(3-guanidinopropyl)-4,7,10,13-tetraoxo-5,8,11,14-tetraazaoctadec-17-ynoic acid

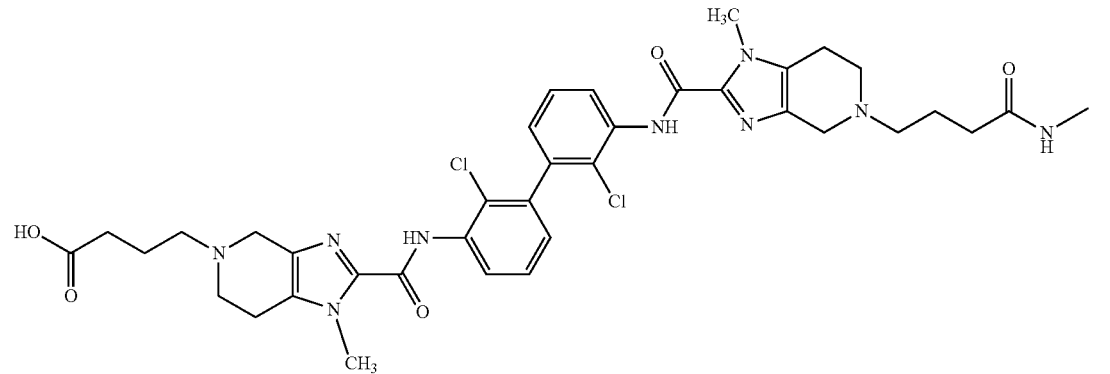

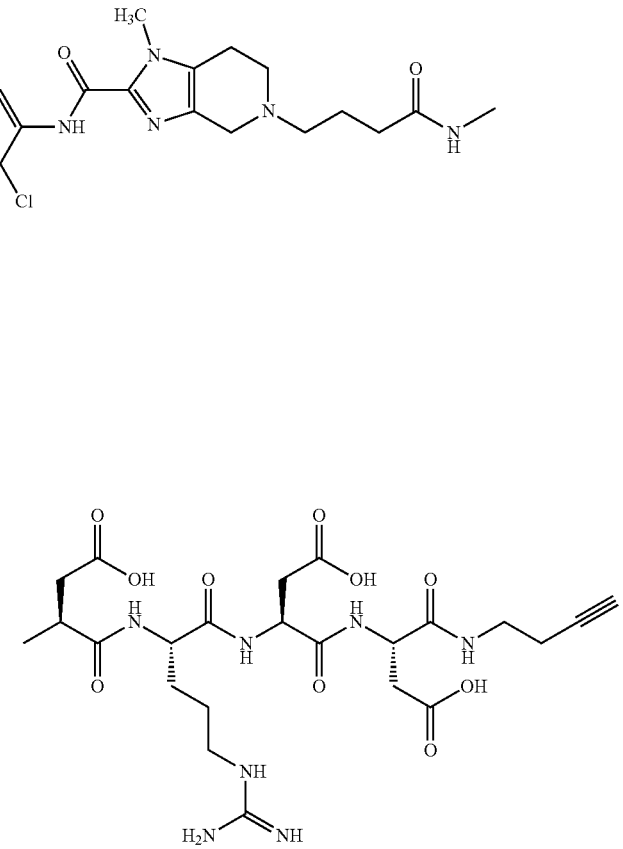

In a 1 dram vial 4-(2-((2,2'-dichloro-3'-(1-methyl-5-((6S,9S,12S,15S)-6,12,15-tris(2-(tert-butoxy)-2-oxoethyl)-4,7,10,13,16-pentaoxo-9-(3-(3-((2,2,4,6,7-pentamethyl-2,3-dihydrobenzofuran-5-yl)sulfonyl)guanidino)propyl)-5,8,11,14,17-pentaazahenicos-20-yn-1-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)butanoic acid (15 mg, 8.7 µmol) was dissolved in DCM (0.5 mL).

Trifluoroacetic acid (0.5 mL) was added. After 1.5 h, the reaction mixture was diluted with MeOH then purified by prep-HPLC (pH=2, acetonitrile/water+TFA) to give the desired product as the TFA salt. LC-MS calculated for $C_{58}H_{74}Cl_2N_{16}O_{15}$ $(M+2H)^{2+}$: m/z=652.3; found 652.3.

Step 4: 4-((S)-2-((S)-2-(2-azidoacetamido)-3-methylbutana-mido)-5-ureidopentanamido)benzyl (3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyltamino)-3-oxopropyl)carbamate

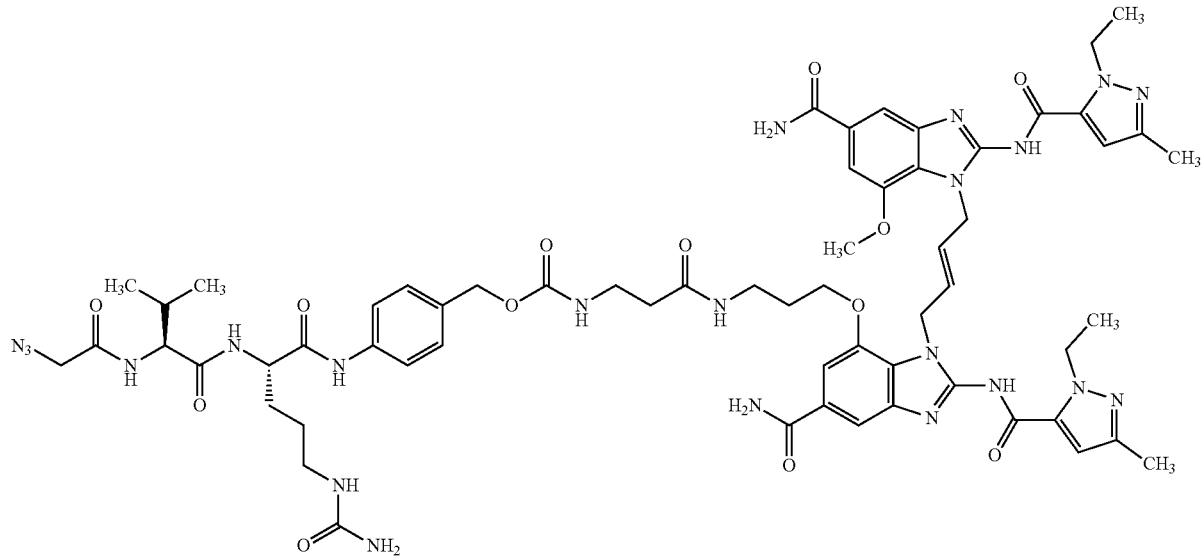 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(=O)CCNC(=O)OCc3ccc(NC(=O)[C@H](CCCNC(N)=O)NC(=O)[C@@H](NC(=O)CN=[N+]=[N-])C(C)C)cc3)c21]

In a 1 dram vial 4-((S)-2-((S)-2-amino-3-methylbutana-mido)-5-ureidopentanamido)benzyl (3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamate (Example 2, Step 2: 5.0 mg, 3.98 μmol) was dissolved in DMF (398 μL). Azidoacetic acid NHS ester (Aldrich, cat #900919: 1.18 mg, 5.97 μmol) and DMAP (1.46 mg, 0.012 mmol) were added to the reaction mixture in one portion. After 1 h, the reaction mixture was diluted with MeOH then purified by prep-HPLC (pH=2, acetonitrile/water+TFA) to give the desired product as the TFA salt. LC-MS calculated for $C_{62}H_{80}N_{22}O_{13}$ $(M+2H)^{2+}$: m/z=670.4; found 670.6.

Step 5: (3S,6S,9S,12S)-3-((2-(1-(2-(((S)-1-(((S)-1-((4-((((3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamoyl)oxy)methyl)phenyl)amino)-1-oxo-5-ureidopentan-2-yl)amino)-3-methyl-1-oxobutan-2-yl)amino)-2-oxoethyl)-1H-1,2,3-triazol-4-yl)ethyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-9-(3-guanidinopropyl)-5,8,11,14-tetraoxo-4,7,10,13-tetraazaheptadecanoic acid In a 1 dram vial (3S,6S,9S,12S)-9,12-bis(carboxym-ethyl)-3-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-6-(3-guanidinopropyl)-4,7,10,13-tetraoxo-5,8,11,14-tetraazaoctadec-17-ynoic acid (Step 3: 1.0 mg, 0.767 μmol), 4-((S)-2-((S)-2-(2-azidoacetamido)-3-methylbutanamido)-5-ureidopentanamido)benzyl (3-((3-((5-carbamoyl-1-((E)-4-(5-carbamoyl-2-(1-ethyl-3-methyl-1H-pyrazole-5-car-boxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamate (Step 4: 1.03 mg, 0.767 μmol) and L(+)-Ascorbic acid (0.135 mg, 0.767 μmol) were dissolved in DMSO (192 μL) to give a colorless solution. Copper(II) sulfate pentahydrate (0.191 mg, 0.767 μmol) in water (192 μL) were added to the reaction mixture in one portion. After 90 min, the reaction mixture was diluted with water and MeOH then purified by prep-HPLC (pH=2, acetonitrile/water+TFA) to give the desired product as the TFA salt. LC-MS calculated for $C_{120}H_{153}Cl_2N_{38}O_{28}$ $(M+3H)^{3+}$: m/z=882.1; found 882.0.

Example 5. (2R,5S,8S,11S,14S)-2-(15-((5-carbamoyl-14(E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-7,11-dioxo-6-oxa-2,3-dithia-8,12-diazapentadecyl)-5,8-bis(carboxymethyl)-14-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-11-(3-guanidinopropyl)-4,7,10,13-tetraoxo-3,6,9,12-tetraazahexadecanedioic acid

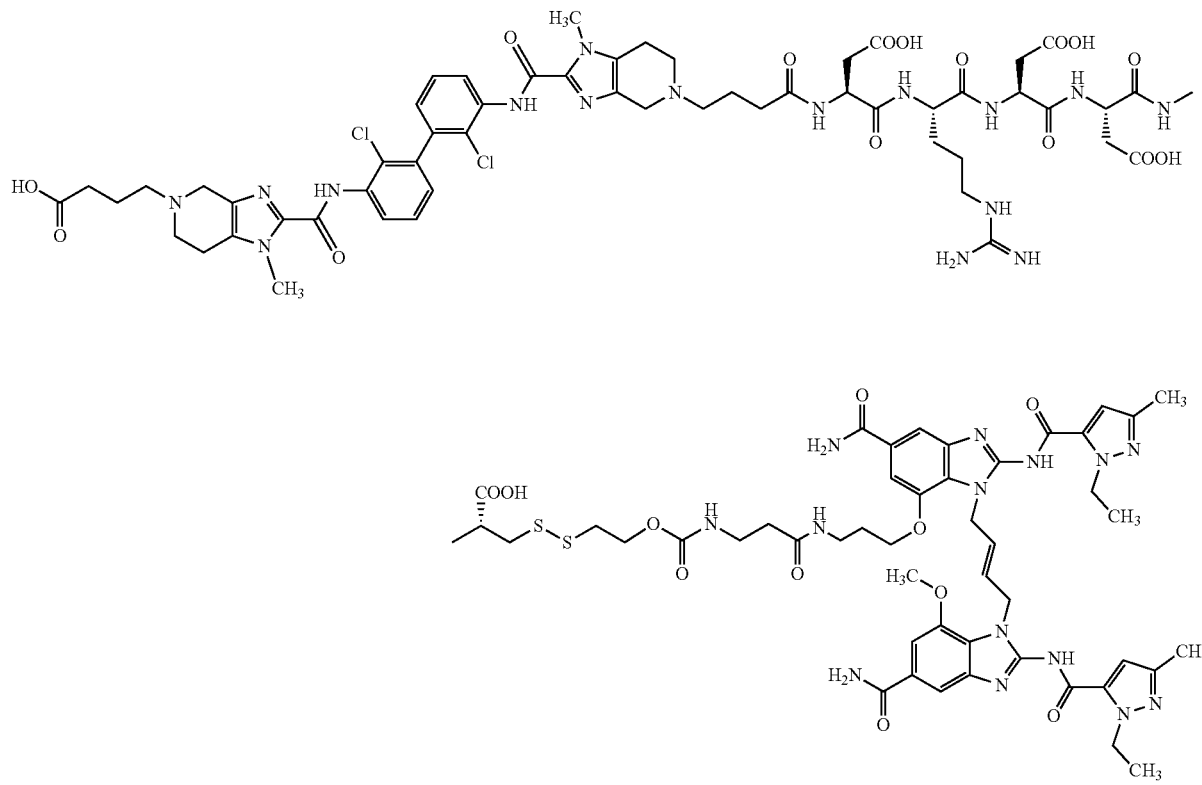

Step 1: tert-butyl (((9H-fluoren-9-yl)methoxy)carbonyl)-L-cysteinate

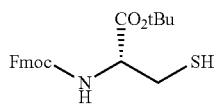

In a 4 dram vial di-tert-butyl 3,3'-disulfanediyl(2R,2'R)-bis(2-((((9H-fluoren-9-yl)methoxy)carbonyl)amino)propanoate) (AstaTech, cat #FD21222: 2.00 g, 2.51 mmol) was dissolved in THF (30 ml) to give a yellow solution. Tri-n-butylphosphine (0.932 ml, 3.76 mmol) was added to the reaction mixture dropwise. After 30 min, water (3 mL) was added. After 16 h, 10% HOAc (50 mL) was added to the reaction mixture followed by extraction with ethyl acetate (25 mL×4). The combined organic layers were dried Na₂SO₄, filtered and concentrated. The crude product was added to a silica gel column and was eluted with ethyl acetate/hexane from 10% to 30% to give tert-butyl (((9H-fluoren-9-yl)methoxy)carbonyl)-L-cysteinate (2.0 g, 2.50 mmol, 99% yield) as a pale yellow oil. LC-MS calculated for $C_{22}H_{26}NO_4S$ $(M+H)^+$: m/z=400.2; found 400.2.

Step 2: tert-butyl N-(((9H-fluoren-9-yl)methoxy)carbonyl)-S-((2-hydroxyethyl)thio)-L-cysteinate

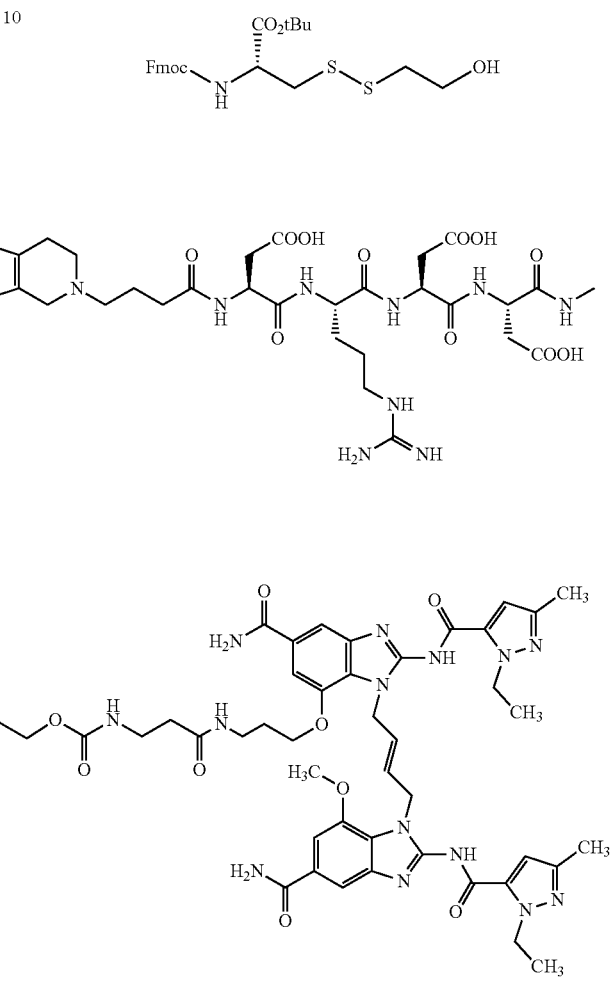

In a 4 dram vial, methoxycarbonylsulfenyl chloride (0.747 mL, 8.26 mmol) was dissolved in acetonitrile (7.5 mL) to give a colorless solution. 2-Mercaptoethan-1-ol (0.579 mL, 8.26 mmol) in acetonitrile (7.52 mL) was added to the reaction mixture dropwise at 0° C. After 30 min, a solution of tert-butyl (((9H-fluoren-9-yl)methoxy)carbonyl)-L-cysteinate (3.00 g, 7.51 mmol) and 2,6-lutidine (4.90 mL, 42.1 mmol) in acetonitrile (18 mL) was added. After 1 h, the reaction mixture was concentrated and the residue was diluted with NH₄Cl, followed by extraction with ethyl acetate (15 mL×4). The combined organic layers were dried Na₂SO₄, filtered and concentrated. The crude product was added to a silica gel column and was eluted with ethyl acetate/dichloromethane from 30% to 50% then ethyl acetate/hexane from 20% to 40% to give tert-butyl N-(((9H-fluoren-9-yl)methoxy)carbonyl)-S-((2-hydroxyethyl)thio)-L-cysteinate (1.79 g, 3.76 mmol, 50.1% yield) as a pale yellow oil. LC-MS calculated for $C_{24}H_{30}NO_5S_2$ $(M+H)^+$: m/z=476.2; found 476.2.

Step 3: tert-butyl S-((2-((((1H-benzo[d][1,2,3]triazol-1-yl)oxy)carbonyl)oxy)ethyl)thio)-N-(((9H-fluoren-9-yl)methoxy)carbonyl)-L-cysteinate

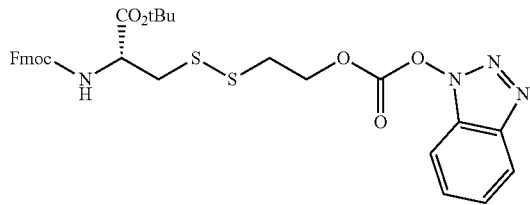

In a 4 dram vial, triphosgene (0.217 g, 0.731 mmol) was dissolved in DCM (5.8 mL) to give a colorless solution. tert-Butyl N-(((9H-fluoren-9-yl)methoxy)carbonyl)-S-((2-hydroxyethyl)thio)-L-cysteinate (0.500 g, 1.05 mmol) and 2,6-lutidine (0.367 mL, 3.15 mmol) in DCM (5.8 mL) was added to the reaction mixture dropwise at 0° C. After 1 h, a solution of HOBt (0.161 g, 1.05 mmol) and 2,6-lutidine (0.367 mL, 3.15 mmol) in DCM (5.8 ml) was added. After 16 h, the reaction mixture was concentrated and the residue was diluted with ethyl acetate (100 mL), followed by washed with aq. NH$_4$Cl (20 mL×6). The organic layers were dried Na$_2$SO$_4$, filtered and concentrated. The crude product was added to a silica gel column and was eluted with ethyl acetate/hexane from 20% to 80% to give tert-butyl S-((2-((((1H-benzo[d][1,2,3]triazol-1-yl)oxy)carbonyl)oxy)ethyl)thio)-N-(((9H-fluoren-9-yl)methoxy)carbonyl)-L-cysteinate (136 mg, 0.214 mmol, 20.3% yield) as a color oil. LC-MS calculated for $C_{31}H_{32}N_4NaO_7S_2$ (M+H)$^+$: m/z=659.2; found 659.2.

Step 4: tert-butyl (R,E)-2-amino-17-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-9,13-dioxo-8-oxa-4,5-dithia-10,14-diazaheptadecanoate

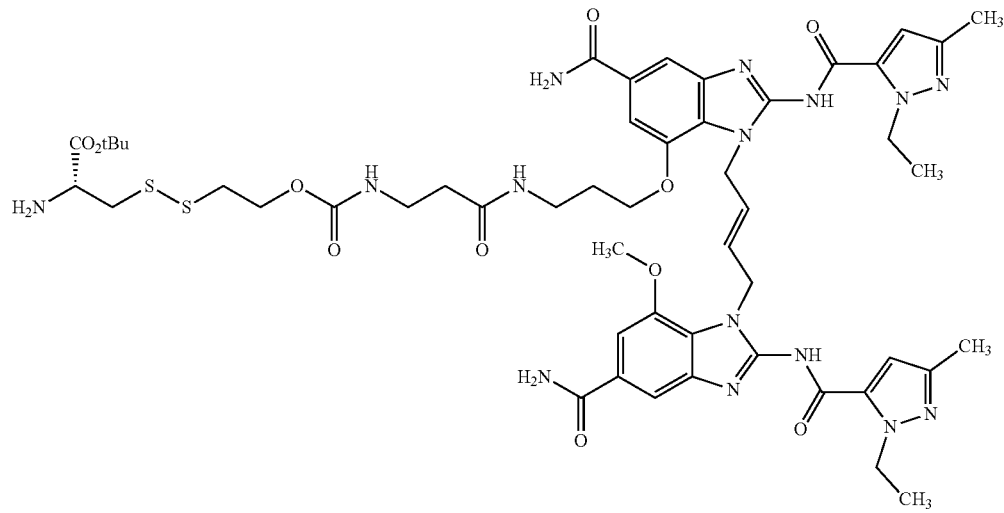 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(=O)CCNC(=O)OCCSSC[C@H](N)C(=O)OC(C)(C)C)c21]

In a 1 dram vial (E)-7-(3-(3-aminopropanamido)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-b enzo[d]imidazole-5-carboxamide (Example 2, Step 1: 5.0 mg, 5.88 μmol) and tert-butyl S-((2-((((1H-benzo[d][1,2,3]triazol-1-yl)oxy)carbonyl)oxy)ethyl)thio)-N-(((9H-fluoren-9-yl)methoxy)carbonyl)-L-cysteinate (7.48 mg, 0.012 mmol) were dissolved in DMF (118 μL) to give a yellow solution. DMAP (3.59 mg, 0.029 mmol) was added to the reaction mixture in one portion. After 1 h, piperidine (0.1 mL) was added. After 1 h, the reaction mixture was diluted with MeOH then purified by prep-HPLC (pH=2, acetonitrile/water+TFA) to give the desired product as the TFA salt. LC-MS calculated for $C_{51}H_{69}N_{15}O_{11}S_2$ (M+2H)$^{2+}$: m/z=565.8; found 566.0.

Step 5: di-tert-butyl (2R,5S,8S,11S,14S)-14-amino-5,8-bis(2-(tert-butoxy)-2-oxoethyl)-2-(15-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-(H-pyrazole-5-carboxamido)-1H-benzo[d]imidazol-7-yl)oxy)-7,11-dioxo-6-oxa-2,3-dithia-8,12-diazapentadecyl)-4,7,10,13-tetraoxo-11-(3-(3-((2,2,4,6,7-pentamethyl-2,3-dihydrobenzofuran-5-yl)sulfonyl)gnanidino)propyl)-3,6,9,12-tetraazahexadecanedioate (5-(3-carboxypropyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)butanamido)-11-(3-guanidinopropyl)-4,7,10,13-tetraoxo-3,6,9,12-tetraazahexadecanedioic acid In a 1 dram vial 4,4'-((((2,2'-dichloro-[1,1'-biphenyl]-3,3'-diyl)bis(azanediyl))bis(carbonyl))bis(1-methyl-1,4,6 7-tetrahydro-5H-imidazo[4,5-c]pyridine-2,5-diyl))dibutyric

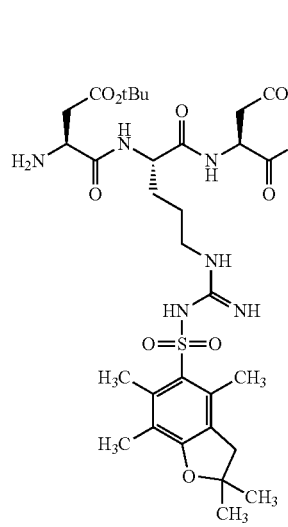

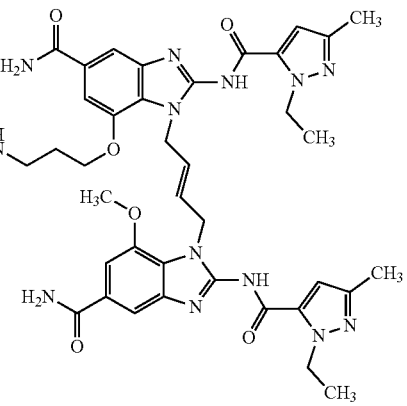

In a 1 dram vial tert-butyl (R,E)-2-amino-17-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-9,13-dioxo-8-oxa-4,5-dithia-10,14-diazaheptadecanoate (7.0 mg, 6.19 μmop was dissolved in DMF (619 μL). Fmoc-Asp(OtBu)-Arg(Pbf)-Asp(OtBu)-Asp(OtBu)-OH (Peptides International, cat #PCS-33379-PI: 10.4 mg, 9.29 μmol), DIPEA (3.24 μL, 0.019 mmol) and BOP (5.48 mg, 0.012 mmol) were added to the reaction mixture in one portion. After 1 h, piperidine (0.1 mL) was added. After 1 h, the reaction mixture was diluted with MeOH then purified by prep-HPLC (pH=2, acetonitrile/water+TFA) to give the desired product as the TFA salt. LC-MS calculated for $C_{94}H_{137}N_{22}O_{24}S_3$ (M+3H)$^{3+}$: m/z=684.9; found 685.1.

Step 6: (2R,5S,8S,11S,14S)-2-(15-((5-carbamoyl-14(E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-7,11-dioxo-6-oxa-2,3-dithia-8,12-diazapentadecyl)-5,8-bis(carboxymethyl)-14-(4-(2-((3'- acid (Example 1, Step 6: 1.76 mg, 2.34 μmol) and di-tert-butyl (2R,5S,8S,11S,14S)-14-amino-5,8-bis(2-(tert-butoxy)-2-oxoethyl)-2-(15-((5-carbamoyl-1-((E)-4-(5-carbamoyl-2-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-7,11-dioxo-6-oxa-2,3-dithia-8,12-diazapentadecyl)-4,7,10,13-tetraoxo-11-(3-(3-((2,2,4,6,7-pentamethyl-2,3-dihydrobenzofuran-5-yl)sulfonyl)guanidino)propyl)-3,6,9,12-tetraazahexadecanedioate (2.4 mg, 1.17 μmol) were dissolved in DMF (117 μL) to give a color solution. DIPEA (1.02 μL, 5.85 μmol) and BOP (0.776 mg, 1.75 μmol) were added to the reaction mixture in one portion. After 1 h, the reaction mixture was concentrated to dryness. Trifluoroacetic acid (0.5 mL) was added. After 90 min, the reaction mixture was concentrated to dryness and diluted with MeOH then purified by prep-HPLC (pH=2, acetonitrile/water+TFA) to give the desired product as the TFA salt.LC-MS calculated for $C_{101}H_{127}Cl_2N_{30}O_{26}S_2$ (M+3H)$^{3+}$: m/z=770.6; found 770.7.

Example 6. (E)-4-(2-((3'-(5-(1-(4-(18-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-10,14-dioxo-2,9-dioxa-5,6-dithia-11,15-diazaoctadecyl)-1H-1,2,3-triazol-1-yl)-28-oxo-3,6,9,12,15,18,21,24-octaoxa-27-azahentriacontan-31-yl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid

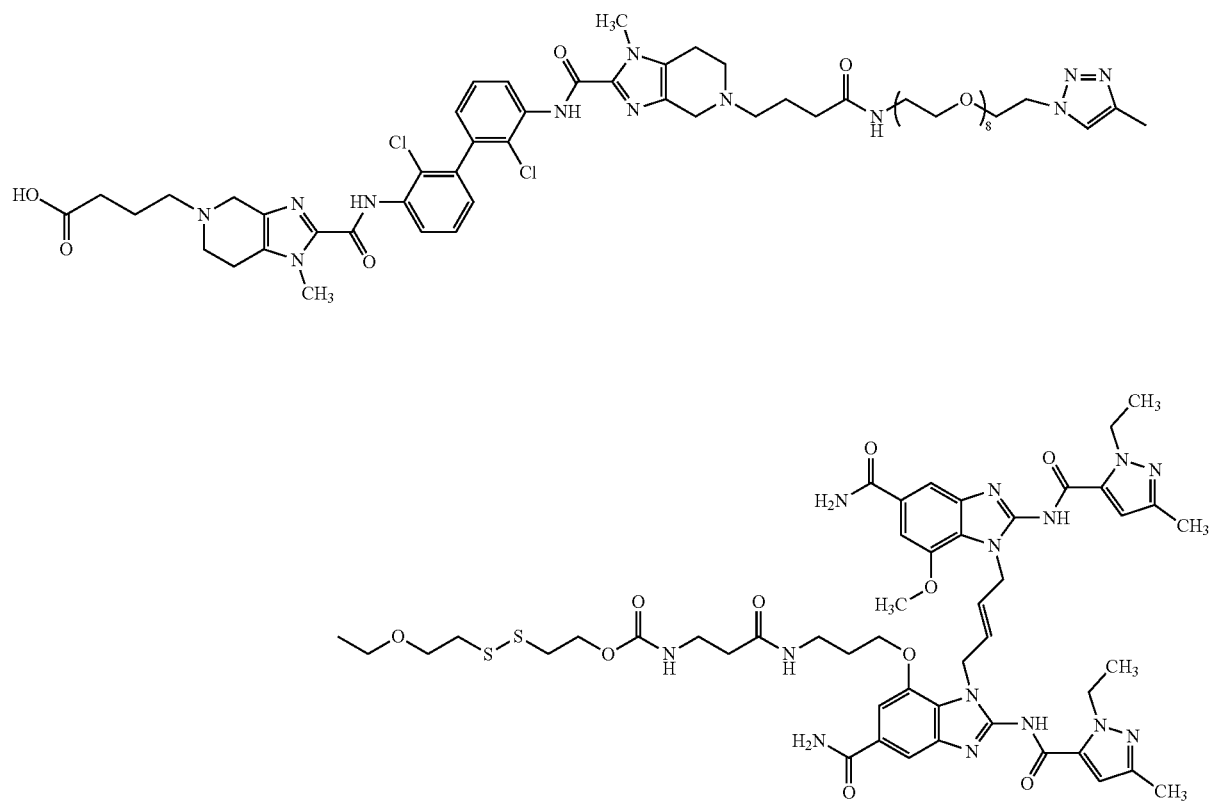

Step 1: 4-(2-((3'-(5-(1-azido-28-oxo-3,6,9,12,15,18,21,24-octaoxa-27-azahentriacontan-31-yl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid

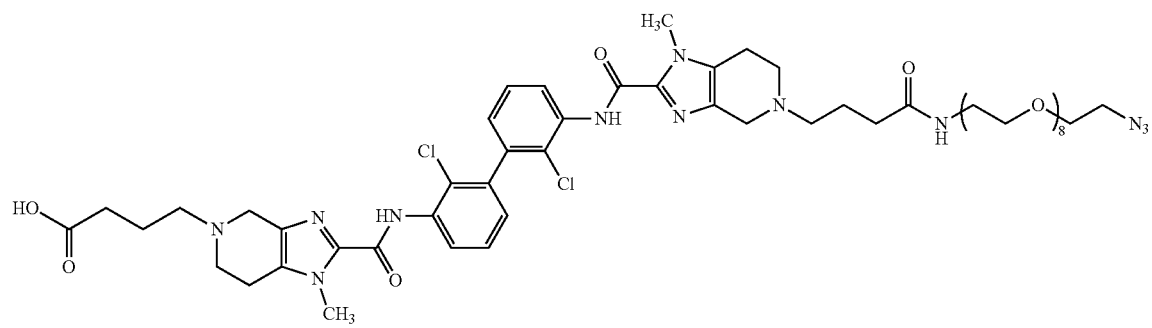

325

In a 1 dram vial 26-azido-3,6,9,12,15,18,21,24-octaoxahexacosan-1-amine (BroadPharm, cat #BP-22225: 3.0 mg, 6.84 μmol) was dissolved in DMF (684 μL). 4,4'-(((((2,2'-Dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))dibutyric acid (Example 1, Step 6: 5.14 mg, 6.84 μmol), DIPEA (5.97 μL, 0.034 mmol) and HATU (5.20 mg, 0.014 mmol) were added to the reaction mixture in one portion. After 1 h, the reaction mixture was diluted with MeOH then purified by prep-HPLC (pH=2, acetonitrile/water+TFA) to give the desired product as the TFA salt. LC-MS calculated for $C_{54}H_{78}Cl_2N_{12}O_{13}$ $(M+2H)^{2+}$: m/z=586.3; found 586.4.

Step 2: 2-((2-(prop-2-yn-1-yloxy)ethyl)disulfanyl)ethyl (E)-(3-((3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propylamino)-3-oxopropyl)carbamate

326

Step 3: (E)-4-(2-((3'-(5-(1-(4-(18-((5-carbamoyl-1-(4-(5-carbamoyl-2-(1-ethyl-3-methyl-1H-benzo[c]imidazol-1-yl)but-2-en-1-yl)-2-(1-ethyl-3-methyl-1H-pyrazole-5-carboxamido)-1H-benzo[d]imidazol-7-yl)oxy)-10,14-dioxo-2,9-dioxa-5,6-dithia-11,15-diazaoctadecyl)-1H-1,2,3-triazol-1-yl)-28-oxo-3,6,9,12,15,18,21,24-octaoxa-27-azahentriacontan-31-yl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid In a 1 dram vial 4-(2-((3'-(5-(1-azido-28-oxo-3,6,9,12,15,18,21,24-octaoxa-27-azahentriacontan-31-yl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Step 1: 1.10 mg, 0.935 μmol), 2-((2-(prop-2-yn-1-yloxy)ethyl)disulfanyl)ethyl (E)-(3-((3-((5-carbamoyl-1-(4-(5-carbamoyl-2-(1-ethyl-3-methyl-1H-pyrazole-5-carboxamido)-

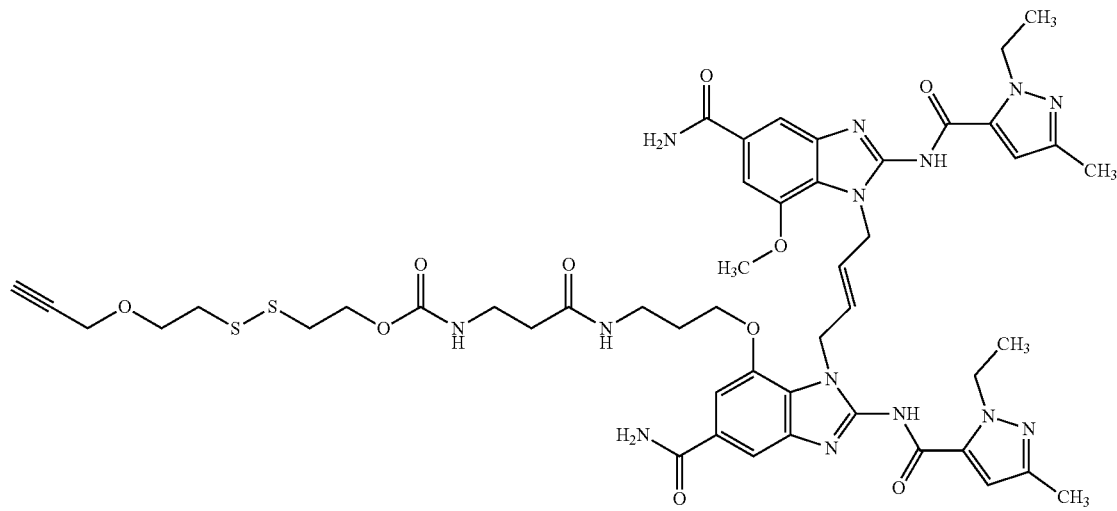 [SMILES: C#CCOCCSSCCOC(=O)NCCC(=O)NCCCOc1cc(C(N)=O)cc2nc(NC(=O)c3cc(C)nn3CC)n(C/C=C/Cn3c(NC(=O)c4cc(C)nn4CC)nc4cc(C(N)=O)cc(OC)c43)c12]

In a 1 dram vial 2-((2-(prop-2-yn-1-yloxy)ethyl)disulfanyl)ethan-1-ol (BroadPharm, cat #BP-22670: 3.39 mg, 0.018 mmol) was dissolved in DMF (588 μL). CDI (2.86 mg, 0.018 mmol) in DMF (100 uL) was added to the reaction mixture in one portion. After 2 h, (E)-7-(3-(3-aminopropanamido)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (Example 2, Step 1: 5.0 mg, 5.88 μmol) and DMAP (2.15 mg, 0.018 mmol) were added. After 16 h, the reaction mixture was diluted with MeOH then purified by prep-HPLC (pH=2, acetonitrile/water+TFA) to give the desired product as the TFA salt. LC-MS calculated for $C_{49}H_{62}N_{14}O_{10}S_2$ $(M+2H)^{2+}$: m/z=535.3; found 535.4.

7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamate (Step 2: 1.0 mg, 0.935 μmol) and (+)-sodium L-ascorbate (0.185 mg, 0.935 μmol) were dissolved in DMSO (234 μL) to give a colorless suspension. Copper(II) sulfate pentahydrate (0.234 mg, 0.935 μmol) in water (234 μL) were added to the reaction mixture in one portion. After 4 h, the reaction mixture was diluted with water and MeOH then purified by prep-HPLC (pH=2, acetonitrile/water+TFA) to give the desired product as the TFA salt. LC-MS calculated for $C_{103}H_{139}Cl_2N_{26}O_{23}S_2$ $(M+3H)^{3+}$: m/z=748.0; found 748.1.

327

Example 7. (3S,6S,9S,12S)-3-((3-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-9-(3-guanidinopropyl)-5,8,11,14-tetraoxo-4,7,10,13-tetraazaheptadecanoic acid

328

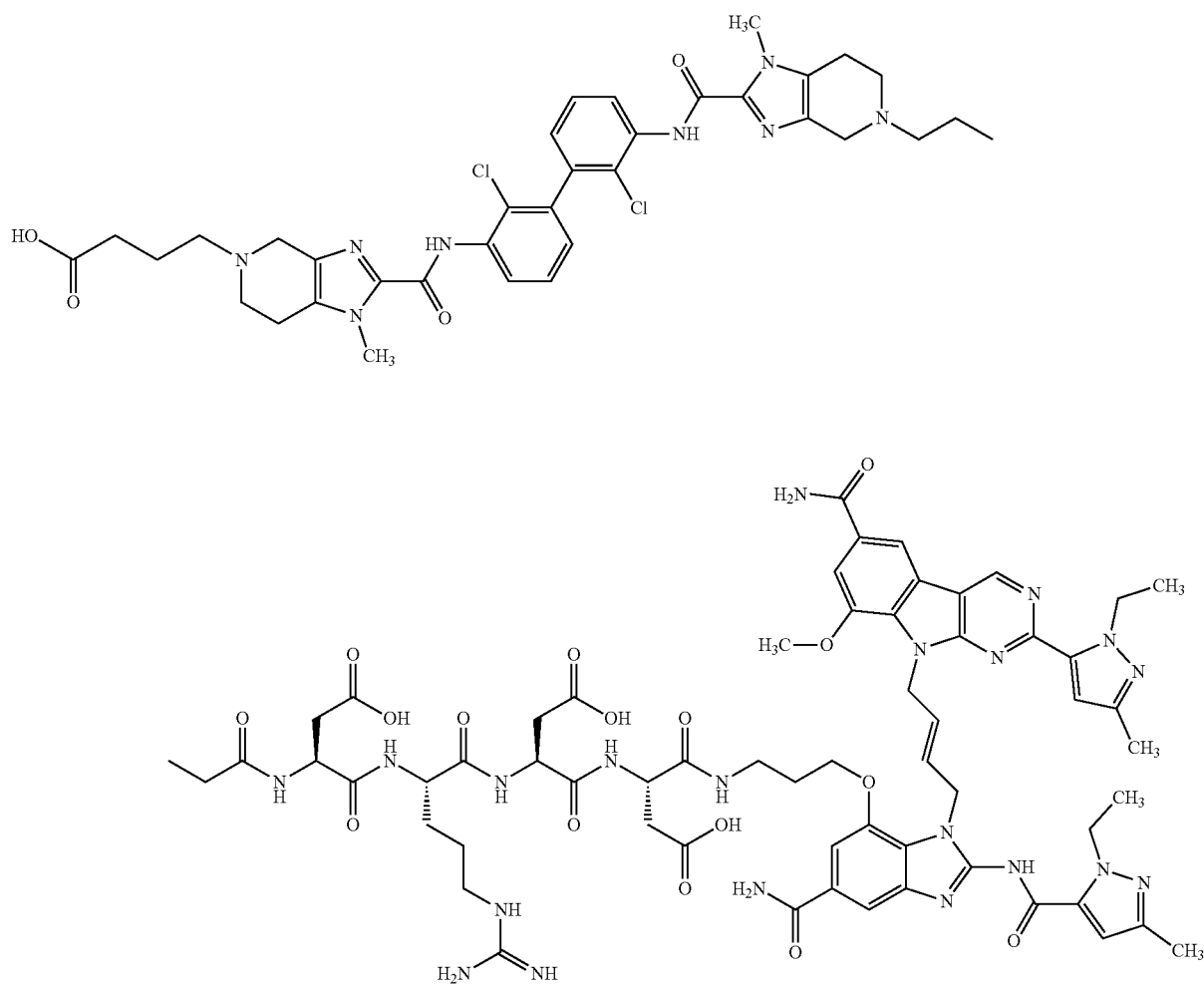

Step 1: (E)-2-(4-hydroxybut-2-en-1-yl)isoindoline-1,3-dione

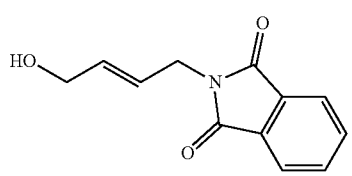 [SMILES: O=C1c2ccccc2C(=O)N1C/C=C/CO]

To a mixture of (E)-but-2-ene-1,4-diol (AstaTech, cat #N10551: 768 mg, 8.72 mmol), triphenylphosphine (2.97 g, 11.3 mmol) and phthalimide (1.28 g, 8.72 mmol) in THF (87 mL) was added DEAD (1.79 mL, 11.3 mmol) dropwise over 1 h at 0° C. The mixture was stirred at r.t. for 16 h and concentrated. The crude product was added to a silica gel column and was eluted with ethyl acetate/hexane from 0% to 80% to give (E)-2-(4-hydroxybut-2-en-1-yl)isoindoline-1,3-dione (1.10 g, 5.09 mmol, 58% yield) as a color oil. LC-MS calculated for $C_{12}H_{10}NO_2$ (M—OH)$^+$: m/z=200.1; found 200.0.

Step 2: (E)-2-(4-(((tert-butyldimethylsilyl)oxy)but-2-en-1-yl)isoindoline-1,3-dione

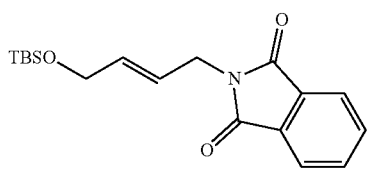 [SMILES: CC(C)(C)[Si](C)(C)OC/C=C/CN1C(=O)c2ccccc2C1=O]

To a mixture of (E)-2-(4-hydroxybut-2-en-1-yl)isoindoline-1,3-dione (500 mg, 2.30 mmol) and TEA (962 μL, 6.91 mmol) in DCM (23 mL) was added TBS-Cl (416 mg, 2.76 mmol). The mixture was stirred at r.t. for 16 h and concentrated. Saturated NaHCO$_3$ (20 mL) was added to the reaction mixture followed by extraction with dichloromethane (10 mL×3). The combined organic layers were dried over Na$_2$SO$_4$, filtered and concentrated. The crude product was added to a silica gel column and was eluted with ethyl acetate/hexane from 0% to 40% to give (E)-2-(4-((tert-butyldimethylsilyl)oxy)but-2-en-1-yl)isoindoline-1,3-dione (598 mg, 1.80 mmol, 78% yield) as a color oil. LC-MS calculated for $C_{12}H_{10}NO_2$ (M-OTBS)$^+$: m/z=200.1; found 200.0.

Step 3: (E)-4-((tert-butyldimethylsilyl)oxy)but-2-en-1-amine

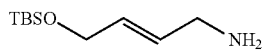

To a solution of (E)-2-(4-((tert-butyldimethylsilyl)oxy)but-2-en-1-yl)isoindoline-1,3-dione (200 mg, 0.603 mmol) in DCM (3.02 mL) and MeOH (3.02 mL) was added hydrazine monohydrate (439 μL, 9.05 mmol). After 4 h, the mixture was filtered to remove the precipitated phthalhydrazide and quenched by adding saturated NaHCO$_3$ (10 mL) followed by extraction with dichloromethane (15 mL×3). The combined organic layers were dried Na$_2$SO$_4$, filtered and concentrated. The crude product was used without further purification. LC-MS calculated for $C_{10}H_{24}NOSi$ (M+H)$^+$: m/z=202.2; found 202.3.

Step 4: tert-butyl (E)-(3-(3-amino-2-((4-((tert-butyldimethylsilyl)oxy)but-2-en-1-yl)amino)-5-carbamoylphenoxy)propyl)carbamate

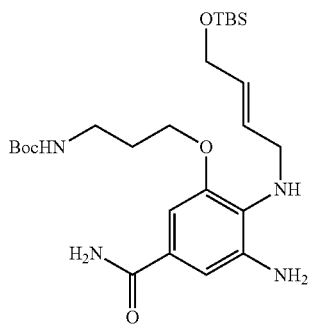 [SMILES: CC(C)(C)OC(=O)NCCCOc1cc(C(N)=O)cc(N)c1NC/C=C/CO[Si](C)(C)C(C)(C)C]

To a solution of (E)-4-((tert-butyldimethylsilyl)oxy)but-2-en-1-amine (53.9 mg, 0.268 mmol) in dry EtOH (1.34 mL) was added tert-butyl (3-(5-carbamoyl-2-chloro-3-nitrophenoxy)propyl)carbamate (Example 1, Step 9: 100 mg, 0.268 mmol) and DIPEA (140 μL, 0.803 mmol). The resulting yellow solution was microwaved at 120° C. with stirring for 2 h. The reaction mixture was added sodium hydrosulfite (233 mg, 1.34 mmol) in water (844 μL, 46.9 mmol) and 30% aq ammonium hydroxide (435 μL, 3.35 mmol) at 0° C. The reaction mixture was then warmed to room temperature. After 10 min, H$_2$O (5 mL) was added to the reaction mixture followed by extraction with ethyl acetate (5 mL×4). The combined organic layers were dried over Na$_2$SO$_4$, filtered and concentrated. LC-MS calculated for $C_{25}H_{45}N_4O_5Si$ (M+H)$^+$: m/z=509.3; found 509.3.

Step 5: tert-butyl (E)-(3-((2-amino-5-carbamoyl-1-(4-hydroxybut-2-en-1-yl)-1H-benzo[d]imidazol-7-yl)oxy)propyl)carbamate

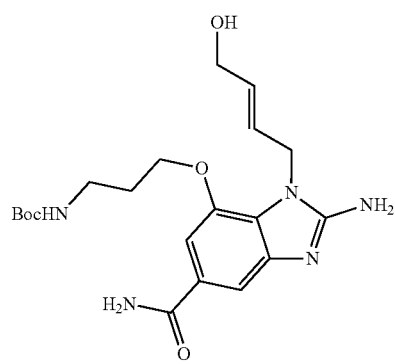 [SMILES: CC(C)(C)OC(=O)NCCCOc1cc(C(N)=O)cc2nc(N)n(C/C=C/CO)c12]

To a solution of above crude mixture in MeOH (4.02 mL) was added BrCN (3M in DCM, 357 μL, 1.07 mmol). After 5 hr, the reaction mixture was concentrated to dryness and used for next step without further purification. LC-MS calculated for $C_{20}H_{30}N_5O_5$ (M+H)$^+$: m/z=420.2; found 420.3.

Step 6: (E)-4-(7-(3-((tert-butoxycarbonyl)amino)propoxy)-5-carbamoyl-2-(1-ethyl-3-methyl-1H-pyrazole-5-carboxamido)-1H-benzo[d]imidazol-1-yl)but-2-en-1-yl 1-ethyl-3-methyl-1H-pyrazole-5-carboxylate

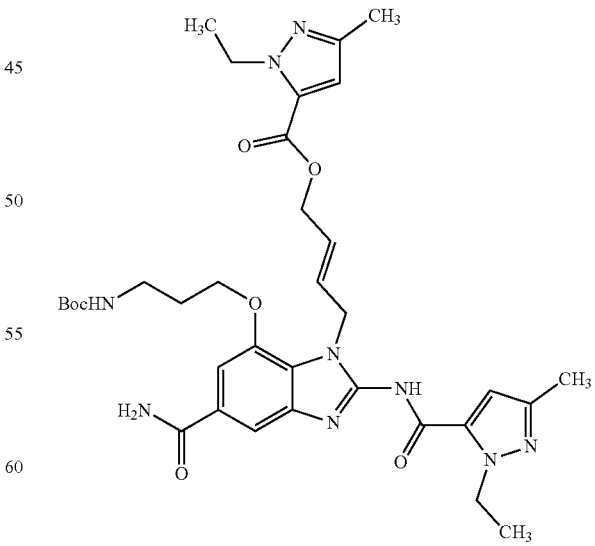

To a solution of above crude mixture in DMF (5 mL) was added DIPEA (374 μL, 2.14 mmol), 1-ethyl-3-methyl-1H-pyrazole-5-carboxylic acid (165 mg, 1.07 mmol) and BOP (474 mg, 1.07 mmol). After 1 h, H$_2$O (5 mL) was added to the reaction mixture followed by extraction with ethyl acetate (5 mL×4). The combined organic layers were dried over Na$_2$SO$_4$, filtered and concentrated. The crude product was added to a silica gel column and was eluted with ethyl acetate/hexane from 30% to 100%, then methanol/dichloromethane from 0% to 10% to give (E)-4-(7-(3-((tert-butoxycarbonyl)amino)propoxy)-5-carbamoyl-2-(1-ethyl-3-methyl-1H-pyrazole-5-carboxamido)-1H-benzo[d]imidazol-1-yl)but-2-en-1-yl 1-ethyl-3-methyl-1H-pyrazole-5-carboxylate (75 mg, 0.109 mmol, 40% yield over three steps) as a yellow solid. LC-MS calculated for C$_{34}$H$_{46}$N$_9$O$_7$ (M+H)$^+$: m/z=692.3; found 692.3.

Step 7: tert-butyl (E)-(3-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)propyl)carbamate

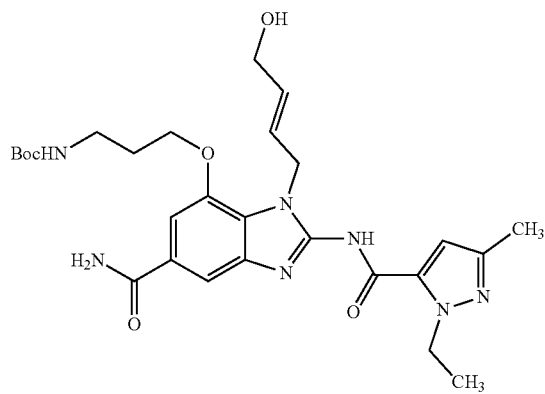 [SMILES: CCn1nc(C)cc1C(=O)Nc1nc2cc(C(N)=O)cc(OCCCNC(=O)OC(C)(C)C)c2n1C/C=C/CO]

To a solution of (E)-4-(7-(3-((tert-butoxycarbonyl)amino)propoxy)-5-carbamoyl-2-(1-ethyl-3-methyl-1H-pyrazole-5-carboxamido)-1H-benzo[d]imidazol-1-yl)but-2-en-1-yl 1-ethyl-3-methyl-1H-pyrazole-5-carboxylate (400 mg, 0.578 mmol) in MeOH (1.45 mL) was added K$_2$CO$_3$ (160 mg, 1.16 mmol). After 1 h, H$_2$O (5 mL) was added to the reaction mixture followed by extraction with IPA/CHCl$_3$ (5 mL×3). The combined organic layers were dried over Na$_2$SO$_4$, filtered, concentrated to dryness and used for next step without further purification. LC-MS calculated for C$_{27}$H$_{38}$N$_7$O$_6$ (M+H)$^+$: m/z=556.3; found 556.4.

Step 8: tert-butyl (E)-(3-((1-(4-bromobut-2-en-1-yl)-5-carbamoyl-2-(1-ethyl-3-methyl-1H-pyrazole-5-carboxamido)-1H-benzo[d]imidazol-7-yl)oxy)propyl)carbamate

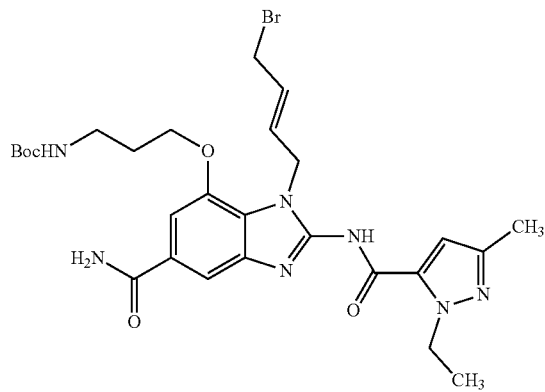 [SMILES: CCn1nc(C)cc1C(=O)Nc1nc2cc(C(N)=O)cc(OCCCNC(=O)OC(C)(C)C)c2n1C/C=C/CBr]

To a solution of above crude in THF (1.45 mL) was added PBr$_3$ (109 μL, 1.16 mmol) and the mixture was stirred at rt for 10 h. Saturated NaHCO$_3$ (15 mL) was added to the reaction mixture followed by extraction with dichloromethane (10 mL×4). The combined organic layers were dried over Na$_2$SO$_4$, filtered and concentrated. The crude product was added to a silica gel column and was eluted with methanol/dichloromethane from 0% to 10% to give tert-butyl (E)-(3-((1-(4-bromobut-2-en-1-yl)-5-carbamoyl-2-(1-ethyl-3-methyl-1H-pyrazole-5-carboxamido)-1H-benzo[d]imidazol-7-yl)oxy)propyl)carbamate (113 mg, 0.183 mmol, 31.6% yield over two steps). LC-MS calculated for C$_{27}$H$_{37}$BrN$_7$O$_5$ (M+H)$^+$: m/z=618.2/620.2; found 618.4/620.4.

Step 9: (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-methoxy-9H-pyrimido[4,5-b]indole-6-carboxamide

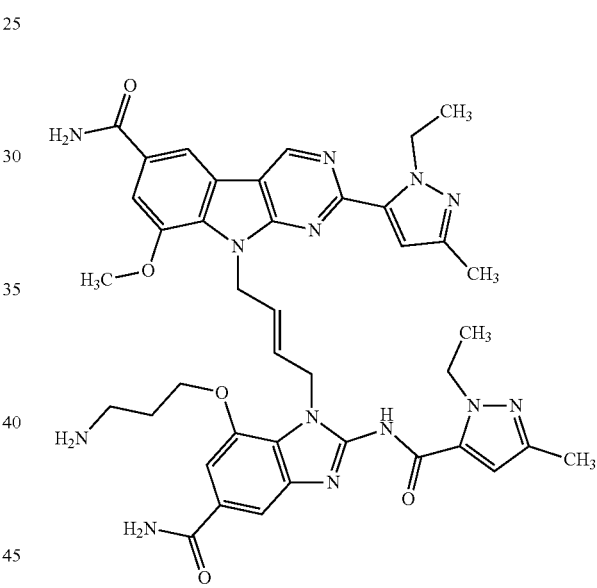

To a mixture of tert-butyl (E)-(3-((1-(4-bromobut-2-en-1-yl)-5-carbamoyl-2-(1-ethyl-3-methyl-1H-pyrazole-5-carboxamido)-1H-benzo[d]imidazol-7-yl)oxy)propyl)carbamate (65 mg, 0.105 mmol) and 2-(1-ethyl-3-methyl-1H-pyrazol-5-yl)-8-methoxy-9H-pyrimido[4,5-b]indole-6-carboxamide (Example S10, Step 4: 36.8 mg, 0.105 mmol) in THF (1.05 mL) was added DIPEA (55.1 μL, 0.315 mmol). After 20 min, Cs$_2$CO$_3$ (103 mg, 0.315 mmol) was added. After 1 hr, the reaction mixture was concentrated to dryness. Trifluoroacetic acid (0.5 mL) was added to the reaction mixture. After 20 min, the reaction mixture was diluted with water and MeOH then purified by prep-HPLC (pH=2, acetonitrile/water+TFA) to give the desired product as the TFA salt. LC-MS calculated for C$_{40}$H$_{46}$N$_{13}$O$_5$ (M+H)$^+$: m/z=788.4; found 788.4.

Step 10: tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate (carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)-9-(3-guanidinopropyl)-5,8,11,14-tetraoxo-4,7,10,13-tetraazaheptadecanoic acid In a 1 dram vial tert-butyl (6S,9S,12S,15S)-15-amino-6,9-bis(2-(tert-butoxy)-2-oxoethyl)-1-((5-carbamoyl-1-((E)-

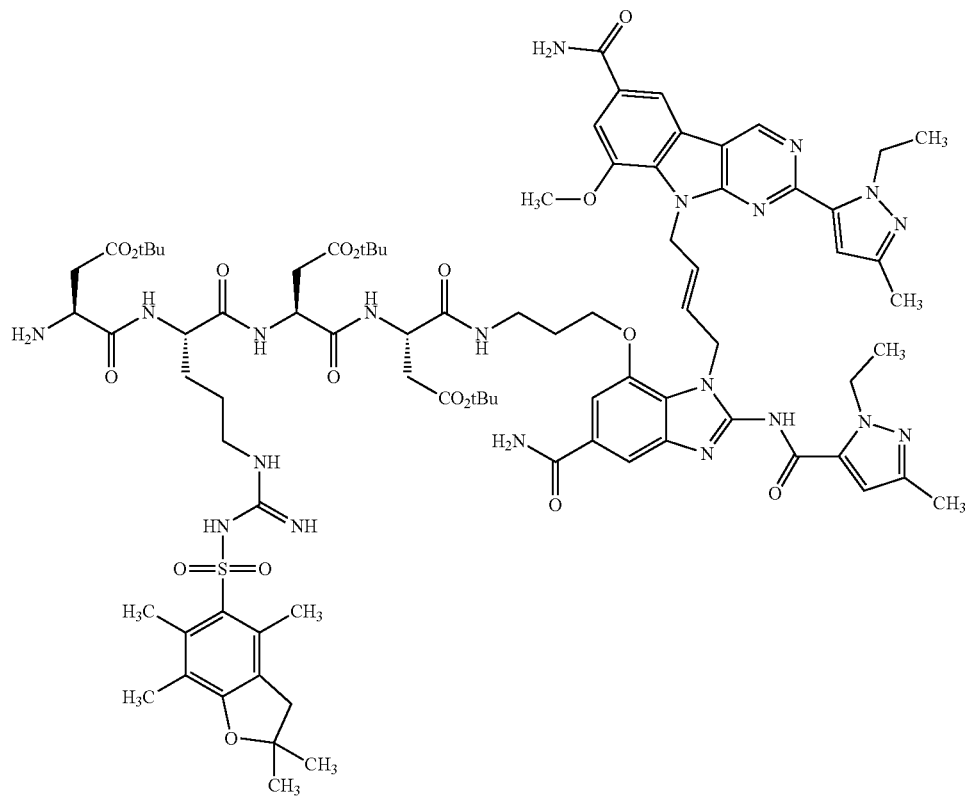 [SMILES: CCn1nc(C)cc1C(=O)Nc1nc2cc(C(N)=O)cc(OCCCNC(=O)[C@H](CC(=O)OC(C)(C)C)NC(=O)[C@H](CC(=O)OC(C)(C)C)NC(=O)[C@H](CCCNC(=N)NS(=O)(=O)c3c(C)c(C)c4c(c3C)CC(C)(C)O4)NC(=O)[C@@H](N)CC(=O)OC(C)(C)C)c2n1C/C=C/Cn1c2nc(-c3cc(C)nn3CC)ncc2c2cc(C(N)=O)cc(OC)c21]

In a 1 dram vial (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-methoxy-9H-pyrimido[4,5-b]indole-6-carboxamide (9 mg, 0.011 mmol) was dissolved in DMF (1.10 mL) to give a colorless solution. Fmoc-Asp(OtBu)-Arg(Pbf)-Asp(OtBu)-Asp(OtBu)—OH (Peptides International, cat #PCS-33379-PI: 15.9 mg, 0.014 mmol), DIPEA (5.99 µL, 0.034 mmol) and BOP (7.58 mg, 0.017 mmol) were added to the reaction mixture in one portion. After 1 h, piperidine (0.1 mL) was added. After 1 h, the reaction mixture was diluted with MeOH then purified by prep-HPLC (pH=2, acetonitrile/water+TFA) to give the desired product as the TFA salt. LC-MS calculated for $C_{83}H_{114}N_{20}O_{18}S$ $(M+2H)^{2+}$: m/z=855.9; found 855.9.

Step 11: (3S,6S,9S,12S)-3-((3-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyhcarbamoyl)-6,12-bis 4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate (6.8 mg, 3.98 µmol) dissolved in DMF (199 µL) to give a pale yellow solution. 4,4'-((((2,2'-dichloro-[1,1'-biphenyl]-3,3'-diyl)bis (azanediyl))bis(carbonyl))bis(1-methyl-1,4,6,7-tetrahydro-5H-imidazo[4,5-c]pyridine-2,5-diyl))dibutyric acid (Example 1, Step 6: 3.21 mg, 3.98 µmol), DIPEA (3.47 µL, 0.020 mmol) and BOP (2.64 mg, 5.96 µmol) were added to the reaction mixture in one portion. After 30 min, the reaction mixture was concentrated to dryness. Trifluoroacetic acid (0.5 mL) was added to the reaction mixture. After 20 min, the reaction mixture was diluted with water and MeOH then purified by prep-HPLC (pH=2, acetonitrile/water+TFA) to give the desired product as the TFA salt. LC-MS calculated for $C_{94}H_{113}Cl_2N_{28}O_2O$ $(M+3H)^{3+}$: m/z=675.2; found 675.3.

Example 8. (7S,10S,13S,16S)-16-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-7,13-bis(carboxymethyl)-1-(1-((7-cyano-2-(3'-((2-(difluoromethyl)-7-yl)(((R)-3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidin-4-yl)-10-(3-guanidinopropyl)-1,5,8,11,14-pentaoxo-2,6,9,12,15-pentaazaoctadecan-18-oic acid

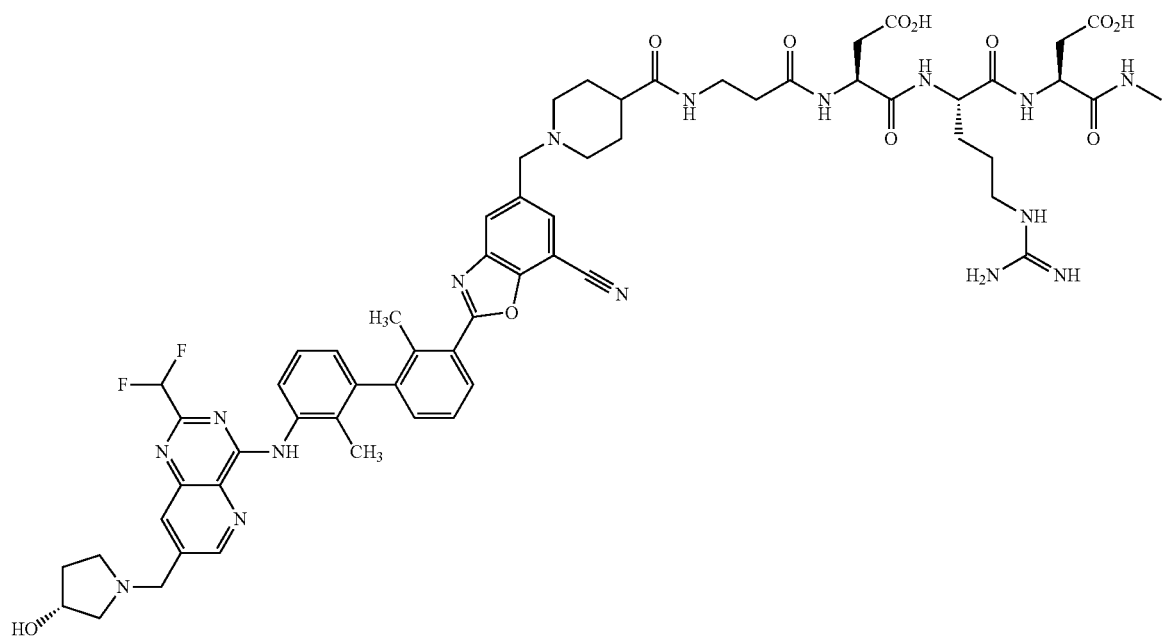

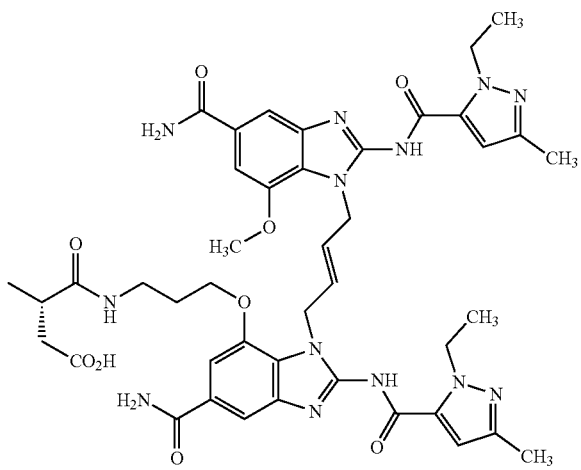

Step 1: methyl 3-chloro-4-hydroxy-5-nitrobenzoate

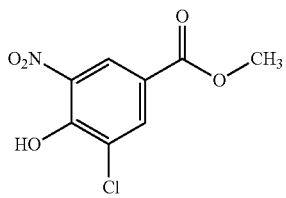

To a solution of methyl 3-chloro-4-hydroxybenzoate (Alfa Aesar, cat #A512389: 10.0 g, 53.6 mmol) in acetic acid (20.0 mL) was added a mixture of acetic acid (20.0 mL) and nitric acid (4.72 mL, 112 mmol) dropwise at 0° C. Then the ice bath was removed and the thick mixture was stirred at room temperature for 2 hrs. Then an equal volume of water was added to the reaction suspension at 0° C. The mixture was filtered and washed with cold water. A yellow solid was obtained as the desired product without further purification. LC-MS calculated for $C_8H_7ClNO_5$ (M+H)$^+$: m/z=232.0; found 232.0.

Step 2: methyl 3-amino-5-chloro-4-hydroxybenzoate

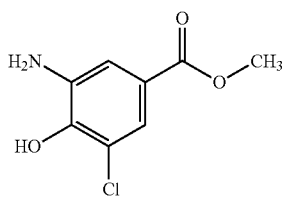

Methyl 3-chloro-4-hydroxy-5-nitrobenzoate (2.08 g, 8.98 mmol) was hydrogenated under ambient pressure of hydrogen using palladium on carbon (10 wt%, 0.57 g, 0.539 mmol) in ethyl acetate (15 mL) for 1 h. The resulting suspension was filtered through a pad of Celite and washed with EtOAc and the solvent was removed under reduced pressure to give a crude product, which was purified by column chromatography (eluting with MeOH/DCM 0%-10%). LC-MS calculated for $C_8H_9ClNO_3$ (M+H)$^+$: m/z=202.0; found 202.0.

Step 3: methyl 2-(3-bromo-2-methylphenyl)-7-chlorobenzo[d]oxazole-5-carboxylate

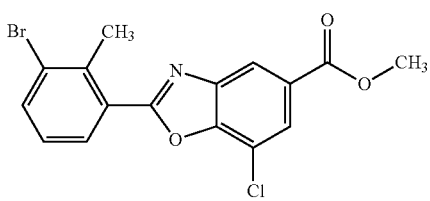 [SMILES: COC(=O)c1cc(Cl)c2oc(-c3cccc(Br)c3C)nc2c1]

A mixture of methyl 3-amino-5-chloro-4-hydroxybenzoate (1.04 g, 5.16 mmol), 3-bromo-2-methylbenzaldehyde (AstaTech, #52940: 0.98 g, 4.92 mmol) in EtOH (25 ml) was placed in a vial and stirred at room temperature for 1 h. The mixture was then concentrated. The residue was redissovled in methylene chloride (25 mL) and dichlorodicyanoquinone (1.12 g, 4.92 mmol) was added. The mixture was stirred at room temperature for 30 min. The reaction was diluted with methylene chloride and washed with an aqueous $Na_2S_2O_3$ solution and $NaHCO_3$ solution. The organic phase was dried over $MgSO_4$, filtered and the filtrate was concentrated. The crude residue was used directly without further purification. LC-MS calculated for $C_{16}H_{12}BrClNO_3$ (M+H)$^+$: m/z=380.0; found 379.9.

Step 4: (2-(3-bromo-2-methylphenyl)-7-chlorobenzo[d]oxazol-5-yl)methanol

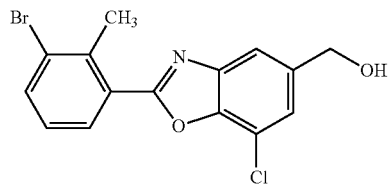 [SMILES: Cc1c(Br)cccc1-c1nc2cc(CO)cc(Cl)c2o1]

To a solution of methyl 2-(3-bromo-2-methylphenyl)-7-chlorobenzo[d]oxazole-5-carboxylate (395.0 mg, 1.04 mmol) in DCM (10.0 ml) was added diisobutylaluminum hydride in DCM (1.0 M, 2.08 ml, 2.08 mmol) dropwise at −78° C. The mixture was slowly warmed up to 0° C. Then the mixture was quenched with EtOAc and DCM, followed by aqueous Rochell's salt solution. The mixture was stirred vigorously at room temperature for 1 h. The organic phase was separated and dried over $MgSO_4$ before filtering through a short pad of Celite to remove solids. The filtrate was concentrated and purified by column chromatography (eluting with MeOH/DCM, 0-5%). LC-MS calculated for $C_{15}H_{12}BrClNO_2$ (M+H)$^+$: m/z=352.0; found 352.0.

Step 5: (7-chloro-2-(2-methyl-3-(4,4,5,5-tetramethyl-1,3,2-dioxaborolan-2-yl)phenyl)benzo[d]oxazol-5-yl)methanol

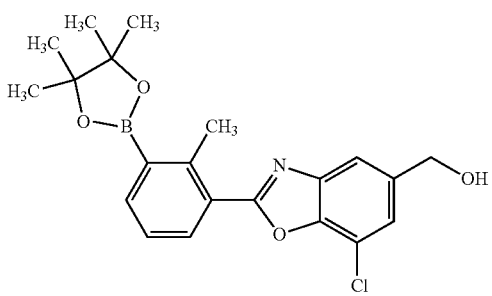 [SMILES: Cc1c(B2OC(C)(C)C(C)(C)O2)cccc1-c1nc2cc(CO)cc(Cl)c2o1]

A mixture of (2-(3-bromo-2-methylphenyl)-7-chlorobenzo[d]oxazol-5-yl)methanol (113 mg, 0.322 mmol), bis(pinacolato)diboron (98 mg, 0.386 mmol), dichloro[1,1'-bis(diphenylphosphino)ferrocene]palladium (II) dichloromethane adduct (26.3 mg, 0.032 mmol) and anhydrous potassium acetate (79 mg, 0.804 mmol) in 1,4-dioxane (3.5 mL) was purged with nitrogen and stirred at 110° C. for 2 h. The crude was diluted with DCM, and then filtered through Celite. The filtrate was concentrated. The residue was purified by flash chromatography (eluting with EtOAc/Hexanes, 0-40%). LC-MS calculated for $C_{21}H_{24}BClNO_4$ (M+H)$^+$: m/z=400.2; found 400.2.

Step 6: 5-(hydroxymethyl)-2-(2-methyl-3-(4,4,5,5-tetramethyl-1,3,2-dioxaborolan-2-yl)phenyl)benzo[d]oxazole-7-carbonitrile

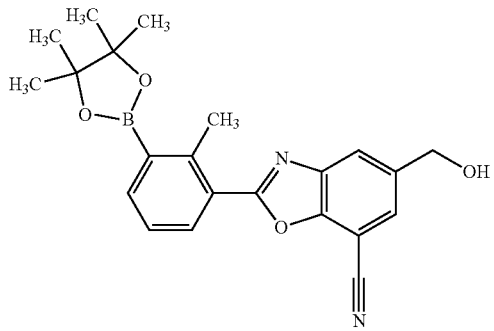 [SMILES: Cc1c(B2OC(C)(C)C(C)(C)O2)cccc1-c1nc2cc(CO)cc(C#N)c2o1]

A stirred mixture of (7-chloro-2-(2-methyl-3-(4,4,5,5-tetramethyl-1,3,2-dioxaborolan-2-yl)phenyl)benzo[d]oxazol-5-yl)methanol (1.08 g, 2.63 mmol), zinc cyanide (0.253 g, 2.11 mmol) and methanesulfonato(2-di-t-butylphosphino-2',4',6'-tri-i-propyl-1,1'-biphenyl)(2'-amino-1,1'-biphenyl-2-yl)palladium(II) (0.171 g, 0.211 mmol) in THF (5.27 ml) and water (5.27 ml) at r.t. was degassed and refilled with $N_2$ three times. It was heated at 90° C. overnight. The reaction mixture was diluted with THF while hot. It was cooled to r.t. and filtered to remove insoluble solid. The filtrate was concentrated in vacuo. Acetonitrile was then added. The resulting slurry was filtered and washed with acetonitrile. The solid was collected and used directly in the next step without further purification. LC-MS calculated for $C_{22}H_{24}BN_2O_4$ (M+H)$^+$: m/z=391.2; found: 391.2.

Step 7: 5-formyl-2-(2-methyl-3-(4,4,5,5-tetramethyl-1,3,2-dioxaborolan-2-yl)phenyl)benzo[d]oxazole-7-carbonitrile

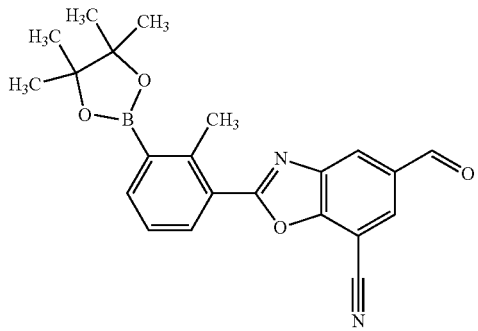 [SMILES: Cc1c(B2OC(C)(C)C(C)(C)O2)cccc1-c1nc2cc(C=O)cc(C#N)c2o1]

To a solution of 5-(hydroxymethyl)-2-(2-methyl-3-(4,4,5,5-tetramethyl-1,3,2-dioxaborolan-2-yl)phenyl)benzo[d]oxazole-7-carbonitrile (1.51 g, 3.68 mmol) in DCM (16.4 mL) and DMF (2.0 ml) was added Dess-Martin periodinane (2.49 g, 5.70 mmol). The mixture was stirred at r.t. for 3 h. The crude mixture was quenched with saturated $Na_2S_2O_3$ and saturated $NaHCO_3$. The mixture was extracted with DCM three times. The organic phase was combined, dried and filtered. The filtrate was concentrated. Diethyl ether was added to the residue to form slurry, which was filtered to give the desired aldehyde. LCMS calculated for $C_{22}H_{22}BN_2O_4$ (M+H)+: m/z=389.2; found 389.2.

Step 8: 7-bromo-2-(difluoromethyl)-4H-pyrido[3,2-d][1,3]oxazin-4-one

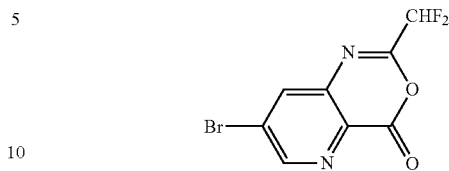

A mixture of 3-amino-5-bromopicolinic acid (PharmBlock cat #PB0554: 645 mg, 2.97 mmol) and 2,2-difluoroacetic anhydride (4.14 g, 23.8 mmol) was stirred at 60° C. for 3 h. After cooling to r.t., the volatiles were removed by rotavap and high vacuum pump. The residue was used directly for next step. LC-MS calculated for $C_8H_4BrF_2N_2O_2$ (M+H)$^+$: m/z=276.9; found 277.0.

Step 9: 7-bromo-2-(difluoromethyl)pyrido[3,2-d]pyrimidin-4-ol

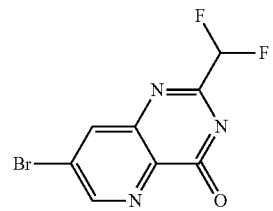

A mixture of 7-bromo-2-(difluoromethyl)-4H-pyrido[3,2-d][1,3]oxazin-4-one (801 mg, 2.89 mmol) and ammonium hydroxide aq. soln, (8.0 ml, 28%) in a heavy wall glass tube was sealed and stirred at 85° C. for 2 h. After cooling to r.t., the solution was then evaporated and the residue was rediluted with $CH_3CN$ and toluene. The suspension was evaporated again and the residue was used in the next step without further purification. LC-MS calculated for $C_8H_5BrF_2N_3O$ (M+H)$^+$: m/z=276.0; found 276.0.

Step 10: 7-bromo-N-(3-chloro-2-methylphenyl)-2-(difluoromethyl)pyrido[3,2-d]pyrimidin-4-amine

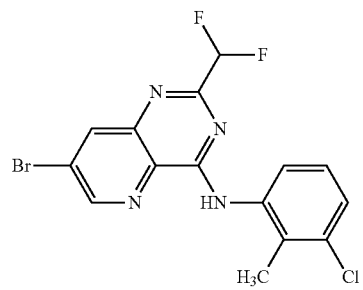 [SMILES: Cc1c(Cl)cccc1Nc1nc(C(F)F)nc2cc(Br)cnc12]

To a mixture of 7-bromo-2-(difluoromethyl)pyrido[3,2-d]pyrimidin-4-ol (crude product from Step 9: 750 mg, 2.72 mmol), benzyltriethylammonium chloride (1238 mg, 5.43 mmol) and N,N-diethylaniline (648 4.08 mmol) in acetonitrile (13.6 ml) was added phosphoryl chloride (1.52 ml, 16.3 mmol). The mixture was stirred at 75° C. for 2 h. Then the reaction was cooled to r.t. The volatiles were removed under reduced pressure.

To a solution of 3-chloro-2-methylaniline (409 mg, 2.89 mmol) and 7-bromo-4-chloro-2-(difluoromethyl)pyrido[3, 2-d]pyrimidine (the residue above) in 2-propanol (14.4 ml) was added methanesulfonic acid (188 µL, 2.89 mmol). The mixture was stirred at 80° C. for 2 h. Then the reaction was cooled to r.t. The mixture was carefully quenched by NaHCO₃ aq solution. The precipitates were filtered, washed by water and dried by air. The solids were used directly for next step. LC-MS calculated for C₁₅H₁₁BrClF₂N₄ (M+H)⁺: m/z=399.0; found 399.0.

Step 11: N-(3-chloro-2-methylphenyl)-2-(difluoromethyl)-7-vinylpyrido[3,2-d]pyrimidin-4-amine

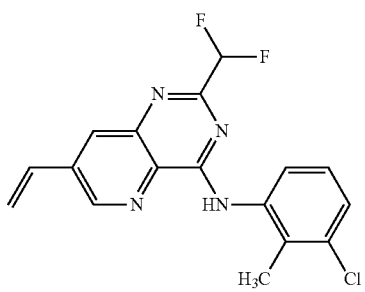 [SMILES: C=Cc1cnc2c(Nc3cccc(Cl)c3C)nc(C(F)F)nc2c1]

A mixture of 7-bromo-N-(3-chloro-2-methylphenyl)-2-(difluoromethyl)pyrido[3,2-d]pyrimidin-4-amine (841 mg, 2.10 mmol), 4,4,5,5-tetramethyl-2-vinyl-1,3,2-dioxaborolane (537 µL, 3.16 mmol), tetrakis(triphenylphosphine) palladium(0) (243 mg, 0.21 mmol) and potassium phosphate (1117 mg, 5.26 mmol) in tert-butanol (7.0 ml) and water (7.0 ml) was purged with N₂ and then stirred at 100° C. for 3 h. The reaction was cooled to room temperature. The reaction mixture was diluted with water and extracted with DCM. The organic layer was dried over MgSO₄, filtered and concentrated to give a crude residue, which was purified by flash chromatography (0-30% EtOAc/DCM). LC-MS calculated for C₁₇H₁₄ClF₂N₄ (M+H)⁺: m/z=347.1; found 347.1.

Step 12: 4-(3-chloro-2-methylphenylamino)-2-(difluoromethyl)pyrido[3,2-d]pyrimidine-7-carbaldehyde

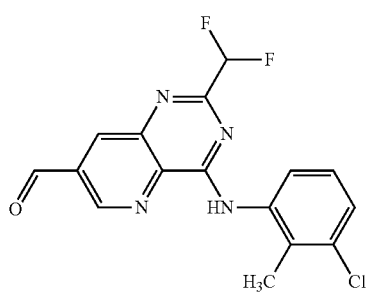 [SMILES: Cc1c(Cl)cccc1Nc1nc(C(F)F)nc2cc(C=O)cnc12]

A vial was charged with N-(3-chloro-2-methylphenyl)-2-(difluoromethyl)-7-vinylpyrido[3,2-d]pyrimidin-4-amine (195 mg, 0.562 mmol), THF (4.5 mL), a stir bar and water (1.1 mL). To this solution was added sodium periodate (601 mg, 2.81 mmol) followed by osmium tetroxide (4% w/w in water, 221 µL, 0.028 mmol). After stirring at r.t. for 1 h, the reaction was quenched with a saturated aqueous solution of sodium thiosulfate. The mixture was then extracted with DCM, and the combined organic layers were washed with water, brine, dried over MgSO₄, filtered, and concentrated in vacuo. The crude residue was used directly in the next step without further purification. LC-MS calculated for C₁₆H₁₂ClF₂N₄O (M+H)⁺: m/z=349.1; found 349.1.

Step 13: (R)-1-((4-(3-chloro-2-methylphenylamino)-2-(difluoromethyl)pyrido[3,2-d]pyrimidin-7-yl)methyl)pyrrolidin-3-ol

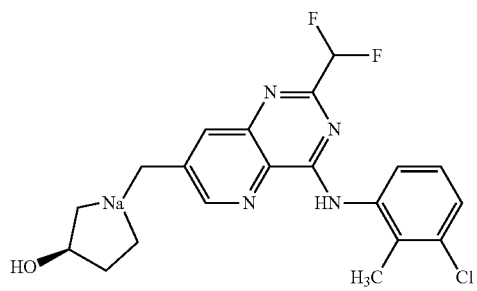

A mixture of 4-((3-chloro-2-methylphenyl)amino)-2-(difluoromethyl)pyrido[3,2-d]pyrimidine-7-carbaldehyde (101 mg, 0.290 mmol) and (R)-pyrrolidin-3-ol (30.3 mg, 0.348 mmol) in DCM (1931 µL) was stirred at r.t. for 30 min. Then sodium triacetoxyborohydride (92 mg, 0.434 mmol) was added. The mixture was further stirred at r.t. for 1 h. The reaction was quenched with NH₄OH aq. solution and extracted by DCM. The organic phase was combined and dried over MgSO₄. After filtration, the DCM solution was concentrated to a residue, which was purified by flash chromatography (0-12% MeOH/DCM). LC-MS calculated for C₂₀H₂₁ClF₂N₅O (M+H)⁺: m/z=420.1; found 420.2.

Step 14: (R)-2-(3'-(2-(difluoromethyl)-7-((3-hydroxypyrrolidin-1-yl)methyl)pyrido[3,2-d]pyrimidin-4-ylamino)-2,2'-dimethylbiphenyl-3-yl)-5-formylbenzo[d]oxazole-7-carbonitrile

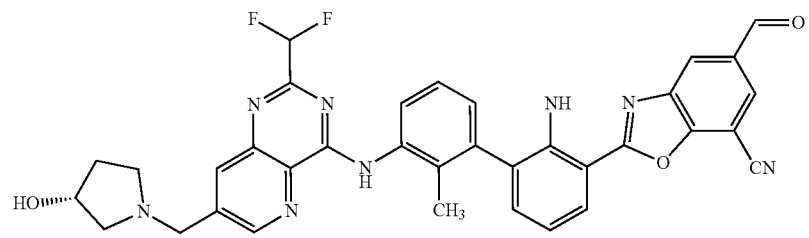 [SMILES: Cc1c(Nc2nc(C(F)F)nc3cc(CN4CC[C@@H](O)C4)cnc23)cccc1-c1cccc(-c2nc3cc(C=O)cc(C#N)c3o2)c1N]

A mixture of (R)-1-((4-((3-chloro-2-methylphenyl)amino)-2-(difluoromethyl)pyrido[3,2-d]pyrimidin-7-yl)methyl)pyrrolidin-3-ol (34.4 mg, 0.082 mmol), 5-formyl-2-(2-methyl-3-(4,4,5,5-tetramethyl-1,3,2-dioxaborolan-2-yl)phenyl)benzo[d]oxazole-7-carbonitrile (Step 7: 35 mg, 0.090 mmol), chloro(2-dicyclohexylphosphino-2',4',6'-triisopropyl-1,1'-biphenyl)[2-(2'-amino-1,1'-biphenyl)]palladium(II) (6.5 mg, 8.2 µmol) and potassium phosphate (43.5 mg, 0.205 mmol) in water (140 µL) and 1,4-dioxane (690 µL) was purged with $N_2$ and then sealed. The reaction was stirred at 100° C. for 2 h. The reaction was cooled to room temperature. The reaction mixture was diluted with DCM and $H_2O$. The layers were separated. The aqueous layer was extracted with DCM three times. The organic layer was dried over $MgSO_4$, filtered and concentrated to give a crude residue, which was used directly in the next step without further purification. LC-MS calculated for $C_{36}H_{30}F_2N_7O_3$ (M+H)⁺: m/z=646.2; found 646.3.

Step 15: (R)-1-((7-cyano-2-(3'-(2-(difluoromethyl)-7-((3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)piperidine-4-carboxylic acid

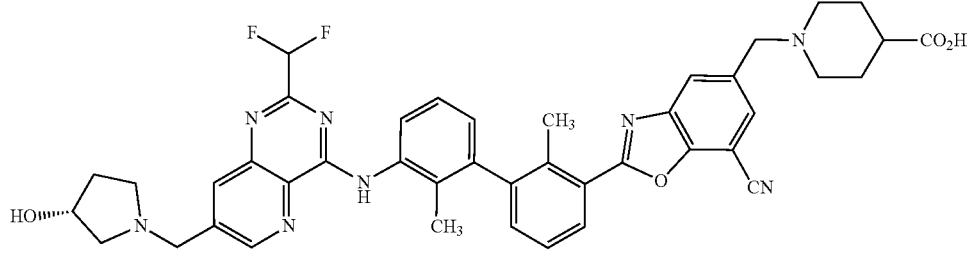 [SMILES: Cc1c(Nc2nc(C(F)F)nc3cc(CN4CC[C@@H](O)C4)cnc23)cccc1-c1cccc(-c2nc3cc(CN4CCC(C(=O)O)CC4)cc(C#N)c3o2)c1C]

A mixture of (R)-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)-5-formylbenzo[d]oxazole-7-carbonitrile (9.5 mg, 0.015 mmol) and tert-butyl piperidine-4-carboxylate (5.45 mg, 0.029 mmol) in DCM (500 µL) was stirred at r.t. for 2 h. Then sodium triacetoxyborohydride (9.36 mg, 0.044 mmol) was added. The mixture was stirred at r.t. for 1 h. Then to the mixture was added trifluoroacetic acid (300 µL) and stirred for 30 min. The volatiles were evaporated and the residue was diluted with MeOH and then purified by prep-HPLC (pH=2, acetonitrile/water+TFA) to give the desired product as TFA salt. LC-MS calculated for $C_{42}H_{41}F_2N_8O_4$ (M+H)⁺: m/z=759.3 ; found 759.6. ¹H NMR (500 MHz, DMSO) δ 10.63 (s, 1H), 9.13 (s, 1H), 8.52 (d, J=2.0 Hz, 1H), 8.39 (d, J=1.6 Hz, 1H), 8.19 (dd, J=7.9, 1.5 Hz, 1H), 8.11 (d, J=2.1 Hz, 1H), 7.64 (dd, J=8.1, 1.3 Hz, 1H), 7.59 (t, J=7.7 Hz, 1H), 7.49 (dd, J=7.5, 1.5 Hz, 1H), 7.41 (t, J=7.8 Hz, 1H), 7.16 (dd, J=7.6, 1.3 Hz, 1H), 6.74 (t, J=54.5 Hz, 1H), 4.85-4.65 (m, 2H), 4.58-4.40 (m, 3H), 3.74-3.00 (m, 8H), 2.78-2.54 (m, 1H), 2.50 (s, 3H), 2.32-1.91 (m, 5H), 1.95 (s, 3H), 1.79-1.67 (m, 1H).

Step 16: (7S,10S,13S,16S)-7,13,16-tris(2-(tert-butoxy)-2-oxoethyl)-1-(1-((7-cyano-2-(3'-((2-(difluoromethyl)-7-(((R)-3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidin-4-yl)-1,5,8,11,14-pentaoxo-10-(3-(3-((2,2,4,6,7-pentamethyl-2,3-dihydrobenzofuran-5-yl)sulfonyl)guanidino)propyl)-2,6,9,12,15-pentaazaheptadecan-17-oic acid

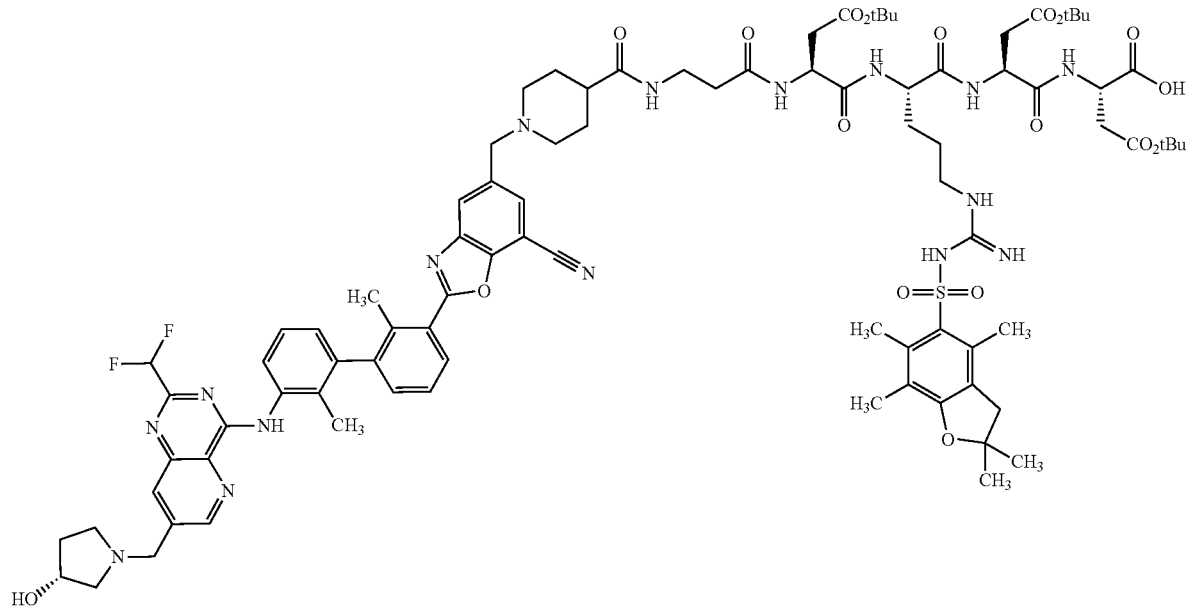 [SMILES: Cc1c(Nc2nc(C(F)F)nc3cc(CN4CC[C@@H](O)C4)cnc23)cccc1-c1cccc(-c2nc3cc(CN4CCC(C(=O)NCCC(=O)N[C@@H](CC(=O)OC(C)(C)C)C(=O)N[C@@H](CCCNC(=N)NS(=O)(=O)c5c(C)c(C)c6c(c5C)CC(C)(C)O6)C(=O)N[C@@H](CC(=O)OC(C)(C)C)C(=O)N[C@@H](CC(=O)OC(C)(C)C)C(=O)O)CC4)cc(C#N)c3o2)c1C]

In a peptide synthesis vessel add H-Asp(OtBu)-2-ClTrt resin (Peptides International, cat #RHD-11054-PI: 25 mg, 0.83 mmol/g, 0.021 mmol), Fmoc-Asp(OtBu)-OH (17.09 mg, 0.042 mmol) solution in DMF (500 mL), DIPEA (14.5 µL, 0.083 mmol) and PyBOP (21.6 mg, 0.042 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated in a sequence of Fmoc-Arg(Pbf)-OH (26.9 mg, 0.042 mmol), Fmoc-Asp(OtBu)-OH (17.09 mg, 0.042 mmol), Fmoc-beta-Ala-OH (12.93 mg, 0.042 mmol) and (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (19.69 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the desired product as the TFA salt. LC-MS calculated for $C_{88}H_{114}F_2N_{16}O_{18}S$ (M+2H)$^{2+}$: m/z=876.9; found 876.8.

Step 17: (7S,10S,13S,16S)-16-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-7,13-bis(carboxymethyl)-1-(1-((7-cyano-2-(3'-((2-(difluoromethyl)-7-(((R)-3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidin-4-yl)-10-(3-guanidinopropyl)-1,5,8,11,14-pentaoxo-2,6,9,12,15-pentaazaoctadecan-18-oic acid In a 1 dram vial (7S,10S,13S,16S)-7,13,16-tris(2-(tert-butoxy)-2-oxoethyl)-1-(1-((7-cyano-2-(3'-((2-(difluoromethyl)-7-(((R)-3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidin-4-yl)-1,5,8,11,14-pentaoxo-10-(3-(3-((2,2,4,6,7-pentamethyl-2,3-dihydrobenzofuran-5-yl)sulfonyl)guanidino)propyl)-2,6,9,12,15-pentaazaheptadecan-17-oic acid (5.6 mg, 3.2 µmol) and (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (Example 1, Step 17: 2.5 mg, 3.2 µmol) were dissolved in DMF (300 µL) to give a yellow solution. DIPEA (2.8 µL, 0.016 mmol) and BOP (2.1 mg, 4.8 µmol) were added to the reaction mixture in one portion. After 30 min, the reaction mixture was concentrated to dryness. Trifluoroacetic acid (0.5 mL) was added to the reaction mixture. After 20 min, the reaction mixture was diluted with water and MeOH then purified by prep-HPLC (pH=2, acetonitrile/water+TFA) to give the desired product as the TFA salt. LC-MS calculated for $C_{101}H_{118}F_2N_{29}O_{20}$ (M+3H)$^{3+}$: m/z=698.6; found 698.7.

Example 9

(3S,6S,9S,12S)-3-((2-(1-(2-(((S)-1-(((S)-1-((4-((((3-((3-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamoyl)oxy)methyl)phenyl)amino)-1-oxo-5-ureidopentan-2-yl)amino)-3-methyl-1-oxobutan-2-yl)amino)-2-oxoethyl)-1H-1,2,3-triazol-4-yl)ethyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-9-(3-guanidinopropyl)-5,8,11,14-tetraoxo-4,7,10,13-tetraazaheptadecanoic acid

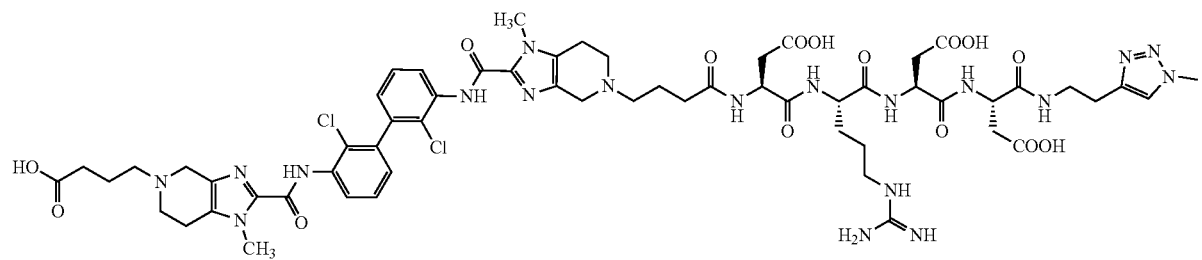

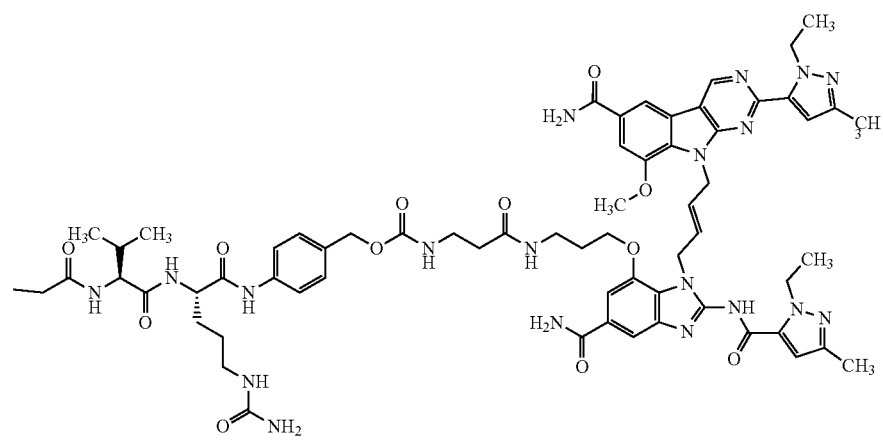

Step 1: 4-((S)-2-((S)-2-amino-3-methylbutanamido)-5-ureidopentanamido)benzyl (3-((3-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-3-oxopropyl) carbamate

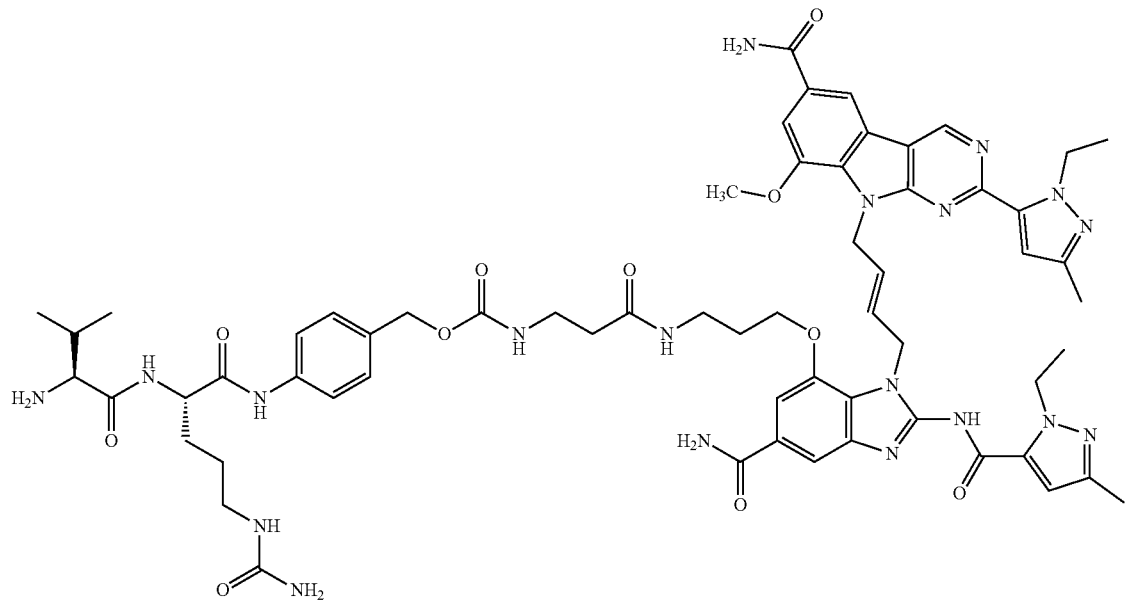 [SMILES: CCn1nc(C)cc1C(=O)Nc1nc2cc(C(N)=O)cc(OCCCNC(=O)CCNC(=O)OCc3ccc(NC(=O)[C@H](CCCNC(N)=O)NC(=O)[C@@H](N)C(C)C)cc3)c2n1C/C=C/Cn1c2nc(-c3cc(C)nn3CC)ncc2c2cc(C(N)=O)cc(OC)c21]

This compound was prepared using similar procedures as described for Example 2, Step 1-2 with (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-methoxy-9H-pyrimido[4,5-b]indole-6-carboxamide (Example 7, Step 9) replacing (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide in Step 1.

Step 2: 4-((S)-2-((S)-2-(2-azidoacetamido)-3-methylbutanamido)-5-ureidopentanamido)benzyl (3-((3-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-3-oxopropyl) carbamate

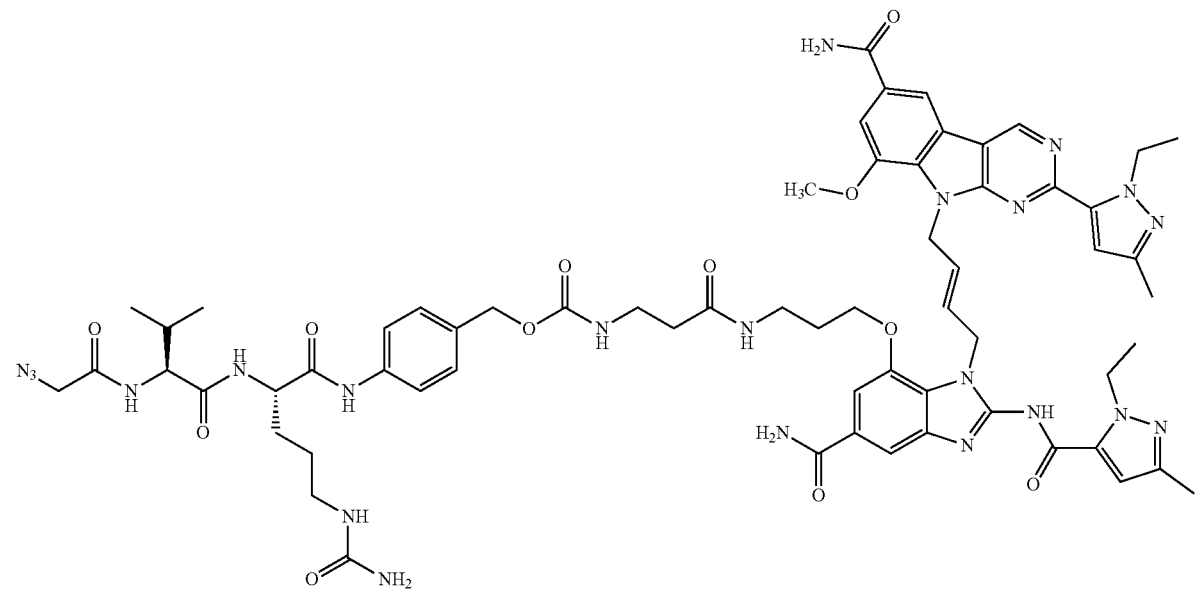 [SMILES: CCn1nc(C)cc1C(=O)Nc1nc2cc(C(N)=O)cc(OCCCNC(=O)CCNC(=O)OCc3ccc(NC(=O)[C@H](CCCNC(N)=O)NC(=O)[C@@H](NC(=O)CN=[N+]=[N-])C(C)C)cc3)c2n1C/C=C/Cn1c2nc(-c3cc(C)nn3CC)ncc2c2cc(C(N)=O)cc(OC)c21]

This compound was prepared using similar procedures as described for Example 4 with 4-((S)-2-((S)-2-amino-3-methylbutanamido)-5-ureidopentanamido)benzyl (3-((3-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamate replacing 4-((S)-2-((S)-2-amino-3-methylbutanamido)-5-ureidopentanamido)benzyl (3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamate in Step 4. LC-MS calculated for $C_{64}H_{80}N_{22}O_{12}$ $(M+2H)^{2+}$: m/z=674.4; found 674.4.

Step 3: (3S,6S,9S,12S)-3-((2-(1-(2-(((S)-1-(((S)-1-((4-(((((3-((3-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamoyl)oxy)methyl)phenyl)amino)-1-oxo-5-ureidopentan-2-yl)amino)-3-methyl-1-oxobutan-2-yl)amino)-2-oxoethyl)-1H-1,2,3-triazol-4-yl)ethyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-9-(3-guanidinopropyl)-5,8,11,14-tetraoxo-4,7,10,13-tetraazaheptadecanoic acid This compound was prepared using similar procedures as described for Example 4 with 4-((S)-2-((S)-2-(2-azidoacetamido)-3-methylbutanamido)-5-ureidopentanamido)benzyl (3-((3-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamate replacing 4-((S)-2-((S)-2-(2-azidoacetamido)-3-methylbutanamido)-5-ureidopentanamido)benzyl (3-((3-((5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-oxopropyl)carbamate in Step 5. LC-MS calculated for $C_{122}H_{153}Cl_2N_{38}O_{27}$ $(M+3H)^{3+}$: m/z=884.7; found 885.2.

Example 10

(S)-4-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-(S)-3-carboxy-2-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)propanamido)-4-oxobutanoic acid

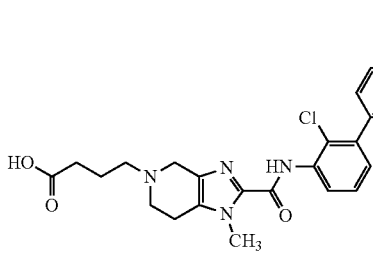
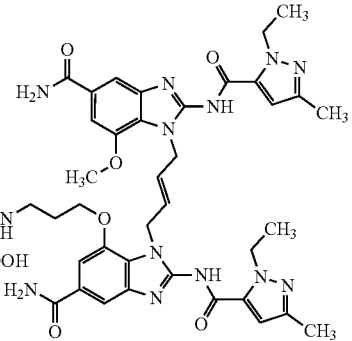
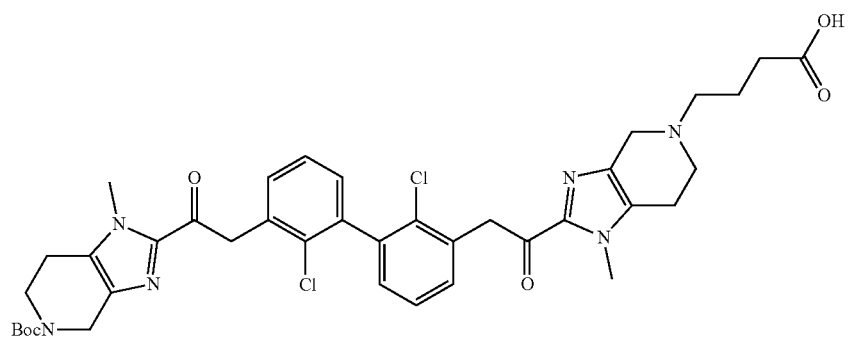 [SMILES: Cn1c(C(=O)Cc2cccc(-c3cccc(CC(=O)c4nc5c(n4C)CCN(C(=O)OC(C)(C)C)C5)c3Cl)c2Cl)nc2c1CCN(CCCC(=O)O)C2]

Step 1: 4-(2-((3'-(5-(tert-butoxycarbonyl)-1-methyl-4,5,6,7-tetrahydro-1H-imidazo[4,5-d]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid A mixture of tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 1, Step 5: 248 mg, 0.365 mmol) in dichloromethane (10.0 mL) was sequentiantly treated with methyl 4-oxobutanoate (127 mg, 1.09 mmol), hunig's base (319 µl, 1.82 mmol) and sodium triacetoxyborohydride (309 mg, 1.46 mmol) in DCM (3649 µl). The mixture was stirred at rt for 2 h. The reaction mixture was quenched with saturated aqueous $NaHCO_3$ solution, and extracted with dichloromethane. The organic layers were washed with brine, dried over $Na_2SO_4$, filtered and concentrated under reduced pressure. The residue was treated with LiOH (87 mg, 3.65 mmol) in a mixture of THF, MeOH and water. After 12 h, the reaction mixture was diluted with MeOH then purified by prep-HPLC (pH=2, acetonitrile/water+TFA) to give the desired product as the TFA salt. LC-MS calculated for $C_{37}H_{43}Cl_2N_8O_6$ $(M+H)^+$: m/z=765.3; found 765.2.

Step 2: 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid

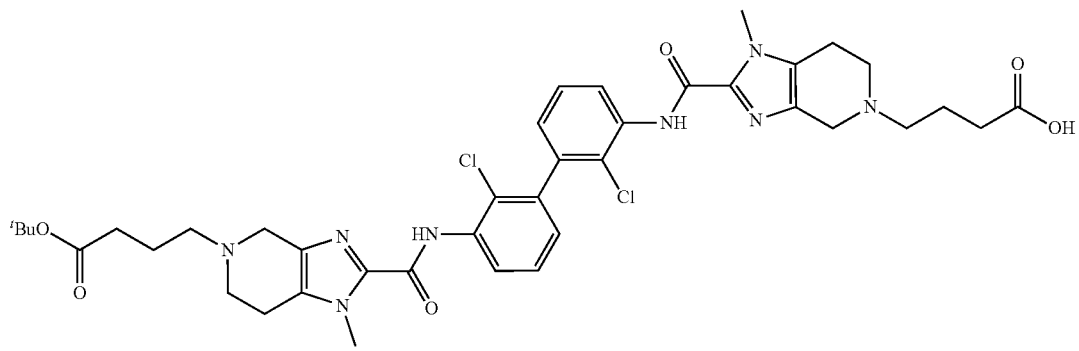 [SMILES: Cn1c(C(=O)Nc2cccc(-c3cccc(NC(=O)c4nc5c(n4C)CCN(CCCC(=O)OC(C)(C)C)C5)c3Cl)c2Cl)nc2c1CCN(CCCC(=O)O)C2]

A mixture of 4-(2-((3'-(5-(tert-butoxycarbonyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (85 mg, 0.111 mmol) in dichloromethane (10.0 mL) and trifluoroacetic acid (5.0 mL) was stirred at room temperature for 1 h. The mixture was concentrated under reduced pressure. The residue was sequentiantly treated with tert-butyl 4-oxobutanoate (Enamine Ltd, cat #EN300-250752: 52.7 mg, 0.333 mmol), hunig's base (97 µl, 0.555 mmol) and sodium triacetoxyborohydride (94 mg, 0.444 mmol) in DCM (1.1 mL). The mixture was stirred at rt for 2 h. The reaction mixture was quenched with saturated aqueous $NaHCO_3$ solution, and extracted with dichloromethane. The organic layers were washed with brine, dried over $Na_2SO_4$, filtered and concentrated under reduced pressure. The residue was diluted with MeOH then purified by prep-HPLC (pH=2, acetonitrile/water+TFA) to give the desired product as the TFA salt. LC-MS calculated for $C_{40}H_{49}Cl_2N_8O_6$ $(M+H)^+$: m/z=807.3; found 807.2.

Step 3: (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid

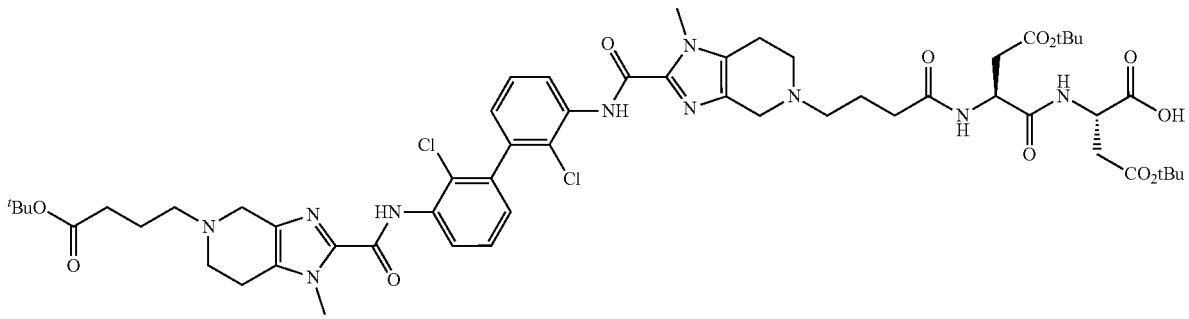 [SMILES: Cn1c(C(=O)Nc2cccc(-c3cccc(NC(=O)c4nc5c(n4C)CCN(CCCC(=O)OC(C)(C)C)C5)c3Cl)c2Cl)nc2c1CCN(CCCC(=O)N[C@@H](CC(=O)OC(C)(C)C)C(=O)N[C@@H](CC(=O)OC(C)(C)C)C(=O)O)C2]

In a peptide synthesis vessel add H-Asp(OtBu)-2-ClTrt resin (Peptides International, cat #RHD-11054-PI : 25 mg, 0.83 mmol/g, 0.021 mmol), Fmoc-Asp(OtBu)-OH (17.09 mg, 0.042 mmol) solution in DMF (500 µL), DIPEA (14.5 µL, 0.083 mmol) and PyBOP (21.6 mg, 0.042 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated with 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (20.6 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the desired product as the TFA salt. LC-MS calculated for $C_{56}H_{76}Cl_2N_{10}O_{12}$ $(M+2H)^{2+}$: m/z=575.3; found 575.5.

Step 4: (S)-4-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-((S)-3-carboxy-2-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-bipheny]-3-yl)carbamoyl)-1- methyl-1,4,6,7-tetrahydro-5H-imidazo[4,5-c]pyridin-5-yl)butanamido)propanamido)-4-oxobutanoic acid In a 1 dram vial (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid dissolved in DMF (227 µl) to give a colorless solution. (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (Example 1, Step 17: 2.66 mg, 3.41 µmol), DIPEA (2.0 µl, 0.011 mmol) and BOP (3.01 mg, 6.81 µmol) were added to the reaction mixture in one portion. After 30 min, the reaction mixture was concentrated to dryness. Trifluoroacetic acid (0.5 mL) was added to the reaction mixture. After 20 min, the reaction mixture was diluted with water and MeOH then purified by prep-HPLC (pH=2, acetonitrile/water+TFA) to give the desired product as the TFA salt. LC-MS calculated for $C_{82}H_{95}Cl_2N_{23}O_{17}$ $(M+2H)^{2+}$: m/z=872.8; found 872.8.

Example 11

(S)-4-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)amino)-3-((S)-3-carboxy-2-((S)-3-carboxy-2-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)propanamido)propanamido)-4-oxobutanoic acid

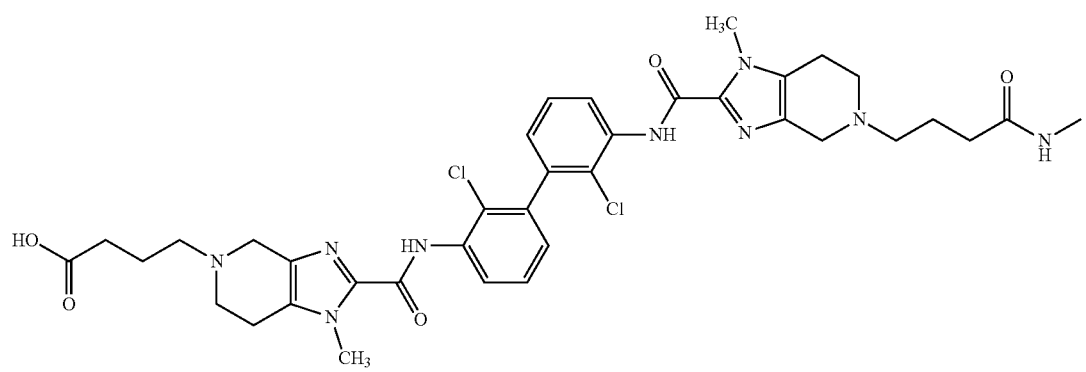

-continued

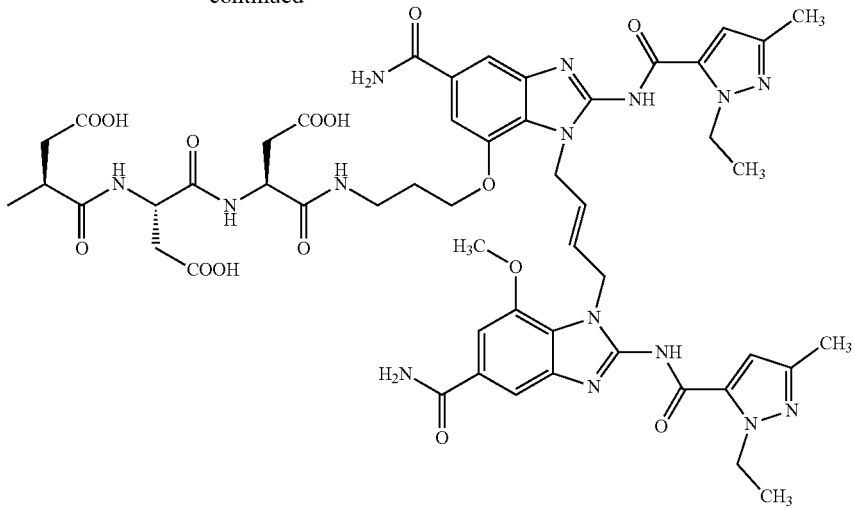

Step 1: (S)-4-(tert-butoxy)-2-((S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanamido)-4-oxobutanoic acid TFA) to give the desired product as the TFA salt. LC-MS calculated for $C_{64}H_{89}Cl_2N_{11}O_{15}$ $(M+2H)^{2+}$: m/z=660.8; found 660.8.

Step 2: (S)-4-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]

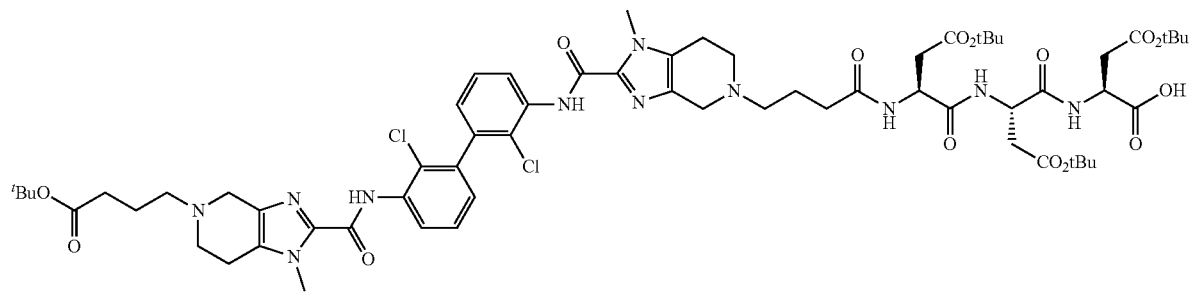 [SMILES: Cn1c(C(=O)Nc2cccc(-c3cccc(NC(=O)c4nc5c(n4C)CCN(CCCC(=O)OC(C)(C)C)C5)c3Cl)c2Cl)nc2c1CCN(CCCC(=O)N[C@@H](CC(=O)OC(C)(C)C)C(=O)N[C@@H](CC(=O)OC(C)(C)C)C(=O)N[C@@H](CC(=O)OC(C)(C)C)C(=O)O)C2]

In a peptide synthesis vessel add H-Asp(OtBu)-2-ClTrt resin (Peptides International, cat #RHD-11054-PI: 25 mg, 0.83 mmol/g, 0.021 mmol), Fmoc-Asp(OtBu)-OH (17.09 mg, 0.042 mmol) solution in DMF (500 μL), DIPEA (14.5 μL, 0.083 mmol) and PyBOP (21.6 mg, 0.042 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated in a sequence of Fmoc-Asp (OtBu)-OH (17.09 mg, 0.042 mmol) and 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Example 10, Step 2: 20.6 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+ imidazol-7-yl)oxy)propyl)amino)-3-((S)-3-carboxy-2-((S)-3-carboxy-2-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)propanamido)propanamido)-4-oxobutanoic acid This compound was prepared using similar procedures as described for Example 10 with (S)-4-(tert-butoxy)-2-((S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanamido)-4-oxobutanoic acid replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid in Step 4. LC-MS calculated for $C_{86}H_{101}Cl_2N_{24}O_{20}$ $(M+3H)^{3+}$: m/z=620.5; found 620.5.

Example 12

(3S,6S,9S,12S)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-17-(2-((3'-(5-(4-carboxybutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-6,9,12-bis(carboxymethyl)-5,8,11,14-tetraoxo-4,7,10,13-tetraazaheptadecanoic acid

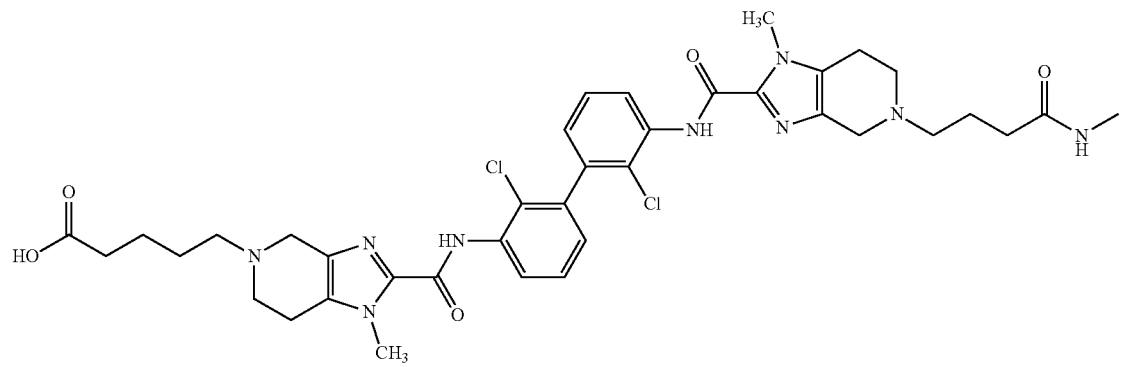

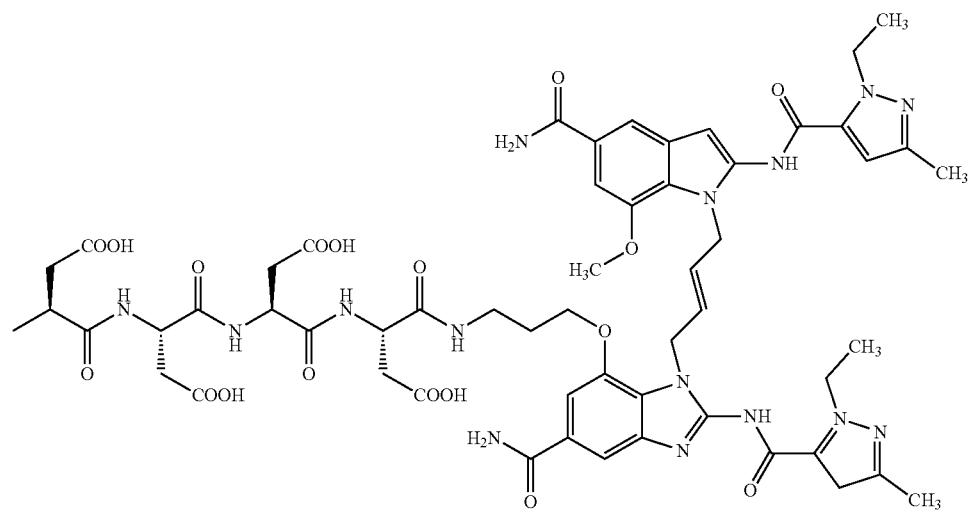

Step 1: (2S,5S,8S,11S)-2,5,8,11-tetrakis(2-(tert-butoxy)-2-oxoethyl)-16-(2-((3'-(5-(5-(tert-butoxy)-5-oxopentyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)-4,7,10,13-tetraoxo-3,6,9,12-tetraazahexadecanoic acid desired product as the TFA salt. LC-MS calculated for $C_{73}H_{104}Cl_2N_{12}O_{18}$ $(M+2H)^{2+}$: m/z=754.3; found 754.3.

Step 2: (3S,6S,9S,12S)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-17-(2-((3'-

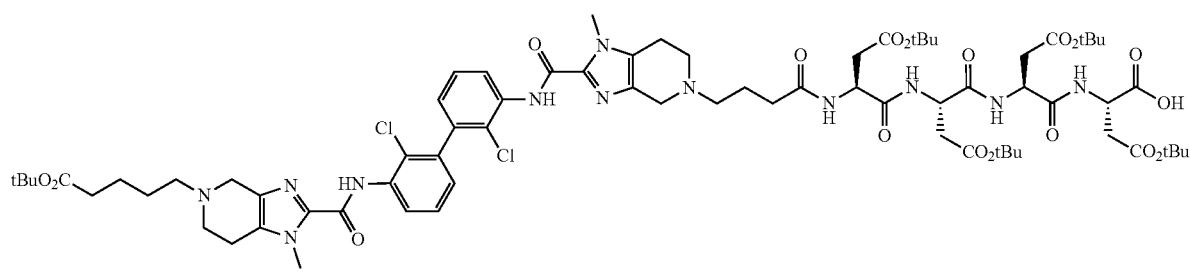 [SMILES: Cn1c(C(=O)Nc2cccc(-c3cccc(NC(=O)c4nc5c(n4C)CCN(CCCC(=O)N[C@@H](CC(=O)OC(C)(C)C)C(=O)N[C@@H](CC(=O)OC(C)(C)C)C(=O)N[C@@H](CC(=O)OC(C)(C)C)C(=O)N[C@@H](CC(=O)OC(C)(C)C)C(=O)O)C5)c3Cl)c2Cl)nc2c1CCN(CCCCC(=O)OC(C)(C)C)C2]

In a peptide synthesis vessel add H-Asp(OtBu)-2-C;Trt resin (Peptides International, cat #RHD-11054-PI: 25 mg, 0.83 mmol/g, 0.021 mmol), Fmoc-Asp(OtBu)-OH (17.09 mg, 0.042 mmol) solution in DMF (500 μL), DIPEA (14.5 μL, 0.083 mmol) and PyBOP (21.6 mg, 0.042 mmol). The resulting mixture was stirred for 1 h and washed repeatly three times with DMF. Use 20% piperidine in DMF (2 mL) for Fmoc deprotection, 3× (10 min), and wash repeatly three times with DMF before each amino acid coupling. This coupling process was repeated in a sequence of Fmoc-Asp(OtBu)-OH (17.09 mg, 0.042 mmol), Fmoc-Asp(OtBu)-OH (17.09 mg, 0.042 mmol) and 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Example 10, Step 2: 20.6 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the (5-(4-carboxybutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-6,9,12-tris(carboxymethyl)-5,8,11,14-tetraoxo-4,7,10,13-tetraazaheptadecanoic acid This compound was prepared using similar procedures as described for Example 10 with (2S,5S,8S,11S)-2,5,8,11-tetrakis(2-(tert-butoxy)-2-oxoethyl)-16-(2-((3'-(5-(5-(tert-butoxy)-5-oxopentyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13-tetraoxo-3,6,9,12-tetraazahexadecanoic acid replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid in Step 4. LC-MS calculated for $C_{91}H_{108}Cl_2N_{25}O_{23}$ $(M+3H)^{3+}$: m/z=663.5; found 663.5.

Example 13

(3S,6S,9S,12S,15S)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-6,9,12-tris(carboxymethyl)-15-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-5,8,11,14-tetraoxo-4,7,10,13-tetraazaheptadecanedioic acid

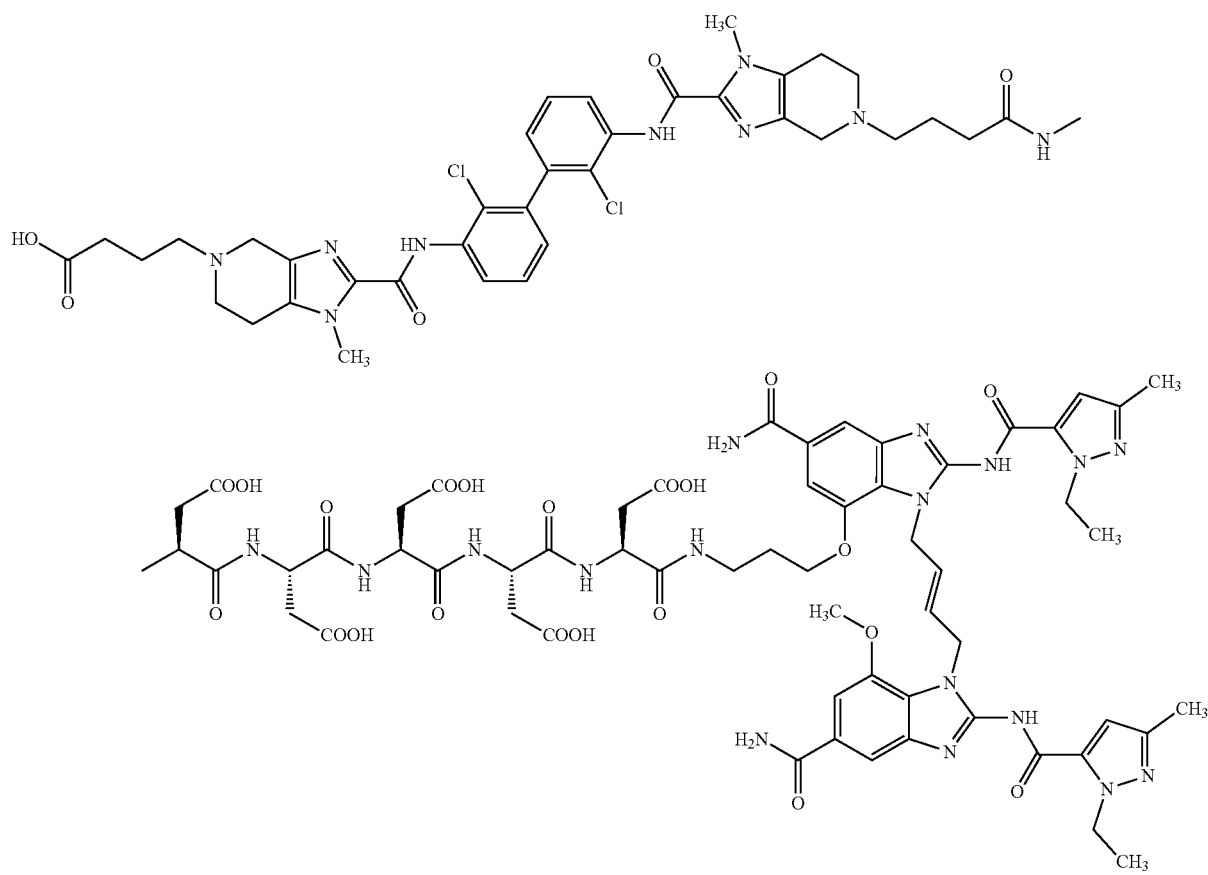

Step 1: (2S,5S,8S,11S,14S)-2,5,8,11,14-pentakis(2-(tert-butoxy)-2-oxoethyl)-19-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13,16-pentaoxo-3,6,9,12,15-pentaazanonadecanoic acid

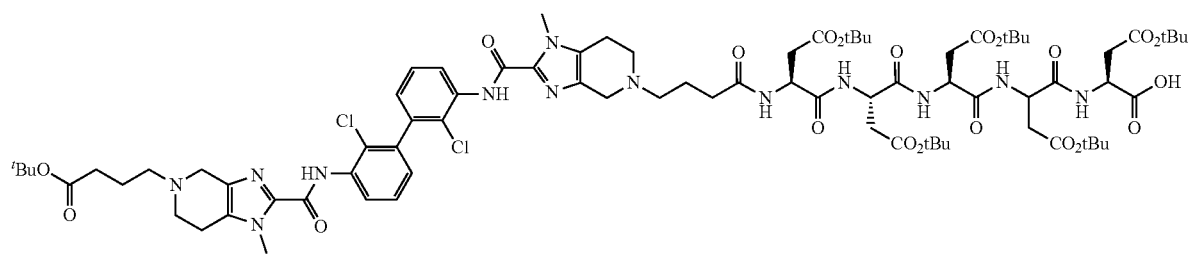 [SMILES: Cn1c(C(=O)Nc2cccc(-c3cccc(NC(=O)c4nc5c(n4C)CCN(CCCC(=O)OC(C)(C)C)C5)c3Cl)c2Cl)nc2c1CCN(CCCC(=O)N[C@@H](CC(=O)OC(C)(C)C)C(=O)N[C@@H](CC(=O)OC(C)(C)C)C(=O)N[C@@H](CC(=O)OC(C)(C)C)C(=O)NC(CC(=O)OC(C)(C)C)C(=O)N[C@@H](CC(=O)OC(C)(C)C)C(=O)O)C2]

In a peptide synthesis vessel add H-Asp(OtBu)-2-ClTrt resin (Peptides International, cat #RHD-11054-PI: 25 mg, 0.83 mmol/g, 0.021 mmol), Fmoc-Asp(OtBu)-OH (17.09 mg, 0.042 mmol) solution in DMF (500 µL), DIPEA (14.5 µL, 0.083 mmol) and PyBOP (21.6 mg, 0.042 mmol). The resulting mixture was stirred for 1 h and washed repeatly three times with DMF. Use 20% piperidine in DMF (2 mL) for Fmoc deprotection, 3× (10 min), and wash repeatly three times with DMF before each amino acid coupling. This coupling process was repeated in a sequence of Fmoc-Asp(OtBu)-OH (17.09 mg, 0.042 mmol), Fmoc-Asp(OtBu)-OH (17.09 mg, 0.042 mmol), Fmoc-Asp(OtBu)-OH (17.09 mg, 0.042 mmol) and 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3- yl)carbamoyl)-1-methyl-1,4,6,7-tetrahydro-5H-imidazo[4,5-c]pyridin-5-yl)butanoic acid (Example 10, Step 2: 20.6 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3×0 with remaining reagent. The filtrate was concentrated and then diluted with MeOH then purified by prep-HPLC (pH=2, acetonitrile/water+TFA) to give the desired product as the TFA salt. LC-MS calculated for $C_{80}H_{115}Cl_2N_{13}O_{21}$ $(M+2H)^{2+}$: m/z=832.0; found 832.0.

Step 2: (3S,6S,9S,12S,15S)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-6,9,12-tris(carboxymethyl)-15-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-5,8,11,14-tetraoxo-4,7,10,13-tetraazaheptadecanedioic acid This compound was prepared using similar procedures as described for Example 10 with (2S,5S,8S,11S,14S)-2,5,8,11,14-pentakis(2-(tert-butoxy)-2-oxoethyl)-19-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13,16-pentaoxo-3,6,9,12,15-pentaazanonadecanoic acid replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid in Step 4. LC-MS calculated for $C_{94}H_{111}Cl_2N_{26}O_{26}$ $(M+3H)^{3+}$: m/z=697.2; found 697.2.

Example 14 di-tert-butyl (3S,6S,9S,12S,15S,18S,21S)-6,9,12,15,18-pentakis(2-(tert-butoxy)-2-oxoethyl)-21-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-5,8,11,14,17,20-hexaoxo-4,7,10,13,16,19-hexaazatricosanedioate acid

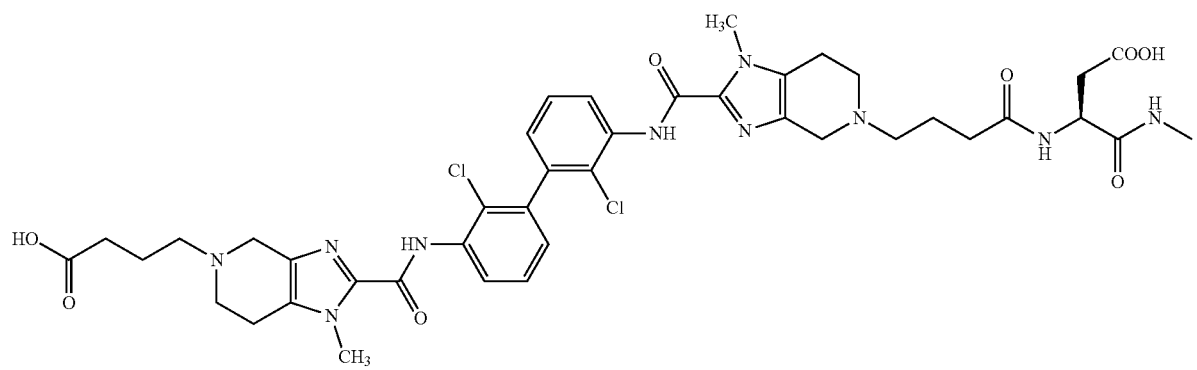

367

-continued

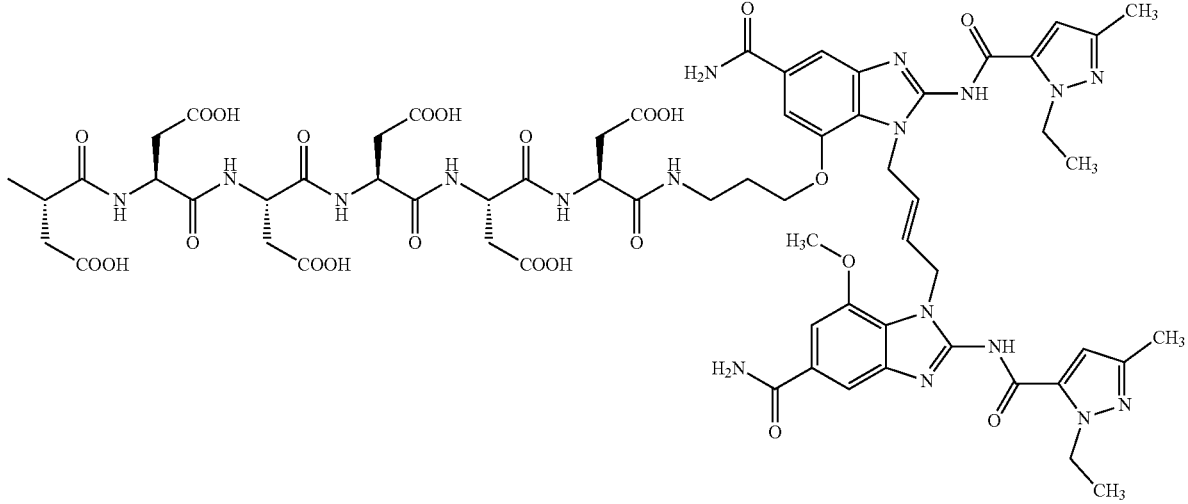

Step 1: (2S,5S,8S,11S,14S,17S,20S)-2,5,8,11,14,17,20-heptakis(2-(tert-butoxy)-2-oxoethyl)-25-(2-((3'-(5-(4-(tert-butoxy)-4-oxobtayl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13,16,19,22-heptaoxo-3,6,9,12,15,18,21-heptaazapentacosanoic acid In a peptide synthesis vessel add H-Asp(OtBu)-2-ClTrt resin (Peptides International, cat #RHD-11054-PI: 25 mg, 0.83 mmol/g, 0.021 mmol), Fmoc-Asp(OtBu)-OH (17.09 mg, 0.042 mmol) solution in DMF (500 µL), DIPEA (14.5 µL, 0.083 mmol) and PyBOP (21.6 mg, 0.042 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated in a sequence of Fmoc-Asp(OtBu)-OH (17.09 mg, 0.042 mmol), Fmoc-Asp(OtBu)-OH (17.09 mg, 0.042 mmol), Fmoc-Asp(OtBu)-OH (17.09 mg, 0.042 mmol), Fmoc-Asp(OtBu)-OH (17.09 mg, 0.042 mmol), Fmoc-Asp(OtBu)-OH (17.09 mg, 0.042 mmol) and

368

4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Example 10, Step 2: 20.6 mg, 0.026 mmol). At the end cleave the peptide from the resin using a cocktail of 10% (0.5 mL) HOAc, 10% (0.5 mL) TFE, 80% (4 mL) DCM, the

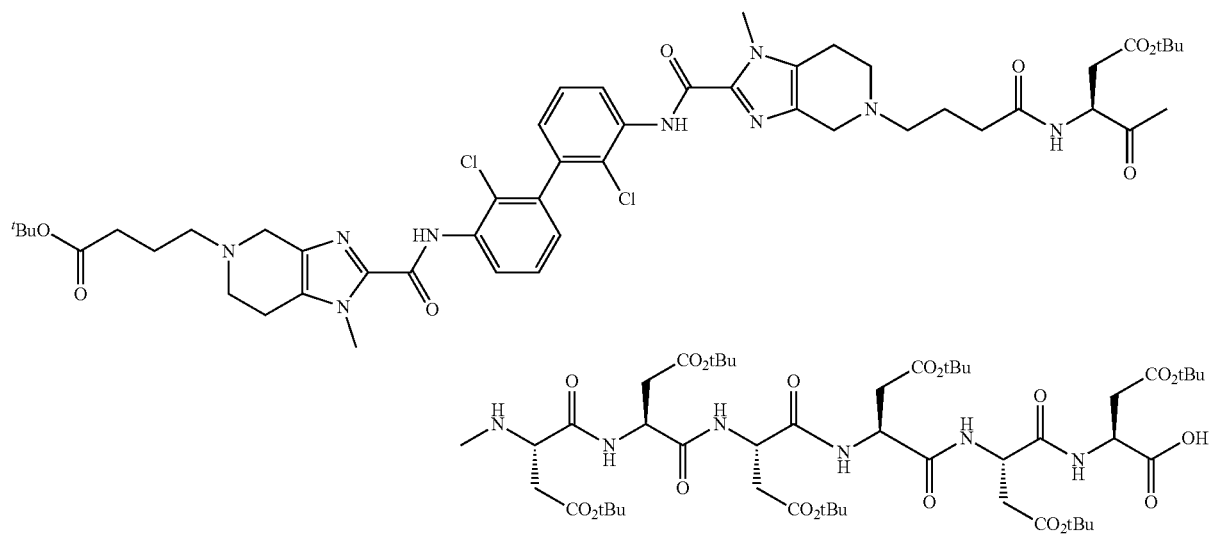

cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the desired product as the TFA salt. LC-MS calculated for $C_{96}H_{141}Cl_2N_{15}O_{27}$ (M+2H)$^{2+}$: m/z=1003.6; found 1003.6.

Step 2: di-tert-butyl (3S,6S,9S,12S,15S,18S,21S)-6,9,12,15,18-pentakis(2-(tert-butoxy)-2-oxoethyl)-21-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-3-((3-((5-carbamoyl-1-((E)-4-(5-carbamoyl-2-(1-ethyl-3-methyl-1H- pyrazole-5-carboxamido)-7-methoxy-1H-benzo[d]
imidazol-1-yl)but-2-en-1-yl)-2-(1-ethyl-3-methyl-1H-
pyrazole-5-carboxamido)-1H-benzo[d]imidazol-7-yl)oxy)
propyl)carbamoyl)-5,8,11,14,17,20-hexaoxo-4,7,10,13,16,
19-hexaazatricosanedioate This compound was prepared using similar procedures as described for Example 10 with (2S,5S,8S,11S,14S,17S,20S)-2,5,8,11,14,17,20-heptakis(2-(tert-butoxy)-2-oxo-ethyl)-25-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13,16,19,22-heptaoxo-3,6,9,12,15,18,21-heptaazapentacosanoic acid replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid in Step 4. LC-MS calculated for $C_{102}H_{121}Cl_2N_{28}O_{32}$ $(M+3H)^{3+}$: m/z=773.9; found 773.9.

Example 15

(3S,6S,9S,12S,15S,18S,21S,24S)-3-((3-((5-carbam-
oyl-1-((E)-4-(5-carbamoyl-2-(1-ethyl-3-methyl-1H-
pyrazole-5-carboxamido)-7-methoxy-1H-benzo[d]
imidazol-1-yl)but-2-en-1-yl)-2-(1-ethyl-3-methyl-
1H-pyrazole-5-carboxamido)-1H-benzo[d]imidazol-
7-yl)oxy)propyl)carbamoyl)-6,12,15,18-tetrakis
(carboxymethyl)-24-(4-(2-((3'-(5-(3-carboxypropyl)-
1-methyl-4,5,6,7-tetrahydro-1H-imidazo[4,5-c]
pyridine-2-carboxamido)-2,2'-dichloro-[1,1'-
biphenyl]-3-yl)carbamoyl)-1-methyl-1,4,6,7-
tetrahydro-5H-imidazo[4,5-c]pyridin-5-yl)
butanamido)-9,21-bis(3-guanidinopropyl)-5,8,11,14,
17,20,23-heptaoxo-4,7,10,13,16,19,22-
heptaazahexacosanedioic acid

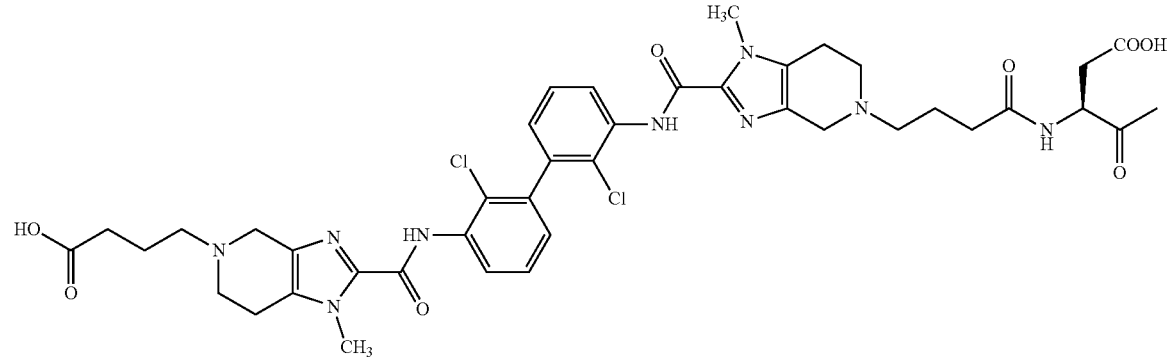

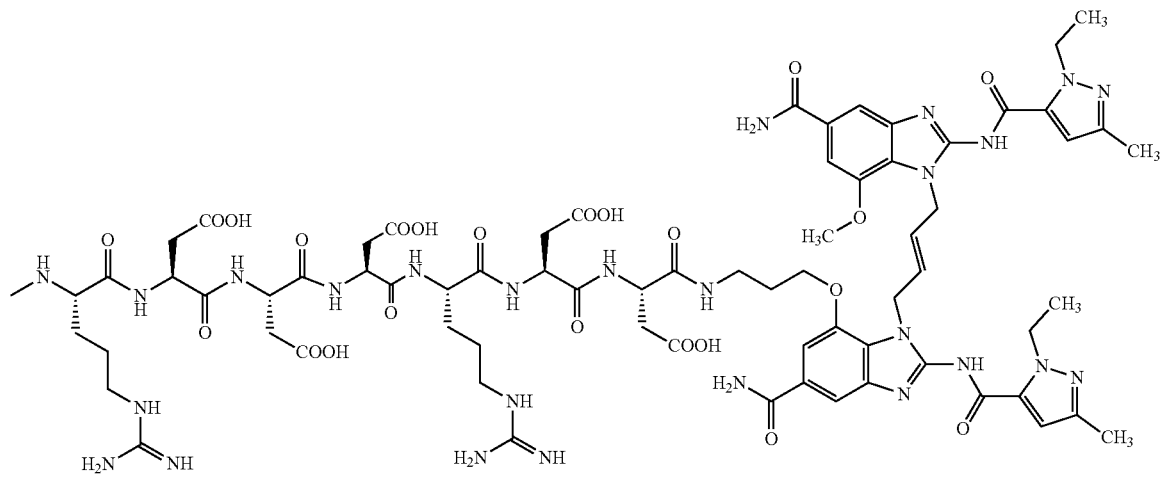

Step 1: (2S,5S,8S,11S,14S,17S,20S,23S)-2,5,11,14,17,23-hexakis(2-(tert-butoxy)-2-oxoethyl)-28-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13,16,19,22,25-octaoxo-8,20-bis(3-(3-((2,2,4,6,7-pentamethyl-2,3-dihydrobenzofuran-5-yl)sulfonyl)guanidino)propyl)-3,6,9,12,15,18,21,24-octaazaoctacosanoic acid

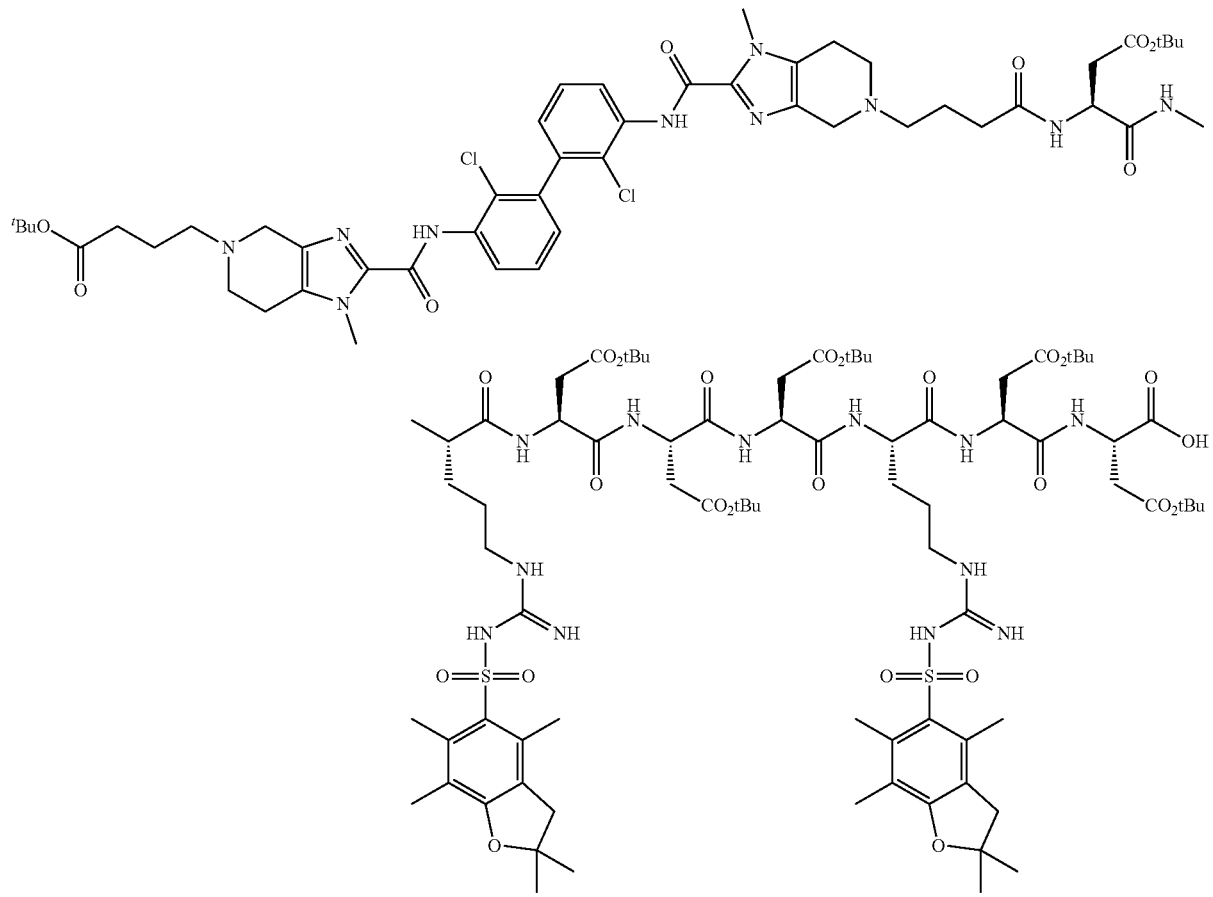

In a peptide synthesis vessel add H-Asp(OtBu)-2-ClTrt resin (Peptides International, cat #RHD-11054-PI: 25 mg, 0.83 mmol/g, 0.021 mmol), Fmoc-Asp(OtBu)-OH (17.09 mg, 0.042 mmol) solution in DMF (500 μL), DIPEA (14.5 μL, 0.083 mmol) and PyBOP (21.6 mg, 0.042 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated in a sequence of Fmoc-Arg(Pbf)-OH (26.9 mg, 0.042 mmol), Fmoc-Asp(OtBu)-OH (17.09 mg, 0.042 mmol), Fmoc-Asp(OtBu)-OH (17.09 mg, 0.042 mmol), Fmoc-Asp(OtBu)-OH (17.09 mg, 0.042 mmol), Fmoc-Arg(Pbf)-OH (26.9 mg, 0.042 mmol), Fmoc-Asp(OtBu)-OH (17.09 mg, 0.042 mmol) and 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Example 10, Step 2: 20.6 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the desired product as the TFA salt. LC-MS calculated for $C_{126}H_{185}Cl_2N_{22}O_{32}S_2$ $(M+3H)^{3+}$: m/z=884.9; found 884.9.

Step 2: (3S,6S,9S,12S,15S,18S,21S,24S)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-6,12,15,18-tetrakis(carboxymethyl)-24-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-9,21-bis(3-guanidinopropyl)-5,8,11,14,17,20,23-heptaoxo-4,7,10,13,16,19,22-heptaazahexacosanedioic acid This compound was prepared using similar procedures as described for Example 10 with (2S,5S,8S,11S,14S,17S,20S, 23S)-2,5,11,14,17,23-hexakis(2-(tert-butoxy)-2-oxoethyl)-28-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13,16,19,22,25-octaoxo-8,20-bis(3-(3-((2,2,4,6,7-pentamethyl-2,3-dihydrobenzofuran-5-yl)sulfonyl)guanidino)propyl)-3,6,9,12,15,18,21,24-octaazaoctacosanoic acid replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid in Step 4. LC-MS calculated for $C_{110}H_{140}Cl_2N_{35}O_{31}$ $(M+3H)^{3+}$: m/z=839.7; found 839.7.

Example 16

(3S,6S,9S,12S)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-9,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-6-(3-guanidinopropyl)-5,8,11,14-tetraoxo-4,7,10,13-tetraazaheptadecanoic acid

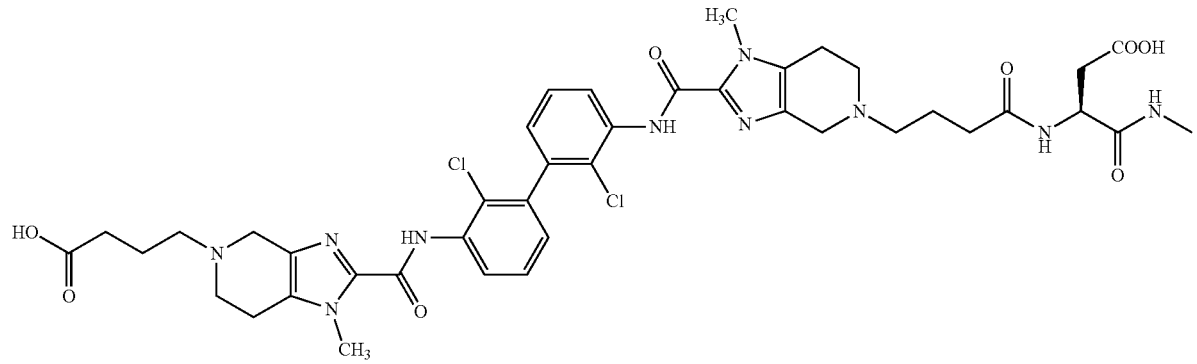

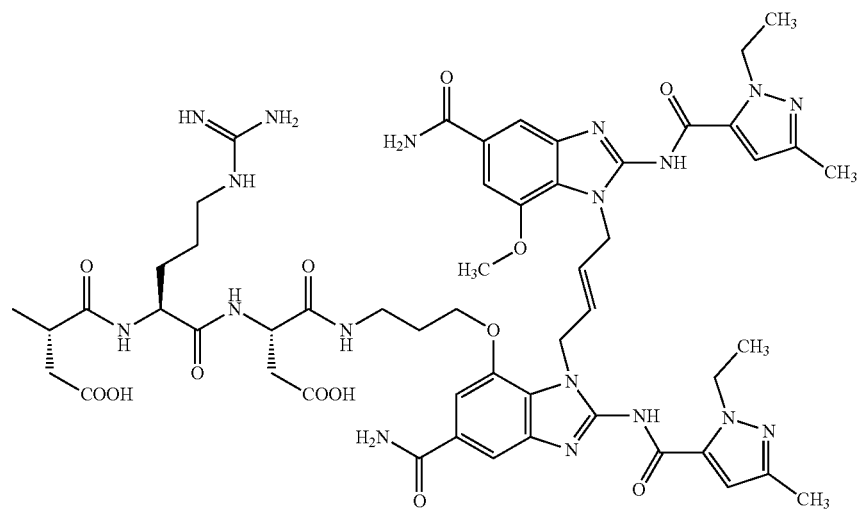

Step 1: (2S,5S,8S,11S)-2,8,11-tris(2-(tert-butoxy)-2-oxoethyl)-16-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)-4,7,10,13-tetraoxo-5-(3-(3-((2,2,4,6,7-pentamethyl-2,3-dihydrobenzofuran-5-yl)sulfonyl)guanidinotpropyl)-3,6,9,12-tetraazahexadecanoic acid

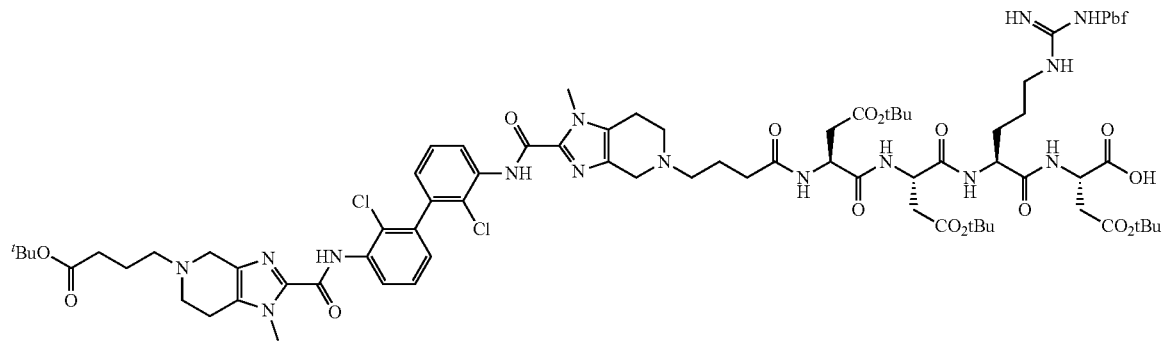

In a peptide synthesis vessel add H-Asp(OtBu)-2-ClTrt resin (Peptides International, cat #RHD-11054-PI: 50 mg, 0.83 mmol/g, 0.042 mmol), Fmoc-Arg(Pbf)-OH (53.9 mg, 0.083 mmol) solution in DMF (500 μL), DIPEA (14.5 μL, 0.083 mmol) and PyBOP (21.6 mg, 0.042 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated in a sequence of Fmoc-Asp(OtBu)-OH (34.2 mg, 0.083 mmol), Fmoc-Asp(OtBu)-OH (34.2 mg, 0.083 mmol) and 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Example 10, Step 2: 20.6 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the desired product as the TFA salt. LC-MS calculated for $C_{83}H_{117}Cl_2N_{15}O_{19}S$ (M+2H)$^{2+}$: m/z=865.9; found 865.9.

Step 2: (3S,6S,9S,12S)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-9,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-6-(3-guanidinopropyl)-5,8,11,14-tetraoxo-4,7,10,13-tetraazaheptadecanoic acid This compound was prepared using similar procedures as described for Example 10 with (2S,5S,8S,11S)-2,8,11-tris(2-(tert-butoxy)-2-oxoethyl)-16-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13-tetraoxo-5-(3-(3-((2,2,4,6,7-pentamethyl-2,3-dihydrobenzofuran-5-yl)sulfonyl)guanidino)propyl)-3,6,9,12-tetraazahexadecanoic acid replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid in Step 4. LC-MS calculated for $C_{92}H_{113}Cl_2N_{28}O_{21}$ (M+3H)$^{3+}$: m/z=672.5; found 672.3.

Example 17

(3S,6S)-6-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-3-((S)-3-carboxy-2-((S)-2-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-5-guanidinopentanamido)propanamido)-4-oxooctanedioic acid

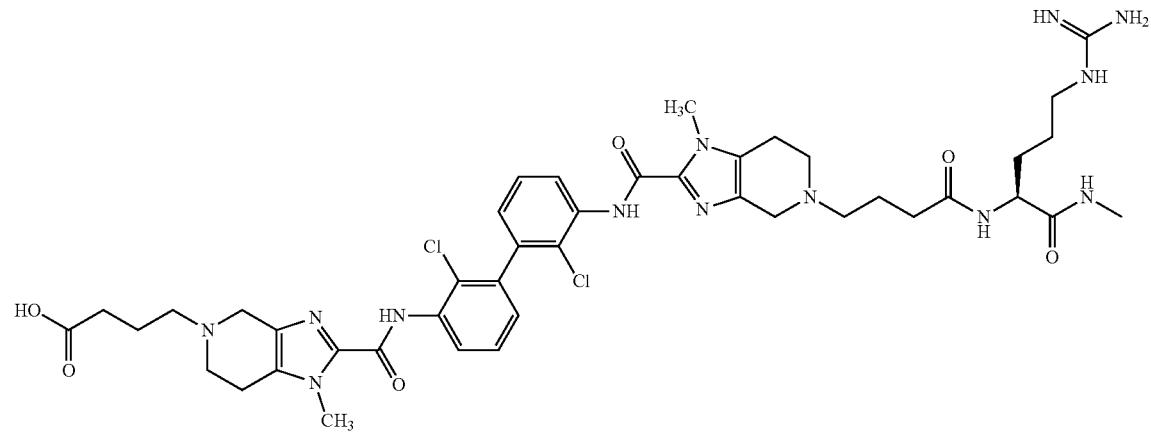

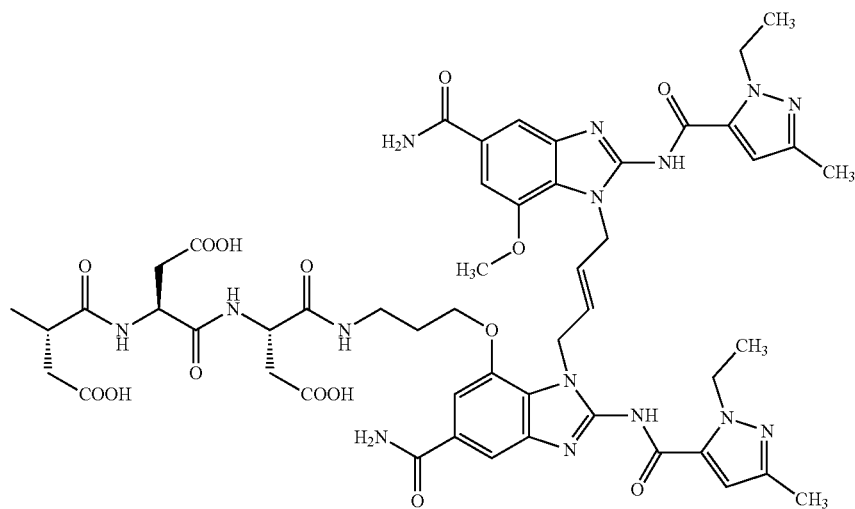

Step 1: (6S,9S,12S,15S)-9,12,15-tris(2-(tert-butoxy)-2-oxoethyl)-6-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)butanamido)-1-imino-7,10,13-trioxo-1-((2,2,4,6,7-pentamethyl-2,3-dihydrobenzofuran)-5-sulfonamido)-2,8,11,14-tetraazahexadecan-16-oic acid

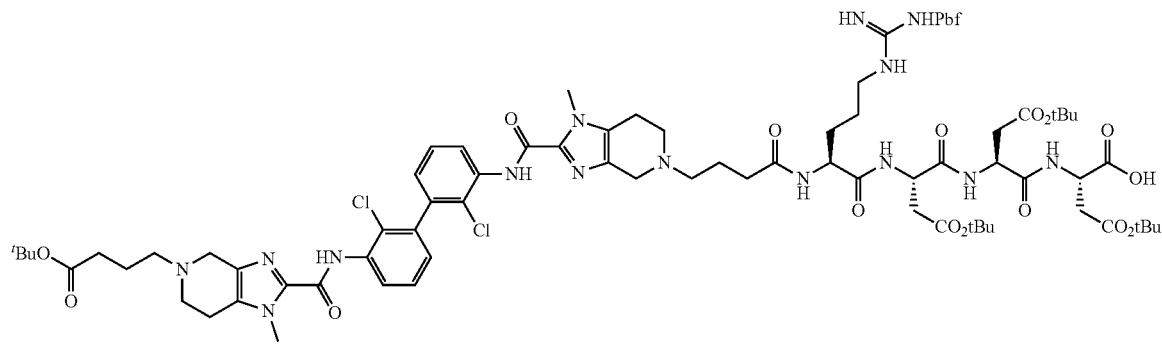

In a peptide synthesis vessel add H-Asp(OtBu)-2-ClTrt resin (Peptides International, cat #RHD-11054-PI: 50 mg, 0.83 mmol/g, 0.042 mmol), Fmoc-Asp(OtBu)-OH (34.2 mg, 0.083 mmol) solution in DMF (500 μL), DIPEA (29.0 μL, 0.166 mmol) and PyBOP (43.2 mg, 0.083 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated in a sequence of Fmoc-Asp(OtBu)-OH (34.2 mg, 0.083 mmol), Fmoc-Arg(Pbf)-OH (53.9 mg, 0.083 mmol) and 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Example 10, Step 2: 20.6 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the desired product as the TFA salt. LC-MS calculated for $C_{83}H_{117}Cl_2N_{15}O_{19}S$ $(M+2H)^{2+}$: m/z=865.9; found 865.9.

Step 2: (3S,6S)-6-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-3-((S)-3-carboxy-2-((S)-2-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)butanamido)-5-guanidinopentanamido)propanamido)-4-oxooctanedioic acid This compound was prepared using similar procedures as described for Example 10 with (6S,9S,12S,15S)-9,12,15-tris(2-(tert-butoxy)-2-oxoethyl)-6-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-1-imino-7,10,13-trioxo-1-(4(2,2,4,6,7-pentamethyl-2,3-dihydrobenzofuran)-5-sulfonamido)-2,8,11,14-tetraazahexadecan-16-oic acid replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid in Step 4. LC-MS calculated for $C_{92}H_{113}Cl_2N_{28}O_{21}$ $(M+3H)^{3+}$: m/z=672.5; found 672.3.

Example 18

(3S,6S,9S,12S)-9-(4-aminobutyl)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-5,8,11,14-tetraoxo-4,7,10,13-tetraazaheptadecanoic acid

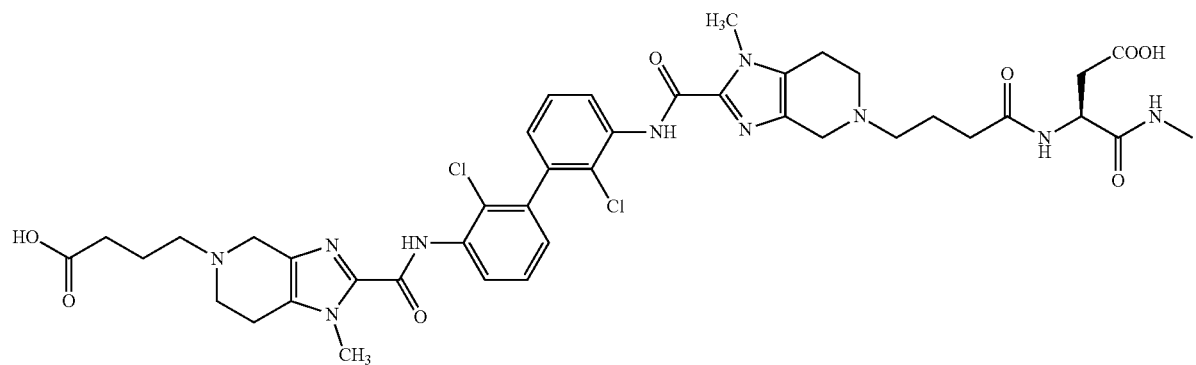

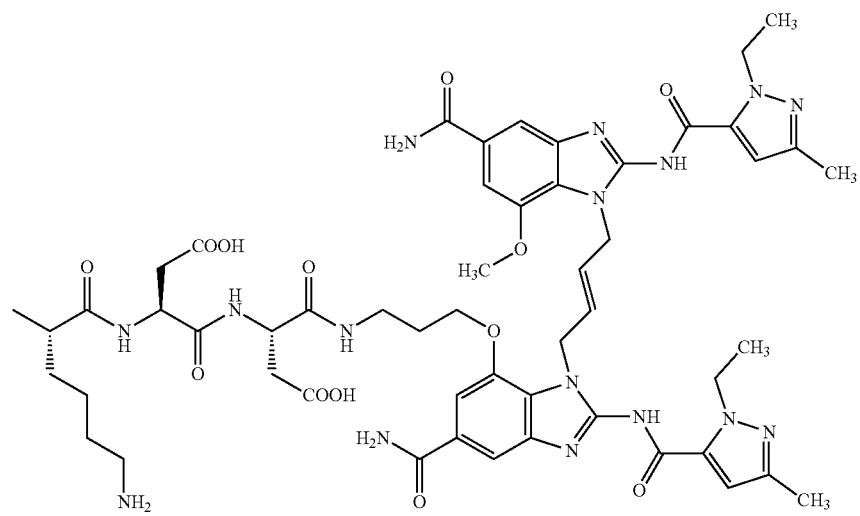

Step 1: (10S,13S,16S)-10-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)butanamido)-4-oxobutanamido)-13,16-bis(2-(tert-butoxy)-2-oxoethyl)-2,2-dimethyl-4,11,14-trioxo-3-oxa-5,12,15-triazaheptadecan-17-oic acid

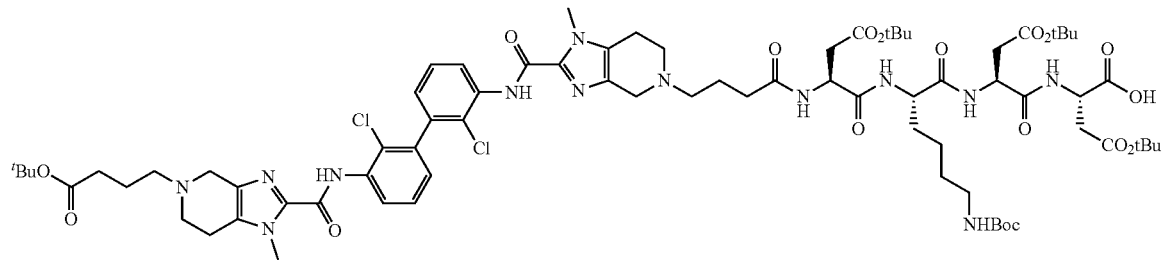 [SMILES: Cn1c(C(=O)Nc2cccc(-c3cccc(NC(=O)c4nc5c(n4C)CCN(CCCC(=O)OC(C)(C)C)C5)c3Cl)c2Cl)nc2c1CCN(CCCC(=O)N[C@@H](CC(=O)OC(C)(C)C)C(=O)N[C@@H](CCCCNC(=O)OC(C)(C)C)C(=O)N[C@@H](CC(=O)OC(C)(C)C)C(=O)N[C@@H](CC(=O)OC(C)(C)C)C(=O)O)C2]

In a peptide synthesis vessel add H-Asp(OtBu)-2-ClTrt resin (Peptides International, cat #RHD-11054-PI: 50 mg, 0.83 mmol/g, 0.042 mmol), Fmoc-Asp(OtBu)-OH (34.2 mg, 0.083 mmol) solution in DMF (500 µL), DIPEA (29.0 µL, 0.166 mmol) and PyBOP (43.2 mg, 0.083 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated in a sequence of Fmoc-Lys(Boc)-OH (38.9 mg, 0.083 mmol), Fmoc-Asp(OtBu)-OH (34.2 mg, 0.083 mmol) and 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Example 10, Step 2: 20.6 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the desired product as the TFA salt. LC-MS calculated for $C_{75}H_{109}Cl_2N_{13}O_{18}$ (M+2H)$^{2+}$: m/z=775.8; found 775.8.

Step 2: (3S,6S,9S,12S)-9-(4-aminobtayl)-3-((3-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)-5,8,11,14-tetraoxo-4,7,10,13-tetraazaheptadecanoic acid This compound was prepared using similar procedures as described for Example 10 with (10S,13S,16S)-10-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-13,16-bis(2-(tert-butoxy)-2-oxoethyl)-2,2-dimethyl-4,11,14-trioxo-3-oxa-5,12,15-triazaheptadecan-17-oic acid replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid in Step 4. LC-MS calculated for $C_{92}H_{113}Cl_2N_{26}O_{21}$ (M+3H)$^{3+}$: m/z=663.2; found 663.1.

Example 19

(6S,9S,12S,15S)-1-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-6,9-bis(2-carboxyethyl)-15-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-12-(3-guanidinopropyl)-5,8,11,14-tetraoxo-4,7,10,13-tetraazaoctadecan-18-oic acid

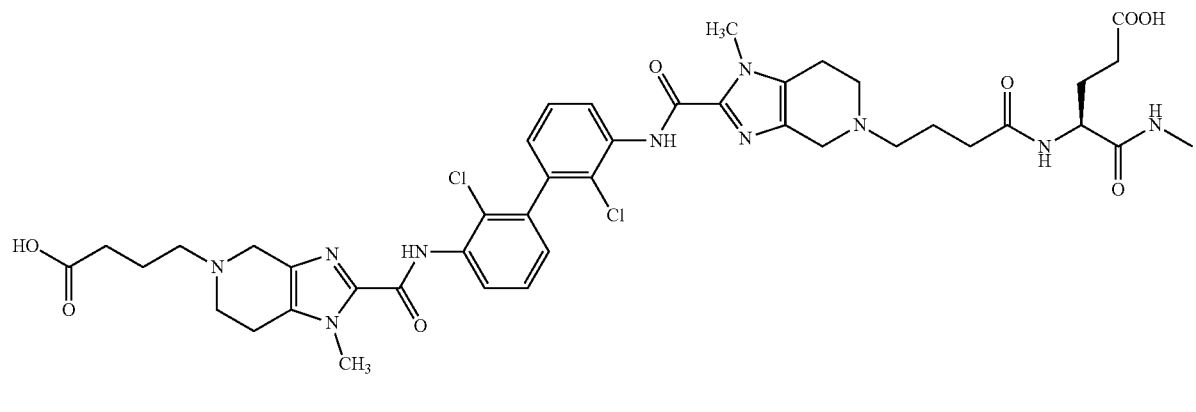

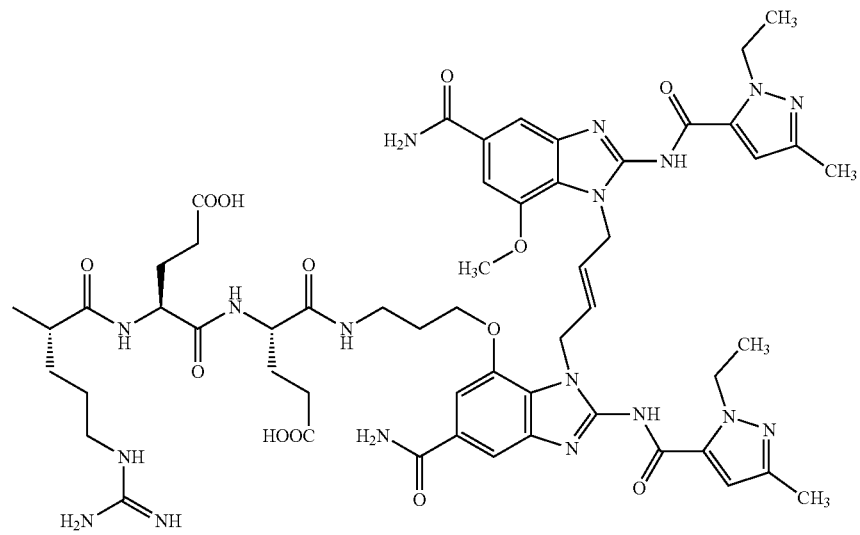

Step 1: (2S,5S,8S,11S)-2,5-bis(3-(tert-butoxy)-3-oxopropyl)-11-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)butanamido)-16,16-dimethyl-4,7,10,14-tetraoxo-8-(3-(3-((2,2,4,6,7-pentamethyl-2,3-dihydrobenzofuran-5-yl)sulfonyl)gnanidino)propyl)-15-oxa-3,6,9-triazaheptadecanoic acid

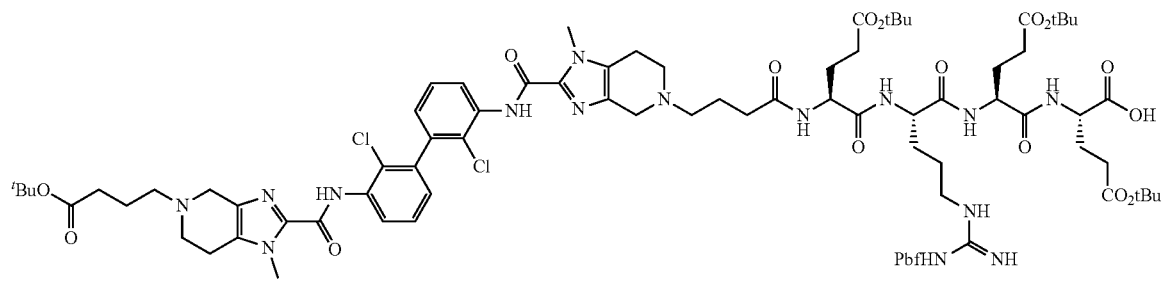

In a peptide synthesis vessel add H-Glu(OtBu)-2-ClTrt resin (aapptec, cat #RTE105: 55.5 mg, 0.757 mmol/g, 0.042 mmol), Fmoc-Glu(OtBu)-OH (35.4 mg, 0.083 mmol) solution in DMF (500 µL), DIPEA (29.0 µL, 0.166 mmol) and PyBOP (43.2 mg, 0.083 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated in a sequence of Fmoc-Arg(Pbf)-OH (53.9 mg, 0.083 mmol), Fmoc-Glu(OtBu)-OH (35.4 mg, 0.083 mmol) and 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Example 10, Step 2: 20.6 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the desired product as the TFA salt. LC-MS calculated for $C_{86}H_{123}Cl_2N_{15}O_{19}S$ $(M+2H)^{2+}$: m/z=886.6; found 886.6.

Step 2: (6S,9S,12S,15S)-1-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-6,9-bis(2-carboxyethyl)-15-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-12-(3-guanidinopropyl)-5,8,11,14-tetraoxo-4,7,10,13-tetraazaoctadecan-18-oic acid This compound was prepared using similar procedures as described for Example 10 with (2S,5S,8S,11S)-2,5-bis(3-(tert-butoxy)-3-oxopropyl)-11-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-16,16-dimethyl-4,7,10,14-tetraoxo-8-(3-(3-((2,2,4,6,7-pentamethyl-2,3-dihydrobenzofuran-5-yl)sulfonyl)guanidino)propyl)-15-oxa-3,6,9-triazaheptadecanoic acid replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl) carbamoyl)-1-methyl-1,4,6,7-tetrahydro-5H-imidazo[4,5-c]pyridin-5-yl)butanamido)-4-oxobutanamido)-4-oxobutanoic acid in Step 4. LC-MS calculated for $C_{95}H_{119}Cl_2N_{28}O_{21}$ $(M+3H)^{3+}$: m/z=686.6; found 686.6.

Example 20

(6S,9S,12S,15S,18S)-6-(tert-butyl)-1-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-9,12-bis(carboxymethyl)-18-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-15-(3-guanidinopropyl)-5,8,11,14,17-pentaoxo-4,7,10,13,16-pentaazaicosan-20-oic acid

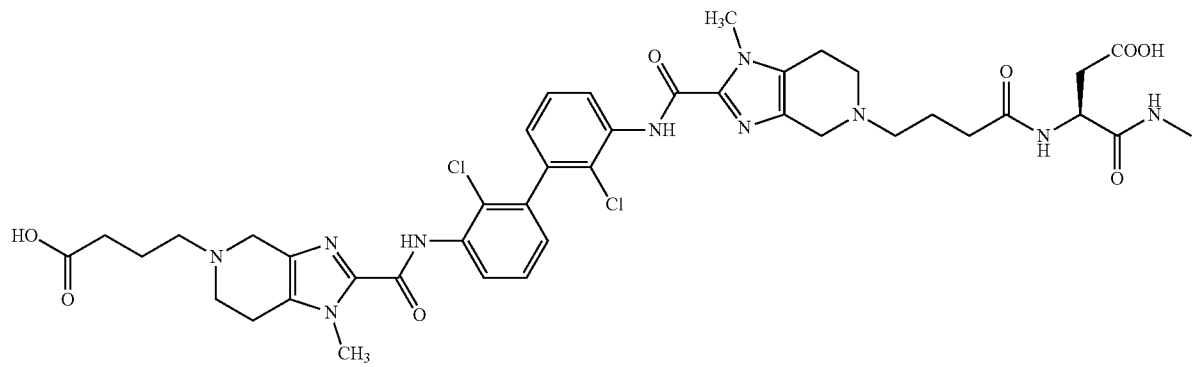

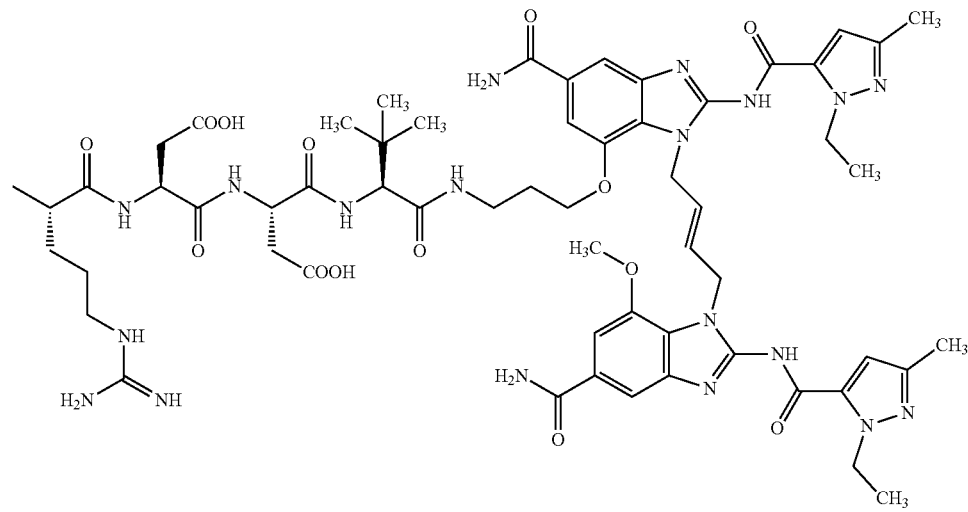

Step 1: (2S,5S,8S,11S)-2,5,11-tris(2-(tert-butoxy)-2-oxo-ethyl)-16-(2-((3'-(5-(4-(tert-butoxy)-4-oxobutyl)-1-methyl-4,5,6,7-tetrahydro-1H-imidazo[4,5-c]pyridine-2-carbox-amido)-2,2'-dichloro-[1,1'-bipheny]-3-yl)carbamoyl)-1-methyl-1,4,6,7-tetrahydro-5H-imidazo[4,5-c]pyridin-5-yl)-4,7,10,13-tetraoxo-8-(3-(3-((2,2,4,6,7-pentamethyl-2,3-dihydrobenzofuran-5-yl)sulfonyl)guanidinotpropyl)-3,6,9,12-tetraazahexadecanoic acid

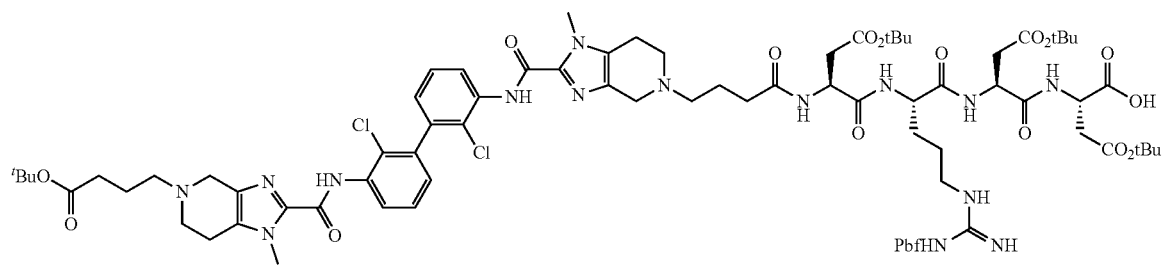

In a peptide synthesis vessel add H-Asp(OtBu)-2-ClTrt resin (Peptides International, cat #RHD-11054-PI: 100 mg, 0.83 mmol/g, 0.083 mmol), Fmoc-Asp(OtBu)-OH (68.3 mg, 0.166 mmol) solution in DMF (2 mL), DIPEA (58.0 µL, 0.332 mmol) and PyBOP (86.4 mg, 0.168 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated in a sequence of Fmoc-Arg (Pbf)-OH (108 mg, 0.166 mmol), Fmoc-Asp(OtBu)-OH (68.3 mg, 0.166 mmol) and 4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Example 10, Step 2: 40.3 mg, 0.050 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the desired product as the TFA salt. LC-MS calculated for $C_{83}H_{117}Cl_2N_{15}O_{19}S$ $(M+2H)^{2+}$: m/z=865.9; found 865.9.

Step 2: (S,E)-7-(3-(2-amino-3,3-dimethylbutanamido)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide

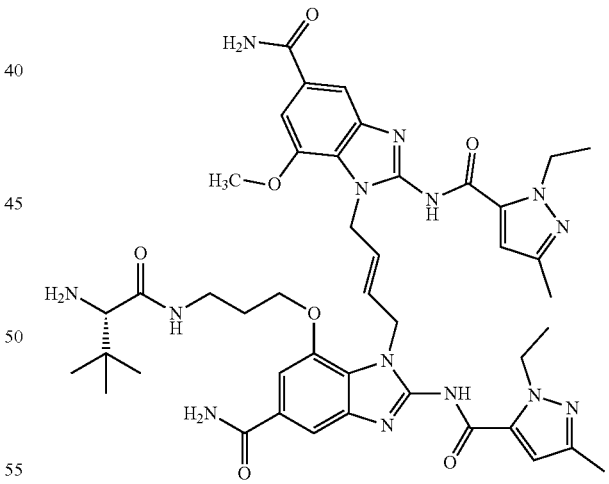

This compound was prepared using similar procedures as described for Example S32 with Fmoc-Tle-OH replacing Boc-beta-alanine. LC-MS calculated for $C_{44}H_{57}N_{14}O_7$ $(M+H)^+$: m/z=893.4; found 893.6.

Step 3: (6S,9S,12S,15S,18S)-6-(tert-butyl)-1-((5-carbamoyl-1-((E)-4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)-9,12-bis(carboxymethyl)-18-(4-(2-((3'-(5-(3-carboxypropyl)-1- methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-15-(3-guanidinopropyl)-5,8,11,14,17-pentaoxo-4,7,10,13,16-pentaazaicosan-20-oic acid This compound was prepared using similar procedures as described for Example 10 with (2S,5S,8S,11S)-2,5,11-tris(2-(tert-butoxy)-2-oxoethyl)-16-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13-tetraoxo-8-(3-(3-((2,2,4,6,7-pentamethyl-2,3-dihydrobenzofuran-5-yl)sulfonyl)guanidino)propyl)-3,6,9,12-tetraazahexadecanoic acid (Step 1) replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-xobutanoic acid and (S,E)-7-(3-(2-amino-3,3-dimethylbutanamido)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide replacing (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide in Step 4. LC-MS calculated for $C_{98}H_{124}Cl_2N_{29}O_{22}$ $(M+3H)^{3+}$: m/z=710.3; found 710.2.

Example 21

(3S,6S,9S,12S)-3-((3-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-5,8,11,14-tetraoxo-9-(3-ureidopropyl)-4,7,10,13-tetraazaheptadecanoic acid

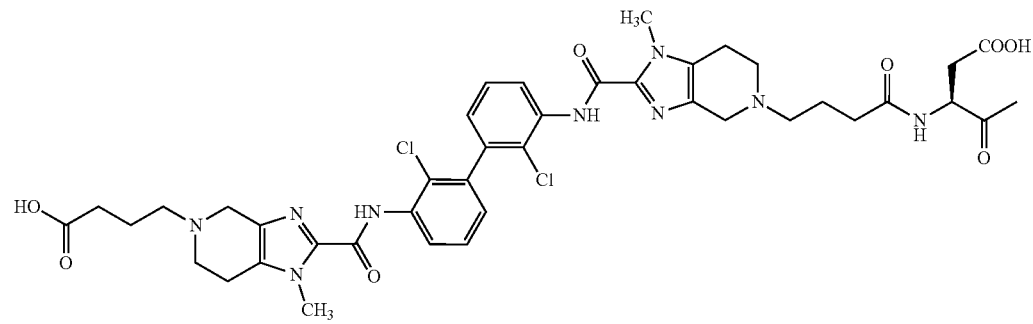

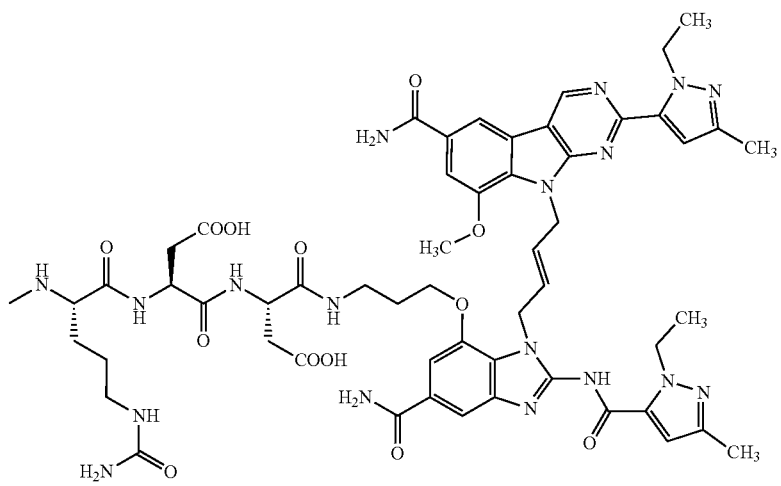

Step 1: (2S,5S,8S,11S)-2,5,11-tris(2-(tert-butoxy)-2-oxo-ethyl)-16-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)-4,7,10,13-tetraoxo-8-(3-nreidopropyl)-3,6,9,12-tetraazahexadecanoic acid

[d]imidazol-7-yl)oxy)propyhcarbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-bipheny]-3-yl)carbamoyl)-1-methyl-1,4,6,7-tetrahydro-5H-imidazo[4,5-c]pyridin-5-yl)-5,8,11,14-tetraoxo-9-(3-nreidopropyl)-4,7,10,13-tetraazaheptadecanoic acid

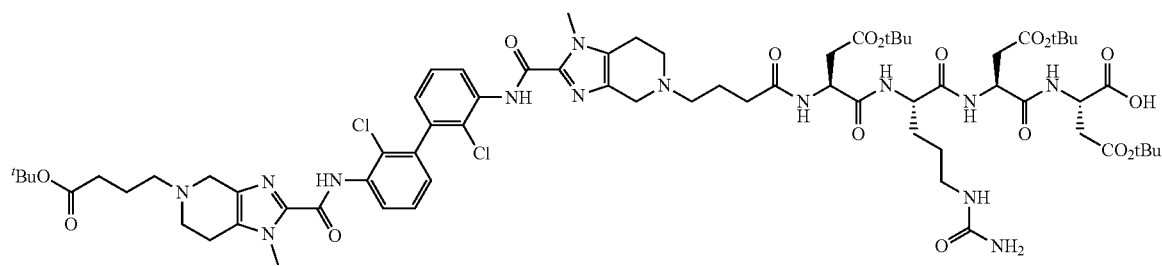 [SMILES: Cn1c(C(=O)Nc2cccc(-c3cccc(NC(=O)c4nc5c(n4C)CCN(CCCC(=O)OC(C)(C)C)C5)c3Cl)c2Cl)nc2c1CCN(CCCC(=O)N[C@@H](CC(=O)OC(C)(C)C)C(=O)N[C@@H](CCCNC(N)=O)C(=O)N[C@@H](CC(=O)OC(C)(C)C)C(=O)N[C@@H](CC(=O)OC(C)(C)C)C(=O)O)C2]

In a peptide synthesis vessel add H-Asp(OtBu)-2-ClTrt resin (Peptides International, cat #RHD-11054-PI: 25 mg, 0.83 mmol/g, 0.021 mmol), Fmoc-Asp(OtBu)-OH (17.09 mg, 0.042 mmol) solution in DMF (500 μL), DIPEA (14.5 μL, 0.083 mmol) and PyBOP (21.6 mg, 0.042 mmol). The resulting mixture was stirred for 1 h and washed repeatedly three times with DMF. Use 20% piperidine in DMF (2 mL) for Fmoc deprotection, 3× (10 min), and wash repeatedly three times with DMF before each amino acid coupling. This coupling process was repeated in a sequence of Fmoc-Cit-OH (16.50 mg, 0.042 mmol), Fmoc-Asp(OtBu)-OH (17.09 mg, 0.042 mmol) and 4-((2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanoic acid (Example 10, Step 2: 20.6 mg, 0.026 mmol). At the end cleave the peptide from the resin using a cocktail of 10% (0.5 mL) HOAc, 10% (0.5 mL) TFE, 80% (4 mL) DCM, the cleavage step was performed as follows: add 2.5 mL cleavage reagent and stirred for 1 hr, drain and wash 3× with remaining reagent. The filtrate was concentrated and then diluted with MeOH then purified by prep-HPLC (pH=2, acetonitrile/water+TFA) to give the desired product as the TFA salt. LC-MS calculated for $C_{70}H_{100}Cl_2N_{14}O_{17}$ $(M+2H)^{2+}$: m/z=740.4; found 740.4.

Step 2: (3S,6S,9S,12S)-3-((3-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-1H-benzo[d]imidazol-2-(1-ethyl-3-methyl-1H-pyrazole-5-carboxamido)-1H-benzo This compound was prepared using similar procedures as described for Example 10 with (2S,5S,8S,11S)-2,5,11-tris(2-(tert-butoxy)-2-oxoethyl)-16-(2-((3'-(5-(4-(tert-butoxy)-4-oxobutyl)-1-methyl-4,5,6,7-tetrahydro-1H-imidazo [4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13-tetraoxo-8-(3-ureidopropyl)-3,6,9,12-tetraazahexadecanoic acid replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid and (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-methoxy-9H-pyrimido[4,5-b]indole-6-carboxamide (Example 7, Step 9) replacing (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide in Step 4. LC-MS calculated for $C_{94}H_{112}Cl_2N_{27}O_{21}$ $(M+3H)^{3+}$: m/z=675.5; found 675.6.

Example 22

(3S,6S,9S,12S,15S,18S,21S,24S)-3-((3-05-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)-6,12,15,18-tetrakis(carboxymethyl)-24-(4-(2-((3'-((5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-9,21-bis(3-guanidinopropyl)-5,8,11,14,17,20,23-heptaoxo-4,7,10,13,16,19,22-heptaazahexacosanedioic acid

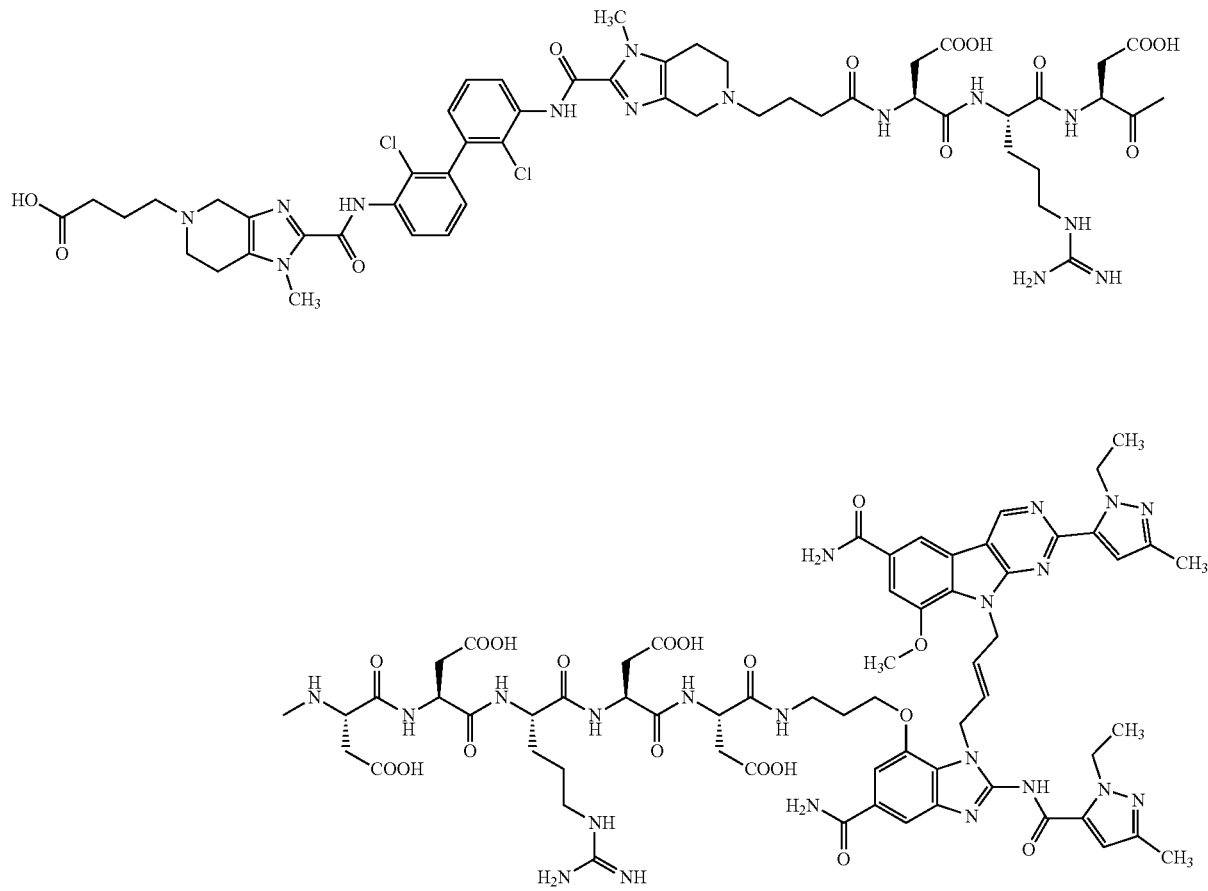

This compound was prepared using similar procedures as described for Example 10 with (2S,5S,8S,11S,14S,17S,20S,23S)-2,5,11,14,17,23-hexakis(2-(tert-butoxy)-2-oxoethyl)-28-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13,16,19,22,25-octaoxo-8,20-bis (3-(3-((2,2,4,6,7-pentamethyl-2,3-dihydrobenzofuran-5-yl)sulfonyl)guanidino)propyl)-3,6,9,12,15,18,21,24-octaazaoctacosanoic acid (Example 15, Step 1) replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid and (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-methoxy-9H-pyrimido[4,5-b]indol-6-carboxamide (Example 7, Step 9) replacing (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide in Step 4. LC-MS calculated for $C_{112}H_{140}Cl_2N_{35}O_{30}$ $(M+3H)^{3+}$: m/z=842.3; found 842.2.

Example 23

(3S,6S,9S,12S)-3-((3-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-9-(3-guanidinopropyl)-5,8,11,14-tetraoxo-4,7,10,13-tetraazaheptadecanoic acid

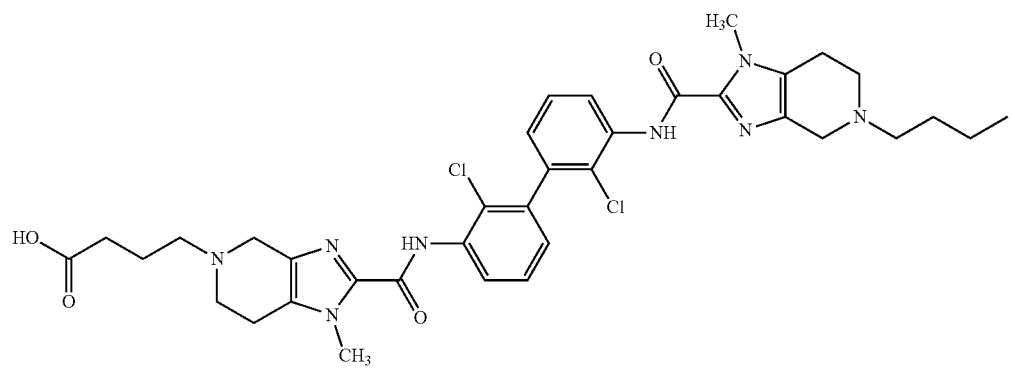

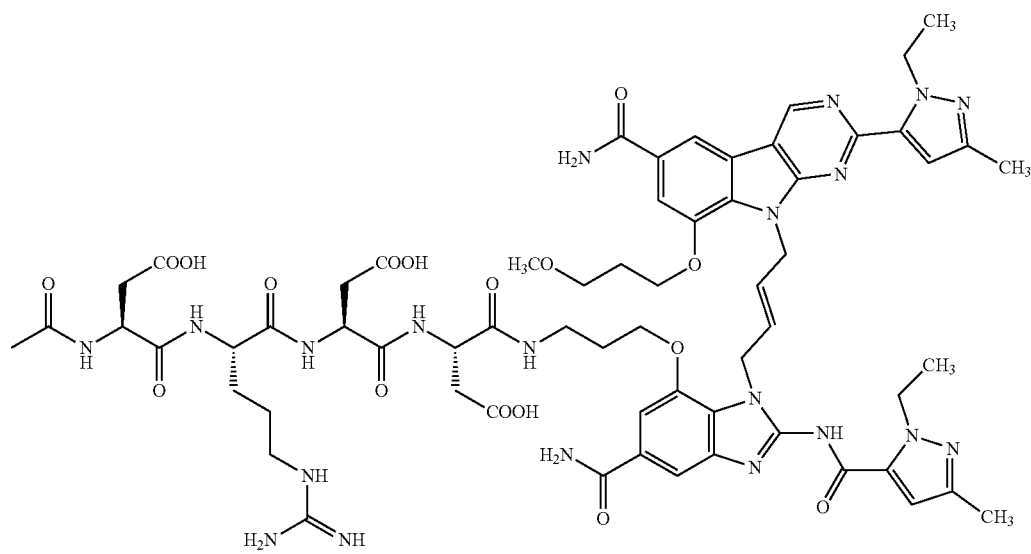

401

Step 1: (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

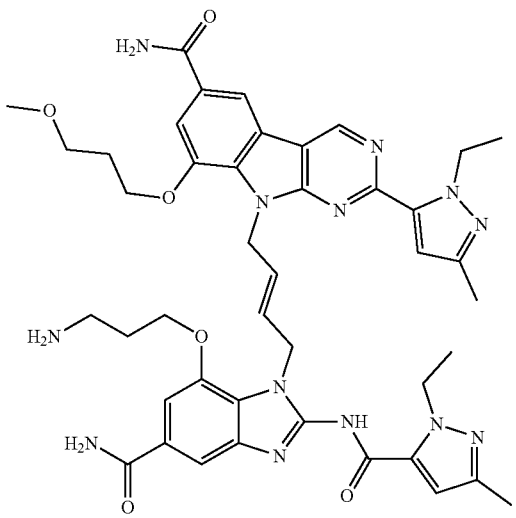

This compound was prepared using similar procedures as described for Example 7 with 2-(1-ethyl-3-methyl-1H-pyrazol-5-yl)-8-(3-methoxypropoxy)-9H-pyrimido[4,5-b]indole-6-carboxamide (Example S12, Step 3) replacing 2-(1-ethyl-3-methyl-1H-pyrazol-5-yl)-8-methoxy-9H-pyrimido[4,5-b]indole-6-carboxamide in Step 9. LC-MS calculated for $C_{43}H_{52}N_{13}O_6$ $(M+H)^+$: m/z=846.4; found 846.5.

Step 2: (3S,6S,9S,12S)-3-((3-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)-6,12-bis(carboxymethyl)-17-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-9-(3-guanidinopropyl)-5,8,11,14-tetraoxo-4,7,10,13-tetraazaheptadecanoic acid

402

This compound was prepared using similar procedures as described for Example 10 with (2S,5S,8S,11S)-2,5,11-tris(2-(tert-butoxy)-2-oxoethyl)-16-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13-tetraoxo-8-(3-(3-((2,2,4,6,7-pentamethyl-2,3-dihydrobenzofuran-5-yl)sulfonyl)guanidino)propyl)-3,6,9,12-tetraazahexadecanoic acid (Example 20, Step 1) replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanamido)-4-oxobutanoic acid and (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide replacing (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide in Step 4. LC-MS calculated for $C_{97}H_{119}Cl_2N_{28}O_{21}$ $(M+3H)^{3+}$: m/z=694.6; found 694.7.

Example 24

(11S,14S,17S,20S)-1-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-11,14-bis(carboxymethyl)-20-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-17-(3-guanidinopropyl)-5,10,13,16,19-pentaoxo-6-oxa-4,9,12,15,18-pentaazadocosan-22-oic acid

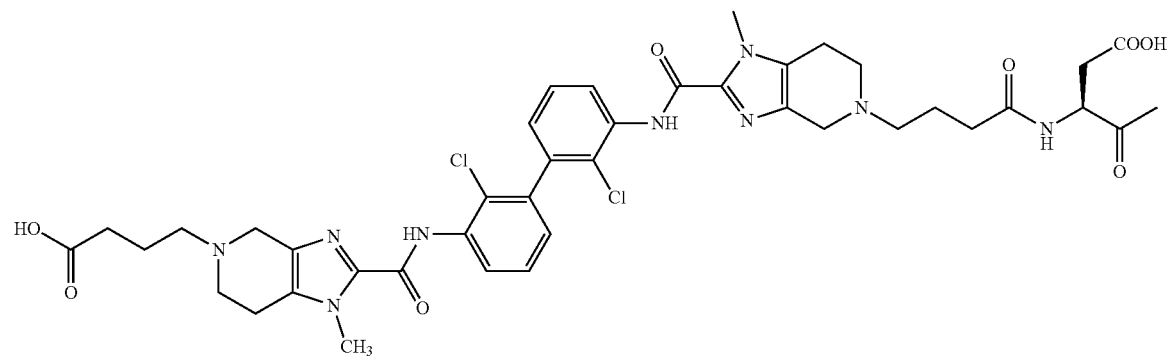

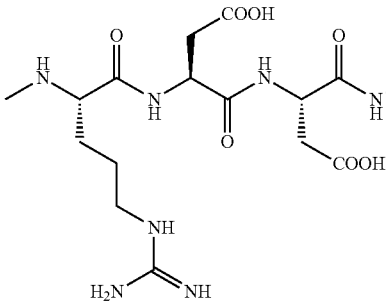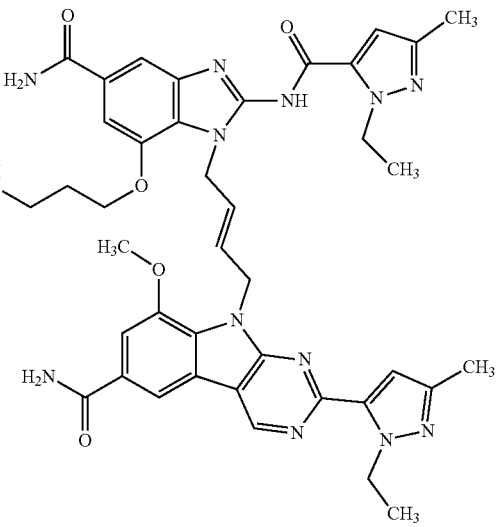

Step 1: tert-butyl (2-(((4-nitrophenoxy)carbonyl)oxy)ethyl)carbamate

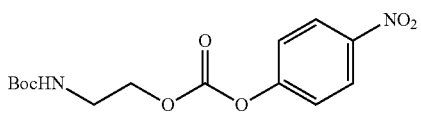 [SMILES: CC(C)(C)OC(=O)NCCOC(=O)Oc1ccc([N+](=O)[O-])cc1]

In a 4 dram vial tert-butyl (2-hydroxyethyl)carbamate (270 mg, 1.675 mmol) and 4- nitrophenyl carbonochloridate (675 mg, 3.35 mmol) were dissolved in THF (8.4 mL) to give a pale yellow solution. Pyridine (474 µL, 5.86 mmol) was added to the reaction mixture dropwise. After 2 h, the crude product was added to a silica gel column and was eluted with dichloromethane to give tert-butyl (2-(((4-nitrophenoxy)carbonyl)oxy)ethyl)carbamate (540 mg, 1.655 mmol, 99% yield) as a colorless oil. LC-MS calculated for $C_{14}H_{18}N_2NaO_7$ (M+Na)$^+$: m/z=349.1; found 349.1.

Step 2: 2-aminoethyl (E)-(3-((5-carbamoyl-1-(4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate

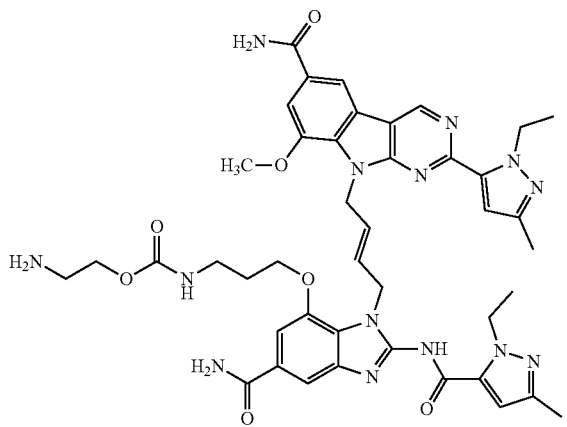 [SMILES: CCn1nc(C)cc1C(=O)Nc1nc2cc(C(N)=O)cc(OCCCNC(=O)OCCN)c2n1C/C=C/Cn1c2nc(-c3cc(C)nn3CC)ncc2c2cc(C(N)=O)cc(OC)c21]

In a 1 dram vial (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-methoxy-9H-pyrimido[4,5-b]indole-6-carboxamide (Example 23, Step 1: 12.4 mg, 0.016 mmol) was dissolved in DMF (1.6 mL) to give a yellow suspension. Tert-butyl (2-(((4-nitrophenoxy)carbonyl)oxy)ethyl)carbamate (10.27 mg, 0.031 mmol) and DMAP (9.61 mg, 0.079 mmol) was added to the reaction mixture. After 30 min, the reaction mixture was concentrated to dryness and TFA (0.5 mL) was added. After 10 min, the reaction mixture was diluted with MeOH then purified by prep-HPLC (pH=2, acetonitrile/water+TFA) to give the desired product as the TFA salt. LC-MS calculated for $C_{43}H_{51}N_{14}O_7$ (M+H)$^+$: m/z=875.4; found 875.5.

Step 3: (11S,14S,17S,20S)-1-((5-carbamoyl-1-((E)-4-(6-carbamoyl-2-(1-ethyl-3-methyl-1H-pyrazol-5-yl)-8-methoxy-9H-pyrimido[4,5-b]indol-9-yl)-but-2-en-1-yl)-2-(1-ethyl-3-methyl-1H-pyrazole-5-carboxamido)-1H-benzo[d]imidazol-7-yl)oxy)-11,14-bis(carboxymethyl)-20-(4-(2-((3'-(5-(3-carboxypropyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-17-(3-guanidinopropyl)-5,10,13,16,19-pentaoxo-6-oxa-4,9,12,15,18-pentaazadocosan-22-oic acid This compound was prepared using similar procedures as described for Example 10 with (2S,5S,8S,11S)-2,5,11-tris(2-(tert-butoxy)-2-oxoethyl)-16-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)-4,7,10,13-tetraoxo-8-(3-(3-((2,2,4,6,7-pentamethyl-2,3-dihydrobenzofuran-5-yl)sulfonyl)guanidino)propyl)-3,6,9,12-tetraazahexadecanoic acid (Example 20, Step 1) replacing (S)-4-(tert-butoxy)-2-((S)-4-(tert-butoxy)-2-(4-(2-((3'-(5-(4-(tert-butoxy)-4-oxobutyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)butanamido)-4-oxobutanoic acid and 2-aminoethyl (E)-(3-((5-carbamoyl-1-(4-(6-carbamoyl-2-(1-ethyl-3-methyl-1H-pyrazol-5-yl)-8-methoxy-9H-pyrimido[4,5-b]indol-9-yl)but-2-en-1-yl)-2-

(1-ethyl-3-methyl-1H-pyrazole-5-carboxamido)-1H-benzo[d]imidazol-7-yl)oxy)propyl)carbamate replacing (E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide in Step 4. LC-MS calculated for $C_{97}H_{118}Cl_2N_{29}O_{22}$ $(M+3H)^{3+}$: m/z=704.2; found 704.3.

Examples 1A and 1B: PD-1/PD-L1 Binding Assay

Example 1A: Alphascreen

Binding assays were conducted in a low volume white 384-well polystyrene plate in a final volume of 20 µL. Compounds to be analyzed were first serially diluted in DMSO and added to the plate wells before the addition of other reaction components. The final concentration of DMSO in the assay was 1%. The assay was carried out at 25° C. in the PBS buffer (pH 7.4) with 0.05% Tween-20 and 0.1% BSA. Recombinant human PD-L1 protein (19-238) with a His-tag at the C-terminus was purchased from Acro-Biosystems (PD1-H5229). Recombinant human PD-1 protein (25-167) with Fc tag at the C-terminus was also from AcroBiosystems (PD1-H5257). PD-L1 and PD-1 proteins were diluted in the assay buffer (final concentration—0.67 and 0.20 nM respectively) and 10 µL was added to the plate well. Plates were centrifuged and proteins were preincubated with compounds for 40 minutes. The incubation was followed by the addition of 10 µL of assay buffer supplemented with Alphascreen Ni chelate donor beads (PerkinElmer—AS101D) and Protein A Acceptor beads (PerkinElmer—6760137) at final concentration 2.5 µg/mL under reduced light. After plate sealing, the plate was incubated in the dark at room temperature for 120 minutes before reading on a PHERAstar FS plate reader (BMG Labtech). $IC_{50}$ determination was performed by fitting the curve of percent control activity versus the log of the compound concentration using the GraphPad Prism 5.0 software.

Example 1B; Homogeneous Time-Resolved Fluorescence (HTRF)

The assays were conducted in a standard black 384-well polystyrene plate with a final volume of 20 µL. Inhibitors were first serially diluted in DMSO and then added to the plate wells before the addition of other reaction components. The final concentration of DMSO in the assay was 1%. The assays were carried out at 25° C. in the PBS buffer (pH 7.4) with 0.05% Tween-20 and 0.1% BSA. Recombinant human PD-L1 protein (19-238) with a His-tag at the C-terminus was purchased from AcroBiosystems (PD1-H5229). Recombinant human PD-1 protein (25-167) with Fc tag at the C-terminus was also purchased from AcroBiosystems (PD1-H5257). PD-L1 and PD-1 proteins were diluted in the assay buffer and 10 µL was added to the plate well. Plates were centrifuged and proteins were preincubated with inhibitors for 40 minutes. The incubation was followed by the addition of 10 µL of HTRF detection buffer supplemented with Europium cryptate-labeled anti-human IgG (PerkinElmer-AD0212) specific for Fc and anti-His antibody conjugated to SureLight®-Allophycocyanin (APC, PerkinElmer-AD0059H). After centrifugation, the plate was incubated at 25° C. for 60 min. before reading on a PHERAstar FS plate reader (665 nm/620 nm ratio). Final concentrations in the assay were ~3 nM PD1, 10 nM PD-L1, 1 nM europium anti-human IgG and 20 nM anti-His-Allophycocyanin. $IC_{50}$ determination was performed by fitting the curve of percent control activity versus the log of the inhibitor concentration using the GraphPad Prism 5.0 software.

Example 2A: PD-L1 Homogeneous Time-Resolved Fluorescence (HTRF) Dimerization Assay Dimerization assays were conducted in a standard black 384-well polystyrene plate in a final volume of 20 µL. Compounds to be analyzed were diluted in DMSO and added to the plate wells before the addition of other reaction components. The final concentration of tested compounds was 10 µM and DMSO was at 1%. The assays were carried out at 25° C. in PBS buffer (pH 7.4) with 0.05% Tween-20 and 0.1% BSA. Recombinant human PD-L1 protein (19-238) with a His-tag at the C-terminus was purchased from AcroBiosystems (PD1-H5229). Recombinant human PD-L1 protein (19-239) with Fc tag at the C-terminus was purchased from BPS Bioscience (#71104). PD-L1 proteins were diluted in the assay buffer, mixed, and 10 ul was added to the plate well. Plates were centrifuged and proteins were preincubated with compounds for 40 minutes. The incubation was followed by the addition of 10 µL of HTRF detection buffer supplemented with Europium cryptate-labeled anti-human IgG (PerkinElmer-AD0074) specific for Fc and anti-His antibody conjugated to SureLight®-Allophycocyanin (APC, PerkinElmer-AD0059H). Final concentrations in the assay were: 30 nM PD-L1 (Fc-tag), 100 nM PD-L1 (His-tag), 10 nM europium anti-human IgG and 200 nM anti-His-Allophycocyanin. After centrifugation, the plate was incubated at 25° C. for 60 minutes before reading on a PHERAstar FS plate reader (665 nm/620 nm ratio). The dimerization ratio was calculated based on the assay signal in the presence of compound divided by the signal in the presence of DMSO.

Example 3A: PD-L1 Internalization Assays

Endocytosis or internalization of PD-L1 was measured by two different methods, one direct and the other indirect. In the direct method, an anti PD-L1 antibody labeled with a pH sensitive fluorophore is incubated with PD-L1 expressing cells. Upon internalization and trafficking of the antibody-PD-L1 complex to low pH endosomes, fluorescence is emitted. In the indirect method, cell surface PD-L1 is measured using an anti PD-L1 antibody after incubation with a compound to determine remaining, non-internalized receptor.

Direct Method Assessing for PD-L1 Internalization

For the direct measurement, biotinylated anti-PD-L1 antibody (BPS Biosciences) or Atezolizumab, biotinylated with a 20-fold excess of biotin using the EZ-Link™ Sulfo-NHS-LC-Biotin reagents (ThermoFisher), were labeled with pHrodo™ Red Avidin (Life Technologies) conjugate. Equimolar solutions of the antibody and pHrodo™ Red avidin (4.2 uM each) were incubated on ice for 2 hours in the dark in a buffer composed of 40 mM Tris-HCl, pH 8.0, 110 mM NaCl, 2.2 mM KCl, 20% glycerol, and 1% bovine serum albumin The mixture was centrifuged for 1 minute at 1000 rpm, and the clarified supernatant was used in subsequent assays. As an isotype control, a biotinylated Human IgG1κ antibody (Ancell) was labeled using the same protocol. For the assay, 2×10^5 CHO-PD-L1 cells (Promega) were seeded into each well of a 6-well tissue culture plate in 2 ml of F-12 medium supplemented with 10% FBS, 200 µg/ml Hydromycin and 250 µg/ml Geneticin. Cells were allowed to attach for 24 hours, and then 40 nM of the anti-PD-L1-biotin/pHrodo-Avidin, Atezolizumab/pHrodo-Avidin or IgG-biotin/pHrodo-Avidin complex was added to the cells and allowed to incubate at 37° C. for 5 to 16 hours. The cells were washed twice with PBS (Mg, Ca free) and harvested using non-enzymatic lift buffer (10 mM Tris (pH 7.5), 140 mM NaCl, 1 mM EDTA), collected by centrifugation, and re-suspended in 400 μL of PBS. The cells were analyzed by flow cytometry, and internalized antibody-receptor complex was detected using a C6 Accuri Flow Cytometer (excitation with 488 nM laser and emission collected with a 585/40 bandpass filter). There was no difference between IgG control and Atezolizumab, demonstrating that Atezolizumab dos not cause PD-L1 internalization.

Indirect Method for Assessing for PD-L1 Internalization

For the indirect analysis, cell surface PD-L1 was detected with fluorescently labeled anti-PD-L1 (CD274) antibodies. CHO-PD-L1 cells were seeded at 2×10^5 cells per well of a 6-well tissue culture plate in 2 ml of F-12 medium supplemented with 10% FBS, 200 μg/ml Hydromycin and 250 μg/ml Geneticin and allowed to attach for 24 hours. After 24 hours, test compounds were added to a final concentration of 1 uM from DMSO stocks, and an equal volume of DMSO was added to control wells. Cells were incubated in the presence of a compound for 16 hours at 37° C., 5% CO2. Prior to analysis, the cells were washed twice with 1 mL of Ca, Mg free PBS and detached with 1 mL of lift buffer (10 mM Tris, 140 mM NaCl, 1 mM EDTA). The collected cells were stained with PE-conjugated mouse anti-human CD274 antibody according to manufacturer instructions: BD Pharmigen #557924 Clone MIH1 (20 μL of Ab per 100 uL of BSA based staining buffer) or eBioscience #12-5983 Clone MIH1 (2 μL per 100 ul of BSA based staining buffer). Cells were incubated at room temperature for 20 minutes, protected from light, washed twice with Ca, Mg free PBS and resuspended in 400 μL of PBS. Antibody binding was detected by flow cytometry using an Accuri C6 instrument. Isotype control antibody-stained cells were used as a negative control. To test that lack of PD-L1 cell surface staining was not due to inhibition of detection antibody binding by the test article, an acid-wash procedure was used. After 16 hours of incubation in the presence of a compound or anti-PD-L1 antibody, the remaining, non-internalized a compound or antibody was stripped from the cell surface using freshly prepared, ice-cold acid stripping buffer (DMEM/0.2% BSA, pH 3.5). Cells were washed in this manner three times for 5 minutes each on a shaking platform. The stripped cells were then washed with ice-cold PBS three times for 5 minutes each with gentle shaking, harvested with lift buffer and stained with PE-mouse anti human CD274 antibodies as described.

For the indirect method of assessing PD-L1 internalization using the MDA-MB231 breast cancer cell line, the procedure for the assays was the same as described for the CHO-PD-L1 cells with the following changes. MDA-MB231 were seeded at 2×10^5 cells per well of a 6-well tissue culture plate in 2 ml of RPMI1640 medium supplemented with 10% FBS. After compound treatment for 16 hrs, the cells were treated with the stripping buffer (DMEM/0.2% BSA, pH 3.5) prior to staining with the anti-CD274 antibodies as described.

Indirect Whole Blood Assay

To determine PD-L1 internalization in human whole blood, normal human blood (Biological Specialty Corp, Colmar. Pa.) was incubated in the presence or absence of a concentration range of test compounds and 1 ng/ml human interferon γ (R&D Systems Inc. Minn. Minn.) in a 96 well round bottom plate (Corning, Corning, N.Y.) for 18 hours at 37° C. Blood was then transferred into 96 well "2 ml Assay Block" (Corning, Corning N.Y.) and stained with PD-L1 (MIH1, eBioscience; or BD Biosciences San Jose, Calif.), CD14 (Life Technologies, Carlsbad, Calif.) for 30 minutes in the dark at room temperature. Whole Blood/red cells were lysed/fixed (lysis buffer BD Biosciences) for 5 minutes at 37° C. in dark and then centrifuged at 1600 RPM for 5 minutes and cells were transferred into 96 well round bottom plates (Corning). Cells were gated on CD14+ (BD Biosciences) and PD-L1 expression determined by mean fluorescence intensity (MFI) (BD LSRFortessa™ X-20). $IC_{50}$ determination was performed by fitting the curve of compound percent inhibition versus the log of the compound concentration using the GraphPad Prism 7.0 software.

Example 4A: Results of Binding, Dimerization, and Internalization Assays

Several compounds were assessed in each of the PD-1-PD-L1 Alphascreen binding assay (Example 1A), the PD-L1 dimerization assay (Example 2A), the indirect CHO/PD-L1 internalization assay (Example 3A), the indirect whole blood PD-L1 internalization assay (Example 3A), and the internalization assays using the MDA-MB231 breast cancer cell line (Example 3A). Compounds described herein were also assessed in PD-1-PD-L1 HTRF binding assay (Example 1B). The cutoffs for ranges of values observed in each of the assays is shown in Table 1. The results obtained for the tested compounds are shown in Table 2 and Table 3.

TABLE 1

| Cutoffs | + | ++ | +++ | ++++ |
|---|---|---|---|---|
| PD-1-PD-L1 Binding $IC_{50}$ (nM) (Alphascreen) | <=0.1 nM | >0.1 to <=1 nM | >1 nM | |
| PD-1-PD-L1 Binding $IC_{50}$ (nM) (HTRF) | <=10 nM | >10 to <=100 | | |
| PD-L1 Dimerization ratio | >=1.88 to <=2.16 | >=1.75 to <1.88 or >2.16 to <=2.29 | <1.75 or >2.29 | |
| Indirect PD-L1 Internalization Assay using CHO-PD-L1 cells | >90% internalized | >=90% internalized | | |
| Indirect PD-L1 Internalization Assay using MDA-MB231 cells $IC_{50}$ (nM) | <10 nM | >=10 nM to <100 nM | >=100 nM to <=500 nM | >500 nM |
| PD-L1 Whole Blood Internalization $IC_{50}$ (nM) | <100 nM | >=100 nM to <1000 nM | >=1000 nM to <=5000 nM | >5000 nM |

TABLE 2

| Cpd | Structure | PD-1-PD-L1 Binding IC$_{50}$ (nM) (Alpha-screen) | PD-L1 Dimerization Cpd/DMSO ratio | PD-L1 Indirect Internalization Assay using CHO-PD-L1 cells | PD-L1 Whole Blood Internalization IC$_{50}$ (nM) |
|---|---|---|---|---|---|
| P7 | 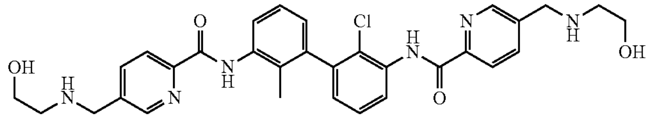 [SMILES: Cc1c(NC(=O)c2ccc(CNCCO)cn2)cccc1-c1cccc(NC(=O)c2ccc(CNCCO)cn2)c1Cl] | + | + | + | + |
| P8 | 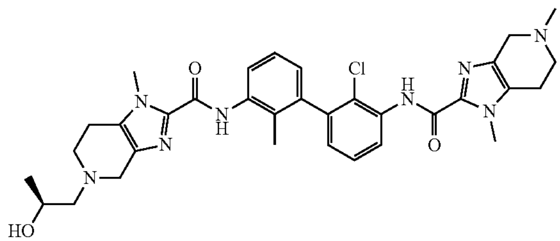 [SMILES: Cc1c(NC(=O)c2nc3c(n2C)CCN(C[C@H](C)O)C3)cccc1-c1cccc(NC(=O)c2nc3c(n2C)CCN(C)C3)c1Cl] | ++ | + | + | + |
| P9 | 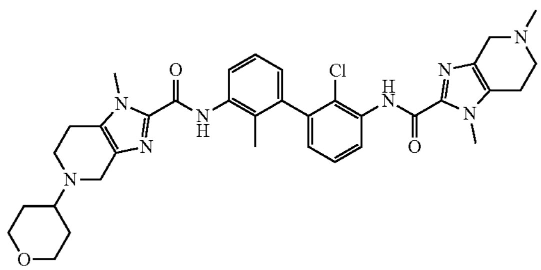 [SMILES: Cc1c(NC(=O)c2nc3c(n2C)CCN(C2CCOCC2)C3)cccc1-c1cccc(NC(=O)c2nc3c(n2C)CCN(C)C3)c1Cl] | ++ | + | + | + |
| P10 | 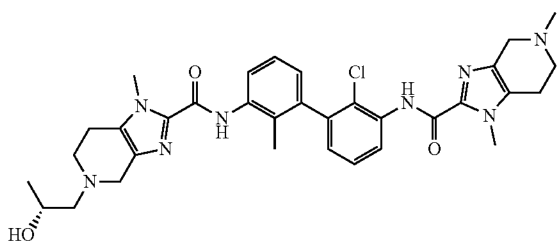 [SMILES: Cc1c(NC(=O)c2nc3c(n2C)CCN(C[C@@H](C)O)C3)cccc1-c1cccc(NC(=O)c2nc3c(n2C)CCN(C)C3)c1Cl] | ++ | + | + | + |
| P11 | 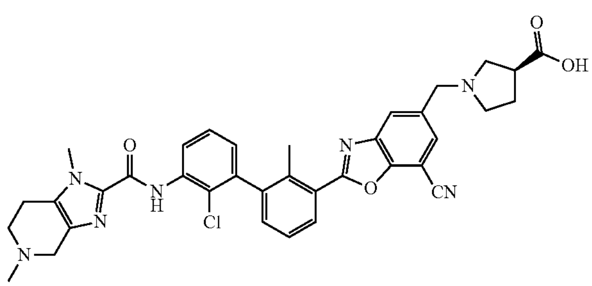 [SMILES: Cc1c(-c2nc3cc(CN4CC[C@H](C(=O)O)C4)cc(C#N)c3o2)cccc1-c1cccc(NC(=O)c2nc3c(n2C)CCN(C)C3)c1Cl] | + | ++ | + | + |
| P12 | 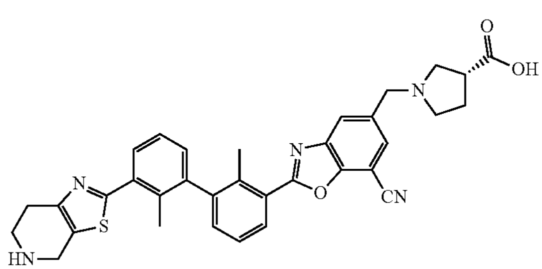 [SMILES: Cc1c(-c2nc3cc(CN4CC[C@@H](C(=O)O)C4)cc(C#N)c3o2)cccc1-c1cccc(-c2nc3c(s2)CNCC3)c1C] | ++ | ++ | + | ++ |

TABLE 2-continued

| Cpd | Structure | PD-1-PD-L1 Binding IC$_{50}$ (nM) (Alpha-screen) | PD-L1 Dimer-ization Cpd/DMSO ratio | PD-L1 Indirect Internal-ization Assay using CHO-PD-L1 cells | PD-L1 Whole Blood Internal-ization IC$_{50}$ (nM) |
|---|---|---|---|---|---|
| P13 | 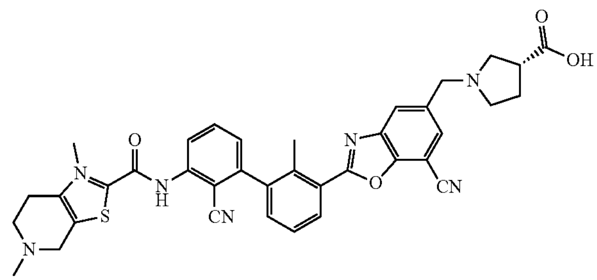 | ++ | ++ | + | ++ |
| P14 | 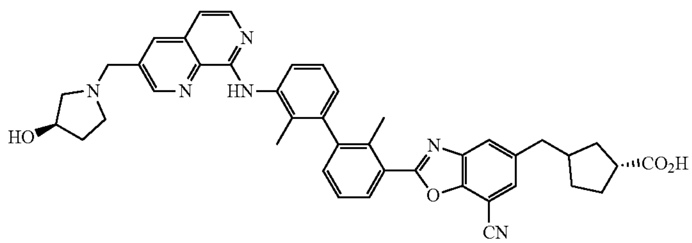 [SMILES: Cc1c(Nc2nccc3cc(CN4CC[C@@H](O)C4)cnc23)cccc1-c1cccc(-c2nc3cc(CC4CC[C@@H](C(=O)O)C4)cc(C#N)c3o2)c1C] | ++ | ++ | + | + |
| P15 | 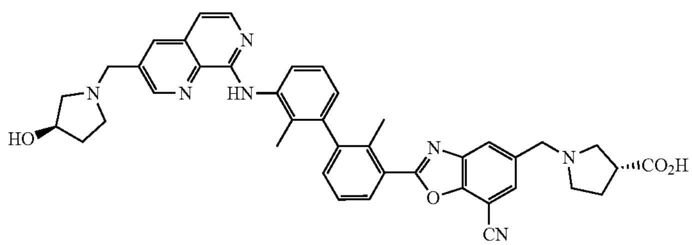 [SMILES: Cc1c(Nc2nccc3cc(CN4CC[C@@H](O)C4)cnc23)cccc1-c1cccc(-c2nc3cc(CN4CC[C@@H](C(=O)O)C4)cc(C#N)c3o2)c1C] | ++ | + | + | ++ |
| P16 | 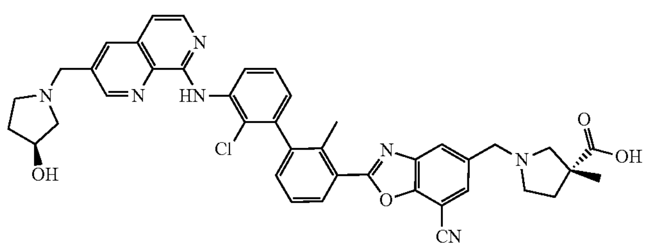 [SMILES: Cc1c(-c2nc3cc(CN4CC[C@@](C)(C(=O)O)C4)cc(C#N)c3o2)cccc1-c1cccc(Nc2nccc3cc(CN4CC[C@H](O)C4)cnc23)c1Cl] | ++ | + | + | ++ |
| P17 | 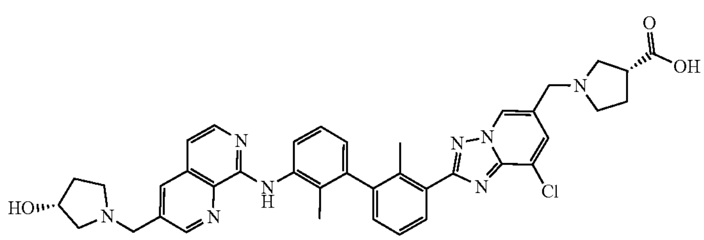 [SMILES: Cc1c(Nc2nccc3cc(CN4CC[C@@H](O)C4)cnc23)cccc1-c1cccc(-c2nc3c(Cl)cc(CN4CC[C@@H](C(=O)O)C4)cn3n2)c1C] | ++ | ++ | + | ++ |
| P18 | 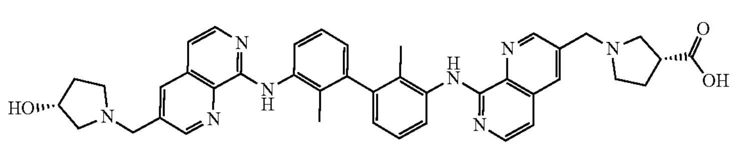 [SMILES: Cc1c(Nc2nccc3cc(CN4CC[C@@H](O)C4)cnc23)cccc1-c1cccc(Nc2nccc3cc(CN4CC[C@@H](C(=O)O)C4)cnc23)c1C] | ++ | + | + | ++ |

TABLE 2-continued

| Cpd | Structure | PD-1-PD-L1 Binding IC$_{50}$ (nM) (Alphascreen) | PD-L1 Dimerization Cpd/DMSO ratio | PD-L1 Indirect Internalization Assay using CHO-PD-L1 cells | PD-L1 Whole Blood Internalization IC$_{50}$ (nM) |
|---|---|---|---|---|---|
| P19 | 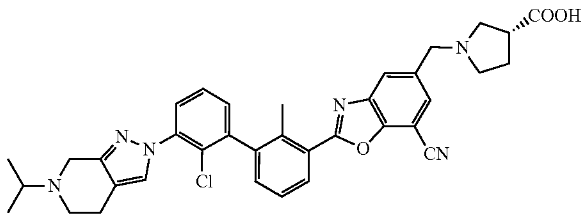 [SMILES: Cc1c(-c2nc3cc(CN4CC[C@@H](C(=O)O)C4)cc(C#N)c3o2)cccc1-c1cccc(-n2cc3c(n2)CN(C(C)C)CC3)c1Cl] | ++ | + | + | ++ |
| P20 | 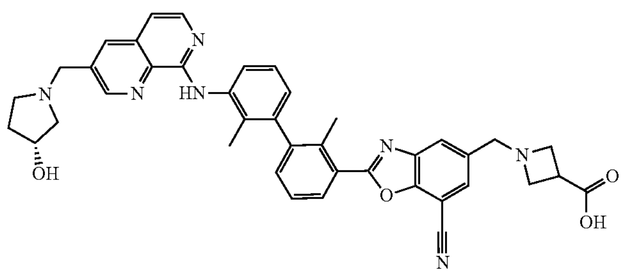 [SMILES: Cc1c(Nc2nccc3cc(CN4CC[C@@H](O)C4)cnc23)cccc1-c1cccc(-c2nc3cc(CN4CC(C(=O)O)C4)cc(C#N)c3o2)c1C] | ++ | + | + | ++ |
| P21 | 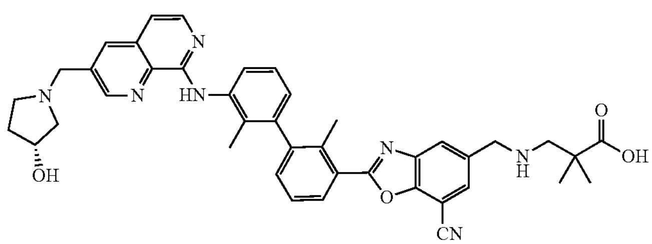 [SMILES: Cc1c(Nc2nccc3cc(CN4CC[C@@H](O)C4)cnc23)cccc1-c1cccc(-c2nc3cc(CNCC(C)(C)C(=O)O)cc(C#N)c3o2)c1C] | ++ | + | + | ++ |
| P22 | 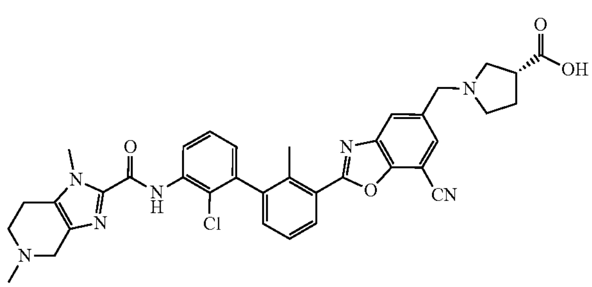 [SMILES: Cc1c(-c2nc3cc(CN4CC[C@@H](C(=O)O)C4)cc(C#N)c3o2)cccc1-c1cccc(NC(=O)c2nc3c(n2C)CCN(C)C3)c1Cl] | ++ | ++ | + | + |
| P23 | 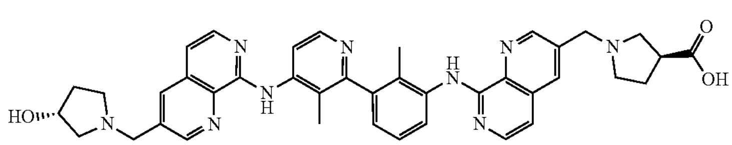 [SMILES: Cc1c(Nc2nccc3cc(CN4CC[C@H](C(=O)O)C4)cnc23)cccc1-c1nccc(Nc2nccc3cc(CN4CC[C@@H](O)C4)cnc23)c1C] | ++ | + | + | ++ |
| P24 | 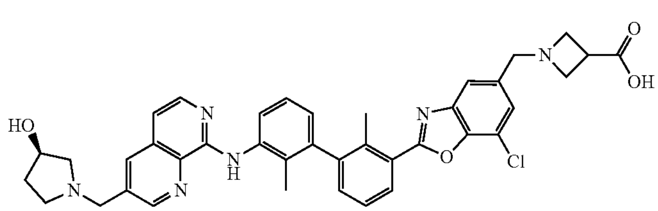 [SMILES: Cc1c(Nc2nccc3cc(CN4CC[C@@H](O)C4)cnc23)cccc1-c1cccc(-c2nc3cc(CN4CC(C(=O)O)C4)cc(Cl)c3o2)c1C] | ++ | + | + | ++ |

TABLE 2-continued

| Cpd | Structure | PD-1-PD-L1 Binding IC$_{50}$ (nM) (Alpha-screen) | PD-L1 Dimer-ization Cpd/DMSO ratio | PD-L1 Indirect Internal-ization Assay using CHO-PD-L1 cells | PD-L1 Whole Blood Internal-ization IC$_{50}$ (nM) |
|---|---|---|---|---|---|
| P25 | (structure) | ++ | + | + | +++ |
| P26 | (structure) | ++ | + | + | ++ |

TABLE 3

| Compound from Table 2 | Indirect PD-L1 Internalization Assay using MDA-MB231 cells IC$_{50}$ (nM) |
|---|---|
| P7 | + |
| P8 | + |
| P9 | + |
| P10 | + |
| P11 | + |
| P12 | ++ |
| P13 | ++ |
| P14 | + |
| P15 | + |
| P16 | ++ |
| P17 | +++ |
| P18 | + |
| P19 | ++++ |
| P20 | + |
| P21 | ++ |
| P22 | + |
| P23 | ++ |
| P24 | ++ |
| P25 | ++ |
| P26 | ++ |

Example 5A: Whole Blood Interferon γ Assay

To determine the increase of Interferon γ in whole blood, normal human blood (Biological Specialty Corp, Colmar. Pa.) diluted 1/10 in AIM-V media (Life Technologies) is incubated in the presence or absence of a concentration range of test compounds and 5 ng/ml *Staphylococcal enterotoxin* B (Toxin Technologies Sarasota, Fla.) in a 96 well U bottom Tissue Culture Plate (Corning) for 3 days at 37° C. Plates are centrifuged at 1400 RPM for 5 minutes, and supernatants collected and tested for presence of Interferon γ in a commercial Interferon γ ELISA kit (R&D Human IFN-γ Quantikine ELISA (R&D Systems, Minneapolis, Minn.).

Example 6A: Animal Models

Studies to assess pharmacokinetics, pharmacodynamics, and efficacy are conducted in mice engrafted with human CD34+ cells and mice engineered to express human checkpoint molecules. Both preclinical models have been validated with approved therapeutics targeting the PD-1:PD-L1-axis Humanized CD34+ Mice Humanized CD34+ mice have been used commonly to study immune-oncology, infectious diseases and graft rejection research. In brief, immune-compromised NSG mice (NOD scid IL2Rg$^{null}$; Jackson Laboratory) receive total body irradiation to deplete existing bone marrow cells. CD34+ human stem cells derived from umbilical cord blood are then engrafted to establish a fully human immune system over a 12-14 week period. Alternative mouse strains may also be used to improve the engraftment of stem cells and enhance the development of myeloid lineage cells, which are the main PD-L1-expressing host immune cells. For example, the NSG-SGM3 mice were engineered to produce human cytokines (SCF, IL-3 and GM-CSF) that allow full differentiation of the myeloid lineage [Jackson Laboratory]. Cell-derived xenograft models are selected based on tumor and host PD-L1 expression, as well as their response to anti-PD-L1 antibody treatment. PD-L1 internalization induced by small molecules targeting PD-L1 are the main pharmacodynamic biomarker and are determined by measuring the remaining PD-L1 expression on both tumor and host immune cells.

Human Checkpoint Molecule Knock-In Mice

Human-mouse chimeric models have been developed to allow binding of human-specific antibodies to the human protein while using fully intact mouse immune biology. This approach is utilized to evaluate small molecules targeting PD-L1. To this end, the relevant extracellular domain of the human gene is integrated into the locus of the mouse gene by homologous recombination ('knock-in'). For example, the HuGEMM model for PD-1 and PD-L1 uses a human PD-1 knock-in strain that is engrafted with the mouse colon carcinoma cell line MC38 recombinantly expressing human PD-L1 [HuCELL; Crown Bioscience]. Human PD-L1 and PD-1 double knock-in animals with engraftment of MC38-huPD-L1 are developed and used to evaluate PD-L1 internalization induced by small molecules targeting PD-L1 in both tumor and host immune cells.

Example 7A. IRF3 and NF-kB Activation Assays

THP-1 Dual Cells (Invivogen) were maintained in RPMI1640 medium with addition of 10% FBS, 100 μg/ml zeocin, 10 μg/ml blasticidin. Cells were added in a 96-well flat bottom assay plate at 100,000 per well in 100 μL complete RPMI medium. Test compounds were prepared by serial dilution in complete RPMI medium and 100 μL test compounds were transferred to each corresponding well. The assay plate was incubated at 37° C., 5% $CO_2$ for 24 hours. After the overnight incubation, 20 μL of the culture supernatants were collected, followed by addition of 180 μL of QUANTI-Blue (Invivogen) to assess IRF3 activity. The amount of IRF3 activation was assessed by reading the absorbance at 620-655 nm with a microplate reader 2 hours later. The culture supernatant from the untreated THP-1 cells was used as the negative control. $EC_{50}$ determination was performed by fitting the curve of percent control activity versus the log of the compound concentration using the GraphPad Prism 6.0 software.

$EC_{50}$ in activating IRF3 for the compounds of the Examples are presented in Tables 4A, 4B, and 4C.

TABLE 4A

| Example No. | THP1 IRF3 $EC_{50}$ (nM) |
|---|---|
| S1 | +++ |
| S2 | ++ |
| S3 | ++ |
| S4 | +++ |
| S5 | + |
| S6 | + |
| S7 | ++ |
| S8 | +++ |
| S9 | ++ |
| S10 | + |
| S11 | + |
| S12 | + |
| S13 | + |
| S14 | + |
| S15 | + |
| S16 | + |
| S17 | + |
| S18 | + |
| S19 | + |
| S20 | + |
| S21 | + |
| S22 | + |
| S23 | ++ |
| S24 | + |
| S25 | ++ |
| S26 | +++ |
| S27 | + |
| S28 | + |
| S29 | + |
| S30 | +++ |
| S31 | + |
| S32 | + |

TABLE 4A-continued

| Example No. | THP1 IRF3 $EC_{50}$ (nM) |
|---|---|
| S33 | + |
| S65 | + |
| S66 | + |
| S67 | + |
| S68 | + |
| S69 | + |

+ Refers to an $EC_{50}$ of ≤100 nM
++ Refers to an $EC_{50}$ of >100 nM to 500 nM
+++ Refers to an $EC_{50}$ of >500 nM to 1000 nM

TABLE 4B

| Example No. | THP1 IRF3 $EC_{50}$ (nM) |
|---|---|
| S1 | + |
| S2 | + |
| S3 | + |
| S4 | + |
| S5 | + |
| S6 | ++ |
| S7 | + |
| S8 | + |
| S9 | + |
| S10 | ++ |
| S11 | ++ |
| S12 | ++ |
| S13 | ++ |
| S14 | ++ |
| S15 | ++ |
| S16 | ++ |
| S17 | ++ |
| S18 | ++ |
| S19 | ++ |
| S20 | ++ |
| S21 | ++ |
| S22 | ++ |
| S23 | ++ |
| S24 | ++ |
| S25 | + |
| S26 | + |
| S27 | ++ |
| S28 | ++ |

+ refers to an $EC_{50}$ of <1000 nM
++ refers to an $EC_{50}$ of <200 nM

TABLE 4C

| Example No. | THP1 IRF3 $EC_{50}$ (nM) |
|---|---|
| S1 | B |
| S2 | C |
| S4 | D |
| S5 | B |
| S6 | A |
| S7 | C |
| S8 | D |
| S9 | C |
| S10 | A |
| S11 | A |
| S12 | A |
| S13 | A |
| S14 | A |
| S15 | A |
| S16 | A |
| S17 | A |
| S18 | A |
| S19 | A |
| S20 | A |
| S21 | A |
| S22 | A |
| S23 | B |
| S24 | A |

TABLE 4C-continued

| Example No. | THP1 IRF3 EC$_{50}$ (nM) |
|---|---|
| S25 | C |
| S26 | D |
| S27 | A |
| S28 | A |
| S34 | A |
| S35 | B |
| S36 | B |
| S37 | A |
| S38 | D |
| S39 | A |
| S40 | A |
| S41 | A |
| S42 | C |
| S43 | B |
| S44 | A |
| S45 | A |
| S46 | A |
| S47 | B |
| S48 | A |
| S49 | A |
| S50 | A |
| S51 | A |
| S52 | A |
| S53 | A |
| S54 | A |
| S55 | A |
| S56 | A |
| S57 | B |
| S58 | B |
| S59 | B |
| S60 | B |
| S61 | B |
| S62 | B |
| S63 | C |
| S64 | B |

A refers to an EC$_{50}$ of ≤50 nM;
B refers to an EC$_{50}$ of >50 to 200 nM;
C refers to an EC$_{50}$ of >200 to 500 nM;
D refers to an EC$_{50}$ of >500 to 1000 nM.

Example 8A and 8B. Determination of IRF3 Activation and PD-L1 Expression in HEK293T STING Reporter Cell Lines Example 8A: Determination of IRF3 Activation in HEK293T STING Reporter Cell Lines HEK293T STING reporter cell line was purchased from Invivogen and expressed low level of PD-L1. This cell line was then engineered at Incyte Research Institute to overexpress human PD-L1. Both PD-L1 high and PD-L1 low HEK293T cell lines were plated at 100,000 cells/100 µL/well in 10% fetal calf serum-containing DMEM culture medium in a 96-well flat bottom plate. Serial dilutions of PD-L1 small molecule-conjugated STING agonists were then added to the corresponding wells, and incubated for 20 hours at 37° C. In a competition study setting, 1 µM of a PD-L1 small molecule was added in the corresponding wells to compete with the binding of PD-L1 small molecule-conjugated STING agonists. At the end of the incubation, the culture supernatants were carefully removed from each well, and the amount of IRF3 activation was determined by adding Quanti-Blue substrate in accordance with the manufacturer's protocol. EC$_{50}$'s for IFR3 activation for the Example compounds were measured and are shown in Tables 5 and 7.

TABLE 5

| | IRF Activation EC$_{50}$ (nM) | | |
|---|---|---|---|
| Example | No competition | With compound P27 (1 µM) | Potency shift |
| 1 | + | +++ | >100 |
| 2 | + | ++ | >20 |
| 3 | + | +++ | >20 |
| 4 | + | +++ | >20 |
| 5 | + | +++ | >20 |
| 6 | + | ++ | >5 |

+ refers to ≤50 nM
++ refers to >50 nM to 200 nM
+++ refers to >200 nM to 1000 nM
++++ refers to >1000 nM Example 8B: Determination of PD-L1 Surface Levels To determine PD-L1 expression on HEK cells after treatment of PD-L1-small molecule conjugated STING agonists, cells were harvested at 20 hours post-treatment. Single cell suspensions were then stained with phycoerythrin-conjugated anti-PD-L1 antibody (BD Bioscience), and the PD-L1 expression were then analyzed by flow cytometry. Mean fluorescence intensity was used as the relative level of surface PD-L1 expression on cells (FIG. 1 and Table 6). High PD-L1 expressing cells have 200-fold more surface PD-L1 expression than a negative control, while and low PD-L1 expressing cells have about 10-fold more surface PD-L1 expression than a negative control. IC$_{50}$'s for reduction of surface PD-L1 for the Example compounds were measured and are shown in Table 7.

TABLE 6

| | Mean Fluorescence Intensity |
|---|---|
| Unstained | 61.5 |
| S293T-hSTING-R323 Cells (low PD-L1) | 617 |
| S293T-hSTING-R323 Cells (high PD-L1) | 12459 |

TABLE 7

| | IRF Activation EC$_{50}$ (nM) | | | PD-L1 Internalization IC$_{50}$ (nM) | |
|---|---|---|---|---|---|
| Example | Low PD-L1 | High PD-L1 | Low PD-L1/ High PD-L1 | Low PD-L1 | High PD-L1 |
| 1 | +++ | + | >100 | ++++ | + |
| 2 | ++ | + | >20 | ++++ | + |
| 3 | +++ | + | >20 | ++++ | + |
| 4 | +++ | + | >100 | ++++ | ++ |
| 5 | +++ | + | >20 | ++++ | + |
| 6 | +++ | + | >5 | ++++ | +++ |
| 7 | ++ | + | >200 | | + |
| 8 | ++ | + | >10 | | +++ |
| 9 | +++ | + | >10 | | ++ |
| 10 | ++ | + | >20 | | + |
| 11 | + | + | | | + |
| 12 | ++ | + | >20 | | + |
| 13 | ++ | + | >5 | | + |
| 14 | ++ | + | >5 | | + |
| 15 | ++ | + | >20 | | + |
| 16 | + | + | >20 | | + |
| 17 | ++ | + | >20 | | + |
| 18 | + | + | >10 | | + |
| 19 | ++ | + | >5 | | + |
| 20 | ++ | + | >20 | | + |

TABLE 7-continued

| | IRF Activation EC$_{50}$ (nM) | | PD-L1 Internalization IC$_{50}$ (nM) | | |
|---|---|---|---|---|---|
| Example | Low PD-L1 | High PD-L1 | Low PD-L1/ High PD-L1 | Low PD-L1 | High PD-L1 |
| 21 | ++ | + | >20 | | + |
| 22 | + | + | >10 | | + |
| 23 | ++ | + | >10 | | + |
| 24 | + | + | >10 | | + |

+ refers to ≤50 nM
++ refers to >50 nM to 200 nM
+++ refers to >200 nM to 1000 nM
++++ refers to >1000 nM Example 9A In-Vitro Assay Using 293T-Dual hSTING-R232

293T-Dual hSTING-R232 (ISG/KI-IFNb) cells that were generated from 293T-Dual Null (ISG/KI-IFNb) cells by stable transfection of the R232 isoform of human STING were purchased from Invivogen (Invivogen #293d-r232).

This cell line expresses an ISRE-inducible SEAP (secreted embryonic alkaline phosphatase) reporter construct, which monitors the activation of interferon regulatory factor (IRF) and its binding to ISRE (IFN-stimulated response elements). These reporter cells express low level of PD-L1. Human PD-L1 was then overexpressed in these cells through stable transfection.

These 293T-Dual hSTING-R232 reporter cells as well as293T-Dual hSTING-R232 reporter cells overexpressing huPD-L1 were treated with various concentrations of STING compounds for 20 hours. After 20 hours, interferon regulatory factor (IRF) activity was assessed by measuring SEAP levels in the supernatant using QUNTI-Blue. EC50 values were generated by curve fit in Prism software.

Also, cells were stained with PE-conjugated anti-human PD-L1 antibody to determine surface PD-L1 expression. Cell acquisition was performed on BD LSRFortessa X-20 (BD Biosciences). Data was analyzed using FlowJo software. IC50 values were calculated using Prism Software.

Baseline PD-L1 Expression in PBMCs and Pleural Effusion Samples by Flow Cytometry Single cell suspension from PBMC and pleural effusions were blocked for 10 min with anti-Fc receptor antibody. The cells were then stained with different fluorochrome-conjugated antibodies for 30 minutes at room temperature to identify different cell populations. Phycoerythrin-conjugated anti-PD-L1 (clone M1H1; 12-5983-42, eBiosciences) was used to determine baseline surface PD-L1 expression on CD11b+ cells as well as HLA-DR+ cells. A commercial kit (Zombie Violet Fixable Viability Kit, Cat #423114, Biolegend) was used to exclude dead cells from data analyses. Cell acquisition was performed on BD LSRFortessa X-20 (BD Biosciences). Data was analyzed using FlowJo software.

IFN-beta Cytokine Analysis

CD11b$^+$ cells were isolated from healthy PBMCs as well as Pleural effusion samples using Miltenyi isolation kit according to manufacturer's protocol. Cells were seeded in 96 well plates at the density of 300,000 cells/wells, and then treated with various concentrations of compounds for 20 hours. After 20 hours, IFN-beta secretion levels were evaluated in the culture supernatants by MSD singleplex assay. EC$_{50}$ values were calculated using Prism software.

Results

Figure 2A:
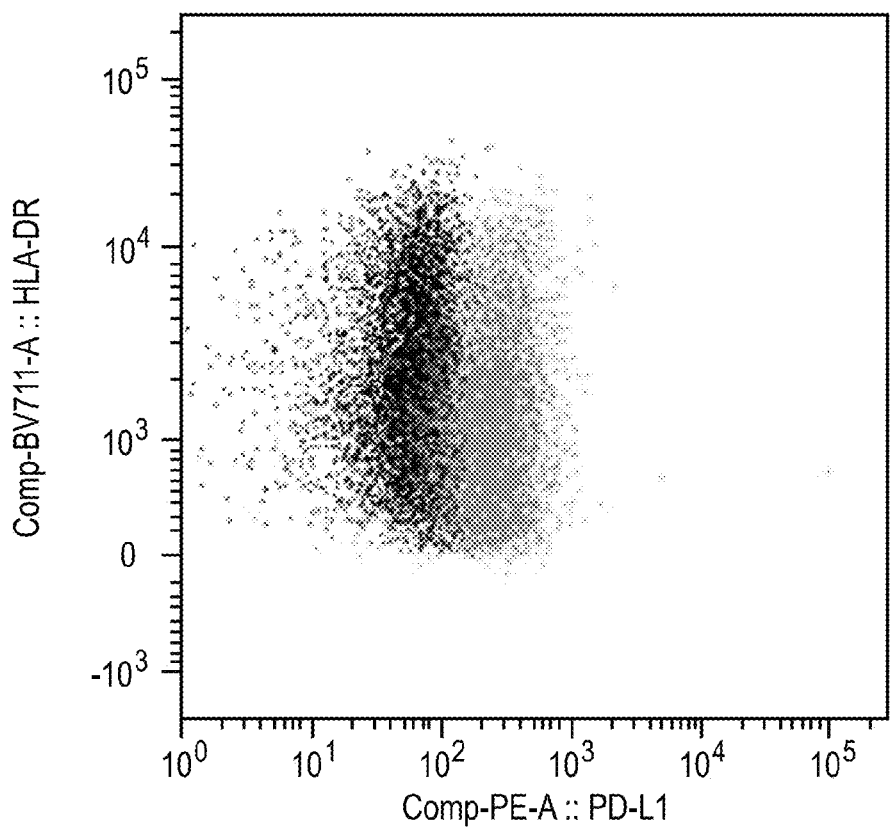
FIG. 2A depicts a representative flow cytometric tracing for surface PD-L1 levels on CD11b$^+$ cells in healthy PBMCs.
Figure 2B:
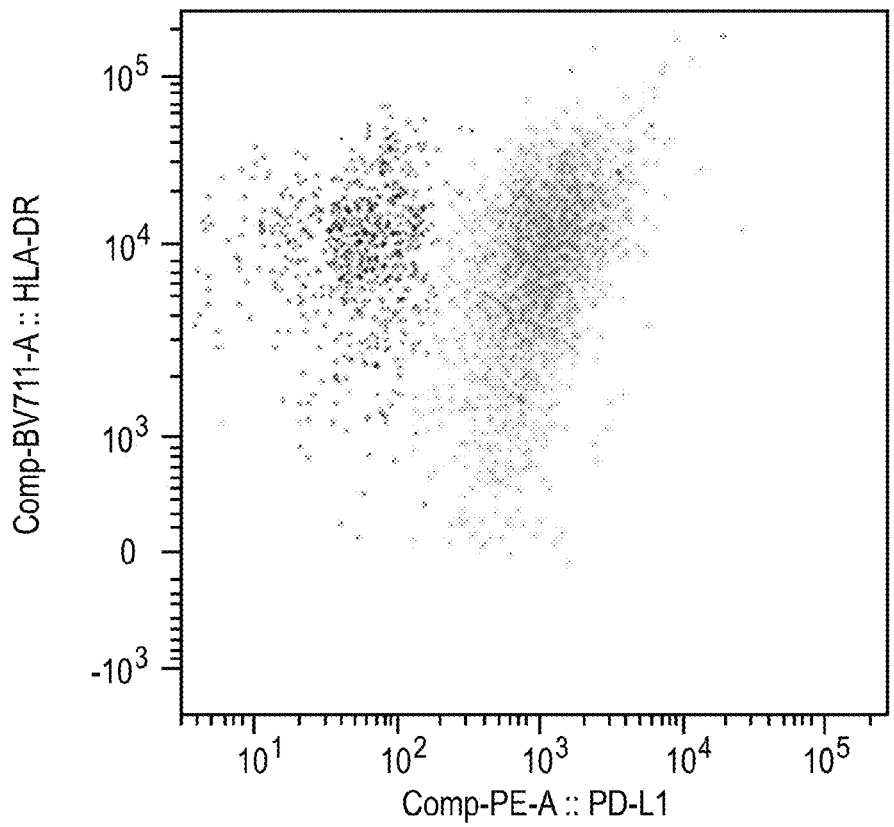
FIG. 2B depicts a representative flow cytometric tracing for surface PD-L1 levels on CD11b$^+$ cells in pleural effusion samples from lung cancer patients.

PD-L1 Expression on CD11b$^+$ Monocytes Isolated from healthy PBMC and Lung Cancer Pleural Effusions Surface PD-L1 levels on CD11b$^+$ cells in healthy PBMCs and pleural effusion samples from lung cancer patients were determined using flow cytometry. Total of 8 healthy donors and 2 lung cancer patients were characterized (FIG. 2), and a representative flow cytometric tracing was shown for both healthy donors (FIG. 2A) and cancer patient sample (FIG. 2B).

Differential IFNβ Induction by PD-L1 Small Molecule Conjugated with STING Agonist in Healthy Donors Versus Cancer Patients Different naked STING agonisst and PD-L1-targeted small molecule-STING agonist conjugates were added to CD11b$^+$ monocytes cultures isolated from healthy donor blood or lung cancer patients' pleural effusions. Culture supernatants were collected 20 hours later and IFNβ production were determined using MSD singleplex assay. The EC$_{50}$ values for the naked and conjugated STING agonists were summarized in Table 8. While naked STING agonists showed equivalent cellular potency in both healthy donor and patients' CD11b$^+$ cultures, PD-L1 small molecule-STING agonist conjugates had a 3-12 fold shift in potency.

TABLE 8

IFNβ induction by naked STING agonists and PD-L1 small molecule-STING conjugates in different CD11b$^+$ cultures

| Example No. | Conjugation | Healthy donor | Cancer patient |
|---|---|---|---|
| S45 | Unconjugated | 119 ± 22 (n = 8) | 56 (n = 2) |
| S48 | Unconjugated | 64 ± 12 (n = 8) | 38 (n = 2) |
| 1 | PD-L1 small molecule | 5030 ± 1261 (n = 8) | 406 (n = 2) |
| 7 | PD-L1 small molecule | 2011 ± 308 (n = 8) | 643 nM (n = 1) |

The values in table indicate the EC$_{50}$ number (in nM; mean ± standard error of mean) for IFNβ induction in monocyte cultures.

All publications, patent applications, patents, and other references mentioned herein are incorporated by reference in their entirety. Unless otherwise defined, all technical and scientific terms used herein have the same meaning as commonly understood by one of ordinary skill in the art to which this invention belongs. In case of conflict, the present specification, including definitions, will control. Suitable methods and materials are described below, although methods and materials similar or equivalent to those described herein can also be used in the practice or testing of the present invention. The materials, methods, and examples are illustrative only and not intended to be limiting.

What is claimed is:

1. A compound of Formula (I):

P-L-S     (I)

or a pharmaceutically acceptable salt thereof, wherein P is a ligand that binds to cell surface PD-L1 protein and induces PD-L1 internalization, L is a linking group, and S is a moiety that agonizes STING, wherein P has Formula (P-1b):

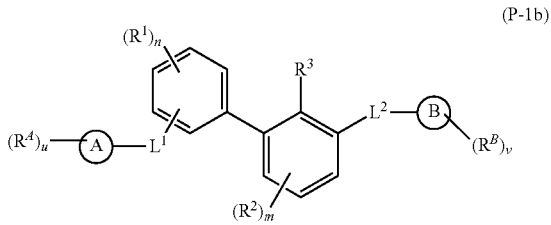

wherein:
L is attached to ring A or ring B by a direct bond or to an $R^A$ or $R^B$ substituent;

$L^1$ and $L^2$ are each independently selected from a bond, —C(O)NR$^{13}$—, —NR$^{13}$C(O)—, —O—, —(CR$^{14}$R$^{15}$)$_{t2}$—, —(CR$^{14}$R$^{15}$)$_{t2}$—O—, —O(CR$^{14}$R$^{15}$)$_{t2}$—, —(CR$^{14}$R$^{15}$)$_{t2}$—NR$^{13}$—, —NR$^{13}$—(CR$^{14}$R$^{15}$)$_{t2}$—, S(O)$_2$NR$^{13}$—, —NR$^{13}$S(O)$_2$—, —NR$^{13}$S(O)$_2$NR$^{13}$—, —NR$^{13}$C(O)O—, —OC(O)NR$^{13}$— and —NR$^{13}$C(O)NR$^{13}$—;

ring A and ring B are each independently selected from 5-10 membered heteroaryl, 4-10 membered heterocycloalkyl, $C_{6-10}$ aryl, and $C_{3-10}$ cycloalkyl;

$R^1$ is $C_{1-4}$ alkyl, $C_{1-4}$ alkoxy, $C_{1-4}$ haloalkyl, $C_{1-4}$ haloalkoxy, CN, halo, OH, —C(O)OH, NH$_2$—, -$C_{1-4}$ alkylamino, or di-($C_{1-4}$ alkyl)amino;

$R^2$ is $C_{1-4}$ alkyl, $C_{1-4}$ alkoxy, $C_{1-4}$ haloalkyl, $C_{1-4}$ haloalkoxy, CN, halo, OH, —C(O)OH, NH$_2$, -$C_{1-4}$ alkylamino, or di-($C_{1-4}$ alkyl)amino;

$R^3$ is methyl, Cl, F, CN, or $C_{1-2}$ haloalkyl;

each subscript t2 is independently an integer of 1, 2, 3 or 4;

the subscript m is an integer of 0, 1, 2, or 3;
the subscript n is an integer of 0, 1, 2, or 3;
the subscript u is an integer of 0, 1, 2, 3, 4, or 5;
the subscript v is an integer of 0, 1, 2, 3, 4, or 5;

$R^A$ and $R^B$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-14}$ aryl, $C_{3-14}$ cycloalkyl, 5-14 membered heteroaryl, 4-14 membered heterocycloalkyl, $C_{6-14}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, C(O)NR$^a$S(O)$_2$R$^a$, OC(O)R$^a$, OC(O)NR$^a$R$^a$, NHR$^a$, NR$^a$R$^a$, NR$^a$C(O)R$^a$, NR$^a$C(=NR$^a$)R$^a$, NR$^a$C(O)OR$^a$, NR$^a$C(O)NR$^a$R$^a$, C(=NR$^a$)R$^a$, C(=NOH)R$^a$, C(=NOH)NR$^a$, C(=NCN)NR$^a$R$^a$, NR$^a$C(=NCN)NR$^a$R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, S(O)$_2$NR$^a$C(O)R$^a$, —P(O)R$^a$R$^a$, —P(O)(OR$^a$)(OR$^a$), —B(OH)$_2$, —B(OR$^a$)$_2$ and S(O)$_2$NR$^a$R$^a$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- are each optionally substituted with 1, 2, 3, 4 or 5 independently selected R$^b$ substituents;

or two R$^A$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected R$^f$ substituents;

or two R$^B$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected R$^f$ substituents;

each R$^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- are each optionally substituted with 1, 2, 3, 4, or 5 independently selected R$^d$ substituents;

each R$^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, NH$_2$, NO$_2$, NHOR$^c$, OR$^c$, SR$^c$, C(O)R$^c$, C(O)NR$^c$R$^c$, C(O)OR$^c$, C(O)NR$^c$S(O)$_2$R$^c$, OC(O)R$^c$, OC(O)NR$^c$R$^c$, C(=NOH)R$^c$, C(=NOH)NR$^c$, C(=NCN)NR$^c$R$^c$, NR$^c$C(=NCN)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(=NR$^c$)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$, S(O)$_2$NR$^c$C(O)R$^c$, —P(O)R$^c$R$^c$, —P(O)(OR$^c$)(OR$^c$), —B(OH)$_2$, —B(OR$^c$)$_2$ and S(O)$_2$NR$^c$R$^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each further optionally substituted with 1, 2 or 3 independently selected R$^d$ substituents;

each R$^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2, 3, 4, or 5 independently selected R$^f$ substituents;

or two R$^c$ attached to the same nitrogen atom are taken together to form a 4-14 membered heterocycloalkyl ring which is optionally substituted with 1, 2, or 3 independently selected R$^f$ substituents;

each R$^d$ is independently selected from $C_{1-6}$ alkyl, $C_{1-6}$ haloalkyl, halo, $C_{2-6}$ alkenyl, $C_{2-6}$ alkynyl, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-10 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $C(O)NR^eS(O)_2R^e$, $OC(O)R^e$, $OC(O)NR^eR^e$, $NHR^e$, $NR^eR^e$, $NR^eC(O)R^e$, $NR^eC(=NR^e)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $S(O)_2NR^eC(O)R^e$, $NR^eS(O)_2R^e$, $NR^eS(O)_2NR^eR^e$, —$P(O)R^eR^e$, —$P(O)(OR^e)(OR^e)$, —$B(OH)_2$, —$B(OR^e)_2$ and $S(O)_2NR^eR^e$, wherein the $C_{1-6}$ alkyl, $C_{2-6}$ alkenyl, $C_{2-6}$ alkynyl, $C_{6-10}$ aryl, 5-10 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-10 membered heteroaryl)-$C_{1-4}$ alkyl-, and (4-14 membered heterocycloalkyl)-$C_{1-4}$ alkyl- are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2 or 3 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $C(O)NR^gS(O)_2R^g$, $OC(O)R^g$, $OC(O)NR^gR^g$, $NHR^g$, $NR^gR^g$, $NR^gC(O)R^g$, $NR^gC(=NR^g)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $S(O)_2NR^gC(O)R^g$, $NR^gS(O)_2R^g$, $NR^gS(O)_2NR^gR^g$, —$P(O)R^gR^g$, —$P(O)(OR^g)(OR^g)$, —$B(OH)_2$, —$B(OR^g)_2$ and $S(O)_2NR^gR^g$; wherein the $C_{1-4}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 independently selected $R^n$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2, or 3 independently selected $R^p$ substituents;

each $R^n$ is substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $C(O)NR^oS(O)_2R^o$, $OC(O)R^o$, $OC(O)NR^oR^o$, $NHR^o$, $NR^oR^o$, $NR^oC(O)R^o$, $NR^oC(=NR^o)R^o$, $NR^oC(O)NR^oR^o$, $NR^oC(O)OR^o$, $C(=NR^oNR^oR^o$, $NR^oC(=NR^oNR^oR^o$, $S(O)R^o$, $S(O)NR^oR^o$, $S(O)_2R^o$, $S(O)_2NR^oC(O)R^o$, $NR^oS(O)_2R^o$, $NR^oS(O)_2NR^oR^o$, —$P(O)R^oR^o$, —$P(O)(OR^o(OR^o)$, —$B(OH)_2$, —$B(OR^o)_2$ and $S(O)_2NR^oR^o$, wherein the $C_{1-4}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2 or 3 independently selected $R^q$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $C(O)NR^rS(O)_2R^r$, $OC(O)R^r$, $OC(O)NR^rR^r$, $NHR^r$, $NR^rR^r$, $NR^rC(O)R^r$, $NR^rC(=NR^r)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $S(O)_2NR^rC(O)R^r$, $NR^rS(O)_2R^r$, $NR^rS(O)_2NR^rR^r$, —$P(O)R^rR^r$, —$P(O)(OR^r)(0R^r)$, —$B(OH)_2$, —$B(OR^r)_2$ and $S(O)_2NR^rR^r$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- is optionally substituted with 1, 2 or 3 independently selected $R^q$ substituents;

each $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl are each optionally substituted with 1, 2 or 3 independently selected $R^q$ substituents; and each $R^q$ is independently selected from OH, $NO_2$, CN, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 4-6 membered heterocycloalkyl, and 5-6 membered heteroaryl, $C_{1-6}$ alkoxy, $C_{1-6}$ haloalkoxy, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, phenyl, $C_{3-7}$ cycloalkyl, 4-6 membered heterocycloalkyl, and 5-6 membered heteroaryl are each optionally substituted with 1, 2 or 3 substituents independently selected from halo, OH, CN, —COOH, $C_{1-4}$ alkyl, $C_{1-4}$ alkoxy, $C_{1-4}$ haloalkyl, $C_{1-4}$ haloalkoxy, amino, $C_{1-3}$ alkylamino, and di($C_{1-3}$ alkyl)amino; and wherein S has Formula (S-1c):

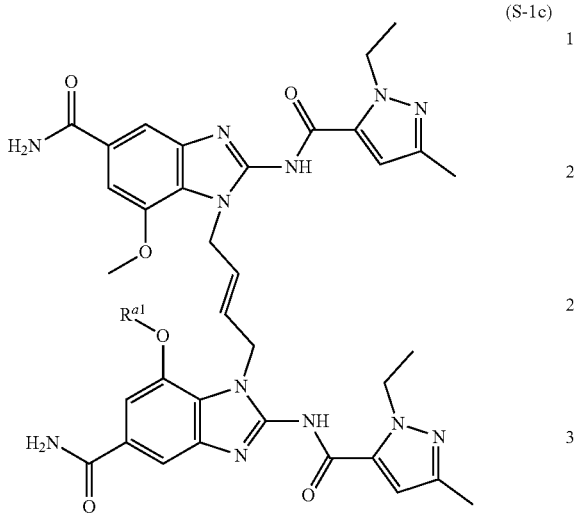

(S-1c)

wherein:
L is attached to $R^{a1}$;
each $R^{a1}$ is independently selected from H, $R^{c1}$, $C(O)R^{c1}$, $C(O)OH$, $C(O)OR^{c1}$, $S(O)R^{c1}$, $S(O)_2R^{c1}$, $C(O)NH_2$, $C(O)NR^{c1}R^{d1}$, $S(O)_2NH_2$, and $S(O)_2NR^{c1}R^{d1}$;
each $R^{c1}$ is independently selected from $C_{1-4}$ alkyl, $C_{1-4}$ haloalkyl, -($C_{1-4}$ alkyl)-OH, -($C_{1-4}$ alkyl)-O—P(O)(OH)$_2$, -($C_{1-4}$ alkyl)-O—P(O)($R^IR^{II}$)$_2$, -($C_{1-4}$ alkyl)-O-($C_{1-4}$ alkyl), -($C_{1-4}$ alkyl)-N($R^{e1}$)($R^{f1}$), -($C_{1-4}$ alkyl)-O—C(O)($C_{1-4}$ alkyl), -($C_{1-4}$ alkyl)-C(O)—O-($C_{1-4}$ alkyl), optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted -$C_{1-4}$ alkyl-$C_{3-6}$ cycloalkyl, optionally substituted -$C_{1-4}$ alkyl-phenyl, optionally substituted -$C_{1-4}$ alkyl-4-6 membered heterocycloalkyl, optionally substituted -$C_{1-4}$ alkyl-5-6 membered heteroaryl, and optionally substituted -$C_{1-4}$ alkyl-9-10 membered heteroaryl;
wherein the $C_{3-6}$ cycloalkyl, phenyl, 4-6 membered heterocycloalkyl, 5-6 membered heteroaryl and 9-10 membered heteroaryl moieties of said optionally substituted $C_{3-6}$ cycloalkyl, optionally substituted phenyl, optionally substituted 4-6 membered heterocycloalkyl, optionally substituted 5-6 membered heteroaryl, optionally substituted 9-10 membered heteroaryl, optionally substituted -$C_{1-4}$ alkyl-$C_{3-6}$ cycloalkyl, optionally substituted -$C_{1-4}$ alkyl-phenyl, optionally substituted -$C_{1-4}$ alkyl-4-6 membered heterocycloalkyl, optionally substituted -$C_{1-4}$ alkyl-5-6 membered heteroaryl, and optionally substituted -$C_{1-4}$ alkyl-9-10 membered heteroaryl are each optionally substituted by 1, 2, 3, or 4 substituents independently selected from halo, OH, OP(O)(OH)$_2$, OP(O)($R^IR^{II}$)$_2$, amino, ($C_{1-4}$ alkyl)NH$_2$, ($C_{1-4}$ alkyl)amino, di-($C_{1-4}$ alkyl)amino, $C_{1-4}$ alkyl, $C_{1-4}$ haloalkyl, $C_{1-4}$ haloalkoxy, $C_{1-6}$ alkoxy-, OH-($C_{2-4}$ alkoxy)-, -($C_{1-4}$ alkyl)-O—P(O)(OH)$_2$, -($C_{1-4}$ alkyl)-O—P(O)($R^IR^{II}$)$_2$, $C_{1-4}$ alkoxy-($C_{1-4}$ alkoxy)-, $C(O)R^{d1}$, $C(O)NR^{d1}R^{f1}$, and $C(O)OR^{d1}$;

each $R^{d1}$ is independently selected from H and $C_{1-4}$ alkyl;
each $R^{e1}$ is independently selected from H, $C_{1-4}$ alkyl, —C(O)($C_{1-4}$ alkyl), —OC(O)($C_{1-4}$ alkyl), —C(O)O($C_{1-4}$ alkyl), -($C_{1-4}$ alkyl)NH$_2$, -($C_{1-4}$ alkyl)-$C_{1-4}$ alkoxy, —C(O)-(optionally substituted 5-6 membered heterocycloalkyl), —C(O)($C_{1-4}$ alkyl)-(optionally substituted 5-6 membered heterocycloalkyl), —C(O) (optionally substituted 5-6 membered heteroaryl), and —C(O)($C_{1-4}$ alkyl)-(optionally substituted 5-6 membered heteroaryl), wherein the optionally substituted 5-6 membered heterocycloalkyl and optionally substituted 5-6 membered heteroaryl are each optionally substituted 1, 2, 3, or 4 substituents independently selected from halo, OH, —OP(O)(OH)$_2$, OP(O)($R^IR^{II}$)$_2$, amino, ($C_{1-4}$ alkyl)NH$_2$, ($C_{1-4}$ alkyl)amino-, di-($C_{1-4}$ alkyl)amino-, $C_{1-4}$ alkyl, $C_{1-4}$ haloalkyl, $C_{1-4}$ haloalkoxy, $C_{1-4}$ alkoxy-, OH-($C_{2-4}$ alkoxy)-, -($C_{1-4}$ alkyl)-O—P(O)(OH)$_2$, -($C_{1-4}$ alkyl)-O—P(O)($R^IR^{II}$)$_2$, $C_{1-4}$ alkoxy-($C_{1-4}$ alkoxy)-, $C_{1-4}$ alkoxy-($C_{1-4}$ alkoxy)-, $C(O)R^{d1}$, $C(O)NR^{d1}R^{f1}$, and $C(O)OR^{d1}$;

each $R^{f1}$ is independently selected from H and $C_{1-4}$ alkyl; and
each occurrence of $R^I$ and $R^{II}$ are independently $C_{1-6}$ alkoxy; or
wherein S has Formula (S-2b):

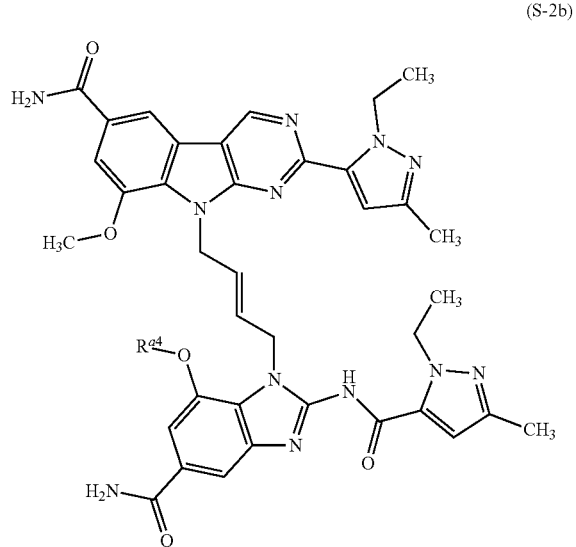

(S-2b)

wherein:
L is attached to $R^{a4}$;
$R^{a4}$ is selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{4,4}$ groups;

each $R^{4,4}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a41}$, $SR^{a41}$, $C(=O)R^{b41}$, $C(=O)NR^{c41}R^{d41}$, $C(=O)OR^{a41}$, $OC(=O)R^{b41}$, $OC(=O)NR^{c41}R^{d41}$, $NR^{c41}R^{d41}$, $NR^{c41}C(=O)R^{b41}$, $NR^{c1}C(=O)OR^{b41}$, $NR^{c1}C(=O)NR^{c41}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}S(=O)_2R^{b41}$, $NR^{c41}S(=O)_2NR^{c41}R^{d41}$, $S(=O)_2R^{b41}$, $S(=O)_2NR^{c41}R^{d41}$, and $OP(O)(OR^{f41})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{4B}$ groups;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ groups;

each $R^{b41}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4B}$ groups;

each $R^{e41}$ is independently selected from H, $C_{1-4}$ alkyl, $C_{1-4}$ alkoxy, $C_{1-4}$ haloalkyl, and $C_{1-4}$ haloalkoxy;

each $R^{f41}$ is independently OH or $C_{1-6}$ alkoxy;

each $R^{4B}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a42}$, $SR^{a42}$, $C(=O)R^{b42}$, $C(=O)NR^{c42}d^{d42}$, $C(=O)OR^{a42}$, $OC(=O)R^{b42}$, $OC(=O)NR^{c42}R^{d42}$, $NR^{c42}R^{d42}$, $NR^{c42}C(=O)R^{b42}$, $NR^{c42}C(=O)OR^{b42}$, $NR^{c42}C(=O)NR^{c42}R^{d42}$, $C(=NR^{e42})R^{b42}$, $C(=NR^{e42})NR^{c42}R^{d42}$, $NR^{c42}C(=NR^{e42})NR^{c42}R^{d42}$, $NR^{c42}S(=O)_{2l}R^{b42}$, $NR^{c42}S(=O)_2NR^{c42}R^{d42}$, $S(=O)_2R^{b42}$, $S(=O)_2NR^{c42}R^{d42}$, and $OP(O)(OR^{f42})$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b42}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ groups;

each $R^{e42}$ is independently selected from H, $C_{1-4}$ alkyl, $C_{1-4}$ alkoxy, $C_{1-4}$ haloalkyl, and $C_{1-4}$ haloalkoxy;

each $R^{f42}$ is independently OH or $C_{1-6}$ alkoxy; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

2. The compound of claim 1, or a pharmaceutically acceptable salt thereof, wherein the compound has Formula (P-1c):

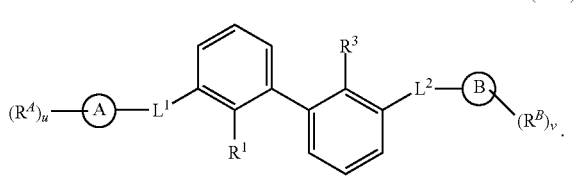

(P-1c)

3. The compound of claim 1, or a pharmaceutically acceptable salt thereof, wherein:

$R^A$ and $R^B$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, and CN, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- are each optionally substituted with 1, 2, or 3 independently selected $R^b$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $OR^c$, $NHR^c$, $NR^cR^c$, $C(O)R^c$, $C(O)NR^cR^c$, and $C(O)OR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, are each optionally substituted with 1, 2, or 3 independently selected $R^f$ substituents;

each $R^d$ is independently selected from $C_{1-6}$ alkyl, $C_{1-6}$ haloalkyl, halo, $OR^e$, $C(O)R^e$, $C(O)NR^eR^e$, and $C(O)OR^e$, wherein the $C_{1-6}$ alkyl is optionally substituted with 1, 2, or 3 independently selected $R^f$ substituents;

each $R^e$ is independently selected from H and $C_{1-6}$ alkyl; and each $R^f$ is independently selected from OH, halo, $C_{1-4}$ alkyl, $C_{2-4}$ alkenyl, $C_{2-4}$ alkynyl, $C_{1-4}$ haloalkyl, and carboxy.

4. The compound of claim 2, or a pharmaceutically acceptable salt thereof, wherein:

$R^A$ and $R^B$ are each independently selected from H, halo, $C_{1-6}$ alkyl, $C_{2-6}$ alkenyl, $C_{2-6}$ alkynyl, $C_{1-6}$ haloalkyl, 4-10 membered heterocycloalkyl, (4-10 membered heterocycloalkyl)-$C_{1-4}$ alkyl-, and CN, wherein the $C_{1-6}$ alkyl, $C_{2-6}$ alkenyl, $C_{2-6}$ alkynyl, 4-10 membered heterocycloalkyl, and (4-10 membered heterocycloalkyl)-$C_{1-4}$ alkyl- are each optionally substituted with 1, 2, or 3 independently selected $R^b$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, 5-10 membered heteroaryl, 4-10 membered heterocycloalkyl, CN, OH, $OR^c$, $NHR^c$, $NR^cR^c$, $C(O)R^c$, $C(O)NR^cR^c$, and $C(O)OR^c$; wherein the $C_{1-6}$ alkyl, $C_{1-6}$ haloalkyl, 5-10 membered heteroaryl, and 4-10 membered heterocycloalkyl, are each further optionally substituted with 1, 2 or 3 independently selected $R^d$ substituents;

each $R^c$ is independently selected from H, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, are each optionally substituted with 1, 2, or 3 independently selected $R^f$ substituents;

each $R^d$ is independently selected from $C_{1-6}$ alkyl and $OR^e$, $C(O)R^e$, wherein the $C_{1-6}$ alkyl is optionally substituted with 1, 2, or 3 independently selected $R^f$ substituents;

each $R^e$ is independently selected from H and $C_{1-6}$ alkyl; and each $R^f$ is independently selected from OH, halo, $C_{1-4}$ alkyl, $C_{2-4}$ alkenyl, $C_{2-4}$ alkynyl, and carboxy.

5. The compound of claim 2, or a pharmaceutically acceptable salt thereof, wherein P is 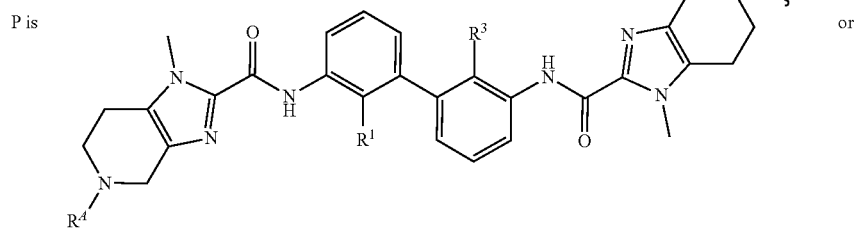 or

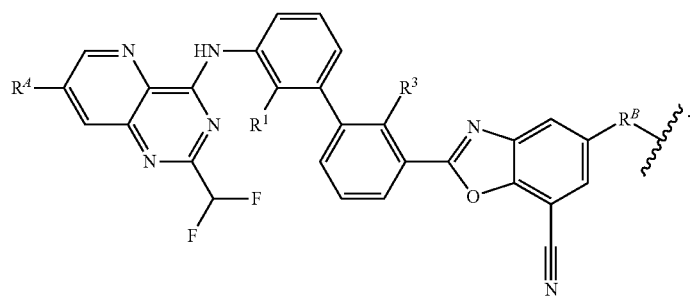

6. The compound of claim 2, or a pharmaceutically acceptable salt thereof, wherein $L^1$ is a bond, —C(O)NH—, —OCH$_2$—, or —NH—.

7. The compound of claim 2, or a pharmaceutically acceptable salt thereof, wherein $L^2$ is a bond, —NHC(O)—, —CH$_2$O—, or —NH—.

8. The compound of claim 2, or a pharmaceutically acceptable salt thereof, wherein ring A is selected from:

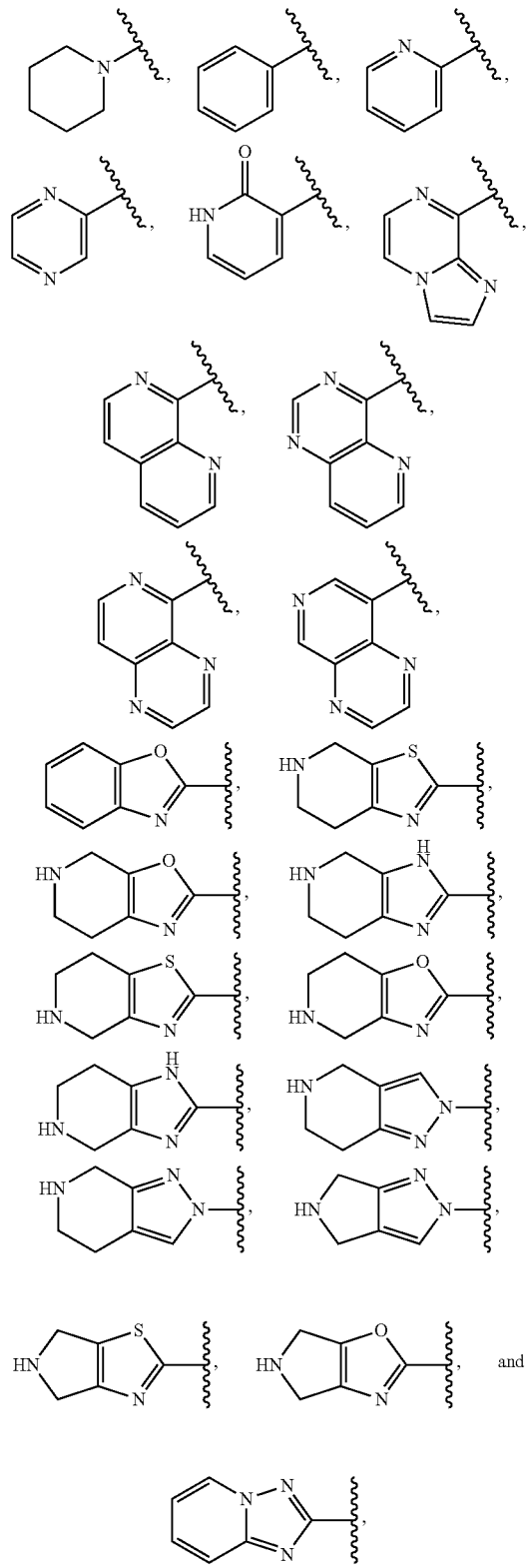

each of which is substituted with u independently selected $R^A$ groups; and wherein

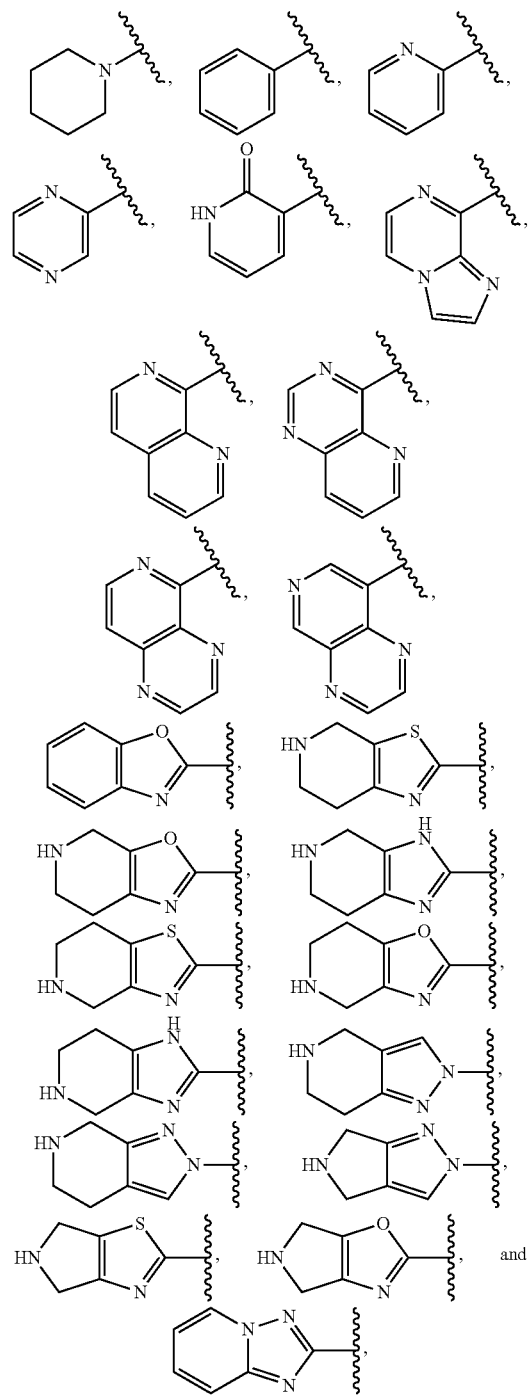

designates the point of attachment to $L^1$.

9. The compound of claim 8, or a pharmaceutically acceptable salt thereof, wherein ring B is selected from:

each of which is substituted with v independently selected $R^B$ groups; and wherein

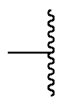

designates the point of attachment to $L^2$.

10. The compound of claim 1, or a pharmaceutically acceptable salt thereof, wherein L is sufficiently polar to avoid the compound or salt to penetrate a cell membrane.

11. The compound of claim 1, or a pharmaceutically acceptable salt thereof, wherein:

L is $-(A^1)_{a1}-(B^1)_{a2}-(C^1)_{a3}-(D^1)_{a4}-(E^1)_{a5}-(F^1)_{a6}-(G^1)_{a7}-(H^1)_{a8}-$;
subscript a1 is 0 or 1;
subscript a2 is 0 or 1;
subscript a3 is 0 or 1;
subscript a4 is 0 or 1;
subscript a5 is 0 or 1;
subscript a6 is 0 or 1;
subscript a7 is 0 or 1;
subscript a8 is 0 or 1;
wherein a1+a2+a3+a4+a5+a6 is 1, 2, 3, 4, 5, 6, 7, or 8;
$A^1$, $B^1$, $C^1$, $D^1$, $E^1$, $F^1$, and $H^1$ are each independently selected from $M^1$, $C_{1-6}$ alkylene, $C_{2-8}$ heteroalkylene, $Cy^1$, $Cy^1$-$C_{1-6}$ alkylene, $C_{1-6}$ alkylene-$Cy^1$, a peptide of 1-8 amino acids, and polyethylene glycol having from 1 to 10 ethylene glycol repeat units, wherein said $C_{1-6}$ alkylene and $C_{2-8}$ heteroalkylene are optionally substituted with 1 or 2 independently selected $R^{k1}$ substituents;
$M^1$ is —O—, —S—, —S—S—, —C(O)—, —NH—, —C(O)NH—, —NHC(O)—, NHC(O)O—, —OC(O)NH—, and —NHC(O)NH—;
$C_{2-8}$ heteroalkylene is a straight-chain alkylene chain, wherein wherein 1, 2, or 3 non-adjacent $C_1$ alkylene chain members are replaced with a group independently selected from —O—, —S—, —S—S—, —C(O)—, —NH—, —C(O)NH—, —NHC(O)—, NHC(O)O—, —OC(O)NH—, and —NHC(O)NH—, provided that said $C_{2-8}$ heteroalkylene retains at least one $C_1$ alkylene chain member;
each $Cy^1$ is independently phenyl, $C_{3-7}$ cycloalkyl, 5-6 membered heteroaryl, and 4-7 membered heterocycloalkyl, each of which is optionally substituted with 1, 2, or 3 independently selected $R^{k1}$ substituents;
each $R^{L1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{k1}$ substituents; and
each $R^{k1}$ is independently selected from —NHC(=NH)NH$_2$, OH, NO$_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, amino-$C_{1-6}$ alkyl, $C_{1-6}$ alkylamino-$C_{1-6}$ alkyl, di($C_{1-6}$ alkyl)amino-$C_{1-6}$ alkyl, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carbamyl-$C_{1-6}$ alkyl, $C_{1-6}$ alkylcarbamyl-$C_{1-6}$ alkyl, di($C_{1-6}$ alkyl)carbamyl-$C_{1-6}$ alkyl, carboxy, carboxy-$C_{1-6}$ alkyl, $C_{1-6}$ alkylcarbonyl, $C_{1-6}$ alkoxycarbonyl, $C_{1-6}$ alkylcarbonyl-$C_{1-6}$ alkyl, $C_{1-6}$ alkoxycarbonyl-$C_{1-6}$ alkyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, alkyl)aminosulfonyl, aminosulfonylamino, $C_{1-6}$ alkylaminosulfonylamino, alkyl)aminosulfonylamino, aminocarbonylamino, $C_{1-6}$ alkylaminocarbonylamino, and di($C_{1-6}$ alkyl)aminocarbonylamino.

12. The compound of claim 11, wherein the peptide comprises 1-8 amino acids independently selected from aspartic acid, glutamic acid, asparagine, proline, arginine, lysine, glycine, and valine.

13. The compound of claim 12, wherein L has a length along the shortest path of 6 atoms to 50 atoms.

14. The compound of claim 1, wherein L comprises a linking group of a formula selected from:

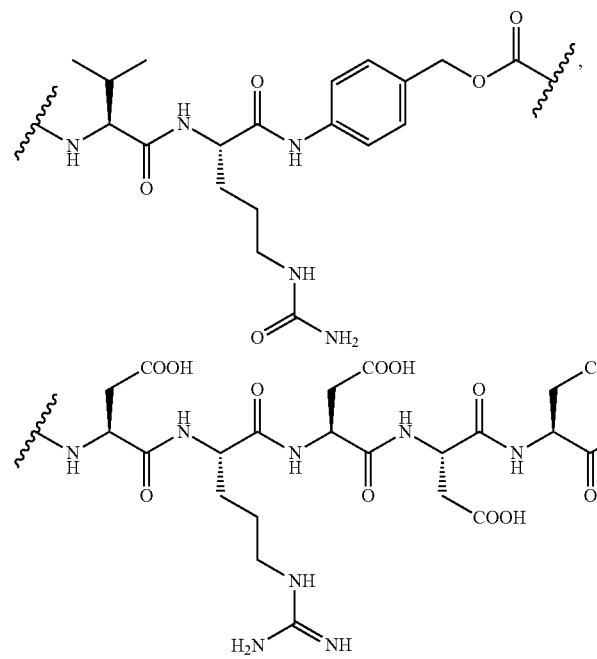

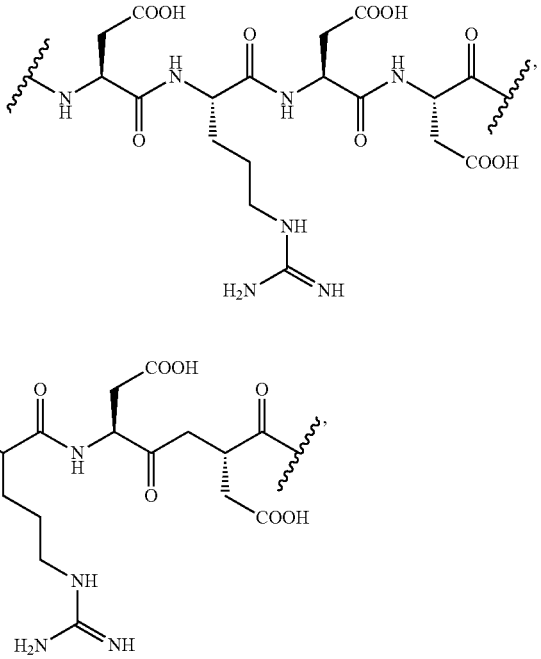

-continued
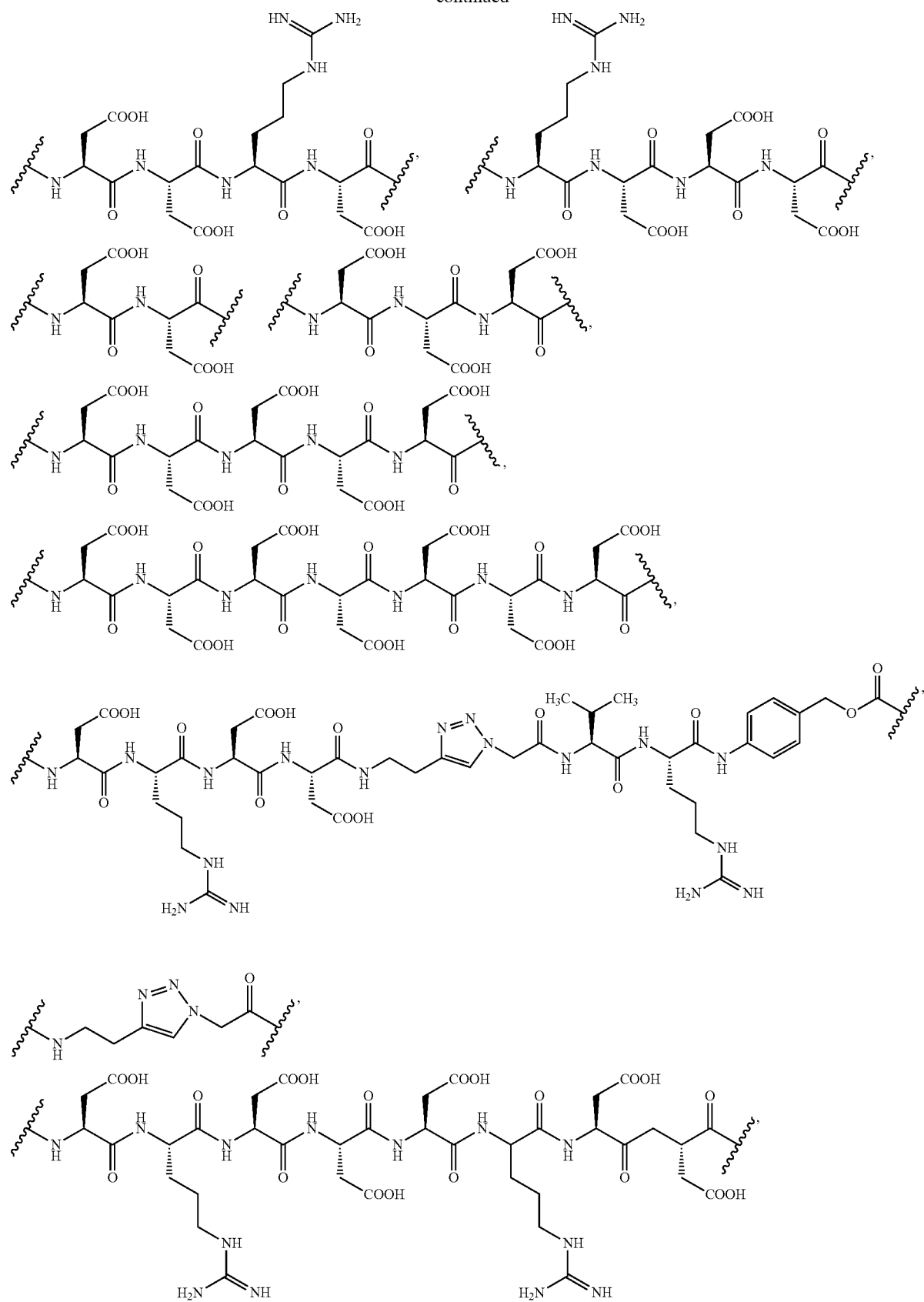

-continued
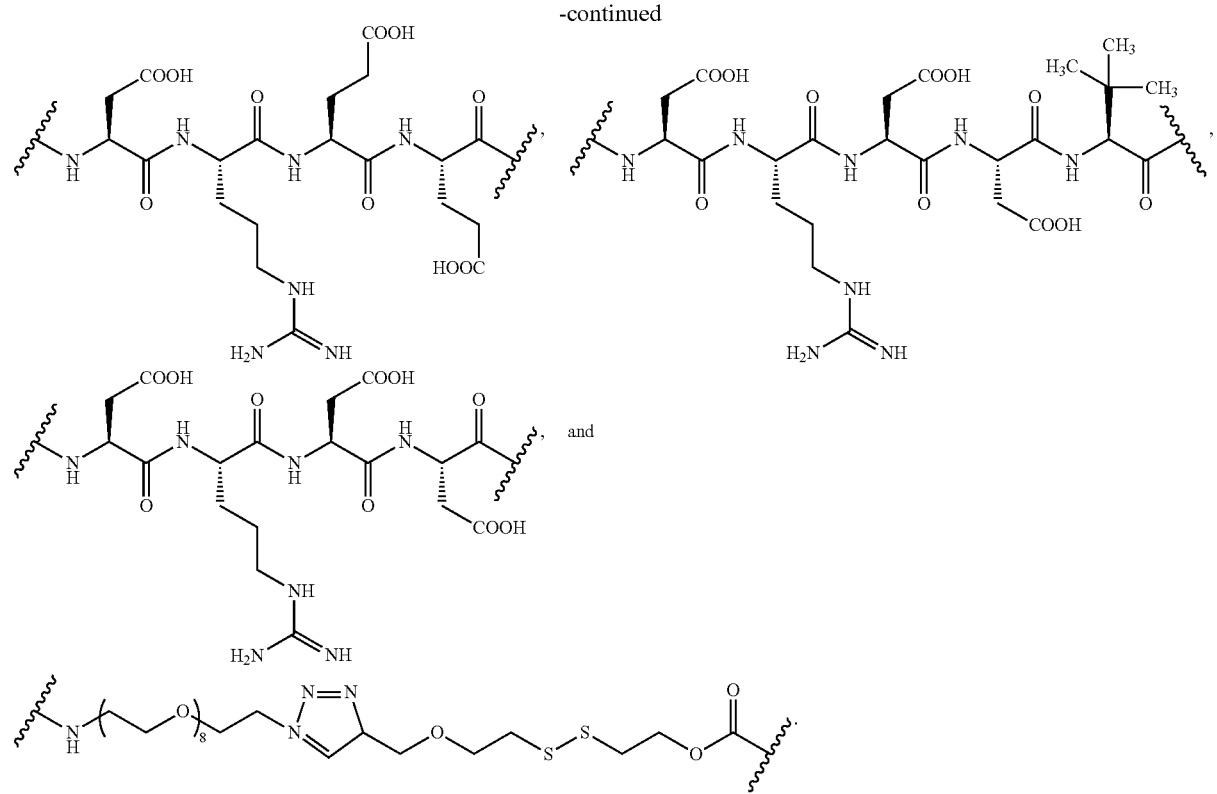
15. The compound of claim 1, wherein the compound is selected from:

441
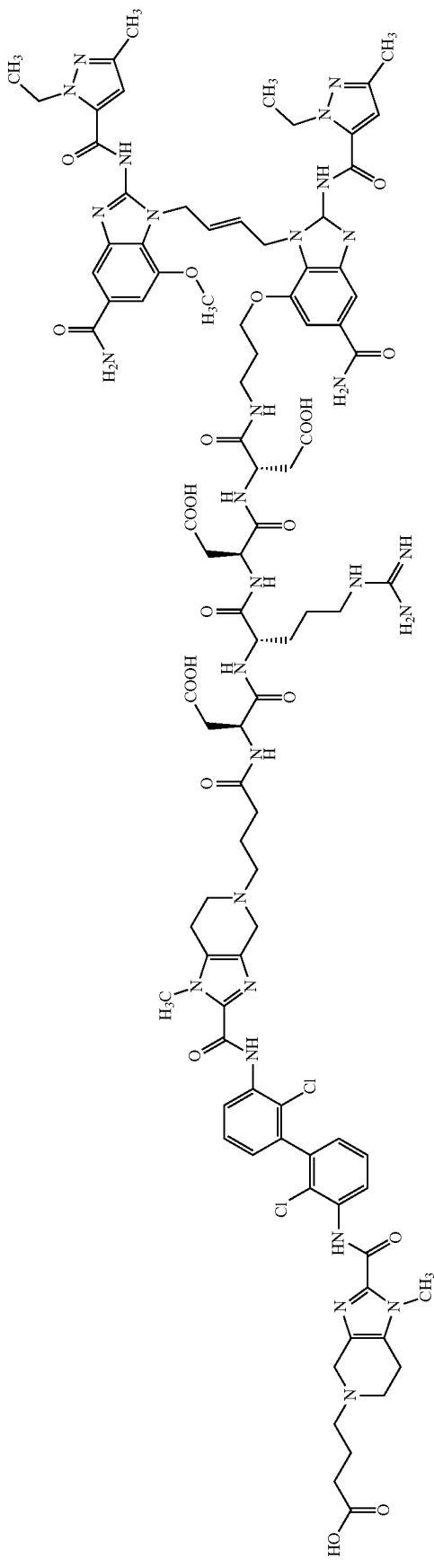
442
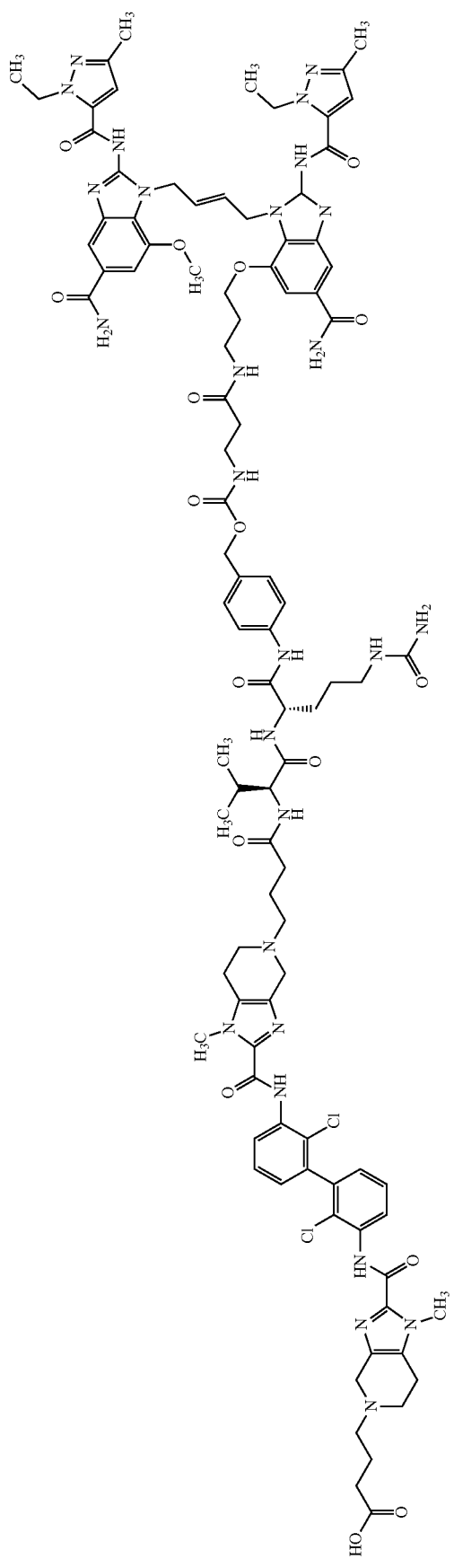

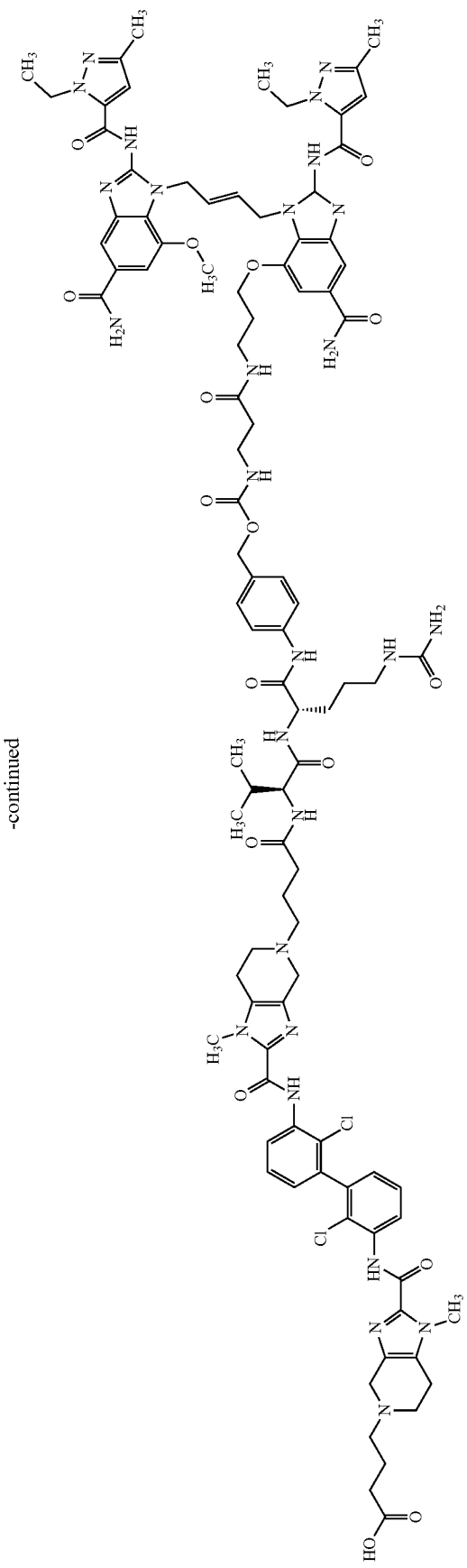

445
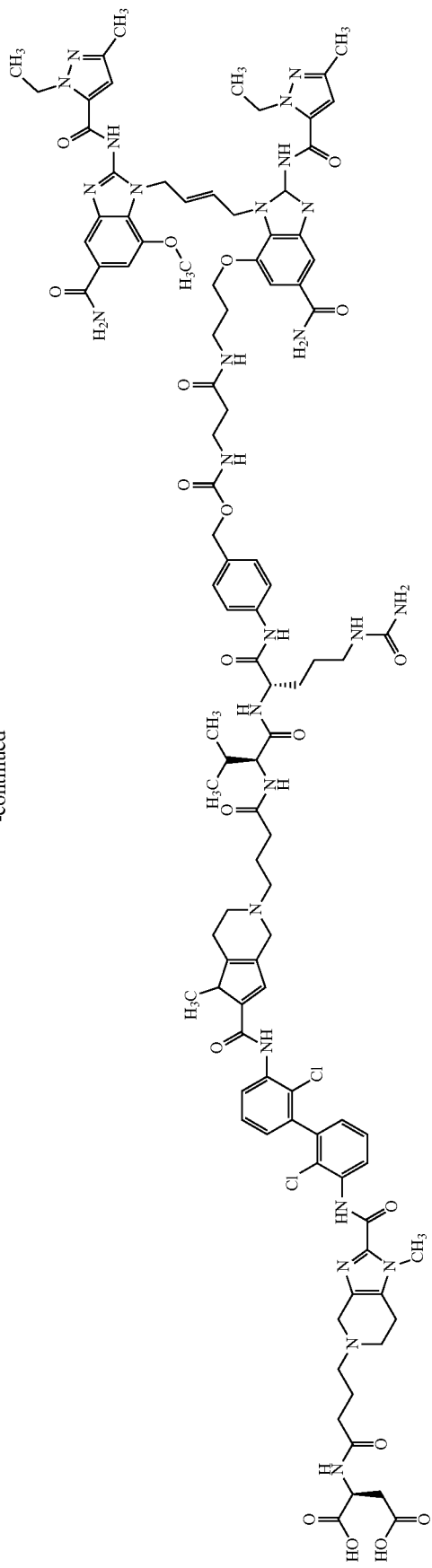
446
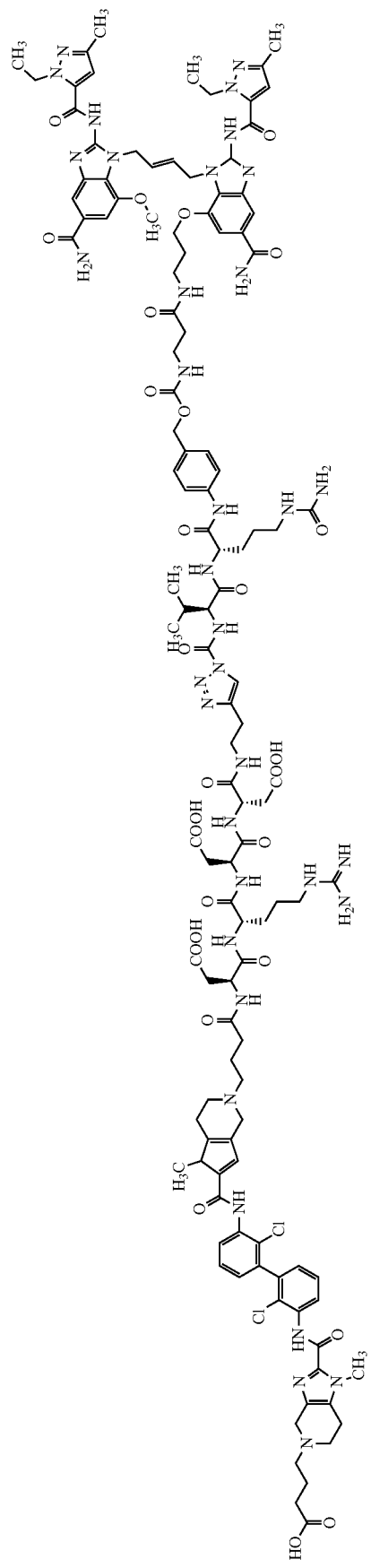

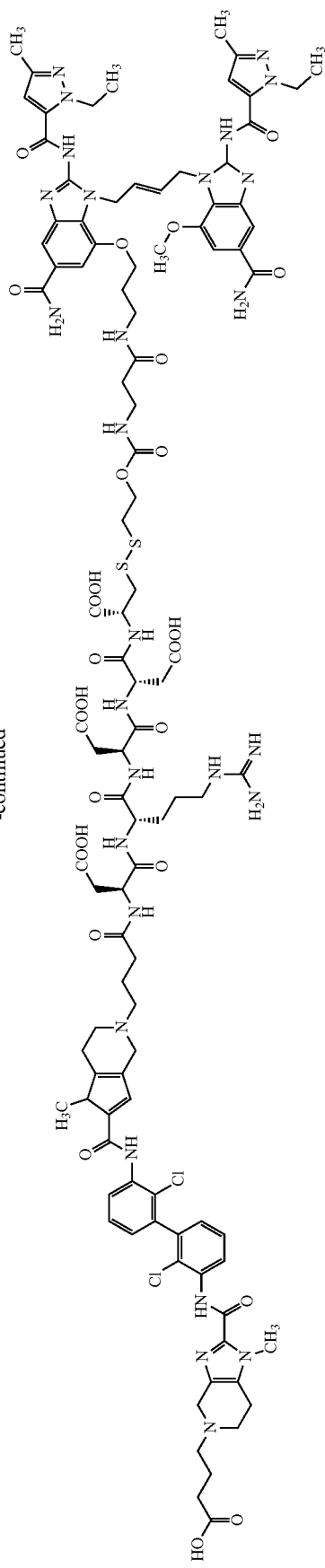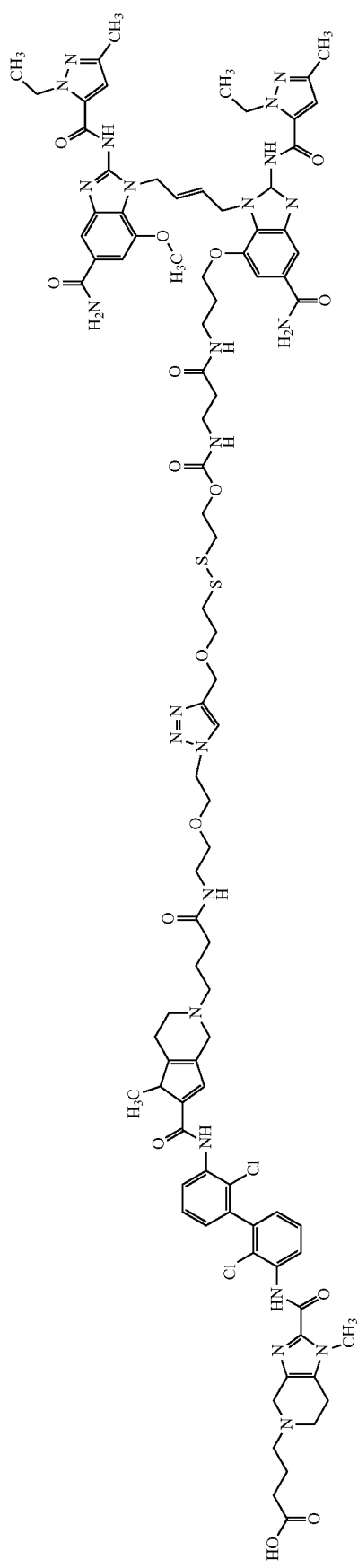

449
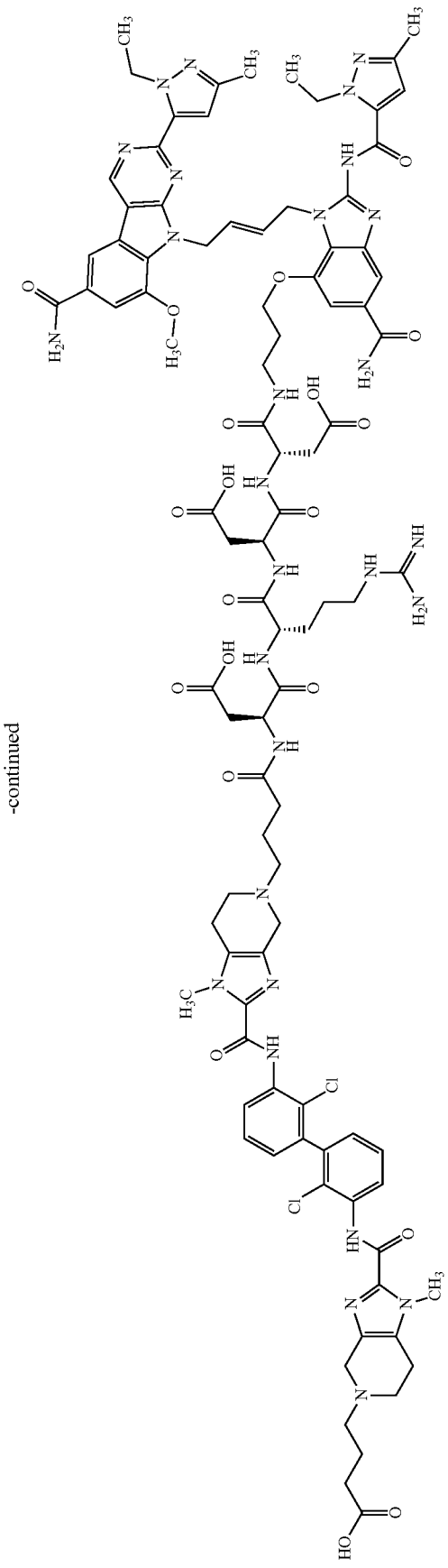
450
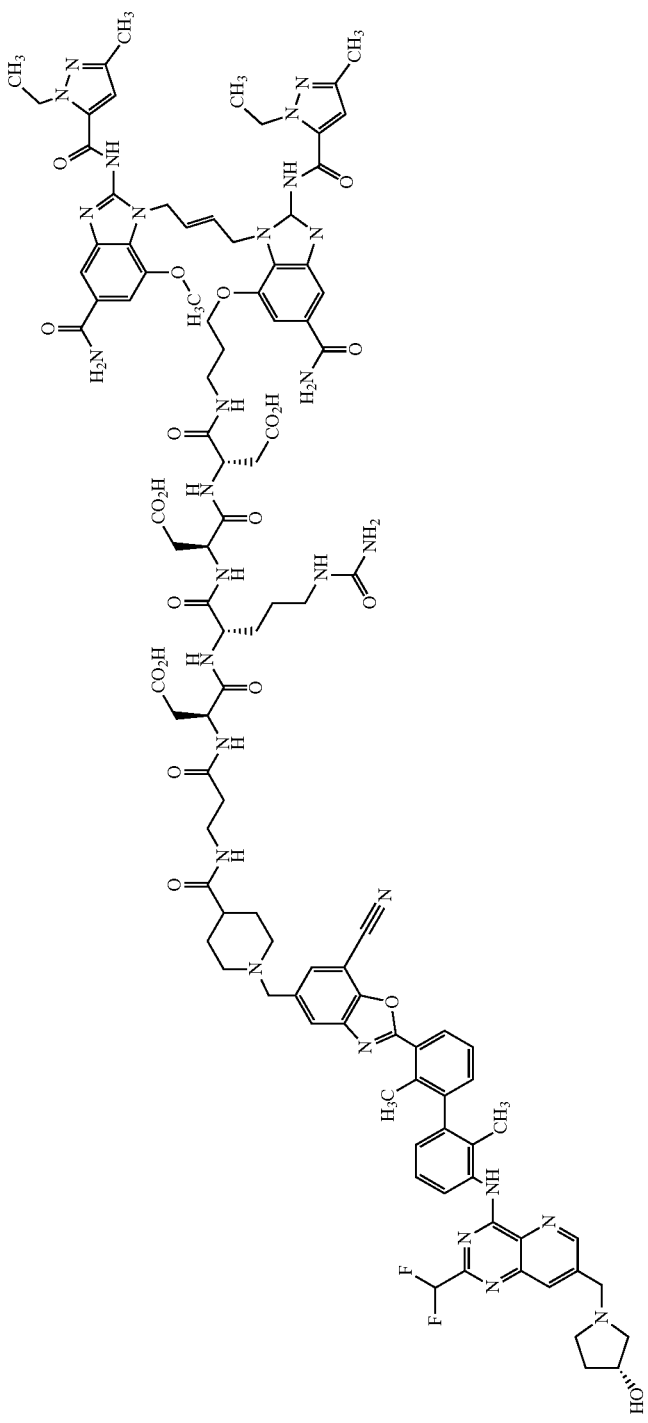

451
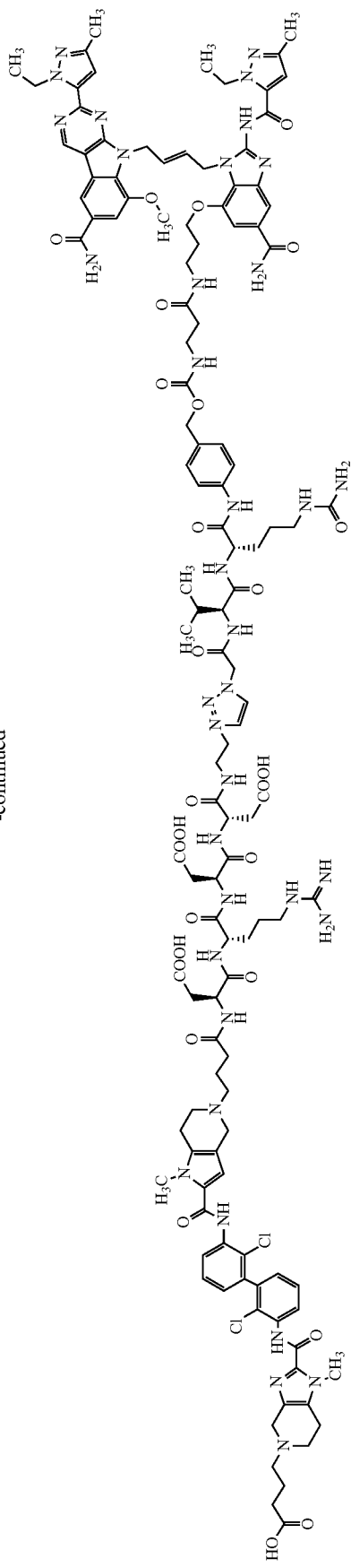
452
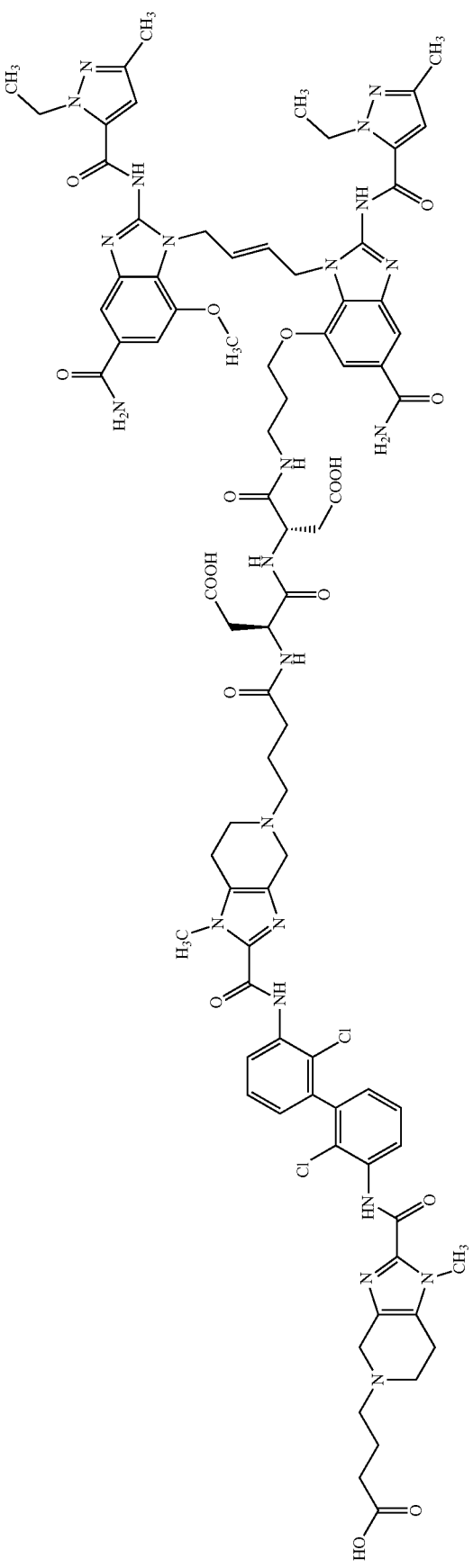

453 454
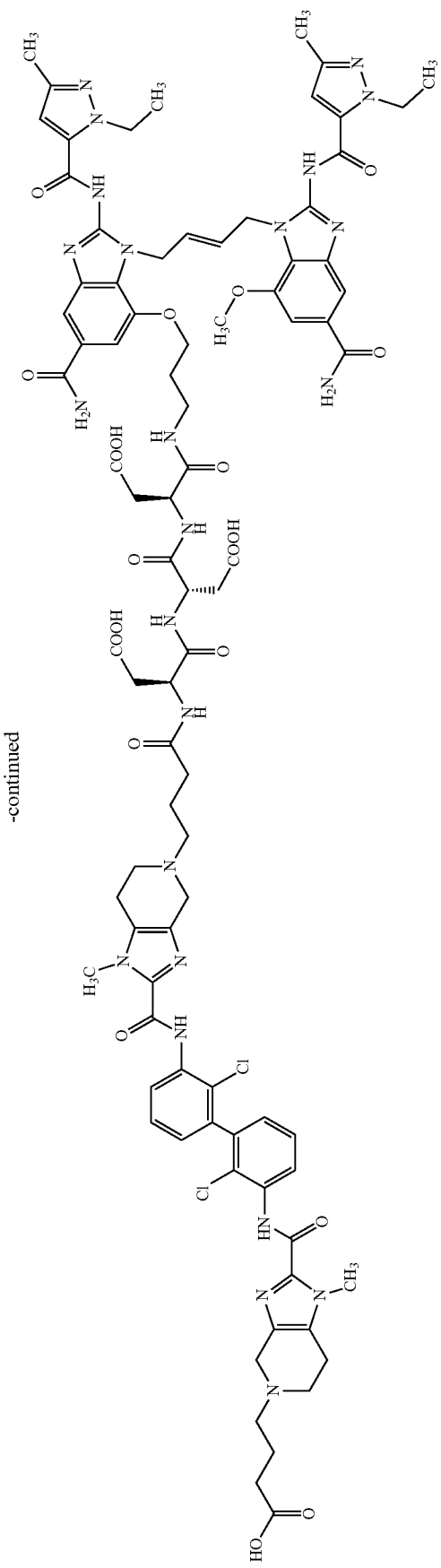
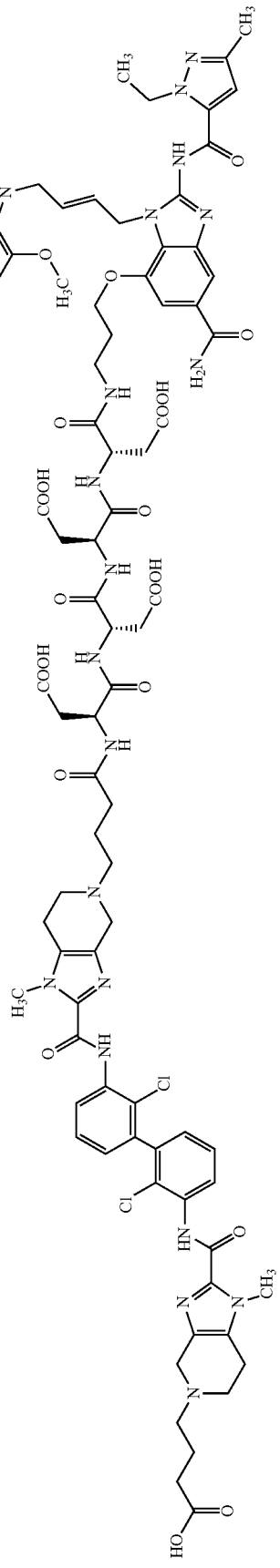

455
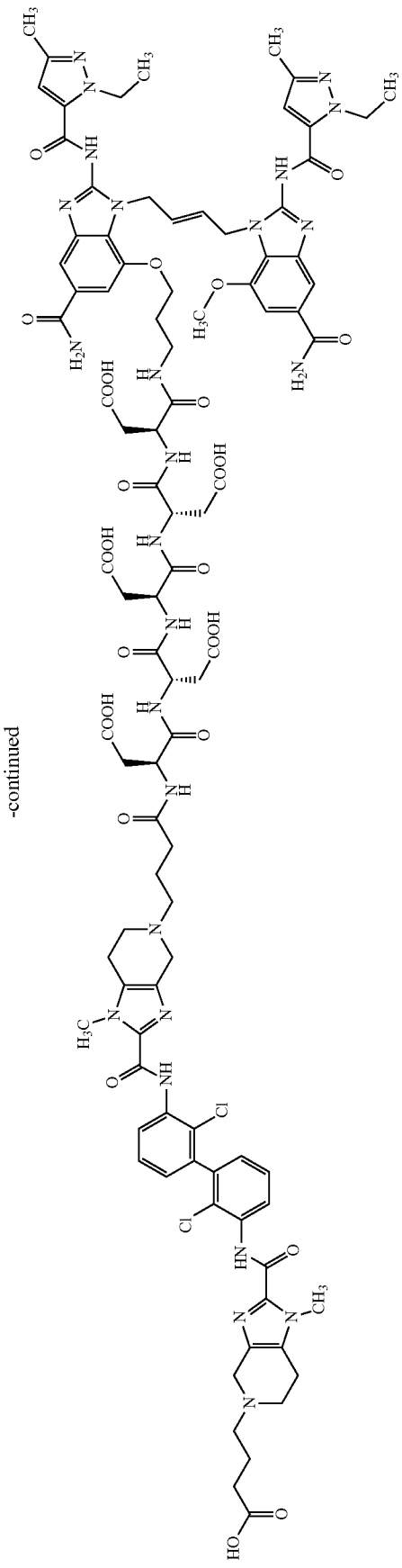
456
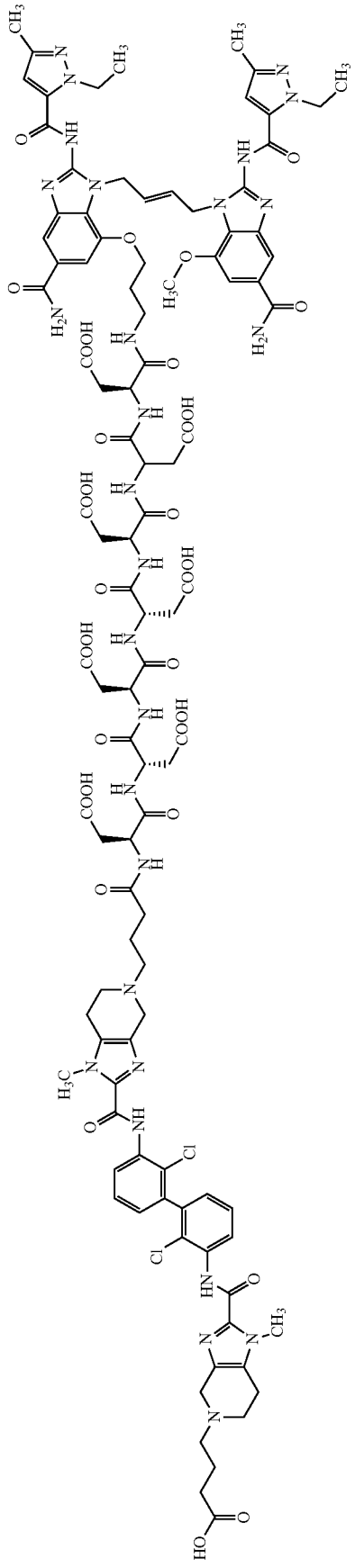

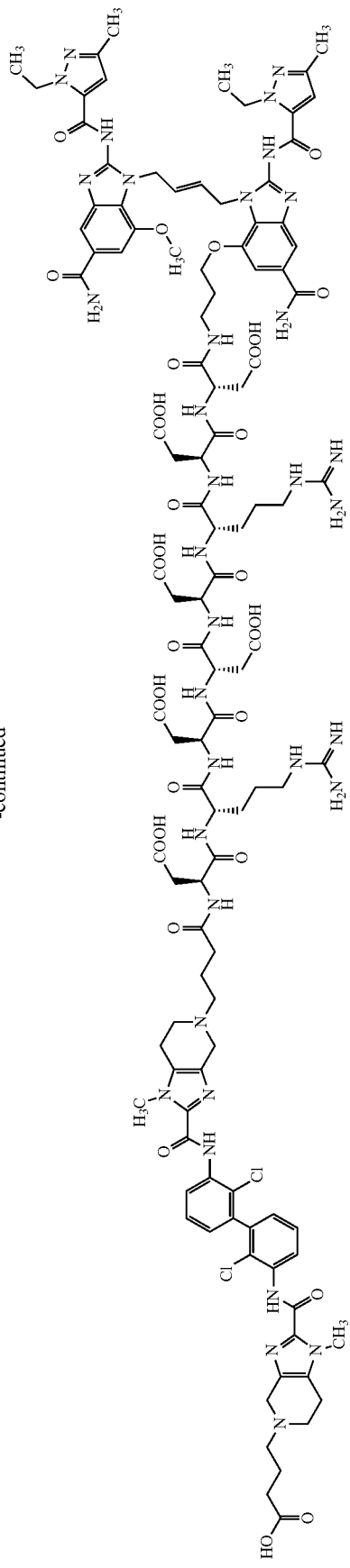
457
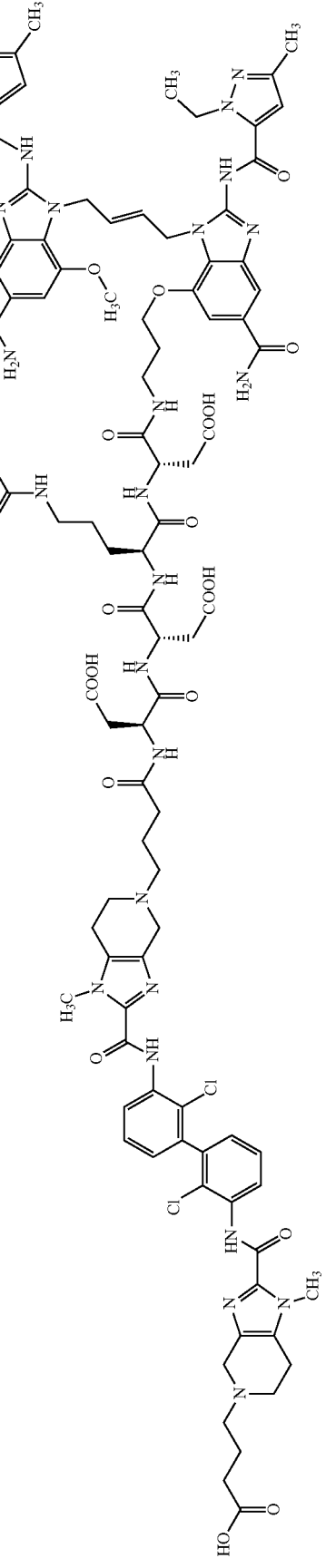
458

459
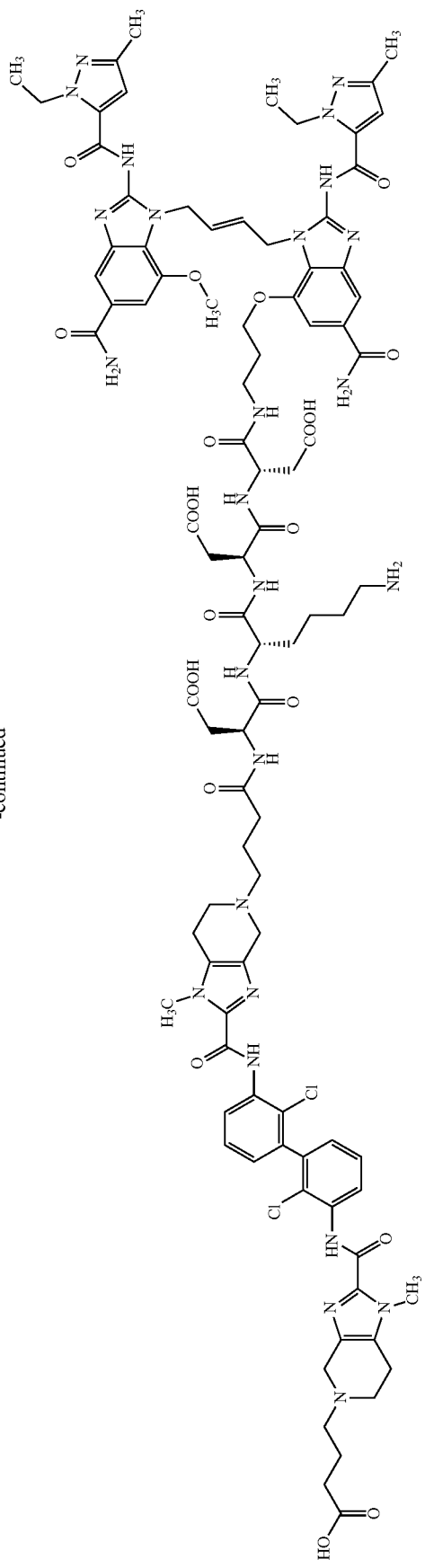
460
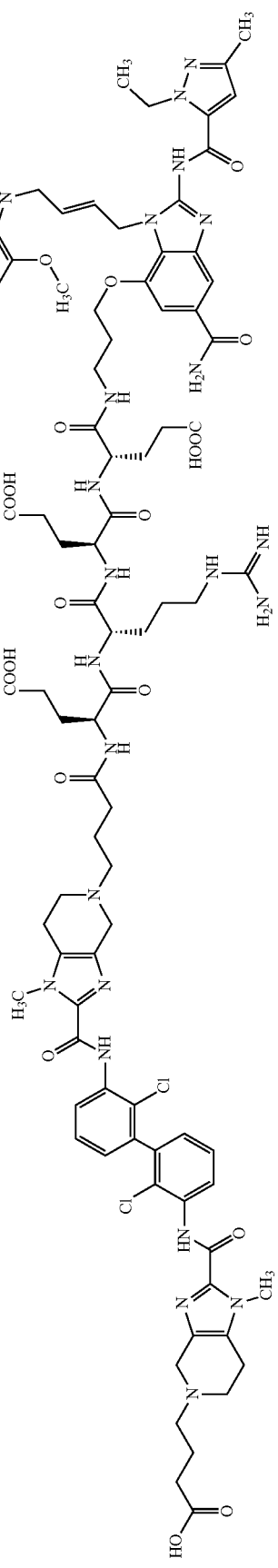

461
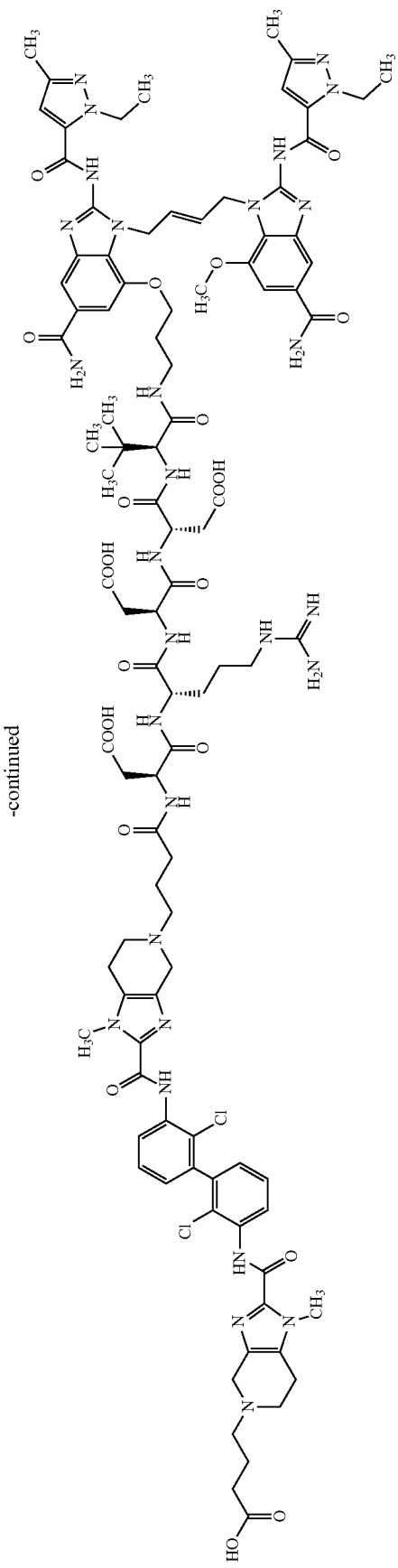
462
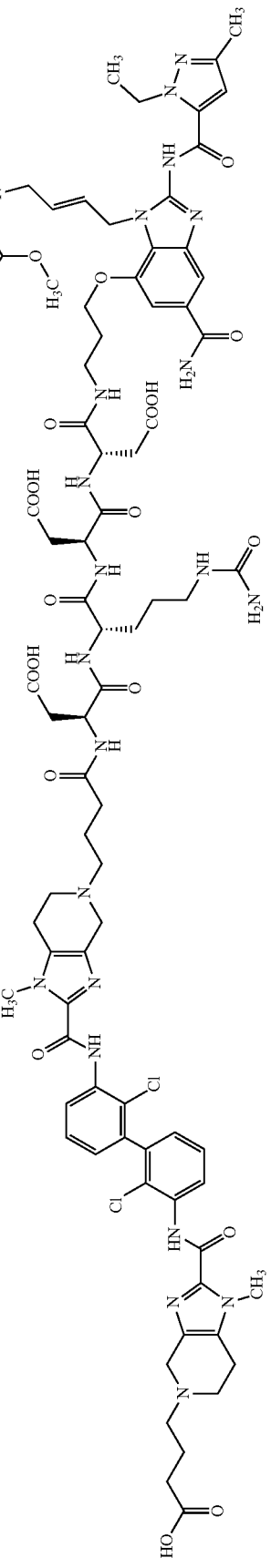

463
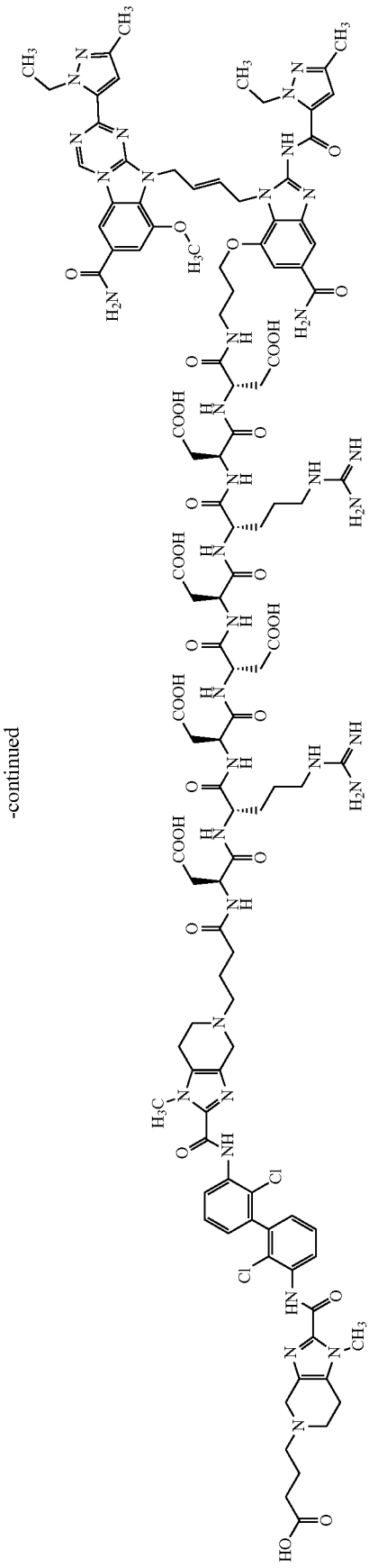
464
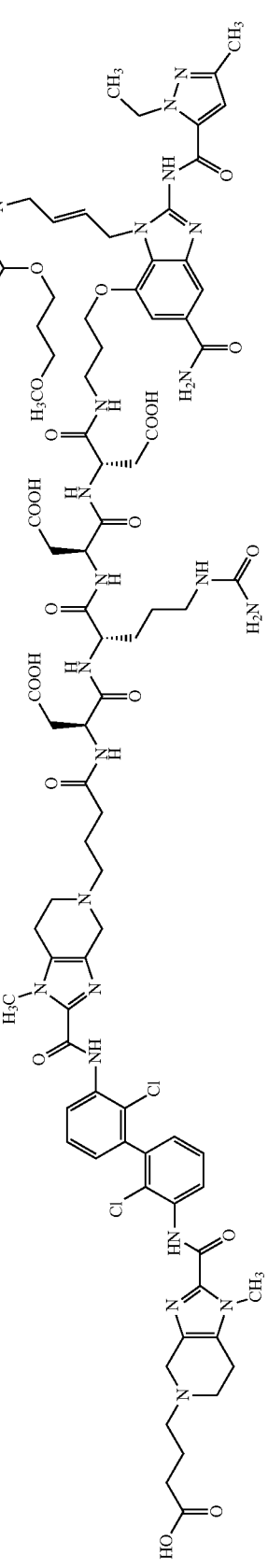
and

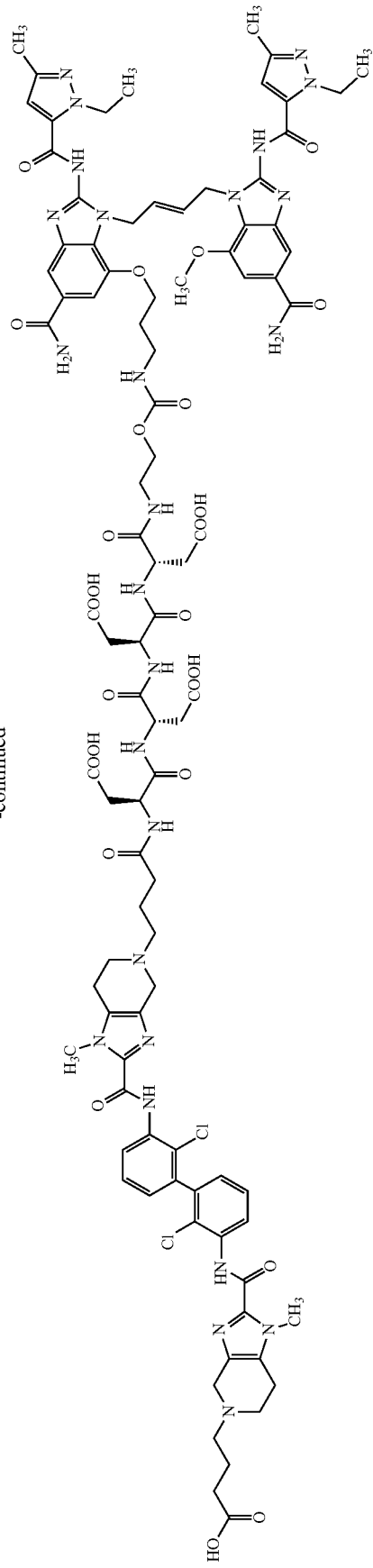
-continued or a pharmaceutically acceptable salt thereof.

16. A method of treating cancer in a patient, comprising administering to the patient a compound of claim 1, or a pharmaceutically acceptable salt thereof, wherein the cancer is selected from bladder cancer, head and neck cancer, uterine cancer (UC), prostate cancer, lung cancer, colon cancer, colorectal cancer, salivary gland cancer, skin cancer, breast cancer, ovarian cancer, lymphoma, pancreatic cancer, and oral cancer.

17. A method of agonizing STING, comprising contacting a cell with a compound of claim 1, or a pharmaceutically acceptable salt thereof.

18. The method of claim 17, wherein the compound or salt selectively agonizes STING in high PD-L1 expressing cells as compared to low PD-L1 expressing cells, wherein the high PD-L1 expressing cells have 200-fold more surface PD-L1 expression than a negative control and the low PD-L1 expressing cells have about 10-fold more surface PD-L1 expression than a negative control.

19. The method of claim 18, wherein the compound or salt is at least 10-fold more selective for the high PD-L1 expressing cells as compared to the low PD-L1 expressing cells.

20. The method of claim 18, wherein the compound or salt is at least 50-fold more selective for the high PD-L1 expressing cells as compared to the low PD-L1 expressing cells.

21. The method of claim 18, wherein the compound or salt is at least 100-fold more selective for the high PD-L1 expressing cells as compared to the low PD-L1 expressing cells.

22. The method of claim 18, wherein the compound or salt is at least 200-fold more selective for the high PD-L1 expressing cells as compared to the low PD-L1 expressing cells.

23. The method of claim 16, wherein the cancer is bladder cancer.

24. The method of claim 16, wherein the cancer is head and neck cancer.

25. The method of claim 24, wherein the head and neck cancer is head and neck squamous cell carcinoma (HNSCC).

26. The method of claim 16, wherein the cancer is uterine cancer (UC).

27. The method of claim 16, wherein the cancer is prostate cancer.

28. The method of claim 16, wherein the cancer is lung cancer.

29. The method of claim 28, wherein the lung cancer is small cell lung carcinoma (SCLC).

30. The method of claim 16, wherein the cancer is melanoma.

31. The method of claim 16, wherein the cancer is colorectal cancer.

32. The method of claim 16, wherein the cancer is salivary gland cancer.

33. The method of claim 16, wherein the cancer is skin cancer.

34. The method of claim 16, wherein the cancer is breast cancer.

35. The method of claim 34, wherein the breast cancer is triple-negative breast cancer.

36. The method of claim 16, wherein the cancer is ovarian cancer.

37. The method of claim 16, wherein the cancer is lymphoma.

38. The method of claim 37, wherein the lymphoma is T-cell lymphoma.

39. The method of claim 16, wherein the cancer is pancreatic cancer.

40. The method of claim 16, wherein the cancer is oral cancer.

* * * * *

UNITED STATES PATENT AND TRADEMARK OFFICE
CERTIFICATE OF CORRECTION

PATENT NO. : 11,596,692 B1
APPLICATION NO. : 16/691150
DATED : March 7, 2023
INVENTOR(S) : Liangxing Wu, Zhenwu Li and Wenqing Yao It is certified that error appears in the above-identified patent and that said Letters Patent is hereby corrected as shown below:

In the Claims

Column 423, Line 18, Claim 1, delete "—0—," and insert -- —O—, --;

Column 425, Line 57, Claim 1, delete "$R^g$is" and insert -- $R^g$ is --;

Column 426, Line 13, Claim 1, delete "(=NR°R°," and insert -- (=NR°)R°, --;

Column 426, Line 14, Claim 1, delete "(=NR°NR°R°," and insert -- (=NR°)NR°R°, --;

Column 426, Line 14, Claim 1, delete "(=NR°NR°R°," and insert -- (=NR°)NR°R°, --;

Column 426, Line 16, Claim 1, delete "—P(O)(OR°(OR°)," and insert -- —P(O)(OR°)(OR°), --;

Column 426, Line 38, Claim 1, delete "—P(O)(OR$^r$)(0R$^r$)," and insert -- —P(O)(OR$^r$)(OR$^r$), --;

Column 428, Lines 16-17, Claim 1, delete "—C(O) (optionally" and insert -- —C(O)(optionally --;

Column 428, Line 26, Claim 1, delete "$C_{1-4}$" and insert -- $C_{1-6}$ --;

Column 429, Line 58, Claim 1, delete "NR$^{c42}$d$^{d42}$," and insert -- NR$^{c42}$Rd$^{d42}$, --;

Column 429, Line 62, Claim 1, delete "NR$^{c42}$S(=O)$_{2I}$ R$^{b42}$," and insert -- NR$^{c42}$S(=O)$_2$R$^{b42}$, --;

Column 435, Line 24, Claim 11, after "F$^1$," insert -- G$^1$, --;

Column 435, Line 37, Claim 11, delete "wherein wherein" and insert -- wherein --;

Column 436, Lines 28-29, Claim 11, delete "alkyl)aminosulfonyl," and insert -- di($C_{1-6}$ alkyl)aminosulfonyl, --;

Signed and Sealed this
Fifteenth Day of August, 2023

Katherine Kelly Vidal
*Director of the United States Patent and Trademark Office*

CERTIFICATE OF CORRECTION (continued)
U.S. Pat. No. 11,596,692 B1

Page 2 of 11

Column 436, Line 30, Claim 11, delete "alkyl)aminosulfonylamino," and insert -- di($C_{1-6}$ alkyl)aminosulfonylamino, --;

Columns 435-436, Lines 60-65, Claim 14, delete

" 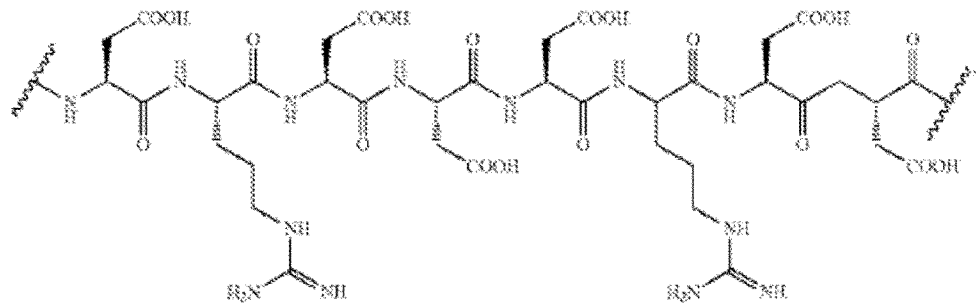 " and insert

-- 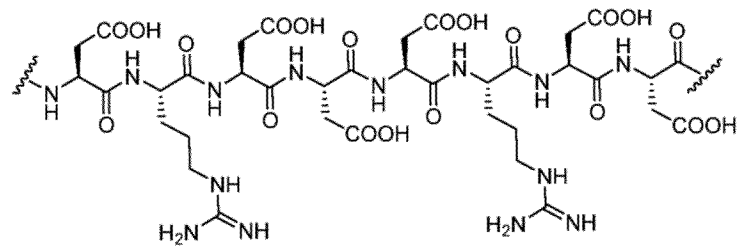 , --;

Column 437, Line 3, Claim 14, after " 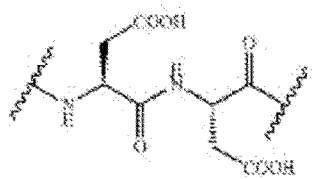 " insert -- , --;

Columns 437-438, Line 6, Claim 14, delete

" 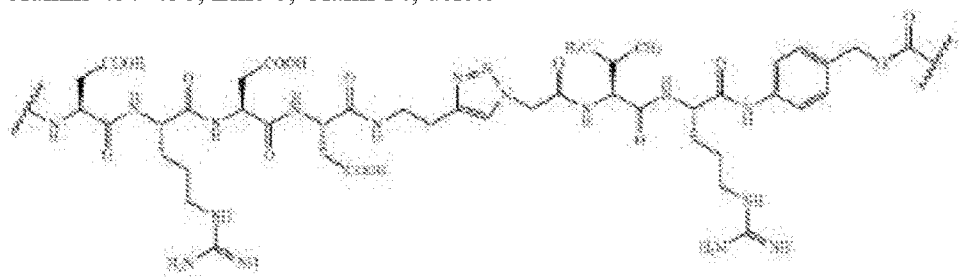 " and insert

-- 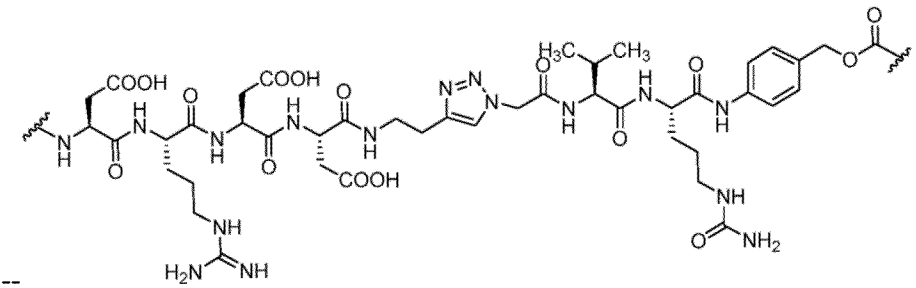 , --;

CERTIFICATE OF CORRECTION (continued)
U.S. Pat. No. 11,596,692 B1

Columns 437-438, Line 8, Claim 14, delete " 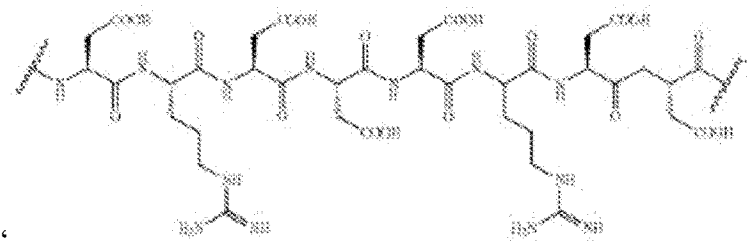 " and insert

-- 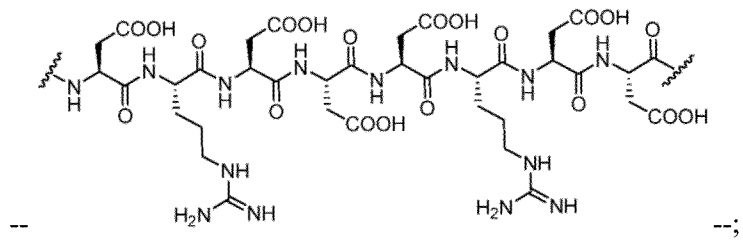 --;

Column 439, Line 2, Claim 14, delete " 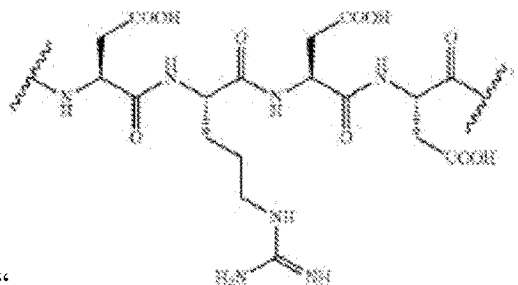 " and insert

-- 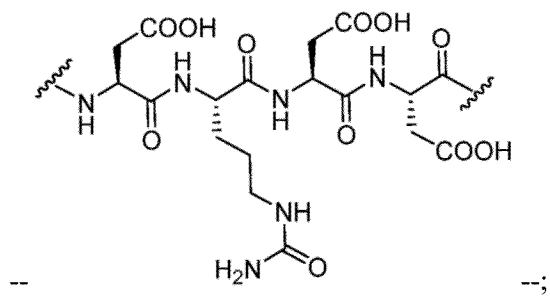 --;

Columns 439-440, Line 3, Claim 14, delete "  " and insert

-- 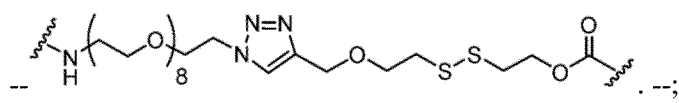 . --;

CERTIFICATE OF CORRECTION (continued)
U.S. Pat. No. 11,596,692 B1

Columns 441-465, delete in entirety and insert

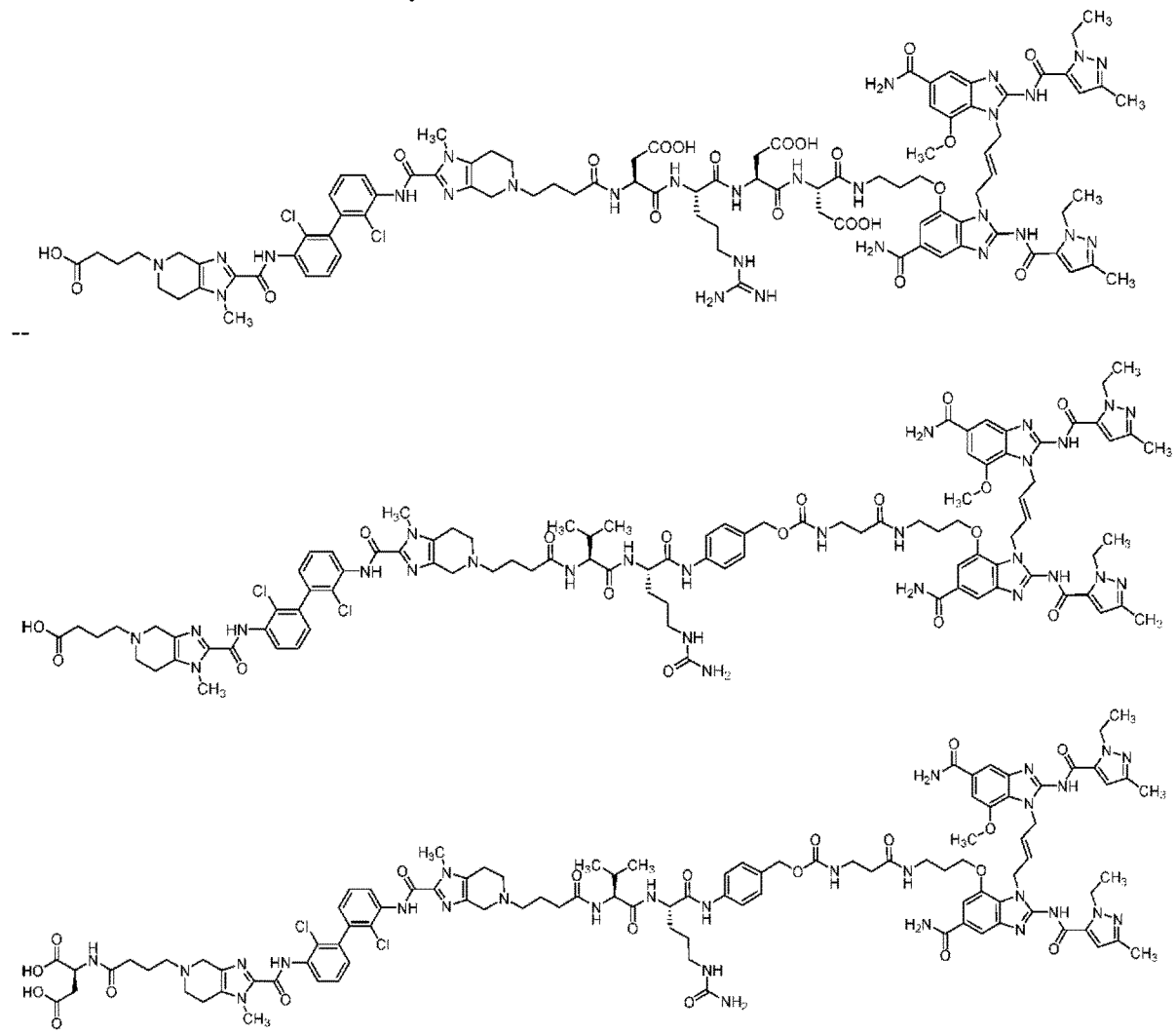

--

CERTIFICATE OF CORRECTION (continued)

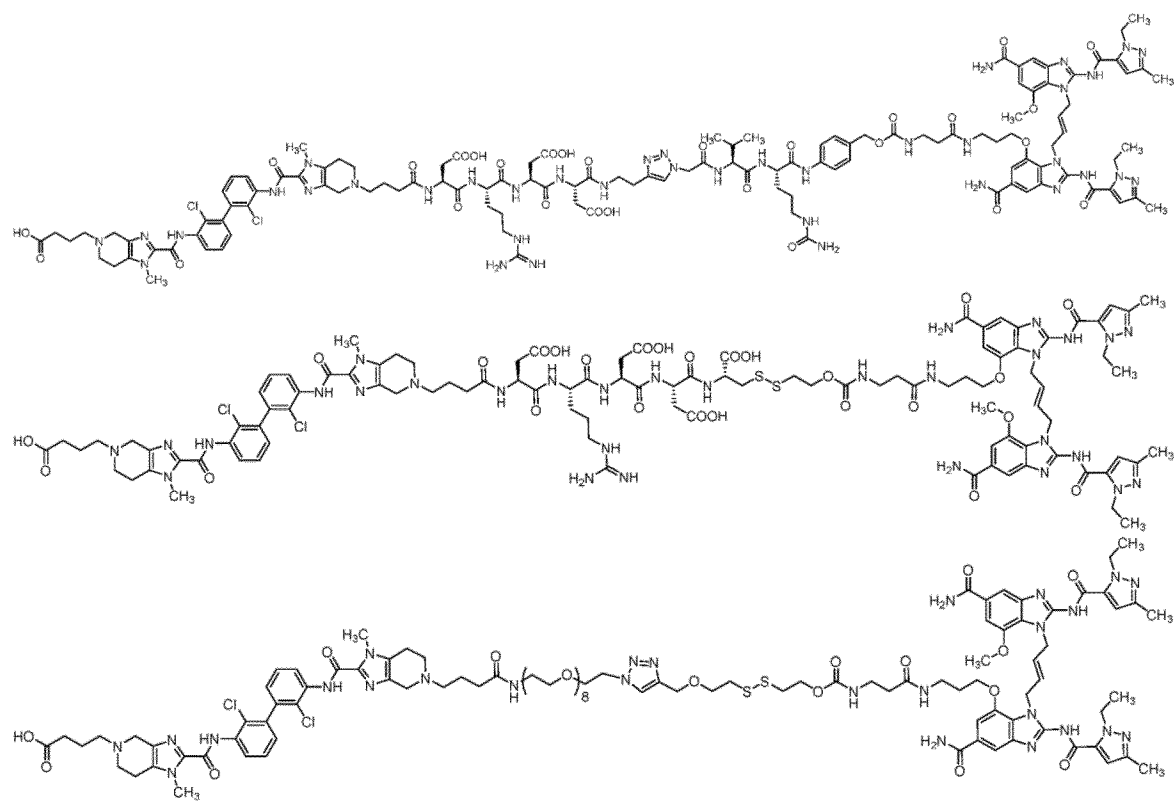

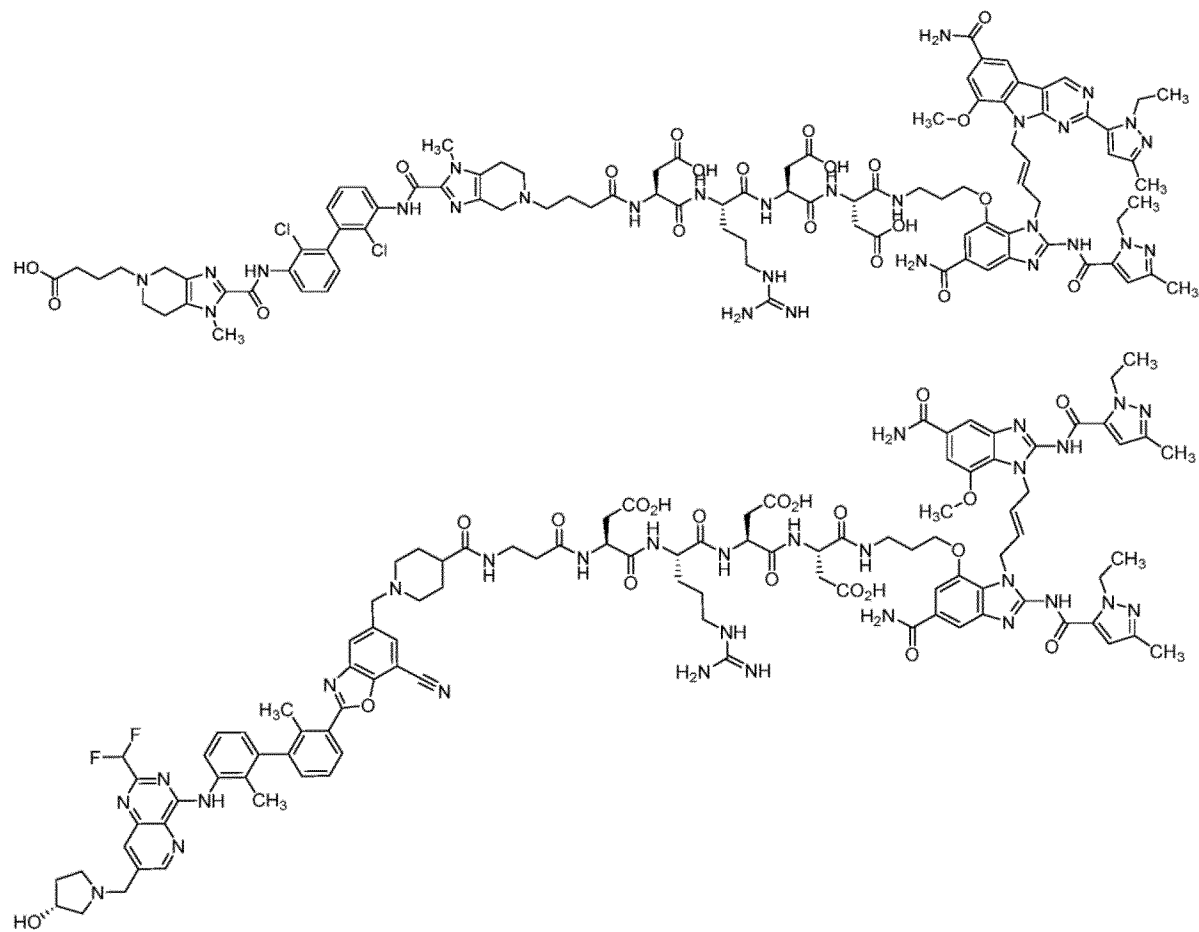

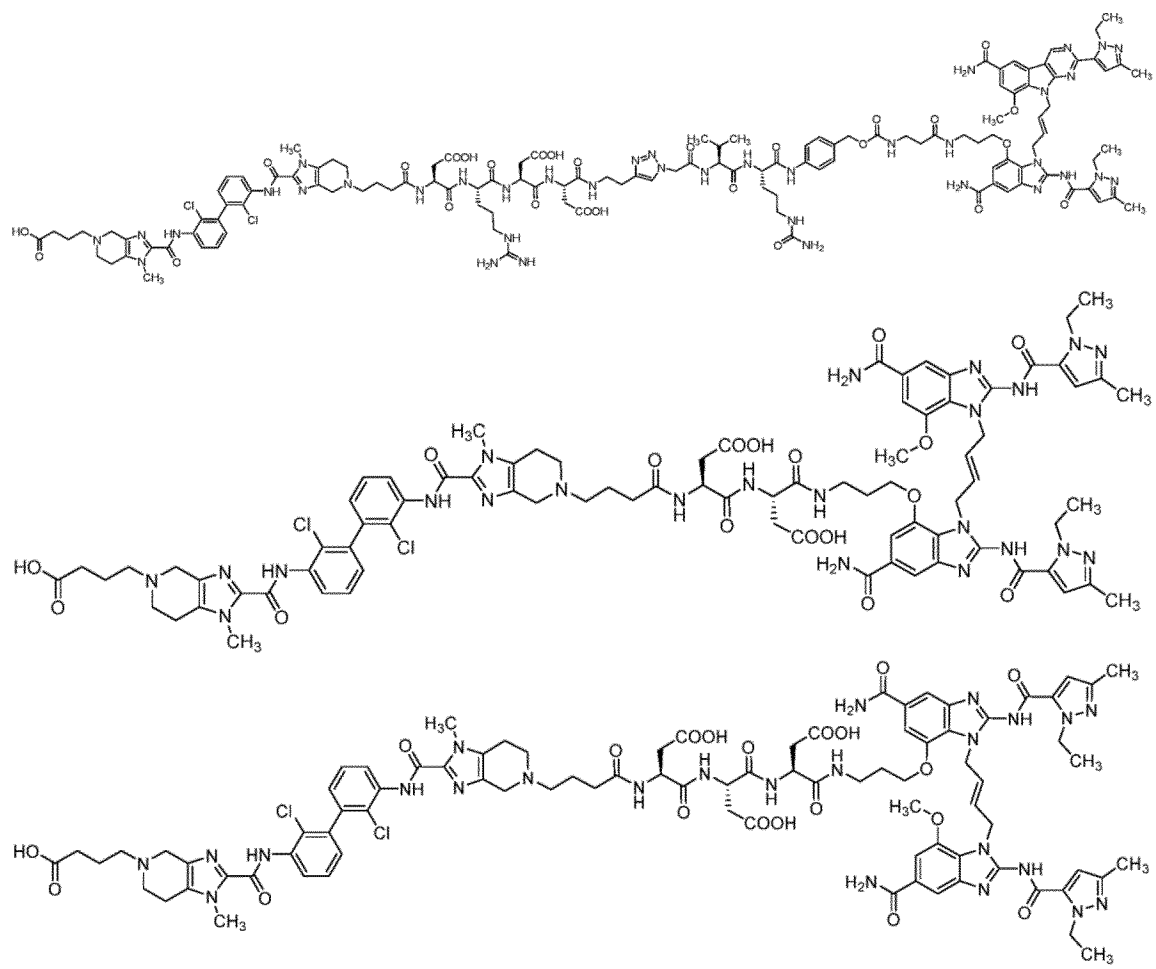

CERTIFICATE OF CORRECTION (continued)
U.S. Pat. No. 11,596,692 B1

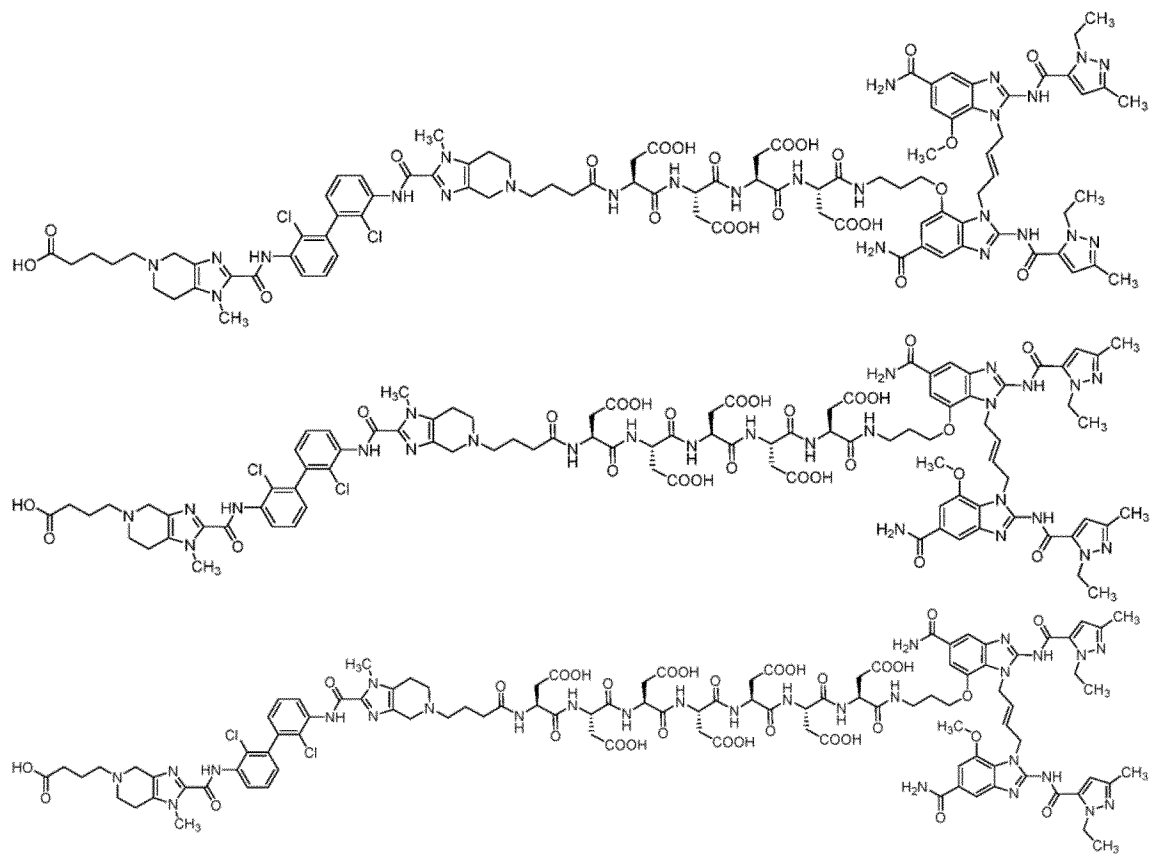

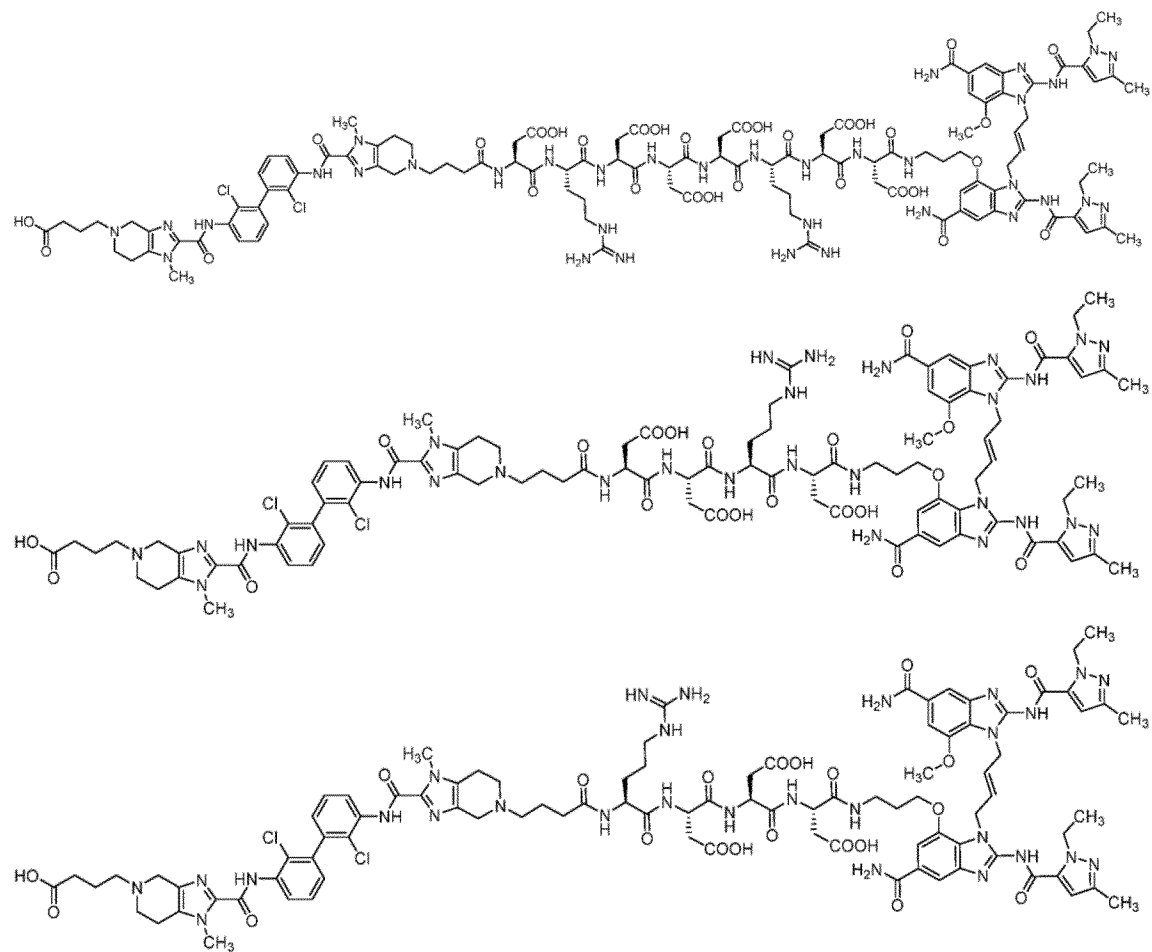

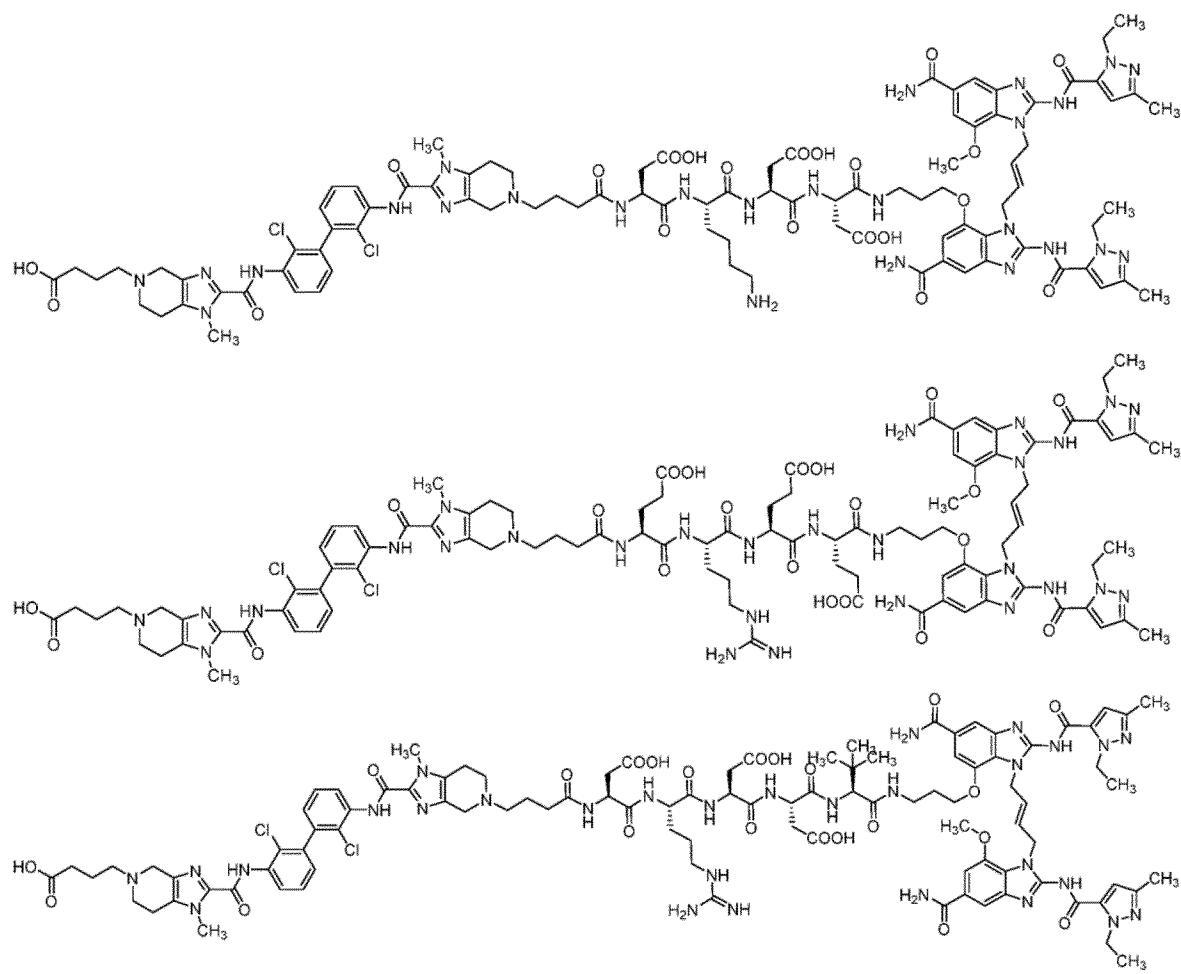

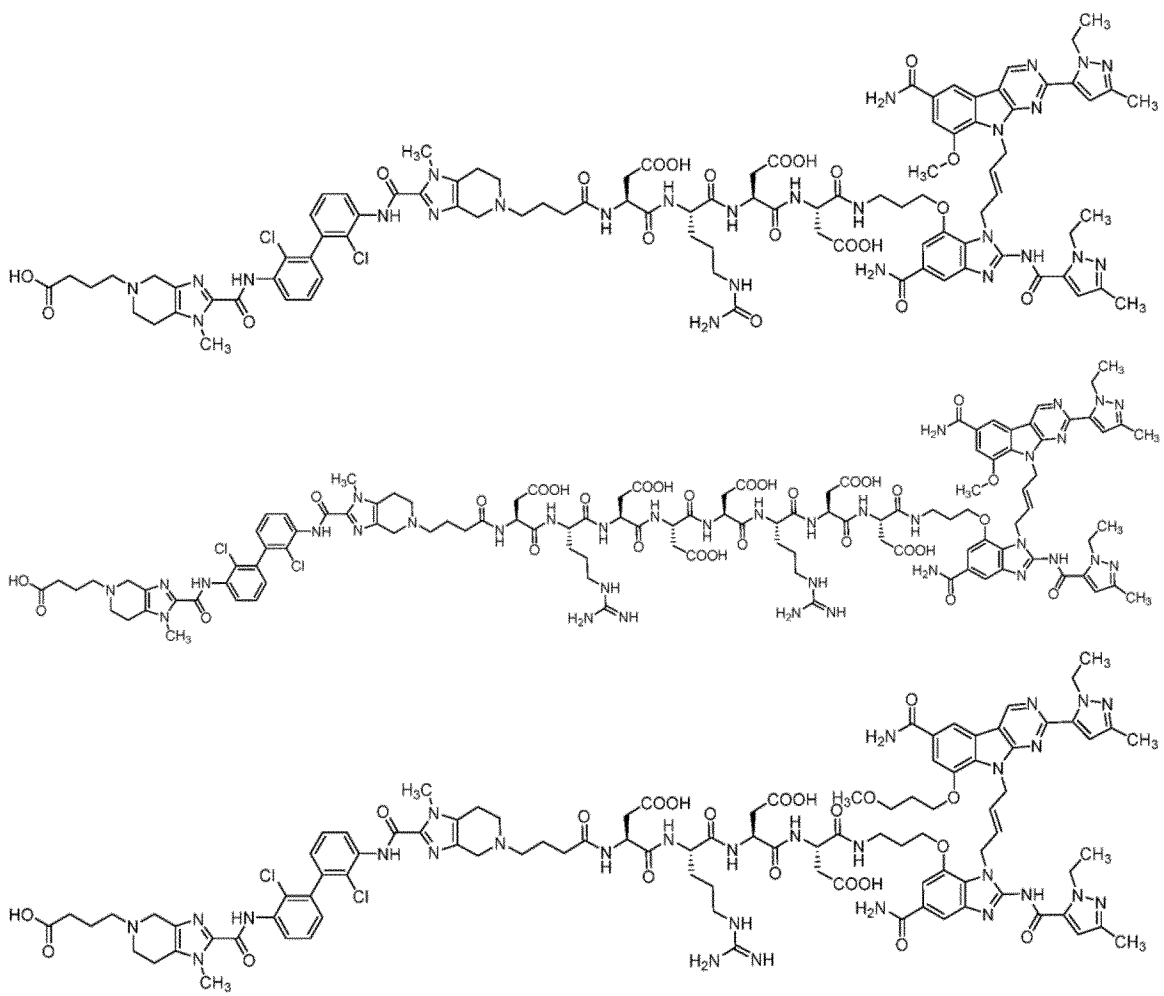
and
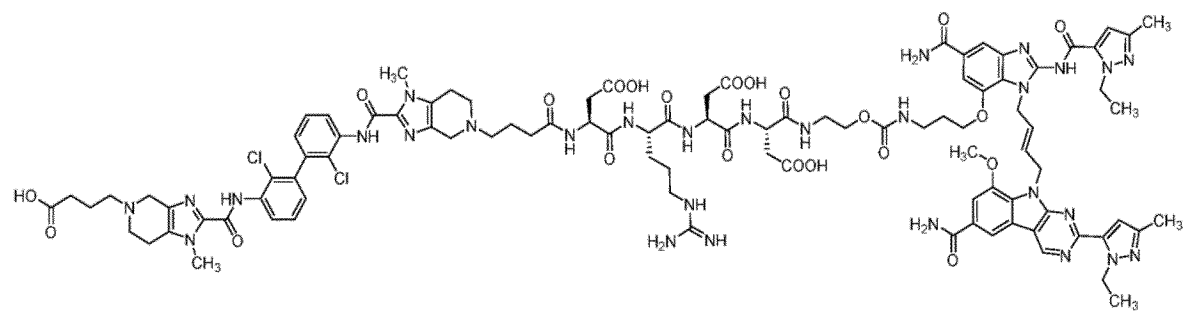
--.